(12) United States Patent
Bucher et al.

(10) Patent No.: US 11,918,582 B2
(45) Date of Patent: Mar. 5, 2024

(54) PYRAZOLE PYRIMIDINE COMPOUNDS AND USES THEREOF

(71) Applicant: RAPT Therapeutics, Inc., South San Francisco, CA (US)

(72) Inventors: Cyril Bucher, San Mateo, CA (US); Adrian Dukes, South San Francisco, CA (US); Blanca Gomez, South San Francisco, CA (US); Hannah Haley, South San Francisco, CA (US); Dennis Hu, San Mateo, CA (US); Jeffrey J. Jackson, San Bruno, CA (US); Michelle Yoo Min Ko, San Francisco, CA (US); Paul Leger, South San Francisco, CA (US); Anqi Ma, South San Francisco, CA (US); Andrew A. Ng, South San Francisco, CA (US); Daniel Poon, South San Francisco, CA (US); Omar Robles, Redwood City, CA (US); Anton Shakhmin, South San Francisco, CA (US); Grant Shibuya, South San Francisco, CA (US); Parcharee Tivitmahaisoon, South San Francisco, CA (US); Vi-Anh Vu, South San Francisco, CA (US); David J. Wustrow, South San Francisco, CA (US); Mikhail Zibinsky, Redwood City, CA (US)

(73) Assignee: RAPT Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 17/694,642

(22) Filed: Mar. 14, 2022

(65) Prior Publication Data

US 2022/0305018 A1   Sep. 29, 2022

Related U.S. Application Data

(60) Provisional application No. 63/161,426, filed on Mar. 15, 2021.

(51) Int. Cl.
  *A61K 31/519* (2006.01)
  *A61K 45/06* (2006.01)
  *C07D 487/04* (2006.01)
  *C07D 519/00* (2006.01)

(52) U.S. Cl.
  CPC ............ *A61K 31/519* (2013.01); *A61K 45/06* (2013.01); *C07D 487/04* (2013.01); *C07D 519/00* (2013.01)

(58) Field of Classification Search
  CPC ....... A61K 31/519; A61K 45/06; A61P 31/00; A61P 31/04; A61P 31/12; A61P 35/00; C07D 487/04; C07D 519/00
  See application file for complete search history.

(56) References Cited

FOREIGN PATENT DOCUMENTS

| CN | 113845531 A | 12/2021 |
|---|---|---|
| WO | WO-2018/049152 A1 | 3/2018 |
| WO | WO-2018/208132 A1 | 11/2018 |
| WO | WO-2019/200120 A1 | 10/2019 |
| WO | WO-2022/197641 A1 | 9/2022 |

OTHER PUBLICATIONS

Alzabin, S. et al. (May 15, 2009). "Hematopoietic progenitor kinase 1 is a negative regulator of dendritic cell activation," *Journal of Immunology* 182(10):6187-6194.
Alzabin, S. et al. (Mar. 2010, e-published Sep. 29, 2009). "Hematopoietic progenitor kinase 1 is a critical component of prostaglandin E2-mediated suppression of the anti-tumor immune response," *Cancer Immunol Immunother* 59(3):419-429.
Di Bartolo, V. et al. (Mar. 19, 2017, e-published Mar. 12, 2007). "A novel pathway down-modulating T cell activation involves HPK-1-dependent recruitment of 14-3-3 proteins on SLP-76," *J Exp. Med.* 204(3):681-691.
Facciabene, A. et al. (May 1, 2012). "T-regulatory cells: key players in tumor immune escape and angiogenesis," *Cancer Res.* 72(9):2162-2171.
International Search Report dated Jun. 30, 2022, for PCT Application No. PCT/US2022/020274, filed Mar. 14, 2022, 4 pages.
Mellman, I. et al. (Dec. 21, 2011). "Cancer immunotherapy comes of age," *Nature* 480(7378):480-489.
Mizoguchi, H. et al. (Dec. 11, 1992). "Alterations in signal transduction molecules in T lymphocytes from tumor-bearing mice," *Science* 258:1795-1798.
Sawasdikosol, S. et al. (Dec. 2012, e-published Apr. 4, 2012). "HPK1 as a novel target for cancer immunotherapy," *Immunol Res.* 54(1-3):262-265.
Shui, Jr-Wen et al. (Jan. 2007, e-published Nov. 19, 2006). "Hematopoietic progenitor kinase 1 negatively regulates T cell receptor signaling and T cell-mediated immune responses," *Nature Immunology* 8(1):84-91.
Sjoblom, T. et al. (Oct. 13, 2006). "The consensus coding sequences of human breast and colorectal cancers," *Science* 314(5797):268-274.
Topalian, S.L. et al. (Apr. 2012, e-published Jan. 9, 2012). "Targeting the PD-1/B7-H1(PD-L1) pathway to activate anti-tumor immunity," *Curr. Opin. Immunol.* 24(2):207-212.
Written Opinion dated Jun. 30, 2022, for PCT Application No. PCT/US2022/020274, filed Mar. 14, 2022, 6 pages.

*Primary Examiner* — Kortney L. Klinkel
*Assistant Examiner* — Padmaja S Rao
(74) *Attorney, Agent, or Firm* — Irina E. Britva; Mintz, Levin, Cohn, Ferris, Glovsky and Popeo, P.C.

(57) ABSTRACT

Disclosed herein are pyrazole pyrimidine compounds that modulate and/or inhibit hematopoietic progenitor kinase 1, as well as methods of making such compounds and therapeutic methods of using same.

57 Claims, No Drawings

PYRAZOLE PYRIMIDINE COMPOUNDS AND USES THEREOF

CROSS-REFERENCES TO RELATED APPLICATIONS

This application claims the benefit of U.S. Provisional Application No. 63/161,426 filed Mar. 15, 2021, which is incorporated herein by reference in its entirety and for all purposes.

TECHNICAL FIELD

The present disclosure generally relates to pyrazole pyrimidine compounds that modulate or inhibit the enzymatic activity of hematopoietic progenitor kinase 1 (HPK1). Provided herein are pyrazole pyrimidine compounds, compositions comprising such compounds, and methods of their use. Also disclosed are pharmaceutical compositions comprising at least one compound according to the disclosure that are useful for the treatment of proliferative disorders, such as cancer, and viral infections.

BACKGROUND

Human cancers harbor numerous genetic and epigenetic alterations, generating neoantigens potentially recognizable by the immune system (Sjoblom et al. (2006) Science 314:268-74). The adaptive immune system, including T and B lymphocytes and dendritic cells, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities. However, although an endogenous immune response to cancer is observed in preclinical models and patients, this response is ineffective, and established cancers are viewed as "self" and tolerated by the immune system. Contributing to this state of tolerance, tumors may exploit several distinct mechanisms to actively subvert anti-tumor immunity. These mechanisms include dysfunctional T-cell signaling (Mizoguchi et al., (1992) Science 258:1795-98), suppressive regulatory cells (Facciabene et al., (2012) Cancer Res. 72:2162-71), and the co-opting of endogenous "immune checkpoints, "which serve to down-modulate the intensity of adaptive immune responses and protect normal tissues from collateral damage, by tumors to evade immune destruction (Topalian et al., (2012a) Curr. Opin. Immunol. 24:1-6; Mellman et al. (2011) Nature 480:480-489).

Hematopoietic progenitor kinase 1 (HPK1) is a STE20-related serine threonine kinase that acts as a down-regulator of T and B cell functions through the AP-1, NFkB, NFAT, Erk2, and Fos pathways. HPK1 has been shown to inducibly associate with the adapter protein SLP-76 and phosphorylate SLP-76 specifically on serine 376. Mutation of serine 376 to alanine resulted in IL-2 gene transcription relative to the wild type (Di Bartolo et al., JExp. Med. (2007) 204:681-691). HPK1 deficiency results in enhanced TCR-induced phosphorylation of SLP-76 and Erk, increased Ca flux, and increased production of cytokines and antigen-specific antibodies indicating that HPK1 negatively regulates TCR signaling and T cell-mediated immune responses (Shui et al., Nature Immunology (2007) Vol 8: 84-91). In addition HPK1 (−/−) T cells are resistant to the suppressive and apoptotic effects of prostaglandin PGE2 (Sawasdikosol et al., Cancer Immunol. Immunother. (2010) 59:419-429). Bone marrow derived DC's from HPK1 deficient mice (HPK1−/−) are superior to DC's derived from wild type mice in stimulating T cell proliferation in vivo and in vitro. These BMDC's are significantly resistant to LPS-induced apoptosis and eliminate s.c. Lewis Lung carcinoma more efficiently than wild type mice in vivo (Alzabin et al., Journal of Immunology (2009), 182: 6187-6194).

Thus, HPK1 is now viewed as a novel target for cancer immunotherapy (Sawasdikosol et al., Immunol Res. (2012) 54: 262-5). Given that HPK1 is not expressed in any major organs outside of the hematopoietic system, it is less likely that an inhibitor of HPK1 kinase activity would cause any serious side effects. Since the result of HPK1 target inhibition in T cells should result in T cell stimulation, sufficient kinase selectivity over kinase targets that result in T cell suppression is necessary to achieving sufficient T cell activation.

Chinese patent application No. 113845531A published Dec. 28, 2021 discloses HPK1-inhibiting compounds having a pyrazole ring structure that can be used alone or in combination with other drugs for the treatment of neoplastic diseases.

There still remains a need for compounds useful as inhibitors of HPK1. Further, there still remains a need for compounds useful as inhibitors of HPK1 with selectivity over kinase targets such as IRAK-4 that result in T cell suppression.

Accordingly, an agent which is safe and effective in inhibiting the function of HPK1, resulting in functional T cell activation would be an important addition for the treatment of patients with diseases or conditions affected by the activity of the enzyme.

SUMMARY

Applicants have found compounds that have activity as HPK1 inhibitors. Applicants have found compounds that have activity as HPK1 inhibitors and have selectivity over IRAK-4. These compounds are provided to be useful as pharmaceuticals with desirable stability, bioavailability, therapeutic index, and toxicity values that are important to their regulatory approval and use in medicinal therapy.

The present disclosure provides pyrazole pyrimidine compounds of Formula (I), which are useful as modulators of HPK1 activity, including salts thereof.

A first aspect of the present disclosure provides a compound of formula (I):

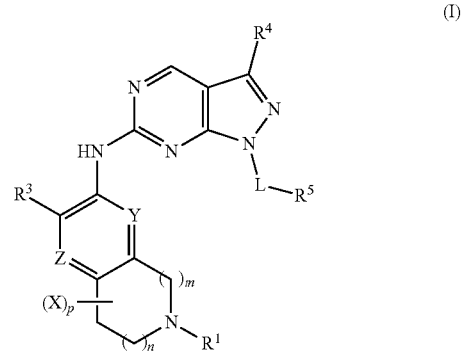

or a pharmaceutically acceptable salt thereof. L is a bond or a substituted or unsubstituted methylene. X is not bonded directly to the N atom of N—R$^1$ and is either absent or if present is a substituted or unsubstituted alkyl. Y is CH or N. Z is CR$^2$ or N. Each of n and m is 0, 1 or 2, and (n+m) equals 1, 2 or 3. p is an integer from 0 to 2. R$^1$ is H, or a substituted or unsubstituted alkyl. R$^2$ is H, a halogen, a substituted or unsubstituted alkyl or a substituted or unsubstituted heteroalkyl. R$^3$ is H, or a substituted or unsubstituted heteroalkyl. R$^4$ is H, a substituted or unsubstituted alkyl or a halogen. R$^5$ is a substituted or unsubstituted alkyl, a substituted or unsubstituted heteroalkyl, a substituted or unsubstituted cycloalkyl or a substituted or unsubstituted heterocycloalkyl.

In one embodiment, a compound of formula (Ia) is provided:

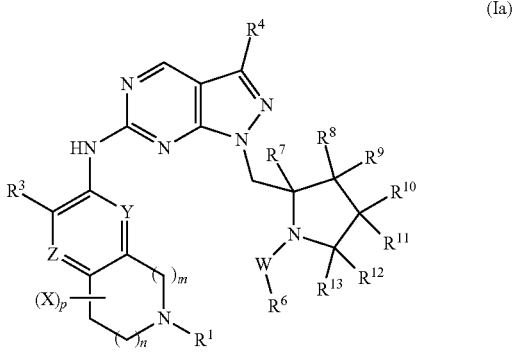

(Ia)

or a pharmaceutically acceptable salt thereof, wherein X, Y, Z, n, m, p, R$^1$, R$^2$, R$^3$ and R$^4$ are as defined in formula (I), including embodiments. W is C(O), S(O), S(O)$_2$ or S(NH)(O). R$^6$ is a substituted or unsubstituted C$_{1-3}$ alkyl, —OCH$_3$ or —NR$^{14}$R$^{15}$. R$^7$ is H or substituted or unsubstituted alkyl. In embodiments, R$^7$ is H or —CH$_3$. R$^8$, R$^9$, R$^{10}$ and R$^{11}$ are each independently H, substituted or unsubstituted C$_{1-3}$ alkyl, —OH or galogen. In embodiments, R$^8$, R$^9$, R$^{10}$ and R$^{11}$ are each independently H, substituted or unsubstituted C$_{1-3}$ alkyl, —OH or —F, —Cl. —Br, or —I. R$^{12}$ and R$^{13}$ are each independently H or C$_{1-3}$ substituted or unsubstituted alkyl; or where one of moiety pairs (i) R$^8$ and R$^9$, (ii) R$^9$ and R$^{10}$, (iii) R$^{10}$ and R$^{11}$, (iv) R$^{11}$ and R$^{12}$ and (v) R$^{12}$ and R$^{13}$ may optionally be joined to form a substituted or unsubstituted C$_{3-6}$ cycloalkyl. R$^{14}$ and R$^{15}$ are each independently H or substituted or unsubstituted alkyl.

In another embodiment, provided is a compound of formula (Ib):

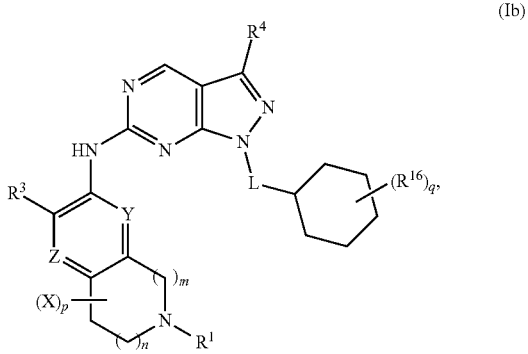

(Ib)

or a pharmaceutically acceptable salt thereof, wherein L, X, Y, Z, n, m, p, R$^1$, R$^2$, R$^3$ and R$^4$ are as defined in formula (I), including embodiments. R$^{16}$ is —OH, a substituted or unsubstituted alkyl, —COOH, —OCH$_3$, —NHC(O)CH$_3$, —NHC(O)CH$_2$OH, —NHSO$_2$CH$_3$ or —C(O)NR$^{17}$R$^{18}$. R$^{17}$ and R$^{18}$ are each independently H or a substituted or unsubstituted C$_{1-3}$ alkyl; and q is 0, 1 or 2.

In another embodiment, provided is a compound of formula (Ic):

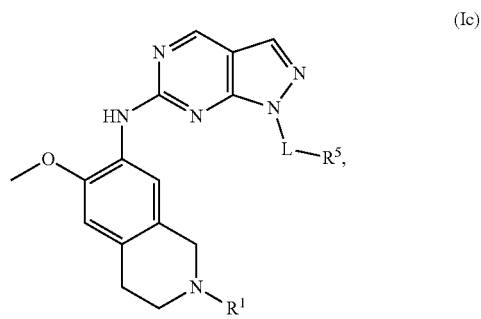

(Ic)

or a pharmaceutically acceptable salt thereof, wherein L, R$^1$ and R$^5$ are as defined in Formula (I).

In another embodiment, provided is a compound of formula (II):

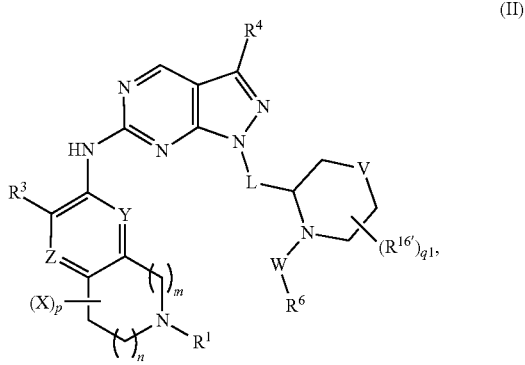

(II)

or a pharmaceutically acceptable salt thereof, wherein L, X, Y, Z, n, m, p, R$^1$, R$^2$, R$^3$ and R$^4$ are as defined in formula (I), including embodiments. V is CR$^{19}$R$^{20}$, O or NR$^{21}$. W is —C(O), —S(O), —S(O)$_2$ or —S(NH)(O). q1 is an integer from 0 to 7. R$^6$ is a substituted or unsubstituted alkyl, —OCH$_3$ or —NR$^{14}$R$^{15}$. R$^{14}$ and R$^{15}$ are each independently H or substituted or unsubstituted alkyl. R$^{19}$ and R$^{20}$ are each H, —OH, —OCH$_3$, —NR$^{14}$R$^{15}$, substituted or unsubstituted alkyl, substituted or unsubstituted heteroalkyl, or substituted or unsubstituted cycloalkyl. R$^{21}$ is H, —OH, substituted or unsubstituted alkyl, or substituted or unsubstituted cycloalkyl. R$^{16'}$ is independently —OH, substituted or unsubstituted alkyl, or halogen. In embodiments, when V is O or NR$^{21}$, then R$^{16'}$ is not —OH or halogen.

In another embodiment, provided is a compound of formula (Ia):

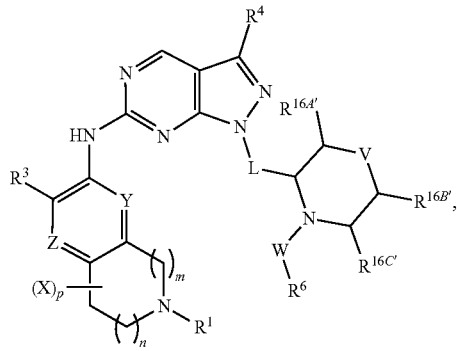

(IIa)

or a pharmaceutically acceptable salt thereof, wherein L, X, Y, Z, n, m, p, $R^1$, $R^2$, $R^3$ and $R^4$ are as defined in formula (I), including embodiments. V, W, $R^6$, $R^{14}$, $R^{15}$, $R^{19}$, $R^{20}$, and $R^{21}$ are as defined in formula (II), including embodiments. $R^{16A'}$, $R^{16B'}$, and $R^{16C'}$ are each independently —OH, halogen, or a substituted or unsubstituted alkyl. In embodiments, when V is O or $NR^{21}$, then $R^{16A'}$, $R^{16B'}$, and $R^{16C'}$ are each independently a substituted or unsubstituted alkyl.

In another embodiment, provided is a compound of formula (III):

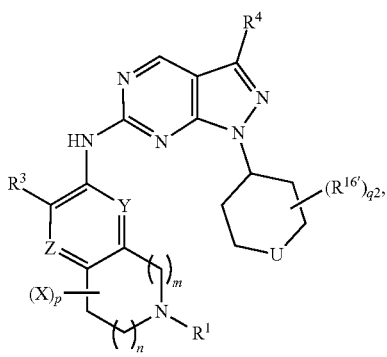

(III)

or a pharmaceutically acceptable salt thereof, wherein X, Y, Z, n, m, p, $R^1$, $R^2$, $R^3$, $R^4$, $R^{14}$, and $R^{15}$ are as defined in formulae (I) and (II), including embodiments. q2 is an integer from 0 to 9. U is O, —$NR^{23}$, —$N(CO)R^{24}$ or —$N(SO_2)R^{25}$. $R^{23}$ and $R^{24}$ are each H, —OH, —$OCH_3$, —$NR^{14}R^{15}$, substituted or unsubstituted alkyl, substituted or unsubstituted heteroalkyl, or substituted or unsubstituted cycloalkyl. $R^{25}$ is H, —OH, substituted or unsubstituted alkyl, or substituted or unsubstituted cycloalkyl. $R^{16'}$ is independently —OH, substituted or unsubstituted alkyl, or halogen. In embodiments, when $R^{16'}$ is adjacent to a heteroatom (U), then $R^{16'}$ is not —OH or halogen.

In another embodiment, provided is a compound of formula (IIIa):

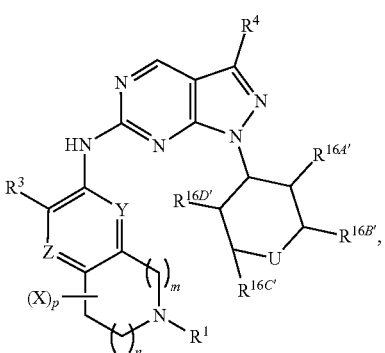

(IIIa)

or a pharmaceutically acceptable salt thereof, wherein X, Y, Z, n, m, p, $R^1$, $R^2$, $R^3$ and $R^4$ are as defined in formula (I), including embodiments. U, $R^{23}$, $R^{24}$ and $R^{25}$ are as defined in formula (III), including embodiments. $R^{16B'}$ and $R^{16C'}$ are each independently a substituted or unsubstituted alkyl. $R^{16A'}$ and $R^{16D'}$ are each independently —OH, substituted or unsubstituted alkyl, or halogen.

In another embodiment, provided is a compound of formula (IV):

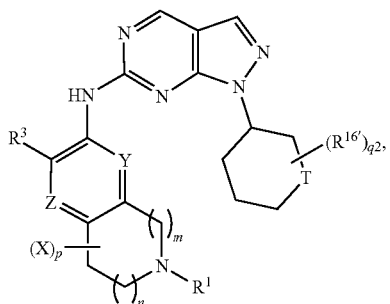

(IV)

or a pharmaceutically acceptable salt thereof, wherein X, Y, Z, n, m, p, $R^1$, $R^2$, $R^3$, $R^4$, and q2 are as defined in formulae (I)-(III), including embodiments. T is O, —$NR^{27}$, —N(CO)$R^{28}$ or —$N(SO_2)R^{29}$. $R^{27}$ and $R^{28}$ are each H, —OH, —$OCH_3$, —$NR^{14}R^{15}$, substituted or unsubstituted alkyl, substituted or unsubstituted heteroalkyl, or substituted or unsubstituted cycloalkyl. $R^{29}$ is H, —OH, substituted or unsubstituted alkyl, or substituted or unsubstituted cycloalkyl. $R^{16'}$ is independently —OH, substituted or unsubstituted alkyl, or halogen. In embodiments, when $R^{16'}$ is adjacent to a heteroatom (T), then $R^{16'}$ is not —OH or halogen.

In another embodiment, provided is a compound of formula (IVa):

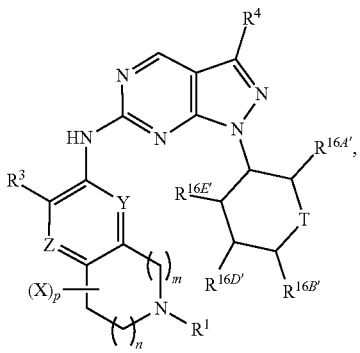

(IVa)

or a pharmaceutically acceptable salt thereof, wherein X, Y, Z, n, m, p, $R^1$, $R^2$, $R^3$ and $R^4$ are as defined in formula (I), including embodiments. T, $R^{27}$, $R^{28}$ and $R^{29}$ are as defined in formula (IV), including embodiments. $R^{16A'}$ and $R^{16B'}$ are each independently a substituted or unsubstituted alkyl. $R^{16D'}$ and $R^{16E'}$ are each independently —OH, substituted or unsubstituted alkyl, or halogen.

The present disclosure also provides pharmaceutical compositions comprising a compound of Formulae (I)-(IVa) and/or a pharmaceutically acceptable salt thereof; and a pharmaceutically acceptable carrier.

The present disclosure also provides a method of treating a disease or disorder associated with the activity of HPK1, the method comprising administering to a mammalian patient a compound of Formulae (I)-(IVa) and/or a pharmaceutically acceptable salt thereof.

The present disclosure also provides processes and intermediates for making the compounds of Formulae (I)-(IVa) and/or salts thereof.

The present disclosure also provides a compound of Formulae (I)-(IVa) and/or a pharmaceutically acceptable salt thereof, for use in therapy.

The present disclosure also provides the use of the compounds of Formulae (I)-(IV) and/or pharmaceutically acceptable salts thereof, for the manufacture of a medicament for the treatment of HPK1 related conditions.

The compounds of Formulae (I)-(IVa) and compositions comprising the compounds of Formulae (I)-(IVa) may be used in treating, preventing, or curing viral infections and various proliferative disorders, such as cancer. The present disclosure also provides a method of treating cancer. The present disclosure also provides a method of treating a hematological cancer. The present disclosure also provides a method of treating a viral infection. Pharmaceutical compositions comprising these compounds are useful in treating, preventing, or slowing the progression of diseases or disorders in a variety of therapeutic areas, such as viral infections and cancer.

These and other features of the disclosure will be set forth in expanded form as the disclosure continues.

DETAILED DESCRIPTION

Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). In embodiments, the alkyl is fully saturated. In embodiments, the alkyl is monounsaturated. In embodiments, the alkyl is polyunsaturated. Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkynylene" by itself or as part of another substituent, means, unless otherwise stated, a divalent radical derived from an alkyne. In embodiments, the alkylene is fully saturated. In embodiments, the alkylene is monounsaturated. In embodiments, the alkylene is polyunsaturated. An alkenylene includes one or more double bonds. An alkynylene includes one or more triple bonds. The term "unsubstituted methylene" refers to the moiety —$CH_2$—. The term "substituted methylene" refers to that moiety wherein one or both hydrogen atoms are replaced with a substituent.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—

$CH_2$—$CH_3$, —$CH_2$—S—$CH_2$, —S(O)—$CH_3$, —$CH_2$—$CH_2$—$S(O)_2$—$CH_3$, —CH=CH—O—$CH_3$, —$Si(CH_3)_3$, —$CH_2$—CH=N—$OCH_3$, —CH=CH—$N(CH_3)$—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—$Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the heteroalkyl is fully saturated. In embodiments, the heteroalkyl is monounsaturated. In embodiments, the heteroalkyl is polyunsaturated.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2R'$— represents both —$C(O)_2R'$— and —$R'C(O)_2$—. As described above, heteroalkyl groups, as used herein, include those groups that are attached to the remainder of the molecule through a heteroatom, such as —C(O)R', —C(O)NR', —NR'R", —OR', —SR', and/or —$SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. The term "heteroalkenylene," by itself or as part of another substituent, means, unless otherwise stated, a divalent radical derived from a heteroalkene. The term "heteroalkynylene" by itself or as part of another substituent, means, unless otherwise stated, a divalent radical derived from a heteroalkyne. In embodiments, the heteroalkylene is fully saturated. In embodiments, the heteroalkylene is monounsaturated. In embodiments, the heteroalkylene is polyunsaturated. A heteroalkenylene includes one or more double bonds. A heteroalkynylene includes one or more triple bonds.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. In embodiments, the cycloalkyl is fully saturated. In embodiments, the cycloalkyl is monounsaturated. In embodiments, the cycloalkyl is polyunsaturated. In embodiments, the heterocycloalkyl is fully saturated. In embodiments, the heterocycloalkyl is monounsaturated. In embodiments, the heterocycloalkyl is polyunsaturated.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. A bicyclic or multicyclic cycloalkyl ring system refers to multiple rings fused together wherein at least one of the fused rings is a cycloalkyl ring and wherein the multiple rings are attached to the parent molecular moiety through any carbon atom contained within a cycloalkyl ring of the multiple rings. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. A representative example of a multicyclic cycloalkyl ring system is adamantane. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. A bicyclic or multicyclic cycloalkenyl ring system refers to multiple rings fused together wherein at least one of the fused rings is a cycloalkenyl ring and wherein the multiple rings are attached to the parent molecular moiety through any carbon atom contained within a cycloalkenyl ring of the multiple rings. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, the term "heterocycloalkyl" means a monocyclic, bicyclic, or a multicyclic heterocycloalkyl ring system. In embodiments, heterocycloalkyl groups are fully saturated. A bicyclic or multicyclic heterocycloalkyl ring system refers to multiple rings fused together wherein at least one of the fused rings is a heterocycloalkyl ring and wherein the multiple rings are attached to the parent molecular moiety through any atom contained within a heterocycloalkyl ring of the multiple rings. In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. In embodiments, a fused ring aryl refers to multiple rings fused together wherein at least one of the fused rings is an aryl ring and wherein the multiple rings are attached to the parent molecular moiety through any carbon atom contained within an aryl ring of the multiple rings. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). In embodiments, the term "heteroaryl" includes fused ring heteroaryl groups (i.e., multiple rings fused together wherein at least one of the fused rings is a heteroaromatic ring and wherein the multiple rings are attached to the parent molecular moiety through any atom contained within a heteroaromatic ring of the multiple rings). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⌇" denotes the point of attachment of a chemical moiety to the remainder of a molecule or chemical formula.

The term "oxo," as used herein, means an oxygen that is double bonded to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

The term "alkylarylene" as an arylene moiety covalently bonded to an alkylene moiety (also referred to herein as an alkylene linker). In embodiments, the alkylarylene group has the formula:

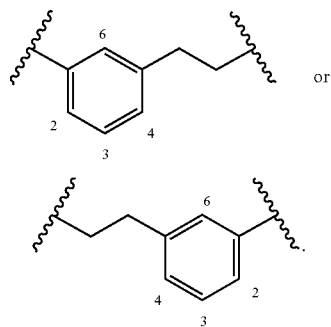

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$ —SO$_3$H, —OSO$_3$H, —SO$_2$NH$_2$, ☐NHNH$_2$, ☐ONH$_2$, ☐NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$) alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr2, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the term "bioconjugate reactive moiety" and "bioconjugate" refers to the resulting association between atoms or molecules of bioconjugate reactive groups. The association can be direct or indirect. For example, a conjugate between a first bioconjugate reactive group (e.g., —NH$_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine).

Useful bioconjugate reactive moieties used for bioconjugate chemistries herein include, for example:
(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
(b) hydroxyl groups which can be converted to esters, ethers, aldehydes, etc.
(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups which are capable of participating in Diels-Alder reactions such as, for example, maleimido or maleimide groups;
(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;
(f) sulfonyl halide groups for subsequent reaction with amines, for example, to form sulfonamides;
(g) thiol groups, which can be converted to disulfides, reacted with acyl halides, or bonded to metals such as gold, or react with maleimides;
(h) amine or sulfhydryl groups (e.g., present in cysteine), which can be, for example, acylated, alkylated or oxidized;
(i) alkenes, which can undergo, for example, cycloadditions, acylation, Michael addition, etc;
(j) epoxides, which can react with, for example, amines and hydroxyl compounds;
(k) phosphoramidites and other standard functional groups useful in nucleic acid synthesis;
(l) metal silicon oxide bonding; and
(m) metal bonding to reactive phosphorus groups (e.g. phosphines) to form, for example, phosphate diester bonds.
(n) azides coupled to alkynes using copper catalyzed cycloaddition click chemistry.
(o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^1$ substituents are present, each $R^1$ substituent may be distinguished as $R_{1A}$, $R_{1B}$, $R_{1C}$, $R^{3D}$, etc., wherein each of $R^{1A}$, $R^{1B}$, $R^{1C}$, $R^{1D}$, etc. is defined within the scope of the definition of $R^1$ and optionally differently.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —$CH_3$). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radio-labeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents. In embodiments, compounds of the present invention contain both basic and acidic functionalities that allow the compounds to be converted into either base or acid addition salts. The neutral forms of the compounds may be regenerated by contacting the salt with a base or acid and isolating the parent compound in a conventional manner. The parent form of the compounds differs from the various salt forms in certain physical properties, such as solubility in polar solvents, but, unless specifically indicated, the salts disclosed herein are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The terms "Pharmaceutically acceptable excipient" and "pharmaceutically acceptable carrier" refer to a substance that aids the administration of a compound to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the terms "HPK1 inhibitor", "HPK1 antagonist" and all other related art-accepted terms, many of which are set forth below, refer to a compound capable of modulating (e.g., reducing), either directly or indirectly, the HPK1 receptor in an in vitro assay, in an in vivo model, and/or other means indicative of therapeutic efficacy. The terms also refer to a compound that exhibits at least some therapeutic benefit in a human subject.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer. In embodiments, the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence; fusion proteins with heterologous and homologous leader sequences, with or without N-terminus methionine residues;

immunologically tagged proteins; and the like.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway (e.g., MAP kinase pathway).

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist. In embodiments, an agonist is a molecule that interacts with a target to cause or promote an increase in the activation of the target. In embodiments, activators are molecules that increase, activate, facilitate, enhance activation, sensitize, or up-regulate, e.g., a gene, protein, ligand, receptor, or cell.

As defined herein, the term "inhibition," "inhibit,", "inhibiting," and the like, in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist. An antagonist prevents, reduces, inhibits, or neutralizes the activity of an agonist, and an antagonist can also prevent, inhibit, or reduce constitutive activity of a target, e.g., a target receptor, even where there is no identified agonist. In embodiments, inhibitors are molecules that decrease, block, prevent, delay activation, inactivate, desensitize, or down-regulate, e.g., a gene, protein, ligand, receptor, or cell. An inhibitor may also be defined as a molecule that reduces, blocks, or inactivates a constitutive activity. An "antagonist" is a molecule that opposes the action(s) of an agonist.

The terms "Hematopoietic Progenitor Kinase 1" and "HPK1", also sometimes referred to in the scientific literature as "Mitogen-activated protein kinase kinase kinase kinase 1" and "MAP4K1", all refer to a protein kinase that in humans is encoded by the MAP4K1 gene. The protein has been shown to play a role in c-Jun N-terminal kinase (JNK) activation and has been identified in the scientific literature as a potential target for cancer immunotherapy. The term "HPK1 inhibitor" refers to an agent capable of inhibiting the activity of hematopoietic progenitor kinase 1 (HPK1) in T cells resulting in T cell stimulation. The HPK1 inhibitor may be a reversible or irreversible HPK1 inhibitor. "A reversible HPK1 inhibitor" is a compound that reversibly inhibits HPK1 enzyme activity either at the catalytic site or at a non-catalytic site and "an irreversible HPK1 inhibitor" is a compound that irreversibly destroys HPK1 enzyme activity by forming a covalent bond with the enzyme.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The terms "disease" or "condition" refer to a state of being or health status of a patient or subject capable of being treated with the compounds or methods provided herein. The disease may be a cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including MDS, AML, ALL, ATLL and CML), or multiple myeloma.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, or carcinoma *villosum*.

The term "infection" or "infectious disease" refers to a disease or condition that can be caused by organisms such as a bacterium, virus, fungi or any other pathogenic microbial agents. In embodiments, the infectious disease is caused by a pathogenic bacteria. Pathogenic bacteria are bacteria which cause diseases (e.g., in humans). In embodiments, the infectious disease is a bacteria associated disease (e.g., tuberculosis, which is caused by *Mycobacterium tuberculosis*). Non-limiting bacteria associated diseases include pneumonia, which may be caused by bacteria such as *Streptococcus* and *Pseudomonas*; or foodborne illnesses, which can be caused by bacteria such as *Shigella, Campylobacter*, and *Salmonella*. Bacteria associated diseases also includes tetanus, typhoid fever, diphtheria, syphilis, and leprosy. In embodiments, the disease is Bacterial vaginosis (i.e. bacteria that change the vaginal microbiota caused by an overgrowth of bacteria that crowd out the Lactobacilli species that maintain healthy vaginal microbial populations) (e.g., yeast infection, or *Trichomonas vaginalis*); Bacterial meningitis (i.e. a bacterial inflammation of the meninges); Bacterial pneumonia (i.e. a bacterial infection of the lungs); Urinary tract infection; Bacterial gastroenteritis; or Bacterial skin infections (e.g. impetigo, or cellulitis). In embodiments, the infectious disease is a *Campylobacter jejuni, Enterococcus faecalis, Haemophilus influenzae, Helicobacter pylori, Klebsiella pneumoniae, Legionella pneumophila, Neisseria gonorrhoeae, Neisseria meningitides, Staphylococcus aureus, Streptococcus pneumonia*, or *Vibrio cholera* infection.

The terms "immune response" and the like refer, in the usual and customary sense, to a response by an organism that protects against disease. The response can be mounted by the innate immune system or by the adaptive immune system, as well known in the art. The terms "modulating immune response" and the like refer to a change in the immune response of a subject as a consequence of administration of an agent, e.g., a compound as disclosed herein, including embodiments thereof. Accordingly, an immune response can be activated or deactivated as a consequence of administration of an agent, e.g., a compound as disclosed herein, including embodiments thereof.

The terms "B Cells" or "B lymphocytes" refer to their standard use in the art. B cells are lymphocytes, a type of white blood cell (leukocyte), that develops into a plasma cell (a "mature B cell"), which produces antibodies. An "immature B cell" is a cell that can develop into a mature B cell. Generally, pro-B cells undergo immunoglobulin heavy chain rearrangement to become pro B pre B cells, and further undergo immunoglobulin light chain rearrangement to become an immature B cells. Immature B cells include T1 and T2 B cells.

The terms "T cells" or "T lymphocytes" as used herein are a type of lymphocyte (a subtype of white blood cell) that plays a central role in cell-mediated immunity. They can be distinguished from other lymphocytes, such as B cells and natural killer cells, by the presence of a T-cell receptor on the cell surface. T cells include, for example, natural killer T (NKT) cells, cytotoxic T lymphocytes (CTLs), regulatory T (Treg) cells, and T helper cells. Different types of T cells can be distinguished by use of T cell detection agents.

The term "memory T cell" is a T cell that has previously encountered and responded to its cognate antigen during prior infection, encounter with cancer or previous vaccination. At a second encounter with its cognate antigen memory T cells can reproduce (divide) to mount a faster and stronger immune response than the first time the immune system responded to the pathogen.

The term "regulatory T cell" or "suppressor T cell" is a lymphocyte which modulates the immune system, maintains tolerance to self-antigens, and prevents autoimmune disease.

The terms "treating", or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "prevent" refers to a decrease in the occurrence of disease symptoms in a patient. As indicated above, the prevention may be complete (no detectable symptoms) or partial, such that fewer symptoms are observed than would likely occur absent treatment. In embodiments, prevent refers to slowing the progression of the disease, disorder or condition or inhibiting progression thereof to a harmful or otherwise undesired state.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, Dosage Calculations (1999); and Remington: *The Science and Practice of Pharmacy*, 20th Edition, 2003, Gennaro, Ed., Lippincott, Williams & Wilkins). The therapeutically effective amount can be ascertained by measuring relevant physiological effects, and it can be adjusted in connection with the dosing regimen and diagnostic analysis of the subject's condition, and the like. By way of example, measurement of the serum level of a HPK1 inhibitor (or, e.g., a metabolite thereof) at a particular time post-administration may be indicative of whether a therapeutically effective amount has been administered.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan. Adjusting the dose to achieve maximal therapeutic window efficacy or toxicity in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent, chemotherapeutic, or treatment for a neurodegenerative disease). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

By "co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). The compositions of the present invention can be delivered transdermally, by a topical route, or formulated as applicator sticks, solutions, suspensions, emulsions, gels, creams, ointments, pastes, jellies, paints, powders, and aerosols.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer (e.g., melanoma, non-small cell lung cancer, bladder cancer, pancreatic cancer, head and neck cancer or brain tumor).

In some embodiments, co-administration includes administering one active agent within 0.5, 1, 2, 4, 6, 8, 10, 12, 16, 20, 24 hours, 2 days, 4 days, 1 week or 1 month of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer (e.g., melanoma, non-small cell lung cancer, bladder cancer, pancreatic cancer, head and neck cancer or brain tumor).

The compounds described herein can be administered to treat numerous types of cancer, in particular melanoma, non-small cell lung cancer, bladder cancer, pancreatic cancer, head and neck cancer or brain tumor. In this regard, the compounds disclosed herein may be administered either alone to treat such diseases or disorders or may be co-administered with another therapeutic agent to treat such diseases or disorders.

The compounds disclosed herein may be co-administered with a cytokine or agonist or antagonist of cytokine function, (including agents which act on cytokine signaling pathways such as modulators of the SOCS system) including alpha-, beta-, and gamma-interferons; insulin-like growth factor type I (IGF-1); interleukins (IL) including IL1 to 17, and interleukin antagonists or inhibitors such as analcinra; tumour necrosis factor alpha (TNF-.alpha.) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec.®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone BI; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexonnaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin Il (including recombinant interleukin Il, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin;

zorubicin hydrochloride, agents that arrest cells in the G2-M phases and/or modulate the formation or stability of microtubules, (e.g. Taxol.™ (i.e. paclitaxel), Taxotere.™, compounds comprising the taxane skeleton, Erbulozole (i.e. R-55104), Dolastatin 10 (i.e. DLS-10 and NSC-376128), Mivobulin isethionate (i.e. as $C_1$-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39·HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and T1-138067), COBRA-1 (Parker Hughes Institute, i.e. DDE-261 and WHI-261), H10 (Kansas State University), H16 (Kansas State University), Oncocidin Al (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta *Medica*), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lso-eleutherobin A, and Z-Eleutherobin), Caribaeoside, Caribaeolin, Halichondrin B, D-64131 (Asta *Medica*), D-68144 (Asta *Medica*), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta *Medica*), D-68836 (Asta *Medica*), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

The term "chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compounds described herein can be co-administered with conventional immunotherapeutic agents including, but not limited to, immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$n, $^{90}$Y, or $^{131}$I, etc.).

The compounds disclosed herein may be co-administered with an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a *vinca* alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin); (ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5.alpha.-reductase such as finasteride; (iii) an agent which inhibits cancer cell invasion (for example a metalloproteinase inhibitor like marimastat or an inhibitor of urokinase plasminogen activator receptor function); (iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazoli- n-4-amine (gefitinib, AZD 1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazoli- n-4-amine (CI 1033)), an inhibitor of the platelet-derived growth factor family, or an inhibitor of the hepatocyte growth factor family; (v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin.alpha.v.beta.3 function or an angiostatin); (vi) a vascular damaging agent such as combretastatin A4, or a compound disclosed in WO 99/02166, WO 00/40529, WO 00/41669, WO 01/92224, WO 02/04434 or WO 02/08213; (vii) an agent used in antisense therapy, for example one directed to one of the targets listed above, such as ISIS 2503, an anti-ras antisense; (viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In embodiments, the compounds disclosed herein can be co-administered with an antibody, such as a monoclonal antibody targeting B-Lymphocytes (such as CD20 (rituximab), MRA-aIL16R and T-Lymphocytes, CTLA4-Ig, HuMax I1-15) or antibody modulating Ig function such as anti-IgE (for example omalizumab).

In embodiments, treatment of cancer includes administration of an effective amount of at least two of the following: a HPK1 inhibitor, an inhibitor of the PD-L1/PD-1 pathway, an inhibitor of CTLA-4, an agonistic antibody of CD137 (4-1BB). In some embodiments, the method may include the use of two or more combinations.

In embodiments, treatment of cancer includes an effective amount of at least two or more of the following: a HPK1 inhibitor and any combination of agent that may be an immune modulator such as, but not limited to, those listed in Table 1. These immune modulators can be depleting antibodies, neutralizing antibodies, blocking antibodies, agonistic antibodies, small molecule modulators (inhibitors or stimulators) or small molecule analogs.

TABLE 1

| Target or Therapy | Examples of Agents | Regulatory Mechanism |
|---|---|---|
| TIM-3 | TSR-022, MGB453 | Checkpoint-receptor |
| LAG-3 | BMS-986016, IMP321 | Checkpoint-receptor |
| B7-H3 | MGA271, MGD-009 | Checkpoint-receptor |
| TIGIT | RG-6058 | Checkpoint-receptor |
| BTLA | | Checkpoint-receptor |
| CD28 | AMG 557, | Checkpoint-receptor |
| CD40 | SEA-CD40, dacetuzumab, CP-870,893, Chi Lob 7/4, lucatumumab | Checkpoint-receptor |
| CD80 | galiximab | Checkpoint-receptor |
| GITR | INCAGN1876, TRX518, | Checkpoint-receptor |
| ICOS | MEDI-570 | Checkpoint-receptor |
| OX40 (CD134) | MEDI-6469, INCAGN1949, huMab OX40L, | Checkpoint-receptor |
| NKG2A | monalizumab | Checkpoint-receptor |
| TGF-beta | Galunisertib, luspatercept, YH-14618, dalantercept, BG-00011, trabedersen, isth-0036 ace-083, | Cytokines |
| IL2 | NKTR-214, recombinant IL2, aldesleukin | Cytokines |
| IL12 | EGEN-001, NHS-IL12 | Cytokines |
| IL7 | Recombinant IL-7, | Cytokines |
| IL15 | NIZ-985, ALT-803, | Cytokines |
| IL21 | Recombinant IL-21, anti-CD20.IL21, | Cytokines |
| IL13 | Tralokinumab, dupilumab | |
| CSF1R | cabiralizumab | Cytokine |
| PI3K delta | INCB50465, idealisib, TGR-1202, AMG319, | Kinase |
| PI3K gamma | IPI-549 | Kinase |
| DNMT (DNA methyl transferase inhibitor) | Azacytidine, decitabine, guadecitabine, | Epigenetic Regulator |
| HDAC (histone deacetylase) | Vorinostat, Panobinostat, belinostat, entinostat, mocetinostat, givinostat, chidamide, quisinostat, abexinostat, chr-3996, ar-42, | Epigenetic Regulator |
| Brd4 | INCN54329, INCB57643, birabresib, apabetalone, alvocidib, PLX-51107, FT-1101, RG-6146, AZD-8186, CPI-0610, JQ1 | Transcription regulator |
| HMT (histone methyl transferases) | | Epigenetic Regulator |
| LSD1 | INCB59872, IMG-7289, RG-6016, CC-90011, GSK-2879552, ORY-2001, 4SC-202, ORY-3001, | Epigenetic Regulator |
| TNFa | Recombinant TNFa, MEDI-1873, FPA-154, LKZ-145 | Cytokine |
| IL1 | Recombinant IL1 | Cytokine |
| IFNa | Recombinant interferon alpha-n1, Recombinant interferon alpha-2b, Recombinant interferon alpha-n3 | Cytokine |
| IFNb | Recombinant IFN beta-1a, | Cytokine |
| IFNg | actimmune | Cytokine |
| STING | Cyclic di-nucleotides | Signaling Molecule |
| TLR | Poly I:C, IMO-2055, TMX-101, imiquimod, CpG, MGN1703, glucopyranosyl lipid A, CBLB502, BCG, HILTONOL, AMPLIGEN, MOTOLIMOD, DUK-CPG-001, AS15 | Pathogen Recognition Receptor |

TABLE 1-continued

| Target or Therapy | Examples of Agents | Regulatory Mechanism |
|---|---|---|
| IL10 | Recombinant IL-10 | Cytokine |
| CCR2 | CCX140, CCX872, BMS-813160, CENICRIVIROC, CNTX-6970. PF-4136309, plozalizumab, INCB-9471, PF-04634817 | Chemokine |
| CCR4 | FLX475, RPT193 | Chemokine |
| CCR5 | Maraviroc, PRO-140, BMS-813160, NIFEVIROC, OHR-118 | Chemokine |
| CXCR4 | Ulocuplumab, plerixafor, x4p-001, usl-311, ly-2510924, APH-0812, BL-8040, BURIXAFOR, BALIXAFORTIDE, PTX-9908, GMI-1359, F-50067 | Chemokine |
| LFA1 | | Adhesion Molecule |
| MICA/B | IPH-4301 | Immune Receptor Ligand |
| VISTA | CA-170 | Checkpoint-Ligand |
| Adenosine | ISTRADEFYLLINE, TOZADENANT, PBF-509, PBF-999, CPI-444 | Nucleoside |
| CD39 | OREG-103. Anti-CD39 antibodies, | Ecto-enzyme |
| CD73 | Oleclumab, PBF-1662, anti-CD73 antibodies | Ecto-Enzyme |
| PD1 | Pembrolizumab, nivolumab, INCSHR1210, CT-011, AMP224 | Checkpoint-receptor |
| PD-L1 | Atezolizumab, avelumab | Checkpoint-Ligand |
| PD-L2 | | Checkpoint-Ligand |
| CTLA4 | Tremelimumab | Checkpoint-receptor |
| CD137 | Urelumab, utomilumab, BMS-663513, PF-05082566 | |
| AXL | BGB-324, BPI-9016M, S-49076 | Kinase |
| MERTK | BGB-324, BPI-9016M, S-49076 | Kinase |
| TYRO | BGB-324, BPI-9016M, S-49076 | |
| BTK | ibrutinib | Kinase |
| ITK | ibrutinib | Kinase |
| LCK | | Kinase |
| TET2 | | Enzyme |
| Arginase | Cb-1158 | Endo/ecto enzyme |
| GCN2 | | Kinase |
| B7-H4 | MDX-1140, AMP-110 | Checkpoint-receptor |
| HIF1alpha | PT2385 | Transcription Factor |
| LIGHT (TNFSF14) | | TNF Superfamily |
| FLT3 | CDX-301, FLX925, quizartinib, gilteritinib, PKC412, midostaurin, crenolanib | Kinase |
| CD158 | Lirlumab, IPH-2101 | |
| CD47 | Anti-CD47, TTI-621, NI-1701, SRF-231, Effi-DEM, RCT-1938 | |
| IDO | Epacadostat, F287, BMS983205, GDC-0919, indoximod, | |
| RORgamma | | |

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

In addition, a HPK1 inhibitor may be combined with the therapeutic administration of immune cells, sometimes referred to as adoptive cell transfer. These cells may be cells from the patient, a genetically related or unrelated donor, they may be genetically modified (e.g. CAR-T cells, NK cells, etc), cell lines, genetically modified cell lines and live or dead versions of the above. HPK1 inhibitors may also be combined with vaccines of any kind (e.g., protein/peptide, viral, bacterial, cellular) to stimulate immune responses to cancer.

In embodiments, treatment is administration of an effective amount of a HPK1 inhibitor in combination with an inhibitor of the PD-L1/PD-1 pathway, an inhibitor of CTLA-4, an agonistic antibody of CD137 (4-1BB) or in combination with another immune modulator as listed in Table 1.

In embodiments, treatment is therapeutic administration of an effective amount of a HPK1 inhibitor in combination with an inhibitor of the PD-L1/PD-1 pathway, an inhibitor of CTLA-4, an agonistic antibody of CD137 (4-1BB) or in combination with another immune modulator as listed in Table 1. Here, treatment starts when tumors reach a size of 40-70 mm$^3$.

The term "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Pro-karyotic cells include but are not limited to bacteria. Eukary-otic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsini-zation.

The term "control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule. In some embodiments, a HPK1 associated disease modulator is a compound that reduces the severity of one or more symptoms of a disease associated with HPK1 (e.g., cancer). A HPK1 modulator is a compound that increases or decreases the activity or function or level of activity or level of function of HPK1. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an activator.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule. In embodiments, the terms "modulate", "modulation" and the like refer to the ability of a molecule (e.g., an activator or an inhibitor) to increase or decrease the function or activity of HPK1, either directly or indirectly, relative to the absence of the molecule.

The term "associated" or "associated with" in the context of a substance or substance activity or function associated with a disease (e.g. a protein associated disease, a cancer associated with HPK1 activity, HPK1 associated cancer, HPK1 associated disease (e.g., cancer, inflammatory disease, autoimmune disease, or infectious disease)) means that the disease (e.g. cancer, inflammatory disease, muscular and/or sensory neuropathic diseases such as Charcot-Marie-Tooth disease, autoimmune disease, or infectious disease) is caused by (in whole or in part), or a symptom of the disease is caused by (in whole or in part) the substance or substance activity or function. For example, a cancer associated with HPK1 activity or function may be a cancer that results (entirely or partially) from aberrant HPK1 function (e.g., enzyme activity, protein-protein interaction, signaling pathway) or a cancer wherein a particular symptom of the disease is caused (entirely or partially) by aberrant HPK1 activity or function. As used herein, what is described as being associated with a disease, if a causative agent, could be a target for treatment of the disease. For example, a cancer associated with HPK1 activity or function or a HPK1 associated disease (e.g., cancer), may be treated with a compound described herein (e.g., HPK1 modulator or HPK1 inhibitor), in the instance where increased HPK1 activity or function (e.g., signaling pathway activity) causes the disease (e.g., cancer).

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extracellular components (e.g., proteins, nucleic acids, small molecules, ions, lipids) that conveys a change in one component to one or more other components, which in turn may convey a change to additional components, which is optionally propagated to other signaling pathway components. For example, binding of HPK1 with a compound as described herein may reduce the level of a product of the HPK1 catalyzed reaction or the level of a downstream derivative of the product or binding may reduce the interactions between the HPK1 or a reaction product and downstream effectors or signaling pathway components (e.g., MAP kinase pathway), resulting in changes in cell growth, proliferation, or survival.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The term "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

The term "substantially pure" indicates that a component makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition (percentage in a weight per weight basis).

The terms "specifically binds" and "selectively binds," when referring to a ligand/receptor, antibody/antigen, or other binding pair, indicate a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant thereof, with an affinity that is at least two-fold greater, at least 10-times greater, at least 20-times greater, or at least 100-times greater than the affinity with any other antibody, or binding composition derived therefrom. In embodiments, the antibody will have an affinity that is greater than about $10^9$ liters/mol, as determined by, e.g., Scatchard analysis (Munsen, et al. (1980) Analyt. Biochem. 107:220-239).

The terms "DNA," "nucleic acid," "nucleic acid molecule," "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

As used herein, the terms "variants" and "homologs" are used interchangeably to refer to amino acid or nucleic acid sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring amino acid and nucleic acid sequences encoded thereby and their isoforms, as well as splice variants of a protein or gene. The terms also encompass nucleic acid sequences that vary in one or more bases from a naturally-occurring nucleic acid sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced; for example, the change is generated in the laboratory by human intervention ("hand of man"). Therefore, non-naturally occurring variants and homologs may also refer to those that differ from the naturally occurring sequences by one or more conservative substitutions and/or tags and/or conjugates.

The compounds of formulae (I)-(IVa) can form salts which are also within the scope of this disclosure. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of formulae (I)-(IVa) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the disclosure. Salts of the compounds of the formulae (I)-(IVa) may be formed, for example, by reacting a compound of the formulae (I)-(IVa) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-.beta.-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of formulae (I)-(IVa) can be provided as amorphous solids or crystalline solids. Lyophilization can be employed to provide the compounds of Formulae (I)-(IV) as a solid.

It should further be understood that solvates (e.g., hydrates) of the compounds of Formula (I) are also within the scope of the present disclosure. The term "solvate" means a physical association of a compound of formulae (I)-(IVa) with one or more solvent molecules, whether organic or inorganic. This physical association includes hydrogen bonding. In certain instances, the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

In addition, compounds of formulae (I)-(IVa), subsequent to their preparation, can be isolated and purified to obtain a composition containing an amount by weight equal to or greater than 99% of a compound of formulae (I)-(IVa) ("substantially pure"), which is then used or formulated as described herein. Such "substantially pure" compounds of formulae (I)-(IVa) are also contemplated herein as part of the present disclosure.

The compounds of the present disclosure are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include .sup.13C and .sup.14C. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed.

Compounds

Provided herein is the compound of formula (I):

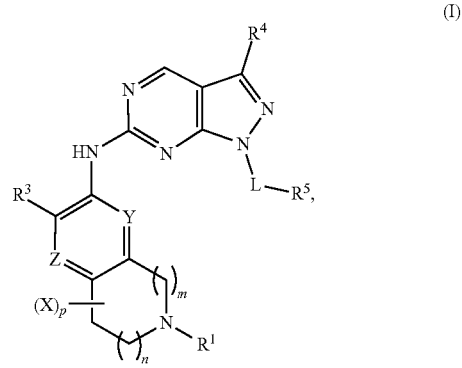

(I)

or a pharmaceutically acceptable salt thereof. L is a bond or a substituted or unsubstituted methylene. X is not bonded directly to the N atom of N—$R^1$ and is either absent or if present is a substituted or unsubstituted alkyl. Y is CH or N. Z is $CR^2$ or N. Each of n and m is 0, 1 or 2, and (n+m) equals 1, 2 or 3. p is an iteger from 0 to 2. $R^1$ is H, or a substituted or unsubstituted alkyl. $R^2$ is H, a halogen, a substituted or unsubstituted alkyl or a substituted or unsubstituted heteroalkyl. $R^3$ is H, or a substituted or unsubstituted heteroalkyl. $R^4$ is H, a substituted or unsubstituted alkyl or a halogen. $R^5$ is a substituted or unsubstituted alkyl, a substituted or unsubstituted heteroalkyl, a substituted or unsubstituted cycloalkyl, or a substituted or unsubstituted heterocycloalkyl.

In embodiments, L is a bond or a substituted (e.g., substituted with a substituent group, a size-limited substituent group, or lower substituent group) or unsubstituted methylene. In embodiments, L is a bond. In embodiments, L is a substituted (e.g., substituted with a substituent group, a size-limited substituent group, or lower substituent group) or unsubstituted methylene. In embodiments, a substituted L (e.g., substituted methylene), is substituted with at least one substituent group, size-limited substituent group, or lower substituent group; wherein if the substituted L is substituted with a plurality of groups selected from substituent groups, size-limited substituent groups, and lower substituent groups; each substituent group, size-limited substituent group, and/or lower substituent group may optionally be different. In embodiments, when L is substituted, it is substituted with at least one substituent group. In embodiments, when L is substituted, it is substituted with at least one size-limited substituent group. In embodiments, when L is substituted, it is substituted with at least one lower substituent group.

In embodiments, X is not bonded directly to the N atom of N—$R^1$ and is either absent or if present is a substituted (e.g., substituted with a substituent group, a size-limited substituent group, or lower substituent group) or unsubstituted alkyl (e.g., $C_1$-$C_8$ alkyl, $C_1$-$C_6$ alkyl, or $C_1$-$C_4$). In embodiments, X is a substituted or unsubstituted $C_{1-3}$ alkyl. In embodiments, a substituted X (e.g., substituted alkyl), is substituted with at least one substituent group, size-limited substituent group, or lower substituent group; wherein if the substituted X is substituted with a plurality of groups selected from substituent groups, size-limited substituent groups, and lower substituent groups; each substituent group, size-limited substituent group, and/or lower substituent group may optionally be different. In embodiments, when X is substituted, it is substituted with at least one substituent group. In embodiments, when X is substituted, it is substituted with at least one size-limited substituent group. In embodiments, when X is substituted, it is substituted with at least one lower substituent group.

In embodiments, Y is CH or N. In embodiments, Y is CH. In embodiments, Y is N.

In embodiments, Z is $CR^2$ or N. In embodiments, Z is $CR^2$. In embodiments, Z is N.

In embodiments, each of n and m is 0, 1 or 2, and (n+m) equals 1, 2 or 3. In embodiments, each of n and m is 0. In embodiments, each of n and m is 1. In embodiments, each of n and m is 2. In embodiments, (n+m) equals 1. In embodiments, (n+m) equals 2. In embodiments, (n+m) equals 3.

In embodiments, p is an integer from 0 to 2. In embodiments, p is 0. In embodiments, p is 1. In embodiments, p is 2.

In embodiments, $R^1$ is H, or a substituted (e.g., substituted with a substituent group, a size-limited substituent group, or lower substituent group) or unsubstituted alkyl (e.g., $C_1$-$C_8$, $C_1$-$C_6$ alkyl, or $C_1$-$C_4$). In embodiments, $R^1$ is H. In embodiments, $R^1$ is a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^1$ is a substituted or unsubstituted $C_{1-3}$ alkyl. In embodiments, a substituted $R^1$ (e.g., substituted alkyl) is substituted with at least one substituent group, size-limited substituent group, or lower substituent group; wherein if the substituted $R^1$ is substituted with a plurality of groups selected from substituent groups, size-limited substituent groups, and lower substituent groups; each substituent group, size-limited substituent group, and/or lower substituent group may optionally be different. In embodiments, when $R^1$ is substituted, it is substituted with at least one substituent group. In embodiments, when $R^1$ is substituted, it is substituted with at least one size-limited substituent group. In embodiments, when $R^1$ is substituted, it is substituted with at least one lower substituent group.

In embodiments, $R^2$ is H, a halogen, a substituted or unsubstituted alkyl or a substituted or unsubstituted heteroalkyl. In embodiments, $R^2$ is H. In embodiments, $R^2$ is a halogen. In embodiments, $R^2$ is —F, —Cl, —Br, or —I. In embodiments, $R^2$ is a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^2$ is a substituted or unsubstituted $C_{1-3}$ alkyl. In embodiments, $R^2$ is a substituted (e.g., substituted with a substituent group, a size-limited substituent group, or lower substituent group) or unsubstituted heteroalkyl (e.g., 2 to 8 membered, 2 to 6 membered, or 2 to 4 membered). In embodiments, a substituted $R^2$ (e.g., substituted alkyl and/or substituted heteroalkyl) is substituted with at least one substituent group, size-limited substituent group, or lower substituent group; wherein if the substituted $R^2$ is substituted with a plurality of groups selected from substituent groups, size-limited substituent groups, and lower substituent groups; each substituent group, size-limited substituent group, and/or lower substituent group may optionally be different. In embodiments, when $R^2$ is substituted, it is substituted with at least one substituent group. In embodiments, when $R^2$ is substituted, it is substituted with at least one size-limited substituent group. In embodiments, when $R^2$ is substituted, it is substituted with at least one lower substituent group.

In embodiments, $R^3$ is H or a substituted or unsubstituted heteroalkyl. In embodiments, $R^3$ is H. In embodiments, $R^3$ is a substituted (e.g., substituted with a substituent group, a size-limited substituent group, or lower substituent group) or unsubstituted heteroalkyl (e.g., 2 to 8 membered, 2 to 6 membered, or 2 to 4 membered). In embodiments, a substituted $R^3$ (e.g., substituted heteroalkyl) is substituted with at least one substituent group, size-limited substituent group, or lower substituent group; wherein if the substituted $R^3$ is substituted with a plurality of groups selected from substituent groups, size-limited substituent groups, and lower substituent groups; each substituent group, size-limited substituent group, and/or lower substituent group may optionally be different. In embodiments, when $R^3$ is substituted, it is substituted with at least one substituent group. In embodiments, when $R^3$ is substituted, it is substituted with at least one size-limited substituent group. In embodiments, when $R^3$ is substituted, it is substituted with at least one lower substituent group.

In embodiments, $R^4$ is H, a substituted or unsubstituted alkyl or a halogen. In embodiments, $R^4$ is H. In embodiments, $R^4$ is halogen. In embodiments, $R^4$ is —F, —Cl, —Br, or —I. In embodiments, $R^4$ is a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^4$ is a substituted or unsubstituted $C_{1-3}$ alkyl. In embodiments, a substituted $R^4$ (e.g., substituted alkyl) is substituted with at least one substituent group, size-limited substituent group, or lower substituent group; wherein if the substituted $R^4$ is substituted with a plurality of groups selected from substituent groups, size-limited substituent groups, and lower substituent groups; each substituent group, size-limited substituent group, and/or lower substituent group may optionally be different. In embodiments, when $R^4$ is substituted, it is substituted with at least one substituent group. In embodiments, when $R^4$ is substituted, it is substituted with at least one size-limited substituent group. In embodiments, when $R^4$ is substituted, it is substituted with at least one lower substituent group.

In embodiments, $R^5$ is a substituted or unsubstituted alkyl, a substituted or unsubstituted heteroalkyl, a substituted or unsubstituted cycloalkyl or a substituted or unsubstituted heterocycloalkyl. In embodiments, $R^5$ is a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^5$ is a substituted or unsubstituted $C_{1-3}$ alkyl. In embodiments, $R^5$ is a substituted (e.g., substituted with a substituent group, a size-limited substituent group, or lower substituent group) or unsubstituted heteroalkyl (e.g., 2 to 8 membered, 2 to 6 membered, or 2 to 4 membered). In embodiments, $R^5$ is a substituted (e.g., substituted with a substituent group, a size-limited substituent group, or lower substituent group) or unsubstituted cycloalkyl (e.g., $C_3$-$C_5$, $C_3$-$C_6$, or $C_5$-$C_6$). In embodiments, $R^5$ a substituted or unsubstituted $C_{3-6}$ cycloalkyl. In embodiments, $R^5$ is a substituted (e.g., substituted with a substituent group, a size-limited substituent group, or lower substituent group) or unsubstituted heterocycloalkyl (e.g., 3 to 8 membered, 3 to 6 membered, or 5 to 6 membered). In embodiments, a substituted $R^5$ (e.g., substituted alkyl, substituted heteroalkyl, substituted cycloalkyl, and/or substituted heterocycloalkyl) is substituted with at least one substituent group, size-limited substituent group, or lower substituent group; wherein if the substituted $R^5$ is substituted with a plurality of groups selected from substituent groups, size-limited substituent groups, and lower substituent groups; each substituent group, size-limited substituent group, and/or lower substituent group may optionally be different. In embodiments, when $R^5$ is substituted, it is substituted with at least one substituent group. In embodiments, when $R^5$ is substituted, it is substituted with at least one size-limited substituent group. In embodiments, when $R^5$ is substituted, it is substituted with at least one lower substituent group.

Provided herein is the compound of formula (I):

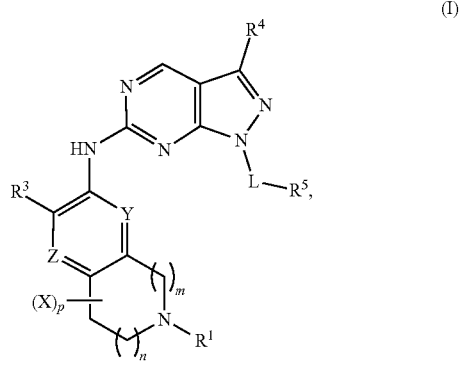

(I)

or a pharmaceutically acceptable salt thereof, wherein L, X, Y, Z, m, n, p, $R^1$, $R^2$, $R^3$, $R^4$, and $R^5$ are as defined in formula (I), including embodiments. In embodiments, the compound is not N-(1-isopropylpyrazolo[3,4-d]pyrimidin-6-yl)-6-methoxy-2-methyl-3,4-dihydro-1H-isoquinolin-7-amine of formula:

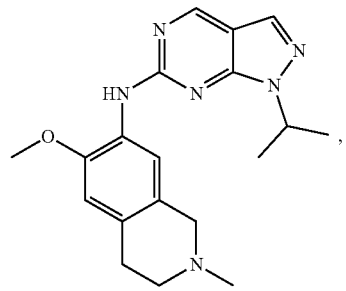 [SMILES: COc1cc2c(cc1Nc1ncc3cnn(C(C)C)c3n1)CN(C)CC2]

or a pharmaceutically acceptable salt thereof.

Provided herein is the compound of formula (I):

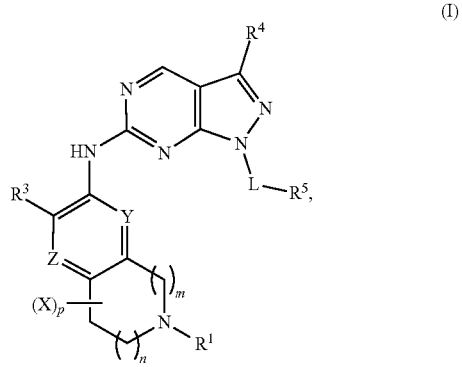

(I)

or a pharmaceutically acceptable salt thereof, wherein L, X, Y, Z, m, n, p, $R^1$, $R^2$, $R^3$, and $R^4$ are as defined in formula (I) including embodiments. In embodiments, $R^5$ is a substituted or unsubstituted heteroalkyl, a substituted or unsubstituted cycloalkyl or a substituted or unsubstituted heterocycloalkyl. In embodiments, $R^5$ is a substituted (e.g., substituted with a substituent group, a size-limited substituent group, or lower substituent group) or unsubstituted heteroalkyl (e.g., 2 to 8 membered, 2 to 6 membered, or 2 to 4 membered). In embodiments, $R^5$ is a substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$). In embodiments, $R^5$ a substituted or unsubstituted $C_{3-6}$ cycloalkyl. In embodiments, $R^5$ is a substituted (e.g., substituted with a substituent group, a size-limited substituent group, or lower substituent group) or unsubstituted heterocycloalkyl (e.g., 3 to 8 membered, 3 to 6 membered, or 5 to 6 membered). In embodiments, a substituted $R^5$ (e.g., substituted heteroalkyl, substituted cycloalkyl, and/or substituted heterocycloalkyl) is substituted with at least one substituent group, size-limited substituent group, or lower substituent group; wherein if the substituted $R^5$ is substituted with a plurality of groups selected from substituent groups, size-limited substituent groups, and lower substituent groups; each substituent group, size-limited substituent group, and/or lower substituent group may optionally be different. In embodiments, when $R^5$ is substituted, it is substituted with at least one substituent group. In embodiments, when $R^5$ is substituted, it is substituted with at least one size-limited substituent group. In embodiments, when $R^5$ is substituted, it is substituted with at least one lower substituent group.

Provided herein is the compound of formula (I):

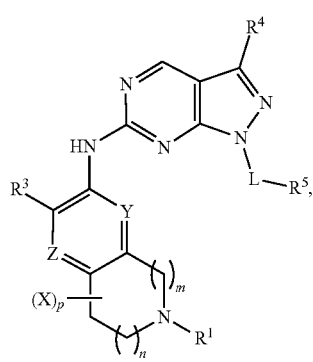

(I)

or a pharmaceutically acceptable salt thereof, wherein L, X, Y, Z, m, n, p, $R^1$, $R^2$, and $R^4$ are as defined in Formula (I) including embodiments. In embodiments, $R^3$ is H or a substituted heteroalkyl. In embodiments, $R^3$ is H. In embodiments, $R^3$ is a substituted (e.g., substituted with a substituent group, a size-limited substituent group, or lower substituent group) or unsubstituted heteroalkyl (e.g., 2 to 8 membered, 2 to 6 membered, or 2 to 4 membered). In embodiments, a substituted $R^3$ (e.g., substituted heteroalkyl) is substituted with at least one substituent group, size-limited substituent group, or lower substituent group; wherein if the substituted $R^3$ is substituted with a plurality of groups selected from substituent groups, size-limited substituent groups, and lower substituent groups; each substituent group, size-limited substituent group, and/or lower substituent group may optionally be different. In embodiments, when $R^3$ is substituted, it is substituted with at least one substituent group. In embodiments, when $R^3$ is substituted, it is substituted with at least one size-limited substituent group. In embodiments, when $R^3$ is substituted, it is substituted with at least one lower substituent group. In embodiments, $R^5$ is a substituted or unsubstituted alkyl. In embodiments, $R^5$ is a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^5$ is a substituted or unsubstituted $C_{1-3}$ alkyl. In embodiments, a substituted $R^5$ (e.g., substituted alkyl) is substituted with at least one substituent group, size-limited substituent group, or lower substituent group; wherein if the substituted $R^5$ is substituted with a plurality of groups selected from substituent groups, size-limited substituent groups, and lower substituent groups; each substituent group, size-limited substituent group, and/or lower substituent group may optionally be different. In embodiments, when $R^5$ is substituted, it is substituted with at least one substituent group. In embodiments, when $R^5$ is substituted, it is substituted with at least one size-limited substituent group. In embodiments, when $R^5$ is substituted, it is substituted with at least one lower substituent group.

In embodiments, the compound of formula (I) is:

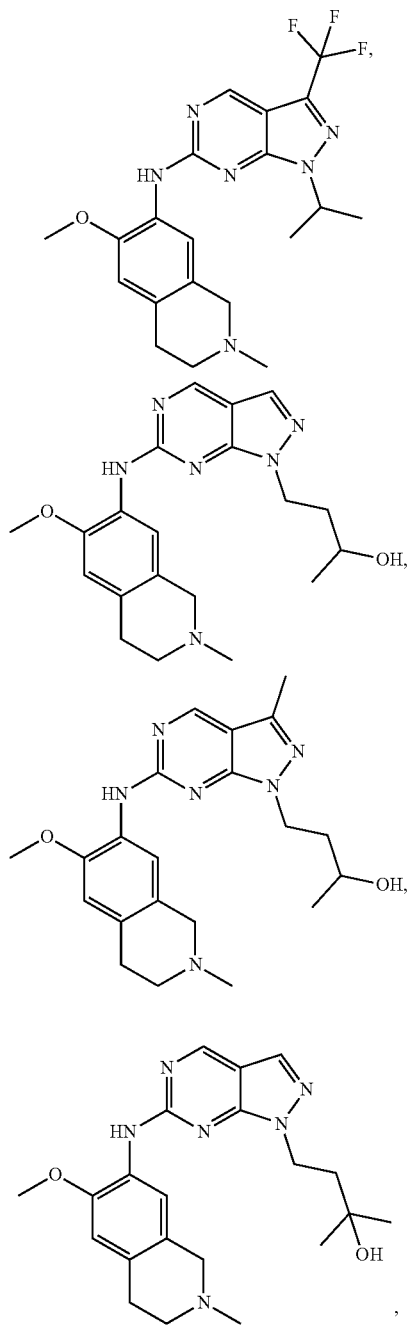

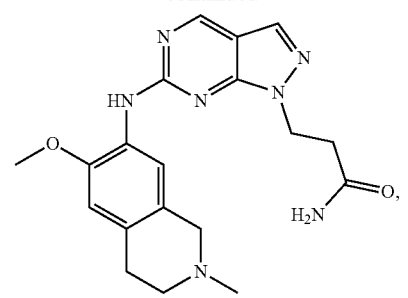

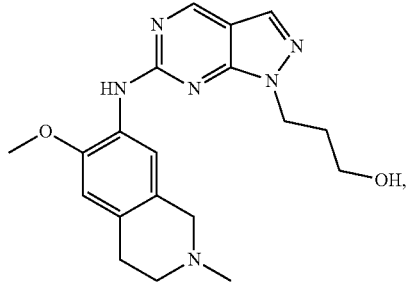

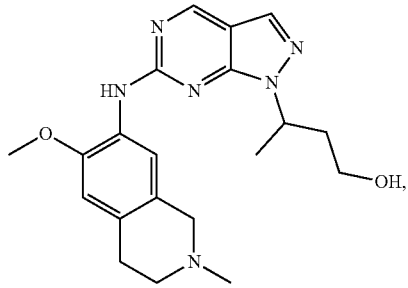

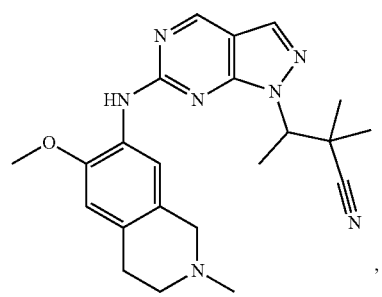

or a pharmaceutically acceptable salt thereof.

In embodiments, the compound is a compound of formula (I) is:

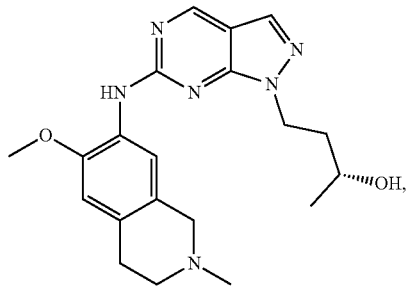

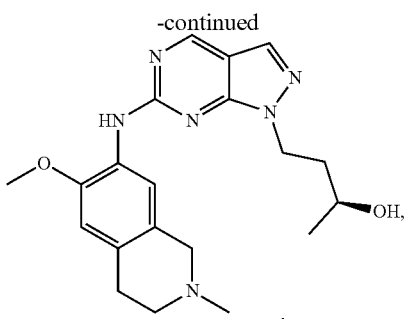

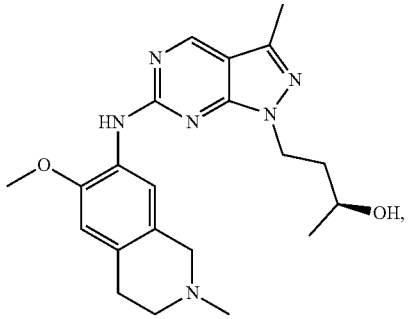

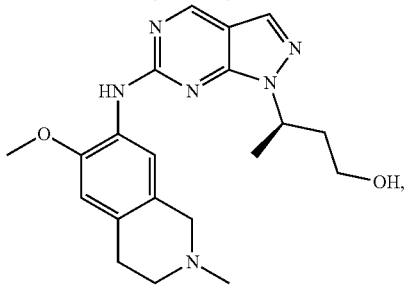

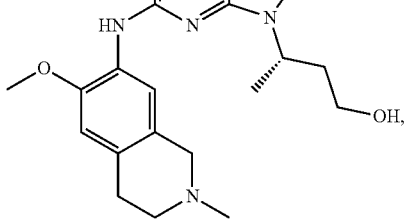

or a pharmaceutically acceptable salt thereof.

In embodiments, the compound is a compound of formula (I), wherein $R^5$ is:

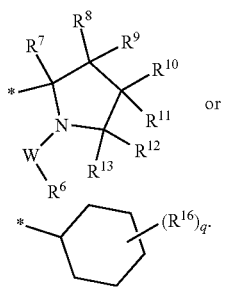

W is —C(O), —S(O), —S(O)$_2$ or —S(NH)(O). $R^6$ is a substituted or unsubstituted alkyl, —OCH$_3$ or —NR$^{14}$R$^{15}$. $R^7$ is H or substituted or unsubstituted alkyl. In embodiments, $R^7$ is H or —$CH_3$. $R^8$, $R^9$, $R^{10}$ and $R^{11}$ are each independently H, substituted or unsubstituted alkyl, —OH or halogen. In embodiments, $R^8$, $R^9$, $R^{10}$ and $R^{11}$ are each independently H, substituted or unsubstituted alkyl, —OH, —F, —Cl, —Br, or —I. $R^{12}$ and $R^{13}$ are each independently H or substituted or unsubstituted alkyl, or $R^8$ and $R^9$, $R^9$ and $R^{10}$, $R^{10}$ and $R^{11}$, $R^{11}$ and $R^{12}$, and $R^{12}$ and $R^{13}$ may optionally be joined to form a substituted or unsubstituted cycloalkyl. $R^{14}$ and $R^{15}$ are each independently H or substituted or unsubstituted alkyl. $R^{16}$ is —OH, a substituted or unsubstituted alkyl, —COOH, —$OCH_3$, —NHC(O)$CH_3$, —NHC(O)$CH_2$OH, —NH$SO_2CH_3$ or —C(O)N$R^{17}R^{18}$. $R^{17}$ and $R^{18}$ are each independently H or a substituted or unsubstituted alkyl. q is 0, 1 or 2.

In embodiments, the compound is a compound of formula (Ia),

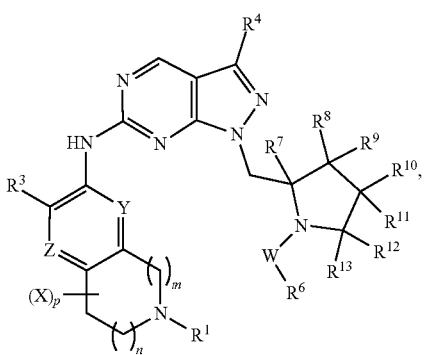

or a pharmaceutically acceptable salt thereof. X, Y, Z, n, m, p, $R^1$, $R^2$, $R^3$ and $R^4$ are as defined in formula (I), including embodiments. W is C(O), S(O), S(O)$_2$ or S(NH)(O). $R^6$ is a substituted or unsubstituted alkyl, —$OCH_3$ or —$NR^{14}R^{15}$; $R^7$ is H or —$CH_3$. $R^8$, $R^9$, $R^{10}$ and $R^{11}$ are each independently H, substituted or unsubstituted alkyl, —OH, or halogen. In embodiments, $R^8$, $R^9$, $R^{10}$ and $R^{11}$ are each independently H, substituted or unsubstituted alkyl, —OH, —F, —Cl, —Br, or —I. $R^{12}$ and $R^{13}$ are each independently H or substituted or unsubstituted alkyl; or where one of moiety pairs (i) $R^8$ and $R^9$, (ii) $R^9$ and $R^{10}$, (iii) $R^{10}$ and $R^{11}$, (iv) $R^{11}$ and $R^{12}$ and (v) $R^{12}$ and $R^{13}$ may optionally be joined to form a substituted or unsubstituted $C_{3-6}$ cycloalkyl. $R^{14}$ and $R^{15}$ are each independently H or substituted or unsubstituted alkyl.

In embodiments, W is C(O), S(O), S(O)$_2$ or S(NH)(O). In embodiments, W is C(O). In embodiments, W is S(O). In embodiments, W is S(O)$_2$. In embodiments, W is S(NH)(O).

In embodiments, $R^6$ is a substituted or unsubstituted $C_{1-3}$ alkyl, —$OCH_3$ or —$NR^{14}R^{15}$, wherein $R^{14}$ and $R^{15}$ are each independently H or substituted or unsubstituted alkyl. In embodiments, $R^6$ is —$OCH_3$. In embodiments, $R^6$ is a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^6$ a substituted or unsubstituted $C_{1-3}$ alkyl. In embodiments, a substituted $R^6$ (e.g., substituted alkyl) is substituted with at least one substituent group, size-limited substituent group, or lower substituent group; wherein if the substituted $R^6$ is substituted with a plurality of groups selected from substituent groups, size-limited substituent groups, and lower substituent groups; each substituent group, size-limited substituent group, and/or lower substituent group may optionally be different. In embodiments, when $R^6$ is substituted, it is substituted with at least one substituent group. In embodiments, when $R^6$ is substituted, it is substituted with at least one size-limited substituent group. In embodiments, when $R^6$ is substituted, it is substituted with at least one lower substituent group. In embodiments, $R^6$ is —$N^{14}R^{15}$, wherein $R^{14}$ and $R^{15}$ are each independently H or substituted or unsubstituted alkyl. In embodiments, $R^{14}$ and $R^{15}$ are each independently H. In embodiments, $R^{14}$ and $R^{15}$ are each independently substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^6$ a substituted or unsubstituted $C_{1-3}$ alkyl. In embodiments, a substituted $R^{14}$ or $R^{15}$ (e.g., substituted alkyl) are each substituted with at least one substituent group, size-limited substituent group, or lower substituent group; wherein if the substituted $R^{14}$ or $R^{15}$ are each substituted with a plurality of groups selected from substituent groups, size-limited substituent groups, and lower substituent groups; each substituent group, size-limited substituent group, and/or lower substituent group may optionally be different. In embodiments, when $R^{14}$ or $R^{15}$ are each substituted, it is substituted with at least one substituent group. In embodiments, when $R^{14}$ or $R^{15}$ are each substituted, it is substituted with at least one size-limited substituent group. In embodiments, when $R^{14}$ or $R^{15}$ are each substituted, it is substituted with at least one lower substituent group.

In embodiments, $R^7$ is H or —$CH_3$. In embodiments, $R^7$ is H. In embodiments, $R^7$ is —$CH_3$.

In embodiments, $R^8$, $R^9$, $R^{10}$ and $R^{11}$ are each independently H, substituted or unsubstituted alkyl, —OH or halogen. In embodiments, halogen is —F, —Cl, —Br, or —I. In embodiments, $R^8$, $R^9$, $R^{10}$ and $R^{11}$ are each independently H. In embodiments, $R^8$, $R^9$, $R^{10}$ and $R^{11}$ are each independently —OH. In embodiments, $R^8$, $R^9$, $R^{10}$ and $R^{11}$ are each independently halogen. In embodiments, $R^8$, $R^9$, $R^{10}$ and $R^{11}$ are each independently substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^8$, $R^9$, $R^{10}$ and $R^{11}$ are each independently a substituted or unsubstituted $C_{1-3}$ alkyl. In embodiments, a substituted $R^8$, $R^9$, $R^{10}$ and $R^{11}$ (e.g., substituted alkyl) are each substituted with at least one substituent group, size-limited substituent group, or lower substituent group; wherein if the substituted $R^8$, $R^9$, $R^{10}$ and $R^1$ are each substituted with a plurality of groups selected from substituent groups, size-limited substituent groups, and lower substituent groups; each substituent group, size-limited substituent group, and/or lower substituent group may optionally be different. In embodiments, when $R^8$, $R^9$, $R^{10}$ and $R^{11}$ are each substituted, it is substituted with at least one substituent group. In embodiments, when $R^8$, $R^9$, $R^{10}$ and $R^{11}$ are each substituted, it is substituted with at least one size-limited substituent group. In embodiments, when $R^8$, $R^9$, $R^{10}$ and $R^{11}$ are each substituted, it is substituted with at least one lower substituent group.

In embodiments, $R^{12}$ and $R^{13}$ are each independently H or substituted or unsubstituted alkyl; or where one of moiety pairs (i) $R^8$ and $R^9$, (ii) $R^9$ and $R^{10}$, (iii) $R^{10}$ and $R^{11}$, (iv) $R^{11}$ and $R^{12}$ and (v) $R^{12}$ and $R^{13}$ may optionally be joined to form a substituted or unsubstituted cycloalkyl. In embodiments, $R^{12}$ and $R^{13}$ are each independently H. In embodiments, $R^{12}$ and $R^{13}$ are each independently substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{12}$ and $R^{13}$ are each independently a substituted or unsubstituted $C_{1-3}$ alkyl. In embodiments, a substituted $R^{12}$ and $R^{13}$ (e.g., substituted alkyl) are each substituted with at least one substituent group, size-limited substituent group, or lower substituent group; wherein if the substituted $R^{12}$ and $R^{13}$ are each substituted with a plurality of groups selected from substituent groups, size-limited substituent groups, and lower substituent groups; each substituent group, size-limited substituent group, and/or lower substituent group may optionally be different. In embodiments, when $R^{12}$ and $R^{13}$ are each substituted, it is substituted with at least one substituent group. In embodiments, when $R^{12}$ and $R^{13}$ are each substituted, it is substituted with at least one size-limited substituent group. In embodiments, when $R^{12}$ and $R^{13}$ are each substituted, it is substituted with at least one lower substituent group.

In embodiments, $R^8$ and $R^9$ may optionally be joined to form a substituted (e.g., substituted with a substituent group, a size-limited substituent group, or lower substituent group) or unsubstituted cycloalkyl. In embodiments, a substituted ring formed when $R^8$ and $R^9$ are joined (e.g., substituted cycloalkyl) is substituted with at least one substituent group, size-limited substituent group, or lower substituent group; wherein if the substituted ring formed when $R^8$ and $R^9$ are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^8$ and $R^9$ are joined is substituted, it is substituted with at least one substituent group. In embodiments, when the substituted ring formed when $R^8$ and $R^9$ are joined is substituted, it is substituted with at least one size-limited substituent group. In embodiments, when the substituted ring formed when $R^8$ and $R^9$ are joined is substituted, it is substituted with at least one lower substituent group. In embodiments, $R^8$ and $R^9$ may optionally be joined to form a substituted or unsubstituted $C_{3-6}$ cycloalkyl.

In embodiments, $R^9$ and $R^{10}$ may optionally be joined to form a substituted (e.g., substituted with a substituent group, a size-limited substituent group, or lower substituent group) or unsubstituted cycloalkyl. In embodiments, a substituted ring formed when $R^9$ and $R^{10}$ are joined (e.g., substituted cycloalkyl) is substituted with at least one substituent group, size-limited substituent group, or lower substituent group; wherein if the substituted ring formed when $R^9$ and $R^{10}$ are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^9$ and $R^{10}$ are joined is substituted, it is substituted with at least one substituent group. In embodiments, when the substituted ring formed when $R^9$ and $R^{10}$ are joined is substituted, it is substituted with at least one size-limited substituent group. In embodiments, when the substituted ring formed when $R^9$ and $R^{10}$ are joined is substituted, it is substituted with at least one lower substituent group. In embodiments, $R^9$ and $R^{10}$ may optionally be joined to form a substituted or unsubstituted $C_{3-6}$ cycloalkyl.

In embodiments, $R^{10}$ and $R^{11}$ may optionally be joined to form a substituted (e.g., substituted with a substituent group, a size-limited substituent group, or lower substituent group) or unsubstituted cycloalkyl. In embodiments, a substituted ring formed when $R^{10}$ and $R^{11}$ are joined (e.g., substituted cycloalkyl) is substituted with at least one substituent group, size-limited substituent group, or lower substituent group; wherein if the substituted ring formed when $R^{10}$ and $R^{11}$ are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{10}$ and $R^{11}$ are joined is substituted, it is substituted with at least one substituent group. In embodiments, when the substituted ring formed when $R^{10}$ and $R^1$ are joined is substituted, it is substituted with at least one size-limited substituent group. In embodiments, when the substituted ring formed when $R^{10}$ and $R^{11}$ are joined is substituted, it is substituted with at least one lower substituent group. In embodiments, $R^{10}$ and $R^{11}$ may optionally be joined to form a substituted or unsubstituted $C_{3-6}$ cycloalkyl.

In embodiments, $R^{11}$ and $R^{12}$ may optionally be joined to form a substituted (e.g., substituted with a substituent group, a size-limited substituent group, or lower substituent group) or unsubstituted cycloalkyl. In embodiments, a substituted ring formed when $R^{11}$ and $R^{12}$ are joined (e.g., substituted cycloalkyl) is substituted with at least one substituent group, size-limited substituent group, or lower substituent group; wherein if the substituted ring formed when $R^{11}$ and $R^{12}$ are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{11}$ and $R^{12}$ are joined is substituted, it is substituted with at least one substituent group. In embodiments, when the substituted ring formed when $R^{11}$ and $R^{12}$ are joined is substituted, it is substituted with at least one size-limited substituent group. In embodiments, when the substituted ring formed when $R^{11}$ and $R^{12}$ are joined is substituted, it is substituted with at least one lower substituent group. In embodiments, $R^{11}$ and $R^{12}$ may optionally be joined to form a substituted or unsubstituted $C_{3-6}$ cycloalkyl.

In embodiments, $R^{12}$ and $R^{13}$ may optionally be joined to form a substituted (e.g., substituted with a substituent group, a size-limited substituent group, or lower substituent group) or unsubstituted cycloalkyl. In embodiments, a substituted ring formed when $R^{12}$ and $R^{13}$ are joined (e.g., substituted cycloalkyl) is substituted with at least one substituent group, size-limited substituent group, or lower substituent group; wherein if the substituted ring formed when $R^{12}$ and $R^{13}$ are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{12}$ and $R^{13}$ are joined is substituted, it is substituted with at least one substituent group. In embodiments, when the substituted ring formed when $R^{12}$ and R are joined is substituted, it is substituted with at least one size-limited substituent group. In embodiments, when the substituted ring formed when $R^{12}$ and $R^{13}$ are joined is substituted, it is substituted with at least one lower substituent group. In embodiments, $R^{12}$ and $R^{13}$ may optionally be joined to form a substituted or unsubstituted $C_{3-6}$ cycloalkyl.

In embodiments, the compound is a compound of formula (Ib):

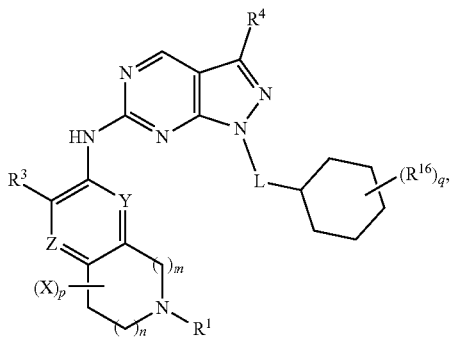

(Ib)

or a pharmaceutically acceptable salt thereof. L, X, Y, Z, n, m, p, $R^1$, $R^2$, $R^3$ and $R^4$ are as defined in formula (I) including embodiments. $R^{16}$ is —OH, a substituted or unsubstituted alkyl, —COOH, —OCH$_3$, —NHC(O)CH$_3$, —NHC(O)CH$_2$OH, —NHSO$_2$CH$_3$ or —C(O)NR$^{17}$R$^{18}$. $R^{17}$ and $R^{18}$ are each independently H or a substituted or unsubstituted $C_{1-3}$ alkyl. q is 0, 1 or 2.

In embodiments, $R^{16}$ is —OH, a substituted or unsubstituted alkyl, —COOH, —OCH$_3$, —NHC(O)CH$_3$, —NHC(O)CH$_2$OH, —NHSO$_2$CH$_3$ or —C(O)NR$^{17}$R$^{18}$. In embodiments, $R^{16}$ is —OH. In embodiments, $R^{16}$ is —COOH. In embodiments, $R^{16}$ is —OCH$_3$. In embodiments, $R^{16}$ is —NHC(O)CH$_3$. In embodiments, $R^{16}$ is —NHC(O)CH$_2$OH. In embodiments, $R^{16}$ is —NHSO$_2$CH$_3$. In embodiments, $R^{16}$ is —C(O)NR$^{17}$R$^{18}$. In embodiments, $R^{16}$ is a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{16}$ is a substituted or unsubstituted $C_{1-3}$ alkyl. In embodiments, a substituted $R^{16}$ (e.g., substituted alkyl) is substituted with at least one substituent group, size-limited substituent group, or lower substituent group; wherein if the substituted $R^{16}$ is substituted with a plurality of groups selected from substituent groups, size-limited substituent groups, and lower substituent groups; each substituent group, size-limited substituent group, and/or lower substituent group may optionally be different. In embodiments, when $R^{16}$ is substituted, it is substituted with at least one substituent group. In embodiments, when $R^{16}$ is substituted, it is substituted with at least one size-limited substituent group. In embodiments, when $R^{16}$ is substituted, it is substituted with at least one lower substituent group.

In embodiments, $R^{17}$ and $R^{18}$ are each independently H or a substituted or unsubstituted alkyl. In embodiments, $R^{17}$ and $R^{18}$ are each independently H. In embodiments, $R^{17}$ and $R^{18}$ are each independently a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{17}$ and $R^{18}$ are each independently a substituted or unsubstituted $C_{1-3}$ alkyl. In embodiments, a substituted $R^{17}$ and $R^{18}$ (e.g., substituted alkyl) are each substituted with at least one substituent group, size-limited substituent group, or lower substituent group; wherein if the substituted $R^{17}$ and $R^{18}$ are each substituted with a plurality of groups selected from substituent groups, size-limited substituent groups, and lower substituent groups; each substituent group, size-limited substituent group, and/or lower substituent group may optionally be different. In embodiments, when $R^{17}$ and $R^{18}$ are each substituted, it is substituted with at least one substituent group. In embodiments, when $R^{17}$ and $R^{18}$ are each substituted, it is substituted with at least one size-limited substituent group. In embodiments, when $R^{17}$ and $R^{18}$ are each substituted, it is substituted with at least one lower substituent group.

In embodiments, q is 0, 1 or 2. In embodiments, q is 0. In embodiments, q is 1. In embodiments, q is 2.

In embodiments, the compound is a compound of formula (Ic):

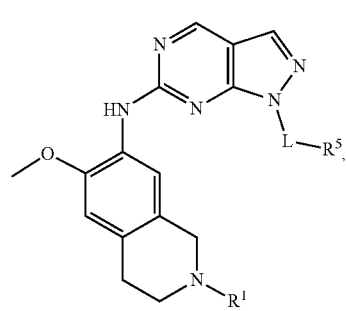

(Ic)

or a pharmaceutically acceptable salt thereof. L, $R^1$ and $R^5$ are as defined in Formula (I), including embodiments.

In embodiment, the compound is a compound of formula (II):

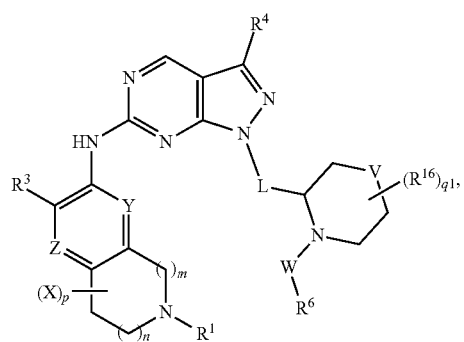

(II)

or a pharmaceutically acceptable salt thereof. L, X, Y, Z, n, m, p, $R^1$, $R^2$, $R^3$, $R^4$ and $R^6$ are as defined in formulae (I) and (Ia), including embodiments. V is CR$^{19}$R$^{20}$, O or NR$^{21}$. W is —C(O), —S(O), —S(O)$_2$ or —S(NH)(O). q1 is an integer from 0 to 7. $R^6$ is a substituted or unsubstituted alkyl, —OCH$_3$ or —NR$^{14}$R$^{15}$. $R^{14}$ and $R^{15}$ are each independently H or substituted or unsubstituted alkyl. $R^{19}$ and $R^{20}$ are each H, —OH, —OCH$_3$, —NR$^{14}$R$^{15}$, substituted or unsubstituted alkyl, substituted or unsubstituted heteroalkyl, or substituted or unsubstituted cycloalkyl. $R^{21}$ is H, —OH, substituted or unsubstituted alkyl, or substituted or unsubstituted cycloalkyl. $R^{16'}$ is independently —OH, substituted or unsubstituted alkyl, or halogen. In embodiments, when V is O or NR$^{21}$, then $R^{16'}$ is not —OH or halogen.

In embodiments, V is CR$^{19}$R$^{20}$, O or NR$^{21}$.

In embodiments, V is O.

In embodiments, V is CR$^{19}$R$^{20}$. In embodiments, $R^{19}$ and $R^{20}$ are each independently H, —OH, —OCH$_3$, —NR$^{14}$R$^{15}$, substituted or unsubstituted alkyl, substituted or unsubstituted heteroalkyl, or substituted or unsubstituted cycloalkyl. In embodiments, $R^{19}$ and $R^{20}$ are each H. In embodiments, $R^{19}$ and $R^{20}$ are each —OH. In embodiments, $R^{19}$ and $R^{20}$ are each —OCH$_3$. In embodiments, $R^{19}$ and $R^{20}$ are each —NR$^{14}$R$^{15}$. In embodiments, $R^{19}$ and $R^{20}$ are each independently a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{19}$ and $R^{20}$ are each independently substituted or unsubstituted $C_{1-3}$ alkyl. In embodiments, $R^{19}$ and $R^{20}$ are each independently a substituted (e.g., substituted with a substituent group, a size-limited substituent group, or lower substituent group) or unsubstituted heteroalkyl (e.g., 2 to 8 membered, 2-6 membered, or 2 to 4 membered). In embodiments, $R^{19}$ and $R^{20}$ are each independently a substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$). In embodiments, $R^{19}$ and $R^{20}$ are each independently substituted or unsubstituted $C_{3-6}$ cycloalkyl. In embodiments, a substituted $R^{19}$ and $R^{20}$ (e.g., substituted alkyl, substituted heteroalkyl, and/or substituted cycloalkyl) are each substituted with at least one substituent group, size-limited substituent group, or lower substituent group; wherein if the substituted $R^{19}$ and $R^{20}$ are each substituted with a plurality of groups selected from substituent groups, size-limited substituent groups, and lower substituent groups; each substituent group, size-limited substituent group, and/or lower substituent group may optionally be different. In embodiments, when $R^{19}$ and $R^{20}$ are each substituted, it is substituted with at least one substituent group. In embodiments, when $R^{19}$ and $R^{20}$ are each substituted, it is substituted with at least one size-limited substituent group. In embodiments, when $R^{19}$ and $R^{20}$ are each substituted, it is substituted with at least one lower substituent group.

In embodiments, $R^{14}$ and $R^{15}$ are each independently H or substituted or unsubstituted alkyl. In embodiments, $R^{14}$ and $R^{15}$ are each independently H. In embodiments, $R^{14}$ and $R^{15}$ are each independently substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{14}$ and $R^{15}$ are each independently substituted or unsubstituted $C_{1-3}$ alkyl. In embodiments, a substituted $R^{14}$ and $R^{15}$ (e.g., substituted alkyl) are each substituted with at least one substituent group, size-limited substituent group, or lower substituent group; wherein if the substituted $R^{14}$ and $R^{15}$ are each substituted with a plurality of groups selected from substituent groups, size-limited substituent groups, and lower substituent groups; each substituent group, size-limited substituent group, and/or lower substituent group may optionally be different. In embodiments, when $R^{14}$ and $R^{15}$ are each substituted, it is substituted with at least one substituent group. In embodiments, when $R^{14}$ and $R^{15}$ are each substituted, it is substituted with at least one size-limited substituent group. In embodiments, when $R^{14}$ and $R^{15}$ are each substituted, it is substituted with at least one lower substituent group.

In embodiments, V is NR$^{21}$. In embodiments, $R^{21}$ is H, —OH, substituted or unsubstituted alkyl, or substituted or unsubstituted cycloalkyl. In embodiments, $R^{21}$ is H. In embodiments, $R^{21}$ is —OH. In embodiments, $R^{21}$ is a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{21}$ is substituted or unsubstituted $C_{1-3}$ alkyl. In embodiments, $R^{21}$ is a substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$). In embodiments, $R^{21}$ is substituted or unsubstituted $C_{3-6}$ cycloalkyl. In embodiments, a substituted $R^{21}$ (e.g., substituted alkyl and/or substituted cycloalkyl) is substituted with at least one substituent group, size-limited substituent group, or lower substituent group; wherein if the substituted $R^{21}$ is substituted with a plurality of groups selected from substituent groups, size-limited substituent groups, and lower substituent groups; each substituent group, size-limited substituent group, and/or lower substituent group may optionally be different. In embodiments, when $R^{21}$ is substituted, it is substituted with at least one substituent group. In embodiments, when $R^{21}$ is substituted, it is substituted with at least one size-limited substituent group. In embodiments, when $R^{21}$ is substituted, it is substituted with at least one lower substituent group.

In embodiments, W is —C(O), —S(O), —S(O)$_2$ or —S(NH)(O). In embodiments, W is —C(O). In embodiments, W is —S(O). In embodiments, W is —S(O)$_2$. In embodiments, W is —S(NH)(O).

In embodiments, q1 is an integer from 0 to 7. In embodiments, q1 is 0. In embodiments, q1 is 1. In embodiments, q1 is 2. In embodiments, q1 is 3. In embodiments, q1 is 4. In embodiments, q1 is 5. In embodiments, q1 is 6. In embodiments, q1 is 7.

In embodiments, $R^{16'}$ is independently —OH, substituted or unsubstituted alkyl, or halogen, wherein when V is O or NR$^{21}$, then $R^{16'}$ is not —OH or halogen. In embodiments, $R^{16'}$ is —OH. In embodiments, $R^{16'}$ is halogen. In embodiments, $R^{16'}$ is a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{16'}$ is substituted or unsubstituted $C_{1-3}$ alkyl. In embodiments, a substituted $R^{16'}$ (e.g., substituted alkyl) is substituted with at least one substituent group, size-limited substituent group, or lower substituent group; wherein if the substituted $R^{16'}$ is substituted with a plurality of groups selected from substituent groups, size-limited substituent groups, and lower substituent groups; each substituent group, size-limited substituent group, and/or lower substituent group may optionally be different. In embodiments, when $R^{16'}$ is substituted, it is substituted with at least one substituent group. In embodiments, when $R^{16'}$ is substituted, it is substituted with at least one size-limited substituent group. In embodiments, when $R^{16'}$ is substituted, it is substituted with at least one lower substituent group.

In embodiment, the compound is a compound of formula (IIa):

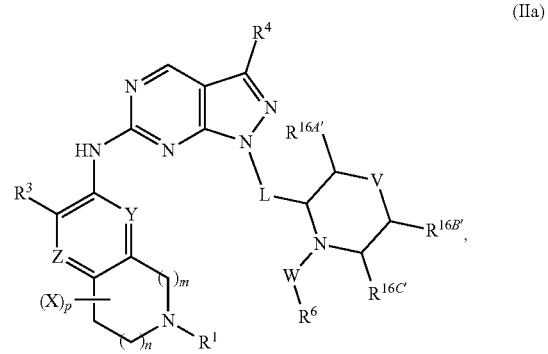

(IIa)

or a pharmaceutically acceptable salt thereof. L, X, Y, Z, n, m, p, $R^1$, $R^2$, $R^3$, $R^4$ and $R^6$ are as defined in formula (I), including embodiments. V, W, $R^{14}$, $R^{15}$, $R^{19}$, $R^{20}$, and $R^{21}$ are as defined in formula (II), including embodiments. $R^{16A'}$, $R^{16B'}$, and $R^{16C'}$ are each independently —OH, halogen, or a substituted or unsubstituted alkyl. In embodiments, $R^{16A'}$, $R^{16B'}$, and $R^{16C'}$ are each independently —OH, halogen, or a substituted or unsubstituted alkyl. In embodiments, when V is O or $NR^{21}$, then $R^{16A'}$, $R^{16B'}$, and $R^{16C'}$ are each independently a substituted or unsubstituted alkyl.

In embodiments, $R^{16A'}$, $R^{16B'}$, and $R^{16C'}$ are each independently —OH. In embodiments, $R^{16A'}$, $R^{16B'}$, and $R^{16C'}$ are each independently halogen. In embodiments, $R^{16A'}$, $R^{16B'}$, and $R^{16C'}$ are each independently —F, —Cl, —Br, or —I. In embodiments, $R^{16A'}$, $R^{16B'}$, and $R^{16C'}$ are each independently a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{16A'}$, $R^{16B'}$, and $R^{16C'}$ are each independently a substituted or unsubstituted $C_{1-3}$ alkyl. In embodiments, a substituted $R^{16A'}$, $R^{16B'}$, and $R^{16C'}$ (e.g., substituted alkyl) are each substituted with at least one substituent group, size-limited substituent group, or lower substituent group; wherein if the substituted $R^{16A'}$, $R^{16B'}$, and $R^{16C'}$ are each substituted with a plurality of groups selected from substituent groups, size-limited substituent groups, and lower substituent groups; each substituent group, size-limited substituent group, and/or lower substituent group may optionally be different. In embodiments, when $R^{16A'}$, $R^{16B'}$, and $R^{16C'}$ are each substituted, it is substituted with at least one substituent group. In embodiments, when $R^{16A'}$, $R^{16B'}$, and $R^{16C'}$ are each substituted, it is substituted with at least one size-limited substituent group. In embodiments, when $R^{16A'}$, $R^{16B'}$, and $R^{16C'}$ are each substituted, it is substituted with at least one lower substituent group.

In embodiment, the compound is a compound of formula (III):

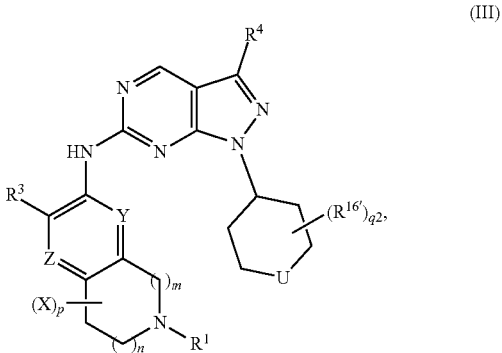

or a pharmaceutically acceptable salt thereof. X, Y, Z, n, m, p, $R^1$, $R^2$, $R^3$, $R^4$, $R^{14}$, $R^{15}$, and $R^{16'}$ are as defined in formulae (I) and (II), including embodiments. q2 is an integer from 0 to 9. U is O, —$NR^{23}$, —$N(CO)R^{24}$ or —$N(SO_2)R^{25}$. $R^{23}$ and $R^{24}$ are each H, —OH, —$OCH_3$, —$NR^{14}R^{15}$, substituted or unsubstituted alkyl, substituted or unsubstituted heteroalkyl, or substituted or unsubstituted cycloalkyl. $R^{25}$ is H, —OH, substituted or unsubstituted alkyl or substituted or unsubstituted cycloalkyl. $R^{16'}$ is independently —OH, substituted or unsubstituted alkyl, or halogen. In embodiments, when $R^{16'}$ is adjacent to a heteroatom (U), then $R^{16'}$ is not —OH or halogen.

In embodiments, q2 is an integer from 0 to 9. In embodiments, q2 is 0. In embodiments, q2 is 1. In embodiments, q2 is 2. In embodiments, q2 is 3. In embodiments, q2 is 4. In embodiments, q2 is 5. In embodiments, q2 is 6. In embodiments, q2 is 7. In embodiments, q2 is 8. In embodiments, q2 is 9.

In embodiments, U is O, —$NR^{23}$, —$N(CO)R^{24}$ or —$N(SO_2)R^{25}$. In embodiments, U is O. In embodiments, U is —$NR^{23}$. In embodiments, U is —$N(CO)R^{24}$. In embodiments, U is —$N(SO_2)R^{25}$.

In embodiments, $R^{23}$ and $R^{24}$ are each independently H, —OH, —$OCH_3$, —$NR^{14}R^{15}$, substituted or unsubstituted alkyl, substituted or unsubstituted heteroalkyl, or substituted or unsubstituted cycloalkyl. In embodiments, $R^{23}$ and $R^{24}$ are each independently H. In embodiments, $R^{23}$ and $R^{24}$ are each independently —OH. In embodiments, $R^{23}$ and $R^{24}$ are each independently —$OCH_3$. In embodiments, $R^{23}$ and $R^{24}$ are each independently —$NR^{14}R^{15}$. In embodiments, $R^{23}$ and $R^{24}$ are each independently a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{23}$ and $R^{24}$ are each independently substituted or unsubstituted $C_{1-3}$ alkyl. In embodiments, $R^{23}$ and $R^{24}$ are each independently a substituted (e.g., substituted with a substituent group, a size-limited substituent group, or lower substituent group) or unsubstituted heteroalkyl (e.g., 2 to 8 membered, 2-6 membered, or 2 to 4 membered). In embodiments, $R^{23}$ and $R^{24}$ are each independently a substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$). In embodiments, $R^{23}$ and $R^{24}$ are each independently substituted or unsubstituted $C_{3-6}$ cycloalkyl. In embodiments, a substituted $R^{23}$ and $R^{24}$ (e.g., substituted alkyl, substituted heteroalkyl, and/or substituted cycloalkyl) are each substituted with at least one substituent group, size-limited substituent group, or lower substituent group; wherein if the substituted $R^{23}$ and $R^{24}$ are each substituted with a plurality of groups selected from substituent groups, size-limited substituent groups, and lower substituent groups; each substituent group, size-limited substituent group, and/or lower substituent group may optionally be different. In embodiments, when $R^{23}$ and $R^{24}$ are each substituted, it is substituted with at least one substituent group. In embodiments, when $R^{23}$ and $R^{24}$ are each substituted, it is substituted with at least one size-limited substituent group. In embodiments, when $R^{23}$ and $R^{24}$ are each substituted, it is substituted with at least one lower substituent group.

In embodiments, $R^{25}$ is H, —OH, substituted or unsubstituted alkyl, or substituted or unsubstituted cycloalkyl. In embodiments, $R^{25}$ is H. In embodiments, $R^{25}$ is —OH. In embodiments, $R^{25}$ is a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{25}$ is substituted or unsubstituted $C_{1-3}$ alkyl. In embodiments, $R^{25}$ is a substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$). In embodiments, $R^{25}$ is substituted or unsubstituted $C_{3-6}$ cycloalkyl. In embodiments, a substituted $R^{25}$ (e.g., substituted alkyl and/or substituted cycloalkyl) is substituted with at least one substituent group, size-limited substituent group, or lower substituent group; wherein if the substituted $R^{25}$ is substituted with a plurality of groups selected from substituent groups, size-limited substituent groups, and lower substituent groups; each substituent group, size-limited substituent group, and/or lower substituent group may optionally be different. In embodiments, when $R^{25}$ is substituted, it is substituted with at least one substituent group. In embodiments, when $R^{25}$ is substituted, it is substituted with at least one size-limited substituent group. In embodiments, when $R^{25}$ is substituted, it is substituted with at least one lower substituent group.

In embodiments, $R^{16'}$ is independently —OH, substituted or unsubstituted alkyl, or halogen. In embodiments, $R^{16'}$ is —OH. In embodiments, $R^{16'}$ is halogen. In embodiments, $R^{16'}$ is —F, —Cl, —Br, or —I. In embodiments, $R^{16'}$ is a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{16'}$ is substituted or unsubstituted $C_{1-3}$ alkyl. In embodiments, when $R^{16'}$ is adjacent to a heteroatom (U), then $R^{16'}$ is not —OH or halogen.

In another embodiment, the compound is a compound of formula (IIIa):

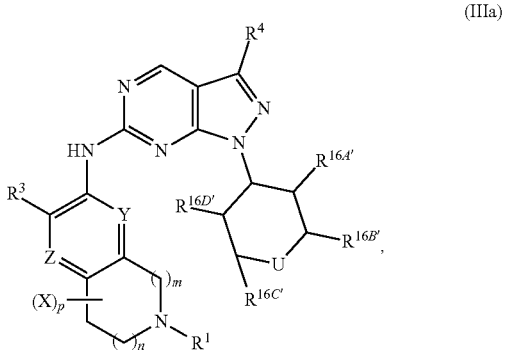

(IIIa)

or a pharmaceutically acceptable salt thereof. X, Y, Z, n, m, p, $R^1$, $R^2$, $R^3$ and $R^4$ are as defined in formula (I), including embodiments. U, $R^{23}$, $R^{24}$ and $R^{25}$ are as defined in formula (III), including embodiments. $R^{16B'}$ and $R^{16C'}$ are each independently a substituted or unsubstituted alkyl. $R^{16A'}$ and $R^{16D'}$ are each independently —OH, substituted or unsubstituted alkyl, or halogen.

In embodiments, $R^{16B'}$ and $R^{16C'}$ are each independently a substituted or unsubstituted alkyl. In embodiments, $R^{16B'}$ and $R^{16C'}$ are each independently a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{16B'}$ and $R^{16C'}$ are each independently substituted or unsubstituted $C_{1-3}$ alkyl. In embodiments, a substituted $R^{16B'}$ and $R^{16C'}$ (e.g., substituted alkyl) are each substituted with at least one substituent group, size-limited substituent group, or lower substituent group; wherein if the substituted $R^{16B'}$ and $R^{16C'}$ are each substituted with a plurality of groups selected from substituent groups, size-limited substituent groups, and lower substituent groups; each substituent group, size-limited substituent group, and/or lower substituent group may optionally be different. In embodiments, when $R^{16B'}$ and $R^{16C'}$ are each substituted, it is substituted with at least one substituent group. In embodiments, when $R^{16B'}$ and $R^{16C'}$ are each substituted, it is substituted with at least one size-limited substituent group. In embodiments, when $R^{16B'}$ and $R^{16C'}$ are each substituted, it is substituted with at least one lower substituent group.

In embodiments, $R^{16D'}$ and $R^{16E'}$ are each independently —OH, substituted or unsubstituted alkyl, or halogen. In embodiments, $R^{16D'}$ and $R^{16E'}$ are each independently —OH. In embodiments, $R^{16D'}$ and $R^{16E'}$ are each independently halogen. In embodiments, $R^{16D'}$ and $R^{16E'}$ are each independently —F, —Cl, —Br, or —I. In embodiments, $R^{16D'}$ and $R^{16E'}$ are each independently a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{16D'}$ and $R^{16E'}$ are each independently substituted or unsubstituted $C_{1-3}$ alkyl. In embodiments, a substituted $R^{16D'}$ and $R^{16E'}$ (e.g., substituted alkyl) are each substituted with at least one substituent group, size-limited substituent group, or lower substituent group; wherein if the substituted $R^{16D'}$ and $R^{16E'}$ are each substituted with a plurality of groups selected from substituent groups, size-limited substituent groups, and lower substituent groups; each substituent group, size-limited substituent group, and/or lower substituent group may optionally be different. In embodiments, when $R^{16D'}$ and $R^{16E'}$ are each substituted, it is substituted with at least one substituent group. In embodiments, when $R^{16D'}$ and $R^{16E'}$ are each substituted, it is substituted with at least one size-limited substituent group. In embodiments, when $R^{16D'}$ and $R^{16E'}$ are each substituted, it is substituted with at least one lower substituent group.

In another embodiment, the compound is a compound of formula (IV):

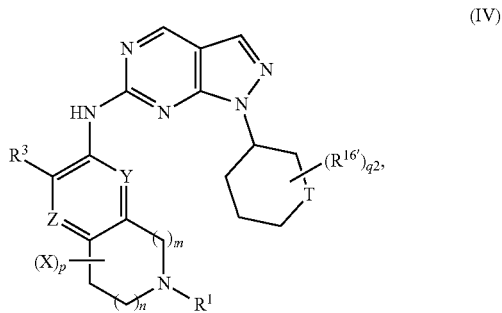

(IV)

or a pharmaceutically acceptable salt thereof. X, Y, Z, n, m, p, $R^1$, $R^2$, $R^3$, $R^4$, $R^{16'}$, and q2 are as defined in formulae (I)-(III), including embodiments. T is O, —$NR^{27}$, —N(CO)$R^{28}$ or —N(SO$_2$)$R^{29}$. $R^{27}$ and $R^{28}$ are each H, —OH, —OCH$_3$, —NR$^{14}$R$^{15}$, substituted or unsubstituted alkyl, substituted or unsubstituted heteroalkyl, or substituted or unsubstituted cycloalkyl. $R^{29}$ is H, —OH, substituted or unsubstituted alkyl, or substituted or unsubstituted cycloalkyl. $R^{16'}$ is independently —OH, substituted or unsubstituted alkyl, or halogen. In embodiments, when $R^{16'}$ is adjacent to a heteroatom (T), then $R^{16'}$ is not —OH or halogen.

In embodiments, T is O, —$NR^{27}$, —N(CO)$R^{28}$ or —N(SO$_2$)$R^{29}$. In embodiments, T is O. In embodiments, T is —$NR^{27}$. In embodiments, T is —N(CO)$R^{28}$. In embodiments, T is —N(SO$_2$)$R^{29}$.

In embodiments, $R^{27}$ and $R^{28}$ are each independently H, —OH, —OCH$_3$, —NR$^{14}$R$^{15}$, substituted or unsubstituted alkyl, substituted or unsubstituted heteroalkyl, or substituted or unsubstituted cycloalkyl. In embodiments, $R^{27}$ and $R^{28}$ are each independently H. In embodiments, $R^{27}$ and $R^{28}$ are each independently —OH. In embodiments, $R^{27}$ and $R^{28}$ are each independently —OCH$_3$. In embodiments, $R^{27}$ and $R^{28}$ are each independently —NR$^{14}$R$^{15}$. In embodiments, $R^{27}$ and $R^{28}$ are each independently a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{27}$ and $R^{28}$ are each independently substituted or unsubstituted $C_{1-3}$ alkyl. In embodiments, $R^{27}$ and $R^{28}$ are each independently a substituted (e.g., substituted with a substituent group, a size-limited substituent group, or lower substituent group) or unsubstituted heteroalkyl (e.g., 2 to 8 membered, 2-6 membered, or 2 to 4 membered). In embodiments, $R^{27}$ and $R^{28}$ are each independently a substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$). In embodiments, $R^{27}$ and $R^{28}$ are each independently substituted or unsubstituted $C_{3-6}$ cycloalkyl. In embodiments, a substituted $R^{27}$ and $R^{28}$ (e.g., substituted alkyl, substituted heteroalkyl, and/or substituted cycloalkyl) are each substituted with at least one substituent group, size-limited substituent group, or lower substituent group; wherein if the substituted $R^{27}$ and $R^{28}$ are each substituted with a plurality of groups selected from substituent groups, size-limited substituent groups, and lower substituent groups; each substituent group, size-limited substituent group, and/or lower substituent group may optionally be different. In embodiments, when $R^{27}$ and $R^{28}$ are each substituted, it is substituted with at least one substituent group. In embodiments, when $R^{27}$ and $R^{28}$ are each substituted, it is substituted with at least one size-limited substituent group. In embodiments, when $R^{27}$ and $R^{28}$ are each substituted, it is substituted with at least one lower substituent group.

In embodiments, $R^{29}$ is H, —OH, substituted or unsubstituted alkyl, or substituted or unsubstituted cycloalkyl. In embodiments, $R^{29}$ is H. In embodiments, $R^{29}$ is —OH. In embodiments, $R^{29}$ is a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{29}$ is substituted or unsubstituted $C_{1-3}$ alkyl. In embodiments, $R^{29}$ is a substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$). In embodiments, $R^{29}$ is substituted or unsubstituted $C_{3-6}$ cycloalkyl. In embodiments, a substituted $R^{29}$ (e.g., substituted alkyl and/or substituted cycloalkyl) is substituted with at least one substituent group, size-limited substituent group, or lower substituent group; wherein if the substituted $R^{29}$ is substituted with a plurality of groups selected from substituent groups, size-limited substituent groups, and lower substituent groups; each substituent group, size-limited substituent group, and/or lower substituent group may optionally be different. In embodiments, when $R^{29}$ is substituted, it is substituted with at least one substituent group. In embodiments, when $R^{29}$ is substituted, it is substituted with at least one size-limited substituent group. In embodiments, when $R^{29}$ is substituted, it is substituted with at least one lower substituent group.

In embodiments, $R^{16'}$ is independently —OH, substituted or unsubstituted alkyl, or halogen. In embodiments, $R^{16'}$ is —OH. In embodiments, $R^{16'}$ is halogen. In embodiments, $R^{16'}$ is —F, —Cl, —Br, or —I. In embodiments, $R^{16'}$ is a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{16'}$ is substituted or unsubstituted $C_{1-3}$ alkyl. In embodiments, when $R^{16'}$ is adjacent to a heteroatom (T), then $R^{16'}$ is not —OH or halogen.

In another embodiment, the compound is a compound of formula (IVa):

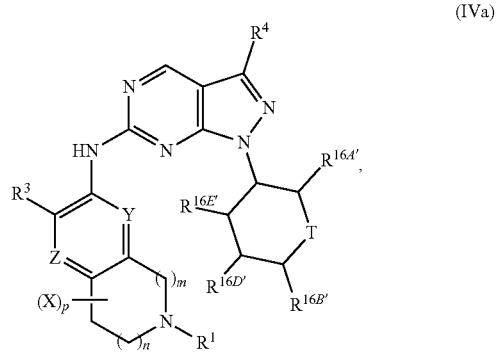

(IVa)

or a pharmaceutically acceptable salt thereof. X, Y, Z, n, m, p, $R^1$, $R^2$, $R^3$ and $R^4$ are as defined in formula (I), including embodiments. T, $R^{27}$, $R^{28}$ and $R^{29}$ are as defined in formula (IV), including embodiments. $R^{16A'}$ and $R^{16B'}$ are each independently a substituted or unsubstituted alkyl. $R^{16D'}$ and $R^{16E'}$ are each independently —OH, substituted or unsubstituted alkyl, or halogen.

In embodiments, $R^{16A'}$ and $R^{16B'}$ are each independently a substituted or unsubstituted alkyl. In embodiments, $R^{16A'}$ and $R^{16B'}$ are each independently a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{16A'}$ and $R^{16B'}$ are each independently substituted or unsubstituted $C_{1-3}$ alkyl. In embodiments, a substituted $R^{16A'}$ and $R^{16B'}$ (e.g., substituted alkyl) are each substituted with at least one substituent group, size-limited substituent group, or lower substituent group; wherein if the substituted $R^{16A'}$ and $R^{16B'}$ are each substituted with a plurality of groups selected from substituent groups, size-limited substituent groups, and lower substituent groups; each substituent group, size-limited substituent group, and/or lower substituent group may optionally be different. In embodiments, when $R^{16A'}$ and $R^{16B'}$ are each substituted, it is substituted with at least one substituent group. In embodiments, when $R^{16A'}$ and $R^{16B'}$ are each substituted, it is substituted with at least one size-limited substituent group. In embodiments, when $R^{16A'}$ and $R^{16B'}$ are each substituted, it is substituted with at least one lower substituent group.

In embodiments, $R^{16D'}$ and $R^{16E'}$ are each independently —OH, substituted or unsubstituted alkyl, or halogen. In embodiments, $R^{16D'}$ and $R^{16E'}$ are each independently —OH. In embodiments, $R^{16D'}$ and $R^{16E'}$ are each independently halogen. In embodiments, $R^{16D'}$ and $R^{16E'}$ are each independently —F, —Cl, —Br, or —I. In embodiments, $R^{16D'}$ and $R^{16E'}$ are each independently a substituted (e.g., substituted with a substituent group, a size-limited substituent group, or lower substituent group) or unsubstituted alkyl (e.g., $C_1$-$C_8$, $C_1$-$C_6$, or $C_1$-$C_4$). In embodiments, $R^{16D'}$ and $R^{16E'}$ are each independently substituted or unsubstituted $C_{1-3}$ alkyl. In embodiments, a substituted $R^{16D'}$ and $R^{16E'}$ (e.g., substituted alkyl) are each substituted with at least one substituent group, size-limited substituent group, or lower substituent group; wherein if the substituted $R^{16D'}$ and $R^{16E'}$ are each substituted with a plurality of groups selected from substituent groups, size-limited substituent groups, and lower substituent groups; each substituent group, size-limited substituent group, and/or lower substituent group may optionally be different. In embodiments, when $R^{16D'}$ and $R^{16E'}$ are each substituted, it is substituted with at least one substituent group. In embodiments, when $R^{16D'}$ and $R^{16E'}$ are each substituted, it is substituted with at least one size-limited substituent group. In embodiments, when $R^{16D'}$ and $R^{16E'}$ are each substituted, it is substituted with at least one lower substituent group.

In embodiments, the compound of formulae (I) to (IVa) is:

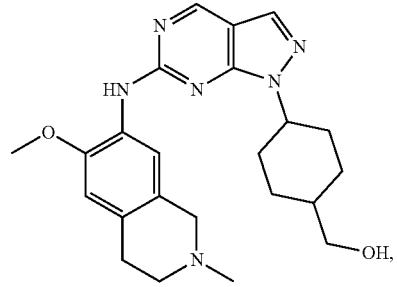

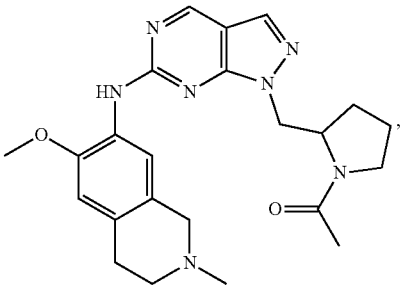

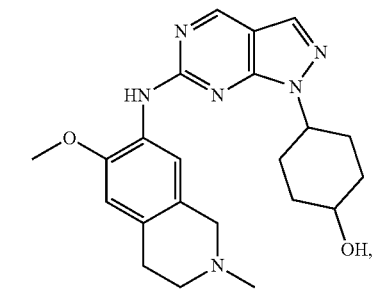

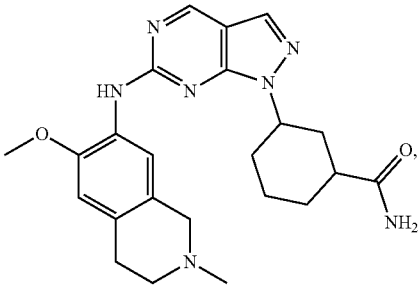

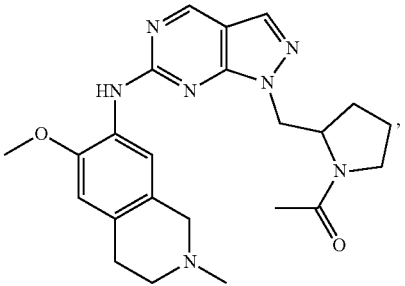

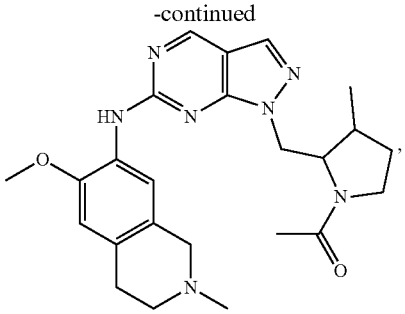

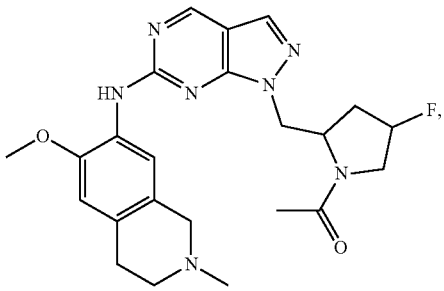

or a pharmaceutically acceptable salt thereof.

In embodiments, the compound of formulae (I) to (IVa) is:

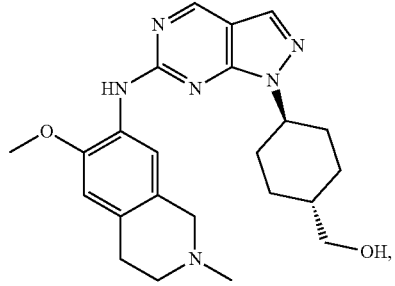

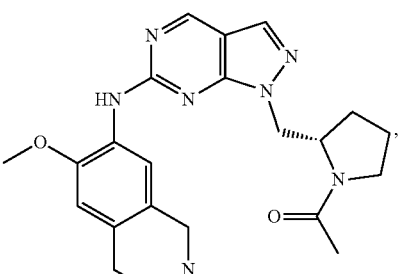

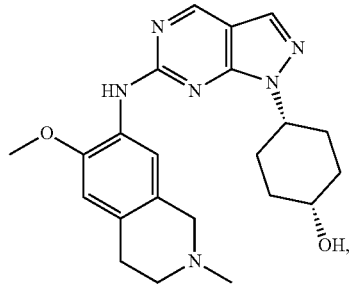

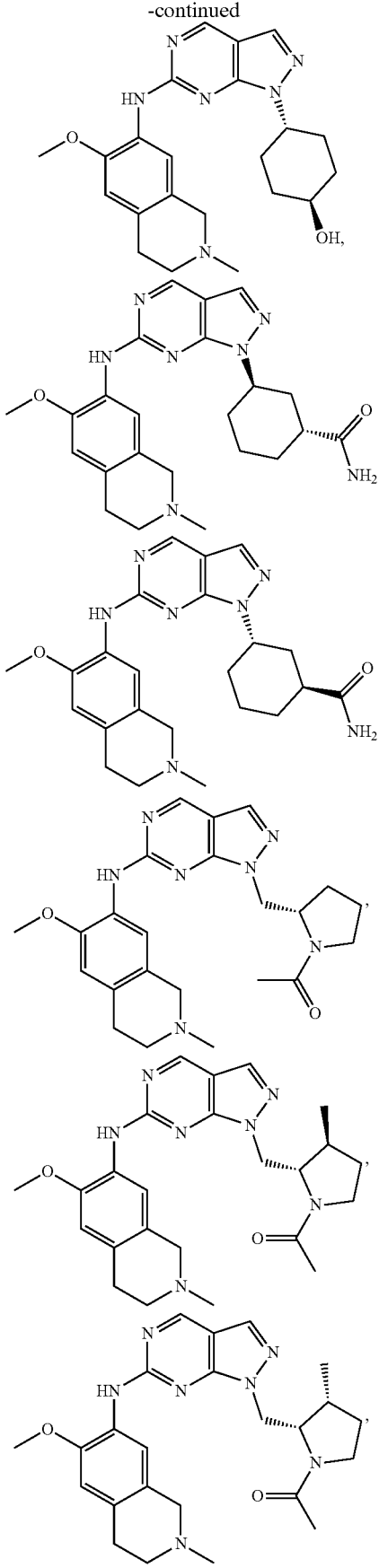

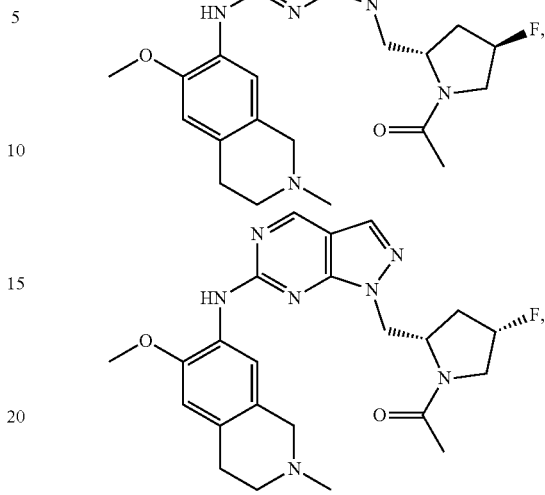

or a pharmaceutically acceptable salt thereof.

In embodiments, the compound of formula (I)-(IVa) is useful as a comparator compound. In embodiments, the comparator compound can be used to assess the activity of a test compound in an assay (e.g., an assay as described herein, for example in the examples section, figures, or tables).

Pharmaceutical Compositions

Compounds in accordance with formulae (I)-(IVa) and/or pharmaceutically acceptable salts thereof can be administered by any means suitable for the condition to be treated, which can depend on the need for site-specific treatment or quantity of formulae (I)-(IVa) compound to be delivered.

Also embraced within this disclosure is a class of pharmaceutical compositions comprising a compound of formulae (I)-(IVa) and/or pharmaceutically acceptable salts thereof, and one or more non-toxic, pharmaceutically-acceptable carriers and/or diluents and/or adjuvants (collectively referred to herein as "carrier" materials) and, if desired, other active ingredients. The compounds of formulae (I)-(IVa) may be administered by any suitable route, preferably in the form of a pharmaceutical composition adapted to such a route, and in a dose effective for the treatment intended. The compounds and compositions of the compound of formulae (I)-(IVa) may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the disclosure can contain at least one agent selected from sweetening agents, flavoring agents, coloring agents, demulcents, anti-oxidants, and preserving agents.

A tablet can, for example, be prepared by admixing at least one compound of Formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of formulae (I)-(IVa) and/or at least one salt thereof with at least one inert solid diluent, such as, for example, calcium carbonate; calcium phosphate; and kaolin.

Soft gelatin capsules can, for example, be prepared by mixing at least one compound of formulae (I)-(IVa)) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of formulae (I)-(IVa) and/or at least one pharmaceutically acceptable salt thereof with at least one excipient suitable for the manufacture of an aqueous suspension. Exemplary excipients suitable for the manufacture of an aqueous suspension, include, but are not limited to, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of formulae (I)-(IVa) and/or at least one pharmaceutically acceptable salt thereof in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of formulae (I)-(IVa) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of formulae (I)-(IVa) and/or at least one pharmaceutically acceptable salt thereof can, for example, be prepared as an oil-in-water emulsion. The oily phase of the emulsions comprising compounds of formulae (I)-(IVa) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present disclosure include Tween 60, Span 80, cetostearyl alcohol, myristyl alcohol, glyceryl monostearate, sodium lauryl sulfate, glyceryl distearate alone or with a wax, or other materials well known in the art.

The compounds of formulae (I)-(IVa) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer'ssolution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of formulae (I)-(IVa) in an oily phase, such as, for example, a mixture of soybean oil and lecithin; 2) combining the formulae (I)-(IVa) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this disclosure include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this disclosure can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this disclosure depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two-day cycle.

For therapeutic purposes, the active compounds of this disclosure are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this disclosure comprise at least one compound of formulae (I)-(IVa) and/or at least one pharmaceutically acceptable salt thereof, and optionally an additional agent selected from any pharmaceutically acceptable carrier, adjuvant, and vehicle. Alternate compositions of this disclosure comprise a compound of the formulae (I)-(IVa) described herein, or a prodrug thereof, and a pharmaceutically acceptable carrier, adjuvant, or vehicle.

Therapeutic Uses

The compounds of formulae (I)-(IVa) are useful for the treatment of diseases and conditions associated with undesirable HPK1 activity, such as cancer.

In another embodiment, the present disclosure provides a combined preparation of a compound of formulae (I)-(IVa), and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with HPK1 target inhibition in T cells.

In another aspect, the disclosure provides a method of treating a patient suffering from or susceptible to a medical condition that is associated with HPK1 target inhibition in T cells. A number of medical conditions can be treated. The method comprises administering to the patient a therapeutically effective amount of a composition comprising a compound of formulae (I)-(IVa) and/or a pharmaceutically acceptable salt thereof, a stereoisomer thereof or a tautomer thereof. For example, the compounds described herein may be used to treat or prevent viral infections and proliferative diseases such as cancer.

The compounds for formulae (I)-(IVa) and pharmaceutical compositions comprising at least one compound of formulae (I)-(IVa) are useful in treating or preventing any disease or conditions that are associated with HPK1 target inhibition in T cells. These include viral and other infections (e.g., skin infections, GI infection, urinary tract infections, genito-urinary infections, systemic infections), and proliferative diseases (e.g., cancer). The compounds of formulae (I)-(IVa) and pharmaceutical compositions comprising in at least one compound of formulae (I)-(IVa) may be administered to animals, preferably mammals (e.g., domesticated animals, cats, dogs, mice, rats), and more preferably humans. Any method of administration may be used to deliver the compound or pharmaceutical composition to the patient. In certain embodiments, the compound of formulae (I)-(IVa) or pharmaceutical composition comprising at least compound of formulae (I)-(IVa) is administered orally. In other embodiments, the formulae (I)-(IVa) or pharmaceutical composition comprising at least a compound of formulae (I)-(IVa) is administered parenterally.

The compounds of formulae (I)-(IVa) can inhibit activity of the hematopoietic progenitor kinase 1 (HPK). For example, the compounds of formulae (I)-(IVa) can be used to inhibit activity of HPK1 in a cell or in an individual in need of modulation of the HPK1 by administering an inhibiting amount of a compound of formulae (I)-(IVa) or a salt thereof.

The present disclosure further provides methods of treating diseases associated with activity or expression, including abnormal activity and/or overexpression, of HPK1 in an individual (e.g., patient) by administering to the individual in need of such treatment a therapeutically effective amount or dose of a compound of formulae (I)-(IVa) or a pharmaceutical composition thereof. Example diseases can include any disease, disorder or condition that is directly or indirectly linked to expression or activity of the HPK1 enzyme, such as over expression or abnormal activity. An HPK1-associated disease can also include any disease, disorder or condition that can be prevented, ameliorated, or cured by modulating HPK1 enzyme activity. Examples of HPK1 associated diseases include cancer and viral infections such as HIV infection, hepatitis B, and hepatitis C.

In one aspect, the compound(s) of formulae (I)-(IVa) are sequentially administered prior to administration of the immuno-oncology agent. In another aspect, compound(s) of formulae (I)-(IVa) are administered concurrently with the immuno-oncology agent. In yet another aspect, compound(s) of formulae (I)-(IVa) are sequentially administered after administration of the immuno-oncology agent.

In another aspect, compounds of formulae (I)-(IVa) may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTOR, LIGHT, DcR3, HVEM, VEGI/TLIA, TRAMP/DR3, EDAR, EDA1, XEDAR, EDA2, TNFR1, Lymphotoxin.alpha./TNFβ, TNFR2, TNFα, LTβR, Lymphotoxin α1β2, FAS, FASL, RELT, DR6, TROY, NGFR.

In one aspect, T cell responses can be stimulated by a combination of a compound of Formula (I) and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of formulae (I)-(IVa) for the treatment of cancer include antagonists of inhibitory receptors on NK cells or agonists of activating receptors on NK cells. For example, compounds of formulae (I)-(IVa) can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of formulae (I)-(IVa) can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493).

The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Types of cancers that may be treated with the compound of formulae (I)-(IVa) include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of formulae (I)-(IVa) for treatment of HPK1 associated diseases, disorders or conditions. The agents can be combined with the present compounds in a single dosage form, or the agents can be administered simultaneously or sequentially as separate dosage forms.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN.®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of formulae (I)-(IVa) include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY.™. Compounds of formulae (I)-(IVa) may also be combined with immunotherapy drugs, including cytokines such as interferon alpha, interleukin 2, and tumor necrosis factor (TNF) in the treatment of melanoma.

Compounds of formulae (I)-(IVa) may also be used in combination with vaccine therapy in the treatment of melanoma. Antimelanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of formulae (I)-(IVa), using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 38.9.degree. C. to 40.degree. C. Melphalan is the drug most often used in this chemotherapy procedure. This can be given with another agent called tumor necrosis factor (TNF).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-.alpha.), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (HERCEPTIN.®), antibodies to costimulatory molecules such as CTLA-4, 4-1BB and PD-1, or antibodies to cytokines (IL-1O or TGF-.beta.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

The pharmaceutical composition of the disclosure may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC.®); (ii) epidermal growth factor (EGF) receptor inhibitors such as, for example, kinase inhibitors (IRESSA.®, SSI-774) and antibodies (Imclone: C225 [Goldstein et al., Clin. Cancer Res., 1:1311-1318 (1995)], and Abgenix: ABX-EGF); (iii) her-2/neu receptor inhibitors such as famesyl transferase inhibitors (FTI) such as, for example, L-744,832 (Kohl et al., Nat. Med., 1(8):792-797 (1995)); (iv) inhibitors of Akt family kinases or the Akt pathway, such as, for example, rapamycin (see, for example, Sekulic et al., Cancer Res., 60:3504-3513 (2000)); (v) cell cycle kinase inhibitors such as, for example, flavopiridol and UCN-O1 (see, for example, Sausville, Curr. Med. Chem. Anti-Canc. Agents, 3:47-56 (2003)); and (vi) phosphatidyl inositol kinase inhibitors such as, for example, LY294002 (see, for example, Vlahos et al., J. Biol. Chem., 269:5241-5248 (1994)). Alternatively, at least one STI and at least one compound of Formula (I) may be in separate pharmaceutical compositions. In a specific embodiment of the present disclosure, at least one compound of Formula (I) and at least one STI may be administered to the patient concurrently or sequentially. In other words, at least one compound of Formula (I) may be administered first, at least one STI may be administered first, or at least one compound of Formula (I) and at least one STI may be administered at the same time. Additionally, when more than one compound of Formula (I) and/or STI is used, the compounds may be administered in any order.

The present disclosure further provides a pharmaceutical composition for the treatment of a chronic viral infection in a patient comprising at least one compound of formulae (I)-(IVa), optionally, at least one chemotherapeutic drug, and, optionally, at least one antiviral agent, in a pharmaceutically acceptable carrier.

Also provided is a method for treating a chronic viral infection in a patient by administering an effective amount of the above pharmaceutical composition.

In a specific embodiment of the present disclosure, at least one compound of formulae (I)-(IVa) and at least one chemotherapeutic agent are administered to the patient concurrently or sequentially. In other words, at least one compound of formulae (I)-(IVa) may be administered first, at least one chemotherapeutic agent may be administered first, or at least one compound of formulae (I)-(IVa) and the at least one STI may be administered at the same time. Additionally, when more than one compound of formulae (I)-(IVa) and/or chemotherapeutic agent is used, the compounds may be administered in any order. Similarly, any antiviral agent or STI may also be administered at any point in comparison to the administration of the compound of formulae (I)-(IVa).

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV). Notably, parasitic infections (e.g., malaria) may also be treated by the above methods wherein compounds known to treat the parasitic conditions are optionally added in place of the antiviral agents.

Suitable antiviral agents contemplated for use in combination with the compound of Formula (I) can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (dd1); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimid-inedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

The present disclosure also includes pharmaceutical kits useful, for example, in the treatment or prevention of HPK1-associated diseases or disorders, and other diseases referred to herein which include one or more containers containing a pharmaceutical composition comprising a therapeutically effective amount of a compound of formulae (I)-(IVa). Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be affected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The disclosure also provides pharmaceutically acceptable compositions which comprise a therapeutically effective amount of one or more of the compounds of formulae (I)-(IVa), formulated together with one or more pharmaceutically acceptable carriers (additives) and/or diluents, and optionally, one or more additional therapeutic agents described above.

The compounds of formulae (I)-(IVa) can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. Remington: The Science and Practice of Pharmacy (2 Volumes), 22nd Edition (2012), Pharmaceutical Press.

The dosage regimen for the compounds of the present disclosure will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of formulae (I)-(IVa) may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of formulae (I)-(IVa) (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of formulae (I)-(IVa) (250 mg) into a vial, aseptically freeze-drying and sealing. For use, the contents of the vial are mixed with 2 mL of physiological saline, to produce an injectable preparation.

The present disclosure includes within its scope pharmaceutical compositions comprising, as an active ingredient, a therapeutically effective amount of at least one of the compounds of formulae (I)-(IVa), alone or in combination with a pharmaceutical carrier. Optionally, compounds of formulae (I)-(IVa) can be used alone, in combination with other compounds of formulae (I)-(IVa), or in combination with one or more other therapeutic agent(s), e.g., an anti-cancer agent or other pharmaceutically active material.

Regardless of the route of administration selected, the compounds of formulae (I)-(IVa), which may be used in a suitable hydrated form, and/or the pharmaceutical compositions of the present disclosure, are formulated into pharmaceutically acceptable dosage forms by conventional methods known to those of skill in the art.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of formulae (I)-(IVa) employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of formulae (I)-(IVa) employed in the pharmaceutical composition at levels lower than that required in order to achieve the desired therapeutic effect and gradually increase the dosage until the desired effect is achieved.

In general, a suitable daily dose of a compound of formulae (I)-(IVa) will be that amount of the compound which is the lowest dose effective to produce a therapeutic effect. Such an effective dose will generally depend upon the factors described above. Generally, oral, intravenous, intracerebroventricular and subcutaneous doses of the compounds of formulae (I)-(IVa) for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the disclosure, dosing is one administration per day.

While it is possible for a compound of formulae (I)-(IVa) to be administered alone, it is preferable to administer the compound as a pharmaceutical formulation (composition).

The above other therapeutic agents, when employed in combination with the compounds of formulae (I)-(IVa), may be used, for example, in those amounts indicated in the Physicians' Desk Reference (PDR) or as otherwise determined by one of ordinary skill in the art. In the methods of the present disclosure, such other therapeutic agent(s) may be administered prior to, simultaneously with, or following the administration of the inventive compounds.

Methods of Preparation of Compounds

The compounds of the present disclosure may be synthesized by many methods available to those skilled in the art of organic chemistry. General synthetic schemes for preparing compounds of the present disclosure are described below. These schemes are illustrative and are not meant to limit the possible techniques one skilled in the art may use to prepare the compounds disclosed herein. Different methods to prepare the compounds of the present disclosure will be evident to those skilled in the art. Examples of compounds of the present disclosure prepared by methods described in the general schemes are given in the Examples section set out hereinafter. Preparation of homochiral examples may be carried out by techniques known to one skilled in the art. For example, homochiral compounds may be prepared by separation of racemic products or diastereomers by chiral phase preparative HPLC. Alternatively, the example compounds may be prepared by methods known to give enantiomerically or diastereomerically enriched products.

The reactions and techniques described in this section are performed in solvents appropriate to the reagents and materials employed and are suitable for the transformations being affected. Also, in the description of the synthetic methods given below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art, with alternatives required when incompatible substituents are present. This will sometimes require a judgment to modify the order of the synthetic steps or to select one particular process scheme over another in order to obtain a desired compound of the disclosure. It will also be recognized that another major consideration in the planning of any synthetic route in this field is the judicious choice of a protecting group used for protection of reactive functional groups present in the compounds described in this disclosure. An authoritative account describing the many alternatives to the trained practitioner is Wuts and Greene, Greene's Protective Groups in Organic Synthesis, Fourth Edition, Wiley and Sons (2007).

Commercially available starting materials, reagents, and solvents were used as received. In general, anhydrous reactions were performed under an inert atmosphere such as nitrogen or Argon.

Microwave reactions were performed with a Biotage Initiator microwave reactor. Reaction progress was generally monitored by LCMS (Waters Acquity UPLC system) or TLC. Silica gel column chromatography purification of intermediates or final products was performed using an ISCO CombiFlash system with normal-phase RediSep columns. Reverse-phase HPLC purification was performed on an ISCO ACCQPrep HPLC system with a Phenomenex, Gemini-NX, 10 um, 250×30 mm, C18 column using a gradient of 20% MeCN/0.1% TFA-water to 100% MeCN/0.1% TFA-water over a 30-min period at a flow rate of 40 to 45 mL/min. Proton NMRs were recorded on a Varian 400 MHz spectrometer, and mass spectra were obtained using a Waters Acquity UPLC system.

Compound names were generated using the software built into CambridgeSoft-PerkinElmer'sChemDraw.

Abbreviations Used in the General Synthetic Methods and Examples

BINAP—2,2'-Bis(diphenylphosphino)-1,1'-binaphthyl
DMF—Dimethylformamide
DCM—Dichloromethane
EDC—1-Ethyl-3-(3-dimethylaminopropyl)carbodiimide
d—doublet
dd—doublet of doublet
DDQ—2,3-Dichloro-5,6-dicyano-1,4-benzoquinone
DEAD—Diethyl azodicarboxylate
DIAD—Diisopropyl azodicarboxylate
DIBAL—Diisobutylaluminium hydride
DIEA—N,N-Diisopropylethylamine
EtOAc—Ethyl acetate h—hour(s)
HATU—2-(7-Aza-1H-benzotriazol-1-yl)-1,1,3,3-tetramethyluronium hexafluorophosphate
HCl—Hydrochloride
$KMnO_4$—Potassium permanganate
LAH—Lithium aluminum hydride
LiOH—Lithium hydroxide
m—multiplet
MeCN—Acetonitrile
MecOH—Methanol
NaOH—Sodium hydroxide
Na2SO4—Sodium sulfate
NMP—N-Methyl-2-pyrrolidone
$Pd_2dba_3$—Tris(dibenzylideneacetone)dipalladium(0)
Ph3P—Triphenyl phosphine
PyBop—Benzotriazol-1-yloxytripyrrolidinophosphonium hexafluorophosphate
rt—room temperature
s—singlet
soln—solution
STAB-H—sodium triacetoxyborohydride
t—triplet
TEA—Triethylamine
TFA—Trifluoroacetic acid
THF—Tetrahydrofuran
p-TSA—p-Toluenesulfonic acid monohydrate
XPhos—Dicyclohexyl[2',4',6'-tris(propan-2-yl)[1,1'-biphenyl]-2-yl]phosphane General Procedure A: Nucleophilic aromatic substitution with anilines.

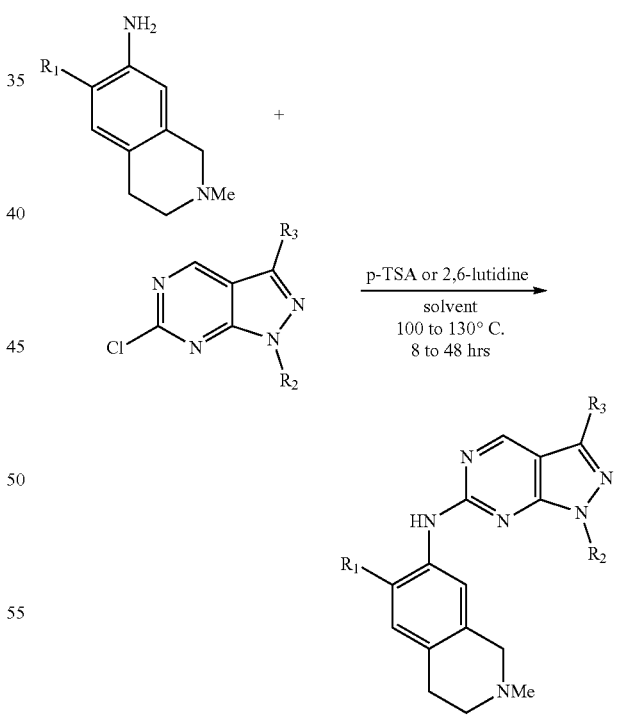

A substituted aniline (0.095 mmol) and the appropriate pyrazolopyrimidine precursor (0.063 mmol) were dissolved in dry NMP, DMF, 2-butanol or 1,4-dioxane (2 mL). p-TSA (0.19 mmol) or 2,6-lutidine (0.19 mmol) was added and the mixture was stirred at 80 to 130° C. The reaction progress was monitored by LCMS or TLC. Upon completion, the reaction mixture was cooled to room temperature and either (a) diluted with 2 mL of acetonitrile and injected directly on a reversed phase HPLC for purification or (b) concentrated under reduced pressure and purified by normal silica gel chromatography using a gradient of methanol in dichloromethane or ethyl acetate in methanol as eluent.

General Procedure B: Buchwald-Hartwig amination with anilines.

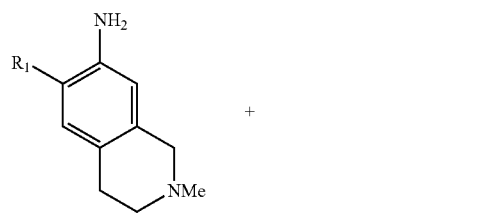

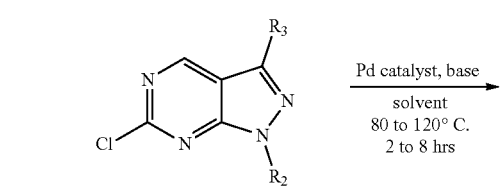

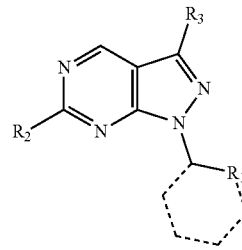

A substituted alkyl halide (0.44 mmol) and the appropriate pyrazolopyrimidine precursor (0.57 mmol) were dissolved in dry DMF, acetonitrile, or 1,4-dioxane (2.2 mL). Cesium carbonate (0.57 mmol) was added, and the mixture was stirred at 22° C. or 80° C. The reaction progress was monitored by LCMS or TLC. Upon completion, the reaction mixture was cooled to room temperature, filtered through a celite pad and concentrated under reduced pressure. The residue was either (a) diluted with 4 mL of acetonitrile and injected directly on a reversed phase HPLC for purification or (b) purified by normal silica gel chromatography.

General Procedure D: Alkylation of pyrazolopyrimidines through Mitsunobu reactions.

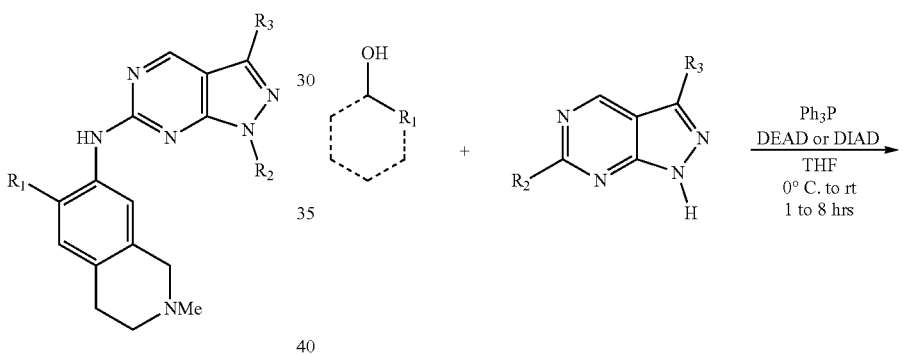

A substituted aniline (0.375 mmol) and the appropriate pyrazolopyrimidine precursor (0.25 mmol) were dissolved in dry 1,2-dimethoxyethane (2.5 mL). Cesium carbonate (0.75 mmol) and Pd-PEPPSI-iPent catalyst (0.025 mmol) were added and the mixture was stirred at 80° C. The reaction progress was monitored by LCMS or TLC. Upon completion, the reaction mixture was cooled to room temperature, filtered through a celite pad and concentrated under reduced pressure. The residue was either (a) diluted with 4 mL of acetonitrile and injected directly on a reversed phase HPLC for purification or (b) purified by normal silica gel chromatography.

General Procedure C: Alkylation of pyrazolopyrimidines with alkyl halides.

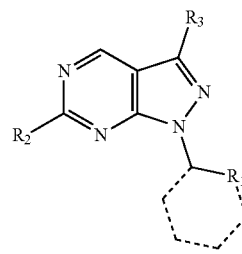

A substituted alcohol (3.88 mmol) and the appropriate pyrazolopyrimidine precursor (1.94 mmol) were dissolved in dry THF (2.2 mL). Triphenylphosphine (5.82 mmol) was added and the mixture was cooled to 0° C. Diethyl azodicarboxylate (5.82 mmol, 40% solution in toluene) was added dropwise to the cooled reaction mixture and the mixture was warmed to room temperature. The reaction progress was monitored by LCMS or TLC. Upon completion, the reaction mixture was concentrated under reduced pressure. The residue was either (a) diluted with 4 mL of acetonitrile and injected directly on a reversed phase HPLC for purification or (b) purified by normal silica gel chromatography.

Precursor 1:

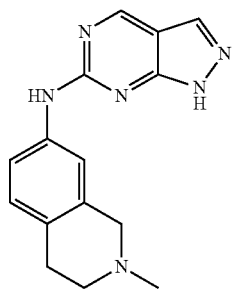

2-methyl-N-(1H-pyrazolo[3,4-d]pyrimidin-6-yl)-1,2,3,4-tetrahydroisoquinolin-7-amine A suspension of 6-chloro-1H-pyrazolo[3,4-d]pyrimidine (500 mg, 3.23 mmol), 2-methyl-3,4-dihydro-1H-isoquinolin-7-amine (525 mg, 3.23 mmol), and p-TSA (1.35 g, 7.12 mmol) in 1,4-dioxane (10 mL) was heated at 100° C. for 18 h. The reaction mixture was cooled to rt and then poured into a saturated bicarbonate solution (100 mL). The mixture was stirred at rt for 1 h. The crude product was collected by filtration to provide 2-methyl-N-(1H-pyrazolo[3,4-d]pyrimidin-6-yl)-3,4-dihydro-1H-isoquinolin-7-amine (800 mg, 88% yield) as a solid. This material was taken on without further purification.

Precursor 2:

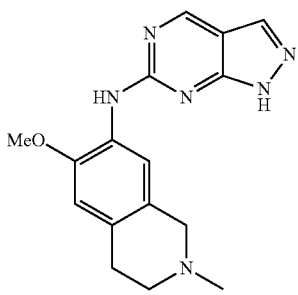 [SMILES: COc1cc2c(cc1Nc1ncc3cn[nH]c3n1)CN(C)CC2]

6-methoxy-2-methyl-N-(1H-pyrazolo[3,4-d]pyrimidin-6-yl)-1,2,3,4-tetrahydroisoquinolin-7-amine Prepared according to general procedure A using 6-chloro-1H-pyrazolo[3,4-d]pyrimidine (402 mg, 2.6 mmol), 6-methoxy-2-methyl-3,4-dihydro-1H-isoquinolin-7-amine (500 mg, 2.6 mmol), and p-TSA in 1,4-dioxane at 100° C. After completion, the reaction mixture was added to 200 mL saturated aqueous sodium bicarbonate and stirred at room temperature for 1 h. The mixture was filtered to afford 6-methoxy-2-methyl-N-(1H-pyrazolo[3,4-d]pyrimidin-6-yl)-1,2,3,4-tetrahydroisoquinolin-7-amine as an off-white solid (500 mg). The material was taken forward without further purification.

Precursor 3.

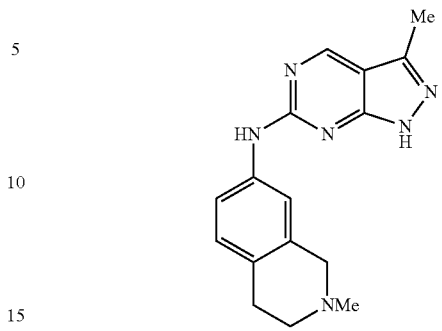

2-methyl-N-(3-methyl-1H-pyrazolo[3,4-d]pyrimidin-6-yl)-3,4-dihydro-1H-isoquinolin-7-amine Prepared according to general procedure A using 6-Chloro-3-methyl-1H-pyrazolo[3,4-d]pyrimidine (500 mg, 2.97 mmol), 2-methyl-1,2,3,4-tetrahydroisoquinolin-7-amine (481 mg, 2.97 mmol), and p-TSA in 1,4-dioxane at 100° C. After completion, the reaction mixture was added to 200 mL saturated aqueous sodium bicarbonate and stirred at room temperature for one hour. The mixture was filtered to afford 2-methyl-N-(3-methyl-1H-pyrazolo[3,4-d]pyrimidin-6-yl)-3,4-dihydro-1H-isoquinolin-7-amine as an off-white solid (400 mg). The material was taken forward without further purification.

Precursor 4.

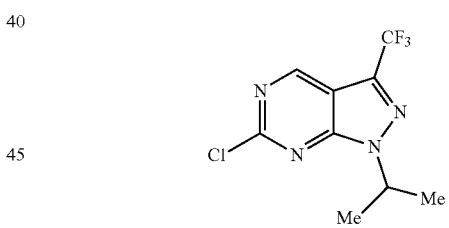

6-chloro-1-isopropyl-3-(trifluoromethyl)-1H-pyrazolo[3,4-d]pyrimidine

Prepared according to general procedure C using 6-chloro-1H-pyrazolo[3,4-d]pyrimidine (150 mg, 0.67 mmol), 2-iodopropane (137 mg, 0.81 mmol), and potassium carbonate in acetonitrile at 80° C. After completion the reaction was concentrated onto celite and purified by silica gel column chromatography using a 0-100% mixture of EtOAc and DCM as the eluent to afford 6-chloro-1-isopropyl-3-(trifluoromethyl)-1H-pyrazolo[3,4-d]pyrimidine as an off-white solid (108 mg). The material was taken forward without further purification.

Precursor 5

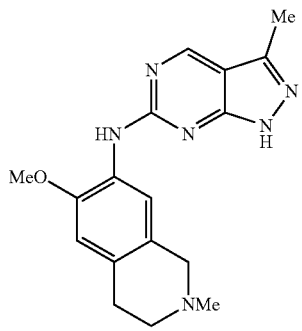 [SMILES: COc1cc2c(cc1Nc1ncc3c(C)n[nH]c3n1)CN(C)CC2]

6-methoxy-2-methyl-N-(3-methyl-1H-pyrazolo[3,4-d]pyrimidin-6-yl)-1,2,3,4-tetrahydroisoquinolin-7-amine Prepared according to general procedure A using 6-chloro-3-methyl-1H-pyrazolo[3,4-d]pyrimidine (500 mg, 2.97 mmol), 6-methoxy-2-methyl-3,4-dihydro-1H-isoquinolin-7-amine (570 mg, 2.97 mmol), and p-TSA (1.18 g, 6.23 mmol) in 1,4-dioxane at 100° C. After completion, the reaction mixture was added to 200 mL saturated aqueous sodium bicarbonate and stirred at room temperature for 1 h. The mixture was filtered to afford 6-methoxy-2-methyl-N-(1H-pyrazolo[3,4-d]pyrimidin-6-yl)-1,2,3,4-tetrahydroisoquinolin-7-amine as an off-white solid 6500 mg). The material was taken forward without further purification.

EXAMPLES

The following examples illustrate the particular embodiments of the present disclosure and do not limit the scope of the present disclosure. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example. Compounds of the Examples are identified by the example and step in which they were prepared (e.g., "1-A" denotes the Example 1, step A), or by the example only where the compound is the title compound of the example (for example, "1" denotes the title compound of Example 1). In some instances, alternate preparations of intermediates or examples are described. Frequently chemists skilled in the art of synthesis may devise alternative preparations which may be desirable based on one or more considerations such as shorter reaction time, less expensive starting materials, ease of operation or isolation, improved yield, amenable to catalysis, avoidance of toxic reagents, accessibility of specialized instrumentation, and decreased number of linear steps, etc. The intent of describing alternative preparations is to further enable the preparation of the examples of this disclosure. In some instances, some functional groups in the outlined examples and claims may be replaced by well known bioisosteric replacements known in the art, for example, replacement of a carboxylic acid group with a tetrazole or a phosphate moiety.

Example 1

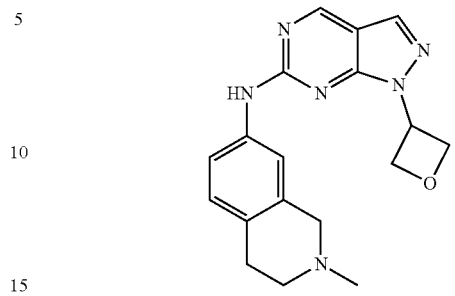

2-methyl-N-(1-(oxetan-3-yl)-1H-pyrazolo[3,4-d]pyrimidin-6-yl)-1,2,3,4-tetrahydroisoquinolin-7-amine The above compound was prepared according to general procedure C using 3-iodooxetane (16.4 mg, 0.090 mmol), 2-methyl-N-(1H-pyrazolo[3,4-d]pyrimidin-6-yl)-3,4-dihydro-1H-isoquinolin-7-amine (Precursor 1) (25 mg, 0.090 mmol) and cesium carbonate (29.1 mg, 0.090 mmol) in DMF at 80° C. for 18 h. The reaction mixture was diluted with EtOAc (10 mL), washed with water (2 mL), and concentrated. The crude product was purified by silica column chromatography eluting with 0% to 10% MeOH in DCM to afford the title compound as an off-white solid (16.5 mg). $^1$H NMR (DMSO-$d_6$) δ: 9.84 (s, 1H), 8.98 (s, 1H), 8.18 (s, 1H), 7.65 (s, 11H), 7.55 (dd, J=8.2, 1.9 Hz, 1H), 7.04 (d, J=8.3 Hz, 1H), 5.90 (p, J=7.1 Hz, 1H), 5.12 (t, J=6.5 Hz, 2H), 5.06-4.98 (m, 2H), 3.50 (s, 2H), 2.77 (t, J=5.8 Hz, 2H), 2.59 (t, J=5.6 Hz, 2H), 2.35 (s, 3H). LCMS [M+H]: 337.2

Example 2

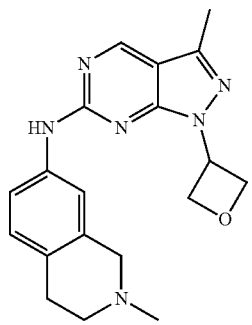 [SMILES: Cc1nn(C2COC2)c2nc(Nc3ccc4c(c3)CN(C)CC4)ncc12]

2-methyl-N-[3-methyl-1-(oxetan-3-yl)pyrazolo[3,4-d]pyrimidin-6-yl]-3,4-dihydro-1H-isoquinolin-7-amine The above compound was prepared according to general procedure E using Precursor 3 (40 mg, 0.14 mmol) and 3-iodooxetane (25 mg, 0.14 mmol), and cesium carbonate (48.7 mg, 0.149 mmol) in DMF at 80° C. and purifying directly by silica gel column chromatography using a mixture of 0-20% MeOH and DCM as the eluent. $^1$H NMR (400 MHz, Acetonitrile-d3, freebase) δ 8.79 (s, 1H), 8.00 (s, 1H), 7.62 (s, 1H), 7.49 (d, J=8.4 Hz, 11H), 7.09 (d, J=8.4 Hz, 1H), 5.87 (t, J=7.3 Hz, 1H), 5.15 (t, J=6.6 Hz, 2H), 5.00 (t, J=7.3 Hz, 2H), 3.63 (s, 2H), 2.86 (s, 2H), 2.73 (s, 2H), 2.50 (s, 3H), 2.45 (d, J=2.2 Hz, 3H). LCMS [M+H]: 381.1.

Example 3

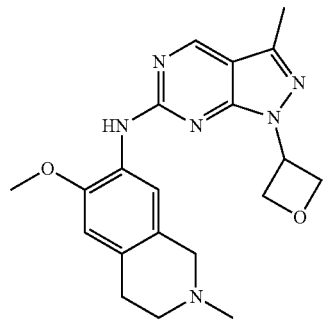 [SMILES: COc1cc2c(cc1Nc1ncc3c(C)nn(C4COC4)c3n1)CN(C)CC2]

6-methoxy-2-methyl-N-[3-methyl-1-(oxetan-3-yl)pyrazolo[3,4-d]pyrimidin-6-yl]-3,4-dihydro-1H-isoquinolin-7-amine The above compound was prepared according to general procedure E using precursor 5 (44 mg, 0.14 mmol) and 3-iodooxetane (25 mg, 0.14 mmol), and cesium carbonate (48.7 mg, 0.149 mmol) in DMF at 80° C. and purifying directly by silica gel column chromatography using a mixture of 0-20% MeOH and DCM as the eluent. ¹H NMR (400 MHz, Acetonitrile-d3, freebase) δ 8.80 (s, 11H), 8.34 (s, 11H), 7.83 (s, 1H), 6.78 (s, 1H), 5.97-5.81 (m, 11H), 5.18 (t, J=6.5 Hz, 2H), 5.03 (t, J=7.3 Hz, 2H), 3.88 (s, 3H), 3.75 (s, 2H), 2.91 (s, 2H), 2.86 (s, 2H), 2.54 (s, 3H), 2.50 (s, 3H).

Example 4

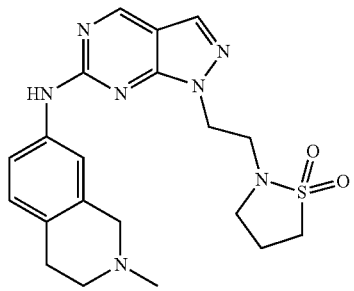 [SMILES: CN1CCc2ccc(Nc3ncc4cnn(CCN5CCCS5(=O)=O)c4n3)cc2C1]

N-[1-[2-(1,1-dioxo-1,2-thiazolidin-2-yl)ethyl]pyrazolo[3,4-d]pyrimidin-6-yl]-2-methyl-3,4-dihydro-1H-isoquinolin-7-amine trifluoroacetate The above compound was prepared according to general procedure E using Precursor 1 (20 mg, 0.07 mmol) and 2-(2-bromoethyl)-1,2-thiazolidine-1,1-dione (16.0 mg, 0.070 mmol), and potassium carbonate in DMF at 80° C. and purifying directly on reverse phase HPLC (Phenomenex, Gemini-NX, 10 um, 250×30 mm, C18 column; gradient of 20% MeCN/0.1% TFA-water to 100% MeCN/0.1% TFA).

¹H NMR (400 MHz, DMSO-d6, TFA salt) δ 8.99 (s, 1H), 8.12 (s, 1H), 7.86 (d, J=2.2 Hz, 1H), 7.71 (dd, J=8.4, 2.2 Hz, 1H), 7.20 (d, J=8.5 Hz, ¹H), 4.58-4.47 (m, 4H), 4.31 (dd, J=15.5, 8.2 Hz, 1H), 3.67 (s, 1H), 3.43 (t, J=6.3 Hz, 2H), 3.40-3.28 (m, 1H), 3.23 (t, J=6.7 Hz, 2H), 3.13-3.05 (m, 2H), 3.02 (d, J=5.4 Hz, 1H), 2.95 (d, J=4.5 Hz, 3H), 2.14-2.03 (m, 2H). LCMS [M+H]: 428.1.

Example 5

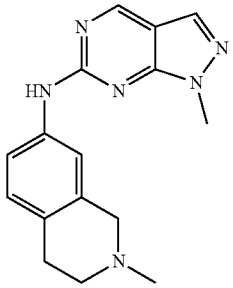 [SMILES: CN1CCc2ccc(Nc3ncc4cnn(C)c4n3)cc2C1]

2-methyl-N-(1-methylpyrazolo[3,4-d]pyrimidin-6-yl)-3,4-dihydro-1H-isoquinolin-7-amine The above compound was prepared according to general procedure E using Precursor 1 (22.0 mg, 0.08 mmol) and methyl iodide (5 mL, 0.08 mmol), and potassium carbonate (21.7 mg, 0.157 mmol) in DMF at rt and purifying directly on reverse phase HPLC (Phenomenex, Gemini-NX, 10 um, 250×30 mm, C18 column; gradient of 20% MeCN/0.1% TFA-water to 100% MeCN/0.1% TFA). ¹H NMR (400 MHz, DMSO-d6, freebase) δ 9.93 (s, 1H), 9.01 (d, J=1.2 Hz, 1H), 8.08 (d, J=1.3 Hz, 11H), 7.85 (d, J=8.4 Hz, 1H), 7.64 (d, J=2.3 Hz, 1H), 7.26 (d, J=8.4 Hz, 1H), 4.60 (s, 3H), 3.68 (t, J=6.5 Hz, 2H), 3.13 (m, 4H), 2.50 (s, 3H). LCMS [M+H]: 295.1.

Example 6

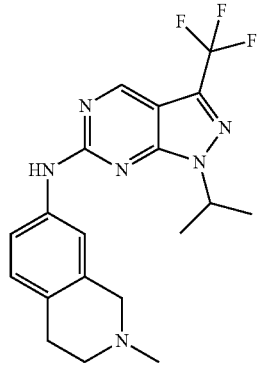 [SMILES: CC(C)n1nc(C(F)(F)F)c2cnc(Nc3ccc4c(c3)CN(C)CC4)nc21]

N-[1-isopropyl-3-(trifluoromethyl)pyrazolo[3,4-d]pyrimidin-6-yl]-2-methyl-3,4-dihydro-1H-isoquinolin-7-amine The above compound was prepared according to general procedure A using Precursor 4 (30.0 mg, 0.11 mmol) and 2-methyl-3,4-dihydro-1H-isoquinolin-7-amine (18.0 mg, 0.11 mmol),p-TSA in 1,4-dioxane at 100° C. and purifying by silica gel column chromatography using a gradient of 0-20% MeOH in DCM. ¹H NMR (400 MHz, DMSO-d6, freebase) δ 10.11 (s, 11H), 9.08 (s, 1H), 7.57 (m, 2H), 7.07 (d, J=8.2 Hz, 1H), 5.09-4.95 (m, 1H), 3.47 (s, 2H), 2.77 (s, 2H), 2.59 (d, J=6.2 Hz, 2H), 2.34 (s, 3H), 1.53 (d, J=6.7 Hz, 6H).

Example 7

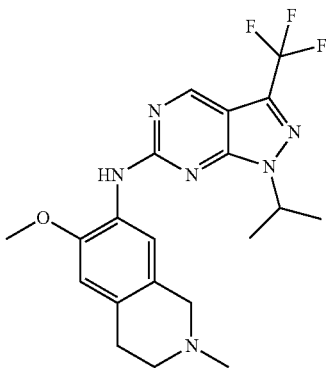 [SMILES: COc1cc2c(cc1Nc1ncc3c(C(F)(F)F)nn(C(C)C)c3n1)CN(C)CC2]

N-(1-isopropyl-3-(trifluoromethyl)-1H-pyrazolo[3,4-d]pyrimidin-6-yl)-6-methoxy-2-methyl-1,2,3,4-tetrahydroisoquinolin-7-amine The above compound was prepared according to general procedure A using Precursor 4 (30 mg, 0.11 mmol) and 6-methoxy-2-methyl-3,4-dihydro-1H-isoquinolin-7-amine (22 mg, 0.11 mmol),p-TSA in 1,4-dioxane at 100° C. and purifying by silica gel column chromatographyy using a gradient of 0-20% MeOH and DCM. ¹H NMR (400 MHz, DMSO-d6, freebase) δ 9.04 (s, 1H), 8.72 (s, 1H), 7.69 (s, 1H), 6.81 (s, 1H), 4.96 (m, 1H), 3.79 (s, 3H), 3.44 (s, 2H), 2.81 (s, 2H), 2.59 (s, 2H), 2.35 (s, 3H), 1.50 (d, J=6.6 Hz, 6H).

Example 8

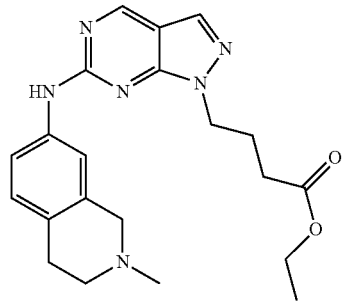 [SMILES: CCOC(=O)CCCn1ncc2cnc(Nc3ccc4c(c3)CN(C)CC4)nc21]

Ethyl 4-(6-((2-methyl-1,2,3,4-tetrahydroisoquinolin-7-yl)amino)-1H-pyrazolo[3,4-d]pyrimidin-1-yl)butanoate The above compound was prepared according to general procedure E using Precursor 1 (50 mg, 0.18 mmol) and Ethyl 4-bromobutanoate (35 mg, 0.18 mmol), and cesium carbonate in DMF at 80° C. and purifying directly by silica gel column chromatography using a mixture of 0-20% MeOH and DCM as the eluent. ¹H NMR (400 MHz, DMSO-d6, freebase) δ 8.94 (s, 1H), 8.05 (s, 1H), 7.66 (s, 1H), 7.58-7.49 (m, 1H), 7.03 (d, J=8.4 Hz, 1H), 4.32 (t, J=6.7 Hz, 2H), 3.50 (s, 2H), 2.75 (d, J=5.9 Hz, 2H), 2.59 (m, 2H), 2.37-2.24 (m, 7H), 2.10 (m, 2H), 1.14-1.02 (t, 3H). LCMS [M+H]: 395.1.

Example 9

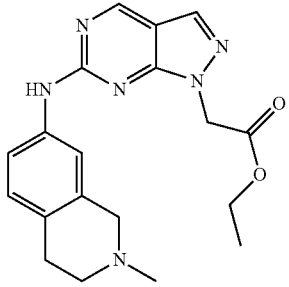 [SMILES: CCOC(=O)Cn1ncc2cnc(Nc3ccc4c(c3)CN(C)CC4)nc21]

Ethyl 2-[6-[(2-methyl-3,4-dihydro-1H-isoquinolin-7-yl)amino]pyrazolo[3,4-d]pyrimidin-1-yl]acetate The above compound was prepared according to general procedure E using Precursor 1 (50 mg, 0.18 mmol), ethyl bromoacetate (30 mg, 0.18 mmol), and cesium carbonate in DMF at 80° C. and purifying directly by silica gel column chromatography using a mixture of 0-20% MeOH and DCM as the eluent. ¹H NMR (400 MHz, Acetonitrile-d3, freebase) δ 8.86 (s, 1H), 7.98 (s, 1H), 7.53 (s, 1H), 7.50-7.42 (m, 1H), 7.07 (d, J=8.3 Hz, 1H), 5.09 (s, 2H), 4.20 (q, J=7.1 Hz, 2H), 3.51 (s, 2H), 2.82 (t, J=5.9 Hz, 2H), 2.62 (t, J=5.9 Hz, 2H), 2.38 (s, 3H), 1.24 (t, J=7.1 Hz, 3H). LCMS [M+H]: 367.1.

Example 10

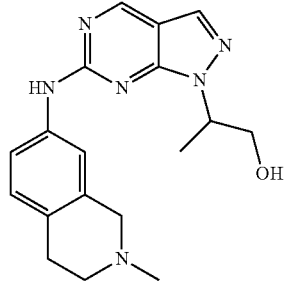 [SMILES: CC(CO)n1ncc2cnc(Nc3ccc4c(c3)CN(C)CC4)nc21]

2-[6-[(2-methyl-3,4-dihydro-1H-isoquinolin-7-yl)amino]pyrazolo[3,4-d]pyrimidin-1-yl]propan-1-ol trifluoroacetate The above compound was prepared according to general procedure E using Precursor 1 (50 mg, 0.18 mmol) and 2-bromopropoxy-tert-butyl-dimethyl-silane (54 mg, 0.21 mmol), and cesium carbonate in DMF at 100° C. and purifying directly by silica gel column chromatography using a mixture of 0-20% MeOH and DCM as the eluent.

The resulting material was dissolved in DCM (1 mL) and 2N HCl in ether was added (1 mL). The reaction mixture was stirred for 3 h, after which it was concentrated and purified directly on reverse phase HPLC (Phenomenex, Gemini-NX, 10 um, 250×30 mm, C18 column; gradient of 20% MeCN/ 0.1% TFA-water to 100% MeCN/0.1% TFA). 1H NMR (400 MHz, DMSO-d6, TFA salt) δ 8.98 (s, 1H), 8.09 (s, 1H), 7.77 (d, J=8.4 Hz, 1H), 7.70 (s, 1H), 7.21 (d, J=8.5 Hz, 1H), 4.88-4.77 (m, 1H), 4.49 (m, 1H), 4.33 (s, 1H), 3.84 (dd, 1H), 3.72 (m, 1H), 3.34 (s, 1H), 3.16-3.00 (m, 1H), 2.96 (m, 4H), 1.44 (d, J=6.8 Hz, 3H). LCMS [M+H]: 339.1.

Example 11

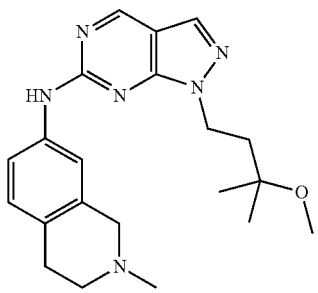 [SMILES: COC(C)(C)CCn1ncc2cnc(Nc3ccc4c(c3)CN(C)CC4)nc21]

N-(1-(3-methoxy-3-methylbutyl)-1H-pyrazolo[3,4-d]pyrimidin-6-yl)-2-methyl-1,2,3,4-tetrahydroisoquinolin-7-amine The above compound was prepared according to general procedure C using 1-bromo-3-methoxy-3-methylbutane (32.3 mg, 0.18 mmol), 2-methyl-N-(1H-pyrazolo[3,4-d]pyrimidin-6-yl)-3,4-dihydro-1H-isoquinolin-7-amine (Precursor 1) (50.0 mg, 0.18 mmol), and cesium carbonate (61.0 mg, 0.18 mmol) in DMF (0.50 mL) at 80° C. for 18 h. The crude product was purified by silica column chromatography eluting with 0% to 10% MeOH in DCM to afford the title compound as a solid (13.6 mg). 1H NMR (DMSO-d6, free base) δ: 9.79 (s, 1H), 8.94 (s, 1H), 8.04 (s, 1H), 7.74 (br s, 1H), 7.54 (dd, J=8.4, 2.2 Hz, 1H), 7.01 (d, J=8.3 Hz, 1H), 4.36-4.29 (m, 2H), 3.46 (s, 2H), 3.14 (s, 3H), 2.76 (t, J=5.8 Hz, 2H), 2.58 (t, J=5.9 Hz, 2H), 2.33 (s, 3H), 2.05-1.97 (m, 2H), 1.18 (s, 6H). LCMS [M+H]: 381.2

Example 12

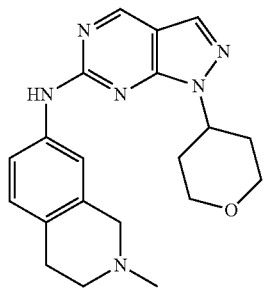 [SMILES: CN1CCc2ccc(Nc3ncc4cnn(C5CCOCC5)c4n3)cc2C1]

2-methyl-N-(1-(tetrahydro-2H-pyran-4-yl)-1H-pyrazolo[3,4-d]pyrimidin-6-yl)-1,2,3,4-tetrahydroisoquinolin-7-amine The above compound was prepared according to general procedure C using 4-bromotetrahydropyran (16.4 mg, 0.10 mmol), 2-methyl-N-(1H-pyrazolo[3,4-d]pyrimidin-6-yl)-3,4-dihydro-1H-isoquinolin-7-amine (Precursor 1) (30.0 mg, 0.107 mmol), and cesium carbonate (34.9 mg, 0.107 mmol) in DMF (0.30 mL) at 80° C. for 18 h. The crude product was purified by silica column chromatography eluting with 0% to 10% MeOH in DCM to afford the title compound. 1H NMR (DMSO-d6, free base) δ: 9.79 (s, 1H), 8.96 (s, 1H), 8.06 (s, 1H), 7.69 (s, 1H), 7.50 (dd, J=8.2, 2.1 Hz, 1H), 7.04 (d, J=8.3 Hz, 1H), 4.83-4.72 (m, 1H), 4.03 (dd, J=11.0, 3.8 Hz, 2H), 3.54 (dd, J=12.2, 10.2 Hz, 2H), 3.48 (s, 2H), 2.76 (t, J=5.6 Hz, 2H), 2.58 (t, J=5.9 Hz, 2H), 2.34 (s, 3H), 2.25 (qd, J=12.2, 4.2 Hz, 2H), 1.93 (d, J=12.6 Hz, 2H). LCMS [M+H]: 365.2

Example 13

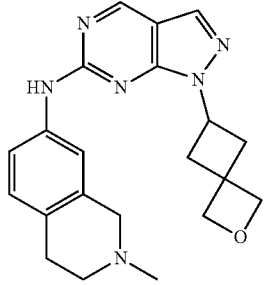 [SMILES: CN1CCc2ccc(Nc3ncc4cnn(C5CC6(COC6)C5)c4n3)cc2C1]

N-(1-(2-oxaspiro[3.3]heptan-6-yl)-1H-pyrazolo[3,4-d]pyrimidin-6-yl)-2-methyl-1,2,3,4-tetrahydroisoquinolin-7-amine The above compound was prepared according to general procedure C using 6-bromo-2-oxaspiro[3.3]heptane (47.4 mg, 0.268 mmol), 2-methyl-N-(1H-pyrazolo[3,4-d]pyrimidin-6-yl)-3,4-dihydro-1H-isoquinolin-7-amine (Precursor 1) (75.0 mg, 0.268 mmol), and cesium carbonate (87.2 mg, 0.268 mmol) in DMF (1.0 mL) at 80° C. for 18 h. The crude product was purified by silica column chromatography eluting with 0% to 10% MeOH in DCM to afford the title compound (27.6 mg). 1H NMR (Chloroform-d, free base) δ: 8.77 (s, 1H), 7.88 (s, 1H), 7.55 (s, 1H), 7.52 (dd, J=8.3, 2.3 Hz, 1H), 7.24 (d, J=2.3 Hz, 1H), 7.11 (d, J=8.3 Hz, 1H), 5.08 (p, J=8.2 Hz, 1H), 4.85 (s, 2H), 4.77 (s, 2H), 3.59 (s, 2H), 3.01-2.95 (m, 2H), 2.90 (t, J=5.9 Hz, 2H), 2.87-2.80 (m, 2H), 2.70 (t, J=5.9 Hz, 2H), 2.47 (s, 3H). LCMS [M+H]: 377.2

Example 14

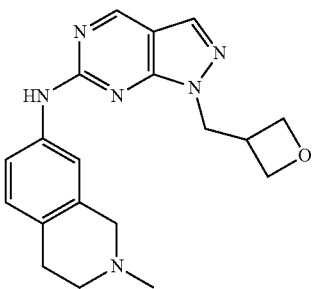 [SMILES: CN1CCc2ccc(Nc3ncc4cnn(CC5COC5)c4n3)cc2C1]

2-methyl-N-(1-(oxetan-3-ylmethyl)-1H-pyrazolo[3,4-d]pyrimidin-6-yl)-1,2,3,4-tetrahydroisoquinolin-7-amine The above compound was prepared according to general procedure C using 3-(bromomethyl)oxetane (40.4 mg, 0.268 mmol), 2-methyl-N-(1H-pyrazolo[3,4-d]pyrimidin-6-yl)-3,4-dihydro-1H-isoquinolin-7-amine (Precursor 1) (75.0 mg, 0.268 mmol), and cesium carbonate (87.2 mg, 0.268 mmol) in DMF (1.0 mL) at 80° C. for 18 h. The crude product was purified by silica column chromatography eluting with 0% to 10% MeOH in DCM to afford the title compound (30.0 mg). 1H NMR (Chloroform-d, free base) δ: 8.78 (s, 1H), 7.87 (s, 1H), 7.67 (s, 1H), 7.47 (dd, J=8.2, 2.3 Hz, 1H), 7.34 (d, J=2.3 Hz, 1H), 7.11 (d, J=8.2 Hz, 1H), 4.82 (dd, J=7.8, 6.4 Hz, 2H), 4.67-4.60 (m, 4H), 3.59 (s, 2H), 3.67-3.52 (m, 1H), 2.90 (t, J=5.9 Hz, 2H), 2.70 (t, J=5.9 Hz, 2H), 2.46 (s, 3H). LCMS [M+H]: 351.1

Example 15

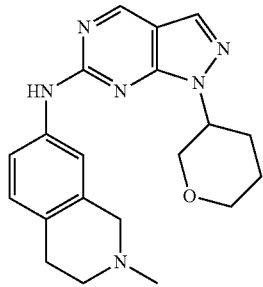 [SMILES: CN1CCc2ccc(Nc3ncc4cnn(C5CCCOC5)c4n3)cc2C1]

2-methyl-N-(1-(tetrahydro-2H-pyran-3-yl)-1H-pyrazolo[3,4-d]pyrimidin-6-yl)-1,2,3,4-tetrahydroisoquinolin-7-amine The above compound was prepared according to general procedure C using 3-bromotetrahydropyran (49.0 mg, 0.175 mmol), 2-methyl-N-(1H-pyrazolo[3,4-d]pyrimidin-6-yl)-3,4-dihydro-1H-isoquinolin-7-amine (Precursor 1) (28.8 mg, 0.175 mmol), sodium iodide (26.2 mg, 0.175 mmol), and cesium carbonate (57.0 mg, 0.175 mmol) in DMF (0.50 mL) at 80° C. for 18 h. The crude product was purified by silica column chromatography eluting with 0% to 20% MeOH in DCM to afford the title compound (1.7 mg). 1H NMR (400 MHz, Chloroform-d, free base) δ 8.80 (s, 1H), 7.90 (s, 1H), 7.51 (dd, J=8.2, 2.4 Hz, 1H), 7.41 (d, J=2.3 Hz, 1H), 7.29 (s, 1H), 7.14 (d, J=8.2 Hz, 1H), 4.81 (ddd, J=15.4, 10.5, 4.4 Hz, 1H), 4.11 (ddd, J=11.2, 4.8, 2.1 Hz, 1H), 4.02 (d, J=11.3 Hz, 1H), 3.91 (t, J=10.6 Hz, 1H), 3.73 (s, 2H), 3.58-3.49 (m, 1H), 2.98 (t, J=5.9 Hz, 2H), 2.83 (t, J=6.0 Hz, 2H), 2.55 (s, 3H), 2.45-2.31 (m, 1H), 2.21 (d, J=12.4 Hz, 1H) (1 aliphatic proton obscured under residual solvent). LCMS [M+H]: 365.0

Example 16

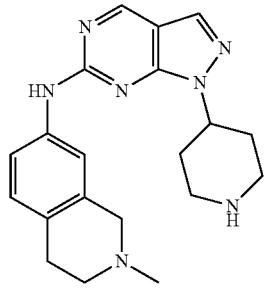 [SMILES: CN1CCc2ccc(Nc3ncc4cnn(C5CCNCC5)c4n3)cc2C1]

2-methyl-N-(1-(piperidin-4-yl)-1H-pyrazolo[3,4-d]pyrimidin-6-yl)-1,2,3,4-tetrahydroisoquinolin-7-amine hydrochloride The above compound was prepared according to general procedure C using 1-boc-4-iodo-piperidine (111 mg, 0.357 mmol), 2-methyl-N-(1H-pyrazolo[3,4-d]pyrimidin-6-yl)-3,4-dihydro-1H-isoquinolin-7-amine (Precursor 1) (100 mg, 0.357 mmol), and cesium carbonate (122 mg, 0.375 mmol) in DMF (0.50 mL) at 80° C. for 18 h. The crude intermediate was purified by silica column chromatography eluting with 0% to 20% MeOH in DCM with 0.1% NH4OH to provide the boc-protected intermediate. This material was dissolved in a solution of acetyl chloride (11 mg, 0.140 mmol) in MeOH (1 mL) and stirred at rt for 17 h. The resulting suspension was concentrated. The crude product was triturated with DCM to afford the title compound (6.8 mg) as a yellow solid. 1H NMR (DMSO-d6, HCl salt) δ: 10.87 (s, 1H), 10.00 (s, 1H), 9.19 (d, J=9.3 Hz, 1H), 9.01 (s, 1H), 8.87 (dd, J=21.2, 10.9 Hz, 1H), 8.14 (s, 1H), 7.76 (dd, J=8.5, 2.2 Hz, 1H), 7.67 (d, J=2.2 Hz, 1H), 7.22 (d, J=8.4 Hz, 1H), 4.91 (ddd, J=15.6, 11.0, 4.1 Hz, 1H), 4.52 (d, J=15.2 Hz, 1H), 4.30 (dd, J=15.5, 8.5 Hz, 1H), 3.45 (d, J=12.4 Hz, 2H), 3.37-3.09 (m, 5H), 2.97 (d, J=16.5 Hz, 1H), 2.91 (d, J=4.8 Hz, 3H), 2.41-2.25 (m, 2H), 2.18 (d, J=13.3 Hz, 2H). LCMS [M+H]: =362.0

Example 17

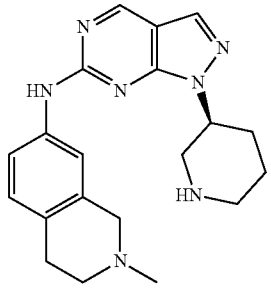 [SMILES: CN1CCc2ccc(Nc3ncc4cnn([C@H]5CCCNC5)c4n3)cc2C1]

(S)-2-methyl-N-(1-(piperidin-3-yl)-1H-pyrazolo[3,4-d]pyrimidin-6-yl)-1,2,3,4-tetrahydroisoquinolin-7-amine hydrochloride The above compound was prepared according to general procedure C using tert-butyl (3R)-3-methylsulfonyloxypiperidine-1-carboxylate (99.7 mg, 0.357 mmol), 2-methyl-3,4-dihydro-1H-isoquinolin-7-amine (100 mg, 0.357 mmol), and cesium carbonate (122 mg, 0.375 mmol) in DMF (0.5 mL) at 80° C. for 18 h. The crude intermediate was purified by silica column chromatography eluting with 0% to 100% MeOH in DCM to provide the boc-protected intermediate. This material was dissolved in a solution of acetyl chloride (31.3 mg, 0.399 mmol) in MeOH (1.5 mL) and stirred at rt for 20 h. The resulting suspension was concentrated to afford the title compound as an off-white solid (33.0 mg). 1H NMR (400 MHz, DMSO-d6, HCl salt) δ 10.09 (d, J=9.7 Hz, 1H), 9.32 (d, J=10.9 Hz, 1H), 9.02 (s, 1H), 8.16 (s, 1H), 7.59 (ddd, J=7.2, 4.5, 2.1 Hz, 1H), 7.21 (dd, J=8.4, 2.2 Hz, 1H), 5.26-5.13 (m, 1H), 4.82 (dd, J=36.2, 15.6 Hz, 1H), 3.63 (d, J=11.9 Hz, 1H), 3.54 (d, J=11.4 Hz, 1H), 3.42 (t, J=11.2 Hz, 1H), 3.30 (d, J=12.3 Hz, 2H), 3.24-3.10 (m, 1H), 3.04-2.96 (m, 2H), 2.95 (d, J=4.7 Hz, 3H), 2.10 (s, 3H), 1.95 (s, 1H). LCMS [M+H]: 364.1

Example 18

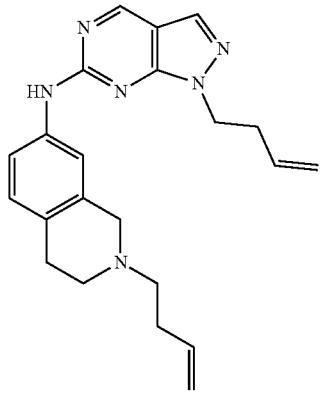 [SMILES: C=CCCN1CCc2ccc(Nc3ncc4cnn(CCC=C)c4n3)cc2C1]

2-(but-3-en-1-yl)-N-(1-(but-3-en-1-yl)-1H-pyrazolo[3,4-d]pyrimidin-6-yl)-1,2,3,4-tetrahydroisoquinolin-7-amine Step 1: Preparation of tert-butyl 7-[(1-but-3-enylpyrazolo[3,4-d]pyrimidin-6-yl)amino]-3,4-dihydro-1H-isoquinoline-2-carboxylate. This was prepared according to general procedure C using 4-bromo-1-butene (41.3 mg, 0.306 mmol), tert-butyl 7-(1H-pyrazolo[3,4-d]pyrimidin-6-ylamino)-3,4-dihydro-1H-isoquinoline-2-carboxylate (107 mg, 0.291 mmol), and cesium carbonate (104 mg, 0.320 mmol) in DMF (1 mL) at 65° C. for 18 h. The crude intermediate was purified by silica column chromatography eluting with 0% to 100% EtOAc in hexanes to afford the title compound (76.6 mg). This material was taken directly to the next step.

Step 2: Preparation of N-(1-but-3-enylpyrazolo[3,4-d]pyrimidin-6-yl)-1,2,3,4-tetrahydroisoquinolin-7-amine dihydrochloride. To a cooled solution (0° C.) of tert-butyl 7-[(1-but-3-enylpyrazolo[3,4-d]pyrimidin-6-yl)amino]-3,4-dihydro-1H-isoquinoline-2-carboxylate (76.0 mg, 0.180 mmol) in MeOH (25 mL) was added acetyl chloride (0.13 mL, 1.81 mmol). After 30 min, the cooling bath was removed, and reaction stirred at rt for 18 h. The reaction was concentrated to provide N-(1-but-3-enylpyrazolo[3,4-d]pyrimidin-6-yl)-1,2,3,4-tetrahydroisoquinolin-7-amine dihydrochloride (70 mg) as a white solid. This material was taken directly to the next step.

Step 3: Preparation of 2-(but-3-en-1-yl)-N-(1-(but-3-en-1-yl)-1H-pyrazolo[3,4-d]pyrimidin-6-yl)-1,2,3,4-tetrahydroisoquinolin-7-amine. This was prepared according to general procedure C using 4-bromo-1-butene (18.9 mg, 0.140 mmol), N-(1-but-3-enylpyrazolo[3,4-d]pyrimidin-6-yl)-1,2,3,4-tetrahydroisoquinolin-7-amine dihydrochloride (55.0 mg, 0.140 mmol), and potassium carbonate (58.0 mg, 0.420 mmol) in DMF (1 mL) at 80° C. for 18 h. The crude intermediate was purified by silica column chromatography eluting with 0% to 20% MeOH in DCM with 0.1% NH4OH to afford the title compound (30.0 mg) as an off-white solid. 1H NMR (400 MHz, DMSO-d6) δ 9.79 (s, 1H), 8.95 (s, 1H), 8.05 (s, 1H), 7.67 (s, 1H), 7.54 (dd, J=8.4, 2.2 Hz, 1H), 7.03 (d, J=8.3 Hz, 1H), 5.83 (dddt, J=19.8, 16.9, 10.1, 6.7 Hz, 2H), 5.08 (ddt, J=16.9, 11.4, 1.8 Hz, 2H), 4.98 (ddd, J=10.4, 7.8, 1.8 Hz, 2H), 4.36 (t, J=7.0 Hz, 2H), 3.55 (s, 2H), 2.74 (t, J=5.8 Hz, 2H), 2.67-2.62 (m, 4H), 2.54 (d, J=7.3 Hz, 2H), 2.30 (q, J=7.0 Hz, 2H). LCMS [M+H]: 375.2

Example 19

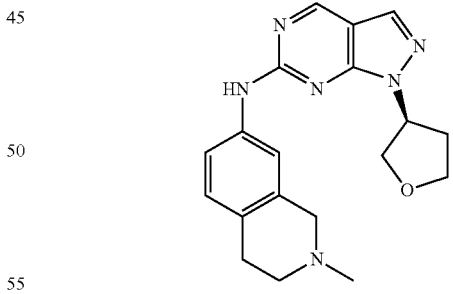

(S)-2-methyl-N-(1-(tetrahydrofuran-3-yl)-1H-pyrazolo[3,4-d]pyrimidin-6-yl)-1,2,3,4-tetrahydroisoquinolin-7-amine Step 1: Preparation of 6-chloro-1-[(3S)-tetrahydrofuran-3-yl]pyrazolo[3,4-d]pyrimidine. This was prepared similar to general procedure D. A solution of (R)-(−)-3-hydroxytetrahydrofuran (54.9 mg, 0.620 mmol), 6-chloro-1H-pyrazolo[3,4-d]pyrimidine (114.7 mg, 0.7400 mmol), and triphenylphosphine (204.4 mg, 0.780 mmol) in THF (5 mL) was cooled to −78° C. bath followed by dropwise addition of DIAD (0.15 mL, 0.780 mmol). The reaction mixture was stirred at rt for 24 h. The crude product was purified by silica column chromatography eluting with a gradient of 0% to 25% EtOAc in DCM to afford the title compound (57.5 mg) as a white solid. This material was taken on directly to the next step without further purification.

Step 2: Preparation of (S)-2-methyl-N-(1-(tetrahydrofuran-3-yl)-1H-pyrazolo[3,4-d]pyrimidin-6-yl)-1,2,3,4-tetrahydroisoquinolin-7-amine. This was prepared according to general procedure A using of 6-chloro-1-[(3S)-tetrahydrofuran-3-yl]pyrazolo[3,4-d]pyrimidine (25.0 mg, 0.111 mmol), 2-methyl-3,4-dihydro-1H-isoquinolin-7-amine (21.7 mg, 0.134 mmol), and p-TSA (63.5 mg, 0.334 mmol) in 1,4-dioxane at 80° C. for 48 h. The crude product was purified by silica column chromatography eluting with a gradient of 0% to 20% MeOH in DCM to afford the title compound as a white solid (11 mg). 1H NMR (Chloroform-d, free base) δ: 8.80 (s, 1H), 7.92 (s, 1H), 7.47 (dd, J=8.3, 2.2 Hz, 1H), 7.40 (s, 1H), 7.12 (d, J=8.1 Hz, 1H), 5.46-5.40 (m, 1H), 4.27-4.20 (m, 2H), 4.15 (dd, J=9.4, 4.9 Hz, 1H), 4.04 (td, J=8.1, 5.7 Hz, 1H), 3.63 (s, 2H), 2.92 (t, J=6.0 Hz, 2H), 2.72 (t, J=6.0 Hz, 2H), 2.49 (s, 3H), 2.26-2.18 (m, 1H). LCMS [M+H]: 351.2

Example 20

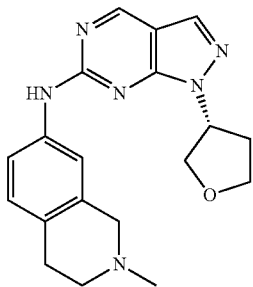 [SMILES: CN1CCc2ccc(Nc3ncc4cnn([C@@H]5CCOC5)c4n3)cc2C1]

(R)-2-methyl-N-(1-(tetrahydrofuran-3-yl)-1H-pyrazolo[3,4-d]pyrimidin-6-yl)-1,2,3,4-tetrahydroisoquinolin-7-amine Step 1: Preparation of 6-chloro-1-[(3R)-tetrahydrofuran-3-yl]pyrazolo[3,4-d]pyrimidine. This was prepared according to general procedure D. A solution of (S)-(−)-3-hydroxytetrahydrofuran (54.9 mg, 0.620 mmol), 6-chloro-1H-pyrazolo[3,4-d]pyrimidine (114.7 mg, 0.74 mmol), and triphenylphosphine (204.3 mg, 0.780 mmol) in THF (5 mL) was cooled to −78° C., followed by dropwise addition of DIAD (0.15 mL, 0.780 mmol). The reaction mixture was stirred at rt for 24 h. The crude product was purified by silica column chromatography eluting with a gradient of 0% to 25% EtOAc in DCM to afford the title compound (43.5 mg) as a white solid. This material was used without further purification.

Step 2: Preparation of (R)-2-methyl-N-(1-(tetrahydrofuran-3-yl)-1H-pyrazolo[3,4-d]pyrimidin-6-yl)-1,2,3,4-tetrahydroisoquinolin-7-amine. This was prepared according to general procedure A using of 6-chloro-1-[(3R)-tetrahydrofuran-3-yl]pyrazolo[3,4-d]pyrimidine (25.0 mg, 0.111 mmol), 2-methyl-3,4-dihydro-1H-isoquinolin-7-amine (21.7 mg, 0.134 mmol), and p-TSA (63.5 mg, 0.334 mmol) in 1,4-dioxane at 80° C. for 48 h. The crude product was purified by silica column chromatography eluting with 0% to 20% MeOH in DCM to afford the title compound as a white solid (5.7 mg). 1H NMR (400 MHz, Chloroform-d, free base) δ 8.79 (s, 1H), 7.92 (s, 1H), 7.47 (dd, J=8.2, 2.3 Hz, 1H), 7.40 (d, J=2.3 Hz, 1H), 7.12 (d, J=8.2 Hz, 1H), 5.49-5.38 (m, 1H), 4.27-4.18 (m, 2H), 4.15 (dd, J=9.3, 4.8 Hz, 1H), 4.04 (td, J=8.2, 5.5 Hz, 1H), 3.62 (s, 2H), 2.92 (t, J=6.0 Hz, 2H), 2.72 (t, J=5.9 Hz, 2H), 2.60-2.50 (m, 2H), 2.49 (s, 3H). LCMS [M+H]: 351.2

Example 21

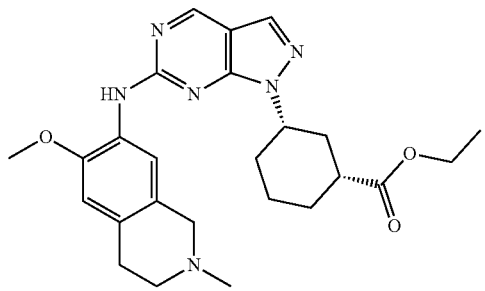 [SMILES: CCOC(=O)[C@@H]1CCC[C@H](n2ncc3cnc(Nc4cc5c(cc4OC)CCN(C)C5)nc32)C1]

ethyl cis-3-(6-((6-methoxy-2-methyl-1,2,3,4-tetrahydroisoquinolin-7-yl)amino)-1H-pyrazolo[3,4-d]pyrimidin-1-yl)cyclohexane-1-carboxylate Step 1: Preparation of ethyl cis-3-(6-chloro-1H-pyrazolo[3,4-d]pyrimidin-1-yl)cyclohexane-1-carboxylate. Prepared according to general procedure D using ethyl trans-3-hydroxycyclohexanecarboxylate, 6-chloro-1H-pyrazolo[3,4-d]pyrimidine, triphenylphosphine, and DEAD (40% solution in toluene) in THF. The crude product was purified by silica column chromatography eluting with 0% to 40% EtOAc in hexanes to afford the title compound as an off-white solid. This material was taken directly to the next step.

Step 2: Preparation of ethyl cis-3-[6-[(6-methoxy-2-methyl-3,4-dihydro-1H-isoquinolin-7-yl)amino]pyrazolo[3,4-d]pyrimidin-1-yl]cyclohexanecarboxylate trifluoroacetate. Prepared according to general procedure B using ethyl cis-3-(6-chloropyrazolo[3,4-d]pyrimidin-1-yl)cyclohexanecarboxylate (90.0 mg, 0.291 mmol), 6-methoxy-2-methyl-3,4-dihydro-1H-isoquinolin-7-amine (67.2 mg, 0.350 mmol), Pd₂dba₃ (26.7 mg, 0.029 mmol), BINAP (54.5 mg, 0.087 mmol), and sodium t-butoxide (33.6 mg, 0.350 mmol) in THF (2.0 mL) at 120° C. for 3 h. The crude product was purified by silica column chromatography eluting with 0% to 100% MeOH in EtOAc followed by reverse phase HPLC (Phenomenex, Gemini-NX, 10 um, 250×30 mm, C18 column; gradient of 20% MeCN/0.1% TFA-water to 100% MeCN/0.1% TFA) to afford the title compound as a yellow solid (44.0 mg). 1H NMR (400 MHz, dmso) δ 9.91 (s, 1H), 8.97 (s, 1H), 8.38 (s, 1H), 8.10 (s, 1H), 8.07 (d, J=5.1 Hz, 1H), 6.97 (s, 1H), 4.70-4.59 (m, 1H), 4.46 (d, J=15.9 Hz, 1H), 4.35-4.21 (m, 1H), 4.07 (q, J=7.1 Hz, 3H), 3.87 (s, 3H), 3.69 (s, 1H), 3.34 (d, J=10.7 Hz, 1H), 3.12-2.99 (m, 1H), 2.95 (d, J=4.7 Hz, 3H), 2.75-2.61 (m, 1H), 2.17 (d, J=12.5 Hz, 2H), 2.08 (qd, J=12.1, 7.3 Hz, 1H), 1.95 (t, J=14.2 Hz, 5H), 1.58 (s, 1H), 1.39 (t, J=13.0 Hz, 1H), 1.17 (t, J=7.1 Hz, 3H). LCMS [M+H]: 465.3

Example 22

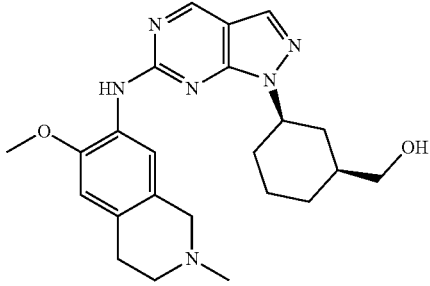 [SMILES: COc1cc2c(cc1Nc1ncc3cnn([C@@H]4CCC[C@H](CO)C4)c3n1)CN(C)CC2]

cis-3-(6-((6-methoxy-2-methyl-1,2,3,4-tetrahydroisoquinolin-7-yl)amino)-1H-pyrazolo[3,4-d]pyrimidin-1-yl cyclohexyl)methanol Step 1: Preparation of ethyl cis-3-(6-chloro-1H-pyrazolo[3,4-d]pyrimidin-1-yl)cyclohexane-1-carboxylate. Prepared according to general procedure D using ethyl trans-3-hydroxycyclohexanecarboxylate, 6-chloro-1H-pyrazolo[3,4-d]pyrimidine, triphenylphosphine, and DEAD (40% solution in toluene) in THF. The crude product was purified by silica column chromatography eluting with 0% to 40% EtOAc in hexanes to afford the title compound as an off-white solid. This material was taken directly to the next step.

Step 2: Preparation of cis-3-[6-[(6-methoxy-2-methyl-3,4-dihydro-1H-isoquinolin-7-yl)amino]pyrazolo[3,4-d]pyrimidin-1-yl]cyclohexanecarboxylic acid. Prepared according to general procedure B using methyl cis-3-(6-chloropyrazolo[3,4-d]pyrimidin-1-yl)cyclohexanecarboxylate (195 mg, 0.662 mmol), 6-methoxy-2-methyl-3,4-dihydro-1H-isoquinolin-7-amine (254 mg, 1.32 mmol), Pd$_2$dba$_3$ (60.6 mg, 0.066 mmol), BINAP (124 mg, 0.198 mmol), and potassium t-butoxide (105 mg, 1.09 mmol) in THF (2.0 mL) under microwave heating at 120° C. for 1.5 h. The crude product was purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (29.4 mg).

Step 3: Preparation of [(cis)-3-[6-[(6-methoxy-2-methyl-3,4-dihydro-1H-isoquinolin-7-yl)amino]pyrazolo[3,4-d]pyrimidin-1-yl]cyclohexyl]methanol. A solution of cis-3-[6-[(6-methoxy-2-methyl-3,4-dihydro-1H-isoquinolin-7-yl)amino]pyrazolo[3,4-d]pyrimidin-1-yl]cyclohexanecarboxylic acid (25.0 mg, 0.0454 mmol), PyBop (35.4 mg, 0.0681 mmol), DIEA (8.80 mg, 0.0681 mmol) in THF (0.50 mL) was stirred at rt for 20 min. Sodium borohydride (2.6 mg, 0.068 mmol) was added. After 3 h at rt, water (2 mL) was added, and the reaction mixture was concentrated. The residue was suspended in 0.1% TFA (aq, 5 mL) and purified by reverse phase HPLC (Phenomenex, Gemini-NX, 10 um, 250×30 mm, C18 column; gradient of 20% MeCN/0.1% TFA-water to 100% MeCN/0.1% TFA) to provide the intermediate dihydropyrazolo[3,4-d]pyrimidin-1-yl]cyclohexyl] methanol. This material was dissolved in THF (0.4 mL) and cooled to 0° C. Under a nitrogen atmosphere, a solution of DDQ (3.41 mg, 0.020 mmol) in dioxane (0.25 mL) was added dropwise. After 2.5 h at 0° C., a saturated solution of sodium bicarbonate (2 mL) was added. The reaction mixture was extracted with EtOAc. The combined organics was concentrated, and the crude product was purified by silica column chromatography eluting with 0% to 100% MeOH in EtOAc to afford the title compound as an off-white solid (0.9 mg). 1H NMR (400 MHz, Methanol-d4, free base) δ 8.87 (s, 1H), 8.31 (s, 1H), 7.98 (s, 1H), 6.80 (s, 1H), 3.92 (s, 3H), 3.63 (s, 2H), 3.49 (qd, J=10.8, 5.8 Hz, 3H), 2.99 (s, 2H), 2.94 (t, J=6.0 Hz, 2H), 2.76 (t, J=6.0 Hz, 2H), 2.48 (s, 3H), 2.17-2.11 (m, 2H), 2.11-2.02 (m, 4H), 1.66-1.54 (m, 2H). LCMS [M+H]: =523.1

Example 23

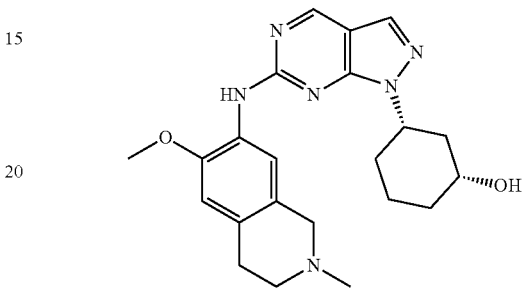

cis-3-(6-((6-methoxy-2-methyl-1,2,3,4-tetrahydroisoquinolin-7-yl)amino)-1H-pyrazolo[3,4-d]pyrimidin-1-yl)cyclohexan-1-ol Step 1: Preparation of cis-3-(6-chloro-1H-pyrazolo[3,4-d]pyrimidin-1-yl)cyclohexan-1-ol. Prepare by general procedure B using trans-cyclohexane-1,3-diol (543.mg, 4.67 mmol), 6-chloro-1H-pyrazolo[3,4-d]pyrimidine (650.2 mg, 4.21 mmol), triphenylphosphine (2.452 g, 9.35 mmol), and DEAD (40% solution in toluene, 2.24 mL, 4.91 mmol) in THF (15 mL) at rt for 2 h. The crude product was purified by silica column chromatography eluting with 0% to 100% EtOAc in hexanes to afford the title compound (74 mg).

Step 2: Preparation of cis-3-(6-((6-methoxy-2-methyl-1,2,3,4-tetrahydroisoquinolin-7-yl)amino)-1H-pyrazolo[3,4-d]pyrimidin-1-yl)cyclohexan-1-ol hydrochloride. Prepare by general method A using cis-3-(6-chloro-1H-pyrazolo[3,4-d]pyrimidin-1-yl)cyclohexan-1-ol (30 mg, 0.119 mmol), 6-methoxy-2-methyl-3,4-dihydro-1H-isoquinolin-7-amine (25.1 mg, 0.131 mmol), and p-TSA (45.2 mg, 0.237 mmol) in 1,4-dioxane (0.5 mL) and sec-butanol (0.5 mL) at 120° C. for 18 h. The crude product was purified by reverse phase HPLC (Phenomenex, Gemini-NX, 10 um, 250×30 mm, C18 column; gradient of 20% MeCN/0.1% TFA-water to 100% MeCN/0.1% TFA) to provide the TFA salt. This material was free based with 1M NaOH and extracted with EA. The combined organics was concentrated. The residue was suspended with 1M HCl followed by lyopholization to afford the title compound (10.9 mg) as a white solid. 1H NMR (400 MHz, dmso) δ 10.36 (s, 1H), 8.97 (s, 1H), 8.37 (s, 1H), 8.09 (s, 11H), 8.07 (d, J=4.0 Hz, 1H), 6.96 (s, 1H), 4.57 (t, J=11.8 Hz, 1H), 4.52-4.39 (m, 1H), 4.32-4.18 (m, 1H), 3.87 (s, 3H), 3.39-3.25 (m, 2H), 3.21-3.11 (m, 11H), 3.01 (d, J=17.1 Hz, 1H), 2.92 (d, J=4.7 Hz, 3H), 2.17 (d, J=11.5 Hz, 1H), 2.05-1.74 (m, 6H), 1.44 (d, J=13.5 Hz, 2H). LCMS [M+H]: 409.1

Example 24

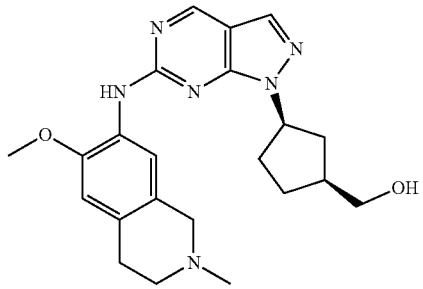 [SMILES: COc1cc2c(cc1Nc1ncc3cnn([C@@H]4CC[C@H](CO)C4)c3n1)CN(C)CC2]

cis-3-(6-((6-methoxy-2-methyl-1,2,3,4-tetrahydroisoquinolin-7-yl)amino)-1H-pyrazolo[3,4-d]pyrimidin-1-yl)cyclopentyl)methanol Step 1: Preparation of cis-3-(6-chloro-1H-pyrazolo[3,4-d]pyrimidin-1-yl)cyclopentyl)methyl acetate. Prepare by general method D using trans-3-hydroxycyclopentyl]methyl acetate (177 mg, 1.12 mmol), 6-chloro-1H-pyrazolo[3,4-d]pyrimidine (181.5 mg, 1.17 mmol), triphenylphosphine (880.4 mg, 3.36 mmol), and DEAD (40% solution in toluene, 0.54 mL, 1.17 mmol) in THF (5.0 mL) at 5° C. for 3 h. The crude product was purified by silica column chromatography eluting with 0% to 30% EtOAc in hexanes to afford the title compound (132.0 mg) as a clear oil. LCMS [M+H]: 338.4

Step 2: Preparation of cis-3-(6-((6-methoxy-2-methyl-1,2,3,4-tetrahydroisoquinolin-7-yl)amino)-1H-pyrazolo[3,4-d]pyrimidin-1-yl)cyclopentyl)methanol. Prepared according to general procedure A using cis-3-(6-chloro-1H-pyrazolo[3,4-d]pyrimidin-1-yl)cyclopentyl)methyl acetate (64 mg, 0.217 mmol), 6-methoxy-2-methyl-3,4-dihydro-1H-isoquinolin-7-amine (43.8 mg, 0.228 mmol), and p-TSA (82.6 mg, 0.434 mmol) in 1,4-dioxane (0.5 mL) and sec-butanol (0.5 mL) at 120° C. for 18 h. The crude product was purified by reverse phase HPLC (Phenomenex, Gemini-NX, 10 um, 250×30 mm, C18 column; gradient of 20% MeCN/0.1% TFA-water to 100% MeCN/0.1% TFA). The purified material was free based with 1M NaOH followed by conversion to the HCl salt with 1M HCl to afford the title compound. 1H NMR (400 MHz, dmso) δ 9.91 (s, 1H), 8.96 (s, 1H), 8.37 (s, 1H), 8.10 (s, 1H), 8.02 (s, 1H), 6.96 (s, 1H), 5.11-5.05 (m, 1H), 4.47 (d, J=14.8 Hz, 1H), 4.27 (dd, J=15.3, 8.2 Hz, 1H), 3.86 (s, 3H), 3.67 (s, 1H), 3.42 (d, J=6.0 Hz, 2H), 3.34 (s, 1H), 2.96 (d, J=4.6 Hz, 3H), 2.22 (td, J=14.9, 13.4, 7.3 Hz, 2H), 2.08 (q, J=7.7 Hz, 2H), 1.81 (q, J=6.9, 6.3 Hz, 2H), 1.74-1.59 (m, 1H). LCMS [M+H]: 409.1

Example 25

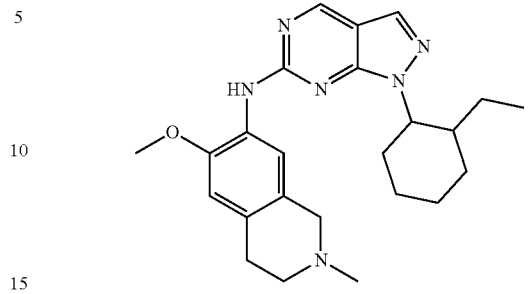

N-(1-(2-ethylcyclohexyl)-1H-pyrazolo[3,4-d]pyrimidin-6-yl)-6-methoxy-2-methyl-1,2,3,4-tetrahydroisoquinolin-7-amine Step 1: Preparation of 6-chloro-1-(2-ethylcyclohexyl)-1H-pyrazolo[3,4-d]pyrimidine. Prepared according to general procedure D using 6-chloro-1H-pyrazolo[3,4-d]pyrimidine (200 mg, 1.29 mmol), 2-ethylcyclohexanol (249 mg, 1.94 mmol), triphenylphosphine (509 mg, 1.94 mmol) and DEAD (40% solution in toluene, 845 mg, 1.94 mmol) in THF (10 mL) at rt for 0.5 h. The crude product was purified by silica column chromatography eluting with 0% to 100% EtOAc in hexanes to afford the title compound as a solid (97 mg). This material was taken directly to the next step without further purification.

Step 2: Preparation of N-(1-(2-ethylcyclohexyl)-1H-pyrazolo[3,4-d]pyrimidin-6-yl)-6-methoxy-2-methyl-1,2,3,4-tetrahydroisoquinolin-7-amine. Prepared according to general procedure A using 6-chloro-1-(2-ethylcyclohexyl)-1H-pyrazolo[3,4-d]pyrimidine (40 mg, 0.15 mmol), 6-methoxy-2-methyl-3,4-dihydro-1H-isoquinolin-7-amine (52 mg, 0.27 mmol), and p-TSA (86 mg, 0.45 mmol) in 2-butanol (2 mL) at 101° C. for 48 h. The reaction mixture was purified by reverse phase HPLC (Phenomenex, Gemini-NX, 10 um, 250×30 mm, C18 column; gradient of 20% MeCN/0.1% TFA-water to 100% MeCN/0.1% TFA) providing the title compound as a solid (26 mg). 1H NMR (400 MHz, Methanol-d4, TFA salt) δ 9.15 (d, J=1.2 Hz, 1H), 8.45-8.39 (m, 1H), 7.85 (d, J=6.7 Hz, 1H), 7.09 (s, 1H), 4.61-4.50 (m, 1H), 4.43-4.32 (m, 2H), 3.94 (s, 3H), 3.85-3.75 (m, 1H), 3.48 (td, J=11.6, 4.8 Hz, 1H), 3.42-3.33 (m, 1H), 3.25-3.14 (m, 1H), 3.10 (s, 3H), 2.15-2.01 (m, 3H), 1.91 (dd, J=29.1, 12.8 Hz, 3H), 1.60-1.34 (m, 2H), 1.33-1.16 (m, 1H), 1.14-0.89 (m, 2H), 0.77 (td, J=7.4, 1.7 Hz, 3H). LCMS [M+H]: 421.3.

Example 26

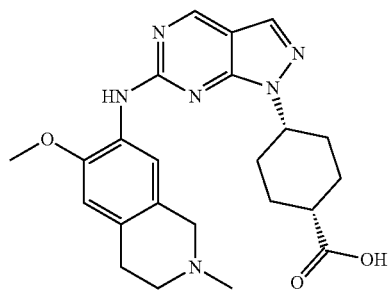 [SMILES: COc1cc2c(cc1Nc1ncc3cnn([C@H]4CC[C@@H](C(=O)O)CC4)c3n1)CN(C)CC2]

(1s,4s)-4-(6-(((6-methoxy-2-methyl-1,2,3,4-tetrahydroisoquinolin-7-yl)amino)-1H-pyrazolo[3,4-d]pyrimidin-1-yl)cyclohexane-1-carboxylic acid Step 1: Preparation of methyl (1s,4s)-4-(6-chloro-1H-pyrazolo[3,4-d]pyrimidin-1-yl)cyclohexane-1-carboxylate. Prepared according to general procedure D using 6-chloro-1H-pyrazolo[3,4-d]pyrimidine (400 mg, 2.59 mmol), trans-methyl 4-hydroxycyclohexanecarboxylate (737 mg, 4.66 mmol), triphenylphosphine (1.02 g, 3.88 mmol) and DEAD (40% solution in toluene, 2.03 g, 4.66 mmol) in THF (20 mL) at rt for 1 h. The crude product was purified by silica column chromatography eluting with 0% to 20% MeOH in DCM to afford the title compound as a solid (560 mg). This material was taken directly to the next step without further purification.

Step 2: Preparation of methyl (1s,4s)-4-(6-((6-methoxy-2-methyl-1,2,3,4-tetrahydroisoquinolin-7-yl)amino)-1H-pyrazolo[3,4-d]pyrimidin-1-yl)cyclohexane-1-carboxylate. Prepared according to general procedure B using methyl (1s,4s)-4-(6-chloro-1H-pyrazolo[3,4-d]pyrimidin-1-yl)cyclohexane-1-carboxylate (200 mg, 0.68 mmol), 6-methoxy-2-methyl-3,4-dihydro-1H-isoquinolin-7-amine (157 mg, 0.81 mmol), Pd$_2$(dba)$_3$ (62 mg, 0.07 mmol), potassium tert-butoxide (91 mg, 0.81 mmol), and (S)-BINAP (127 mg, 0.2 mmol) in THF (10 mL) at 120° C. using microwave reactor for 75 min. The crude product was purified by silica column chromatography eluting with 0% to 20% MeOH in DCM to afford the title compound as a solid (140 mg). This material was taken directly to the next step without further purification.

Step 3: Preparation of (1s,4s)-4-(6-((6-methoxy-2-methyl-1,2,3,4-tetrahydroisoquinolin-7-yl)amino)-1H-pyrazolo[3,4-d]pyrimidin-1-yl)cyclohexane-1-carboxylic acid. To the solution of methyl (1s,4s)-4-(6-((6-methoxy-2-methyl-1,2,3,4-tetrahydroisoquinolin-7-yl)amino)-1H-pyrazolo[3,4-d]pyrimidin-1-yl)cyclohexane-1-carboxylate (140 mg, 0.31 mmol) in MeOH (6 mL) and water (3 mL) were added LiOH (22 mg, 0.93 mmol) and NaOH (2M aqueous solution, 0.31 mL, 0.62 mmol). The mixture was stirred at rt for 48 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the title compound (133 mg). 1H NMR (400 MHz, Methanol-d4) δ 8.91 (s, 1H), 8.39 (s, 1H), 8.02 (s, 1H), 6.94 (s, 1H), 4.78-4.66 (m, 1H), 4.58 (d, J=14.8 Hz, 1H), 4.38 (d, J=14.8 Hz, 1H), 3.97 (s, 3H), 3.84-3.72 (m, 1H), 3.52-3.38 (m, 1H), 3.29-3.21 (m, 1H), 3.20-3.12 (m, 1H), 3.10 (s, 3H), 2.78-2.71 (m, 1H), 2.41-2.32 (m, 2H), 2.32-2.22 (m, 2H), 2.07-1.95 (m, 2H), 1.89-1.76 (m, 2H). LCMS [M+H]: 437.1.

Example 27

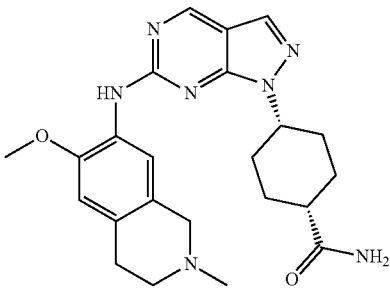 [SMILES: COc1cc2c(cc1Nc1ncc3cnn([C@H]4CC[C@@H](C(N)=O)CC4)c3n1)CN(C)CC2]

(1s,4s)-4-(6-(((6-methoxy-2-methyl-1,2,3,4-tetrahydroisoquinolin-7-yl)amino)-1H-pyrazolo[3,4-d]pyrimidin-1-yl)cyclohexane-1-carboxamide To the solution of (1s,4s)-4-(6-(((6-methoxy-2-methyl-1,2,3,4-tetrahydroisoquinolin-7-yl)amino)-1H-pyrazolo[3,4-d]pyrimidin-1-yl)cyclohexane-1-carboxylic acid (EXAMPLE 26) (50 mg, 0.09 mmol) in DMF (2 mL) and EtOAc (1 mL) were added methylimidazole (90 mg, 1.1 mmol), ammonium chloride (49 mg, 0.91 mmol) and 1-propylphosphonic acid cyclic anhydride, 50+% soln. in EtOAc (0.14 mL, 0.23 mmol). The mixture was stirred at rt for 48 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the desire product as a solid (20 mg). 1H NMR (400 MHz, DMSO-d6) δ 10.82 (s, 11H), 8.99 (s, 1H), 8.46 (s, 1H), 8.11 (s, 1H), 8.03 (s, 1H), 7.30 (s, 1H), 6.96 (s, 1H), 6.85 (s, 1H), 4.70-4.57 (m, 1H), 4.44 (d, J=14.6 Hz, 1H), 4.24 (dd, J=15.2, 8.4 Hz, 1H), 3.86 (s, 3H), 3.68-3.60 (m, 1H), 3.38-3.25 (m, 1H), 3.24-3.12 (m, 1H), 3.08-2.94 (m, 1H), 2.91 (d, J=4.8 Hz, 3H), 2.46-2.38 (m, 1H), 2.31-2.19 (m, 2H), 2.16-2.00 (m, 2H), 1.92-1.75 (m, 2H), 1.72-1.59 (m, 2H). LCMS [M+H]: 436.1.

Example 28

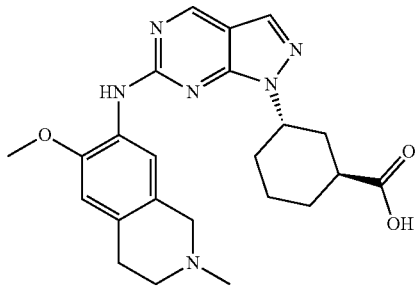 [SMILES: COc1cc2c(cc1Nc1ncc3cnn([C@H]4CCC[C@H](C(=O)O)C4)c3n1)CN(C)CC2]

rac-(1S,3S)-3-(6-(((6-methoxy-2-methyl-1,2,3,4-tetrahydroisoquinolin-7-yl)amino)-1H-pyrazolo[3,4-d]pyrimidin-1-yl)cyclohexane-1-carboxylic acid Step 1: Preparation of methyl rac-(1S,3S)-3-(6-chloro-1H-pyrazolo[3,4-d]pyrimidin-1-yl)cyclohexane-1-carboxylate. Prepared according to general procedure D using 6-chloro-1H-pyrazolo[3,4-d]pyrimidine (800 mg, 5.18 mmol), methyl rac-(1R,3S)-3-hydroxycyclohexanecarboxylate (983 mg, 6.21 mmol), triphenylphosphine (2.72 g, 10.4 mmol) and DEAD (40% solution in toluene, 4.51 g, 10.4 mmol) in THF (30 mL) at rt for 1 h. The crude product was purified by silica column chromatography eluting with 0% to 100% EtOAc in hexane to afford the title compound as a solid (1 g). This material was taken directly to the next step without further purification.

Step 2: Preparation of methyl rac-(1S,3S)-3-(6-((6-methoxy-2-methyl-1,2,3,4-tetrahydroisoquinolin-7-yl)amino)-1H-pyrazolo[3,4-d]pyrimidin-1-yl)cyclohexane-1-carboxylate. Prepared according to general procedure B using methyl rac-(1S,3S)-3-(6-chloro-1H-pyrazolo[3,4-d]pyrimidin-1-yl)cyclohexane-1-carboxylate (300 mg, 1.02 mmol), 6-methoxy-2-methyl-3,4-dihydro-1H-isoquinolin-7-amine (235 mg, 1.22 mmol), Pd$_2$(dba)$_3$ (93 mg, 0.10 mmol), potassium tert-butoxide (137 mg, 1.22 mmol), and (S)-

BINAP (190 mg, 0.31 mmol) in THF (12 mL) at 120° C. using microwave reactor for 75 min. The crude product was purified by silica column chromatography eluting with 0% to 20% MeOH in DCM to afford the title compound as a solid (500 mg). This material was taken directly to the next step without further purification.

Step 3: Preparation of rac-(1S,3S)-3-(6-((6-methoxy-2-methyl-1,2,3,4-tetrahydroisoquinolin-7-yl)amino)-1H-pyrazolo[3,4-d]pyrimidin-1-yl)cyclohexane-1-carboxylic acid. To the solution of methyl rac-(1S,3S)-3-(6-((6-methoxy-2-methyl-1,2,3,4-tetrahydroisoquinolin-7-yl)amino)-1H-pyrazolo[3,4-d]pyrimidin-1-yl)cyclohexane-1-carboxylate (500 mg, 0.88 mmol) in MeOH (8 mL) and water (4 mL) were added LiOH (64 mg, 2.66 mmol) and NaOH (2M water solution, 0.89 mL, 1.77 mmol). The mixture was stirred at rt for 48 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the title compound (143 mg). 1H NMR (400 MHz, Methanol-d4) δ 8.93 (s, 1H), 8.53 (d, J=10.5 Hz, 1H), 8.09 (s, 1H), 6.93 (s, 1H), 5.30-5.17 (m, 1H), 4.68 (dd, J=23.8, 15.2 Hz, 1H), 4.48-4.31 (m, 1H), 3.95 (s, 3H), 3.82-3.74 (m, 1H), 3.46-3.37 (m, 1H), 3.30-3.22 (m, 1H), 3.18-3.13 (m, 1H), 3.11 (d, J=3.0 Hz, 3H), 3.06-2.99 (m, 1H), 2.37-2.25 (m, 11H), 2.23-2.05 (m, 3H), 2.01-1.91 (m, 1H), 1.91-1.83 (m, 1H), 1.79-1.65 (m, 2H). LCMS [M+H]: 437.1.

Example 29 rac-(1S,3S)-3-(6-((6-methoxy-2-methyl-1,2,3,4-tetrahydroisoquinolin-7-yl)amino)-1H-pyrazolo[3,4-d]pyrimidin-1-yl)cyclohexane-1-carboxamide To the solution of rac-(1S,3S)-3-(6-((6-methoxy-2-methyl-1,2,3,4-tetrahydroisoquinolin-7-yl)amino)-1H-pyrazolo[3,4-d]pyrimidin-1-yl)cyclohexane-1-carboxylic acid (EXAMPLE 28) (42 mg, 0.07 mmol) in EtOAc (1 mL) were added methylimidazole (19 mg, 0.23 mmol), ammonium chloride (41 mg, 0.76 mmol) and 1-propylphosphonic acid cyclic anhydride (50+% soln. in EtOAc, 0.11 mL, 0.19 mmol). The mixture was stirred at rt for 48 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the desire product as a solid (20 mg). 11H NMR (400 MHz, Methanol-d4) δ 9.20 (s, 1H), 8.41 (s, 1H), 8.32 (d, J=23.7 Hz, 1H), 7.05 (s, 11H), 5.54-5.39 (m, 11H), 4.77 (t, J=14.3 Hz, 1H), 4.43 (dd, J=15.1, 9.4 Hz, 1H), 3.98 (s, 3H), 3.78 (s, 1H), 3.56-3.41 (m, 1H), 3.40-3.32 (m, 1H), 3.25-3.15 (m, 1H), 3.12 (s, 3H), 3.02-2.89 (m, 1H), 2.29-2.07 (m, 3H), 2.09-1.92 (m, 2H), 1.91-1.73 (m, 3H). LCMS [M+H]: 436.1.

Example 30 rac-6-methoxy-2-methyl-N-(1-((1S,2S)-2-methylcyclohexyl)-1H-pyrazolo[3,4-d]pyrimidin-6-yl)-1,2,3,4-tetrahydroisoquinolin-7-amine Step 1: Preparation of rac-6-chloro-1-((1S,2S)-2-methylcyclohexyl)-1H-pyrazolo[3,4-d]pyrimidine. Prepared according to general procedure D using 6-chloro-1H-pyrazolo[3,4-d]pyrimidine (200 mg, 1.29 mmol), cis-2-methylcyclohexanol (237 uL, 1.94 mmol), triphenylphosphine (0.51 g, 1.94 mmol) and DEAD (40% solution in toluene, 0.88 mL, 1.94 mmol) in THF (10 mL) at rt for 0.5 h. The crude product was purified by silica column chromatography eluting with 0% to 100% EtOAc in hexanes to afford the title compound (151 mg). This material was taken directly to the next step without further purification.

Step 2: Preparation of rac-6-methoxy-2-methyl-N-(1-((1S,2S)-2-methylcyclohexyl)-1H-pyrazolo[3,4-d]pyrimidin-6-yl)-1,2,3,4-tetrahydroisoquinolin-7-amine. Prepared according to general procedure A using rac-6-chloro-1-((1S,2S)-2-methylcyclohexyl)-1H-pyrazolo[3,4-d]pyrimidine (40 mg, 0.16 mmol), 6-methoxy-2-methyl-3,4-dihydro-1H-isoquinolin-7-amine (55 mg, 0.29 mmol), and p-TSA (91 mg, 0.48 mmol) in 2-butanol (2 mL) at 120° C. for 4 h. The reaction mixture was purified using reverse phase HPLC (Phenomenex, Gemini-NX, 10 um, 250×30 mm, C18 column; gradient of 20% MeCN/0.1% TFA-water to 100% MeCN/0.1% TFA) providing the title compound as a solid (15 mg). 1H NMR (400 MHz, Methanol-d4) δ 9.14 (s, 1H), 8.40 (s, 1H), 7.88 (d, J=4.0 Hz, 1H), 7.08 (s, 1H), 4.56 (dd, J=15.0, 4.7 Hz, 1H), 4.38 (d, J=14.9 Hz, 1H), 4.27 (t, J=11.0 Hz, 1H), 3.94 (s, 3H), 3.85-3.76 (m, 11H), 3.52-3.43 (m, 1H), 3.40-3.33 (m, 1H), 3.26-3.16 (m, 1H), 3.09 (s, 3H), 2.29-2.14 (m, 1H), 2.14-2.01 (m, 1H), 2.00-1.90 (m, 3H), 1.87-1.78 (m, 1H), 1.62-1.36 (m, 2H), 1.36-1.21 (m, 1H), 0.70 (dd, J=6.5, 2.6 Hz, 3H). LCMS [M+H]: 407.2.

Example 31

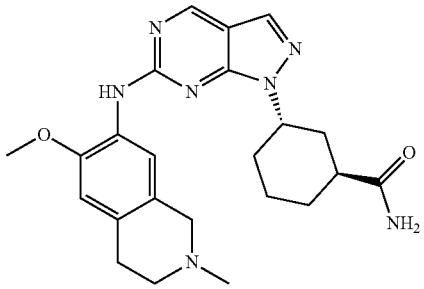 [SMILES: COc1cc2c(cc1Nc1ncc3cnn([C@H]4CCC[C@H](C(N)=O)C4)c3n1)CN(C)CC2]

(1S,3S)-3-(6-((6-methoxy-2-methyl-1,2,3,4-tetrahydroisoquinolin-7-yl)amino)-1H-pyrazolo[3,4-d]pyrimidin-1-yl)cyclohexane-1-carboxamide Step 1: Preparation of methyl (1 S,3S)-3-(6-chloro-1H-pyrazolo[3,4-d]pyrimidin-1-yl)cyclohexane-1-carboxylate. Prepared according to general procedure D using 6-chloro-1H-pyrazolo[3,4-d]pyrimidine (400 mg, 2.6 mmol), methyl (1R,3S)-3-hydroxycyclohexanecarboxylate (491 mg, 3.1 mmol), triphenylphosphine (1.36 g, 5.2 mmol) and DEAD (40% solution in toluene, 2.36 mL, 5.2 mmol) in THF (10 mL) at rt for 1 h. The crude product was purified by silica column chromatography eluting with 0% to 100% EtOAc in hexanes to afford the title compound as a solid (470 mg). This material was taken directly to the next step without further purification.

Step 2: Preparation of methyl (1S,3S)-3-(6-((6-methoxy-2-methyl-1,2,3,4-tetrahydroisoquinolin-7-yl)amino)-1H-pyrazolo[3,4-d]pyrimidin-1-yl)cyclohexane-1-carboxylate. Prepared according to general procedure B using methyl (1S,3S)-3-(6-chloro-1H-pyrazolo[3,4-d]pyrimidin-1-yl)cyclohexane-1-carboxylate (300 mg, 1.02 mmol), 6-methoxy-2-methyl-3,4-dihydro-1H-isoquinolin-7-amine (235 mg, 1.22 mmol), $Pd_2(dba)_3$ (93 mg, 0.10 mmol), potassium tert-butoxide (137 mg, 1.22 mmol), and (S)-BINAP (190 mg, 0.31 mmol) in THF (12 mL) at 120° C. using microwave reactor for 90 min. The crude product was purified by silica column chromatography eluting with 0% to 20% MeOH in DCM to afford the title compound as a solid (414 mg). This material was taken directly to the next step without further purification.

Step 3: Preparation of (1S,3S)-3-(6-((6-methoxy-2-methyl-1,2,3,4-tetrahydroisoquinolin-7-yl)amino)-1H-pyrazolo[3,4-d]pyrimidin-1-yl)cyclohexane-1-carboxylic acid. To the solution of methyl (1S,3S)-3-(6-((6-methoxy-2-methyl-1,2,3,4-tetrahydroisoquinolin-7-yl)amino)-1H-pyrazolo[3,4-d]pyrimidin-1-yl)cyclohexane-1-carboxylate (414 mg, 0.92 mmol) in MeOH (8 mL) and water (4 mL) were added LiOH (44 mg, 1.84 mmol) and NaOH (2M water solution, 0.55 mL, 1.1 mmol). The mixture was stirred at rt for 48 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the title compound (192 mg).

Step 4: Preparation of (1S,3S)-3-(6-((6-methoxy-2-methyl-1,2,3,4-tetrahydroisoquinolin-7-yl)amino)-1H-pyrazolo[3,4-d]pyrimidin-1-yl)cyclohexane-1-carboxamide. To the solution of (1S,3S)-3-(6-((6-methoxy-2-methyl-1,2,3,4-tetrahydroisoquinolin-7-yl)amino)-1H-pyrazolo[3,4-d]pyrimidin-1-yl)cyclohexane-1-carboxylic acid (80 mg, 0.15 mmol) in DMF (3 mL) and EtOAc (1.5 mL) were added methylimidazole (143 mg, 1.74 mmol), ammonium chloride (78 mg, 1.45 mmol) and 1-propylphosphonic acid cyclic anhydride, 50+% soln. in EtOAc (0.22 mL, 0.36 mmol). The mixture was stirred at rt for 48 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the desire product as a solid (46 mg). 1H NMR is identical to EXAMPLE 29 LCMS [M+H]: 436.1.

Example 32

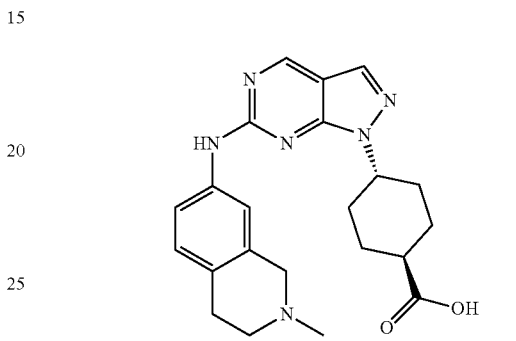

(1r,4r)-4-(6-((2-methyl-1,2,3,4-tetrahydroisoquinolin-7-yl)amino)-1H-pyrazolo[3,4-d]pyrimidin-1-yl)cyclohexane-1-carboxylic acid Step 1: Preparation of methyl (1r,4r)-4-(6-chloro-1H-pyrazolo[3,4-d]pyrimidin-1-yl)cyclohexane-1-carboxylate. Prepared according to general procedure D using 6-chloro-1H-pyrazolo[3,4-d]pyrimidine (400 mg, 2.59 mmol), cis-methyl 4-hydroxycyclohexanecarboxylate (614 mg, 3.88 mmol), triphenylphosphine (1.36 g, 5.18 mmol) and DEAD (40% solution in toluene, 2.36 mL, 5.18 mmol) in THF (20 mL) at rt for 1 h. The crude product was purified by silica column chromatography eluting with 0% to 20% MeOH in DCM to afford the title compound as a solid (345 mg). This material was taken directly to the next step without further purification.

Step 2: Preparation of methyl (1r,4r)-4-(6-((2-methyl-1,2,3,4-tetrahydroisoquinolin-7-yl)amino)-1H-pyrazolo[3,4-d]pyrimidin-1-yl)cyclohexane-1-carboxylate. Prepared according to general procedure B using methyl (1r,4r)-4-(6-chloro-1H-pyrazolo[3,4-d]pyrimidin-1-yl)cyclohexane-1-carboxylate (44 mg, 0.15 mmol), 2-methyl-3,4-dihydro-1H-isoquinolin-7-amine (29 mg, 0.18 mmol), $Pd_2(dba)_3$ (14 mg, 0.02 mmol), potassium tert-butoxide (20 mg, 0.18 mmol), and (S)-BINAP (28 mg, 0.05 mmol) in THF (2.5 mL) at 120° C. using microwave reactor for 50 min. The crude product was purified by silica column chromatography eluting with 0% to 20% MeOH in DCM to afford the title compound as a solid (28 mg). This material was taken directly to the next step without further purification.

Step 3: Preparation of (1r,4r)-4-(6-((2-methyl-1,2,3,4-tetrahydroisoquinolin-7-yl)amino)-1H-pyrazolo[3,4-d]pyrimidin-1-yl)cyclohexane-1-carboxylic acid. To the solution of methyl (1r,4r)-4-(6-((2-methyl-1,2,3,4-tetrahydroisoquinolin-7-yl)amino)-1H-pyrazolo[3,4-d]pyrimidin-1-yl)cyclohexane-1-carboxylate (28 mg, 0.05 mmol) in McOH (2.5 mL) and water (1 mL) were added LiOH (2.5 mg, 0.11 mmol) and NaOH (2M water solution, 53 uL, 0.11 mmol).

The mixture was stirred at rt for 48 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the title compound (9 mg). 1H NMR (400 MHz, Methanol-d4, TFA salt) δ 8.91 (s, 1H), 8.02 (s, 11H), 7.82 (d, J=2.3 Hz, 1H), 7.68 (dd, J=8.5, 2.3 Hz, 1H), 7.27 (d, J=8.4 Hz, 1H), 4.72-4.62 (m, 1H), 4.58 (d, J=15.1 Hz, 1H), 4.41 (d, J=15.2 Hz, 1H), 3.84-3.73 (m, 1H), 3.50-3.38 (m, 1H), 3.28-3.19 (m, 1H), 3.18-3.12 (m, 1H), 3.09 (s, 3H), 2.50-2.40 (m, 1H), 2.27-2.16 (m, 4H), 2.14-2.09 (m, 2H), 1.78-1.63 (m, 2H). LCMS [M+H]: 407.1.

Example 33

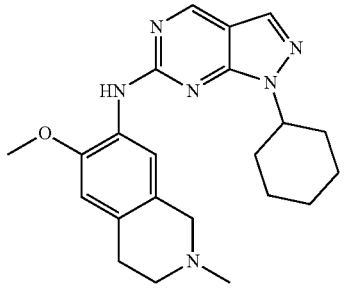 [SMILES: COc1cc2c(cc1Nc1ncc3cnn(C4CCCCC4)c3n1)CN(C)CC2]

N-(1-cyclohexyl-1H-pyrazolo[3,4-d]pyrimidin-6-yl)-6-methoxy-2-methyl-1,2,3,4-tetrahydroisoquinolin-7-amine Step 1: Preparation of 6-chloro-1-cyclohexyl-1H-pyrazolo[3,4-d]pyrimidine. Prepared according to general procedure D using 6-chloro-1H-pyrazolo[3,4-d]pyrimidine (200 mg, 1.29 mmol), cyclohexanol (0.21 mL, 1.94 mmol), triphenylphosphine (509 mg, 1.94 mmol) and DEAD (40% solution in toluene, 0.88 mL, 1.94 mmol) in THF (10 mL) at rt for 3 h. The crude product was purified by silica column chromatography eluting with 0% to 100% EtOAc in hexanes to afford the title compound as a solid (140 mg). This material was taken directly to the next step without further purification.

Step 2: Preparation of N-(1-cyclohexyl-1H-pyrazolo[3,4-d]pyrimidin-6-yl)-6-methoxy-2-methyl-1,2,3,4-tetrahydroisoquinolin-7-amine trifluoroacetate. Prepared according to general procedure A using 6-chloro-1-cyclohexyl-1H-pyrazolo[3,4-d]pyrimidine (45 mg, 0.19 mmol), 6-methoxy-2-methyl-3,4-dihydro-1H-isoquinolin-7-amine (66 mg, 0.34 mmol), and p-TSA (108 mg, 0.57 mmol) in 2-butanol (2 mL) at 101° C. for 48 h. The reaction mixture was purified using reverse phase HPLC (Phenomenex, Gemini-NX, 10 um, 250×30 mm, C18 column; gradient of 20% MeCN/0.1% TFA-water to 100% MeCN/0.1% TFA) providing the title compound as a solid (56 mg). 1H NMR (400 MHz, Methanol-d4, TFA salt) δ 9.12 (s, 1H), 8.34 (s, 1H), 7.82 (s, 1H), 6.96 (s, 1H), 4.69-4.57 (m, 1H), 4.52 (d, J=14.9 Hz, 1H), 4.31 (d, J=14.9 Hz, 1H), 3.92 (s, 3H), 3.81-3.70 (m, 1H), 3.50-3.34 (m, 2H), 3.24-3.09 (m, 1H), 3.06 (s, 31H), 2.08-1.95 (m, 6H), 1.86-1.74 (m, 1H), 1.61-1.43 (m, 2H), 1.41-1.24 (m, 1H). LCMS [M+H]: 393.2.

Example 34

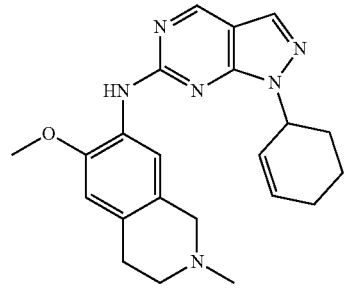 [SMILES: COc1cc2c(cc1Nc1ncc3cnn(C4C=CCCC4)c3n1)CN(C)CC2]

N-(1-(cyclohex-2-en-1-yl)-1H-pyrazolo[3,4-d]pyrimidin-6-yl)-6-methoxy-2-methyl-1,2,3,4-tetrahydroisoquinolin-7-amine Step 1: Preparation of 6-chloro-1-(cyclohex-2-en-1-yl)-1H-pyrazolo[3,4-d]pyrimidine. Prepare by general procedure B using trans-cyclohexane-1,3-diol (543.0 mg, 4.67 mmol), 6-chloro-1H-pyrazolo[3,4-d]pyrimidine (650.2 mg, 4.21 mmol), triphenylphosphine (2.45 g, 9.35 mmol), and DEAD (40% solution in toluene, 2.24 mL, 4.91 mmol) in THF (15 mL) at rt for 2 h. The crude product was purified by silica column chromatography eluting with 0% to 100% EtOAc in hexanes to afford the title compound (105.7 mg). LCMS [M+H]: 235.2

Step 2: Preparation of N-(1-(cyclohex-2-en-1-yl)-1H-pyrazolo[3,4-d]pyrimidin-6-yl)-6-methoxy-2-methyl-1,2,3,4-tetrahydroisoquinolin-7-amine. Prepare by general method A using 6-chloro-1-(cyclohex-2-en-1-yl)-1H-pyrazolo[3,4-d]pyrimidine (55.2 mg, 0.235 mmol), 6-methoxy-2-methyl-3,4-dihydro-1H-isoquinolin-7-amine (47.5 mg, 0.247 mmol), and p-TSA (89.5 mg, 0.470 mmol) in 1,4-dioxane (0.5 mL) and sec-butanol (0.5 mL) at 120° C. for 24 h. The crude product was purified by silica column chromatography eluting with 0% to 30% MeOH in DCM to afford the title compound as an off-white solid (16.5 mg). 1H NMR (400 MHz, Chloroform-d) δ 8.82 (s, 1H), 8.36 (s, 1H), 7.93 (s, 1H), 7.91 (s, 1H), 6.65 (s, 1H), 6.12 (d, J=10.1 Hz, 1H), 5.84 (dd, J=10.2, 2.4 Hz, 1H), 5.47-5.37 (m, 1H), 3.89 (s, 3H), 3.74 (s, 2H), 2.96 (s, 2H), 2.85 (s, 2H), 2.58 (s, 3H), 2.28 (td, J=5.9, 3.0 Hz, 1H), 2.22-2.11 (m, 3H), 1.97 (t, J=4.9 Hz, 1H), 1.80 (dtd, J=13.6, 8.8, 4.9 Hz, 1H). LCMS [M+H]: 391.4

Example 35

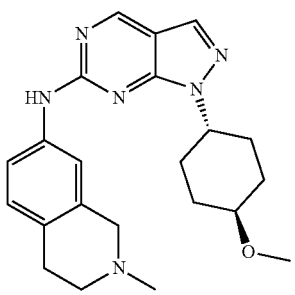 [SMILES: CO[C@H]1CC[C@H](n2ncc3cnc(Nc4ccc5c(c4)CN(C)CC5)nc32)CC1]

N-(1-((1r,4r)-4-methoxycyclohexyl)-1H-pyrazolo[3,4-d]pyrimidin-6-yl)-2-methyl-1,2,3,4-tetrahydroisoquinolin-7-amine Step 1: Preparation of 6-chloro-1-((1r,4r)-4-methoxycyclohexyl)-1H-pyrazolo[3,4-d]pyrimidine. Prepared according to general procedure D using 6-chloro-1H-pyrazolo[3,4-d]pyrimidine (300 mg, 1.94 mmol), 4-methoxycyclohexan-1-ol (505 mg, 3.88 mmol), triphenylphosphine (1.53 g, 5.82 mmol) and DEAD (40% solution in toluene, 2.65 mL, 5.82 mmol) in THF (20 mL) at rt for 1 h. The crude product was purified by silica column chromatography eluting with 0% to 20% MeOH in DCM to afford the title compound as a solid (415 mg). This material was taken directly to the next step without further purification.

Step 2: Preparation of N-(1-((1r,4r)-4-methoxycyclohexyl)-1H-pyrazolo[3,4-d]pyrimidin-6-yl)-2-methyl-1,2,3,4-tetrahydroisoquinolin-7-amine. Prepared according to general procedure B using 6-chloro-1-((1r,4r)-4-methoxycyclohexyl)-1H-pyrazolo[3,4-d]pyrimidine (60 mg, 0.23 mmol), 2-methyl-3,4-dihydro-1H-isoquinolin-7-amine (44 mg, 0.27 mmol), Pd$_2$(dba)$_3$ (21 mg, 0.02 mmol), potassium tert-butoxide (30 mg, 0.27 mmol), and (S)-BINAP (42 mg, 0.07 mmol) in THF (2.5 mL) at 120° C. using a sealed reaction vial overnight. The mixture was purified using reverse phase HPLC (Phenomenex, Gemini-NX, 10 um, 250×30 mm, C18 column; gradient of 20% MeCN/0.1% TFA-water to 100% MeCN/0.1% TFA), providing the title compound (12 mg). 1H NMR (400 MHz, Methanol-d4) δ 8.91 (s, 1H), 8.02 (s, 1H), 7.75 (d, J=2.2 Hz, 1H), 7.72 (dd, J=8.4, 2.3 Hz, 1H), 7.27 (d, J=8.4 Hz, 1H), 4.67 (tt, J=11.4, 4.5 Hz, 1H), 4.57 (d, J=15.0 Hz, 1H), 4.39 (d, J=15.2 Hz, 1H), 3.84-3.72 (m, 1H), 3.49-3.43 (m, 1H), 3.42 (s, 3H), 3.38-3.33 (m, 1H), 3.27-3.19 (m, 1H), 3.18-3.14 (m, 1H), 3.09 (s, 3H), 2.34-2.23 (m, 2H), 2.21-2.14 (m, 1H), 2.14-2.11 (m, 1H), 2.11-2.04 (m, 2H), 1.52-1.39 (m, 2H). LCMS [M+H]: 393.1.

Example 36

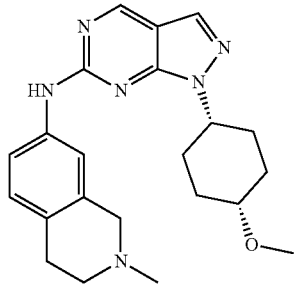 [SMILES: CO[C@H]1CC[C@@H](n2ncc3cnc(Nc4ccc5c(c4)CN(C)CC5)nc32)CC1]

N-(1-((cis)-4-methoxycyclohexyl)-1H-pyrazolo[3,4-d]pyrimidin-6-yl)-2-methyl-1,2,3,4-tetrahydroisoquinolin-7-amine Step 1: Preparation of 6-chloro-1-((cis)-4-methoxycyclohexyl)-1H-pyrazolo[3,4-d]pyrimidine. Prepared according to general procedure D using 6-chloro-1H-pyrazolo[3,4-d]pyrimidine (300 mg, 1.94 mmol), 4-methoxycyclohexan-1-ol (505 mg, 3.88 mmol), triphenylphosphine (1.53 g, 5.82 mmol) and DEAD (40% solution in toluene, 2.65 mL, 5.82 mmol) in THF (20 mL) at rt for 1 h. The crude product was purified by silica column chromatography eluting with 0% to 20% MeOH in DCM to afford the title compound as a solid (183 mg). This material was taken directly to the next step without further purification.

Step 2: Preparation of N-(1-((cis)-4-methoxycyclohexyl)-1H-pyrazolo[3,4-d]pyrimidin-6-yl)-2-methyl-1,2,3,4-tetrahydroisoquinolin-7-amine. Prepared according to general procedure B using 6-chloro-1-((1s,4s)-4-methoxycyclohexyl)-1H-pyrazolo[3,4-d]pyrimidine (40 mg, 0.15 mmol), 2-methyl-3,4-dihydro-1H-isoquinolin-7-amine (29 mg, 0.18 mmol), Pd$_2$(dba)$_3$ (14 mg, 0.02 mmol), potassium tert-butoxide (20 mg, 0.18 mmol), and (S)-BINAP (28 mg, 0.05 mmol) in THF (2.5 mL) at 120° C. using a sealed reaction vial overnight. The mixture was purified using a reverse phase HPLC (Phenomenex, Gemini-NX, 10 um, 250×30 mm, C18 column; gradient of 20% MeCN/0.1% TFA-water to 100% MeCN/0.1% TFA), providing the title compound (30 mg). 1H NMR (400 MHz, Methanol-d4) δ 8.90 (s, 1H), 8.01 (s, 1H), 7.76 (dd, J=8.4, 2.3 Hz, 1H), 7.73 (d, J=2.3 Hz, 1H), 7.27 (d, J=8.4 Hz, 1H), 4.67 (tt, J=11.8, 3.9 Hz, 1H), 4.59 (d, J=15.2 Hz, 1H), 4.38 (d, J=15.3 Hz, 1H), 3.85-3.73 (m, 1H), 3.61-3.54 (m, 1H), 3.49-3.41 (m, 1H), 3.38 (s, 3H), 3.28-3.19 (m, 1H), 3.18-3.13 (m, 1H), 3.08 (s, 3H), 2.43 (qd, J=12.8, 3.6 Hz, 2H), 2.23-2.09 (m, 2H), 1.88-1.77 (m, 2H), 1.69 (tt, J=14.0, 3.6 Hz, 2H). LCMS [M+H]: 393.1.

Example 37

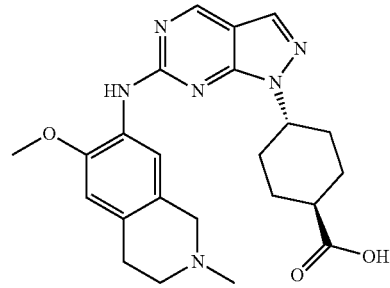 [SMILES: COc1cc2c(cc1Nc1ncc3cnn([C@H]4CC[C@H](C(=O)O)CC4)c3n1)CN(C)CC2]

(1r,4r)-4-(6-((6-methoxy-2-methyl-1,2,3,4-tetrahydroisoquinolin-7-yl)amino)-1H-pyrazolo[3,4-d]pyrimidin-1-yl)cyclohexane-1-carboxylic acid Step 1: Preparation of methyl (1r,4r)-4-(6-chloro-1H-pyrazolo[3,4-d]pyrimidin-1-yl)cyclohexane-1-carboxylate. Prepared according to general procedure D using 6-chloro-1H-pyrazolo[3,4-d]pyrimidine (400 mg, 2.59 mmol), cis-methyl 4-hydroxycyclohexanecarboxylate (614 mg, 3.88 mmol), triphenylphosphine (1.36 g, 5.18 mmol) and DEAD (40% solution in toluene, 2.36 mL, 5.18 mmol) in THF (20 mL) at rt for 1 h. The crude product was purified by silica column chromatography eluting with 0% to 20% MeOH in DCM to afford the title compound as a solid (345 mg). This material was taken directly to the next step without further purification.

Step 2: Preparation of methyl (1r,4r)-4-(6-((6-methoxy-2-methyl-1,2,3,4-tetrahydroisoquinolin-7-yl)amino)-1H-pyrazolo[3,4-d]pyrimidin-1-yl)cyclohexane-1-carboxylate. Prepared according to general procedure B using methyl (1r,4r)-4-(6-chloro-1H-pyrazolo[3,4-d]pyrimidin-1-yl)cyclohexane-1-carboxylate (177 mg, 0.6 mmol), 6-methoxy-2-methyl-3,4-dihydro-1H-isoquinolin-7-amine (139 mg, 0.72 mmol), Pd$_2$(dba)$_3$ (55 mg, 0.06 mmol), potassium tert-butoxide (81 mg, 0.72 mmol), and (S)-BINAP (112 mg, 0.18 mmol) in THF (8 mL) at 120° C. in sealed reaction vial for 2 h. The mixture was purified using reverse phase HPLC (Phenomenex, Gemini-NX, 10 um, 250×30 mm, C18 column; gradient of 20% MeCN/0.1% TFA-water to 100% MeCN/0.1% TFA), providing the desire product as a solid (244 mg).

Step 3: Preparation of (1r,4r)-4-(6-((6-methoxy-2-methyl-1,2,3,4-tetrahydroisoquinolin-7-yl)amino)-1H-pyrazolo[3,4-d]pyrimidin-1-yl)cyclohexane-1-carboxylic acid. To the solution of methyl (1r,4r)-4-(6-((6-methoxy-2-methyl-1,2,3,4-tetrahydroisoquinolin-7-yl)amino)-1H-pyrazolo[3,4-d]pyrimidin-1-yl)cyclohexane-1-carboxylate (244 mg, 0.43 mmol) in MeOH (10 mL) and water (5 mL) was added LiOH (25 mg, 1.0 mmol). The mixture was stirred at rt for 72 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the title compound as a solid (21 mg). 1H NMR (400 MHz, Methanol-d4) δ 9.15 (s, 1H), 8.38 (s, 1H), 7.93 (s, 1H), 7.08 (s, 1H), 4.76-4.64 (m, 1H), 4.59 (d, J=14.9 Hz, 1H), 4.39 (d, J=14.8 Hz, 1H), 3.95 (s, 3H), 3.89-3.76 (m, 1H), 3.47 (dt, J=11.6, 5.6 Hz, 1H), 3.42-3.33 (m, 1H), 3.26-3.16 (m, 1H), 3.10 (s, 3H), 2.56-2.44 (m, 1H), 2.25-2.10 (m, 6H), 1.82-1.60 (m, 2H). LCMS [M+H]: 437.1.

Example 38

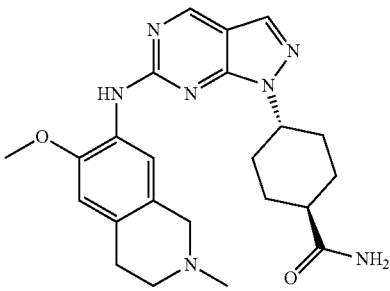 [SMILES: COc1cc2c(cc1Nc1ncc3cnn([C@H]4CC[C@H](C(N)=O)CC4)c3n1)CN(C)CC2]

(1r,4r)-4-(6-((6-methoxy-2-methyl-1,2,3,4-tetrahydroisoquinolin-7-yl)amino)-1H-pyrazolo[3,4-d]pyrimidin-1-yl)cyclohexane-1-carboxamide To the solution of (1r,4r)-4-(6-((6-methoxy-2-methyl-1,2,3,4-tetrahydroisoquinolin-7-yl)amino)-1H-pyrazolo[3,4-d]pyrimidin-1-yl)cyclohexane-1-carboxylic acid (EXAMPLE 37) (24 mg, 0.06 mmol) and ammonium hydroxide solution (10 uL, 0.16 mmol) in DMF (1.5 mL) were added HOBt (1.5 mg, 0.01 mmol), EDC hydrochloride (16 mg, 0.08 mmol) and triethylamine (11 uL, 0.08 mmol). The mixture was stirred at rt for 2 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the desire product as a solid (5.5 mg). 1H NMR (400 MHz, Methanol-d4) δ 9.14 (s, 1H), 8.36 (s, 1H), 8.04 (s, 1H), 7.07 (s, 1H), 4.77-4.64 (m, 1H), 4.58 (d, J=15.0 Hz, 1H), 4.38 (d, J=15.1 Hz, 1H), 3.96 (s, 3H), 3.87-3.75 (m, 1H), 3.53-3.39 (m, 1H), 3.38-3.33 (m, 1H), 3.25-3.18 (m, 1H), 3.14-3.07 (m, 3H), 2.95-2.86 (m, 1H), 2.23-2.03 (m, 6H), 1.90-1.67 (m, 2H). LCMS [M+H]: 436.1.

Example 39

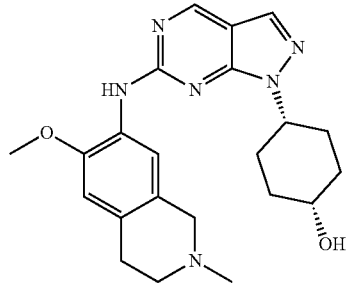 [SMILES: COc1cc2c(cc1Nc1ncc3cnn([C@H]4CC[C@@H](O)CC4)c3n1)CN(C)CC2]

(1s,4s)-4-(6-((6-methoxy-2-methyl-1,2,3,4-tetrahydroisoquinolin-7-yl)amino)-1H-pyrazolo[3,4-d]pyrimidin-1-yl)cyclohexan-1-ol Step 1: Preparation of (1s,4s)-4-(6-chloro-1H-pyrazolo[3,4-d]pyrimidin-1-yl)cyclohexan-1-ol. Prepared according to general procedure D using 6-chloro-1H-pyrazolo[3,4-d]pyrimidine (1 g, 6.47 mmol), trans-cyclohexane-1,4-diol (2.25 g, 19.4 mmol), triphenylphosphine (5.1 g, 19.4 mmol) and DEAD (40% solution in toluene, 8.84 mL, 19.4 mmol) in THF (56 mL) at rt for 30 min. The crude product was purified reversed phase eluting with 0% to 100% acetonitrile (with 0.1% TFA added) in water (with 0.1% TFA added), providing the title compound as a solid (1.06 g). This material was taken directly to the next step without further purification.

Step 2: Preparation of (1s,4s)-4-(6-((6-methoxy-2-methyl-1,2,3,4-tetrahydroisoquinolin-7-yl)amino)-1H-pyrazolo[3,4-d]pyrimidin-1-yl)cyclohexan-1-ol. Prepared according to general procedure A using (1s,4s)-4-(6-chloro-1H-pyrazolo[3,4-d]pyrimidin-1-yl)cyclohexan-1-ol (1.06 g, 4.2 mmol), 6-methoxy-2-methyl-3,4-dihydro-1H-isoquinolin-7-amine (1.45 g, 7.55 mmol), and p-TSA (2.4 g, 12.6 mmol) in 2-butanol (50 mL) at reflux for 48 h. The crude product was purified reversed phase eluting with 0% to 100% acetonitrile (with 0.1% TFA added) in water (with 0.1% TFA added). The TFA salt obtained was then basified, extracted with DCM and purified by silica column chromatography eluting with 0% to 20% MeOH in DCM to afford the title compound as free base. The free base was then converted into HCl salt as a solid (1.2 g). 1H NMR (400 MHz, Methanol-d4) δ 8.92 (s, 1H), 8.33 (s, 1H), 8.04 (s, 1H), 6.86 (s, 1H), 4.68-4.54 (m, 2H), 4.30 (d, J=15.0 Hz, 1H), 4.12-4.05 (m, 1H), 3.95 (s, 3H), 3.78-3.67 (m, 1H), 3.46-3.36 (m, 1H), 3.30-3.25 (m, 1H), 3.17-3.07 (m, 1H), 3.05 (s, 3H), 2.74-2.57 (m, 2H), 2.11-1.96 (m, 2H), 1.92-1.67 (m, 4H). LCMS [M+H]: 409.1.

Example 40

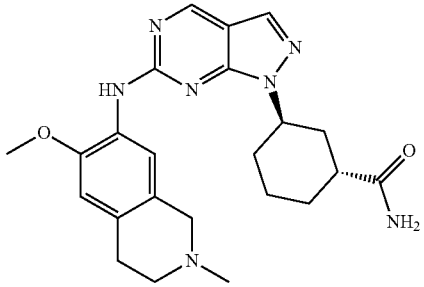 [SMILES: COc1cc2c(cc1Nc1ncc3cnn([C@@H]4CCC[C@@H](C(N)=O)C4)c3n1)CN(C)CC2]

(1S,3S)-3-(6-((6-methoxy-2-methyl-1,2,3,4-tetrahydroisoquinolin-7-yl)amino)-1H-pyrazolo[3,4-d]pyrimidin-1-yl)cyclohexane-1-carboxamide Prepared according to EXAMPLE 31 substituting in Step 1 methyl (1S,3R)-3-hydroxycyclohexanecarboxylate for methyl (1R,3S)-3-hydroxycyclohexanecarboxylate. 1H NMR is identical to EXAMPLE 29 LCMS [M+H]: 436.1.

Example 41

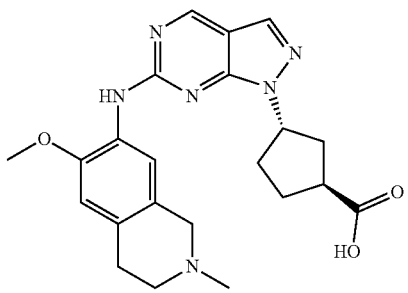 [SMILES: COc1cc2c(cc1Nc1ncc3cnn([C@H]4CC[C@H](C(=O)O)C4)c3n1)CN(C)CC2]

rac-(1S,3S)-3-(6-((6-methoxy-2-methyl-1,2,3,4-tetrahydroisoquinolin-7-yl)amino)-1H-pyrazolo[3,4-d]pyrimidin-1-yl)cyclopentane-1-carboxylic acid Step 1: Preparation of methyl rac-(1S,3S)-3-(6-chloro-1H-pyrazolo[3,4-d]pyrimidin-1-yl)cyclopentane-1-carboxylate. Prepared according to general procedure D using 6-chloro-1H-pyrazolo[3,4-d]pyrimidine (400 mg, 2.59 mmol), methyl cis-3-hydroxycyclopentane-1-carboxylate (448 mg, 3.11 mmol), triphenylphosphine (1.02 g, 3.88 mmol) and DEAD (40% solution in toluene, 1.77 mL, 3.88 mmol) in THF (12 mL) at rt for 30 min. The crude product was purified by silica column chromatography eluting with 0% to 100% EtOAc in hexanes to afford the title compound as a solid (669 mg). This material was taken directly to the next step without further purification.

Step 2: Preparation of methyl rac-(1S,3S)-3-(6-((6-methoxy-2-methyl-1,2,3,4-tetrahydroisoquinolin-7-yl)amino)-1H-pyrazolo[3,4-d]pyrimidin-1-yl)cyclopentane-1-carboxylate. Prepared according to general procedure B using methyl rac-(1S,3S)-3-(6-chloro-1H-pyrazolo[3,4-d]pyrimidin-1-yl)cyclopentane-1-carboxylate (300 mg, 1.1 mmol), 6-methoxy-2-methyl-3,4-dihydro-1H-isoquinolin-7-amine (247 mg, 1.28 mmol), Pd$_2$(dba)$_3$ (98 mg, 0.11 mmol), potassium tert-butoxide (144 mg, 1.28 mmol), and (S)-BINAP (200 mg, 0.32 mmol) in THF (12 mL) at 120° C. in microwave reactor for 90 min. The crude product was purified by silica column chromatography eluting with 0% to 20% MeOH in DCM to afford the title compound as a solid (396 mg). This material was taken directly to the next step without further purification.

Step 3: Preparation of rac-(1S,3S)-3-(6-((6-methoxy-2-methyl-1,2,3,4-tetrahydroisoquinolin-7-yl)amino)-1H-pyrazolo[3,4-d]pyrimidin-1-yl)cyclopentane-1-carboxylic acid. To the solution of methyl rac-(1S,3S)-3-(6-((6-methoxy-2-methyl-1,2,3,4-tetrahydroisoquinolin-7-yl)amino)-1H-pyrazolo[3,4-d]pyrimidin-1-yl)cyclopentane-1-carboxylate (396 mg, 0.91 mmol) in MeOH (8 mL) and water (4 mL) were added LiOH (26 mg, 1.1 mmol) and NaOH (2M water solution, 0.27 mL, 0.54 mmol). The mixture was stirred at rt for 48 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the title compound as a solid (263 mg). 1H NMR (400 MHz, Methanol-d4) δ 8.90 (s, 1H), 8.42 (d, J=15.1 Hz, 1H), 8.05 (s, 1H), 6.93 (s, 1H), 5.33 (p, J=7.7 Hz, 1H), 4.62 (dd, J=15.0, 4.6 Hz, 1H), 4.33 (d, J=15.0 Hz, 1H), 3.95 (s, 3H), 3.84-3.70 (m, 1H), 3.41 (td, J=11.8, 5.2 Hz, 1H), 3.29-3.19 (m, 2H), 3.18-3.13 (m, 1H), 3.10 (s, 3H), 2.57-2.44 (m, 1H), 2.37-2.22 (m, 4H), 2.05-1.94 (m, 1H). LCMS [M+H]: 423.2.

Example 42

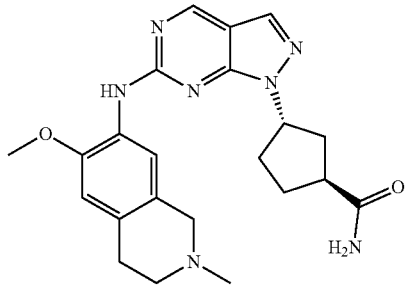 [SMILES: COc1cc2c(cc1Nc1ncc3cnn([C@H]4CC[C@H](C(N)=O)C4)c3n1)CN(C)CC2]

rac-(1S,3S)-3-(6-((6-methoxy-2-methyl-1,2,3,4-tetrahydroisoquinolin-7-yl)amino)-1H-pyrazolo[3,4-d]pyrimidin-1-yl)cyclopentane-1-carboxamide To the solution of rac-(1S,3S)-3-(6-((6-methoxy-2-methyl-1,2,3,4-tetrahydroisoquinolin-7-yl)amino)-1H-pyrazolo[3,4-d]pyrimidin-1-yl)cyclopentane-1-carboxylic acid (EXAMPLE 41) (40 mg, 0.07 mmol) in DMF (1.5 mL) and EtOAc (0.7 mL) were added methylimidazole (74 mg, 0.9 mmol), ammonium chloride (40 mg, 0.75 mmol) and 1-propylphosphonic acid cyclic anhydride (50+% soln. in EtOAc, 0.11 mL, 0.19 mmol). The mixture was stirred at rt for 72 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the desire product as a solid (15 mg). 1H NMR (400 MHz, Methanol-d4) δ 9.18 (s, 1H), 8.40 (s, 1H), 8.13 (d, J=16.0 Hz, 1H), 7.06 (s, 1H), 5.47-5.34 (m, 1H), 4.67 (d, J=15.0 Hz, 1H), 4.37 (dd, J=15.1, 4.2 Hz, 1H), 3.97 (s, 3H), 3.85-3.74 (m, 1H), 3.52-3.41 (m, 1H), 3.39-3.32 (m, 1H), 3.23-3.15 (m, 2H), 3.11 (s, 3H), 2.51-2.40 (m, 1H), 2.40-2.20 (m, 4H), 2.02-1.88 (m, 1H). LCMS [M+H]: 422.2.

Example 43

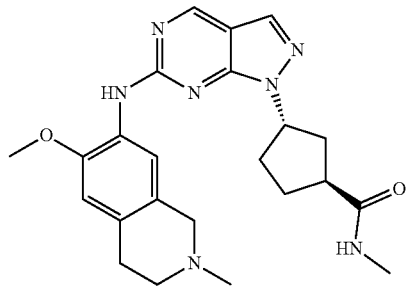 [SMILES: CNC(=O)[C@H]1CC[C@H](n2ncc3cnc(Nc4cc5c(cc4OC)CCN(C)C5)nc32)C1]

rac-(1S,3S)-3-(6-((6-methoxy-2-methyl-1,2,3,4-tetrahydroisoquinolin-7-yl)amino)-1H-pyrazolo[3,4-d]pyrimidin-1-yl)-N-methylcyclopentane-1-carboxamide To the solution of rac-(1S,3S)-3-(6-((6-methoxy-2-methyl-1,2,3,4-tetrahydroisoquinolin-7-yl)amino)-1H-pyrazolo[3,4-d]pyrimidin-1-yl)cyclopentane-1-carboxylic acid (EXAMPLE 41) (40 mg, 0.07 mmol) in DMF (1.5 mL) and EtOAc (0.7 mL) were added methylimidazole (74 mg, 0.9 mmol), methylamine (2M solution in THF, 0.37 mL, 0.75 mmol) and 1-propylphosphonic acid cyclic anhydride (50+% soln. in EtOAc, 0.11 mL, 0.19 mmol). The mixture was stirred at rt for 72 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the desire product as a solid (22 mg). 1H NMR (400 MHz, Methanol-d4) δ 9.19 (s, 1H), 8.42 (s, 1H), 8.10 (d, J=12.5 Hz, 1H), 7.07 (s, 1H), 5.44 (p, J=6.3 Hz, 1H), 4.69 (d, J=15.1 Hz, 1H), 4.40 (dd, J=15.1, 3.8 Hz, 1H), 3.97 (s, 3H), 3.85-3.77 (m, 1H), 3.53-3.43 (m, 1H), 3.41-3.32 (m, 1H), 3.26-3.13 (m, 2H), 3.12 (s, 3H), 2.76 (s, 3H), 2.49-2.31 (m, 2H), 2.31-2.21 (m, 3H), 1.98-1.87 (m, 1H). LCMS [M+H]: 436.2.

Example 44

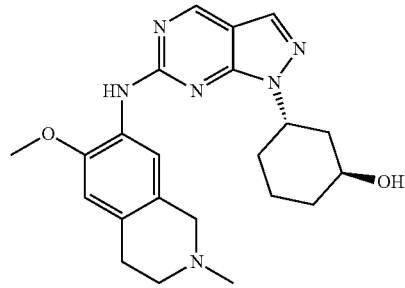 [SMILES: COc1cc2c(cc1Nc1ncc3cnn([C@H]4CCC[C@H](O)C4)c3n1)CN(C)CC2]

rac-(trans)-3-(6-((6-methoxy-2-methyl-1,2,3,4-tetrahydroisoquinolin-7-yl)amino)-1H-pyrazolo[3,4-d]pyrimidin-1-yl)cyclohexan-1-ol Step 1: Preparation of Rac-(trans)-3-(6-chloro-1H-pyrazolo[3,4-d]pyrimidin-1-yl)cyclohexan-1-ol

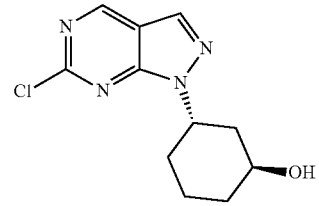 [SMILES: O[C@H]1CCC[C@H](n2ncc3cnc(Cl)nc32)C1]

Prepared according to general procedure D using 6-chloro-1H-pyrazolo[3,4-d]pyrimidine (200 mg, 1.29 mmol), cis-1,3-cyclohexanediol (451 mg, 3.88 mmol), triphenylphosphine (1.02 g, 3.88 mmol) and DEAD (40% solution in toluene, 1.77 mL, 3.88 mmol) in THF (5 mL) at rt for 1 h. The crude product was purified reversed phase eluting with 0% to 100% acetonitrile (with 0.1% TFA added) in water (with 0.1% TFA added), providing the title compound as a solid (200 mg). This material was taken directly to the next step without further purification.

Step 2: rac-(trans)-3-(6-((6-methoxy-2-methyl-1,2,3,4-tetrahydroisoquinolin-7-yl)amino)-1H-pyrazolo[3,4-d]pyrimidin-1-yl)cyclohexan-1-ol Prepared according to general procedure A using rac-(1S,3S)-3-(6-chloro-1H-pyrazolo[3,4-d]pyrimidin-1-yl)cyclohexan-1-ol (50 mg, 0.2 mmol), 6-methoxy-2-methyl-3,4-dihydro-1H-isoquinolin-7-amine (69 mg, 0.36 mmol), and p-TSA (113 mg, 0.6 mmol) in 2-butanol (2 mL) at 105° C. in sealed reaction vial for 48 h. The reaction mixture was purified using reverse phase HPLC (Phenomenex, Gemini-NX, 10 um, 250×30 mm, C18 column; gradient of 20% MeCN/0.1% TFA-water to 100% MeCN/0.1% TFA) providing the title compound as a solid (13 mg). 1H NMR (400 MHz, Methanol-d4) δ 9.12 (s, 1H), 8.31 (s, 1H), 8.23 (d, J=15.9 Hz, 1H), 6.90 (s, 1H), 5.25-5.10 (m, 1H), 4.56 (t, J=13.8 Hz, 1H), 4.37-4.23 (m, 2H), 3.95 (s, 3H), 3.80-3.68 (m, 1H), 3.47-3.34 (m, 2H), 3.18-3.09 (m, 1H), 3.05 (d, J=2.9 Hz, 3H), 2.20-1.92 (m, 5H), 1.91-1.83 (m, 1H), 1.82-1.73 (m, 1H), 1.67-1.54 (m, 1H). LCMS [M+H]: 409.0.]

Example 45

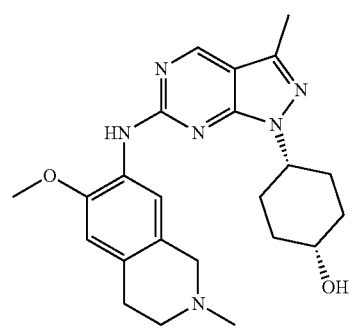 [SMILES: COc1cc2c(cc1Nc1ncc3c(C)nn([C@H]4CC[C@@H](O)CC4)c3n1)CN(C)CC2]

(cis)-4-(6-((6-methoxy-2-methyl-1,2,3,4-tetrahydroisoquinolin-7-yl)amino)-3-methyl-1H-pyrazolo[3,4-d]pyrimidin-1-yl)cyclohexan-1-ol Step 1: Preparation of (cis)-4-(6-chloro-3-methyl-1H-pyrazolo[3,4-d]pyrimidin-1-yl)cyclohexan-1-ol. Prepared according to general procedure D using 6-chloro-3-methyl-1H-pyrazolo[3,4-d]pyrimidine (200 mg, 1.19 mmol), trans-cyclohexane-1,4-diol (413 mg, 3.56 mmol), triphenylphosphine (934 mg, 3.56 mmol) and DEAD (40% solution in toluene, 1.62 mL, 3.56 mmol) in THF (10 mL) at rt for 15 min. The reaction mixture was purified using reverse phase HPLC (Phenomenex, Gemini-NX, 10 um, 250×30 mm, C18 column; gradient of 20% MeCN/0.1% TFA-water to 100% MeCN/0.1% TFA) providing the title compound as a solid (140 mg).

Step 2: Preparation of (cis)-4-(6-((6-methoxy-2-methyl-1,2,3,4-tetrahydroisoquinolin-7-yl)amino)-3-methyl-1H-pyrazolo[3,4-d]pyrimidin-1-yl)cyclohexan-1-ol. Prepared according to general procedure A using (cis)-4-(6-chloro-3-methyl-1H-pyrazolo[3,4-d]pyrimidin-1-yl)cyclohexan-1-ol (50 mg, 0.19 mmol), 6-methoxy-2-methyl-3,4-dihydro-1H-isoquinolin-7-amine (65 mg, 0.34 mmol), and p-TSA (107 mg, 0.56 mmol) in 2-butanol (2.5 mL) in sealed reaction vessel at 120° C. for 48 h. The reaction mixture was purified using reverse phase HPLC (Phenomenex, Gemini-NX, 10 um, 250×30 mm, C18 column; gradient of 20% MeCN/0.1% TFA-water to 100% MeCN/0.1% TFA) providing the title compound as a solid (73 mg). 1H NMR (400 MHz, Methanol-d4) δ 9.11 (s, 1H), 7.99 (s, 1H), 7.01 (s, 1H), 5.44 (s, 1H), 4.71-4.48 (m, 2H), 4.34 (d, J=14.9 Hz, 1H), 4.06 (s, 1H), 3.95 (s, 3H), 3.83-3.68 (m, 1H), 3.53-3.33 (m, 2H), 3.23-3.11 (m, 1H), 3.07 (s, 3H), 2.66-2.38 (m, 5H), 2.09-1.91 (m, 2H), 1.88-1.63 (m, 4H). LCMS [M+H]: 423.1.

Example 46

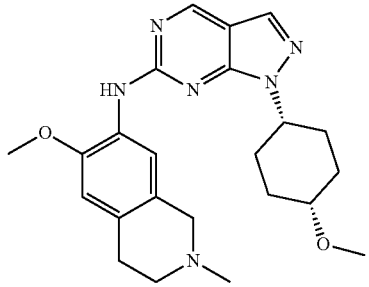

6-methoxy-N-(1-((1s,4s)-4-methoxycyclohexyl)-1H-pyrazolo[3,4-d]pyrimidin-6-yl)-2-methyl-1,2,3,4-tetrahydroisoquinolin-7-amine The above compound was prepared according to general procedure B using 6-chloro-1-((1s,4s)-4-methoxycyclohexyl)-1H-pyrazolo[3,4-d]pyrimidine (Example 36, Step 1) (55 mg, 0.21 mmol), 6-methoxy-2-methyl-3,4-dihydro-1H-isoquinolin-7-amine (48 mg, 0.25 mmol), Pd₂(dba)₃ (19 mg, 0.02 mmol), potassium tert-butoxide (28 mg, 0.25 mmol), and (S)-BINAP (39 mg, 0.06 mmol) in THF (2.5 mL) at 120° C. in sealed reaction vial for 2 h. The mixture was purified using reverse phase HPLC (Phenomenex, Gemini-NX, 10 um, 250×30 mm, C18 column; gradient of 20% MeCN/0.1% TFA-water to 100% MeCN/0.1% TFA), providing the title compound (27 mg). 1H NMR (400 MHz, Methanol-d4) δ 9.09 (s, 1H), 8.31 (s, 1H), 7.87 (s, 1H), 6.93 (s, 1H), 4.70-4.46 (m, 2H), 4.39-4.20 (m, 1H), 3.92 (s, 3H), 3.81-3.70 (m, 1H), 3.68-3.54 (m, 1H), 3.48-3.39 (m, 2H), 3.36 (s, 3H), 3.20-3.09 (m, 1H), 3.06 (s, 3H), 2.46-2.31 (m, 2H), 2.24-2.08 (m, 2H), 1.91-1.78 (m, 2H), 1.75-1.61 (m, 2H). LCMS [M+H]: 423.2.

Example 47

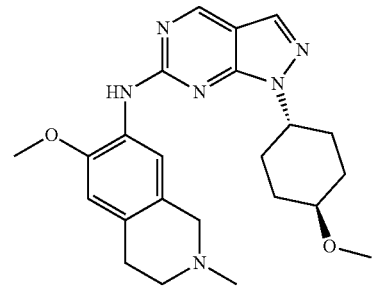

6-methoxy-N-(1-(trans-4-methoxycyclohexyl)-1H-pyrazolo[3,4-d]pyrimidin-6-yl)-2-methyl-1,2,3,4-tetrahydroisoquinolin-7-amine The above compound was prepared according to general procedure B using 6-chloro-1-(trans-4-methoxycyclohexyl)-1H-pyrazolo[3,4-d]pyrimidine (Example 35, Step 1) (55 mg, 0.21 mmol), 2-methyl-3,4-dihydro-1H-isoquinolin-7-amine (48 mg, 0.25 mmol), Pd₂(dba)₃ (19 mg, 0.02 mmol), potassium tert-butoxide (28 mg, 0.25 mmol), and (S)-BINAP (39 mg, 0.06 mmol) in THF (2.5 mL) at 120° C. in sealed reaction vial for 4 h. The mixture was purified using reverse phase HPLC (Phenomenex, Gemini-NX, 10 um, 250×30 mm, C18 column; gradient of 20% MeCN/0.1% TFA-water to 100% MeCN/0.1% TFA), providing the title compound (46 mg). 1H NMR (400 MHz, Methanol-d4) δ 9.12 (s, 1H), 8.35 (s, 1H), 7.87 (s, 1H), 7.00 (s, 1H), 4.76-4.62 (m, 1H), 4.55 (d, J=14.8 Hz, 1H), 4.34 (d, J=14.9 Hz, 1H), 3.93 (s, 3H), 3.83-3.73 (m, 1H), 3.51-3.43 (m, 1H), 3.41 (s, 3H), 3.39-3.33 (m, 2H), 3.23-3.12 (m, 1H), 3.08 (s, 3H), 2.35-2.22 (m, 2H), 2.16-2.03 (m, 4H), 1.56-1.37 (m, 2H). LCMS [M+H]: 423.1.

Example 48

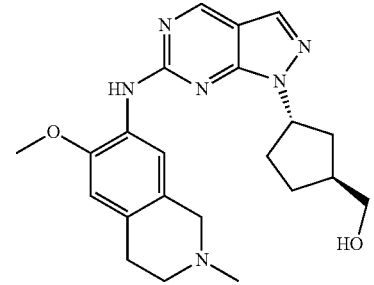 [SMILES: COc1cc2c(cc1Nc1ncc3cnn([C@H]4CC[C@H](CO)C4)c3n1)CN(C)CC2]

rac-(trans-3-(6-((6-methoxy-2-methyl-1,2,3,4-tetrahydroisoquinolin-7-yl)amino)-1H-pyrazolo[3,4-d]pyrimidin-1-yl)cyclopentyl)methanol Step 1: Preparation of rac-(trans-3-(6-chloro-1H-pyrazolo[3,4-d]pyrimidin-1-yl)cyclopentyl)methanol. To a reaction vial containing methyl rac-trans-3-(6-chloro-1H-pyrazolo[3,4-d]pyrimidin-1-yl)cyclopentane-1-carboxylate (for synthesis, see EXAMPLE 41) (351 mg, 1.25 mmol) was added anhydrous THF (9 mL) under nitrogen. The solution was cooled to 0° C. and a solution of diisobutylaluminium hydride was added dropwise (1.2 M in toluene, 2.3 mL, 2.75 mmol). After 10 min, the mixture was warmed to ambient temperature and stirred at ambient temperature for 20 minutes more before being quenched with EtOAc and Rochelle's salt at 0° C. The mixture was stirred at rt for 48 h before being purified by silica column chromatography eluting with 0% to 100% EtOAc in hexane to afford the title compound as a solid (255 mg). This material was taken directly to the next step without further purification.

Step 2: Preparation of rac-(trans-3-(6-((6-methoxy-2-methyl-1,2,3,4-tetrahydroisoquinolin-7-yl)amino)-1H-pyrazolo[3,4-d]pyrimidin-1-yl)cyclopentyl)methanol. Prepared according to general procedure A using rac-((1S,3S)-3-(6-chloro-1H-pyrazolo[3,4-d]pyrimidin-1-yl)cyclopentyl)methanol (48 mg, 0.19 mmol), 6-methoxy-2-methyl-3,4-dihydro-1H-isoquinolin-7-amine (65 mg, 0.34 mmol), and p-TSA (108 mg, 0.57 mmol) in 2-butanol (2 mL) at 101° C. in sealed reaction vessel for 48 h. The reaction mixture was purified using reverse phase HPLC (Phenomenex, Gemini-NX, 10 um, 250×30 mm, C18 column; gradient of 20% MeCN/0.1% TFA-water to 100% MeCN/0.1% TFA) providing the title compound as a solid (58 mg). 1H NMR (400 MHz, Methanol-d4) δ 8.94 (s, 1H), 8.34 (s, 1H), 8.09 (s, 1H), 6.95 (s, 1H), 5.30-5.20 (m, 1H), 4.58 (d, J=14.9 Hz, 1H), 4.34 (dd, J=15.0, 4.8 Hz, 1H), 3.95 (s, 3H), 3.82-3.73 (m, 1H), 3.62-3.51 (m, 2H), 3.42 (dt, J=11.8, 5.7 Hz, 1H), 3.30-3.22 (m, 1H), 3.19-3.12 (m, 1H), 3.08 (s, 3H), 2.60-2.50 (m, 1H), 2.32-2.22 (m, 3H), 2.17-2.08 (m, 1H), 2.08-1.97 (m, 11H), 1.61-1.47 (m, 1H). LCMS [M+H]: 409.1.

Example 49

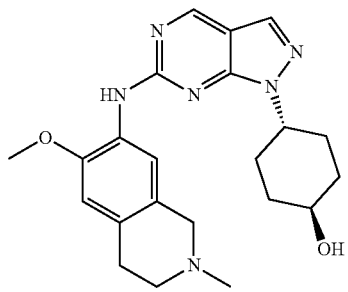 [SMILES: COc1cc2c(cc1Nc1ncc3cnn([C@H]4CC[C@H](O)CC4)c3n1)CN(C)CC2]

trans-4-(6-((6-methoxy-2-methyl-1,2,3,4-tetrahydroisoquinolin-7-yl)amino)-1H-pyrazolo[3,4-d]pyrimidin-1-yl)cyclohexan-1-ol Step 1: Preparation of trans-4-(6-chloro-1H-pyrazolo[3,4-d]pyrimidin-1-yl)cyclohexan-1-ol. Prepared according to general procedure D using 6-chloro-1H-pyrazolo[3,4-d]pyrimidine (1.00 g, 6.47 mmol), cis-cyclohexane-1,4-diol (2.25 g, 19.4 mmol), triphenylphosphine (5.10 g, 19.4 mmol) and DEAD (40% solution in toluene, 8.84 mL, 19.4 mmol) in THF (56 mL) at rt for 30 min. The crude product was purified reversed phase eluting with 0% to 100% acetonitrile (with 0.1% TFA added) in water (with 0.1% TFA added), providing the title compound as a solid (1.09 g). This material was taken directly to the next step without further purification.

Step 2: Preparation of trans-4-(6-((6-methoxy-2-methyl-1,2,3,4-tetrahydroisoquinolin-7-yl)amino)-1H-pyrazolo[3,4-d]pyrimidin-1-yl)cyclohexan-1-ol. Prepared according to general procedure A using (1r,4r)-4-(6-chloro-1H-pyrazolo[3,4-d]pyrimidin-1-yl)cyclohexan-1-ol (1.09 g, 4.3 mmol), 6-methoxy-2-methyl-3,4-dihydro-1H-isoquinolin-7-amine (1.49 g, 7.76 mmol), and p-TSA (2.5 g, 12.9 mmol) in 2-butanol (40 mL) at 120° C. in sealed reaction vial for 4 days. The crude product was purified reversed phase eluting with 0% to 100% acetonitrile (with 0.1% TFA added) in water (with 0.1% TFA added). The TFA salt obtained was then basified, extracted with DCM and purified by silica column chromatography eluting with 0% to 20% MeOH in DCM to afford the title compound as free base. The free base was then converted into HCl salt as a solid (1.26 g). 1H NMR (400 MHz, Methanol-d4) δ 9.11 (s, 1H), 8.27 (s, 1H), 8.21 (s, 1H), 6.97 (s, 1H), 4.78-4.72 (m, 1H), 4.62 (d, J=14.9 Hz, 1H), 4.38 (d, J=14.9 Hz, 1H), 4.05 (s, 3H), 3.89-3.77 (m, 2H), 3.59-3.46 (m, 2H), 3.29-3.20 (m, 1H), 3.18 (s, 3H), 2.35-2.12 (m, 6H), 1.78-1.57 (m, 2H). LCMS [M+H]: 409.1.

Example 50

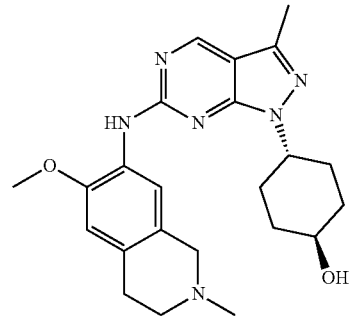 [SMILES: COc1cc2c(cc1Nc1ncc3c(C)nn([C@H]4CC[C@H](O)CC4)c3n1)CN(C)CC2]

trans-4-(6-((6-methoxy-2-methyl-1,2,3,4-tetrahydroisoquinolin-7-yl)amino)-3-methyl-1H-pyrazolo[3,4-d]pyrimidin-1-yl)cyclohexan-1-ol Step 1: Preparation of trans-4-(6-chloro-3-methyl-1H-pyrazolo[3,4-d]pyrimidin-1-yl)cyclohexan-1-ol. Prepared according to general procedure D using 6-chloro-3-methyl-1H-pyrazolo[3,4-d]pyrimidine (400 mg, 2.37 mmol), cis-cyclohexane-1,4-diol (827 mg, 7.12 mmol), triphenylphosphine (1.87 g, 7.12 mmol) and DEAD (40% solution in toluene, 3.24 mL, 7.12 mmol) in THF (20 mL) at rt for 35 min. The crude product was purified by silica column chromatography eluting with 0% to 100% EtOAc in hexanes to afford the title compound as a solid (320 mg). This material was taken directly to the next step without further purification.

Step 2: Preparation of (trans)-4-(6-((6-methoxy-2-methyl-1,2,3,4-tetrahydroisoquinolin-7-yl)amino)-3-methyl-1H-pyrazolo[3,4-d]pyrimidin-1-yl)cyclohexan-1-ol. Prepared according to general procedure A using (1r,4r)-4-

(6-chloro-3-methyl-1H-pyrazolo[3,4-d]pyrimidin-1-yl)cyclohexan-1-ol (50 mg, 0.19 mmol), 6-methoxy-2-methyl-3,4-dihydro-1H-isoquinolin-7-amine (65 mg, 0.34 mmol), and p-TSA (107 mg, 0.56 mmol) in 2-butanol (2.5 mL) in sealed reaction vial at 120° C. for 2.5 h. The reaction mixture was purified using reverse phase HPLC (Phenomenex, Gemini-NX, 10 um, 250×30 mm, C18 column; gradient of 20% MeCN/0.1% TFA-water to 100% MeCN/0.1% TFA) providing the title compound as a solid (21 mg). 1H NMR (400 MHz, Methanol-d4, TFA salt) δ 9.12 (s, 1H), 7.93 (s, 1H), 7.08 (s, 1H), 4.58 (d, J=13.2, 8.6 Hz, 2H), 4.37 (d, J=15.0 Hz, 1H), 3.95 (s, 3H), 3.87-3.76 (m, 1H), 3.76-3.63 (m, 1H), 3.54-3.41 (m, 1H), 3.41-3.32 (m, 11H), 3.27-3.17 (m, 1H), 3.10 (s, 3H), 2.56 (s, 3H), 2.22-2.09 (m, 4H), 2.08-1.97 (m, 2H), 1.61-1.44 (m, 2H). LCMS [M+H]: 423.2.

Example 51

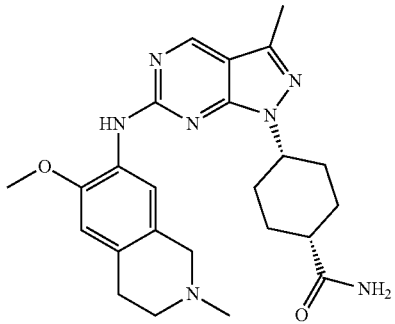 [SMILES: COc1cc2c(cc1Nc1ncc3c(C)nn([C@H]4CC[C@@H](C(N)=O)CC4)c3n1)CN(C)CC2]

(cis)-4-(6-((6-methoxy-2-methyl-1,2,3,4-tetrahydroisoquinolin-7-yl)amino)-3-methyl-1H-pyrazolo[3,4-d]pyrimidin-1-yl)cyclohexane-1-carboxamide Step 1: Preparation of methyl (cis)-4-(6-chloro-3-methyl-1H-pyrazolo[3,4-d]pyrimidin-1-yl)cyclohexane-1-carboxylate. Prepared according to general procedure D using 6-Chloro-3-methyl-1H-pyrazolo[3,4-d]pyrimidine (400 mg, 2.37 mmol), trans-methyl 4-hydroxycyclohexanecarboxylate (450 mg, 2.85 mmol), triphenylphosphine (1.24 g, 4.75 mmol) and DEAD (40% solution in toluene, 2.16 mL, 4.75 mmol) in THF (10 mL) at rt for 1 h. The crude product was purified by silica column chromatography eluting with 0% to 100% EtOAc in hexanes to afford the title compound as a solid (820 mg). This material was taken directly to the next step without further purification.

Step 2: Preparation of methyl (cis)-4-(6-((6-methoxy-2-methyl-1,2,3,4-tetrahydroisoquinolin-7-yl)amino)-3-methyl-1H-pyrazolo[3,4-d]pyrimidin-1-yl)cyclohexane-1-carboxylate. Prepared according to general procedure B using methyl (cis)-4-(6-chloro-3-methyl-1H-pyrazolo[3,4-d]pyrimidin-1-yl)cyclohexane-1-carboxylate (314 mg, 1.0 mmol), 6-methoxy-2-methyl-3,4-dihydro-1H-isoquinolin-7-amine (235 mg, 1.22 mmol), Pd$_2$(dba)$_3$ (93 mg, 0.10 mmol), potassium tert-butoxide (137 mg, 1.22 mmol), and (S)-BINAP (190 mg, 0.31 mmol) in THF (12 mL) at 120° C. using microwave reactor for 90 min. The crude product was purified by silica column chromatography eluting with 0% to 20% MeOH in DCM to afford the title compound as a solid (802 mg). This material was taken directly to the next step without further purification.

Step 3: Preparation of (cis)-4-(6-((6-methoxy-2-methyl-1,2,3,4-tetrahydroisoquinolin-7-yl)amino)-3-methyl-1H-pyrazolo[3,4-d]pyrimidin-1-yl)cyclohexane-1-carboxylic acid. To the solution of methyl (1s,4s)-4-(6-((6-methoxy-2-methyl-1,2,3,4-tetrahydroisoquinolin-7-yl)amino)-3-methyl-1H-pyrazolo[3,4-d]pyrimidin-1-yl)cyclohexane-1-carboxylate (400 mg, 0.86 mmol) in MeOH (8 mL) and water (4 mL) were added LiOH (25 mg, 1.0 mmol) and NaOH (2M water solution, 0.52 mL, 1.0 mmol). The mixture was stirred at rt for 48 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the title compound (383 mg).

Step 4: Preparation of (cis)-4-(6-((6-methoxy-2-methyl-1,2,3,4-tetrahydroisoquinolin-7-yl)amino)-3-methyl-1H-pyrazolo[3,4-d]pyrimidin-1-yl)cyclohexane-1-carboxamide. To the solution of (1s,4s)-4-(6-((6-methoxy-2-methyl-1,2,3,4-tetrahydroisoquinolin-7-yl)amino)-3-methyl-1H-pyrazolo[3,4-d]pyrimidin-1-yl)cyclohexane-1-carboxylic acid (50 mg, 0.09 mmol) in DMF (3 mL) and EtOAc (1.5 mL) were added methylimidazole (87 mg, 1.1 mmol), ammonium chloride (47 mg, 0.89 mmol) and 1-propylphosphonic acid cyclic anhydride, 50+% soln. in EtOAc (0.13 mL, 0.22 mmol). The mixture was stirred at rt for 48 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the desire product as a solid (8 mg). 1H NMR (400 MHz, Methanol-d4) δ 8.94 (s, 1H), 8.21 (s, 1H), 6.97 (s, 1H), 4.69-4.49 (m, 2H), 4.35 (d, J=14.9 Hz, 1H), 3.95 (s, 3H), 3.84-3.73 (m, 1H), 3.50-3.36 (m, 1H), 3.29-3.12 (m, 2H), 3.09 (s, 3H), 2.63-2.55 (m, 1H), 2.52 (s, 3H), 2.49-2.34 (m, 2H), 2.31-2.18 (m, 2H), 2.03-1.90 (m, 2H), 1.87-1.76 (m, 2H). LCMS [M+H]: 450.3.

Example 52

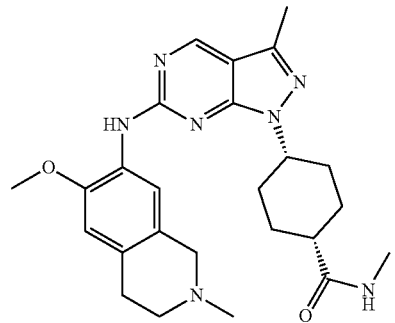

(cis)-4-(6-((6-methoxy-2-methyl-1,2,3,4-tetrahydroisoquinolin-7-yl)amino)-3-methyl-1H-pyrazolo[3,4-d]pyrimidin-1-yl)-N-methylcyclohexane-1-carboxamide To the solution of (cis)-4-(6-((6-methoxy-2-methyl-1,2,3,4-tetrahydroisoquinolin-7-yl)amino)-3-methyl-1H-pyrazolo[3,4-d]pyrimidin-1-yl)cyclohexane-1-carboxylic acid (Example 51, Step 3) (50 mg, 0.09 mmol) in DMF (1.5 mL) and EtOAc (0.7 mL) were added methylimidazole (85 uL, 0.08 mmol), methylamine (2M solution in THF, 0.44 mL, 0.89 mmol) and 1-propylphosphonic acid cyclic anhydride, 50+% soln. in EtOAc (0.13 mL, 0.22 mmol). The mixture was stirred at rt for 48 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the desire product as a solid (30 mg). 1H NMR (400 MHz, Methanol-d4) δ 8.96 (s, 1H), 8.12 (s, 11H), 6.98 (s, 1H), 4.72-4.62 (m, 1H), 4.57 (d, J=15.0 Hz, 1H), 4.35 (d, J=14.9 Hz, 1H), 3.94 (s, 3H), 3.85-3.70 (m, 1H), 3.51-3.38 (m, 1H), 3.30-3.22 (m, 1H), 3.22-3.11 (m, 1H), 3.09 (s, 3H), 2.72 (s, 3H), 2.52 (s, 3H), 2.52-2.47 (m, 1H), 2.45-2.31 (m, 2H), 2.27-2.13 (m, 2H), 1.99-1.87 (m, 2H), 1.85-1.69 (m, 2H). LCMS [M+H]: 464.3.

Example 53

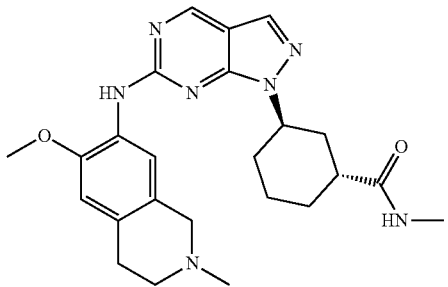

(1R,3R)-3-(6-(((6-methoxy-2-methyl-1,2,3,4-tetrahydroisoquinolin-7-yl)amino)-1H-pyrazolo[3,4-d]pyrimidin-1-yl)-N-methylcyclohexane-1-carboxamide To the solution of (1R,3R)-3-(6-(((6-methoxy-2-methyl-1,2,3,4-tetrahydroisoquinolin-7-yl)amino)-1H-pyrazolo[3,4-d]pyrimidin-1-yl)cyclohexane-1-carboxylic acid (EXAMPLE 31, Step 3) (40 mg, 0.07 mmol) in DMF (1.5 mL) and EtOAc (0.7 mL) were added methylimidazole (70 uL, 0.87 mmol), methylamine (2M solution in THF, 0.36 mL, 0.73 mmol) and 1-propylphosphonic acid cyclic anhydride (50+% soln. in EtOAc, 0.11 mL, 0.11 mmol). The mixture was stirred at rt for 4 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the desire product as a solid (21 mg). 1H NMR (400 MHz, Methanol-d4) δ 8.96 (s, 1H), 8.52 (d, J=18.4 Hz, 1H), 8.11 (s, 1H), 6.95 (s, 1H), 5.50-5.38 (m, 1H), 4.74 (dd, J=23.2, 15.1 Hz, 1H), 4.42 (dd, J=15.1, 10.6 Hz, 1H), 3.97 (s, 3H), 3.83-3.74 (m, 1H), 3.50-3.39 (m, 1H), 3.29-3.22 (m, 1H), 3.19-3.13 (m, 1H), 3.11 (s, 3H), 2.92-2.84 (m, 1H), 2.74 (s, 3H), 2.32-2.21 (m, 1H), 2.20-2.08 (m, 2H), 2.01-1.71 (m, 5H). LCMS [M+H]: 450.3.

Example 54

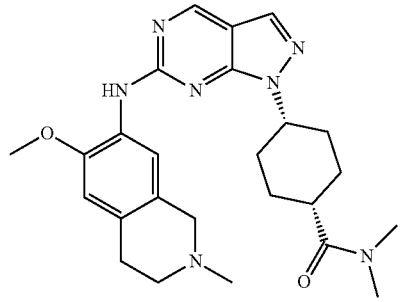

(1s,4s)-4-(6-(((6-methoxy-2-methyl-1,2,3,4-tetrahydroisoquinolin-7-yl)amino)-1H-pyrazolo[3,4-d]pyrimidin-1-yl)-N,N-dimethylcyclohexane-1-carboxamide To the solution of (1s,4s)-4-(6-(((6-methoxy-2-methyl-1,2,3,4-tetrahydroisoquinolin-7-yl)amino)-1H-pyrazolo[3,4-d]pyrimidin-1-yl)cyclohexane-1-carboxylic acid (EXAMPLE 26, Step 3) (40 mg, 0.07 mmol) in EtOAc (1 mL) were added methylimidazole (18 uL, 0.22 mmol), dimethylamine (2M solution in THF, 0.36 mL, 0.73 mmol) and 1-propylphosphonic acid cyclic anhydride, 50+% soln. in EtOAc(0.11 mL, 0.18 mmol). The mixture was stirred at rt for 6 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the desire product as a solid (29 mg). 1H NMR (400 MHz, Methanol-d4) δ 9.12 (s, 1H), 8.35 (s, 1H), 7.99 (s, 1H), 7.06 (s, 11H), 4.88-4.79 (m, 1H), 4.59 (d, J=14.2 Hz, 1H), 4.37 (d, J=14.3 Hz, 1H), 3.95 (s, 3H), 3.85-3.74 (m, 1H), 3.53-3.40 (m, 1H), 3.41-3.33 (m, 1H), 3.25-3.20 (m, 1H), 3.15 (s, 3H), 3.09 (s, 3H), 3.03-2.97 (m, 1H), 2.94 (s, 3H), 2.66-2.43 (m, 2H), 2.17-1.94 (m, 4H), 1.86-1.69 (m, 2H). [M+H]: 464.2.

Example 55

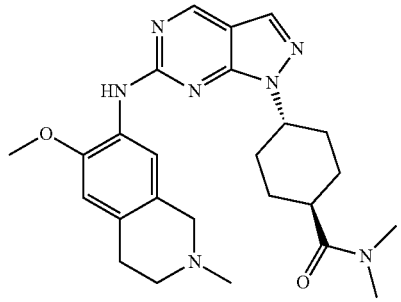

(1r,4r)-4-(6-(((6-methoxy-2-methyl-1,2,3,4-tetrahydroisoquinolin-7-yl)amino)-1H-pyrazolo[3,4-d]pyrimidin-1-yl)-N,N-dimethylcyclohexane-1-carboxamide To the solution of (1r,4r)-4-(6-(((6-methoxy-2-methyl-1,2,3,4-tetrahydroisoquinolin-7-yl)amino)-1H-pyrazolo[3,4-d]

pyrimidin-1-yl)cyclohexane-1-carboxylic acid (EXAMPLE 37) (39 mg, 0.09 mmol) in EtOAc (1 mL) were added methylimidazole (21 uL, 0.27 mmol), dimethylamine (2M solution in THF, 0.45 mL, 0.90 mmol) and 1-propylphosphonic acid cyclic anhydride (50+% soln. in EtOAc, 0.13 mL, 0.22 mmol). The mixture was stirred at rt for 48 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the desire product as a solid (19 mg). 1H NMR (400 MHz, Methanol-d4) δ 9.16 (s, 11H), 8.41 (s, 1H), 7.96 (s, 1H), 7.09 (s, 1H), 4.79-4.66 (m, 11H), 4.59 (d, J=14.7 Hz, 1H), 4.38 (d, J=14.7 Hz, 11H), 3.95 (s, 3H), 3.88-3.75 (m, 1H), 3.53-3.43 (m, 1H), 3.41-3.33 (m, 1H), 3.25-3.21 (m, 1H), 3.18 (s, 3H), 3.11 (s, 3H), 2.97 (s, 3H), 2.93-2.83 (m, 1H), 2.22-2.10 (m, 4H), 2.06-1.96 (m, 2H), 1.85-1.67 (m, 2H). [M+H]: 464.3.

Example 56

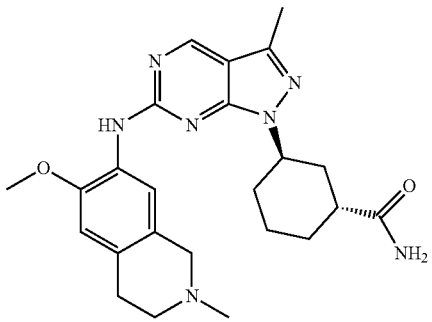 [SMILES: COc1cc2c(cc1Nc1ncc3c(C)nn([C@@H]4CCC[C@@H](C(N)=O)C4)c3n1)CN(C)CC2]

(1R,3R)-3-(6-((6-methoxy-2-methyl-1,2,3,4-tetrahydroisoquinolin-7-yl)amino)-3-methyl-1H-pyrazolo[3,4-d]pyrimidin-1-yl)cyclohexane-1-carboxamide Step 1: Preparation of methyl (1R,3R)-3-(6-chloro-3-methyl-1H-pyrazolo[3,4-d]pyrimidin-1-yl)cyclohexane-1-carboxylate. Prepared according to general procedure D using 6-Chloro-3-methyl-1H-pyrazolo[3,4-d]pyrimidine (400 mg, 2.37 mmol), methyl (1R,3S)-3-hydroxycyclohexanecarboxylate (450 mg, 2.85 mmol), triphenylphosphine (1.24 g, 4.75 mmol) and DEAD (40% solution in toluene, 2.16 mL, 4.75 mmol) in THF (10 mL) at rt for 0.5 h. The crude product was purified by silica column chromatography eluting with 0% to 100% EtOAc in hexanes to afford the title compound as a solid (431 mg). This material was taken directly to the next step without further purification.

Step 2: Preparation of methyl (1R,3R)-3-(6-((6-methoxy-2-methyl-1,2,3,4-tetrahydroisoquinolin-7-yl)amino)-3-methyl-1H-pyrazolo[3,4-d]pyrimidin-1-yl)cyclohexane-1-carboxylate. Prepared according to general procedure B using methyl (1R,3R)-3-(6-chloro-3-methyl-1H-pyrazolo[3,4-d]pyrimidin-1-yl)cyclohexane-1-carboxylate (314 mg, 1.0 mmol), 6-methoxy-2-methyl-3,4-dihydro-1H-isoquinolin-7-amine (235 mg, 1.22 mmol), Pd₂(dba)₃ (93 mg, 0.10 mmol), potassium tert-butoxide (137 mg, 1.22 mmol), and (S)-BINAP (190 mg, 0.30 mmol) in THF (12 mL) at 120° C. using microwave reactor for 90 min. The crude product was purified by silica column chromatography eluting with 0% to 20% MeOH in DCM to afford the title compound as a solid (400 mg). This material was taken directly to the next step without further purification.

Step 3: Preparation of (1R,3R)-3-(6-((6-methoxy-2-methyl-1,2,3,4-tetrahydroisoquinolin-7-yl)amino)-3-methyl-1H-pyrazolo[3,4-d]pyrimidin-1-yl)cyclohexane-1-carboxylic acid. To the solution of methyl (1R,3R)-3-(6-((6-methoxy-2-methyl-1,2,3,4-tetrahydroisoquinolin-7-yl)amino)-3-methyl-1H-pyrazolo[3,4-d]pyrimidin-1-yl)cyclohexane-1-carboxylate (400 mg, 0.86 mmol) in MeOH (8 mL) and water (4 mL) were added LiOH (25 mg, 1.0 mmol) and NaOH (2M water solution, 0.52 mL, 1.0 mmol). The mixture was stirred at rt for 72 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the title compound (209 mg).

Step 4: Preparation of (1R,3R)-3-(6-((6-methoxy-2-methyl-1,2,3,4-tetrahydroisoquinolin-7-yl)amino)-3-methyl-1H-pyrazolo[3,4-d]pyrimidin-1-yl)cyclohexane-1-carboxamide. To the solution of (1R,3R)-3-(6-((6-methoxy-2-methyl-1,2,3,4-tetrahydroisoquinolin-7-yl)amino)-3-methyl-1H-pyrazolo[3,4-d]pyrimidin-1-yl)cyclohexane-1-carboxylic acid (50 mg, 0.09 mmol) in DMF (3 mL) and EtOAc (1.5 mL) were added methylimidazole (85 uL, 1.1 mmol), ammonium chloride (47 mg, 0.89 mmol) and 1-propylphosphonic acid cyclic anhydride, 50+% soln. in EtOAc (0.13 mL, 0.22 mmol). The mixture was stirred at rt for 48 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the title compound as a solid (27 mg). 1H NMR (400 MHz, Methanol-d4) δ 9.23 (d, J=2.6 Hz, 1H), 8.29 (d, J=22.4 Hz, 1H), 7.01 (s, 1H), 5.43-5.30 (m, 1H), 4.76 (t, J=14.8 Hz, 1H), 4.44 (dd, J=15.2, 11.1 Hz, 1H), 3.95 (s, 3H), 3.86-3.74 (m, 1H), 3.48 (td, J=11.6, 5.0 Hz, 1H), 3.40-3.33 (m, 1H), 3.22-3.15 (m, 1H), 3.12 (d, J=1.3 Hz, 3H), 3.01-2.90 (m, 1H), 2.58 (s, 3H), 2.26-2.17 (m, 1H), 2.17-2.06 (m, 2H), 2.05-1.93 (m, 2H), 1.90-1.71 (m, 3H). [M+H] 450.3.

Example 57

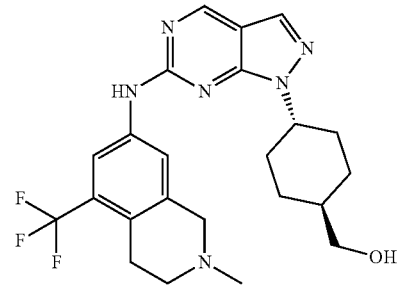 [SMILES: CN1CCc2c(cc(Nc3ncc4cnn([C@H]5CC[C@H](CO)CC5)c4n3)cc2C(F)(F)F)C1]

((1r,4r)-4-(6-((2-methyl-5-(trifluoromethyl)-1,2,3,4-tetrahydroisoquinolin-7-yl)amino)-1H-pyrazolo[3,4-d]pyrimidin-1-yl)cyclohexyl)methanol Step 1: Preparation of (1s,4s)-4-(((tert-butyldiphenylsilyl)oxy)methyl)cyclohexan-1-ol. To a solution of 4-(hydroxymethyl)cyclohexanol (1 g, 7.68 mmol) in DMF (100 mL) was added imidazole (1.05 g, 15.36 mmol) and tert-butyl-chlorodiphenyl-silane (2.11 g, 7.68 mmol, 1.97 mL). The mixture was stirred at 25° C. for 2 h. The mixture was diluted with water (500 mL) and extracted with MTBE:EtOAc=1:1 (2×200 mL). The combined organic layer was dried over anhydrous sodium sulfate, filtered and concentrated. The residue was purified by flash silica gel chromatography eluting with a gradient of 0% to 25% EtOAc in petroleum ether to give 4-[[tert-butyl(diphenyl)silyl]oxymethyl]cyclohexanol (850 mg).

Step 2: Preparation of 1-((1r,4r)-4-(((tert-butyldiphenylsilyl)oxy)methyl)cyclohexyl)-6-chloro-1H-pyrazolo[3,4-d]pyrimidine. To a solution of (1s,4s)-4-(((tert-butyldiphenylsilyl)oxy)methyl)cyclohexan-1-ol (850 mg, 2.31 mmol) and 6-chloro-1H-pyrazolo[3,4-d]pyrimidine (297 mg, 1.92 mmol) in THF (0.5 mL) was added triphenylphosphine (907 mg, 3.46 mmol) and DEAD (40% solution in toluene, 796 mg, 3.46 mmol) at 0° C. The mixture was stirred at 25° C. for 4 h. The mixture was concentrated. The residue was purified by flash silica gel chromatography using 0% to 25% Petroleum ether/Ethyl acetate ether gradient to give 1-((1r,4r)-4-(((tert-butyldiphenylsilyl)oxy)methyl)cyclohexyl)-6-chloro-1H-pyrazolo[3,4-d]pyrimidine (940 mg).

Step 3: Preparation of ((1r,4r)-4-(6-((2-methyl-5-(trifluoromethyl)-1,2,3,4-tetrahydroisoquinolin-7-yl)amino)-1H-pyrazolo[3,4-d]pyrimidin-1-yl)cyclohexyl)methanol. A mixture of 2-methyl-5-(trifluoromethyl)-3,4-dihydro-1H-isoquinolin-7-amine (95.0 mg, 415 umol), 1-((1r,4r)-4-(((tert-butyldiphenylsilyl)oxy)methyl)cyclohexyl)-6-chloro-1H-pyrazolo[3,4-d]pyrimidine (300 mg, 594 umol) and TsOH (307 mg, 1.78 mmol) in 2-butanol (2 mL) was stirred at 100° C. for 12 h. The reaction mixture was diluted with sat. NaHCO₃ (3 mL) and extracted with DCM (3×10 mL). The combined organic layer was dried over sodium sulfate, filtered and concentrated under reduced pressure. The residue was purified by prep-HPLC (column: Welch Xtimate C18 150×30 mm×5 um; mobile phase: [water (0.05% NH3H2O+10 mM NH4HCO3)-CAN]; B %: 40%-70%, 9 min). The product was dissolved with MeCN (1 mL) and H2O (3 mL), then was neutralized with 1N HCl to ~pH 4 to afford the title compound (16 mg). ¹H NMR (400 MHz, DMSO-d6) δ:11.17 (br s, 1H), 10.33 (s, 1H), 9.05 (s, 1H), 8.58 (s, 1H), 8.12 (s, 1H), 7.77 (s, 2H), 4.50-4.59 (m, 2H), 4.35-4.42 (m, 1H), 3.68-3.71 (m, 2H), 3.22-3.40 (m, 4H), 3.10-3.15 (m, 1H), 2.92-2.94 (d, J=4.4 Hz, 2H), 1.93-2.01 (m, 6H), 1.47-1.54 (m, 1H), 1.07-1.18 (m, 2H). LCMS [M+H]: 461.2

Example 58

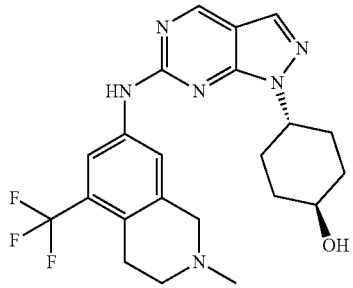 [SMILES: CN1CCc2c(cc(Nc3ncc4cnn([C@H]5CC[C@H](O)CC5)c4n3)cc2C(F)(F)F)C1]

(1r,4r)-4-(6-((2-methyl-5-(trifluoromethyl)-1,2,3,4-tetrahydroisoquinolin-7-yl)amino)-1H-pyrazolo[3,4-d]pyrimidin-1-yl)cyclohexan-1-ol Step 1: Preparation of (1s,4s)-4-((tert-butyldimethylsilyl)oxy)cyclohexan-1-ol. To a solution of cyclohexane-1,4-diol (3.0 g, 25.8 mmol) in DMF (30 mL) were added imidazole (2.2 g, 32.3 mmol) and tert-butyldimethylsilylchloride (4.9 g, 32.3 mmol, 4.0 mL) at 0° C. The mixture was stirred at 25° C. for 15 h. The reaction mixture was diluted with water (100 mL) extracted with EtOAc (3×50 mL). The combined organic layers were washed with brine (50 mL), dried over anhydrous sodium sulfate, filtered and concentrated under reduced pressure. The residue was purified by flash silica gel chromatography eluting with 0% to 7% Ethyl acetate and petroleum ether gradient to give the desired product 4-(tert-butyl-chloro-methyl-silyl)oxycyclohexanol (0.8 g).

Step 2: Preparation of 1-((1r,4r)-4-((tert-butyldimethylsilyl)oxy)cyclohexyl)-6-chloro-1H-pyrazolo[3,4-d]pyrimidine. Prepared according to general procedure D using 6-chloro-1H-pyrazolo[3,4-d]pyrimidine (200 mg, 1.29 mmol), (1s,4s)-4-((tert-butyldimethylsilyl)oxy)cyclohexan-1-ol (447 mg, 1.94 mmol), triphenylphosphine (611 mg, 2.33 mmol), and DEAD (40% solution in toluene, 405 mg, 2.33 mmol) in THF (2 mL) at 25° C. for 16 h. The reaction mixture was extracted with EtOAc. The combined organic layers were washed with brine, dried over sodium sulfate, filtered and concentrated under reduced pressure. The residue was purified by silica column chromatography eluting with 0% to 5% Ethyl acetate/Petroleum ether to afford the title compound (150 mg).

Step 3: Preparation of (1r,4r)-4-(6-((2-methyl-5-(trifluoromethyl)-1,2,3,4-tetrahydroisoquinolin-7-yl)amino)-1H-pyrazolo[3,4-d]pyrimidin-1-yl)cyclohexan-1-ol. Prepared according to general procedure A. To a solution of 2-methyl-5-(trifluoromethyl)-3,4-dihydro-1H-isoquinolin-7-amine (50.0 mg, 0.217 mmol) in 2-butanol (1 mL) was added p-TSA (124.0 mg, 0.651 mmol) and 1-((1r,4r)-4-((tert-butyldimethylsilyl)oxy)cyclohexyl)-6-chloro-1H-pyrazolo[3,4-d]pyrimidine (104.0 mg, 0.282 mmol). The mixture was stirred at 110° C. for 15 h. The reaction mixture was then poured into saturated aq. NaHCO₃ and extracted with DCM/MeOH (10:1). The combined organics were washed with brine, dried over anhydrous sodium sulfate, filtered and concentrated under reduced pressure. The crude product was purified by reversed-phase HPLC (column: Phenomenex Gemini-NX C18 75×30 mm×3 um; mobile phase: [water (0.05% NH3H2O+10 mM NH4HCO3)-ACN]; B %: 36%-66%, 7 min). The partially pure product was purified again by reversed-phase HPLC (column: Phenomenex Synergi C18 150×30 mm×4 um; mobile phase: [water (0.05% HCl)-ACN]; B %: 22%-52%, 9 min) to give the title compound (26 mg). ¹H NMR (400 MHz, DMSO-d6) δ: 11.08 (br s, 1H), 10.34 (s, 1H), 9.04 (s, 1H), 8.64 (s, 1H), 8.12 (s, 1H), 7.72 (s, 1H), 4.52-4.60 (m, 2H), 4.35-4.42 (m, 1H), 3.68-3.72 (m, 1H), 3.53-3.59 (m, 1H), 3.22-3.38 (m, 2H), 3.11-3.16 (m, 2H), 2.92-2.94 (d, J=4.4 Hz, 3H), 1.98-2.07 (m, 6H), 1.35-1.45 (m, 2H). LCMS [M+H]: 447.2.

Example 59

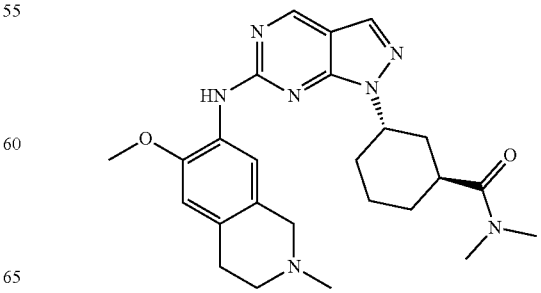

rac-(trans)-3-(6-((6-methoxy-2-methyl-1,2,3,4-tetra-hydroisoquinolin-7-yl)amino)-1H-pyrazolo[3,4-d]pyrimidin-1-yl)-N,N-dimethylcyclohexane-1-carboxamide To the solution of rac-(trans)-3-(6-((6-methoxy-2-methyl-1,2,3,4-tetrahydroisoquinolin-7-yl)amino)-1H-pyrazolo[3,4-d]pyrimidin-1-yl)cyclohexane-1-carboxylic acid (Example 28, Step 3) (42 mg, 0.07 mmol) in EtOAc (1 mL) were added methylimidazole (18 mg, 0.22 mmol), dimethylamine (2M solution in THF, 0.36 mL, 0.73 mmol) and 1-propylphosphonic acid cyclic anhydride, 50+% soln. in EtOAc (0.11 mL, 0.18 mmol). The mixture was stirred at rt for 3 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the title compound as a solid (23 mg). 1H NMR (400 MHz, Methanol-d4) δ 9.20 (s, 1H), 8.43 (s, 11H), 8.25 (d, J=12.3 Hz, 1H), 7.07 (s, 1H), 5.63-5.52 (m, 1H), 4.77-4.65 (m, 1H), 4.44 (d, J=15.2 Hz, 1H), 3.98 (s, 3H), 3.86-3.76 (m, 1H), 3.53-3.42 (m, 2H), 3.39-3.32 (m, 1H), 3.24-3.16 (m, 1H), 3.14-3.07 (m, 6H), 2.98 (d, J=4.1 Hz, 3H), 2.32-2.20 (m, 1H), 2.20-2.09 (m, 2H), 2.03-1.92 (m, 1H), 1.90-1.72 (m, 4H). LCMS [M+H]: 464.2.

Example 60

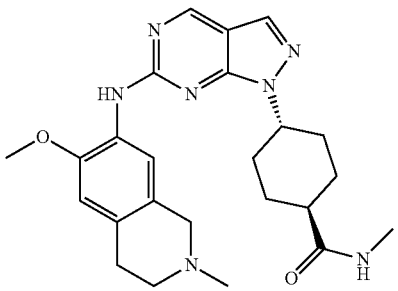

(1r,4r)-4-(6-((6-methoxy-2-methyl-1,2,3,4-tetrahydroisoquinolin-7-yl)amino)-1H-pyrazolo[3,4-d]pyrimidin-1-yl)-N-methylcyclohexane-1-carboxamide To the solution of (1r,4r)-4-(6-((6-methoxy-2-methyl-1,2,3,4-tetrahydroisoquinolin-7-yl)amino)-1H-pyrazolo[3,4-d]pyrimidin-1-yl)cyclohexane-1-carboxylic acid (EXAMPLE 37) (13 mg, 0.03 mmol) in DMF (1.5 mL) and EtOAc (0.7 mL) were added methylimidazole (23 uL, 0.28 mmol), methylamine (2M solution in THF, 0.12 mL, 0.24 mmol) and 1-propylphosphonic acid cyclic anhydride (50+% soln. in EtOAc, 35 uL, 0.06 mmol). The mixture was stirred at rt for 48 h before being purified using reverse phase HPLC (Phenomenex, Gemini-NX, 10 um, 250×30 mm, C18 column; gradient of 20% MeCN/0.1% TFA-water to 100% MeCN/0.1% TFA), providing the desire product as a solid (7 mg). 1H NMR (400 MHz, Methanol-d4) δ 9.15 (s, 1H), 8.39 (s, 1H), 7.98 (s, 1H), 7.08 (s, 1H), 4.78-4.65 (m, 1H), 4.59 (d, J=15.0 Hz, 1H), 4.39 (d, J=14.8 Hz, 1H), 3.96 (s, 3H), 3.88-3.76 (m, 1H), 3.53-3.43 (m, 1H), 3.41-3.34 (m, 1H), 3.25-3.16 (m, 1H), 3.12 (s, 3H), 2.75 (s, 3H), 2.44-2.29 (m, 1H), 2.19-2.08 (m, 4H), 2.08-1.98 (m, 2H), 1.90-1.70 (m, 2H). LCMS [M+H]: 450.1.

Example 61

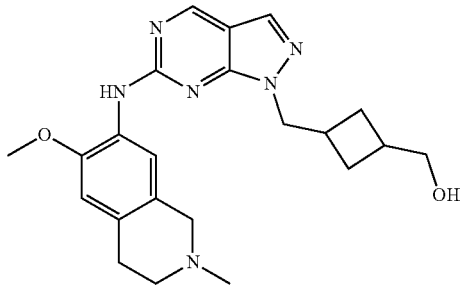 [SMILES: COc1cc2c(cc1Nc1ncc3cnn(CC4CC(CO)C4)c3n1)CN(C)CC2]

(3-((6-((6-methoxy-2-methyl-1,2,3,4-tetrahydroisoquinolin-7-yl)amino)-1H-pyrazolo[3,4-d]pyrimidin-1-yl)methyl)cyclobutyl)methanol Step 1: Preparation of (3-((6-chloro-1H-pyrazolo[3,4-d]pyrimidin-1-yl)methyl)cyclobutyl)methanol. Prepared according to general procedure D using 6-chloro-3-methyl-1H-pyrazolo[3,4-d]pyrimidine (460 mg, 2.98 mmol), [3-(hydroxymethyl)cyclobutyl]methanol (1.0 g, 8.93 mmol), triphenylphosphine (2.34 g, 8.93 mmol) and DEAD (40% solution in toluene, 4.07 mL, 8.93 mmol) in THF (16 mL) at rt for 10 min. The reaction mixture was purified using reverse phase HPLC (Phenomenex, Gemini-NX, 10 um, 250×30 mm, C18 column; gradient of 20% MeCN/0.1% TFA-water to 100% MeCN/0.1% TFA) providing the title compound as a solid (541 mg).

Step 2: Preparation of (3-((6-((6-methoxy-2-methyl-1,2,3,4-tetrahydroisoquinolin-7-yl)amino)-1H-pyrazolo[3,4-d]pyrimidin-1-yl)methyl)cyclobutyl)methanol. Prepared according to general procedure A using (3-((6-chloro-1H-pyrazolo[3,4-d]pyrimidin-1-yl)methyl)cyclobutyl)methanol (75 mg, 0.30 mmol), 6-methoxy-2-methyl-3,4-dihydro-1H-isoquinolin-7-amine (86 mg, 0.45 mmol), and p-TSA (169 mg, 0.89 mmol) in 2-butanol (3 mL) in sealed reaction vial at 120° C. for 48 h. The reaction mixture was purified using reverse phase HPLC (Phenomenex, Gemini-NX, 10 um, 250×30 mm, C18 column; gradient of 20% MeCN/0.1% TFA-water to 100% MeCN/0.1% TFA) providing the title compound as a solid (90 mg). 1H NMR (400 MHz, Methanol-d4). Δ 9.19 (s, 1H), 8.41 (s, 1H), 8.05-7.94 (m, 1H), 7.08 (s, 11H), 4.66-4.57 (m, 1H), 4.49 (d, J=7.5 Hz, 1H), 4.44-4.39 (m, 1H), 4.38-4.35 (m, 1H), 3.95 (d, J=2.4 Hz, 3H), 3.84-3.76 (m, 1H), 3.57 (d, J=6.9 Hz, 1H), 3.52-3.40 (m, 3H), 3.24-3.15 (m, 1H), 3.10 (d, J=3.0 Hz, 3H), 2.95-2.75 (m, 1H), 2.59-2.32 (m, 1H), 2.17-1.87 (m, 3H), 1.78-1.66 (m, 1H). [M+H]: 409.2.

Example 62

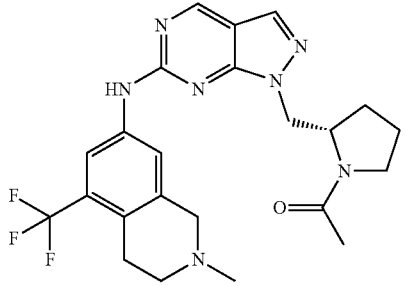 [SMILES: CC(=O)N1CCC[C@H]1Cn1ncc2cnc(Nc3cc4c(c(C(F)(F)F)c3)CCN(C)C4)nc21]

(S)-1-(2-((6-((2-methyl-5-(trifluoromethyl)-1,2,3,4-tetrahydroisoquinolin-7-yl)amino)-1H-pyrazolo[3,4-d]pyrimidin-1-yl)methyl)182thenone182ne-1-yl)ethan-1-one Step 1: Preparation of (S)-1-(2-(hydroxymethyl)182thenone182ne-1-yl)ethan-1-one. To a cooled solution (at 0° C.) of [(2S)-pyrrolidin-2-yl] methanol (2 g, 19.77 mmol, 1.92 mL) in DCM (25 mL) was treated with $K_2CO_3$ (2.73 g, 19.77 mmol) followed by acetic anhydride (2.12 g, 20.76 mmol, 1.94 mL) dropwise. The mixture was stirred at rt for 90 min. The mixture was diluted with water (20 mL) and extracted with EtOAc. The combined organic layer was dried over anhydrous sodium sulfate, filtered and concentrated. The residue was purified by silica gel column chromatography (eluting with 0 to 100% EtOAc/petroleum ether) to provide the title compound (1.76 g).

Step 2: Preparation of (S)-1-(2-((6-chloro-1H-pyrazolo[3,4-d]pyrimidin-1-yl)methyl)182thenone182ne-1-yl)ethan-1-one. Prepared according to general procedure D. A mixture of 6-chloro-1H-pyrazolo[3,4-d]pyrimidine (300 mg, 1.94 mmol), 1-[(2S)-2-(hydroxymethyl)182thenone182ne-1-yl]182thenone (333.5 mg, 2.33 mmol) and triphenylphosphine (1.02 g, 3.88 mmol) in THF (5 mL) was added DIAD (784.99 mg, 3.88 mmol, 754.80 uL) at 0° C. The reaction mixture was stirred at 30° C. for 16 h. The reaction mixture was concentrated and the crude product was purified by prep-HPLC purification (column: Xtimate C18 150×40 mm×5 um; mobile phase: [water (0.05% NH3H2O)-CAN]; B %: 10%-40%,8 min). After lyophilization the product was re-purified by silica gel column chromatography (eluting with 0 to 3% MeOH/DCM) to give the title compound (440 mg).

Step 3: Preparation of (S)-1-(2-((6-((2-methyl-5-(trifluoromethyl)-1,2,3,4-tetrahydroisoquinolin-7-yl)amino)-1H-pyrazolo[3,4-d]pyrimidin-1-yl)methyl)183thenone183ne-1-yl)ethan-1-one. Prepared according to general procedure A using 1-[(2S)-2-[(6-chloropyrazolo[3,4-d]pyrimidin-1-yl)methyl]183thenone183ne-1-yl]183thenone (80 mg, 286.00 umol),2-methyl-5-(trifluoromethyl)-3,4-dihydro-1H-isoquinolin-7-amine (72.43 mg, 314.59 umol) and TsOH (147.75 mg, 857.99 umol) in 2-butanol (2 mL) stirred at 100° C. for 16 h. The reaction mixture was evaporated and purified by prep-HPLC (column: Phenomenex Gemini-NX C18 75×30 mm×3 um; mobile phase: [water (0.05% NH3H2O+10 mM NH4HCO3)-CAN]; B %: 35%-65%,7 min) to provide the title compound (70 mg). The free amine product (25 mg) was dissolved in CAN/H2O (1:20, 30 mL) and 1M HCl was added (3 drops) at 0° C. The solution was lyophilized to give the desired product (15.5 mg, HCl salt). $^1$H NMR (400 MHz, DMSO-d6) δ: 11.41-11.46 (m, 1H), 10.34-10.38 (m, 1H), 9.05-9.10 (m, 1H), 8.33-8.46 (m, 1H), 8.15-8.21 (m, 1H), 7.96-8.05 (m, 1H), 4.73-4.89 (m, 1H), 4.35-4.60 (m, 4H), 3.67-3.71 (m, 1H), 3.21-3.41 (m, 4H), 3.09-3.14 (m, 1H), 2.93 (s, 3H), 1.73-1.94 (m,6H), 1.44-1.61 (m, 1H). LCMS [M+H]: 474.2

Example 63

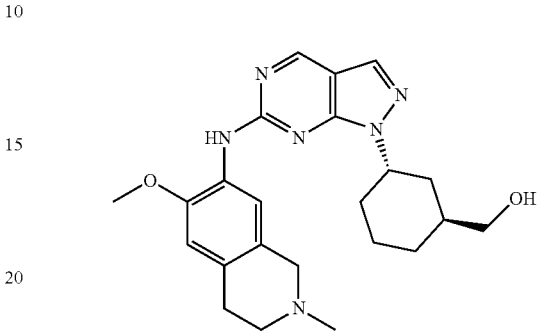

((1S,3S)-3-(6-((6-methoxy-2-methyl-1,2,3,4-tetrahydroisoquinolin-7-yl)amino)-1H-pyrazolo[3,4-d]pyrimidin-1-yl)cyclohexyl)methanol hydrochloride Step 1: Preparation of methyl (1S,3S)-3-(6-chloro-1H-pyrazolo[3,4-d]pyrimidin-1-yl)cyclohexane-1-carboxylate. Prepared according to general procedure D using methyl (1S,3R)-3-hydroxycyclohexanecarboxylate (500 mg, 3.16 mmol, 6-chloro-1H-pyrazolo[3,4-d]pyrimidine (537 mg, 3.48 mmol), triphenylphosphine (2.490 g, 9.48 mmol), and DEAD (40% solution in toluene, 1.58 mL, 3.48 mmol) at rt for 3 h. The crude product was purified by silica column chromatography eluting with 0% to 50% EtOAc/hexanes to provide the title compound (139 mg)

Step 2: Preparation of methyl (1S,3S)-3-(6-((6-methoxy-2-methyl-1,2,3,4-tetrahydroisoquinolin-7-yl)amino)-1H-pyrazolo[3,4-d]pyrimidin-1-yl)cyclohexane-1-carboxylate. Prepared according to general procedure B using methyl (1S,3S)-3-(6-chloro-1H-pyrazolo[3,4-d]pyrimidin-1-yl)cyclohexane-1-carboxylate (60 mg, 0.204 mmol), 6-methoxy-2-methyl-3,4-dihydro-1H-isoquinolin-7-amine (47 mg, 0.244 mmol), potassium tert-butoxide (27.4 mg, 0.244 mmol), Pd2(dba)3 (18.6 mg, 0.10 mol %), BINAP (38.0 mg, 0.061 mmol) in THF. The reaction was heated in a microwave reactor at 130° C. for 30 min. The reaction mixture was suspended in EA and filtered. The filtrate was concentrated and the crude product was purified by silica column chromatography eluting with 0% to 100% MeOH in EtOAc to provide the title compound (33 mg).

Step 3: ((1S,3S)-3-(6-((6-methoxy-2-methyl-1,2,3,4-tetrahydroisoquinolin-7-yl)amino)-1H-pyrazolo[3,4-d]pyrimidin-1-yl)cyclohexyl)methanol hydrochloride. DIBAL (0.15 mL, 0.180 mmol) was added dropwise to a cooled solution (−78° C.) of methyl (1S,3S)-3-[6-[(6-methoxy-2-methyl-3,4-dihydro-1H-isoquinolin-7-yl)amino]pyrazolo[3,4-d]pyrimidin-1-yl]cyclohexanecarboxylate (33.mg, 0.070 mmol) in THF (1 mL). The reaction mixture was stored at 5° C. for 40 h. MeOH (100 uL) was added to quench excess DIBAL. Water (250 uL) was added followed by 1M NaOH (aqueous, 2 mL). The reaction mixture stirred for 45 min then extracted exhaustively with EA. The organic layer was concentrated to provide the crude product. The crude product was purified by reverse phase HPLC (Phenomenex, Gemini-NX, 10 um, 250×30 mm, C18 column; gradient of 20% MeCN/0.1% TFA-water to 100% MeCN/0.1% TFA). The purified product was free based and converted to the HCl salt to provide the title compound. 1H NMR (400 MHz, cd3od) δ 8.92 (s, 1H), 8.49 (d, J=7.5 Hz, 1H), 8.04 (s, 1H), 6.95 (s, 1H), 5.03-4.94 (m, 1H), 4.59 (d, J=14.9 Hz, 1H), 4.37 (dd, J=14.7, 6.8 Hz, 1H), 3.97 (s, 3H), 3.85-3.73 (m, 1H), 3.69 (d, J=7.1 Hz, 2H), 3.49-3.40 (m, 1H), 3.29-3.22 (m, 1H), 3.17 (s, 1H), 3.09 (s, 3H), 2.24 (dddd, J=23.2, 12.9, 9.4, 4.4 Hz, 4H), 2.02-1.82 (m, 3H), 1.79-1.64 (m, 3H). LCMS [M+H]: 423.3

Example 64

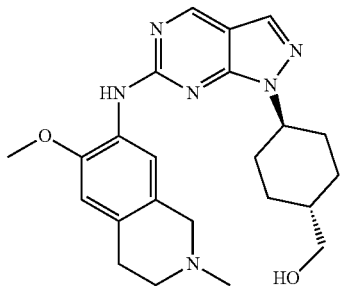 [SMILES: COc1cc2c(cc1Nc1ncc3cnn([C@H]4CC[C@H](CO)CC4)c3n1)CN(C)CC2]

cis-[4-[6-[(6-methoxy-2-methyl-3,4-dihydro-1H-isoquinolin-7-yl)amino]pyrazolo[3,4-d]pyrimidin-1-yl]cyclohexyl]methanol Step 1. Preparation of cis-4-(triisopropylsilyloxymethyl) cyclohexanol. To a cooled (0° C.) solution of cis-4-(hydroxymethyl)cyclohexanol (1.0 g, 7.7 mmol) in DCM (26 mL, 0.3 M) under nitrogen was added imidazole (1.44 g, 21.1 mmol) followed by chloro(triisopropyl)silane (1.8 mL, 8.5 mmol). The reaction mixture was stirred overnight then diluted with DCM and water. The phases were separated, the organic phase washed sequentially with 1 M HCl, saturated NaHCO₃, dried over anhydrous sodium sulfate, filtered, and concentrated to give a viscous colorless oil. The crude product was adsorbed onto silica gel and purified by silica gel chromatography (0-20% EtOAc in hexanes) to afford the title compound (2.3 g).

Step 2. Preparation of trans-[4-(6-chloropyrazolo[3,4-d]pyrimidin-1-yl)cyclohexyl]methoxy-triisopropyl-silane. Prepared according to general procedure D using 6-chloro-1H-pyrazolo[3,4-d]pyrimidine (500 mg, 3.2 mmol), cis-4-(triisopropylsilyloxymethyl)cyclohexanol (1.1 g, 3.9 mmol), and triphenylphosphine (1.7 g, 6.5 mmol) in a solution of THF (16.2 mL). Diethyl azodicarboxylate (2.95 mL, 6.5 mmol) dropwise over 30 min. The reaction mixture was warmed to ambient temperature after 10 min and stirred at rt for 3 h. The reaction mixture was quenched water and brine then extracted with EtOAc. The combined organic phase was dried over anhydrous sodium sulfate, filtered, and concentrated. The crude product was adsorbed onto silica gel then purified by silica gel chromatography (0-30% EtOAc in hexanes) to afford the title compound (489 mg).

Step 3. Preparation of cis-[4-[6-[(6-methoxy-2-methyl-3,4-dihydro-1H-isoquinolin-7-yl)amino]pyrazolo[3,4-d]pyrimidin-1-yl]cyclohexyl]methanol. Prepared according to general procedure B using 6-methoxy-2-methyl-3,4-dihydro-1H-isoquinolin-7-amine (68 mg, 0.35 mmol), trans-[4-(6-chloropyrazolo[3,4-d]pyrimidin-1-yl)cyclohexyl] methoxy-triisopropyl-silane (150 mg, 0.35 mmol), cesium carbonate (347 mg, 1.1 mmol), and Pd-PEPPSI-iPent catalyst (56.2 mg, 0.070 mmol, 20 mol %). 1,2-Dimethoxyethane (3.5 mL, 0.10 M) was added then the mixture was degassed with argon. The reaction mixture was heated to 80° C. and stirred for 3 h. The reaction mixture was cooled to ambient temperature, filtered through Celite, and concentrated. The crude product was adsorbed onto silica gel and purified by silica gel chromatography (0-10% MeOH in DCM). The product was concentrated and dissolved in DCM (1 mL) and treated with 4 N HCl (0.3 mL, 1.2 mmol) and stirred for 4 h. The reaction mixture was concentrated and the crude product was purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (62 mg). ¹H NMR (400 MHz, Methanol-d₄) δ 8.88 (s, 1H), 8.33 (s, 1H), 7.98 (s, 1H), 6.82 (s, 1H), 4.60 (tt, J=12.1, 3.8 Hz, 1H), 3.93 (s, 3H), 3.72 (s, 2H), 3.48 (d, J=6.2 Hz, 2H), 2.98 (t, J=6.0 Hz, 2H), 2.86 (t, J=6.0 Hz, 2H), 2.55 (s, 3H), 2.22 (dq, J=12.5, 3.3 Hz, 2H), 2.15-2.00 (m, 4H), 1.74-1.59 (m, 1H), 1.35-1.19 (m, 2H). LCMS [M+H]: 423.2.

Example 65

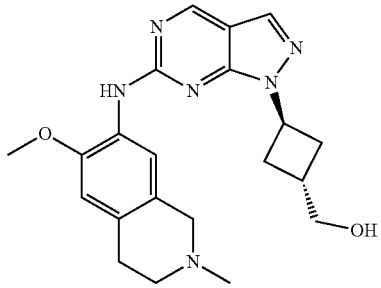 [SMILES: COc1cc2c(cc1Nc1ncc3cnn([C@H]4C[C@H](CO)C4)c3n1)CN(C)CC2]

of trans-[3-[6-[(6-methoxy-2-methyl-3,4-dihydro-1H-isoquinolin-7-yl)amino]pyrazolo[3,4-d]pyrimidin-1-yl]cyclobutyl]methanol Step 1. Preparation of trans-methyl 3-(6-chloropyrazolo[3,4-d]pyrimidin-1-yl)cyclobutanecarboxylate. Prepared according to general procedure D using 6-chloro-1H-pyrazolo[3,4-d]pyrimidine (300 mg, 1.9 mmol), cis-methyl-3-hydroxycyclobutane-1-carboxylate (303 mg, 2.3 mmol), and triphenylphosphine (764 mg, 2.9 mmol) in a solution of THF (9.7 mL). Diethyl azodicarboxylate (0.57 mL, 2.9 mmol) dropwise over 30 min. The reaction mixture was warmed to ambient temperature after 10 min and stirred at rt for 3 h. The reaction mixture was quenched with water and brine then extracted with EtOAc. The combined organic phase was dried over anhydrous sodium sulfate, filtered, and concentrated. The crude product was adsorbed onto silica gel then purified by silica gel chromatography (0-20% EtOAc in DCM) to afford the title compound (702 mg).

Step 2. Preparation of trans-[3-(6-chloropyrazolo[3,4-d]pyrimidin-1-yl)cyclobutyl]methanol. To a cooled (0° C.) solution of trans-methyl 3-(6-chloropyrazolo[3,4-d]pyrimidin-1-yl)cyclobutanecarboxylate (702 mg, 2.6 mmol) in THF (26 mL, 0.10 M) under nitrogen was added a solution of DIBAL (1.2 M in THF, 4.8 mL, 5.8 mmol) dropwise. The reaction mixture was warmed to ambient temperature after 20 min and stirred for 2 h. The reaction was cooled to ° 0 C and quenched with excess EtOAc. An aqueous solution of Rochelle's salt (10% w/v) was added, and the mixture was stirred for 48 h. The phases were separated, the organic phase dried over anhydrous sodium sulfate, filtered, and concentrated. The crude product was adsorbed onto silica gel and purified by flash (0-50% EtOAc in hexanes) to afford the title compound (184 mg).

Step 3. Preparation of trans-[3-[6-[(6-methoxy-2-methyl-3,4-dihydro-1H-isoquinolin-7-yl)amino]pyrazolo[3,4-d]pyrimidin-1-yl]cyclobutyl]methanol. Prepared according to general procedure B using 6-methoxy-2-methyl-3,4-dihydro-1H-isoquinolin-7-amine (60 mg, 0.31 mmol), [3-(6-chloropyrazolo[3,4-d]pyrimidin-1-yl)cyclobutyl]methanol (75 mg, 0.31 mmol), cesium carbonate (307 mg, 0.94 mmol), and Pd-PEPPSI-iPent catalyst (50 mg, 0.063 mmol, 20 mol %) in 1,2-dimethoxyethane (3.1 mL) stirred at 80° C. for 3 h. The reaction mixture was cooled to ambient temperature, filtered through Celite, and concentrated. The crude product was adsorbed onto silica gel and purified by silica gel chromatography (0-10% MeOH in DCM). The product was then repurified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (14 mg). $^1$H NMR (400 MHz, Methanol-d$_4$) δ 8.86 (s, 1H), 8.31 (s, 1H), 8.02 (s, 1H), 6.79 (s, 1H), 5.39 (p, J=8.3 Hz, 1H), 3.91 (s, 3H), 3.77 (d, J=6.4 Hz, 2H), 3.63 (s, 2H), 2.98-2.89 (m, 4H), 2.76 (t, J=6.0 Hz, 2H), 2.69-2.55 (m, 1H), 2.48 (s, 3H), 2.47-2.37 (m, 2H). LCMS [M+H]: 395.2.

Example 66

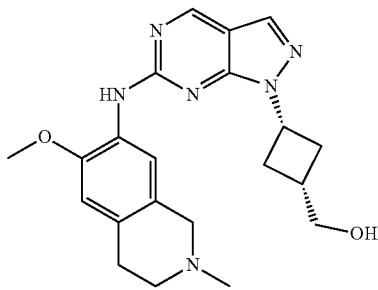 [SMILES: COc1cc2c(cc1Nc1ncc3cnn([C@H]4C[C@@H](CO)C4)c3n1)CN(C)CC2]

cis-[3-[6-[(6-methoxy-2-methyl-3,4-dihydro-1H-isoquinolin-7-yl)amino]pyrazolo[3,4-d]pyrimidin-1-yl]cyclobutyl]methanol Step 1. Preparation of cis-methyl 3-(6-chloropyrazolo[3,4-d]pyrimidin-1-yl)cyclobutanecarboxylate. Prepared according to EXAMPLE 65, Step 1 substituting trans-methyl 3-hydroxycyclobutanecarboxylate (1.0 g, 7.8 mmol) for cis-methyl-3-hydroxycyclobutane-1-carboxylate to afford the title compound (511 mg).

Step 2. Preparation of cis-[3-(6-chloropyrazolo[3,4-d]pyrimidin-1-yl)cyclobutyl]methanol. Prepared according EXAMPLE 65, Step 2 using cis-methyl 3-(6-chloropyrazolo[3,4-d]pyrimidin-1-yl)cyclobutanecarboxylate (250 mg, 0.94 mmol) to the title compound (131 mg).

Step 3. Preparation of cis-[3-[6-[(6-methoxy-2-methyl-3,4-dihydro-1H-isoquinolin-7-yl)amino]pyrazolo[3,4-d]pyrimidin-1-yl]cyclobutyl]methanol. Prepared according to EXAMPLE 65, Step 3 using [3-(6-chloropyrazolo[3,4-d]pyrimidin-1-yl)cyclobutyl]methanol (50 mg, 0.21 mmol) to afford the title compound (35 mg). $^1$H NMR (400 MHz, Methanol-d4) δ 8.85 (d, J=0.9 Hz, 1H), 8.21 (s, 1H), 8.01 (s, 1H), 6.79 (s, 1H), 5.16 (p, J=8.4 Hz, 1H), 3.91 (s, 3H), 3.67-3.61 (m, 4H), 2.98-2.90 (m, 2H), 2.76 (t, J=6.0 Hz, 2H), 2.67-2.57 (m, 2H), 2.57-2.50 (m, 2H), 2.48 (s, 4H), 2.46-2.38 (m, 1H). LCMS [M+H]: 395.2.

Example 67

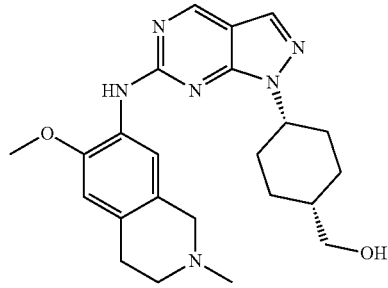 [SMILES: COc1cc2c(cc1Nc1ncc3cnn([C@H]4CC[C@@H](CO)CC4)c3n1)CN(C)CC2]

cis-[4-[6-[(6-methoxy-2-methyl-3,4-dihydro-1H-isoquinolin-7-yl)amino]pyrazolo[3,4-d]pyrimidin-1-yl]cyclohexyl]methanol Step 1. Preparation of trans-4-(triisopropylsilyloxymethyl)cyclohexanol. To a cooled (0° C.) solution of trans-4-(hydroxymethyl)cyclohexanol (2.0 g, 15.4 mmol) in 1:8 DMF:DCM (51 mL) under nitrogen was added imidazole (2.9 g, 42 mmol) followed by chloro(triisopropyl)silane (3.6 mL, 17.0 mmol). The reaction mixture was stirred overnight then diluted with DCM and water. The phases were separated then the organic phase was washed with 1 M HCl, saturated NaHCO$_3$, dried over anhydrous sodium sulfate, filtered, and concentrated to give the title compound (4.8 g) as a viscous colorless oil which was used without further purification.

Step 2. Preparation of cis-[4-(6-chloropyrazolo[3,4-d]pyrimidin-1-yl)cyclohexyl]methoxy-triisopropyl-silane. Prepared according to general procedure D using 6-chloro-1H-pyrazolo[3,4-d]pyrimidine (500 mg, 3.23 mmol), trans-4-(triisopropylsilyloxymethyl)cyclohexanol (1.1 g, 3.9 mmol) and triphenylphosphine (1.3 g, 4.9 mmol) in a solution of THF (16.2 mL). Diisopropyl azodicarboxylate (0.95 mL, 4.9 mmol) dropwise over 30 min. The reaction mixture was warmed to ambient temperature after 10 min and the reaction stirred at rt for 3 h. The reaction mixture was quenched with water and brine then extracted with EtOAc. The combined organic phase was dried over anhydrous sodium sulfate, filtered, and concentrated. The crude product was adsorbed onto silica gel then purified silica gel chromatography (0-50% EtOAc in hexanes) to afford the title compound (736 mg).

Step 3. Preparation of cis-[4-[6-[(6-methoxy-2-methyl-3,4-dihydro-1H-isoquinolin-7-yl)amino]pyrazolo[3,4-d]pyrimidin-1-yl]cyclohexyl]methanol. Prepared according to general procedure B using 6-methoxy-2-methyl-3,4-dihydro-1H-isoquinolin-7-amine (68 mg, 0.36 mmol), cis-[4-(6-chloropyrazolo[3,4-d]pyrimidin-1-yl)cyclohexyl]methoxy-triisopropyl-silane (150 mg, 0.36 mmol), cesium carbonate (347 mg, 1.1 mmol), and Pd-PEPPSI-iPent catalyst (56.2 mg, 0.070 mmol, 20 mol %). 1,2-Dimethoxyethane (3.5 mL) was added then the mixture was degassed with argon. The reaction mixture was heated to 80° C. and stirred for 3 h. The reaction mixture was cooled to ambient temperature, filtered through Celite, and concentrated. The crude product was adsorbed onto silica gel and purified by silica gel chromatography (0-10% MeOH in DCM). The product was concentrated and dissolved in DCM (1 mL) and treated with 4 N HCl (0.3 mL, 1.2 mmol, 3.8 equiv) and stirred for 4 h. The reaction mixture was concentrated and the crude product was purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (64 mg). $^1$H NMR (400 MHz, Methanol-d4) δ 8.85 (s, 1H), 8.24 (s, 1H), 7.96 (s, 1H), 6.77 (s, 1H), 4.76-4.64 (m, 1H), 3.91 (s, 3H), 3.65-3.59 (m, 4H), 2.94 (t, J=6.0 Hz, 2H), 2.77 (t, J=6.0 Hz, 2H), 2.49 (s, 3H), 2.35-2.20 (m, 2H), 1.95-1.83 (m, 5H), 1.80-1.66 (m, 2H). LCMS [M+H]: 423.1 concentrated. The crude product was adsorbed onto silica gel and purified by silica gel chromatography (0-10% MeOH in DCM). The product was concentrated and dissolved in DCM (1 mL) and treated with 4 N HCl (0.21 mL, 0.86 mmol) and stirred for 4 h. The reaction mixture was concentrated and the crude product was purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (38 mg). $^1$H NMR (400 MHz, Methanol-d$_4$) δ 8.82 (s, 1H), 8.30 (s, 1H), 6.79 (s, 1H), 4.50 (tt, J=12.0, 3.9 Hz, 1H), 3.92 (s, 3H), 3.64 (s, 2H), 3.47 (d, J=6.3 Hz, 2H), 2.95 (t, J=6.0 Hz, 2H), 2.79 (t, J=6.0 Hz, 2H), 2.50 (d, J=4.8 Hz, 6H), 2.20 (qd, J=13.4, 13.0, 4.0 Hz, 2H), 2.11-2.00 (m, 4H), 1.71-1.57 (m, 1H), 1.32-1.16 (m, 2H). LCMS [M+H]: 437.3

Example 68

Example 69

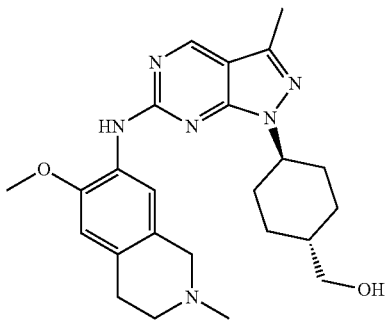 [SMILES: COc1cc2c(cc1Nc1ncc3c(C)nn([C@H]4CC[C@H](CO)CC4)c3n1)CN(C)CC2]

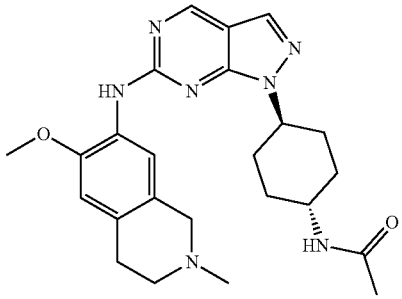 [SMILES: COc1cc2c(cc1Nc1ncc3cnn([C@H]4CC[C@H](NC(C)=O)CC4)c3n1)CN(C)CC2]

trans-[4-[6-[(6-methoxy-2-methyl-3,4-dihydro-1H-isoquinolin-7-yl)amino]-3-methyl-pyrazolo[3,4-d]pyrimidin-1-yl]cyclohexyl]methanol trans-N-[4-[6-[(6-methoxy-2-methyl-3,4-dihydro-1H-isoquinolin-7-yl)amino]pyrazolo[3,4-d]pyrimidin-1-yl]cyclohexyl]acetamide Step 1. Preparation of trans-[4-(6-chloro-3-methyl-pyrazolo[3,4-d]pyrimidin-1-yl)cyclohexyl]methoxy-triisopropyl-silane. Prepared according to general procedure D using 6-chloro-3-methyl-1H-pyrazolo[3,4-d]pyrimidine (500 mg, 3.0 mmol), cis-4-(triisopropylsilyloxymethyl)cyclohexanol (1.0 g, 3.6 mmol), and triphenylphosphine (1.2 g, 4.5 mmol) in a solution of THF (14.8 mL). Diisopropylazodicarboxylate (0.87 mL, 4.5 mmol) was added dropwise over 30 min. The reaction mixture was warmed to ambient temperature after 10 min and the reaction was stirred at rt for 3 h. The reaction mixture was quenched with water and brine then extracted with EtOAc. The combined organic phase was dried over anhydrous sodium sulfate, filtered, and concentrated. The crude product was adsorbed onto silica gel then purified silica gel chromatography (0-30% EtOAc in hexanes) to afford the title compound (404 mg).

Step 2. Preparation of trans-[4-[6-[(6-methoxy-2-methyl-3,4-dihydro-1H-isoquinolin-7-yl)amino]-3-methyl-pyrazolo[3,4-d]pyrimidin-1-yl]cyclohexyl]methanol. Prepared according to general procedure B using 6-methoxy-2-methyl-3,4-dihydro-1H-isoquinolin-7-amine (33 mg, 0.17 mmol), trans-[4-(6-chloro-3-methyl-pyrazolo[3,4-d]pyrimidin-1-yl)cyclohexyl]methoxy-triisopropyl-silane (75 mg, 0.17 mmol), cesium carbonate (168 mg, 0.52 mmol), and Pd-PEPPSI-iPent catalyst (27 mg, 0.034 mmol, 20 mol %) in 1,2-dimethoxyethane (1.7 mL). The reaction mixture was heated to 80° C. and stirred for 3 h. The reaction mixture was cooled to ambient temperature, filtered through Celite, and Step 1. Preparation of tert-butyl trans-N-[4-(6-chloropyrazolo[3,4-d]pyrimidin-1-yl)cyclohexyl]carbamate. Prepared according to general procedure D using 6-chloro-1H-pyrazolo[3,4-d]pyrimidine (1000 mg, 6.0 mmol),tert-butyl cis-4-hydroxycyclohexylcarbamate (1.7 g, 7.8 mmol), triphenylphosphine (3.4 g, 13.0 mmol), and DIAD (2.5 mL, 13.0 mmol) in THF (32 mL). The reaction mixture stirred at ambient temperature for 3 h. The reaction mixture was quenched with water and brine then extracted with EtOAc. The combined organic phase was dried over anhydrous sodium sulfate, filtered, and concentrated. The crude product was adsorbed onto silica gel then purified silica gel chromatography (0-10% MeOH in DCM) to afford the title compound (2.0 mg).

Step 2. Preparation of trans-4-(6-chloropyrazolo[3,4-d]pyrimidin-1-yl)cyclohexanamine 2,2,2-trifluoroacetate. To a solution of tert-butyl N-[4-(6-chloropyrazolo[3,4-d]pyrimidin-1-yl)cyclohexyl]carbamate (2.0 g, 5.7 mmol) in DCM (28 mL) was added trifluoroacetic acid and the solution was stirred for 48 h. The reaction mixture was concentrated to afford trans-4-(6-chloropyrazolo[3,4-d]pyrimidin-1-yl)cyclohexanamine 2,2,2-trifluoroacetate (25% purity), which was used as a crude product.

Step 3. Preparation of trans-N-[4-(6-chloropyrazolo[3,4-d]pyrimidin-1-yl)cyclohexyl]acetamide. To a cooled (0° C.) solution of trans-4-(6-chloropyrazolo[3,4-d]pyrimidin-1-yl)cyclohexanamine 2,2,2-trifluoroacetate (400 mg, 0.27 mmol, 25% purity) in DCM (4.4 mL) was added DIEA (0.24 mL, 1.4 mmol) followed by acetyl chloride (25 μL, 0.36 mmol). The reaction mixture was monitored by LCMS until starting material was completely consumed. The reaction mixture was quenched with water and diluted with DCM, then acidified with 1 M HCl. The phases were separated, and the organic phase was neutralized with saturated aqueous NaHCO$_3$ solution, dried over anhydrous sodium sulfate, filtered, and concentrated. The crude product was adsorbed onto silica gel and purified by silica gel chromatography (0-10% MeOH in DCM) to afford the title compound (23 mg).

Step 4. Preparation of trans-N-[4-[6-[(6-methoxy-2-methyl-3,4-dihydro-1H-isoquinolin-7-yl)amino]pyrazolo[3,4-d]pyrimidin-1-yl]cyclohexyl]acetamide. Prepared according to general procedure A using N-[4-(6-chloropyrazolo[3,4-d]pyrimidin-1-yl)cyclohexyl]acetamide (23 mg, 0.080 mmol), 6-methoxy-2-methyl-3,4-dihydro-1H-isoquinolin-7-amine (20 mg, 0.10 mmol), and p-TSA (46 mg, 0.24 mmol) in 2-butanol (0.32 mL) heated to 120° C. for 16 h. The reaction mixture was cooled to ambient temperature, diluted with MeCN, then purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (16 mg). $^1$H NMR (400 MHz, Methanol-d4) δ 8.87 (s, 1H), 8.28 (s, 1H), 7.98 (s, 1H), 6.81 (s, 1H), 4.61 (tt, J=11.7, 3.7 Hz, 1H), 3.92 (s, 3H), 3.83 (tt, J=11.8, 3.6 Hz, 1H), 3.65 (s, 2H), 2.95 (t, J=6.0 Hz, 2H), 2.78 (t, J=6.0 Hz, 2H), 2.49 (s, 3H), 2.38-2.24 (m, 2H), 2.20-2.04 (m, 4H), 1.95 (s, 3H), 1.59-1.43 (m, 2H). LCMS [M+H]: 450.3

Example 70

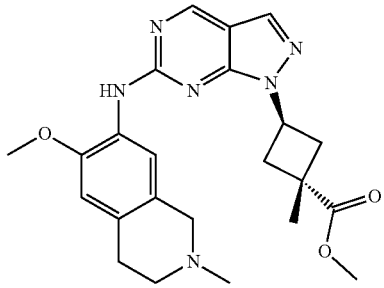 [SMILES: COc1cc2c(cc1Nc1ncc3cnn([C@H]4C[C@](C)(C(=O)OC)C4)c3n1)CN(C)CC2]

trans-methyl 3-[6-[(6-methoxy-2-methyl-3,4-dihydro-1H-isoquinolin-7-yl)amino]pyrazolo[3,4-d]pyrimidin-1-yl]-1-methyl-cyclobutanecarboxylate Step 1. Preparation of cis-methyl 3-(6-chloropyrazolo[3,4-d]pyrimidin-1-yl)-1-methyl-cyclobutanecarboxylate. Prepared according to general procedure D using 6-chloro-1H-pyrazolo[3,4-d]pyrimidine (700 mg, 4.5 mmol), cis-methyl 3-hydroxy-1-methyl-cyclobutanecarboxylate (780 mg, 5.4 mmol), and triphenylphosphine (1.8 g, 6.8 mmol) in a solution of THF (23 mL). DIAD (1.3 mL, 6.8 mmol) added dropwise over 30 min. The reaction was stirred at rt for 1.5 h. The reaction mixture was quenched with water and brine then extracted with EtOAc. The combined organic phase was dried over anhydrous sodium sulfate, filtered, and concentrated. The crude product was adsorbed onto silica gel then purified silica gel chromatography (0-20% EtOAc in hexanes) to afford the title compound (494 mg).

Step 2. Preparation of trans-methyl 3-[6-[(6-methoxy-2-methyl-3,4-dihydro-1H-isoquinolin-7-yl)amino]pyrazolo[3,4-d]pyrimidin-1-yl]-1-methyl-cyclobutanecarboxylate. Prepared according to general procedure B using 6-methoxy-2-methyl-3,4-dihydro-1H-isoquinolin-7-amine (110 mg, 0.57 mmol), methyl 3-(6-chloropyrazolo[3,4-d]pyrimidin-1-yl)-1-methyl-cyclobutanecarboxylate (160 mg, 0.57 mmol), cesium carbonate (557 mg, 1.7 mmol), and Pd-PEPPSI-iPent catalyst (90 mg, 0.11 mmol, 20 mol %) in 1,2-dimethoxyethane (5.7 mL). The reaction mixture was heated to 80° C. and stirred for 3 h. The reaction mixture was cooled to ambient temperature, filtered through Celite, and concentrated. The crude product was adsorbed onto silica gel and purified by silica gel chromatography (0-10% MeOH in DCM) to afford the title compound (186 mg). A small amount (30 mg) of the product was further purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (17 mg $^1$H NMR (400 MHz, Methanol-d4) δ 8.83 (s, 1H), 8.30 (s, 1H), 8.01 (s, 1H), 6.76 (s, 1H), 5.43 (p, J=8.4 Hz, 1H), 3.90 (s, 3H), 3.83 (s, 3H), 3.64 (s, 2H), 2.99-2.88 (m, 4H), 2.79-2.65 (m, 4H), 2.49 (s, 3H), 1.50 (s, 3H). LCMS [M+H]: 437.2.

Example 71

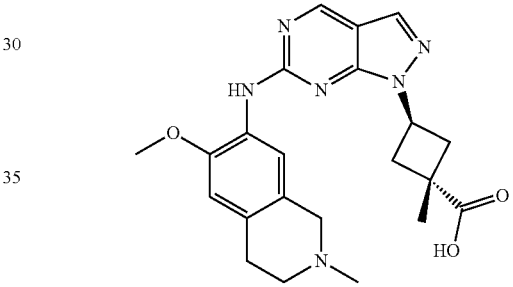

3-[6-[(6-methoxy-2-methyl-3,4-dihydro-1H-isoquinolin-7-yl)amino]pyrazolo[3,4-d]pyrimidin-1-yl]-1-methyl-cyclobutanecarboxylic acid To a solution of trans-methyl 3-[6-[(6-methoxy-2-methyl-3,4-dihydro-1H-isoquinolin-7-yl)amino]pyrazolo[3,4-d]pyrimidin-1-yl]-1-methyl-cyclobutanecarboxylate (155 mg, 0.36 mmol) in MeOH (3.6 mL) was added LiOH (41 mg, 1.8 mmol) and the reaction mixture was stirred for 48 h then. Additional LiOH (24 mg, 1.1 mmol) and the reaction was added and stirred for another 48 h. The reaction was concentrated. The mixture was acidified with 1 M HCl and the phases were separated. The organic phase was dried over anhydrous sodium sulfate, filtered, and concentrated to afford crude material (182 mg). A portion of the crude product (50 mg) was further purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (27 mg). $^1$H NMR (400 MHz, Methanol-d$_4$, TFA salt) δ 8.92 (s, 1H), 8.47 (s, 11H), 8.11 (s, 11H), 6.94 (s, 1H), 5.49 (p, J=8.6 Hz, 11H), 4.57 (d, J=14.9 Hz, 1H), 4.35 (d, J=14.9 Hz, 11H), 3.96 (s, 3H), 3.84-3.74 (m, 1H), 3.43 (td, J=11.6, 5.2 Hz, 11H), 3.29-3.21 (m, 11H), 3.20-3.14 (m, 11H), 3.11 (s, 3H), 3.02-2.91 (m, 2H), 2.76-2.62 (m, 2H), 1.53 (s, 3H). LCMS [M+H]: 423.2.

Example 72

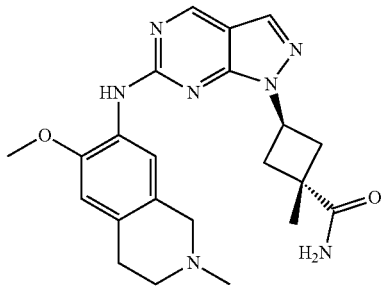 [SMILES: COc1cc2c(cc1Nc1ncc3cnn([C@H]4C[C@](C)(C(N)=O)C4)c3n1)CN(C)CC2]

trans-3-[6-[(6-methoxy-2-methyl-3,4-dihydro-1H-isoquinolin-7-yl)amino]pyrazolo[3,4-d]pyrimidin-1-yl]-1-methyl-cyclobutanecarboxamide To a solution of crude trans-3-[6-[(6-methoxy-2-methyl-3,4-dihydro-1H-isoquinolin-7-yl)amino]pyrazolo[3,4-d]pyrimidin-1-yl]-1-methyl-cyclobutanecarboxylic acid (Example 71) (100 mg, 0.24 mmol) in DMF (0.79 mL) was added a solution of methylamine (60 μL, 1.2 mmol, 2 M in THF), triethylamine (0.20 mL, 1.4 mmol), and a solution of propylphosphonic anhydride (0.28 mL, 0.47 mmol, 50% solution in EtOAc). The reaction mixture was stirred for 48 h then diluted with water and EtOAc. The phases were separated and the aqueous phase was concentrated to give a crude product that was purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (11 mg, 11% yield). $^1$H NMR (400 MHz, Methanol-d4) δ 8.86 (s, 1H), 8.25 (s, 1H), 8.04 (s, 1H), 6.79 (s, 1H), 5.29 (p, J=8.5 Hz, 1H), 3.91 (s, 3H), 3.65 (s, 2H), 3.06-2.97 (m, 2H), 2.94 (t, J=6.0 Hz, 2H), 2.76 (t, J=6.1 Hz, 2H), 2.73-2.64 (m, 2H), 2.50 (s, 3H), 1.55 (s, 3H). LCMS [M+H]: 422.2.

Example 73

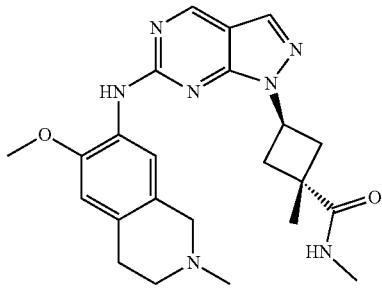 [SMILES: CNC(=O)[C@]1(C)C[C@@H](n2ncc3cnc(Nc4cc5c(cc4OC)CCN(C)C5)nc32)C1]

trans-3-[6-[(6-methoxy-2-methyl-3,4-dihydro-1H-isoquinolin-7-yl)amino]pyrazolo[3,4-d]pyrimidin-1-yl]-N,1-methyl-cyclobutanecarboxamide To a solution of crude trans-3-[6-[(6-methoxy-2-methyl-3,4-dihydro-1H-isoquinolin-7-yl)amino]pyrazolo[3,4-d]pyrimidin-1-yl]-1-methyl-cyclobutanecarboxylic acid (Example 71) (100 mg, 0.24 mmol) in DMF (0.79 mL) was added ammonium chloride (63 mg, 1.2 mmol), triethylamine (0.20 mL, 1.4 mmol), and a solution of propylphosphonic anhydride (0.28 mL, 0.47 mmol, 50% solution in EtOAc). The reaction mixture was stirred for 48 h then diluted with water and EtOAc. The phases were separated and the aqueous phase was concentrated to give a crude product that was purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (9.4 mg). $^1$H NMR (400 MHz, Methanol-d$_4$) δ 8.85 (d, J=1.2 Hz, 1H), 8.26 (s, 1H), 8.03 (s, 1H), 6.78 (s, 1H), 5.28 (p, J=8.6 Hz, 1H), 3.91 (s, 3H), 3.65 (s, 2H), 3.02-2.91 (m, 4H), 2.84 (s, 3H), 2.76 (t, J=6.0 Hz, 2H), 2.73-2.61 (m, 2H), 2.51 (s, 3H), 1.51 (s, 3H). LCMS [M+H]: 436.3.

Example 74

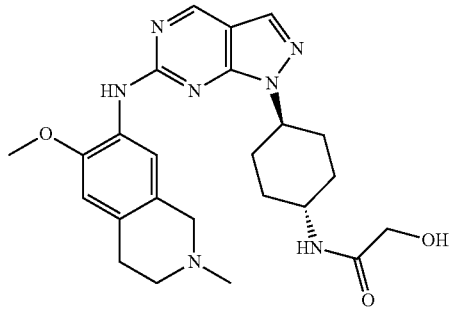 [SMILES: COc1cc2c(cc1Nc1ncc3cnn([C@H]4CC[C@H](NC(=O)CO)CC4)c3n1)CN(C)CC2]

trans-2-hydroxy-N-[4-[6-[(6-methoxy-2-methyl-3,4-dihydro-1H-isoquinolin-7-yl)amino]pyrazolo[3,4-d]pyrimidin-1-yl]cyclohexyl]acetamide Step 1. Preparation of trans-N-[4-(6-chloropyrazolo[3,4-d]pyrimidin-1-yl)cyclohexyl]-2-hydroxy-acetamide. To a cooled solution (0° C.) of crude trans-4-(6-chloropyrazolo[3,4-d]pyrimidin-1-yl)cyclohexanamine 2,2,2-trifluoroacetate (Example 69, Step 2) (400 mg, 0.27 mmol, 25% purity) in DCM (3.0 mL, 0.05 M) was added DIEA (0.24 mL, 1.4 mmol) and the mixture was stirred until completely dissolved. In a separate flask, HATU (135 mg, 0.36 mmol) was dissolved in DCM (3.0 mL) and glycolic acid (25 μL, 0.36 mmol) was added. The solution of amine was then added to the second solution, then the reaction mixture was stirred for 48 h. The reaction mixture was diluted with water and acidified with 1 M HCl. The mixture was extracted with DCM, then the combined organic extract was neutralized with saturated aqueous NaHCO$_3$, dried over anhydrous sodium sulfate, filtered, and concentrated. The crude product was adsorbed onto silica gel and purified by silica gel chromatography (0-10% MeOH in DCM) to afford the title compound (28 mg).

Step 2. Preparation of trans-2-hydroxy-N-[4-[6-[(6-methoxy-2-methyl-3,4-dihydro-1H-isoquinolin-7-yl)amino]pyrazolo[3,4-d]pyrimidin-1-yl]cyclohexyl]acetamide. Prepared according to general procedure A using N-[4-(6-chloropyrazolo[3,4-d]pyrimidin-1-yl)cyclohexyl]-2-hydroxy-acetamide (28 mg, 0.092 mmol), 6-methoxy-2-methyl-3,4-dihydro-1H-isoquinolin-7-amine (23 mg, 0.12 mmol), and p-TSA (52 mg, 0.28 mmol) in 2-butanol (0.37 mL) heated to 120° C. for 16 h. The reaction mixture was cooled to ambient temperature and diluted with MeCN then purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (18 mg). $^1$H NMR (400 MHz, Methanol-d4) δ 8.87 (s, 1H), 8.27 (s, 1H), 7.98 (s, 1H), 6.80 (s, 1H), 4.75-4.54 (m, 1H), 3.98 (s, 2H), 3.92 (s, 3H), 3.66 (s, 2H), 3.03-2.88 (m, 2H), 2.85-2.72 (m, 2H), 2.48 (s, 3H), 2.42-2.24 (m, 2H), 2.21-2.04 (m, 4H), 1.74-1.54 (m, 2H). LCMS [M+H]: 466.3.

Example 75

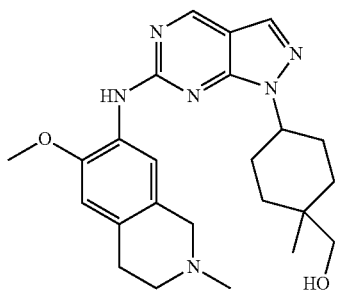 [SMILES: COc1cc2c(cc1Nc1ncc3cnn(C4CCC(C)(CO)CC4)c3n1)CN(C)CC2]

[4-[6-[(6-methoxy-2-methyl-3,4-dihydro-1H-isoquinolin-7-yl)amino]pyrazolo[3,4-d]pyrimidin-1-yl]-1-methyl-cyclohexyl]methanol Step 1. Preparation of cis-methyl 4-[tert-butyl(dimethyl)silyl]oxycyclohexanecarboxylate. To a cooled (0° C.) solution of methyl cis-4-hydroxycyclohexanecarboxylate (2.5 g, 15.8 mmol) in DCM (79 mL) was added imidazole (3.0 g, 44 mmol) and tert-butyldimethylchlorosilane (2.6 g, 17.4 mmol). The reaction mixture was warmed to ambient temperature and stirred overnight. The reaction mixture was diluted with DCM and water, then the phases were separated. The organic phase was washed with 1 M HCl, neutralized with saturated NaHCO₃, dried over anhydrous sodium sulfate, filtered, and concentrated. The crude product was purified by silica gel chromatography (0-25% EtOAc in hexanes) to afford the title compound (3.7 g).

Step 2. Preparation of methyl 4-[tert-butyl(dimethyl)silyl]oxy-1-methyl-cyclohexanecarboxylate. To a cooled (−78° C.) solution of diisopropylamine (0.77 mL, 5.5 mmol) in THF (12.2 mL) was added a 2.5 M solution n-butyllithium (0.77 mL, 1.9 mmol). The mixture was stirred for 30 min then a solution of methyl 4-[tert-butyl(dimethyl)silyl]oxycyclohexanecarboxylate (500 mg, 1.8 mmol) in THF (3.0 mL) was added dropwise and stirred for 1 h. Methyl iodide (0.57 mL, 9.2 mmol) was added and the reaction mixture was slowly warmed to ambient temperature from the cold bath. After 1 h, the reaction mixture was quenched with saturated aqueous ammonium chloride and extracted with EtOAc. The combined organic phase was dried over anhydrous sodium sulfate, filtered, and concentrated. The crude product was purified by silica gel chromatography (0-20% EtOAc in hexanes) to afford the title compound (452 mg) as a mixture of cis- and trans-isomers.

Step 3. Methyl 4-hydroxy-1-methyl-cyclohexanecarboxylate. To a cooled (0° C.) solution of methyl 4-[tert-butyl(dimethyl)silyl]oxy-1-methyl-cyclohexanecarboxylate (452 mg, 1.6 mmol) in THF (5.3 mL) was added a 1 M solution of tetrabutylammonium fluoride (2.4 mL, 2.4 mmol). After 1 h, a second portion of tetrabutylammonium fluoride (3.2 mL, 3.2 mmol) was added and the reaction mixture was stirred for 16 h. The reaction mixture was quenched with saturated aqueous ammonium chloride then extracted with EtOAc. The combined organic phase was dried over anhydrous sodium sulfate, filtered, and concentrated. The crude product was purified by silica gel chromatography (0-100% EtOAc in hexanes) to afford the title compound (189 mg).

Step 4. Preparation of methyl 4-(6-chloropyrazolo[3,4-d]pyrimidin-1-yl)-1-methyl-cyclohexanecarboxylate. Prepared according to general procedure D using 6-chloro-1H-pyrazolo[3,4-d]pyrimidine (140 mg, 0.91 mmol), methyl 4-hydroxy-1-methyl-cyclohexanecarboxylate (190 mg, 1.1 mmol), DEAD (40% solution in toluene, 0.83 mL, 1.8 mmol), and triphenylphosphine (475 mg, 1.8 mmol) in THF (6.1 mL) stirred at rt. Upon completion of the reaction, the mixture was quenched with water and brine then extracted with EtOAc. The combined organic phase was dried over anhydrous sodium sulfate, filtered, and concentrated. The crude product was adsorbed onto silica gel then purified silica gel chromatography (0-30% EtOAc in hexanes) to afford the title compound (195 mg).

Step 5. Preparation of [4-(6-chloropyrazolo[3,4-d]pyrimidin-1-yl)-1-methyl-cyclohexyl]methanol. To a cooled (0° C.) solution of methyl 4-(6-chloropyrazolo[3,4-d]pyrimidin-1-yl)-1-methyl-cyclohexanecarboxylate (300 mg, 0.97 mmol) in THF (9.7 mL) was added a solution of diisobutylaluminum hydride (1.2 M in toluene, 2.4 mL, 2.9 mmol). The reaction mixture was warmed to ambient temperature and stirred for 1 h. EtOAc was added followed by 10% w/v aqueous Rochelle's salt and the mixture was stirred for 48 h. The phases were separated, and the aqueous phase was extracted with EtOAc. The combined organic phase was dried over anhydrous sodium sulfate, filtered, and concentrated. The crude product was purified by silica gel chromatography (0-50% EtOAc in hexanes) to afford the title compound (15 mg).

Step 6. Preparation of [4-[6-[(6-methoxy-2-methyl-3,4-dihydro-1H-isoquinolin-7-yl)amino]pyrazolo[3,4-d]pyrimidin-1-yl]-1-methyl-cyclohexyl]methanol. Prepared according to general procedure A using [4-(6-chloropyrazolo[3,4-d]pyrimidin-1-yl)-1-methyl-cyclohexyl]methanol (15 mg, 0.0.052 mmol), 6-methoxy-2-methyl-3,4-dihydro-1H-isoquinolin-7-amine (13 mg, 0.068 mmol), and p-TSA (30 mg, 0.16 mmol) in 2-butanol (0.21 mL) heated to 120° C. for 16 h. The reaction mixture was cooled to ambient temperature and neutralized with 3 M NaOH (0.52 μL, 0.16 mmol), then diluted with MeCN then purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (2.0 mg, 9% yield) as a 3:1 mixture of cis-trans diastereomers. $^1$H NMR (400 MHz, Methanol-d4, major diastereomer) δ 8.87 (s, 1H), 8.26 (s, 1H), 8.00 (s, 1H), 6.80 (s, 1H), 4.70-4.52 (m, 11H), 3.92 (s, 3H), 3.66-3.57 (m, 3H), 2.95 (t, J=6.0 Hz, 2H), 2.77 (t, J=5.8 Hz, 2H), 2.48 (s, 3H), 2.34-2.10 (m, 2H), 1.88 (d, J=10.2 Hz, 4H), 1.47-1.36 (m, 2H), 1.01 (s, 3H). LCMS [M+H]: 437.3.

Example 76

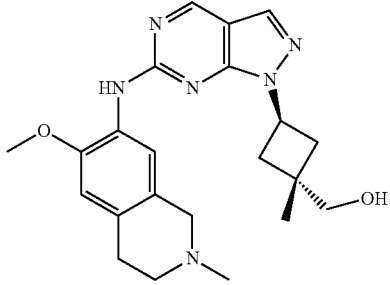 [SMILES: COc1cc2c(cc1Nc1ncc3cnn([C@H]4C[C@](C)(CO)C4)c3n1)CN(C)CC2]

trans-[3-[6-[(6-methoxy-2-methyl-3,4-dihydro-1H-isoquinolin-7-yl)amino]pyrazolo[3,4-d]pyrimidin-1-yl]-1-methyl-cyclobutyl]methanol Step 1. Preparation of trans-[3-(6-chloropyrazolo[3,4-d]pyrimidin-1-yl)-1-methyl-cyclobutyl]methanol. To a cooled (0° C.) solution of trans-methyl 3-(6-chloropyrazolo[3,4-d]pyrimidin-1-yl)-1-methyl-cyclobutanecarboxylate (EXAMPLE 70, Step 1) (186 mg, 0.66 mmol) in THF (10 mL) was added diisobutylaluminum hydride (1.2 M, 1.2 mL, 1.5 mmol) in toluene. The reaction mixture was warmed to ambient temperature and stirred for 1 h. EtOAc was added then 10% w/v aqueous Rochelle's salt was added, and the mixture was stirred for 48 h. The phases were separated, and the aqueous phase was back-extracted with EtOAc. The combined organic phase was dried over anhydrous sodium sulfate, filtered, and concentrated. The crude product was purified by silica gel chromatography (0-50% EtOAc in hexanes) to afford the title compound (126 mg).

Step 2. Preparation of trans-[3-[6-[(6-methoxy-2-methyl-3,4-dihydro-1H-isoquinolin-7-yl)amino]pyrazolo[3,4-d]pyrimidin-1-yl]-1-methyl-cyclobutyl]methanol. Prepared according to general procedure B using 6-methoxy-2-methyl-3,4-dihydro-1H-isoquinolin-7-amine (61 mg, 0.32 mmol), [3-(6-chloropyrazolo[3,4-d]pyrimidin-1-yl)-1-methyl-cyclobutyl]methanol (80 mg, 0.32 mmol), cesium carbonate (309 mg, 0.95 mmol), and Pd-PEPPSI-iPent catalyst (50 mg, 0.063 mmol, 20 mol %) in 1,2-dimethoxyethane (3.2 mL). The reaction mixture was heated to 80° C. and stirred for 3 h. The reaction mixture was cooled to ambient temperature, filtered through Celite, and concentrated. The crude product was purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (41 mg). $^1$H NMR (400 MHz, Methanol-$d_4$) δ 8.85 (s, 1H), 8.30 (s, 1H), 8.03 (s, 1H), 6.78 (s, 1H), 5.31 (p, J=8.5 Hz, 1H), 3.91 (s, 3H), 3.64 (s, 2H), 3.60 (s, 2H), 2.94 (t, J=6.0 Hz, 2H), 2.77 (t, J=6.0 Hz, 2H), 2.57-2.51 (m, 4H), 2.49 (s, 3H), 1.24 (s, 3H). LCMS [M+H]: 409.3.

Example 77

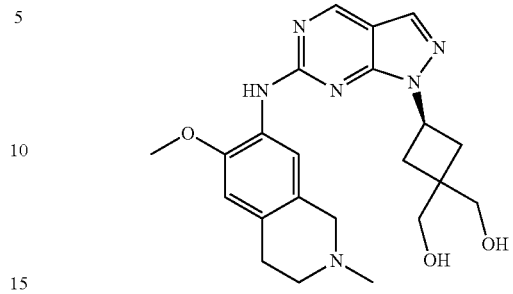

[1-(hydroxymethyl)-3-[6-[(6-methoxy-2-methyl-3,4-dihydro-1H-isoquinolin-7-yl)amino]pyrazolo[3,4-d]pyrimidin-1-yl]cyclobutyl]dimethanol Step 1. Preparation of diethyl 3-(6-chloropyrazolo[3,4-d]pyrimidin-1-yl)201yclobutene-1,1-dicarboxylate. Prepared according to general procedure D using 6-chloro-1H-pyrazolo[3,4-d]pyrimidine (300 mg, 1.9 mmol), diethyl 3-hydroxycyclobutane-1,1-dicarboxylate (500 mg, 2.3 mmol), and triphenylphosphine (1.0 g, 3.9 mmol) in a cooled (0° C.) solution of THF (9.7 mL). DEAD (40% solution in toluene, 1.8 mL, 3.9 mmol) dropwise over 30 min. The reaction mixture was warmed to ambient temperature after 10 min and the reaction stirred for 3 h. The reaction mixture was quenched with water and brine then extracted with EtOAc. The combined organic phase was dried over anhydrous sodium sulfate, filtered, and concentrated. The crude product was adsorbed onto silica gel then purified silica gel chromatography (0-30% EtOAc in hexanes) to afford the title compound (553 mg).

Step 2. Preparation of [3-(6-chloropyrazolo[3,4-d]pyrimidin-1-yl)-1-(hydroxymethyl)cyclobutyl]dimethanol. To a cooled (0° C.) solution of diethyl 3-(6-chloropyrazolo[3,4-d]pyrimidin-1-yl)201yclobutene-1,1-dicarboxylate (200 mg, 0.57 mmol) in THF (5.7 mL) was added diisobutylaluminum hydride (1.2 M, 2.0 mL, 2.4 mmol) in toluene. The reaction mixture was warmed to ambient temperature and stirred for 1 h. EtOAc was added followed by 10% w/v aqueous Rochelle's salt, and the mixture was stirred for 48 h at rt. The phases were separated, and the aqueous phase was extracted with EtOAc. The combined organic phase was dried over anhydrous sodium sulfate, filtered, and concentrated. The crude product was purified by silica gel chromatography (0-10% MeOH in DCM) to afford the title compound (35 mg).

Step 3. Preparation of [1-(hydroxymethyl)-3-[6-[(6-methoxy-2-methyl-3,4-dihydro-1H-isoquinolin-7-yl)amino]pyrazolo[3,4-d]pyrimidin-1-yl]cyclobutyl]dimethanol. Prepared according to general procedure A using [3-(6-chloropyrazolo[3,4-d]pyrimidin-1-yl)-1-(hydroxymethyl)cyclobutyl]dimethanol (35 mg, 0.13 mmol), 6-methoxy-2-methyl-3,4-dihydro-$^1$H-isoquinolin-7-amine (33 mg, 0.17 mmol), and p-TSA (74 mg, 0.0.39 mmo) in 2-butanol (0.52 mL) heated to 120° C. for 16 h. The reaction mixture was cooled to ambient temperature and neutralized with 3 M NaOH (0.13 mL, 0.39 mmol), then diluted with MeCN then purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (23 mg). $^1$H NMR (400 MHz, Methanol-$d_4$)

δ 8.84 (s, 1H), 8.27 (s, 1H), 8.02 (s, 1H), 6.78 (s, 1H), 5.42-5.23 (m, 1H), 3.90 (s, 3H), 3.78 (s, 2H), 3.70-3.56 (m, 4H), 3.01-2.87 (m, 2H), 2.84-2.71 (m, 2H), 2.68-2.54 (m, 2H), 2.54-2.38 (m, 5H). LCMS [M+H]: 425.3.

Example 78

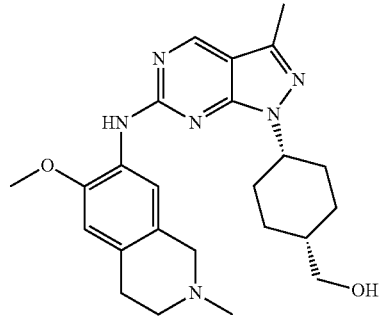 [SMILES: COc1cc2c(cc1Nc1ncc3c(C)nn([C@H]4CC[C@@H](CO)CC4)c3n1)CN(C)CC2]

cis-[4-[6-[(6-methoxy-2-methyl-3,4-dihydro-1H-isoquinolin-7-yl)amino]-3-methyl-pyrazolo[3,4-d]pyrimidin-1-yl]cyclohexyl]methanol The above compound was prepared according to EXAMPLE 68 substituting in Step 1 trans-4-(triisopropylsilyloxymethyl)cyclohexanol for cis-4-(triisopropylsilyloxymethyl)cyclohexanol to afford the title compound (32 mg). $^1$H NMR (400 MHz, Methanol-$d_4$) δ 8.72 (s, 1H), 8.16 (s, 1H), 6.74 (s, 1H), 4.60-4.47 (m, 1H), 3.88 (s, 3H), 3.67-3.59 (m, 2H), 3.56 (s, 2H), 2.90 (t, J=5.8 Hz, 2H), 2.73 (t, J=5.9 Hz, 2H), 2.46 (s, 3H), 2.45 (s, 3H), 2.31-2.13 (m, 2H), 1.97-1.77 (m, 5H), 1.77-1.62 (m, 2H). LCMS [M+H]: 437.1.

Example 79

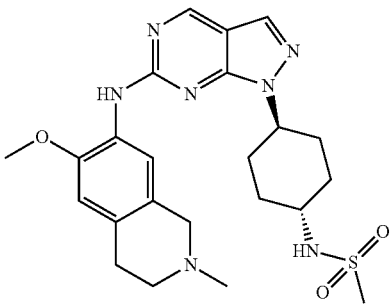 [SMILES: COc1cc2c(cc1Nc1ncc3cnn([C@H]4CC[C@H](NS(C)(=O)=O)CC4)c3n1)CN(C)CC2]

trans-N-[4-[6-[(6-methoxy-2-methyl-3,4-dihydro-1H-isoquinolin-7-yl)amino]pyrazolo[3,4-d]pyrimidin-1-yl]cyclohexyl]methanesulfonamide Step 1. Preparation of trans-N-[4-(6-chloropyrazolo[3,4-d]pyrimidin-1-yl)cyclohexyl]methanesulfonamide. Prepared according to Step 3 of EXAMPLE 69 substituting methanesulfonyl chloride (28 μL, 0.36 mmol) for acetyl chloride to afford the title compound (71 mg).

Step 2. Preparation of trans-N-[4-[6-[(6-methoxy-2-methyl-3,4-dihydro-1H-isoquinolin-7-yl)amino]pyrazolo[3,4-d]pyrimidin-1-yl]cyclohexyl]methanesulfonamide. Prepared according to general procedure A using N-[4-(6-chloropyrazolo[3,4-d]pyrimidin-1-yl)cyclohexyl]methanesulfonamide (40 mg, 0.12 mmol), 6-methoxy-2-methyl-3,4-dihydro-1H-isoquinolin-7-amine (30 mg, 0.16 mmol), and p-TSA (69 mg, 0.36 mmol) in 2-butanol (0.5 mL) heated to 120° C. for 16 h. The reaction mixture was cooled to ambient temperature, neutralized with 3 M NaOH (0.12 mL, 0.36 mmol). The crude product was dissolved in MeCN and purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (15 mg). $^1$H NMR (400 MHz, Methanol-$d_4$) δ 8.87 (s, 1H), 8.25 (s, 1H), 7.99 (s, 1H), 6.81 (s, 1H), 4.68-4.52 (m, 1H), 3.92 (s, 3H), 3.64 (s, 2H), 3.51-3.35 (m, 1H), 3.00 (s, 3H), 2.99-2.88 (m, 2H), 2.83-2.71 (m, 2H), 2.51 (s, 3H), 2.35-2.19 (m, 4H), 2.19-2.03 (m, 2H), 1.70-1.48 (m, 2H). LCMS [M+H]: 486.2.

Example 80

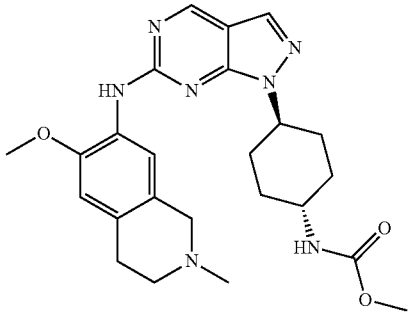

trans-methyl N-[4-[6-[(6-methoxy-2-methyl-3,4-dihydro-1H-isoquinolin-7-yl)amino]pyrazolo[3,4-d]pyrimidin-1-yl]cyclohexyl]carbamate Step 1. Preparation of methyl N-[4-(6-chloropyrazolo[3,4-d]pyrimidin-1-yl)cyclohexyl]carbamate. Prepared according to EXAMPLE 69, Step 3 substituting methylchloroformate (28 μL, 0.36 mmol) for acetyl chloride to provide the title compound (50 mg).

Step 2. Preparation of trans-methyl N-[4-[6-[(6-methoxy-2-methyl-3,4-dihydro-1H-isoquinolin-7-yl)amino]pyrazolo[3,4-d]pyrimidin-1-yl]cyclohexyl]carbamate. Prepared according to general procedure A using methyl N-[4-(6-chloropyrazolo[3,4-d]pyrimidin-1-yl)cyclohexyl]carbamate (50 mg, 0.16 mmol), 6-methoxy-2-methyl-3,4-dihydro-1H-isoquinolin-7-amine (40 mg, 0.21 mmol), and p-TSA (92 mg, 0.48 mmol) in 2-butanol (0.64 mL) heated to 120° C. for 16 h. The reaction mixture was cooled to ambient temperature, neutralized with 3 M NaOH (0.16 mL, 0.48 mmol) and diluted with MeCN then purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compoundound (7.5 mg). $^1$H NMR (400 MHz, Methanol-$d_4$) δ 8.87 (s, 1H), 8.28 (s, 1H), 7.98 (s, 1H), 6.81 (s, 1H), 4.68-4.49 (m, 1H), 3.92 (s, 3H), 3.72-3.51 (m, 3H), 2.95 (t, J=6.0 Hz, 2H), 2.78 (t, J=6.0 Hz, 2H), 2.50 (s, 3H), 2.31 (d, J=13.5 Hz, 2H), 2.22-2.03 (m, 4H), 1.60-1.44 (m, 2H). LCMS [M+H]: 466.3.

Example 81

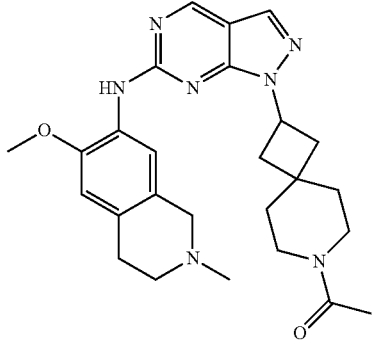 [SMILES: COc1cc2c(cc1Nc1ncc3cnn(C4CC5(CCN(C(C)=O)CC5)C4)c3n1)CN(C)CC2]

1-(2-(6-((6-methoxy-2-methyl-1,2,3,4-tetrahydroiso-quinolin-7-yl)amino)-1H-pyrazolo[3,4-d]pyrimidin-1-yl)-7-azaspiro[3.5]nonan-7-yl)ethan-1-one Step 1: Preparation of tert-butyl 2-(6-chloropyrazolo[3,4-d]pyrimidin-1-yl)-7-azaspiro[3.5]nonane-7-carboxylate. Prepared according to general procedure D using 6-chloro-1H-pyrazolo[3,4-d]pyrimidine (200 mg, 1.29 mmol), tert-butyl 2-hydroxy-7-azaspiro[3.5]nonane-7-carboxylate (468 mg, 1.94 mmol), triphenylphosphine (407 mg, 1.94 mmol) and DEAD (338 mg, 1.94 mmol) in THF (10 mL) at rt for 16 h. The crude product was purified by silica column chromatography (0-35% EtOAc in hexanes) to afford the title compound as a solid (204 mg).

Step 2: Preparation of tert-butyl 2-[6-[(6-methoxy-2-methyl-3,4-dihydro-1H-isoquinolin-7-yl)amino]pyrazolo[3,4-d]pyrimidin-1-yl]-7-azaspiro[3.5]nonane-7-carboxylate. Prepared according to general procedure B using tert-butyl 2-(6-chloropyrazolo[3,4-d]pyrimidin-1-yl)-7-azaspiro[3.5]nonane-7-carboxylate (200 mg, 0.53 mmol), 6-methoxy-2-methyl-3,4-dihydro-1H-isoquinolin-7-amine (153 mg, 0.79 mmol), Pd2(dba)3 (48.5 mg, 0.053 mmol), cesium carbonate (517 mg, 1.59 mmol), and (S)-BINAP (65.9 mg, 0.2 mmol) in tert-butanol (3 mL) and toluene (3 mL) at 100° C. for 3 h. The crude product was purified reversed phase eluting with 0% to 100% acetonitrile (with 0.1% TFA added) in water (with 0.1% TFA added), providing the title compound as a solid (100 mg).

Step 3: Preparation of N-[1-(7-azaspiro[3.5]nonan-2-yl)pyrazolo[3,4-d]pyrimidin-6-yl]-6-methoxy-2-methyl-3,4-dihydro-1H-isoquinolin-7-amine trifluoroacetate. To a solution of tert-butyl 2-[6-[(6-methoxy-2-methyl-3,4-dihydro-1H-isoquinolin-7-yl)amino]pyrazolo[3,4-d]pyrimidin-1-yl]-7-azaspiro[3.5]nonane-7-carboxylate (100.mg, 0.190 mmol) in DCM (2 mL) was added trifluoroacetic acid (0.14 mL, 1.87 mmol) and the solution was stirred at rt until reaction was complete. The reaction mixture was concentrated to the title compound, which was used in the next step without further purification.

Step 4: Preparation of 1-[2-[6-[(6-methoxy-2-methyl-3,4-dihydro-1H-isoquinolin-7-yl)amino]pyrazolo[3,4-d]pyrimidin-1-yl]-7-azaspiro[3.5]nonan-7-yl]ethan-1-one. To a cooled (0° C.) solution of N-[1-(7-azaspiro[3.5]nonan-2-yl)pyrazolo[3,4-d]pyrimidin-6-yl]-6-methoxy-2-methyl-3,4-dihydro-1H-isoquinolin-7-amine; 2,2,2-trifluoroacetic acid (40.0 mg, 0.070 mmol) in DCM (1 mL) was added DIEA (0.24 mL, 1.4 mmol) followed by acetyl chloride (7.8 µL, 0.11 mmol). Upon completion of the reaction, the crude product was purified by reverse phase HPLC (Phenomenex, Gemini-NX, 10 um, 250×30 mm, C18 column; 20% to 100% MeCN/water with 0.1% TFA gradient) to provide the title compound as a solid (15 mg). $^1$H NMR (400 MHz, Chloroform-d) δ 8.99 (s, 11H), 8.23 (s, 1H), 7.76 (s, 1H), 6.73 (s, 1H), 5.24 (s, 11H), 4.55 (s, 1H), 4.07 (s, 1H), 3.85 (s, 3H), 3.66 (s, 1H), 3.54 (s, 1H), 3.34-3.23 (m, 4H), 2.95 (s, 4H), 2.47 (s, 4H), 2.06 (s, 3H), 1.70 (d, J=36.0 Hz, 4H), 1.19 (s, 1H). LCMS [M+H]: 476.3.

Example 82

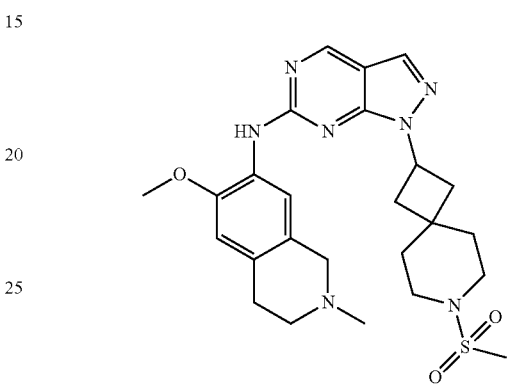

6-methoxy-2-methyl-N-[1-(7-methylsulfonyl-7-azaspiro[3.5]nonan-2-yl)pyrazolo[3,4-d]pyrimidin-6-yl]-3,4-dihydro-1H-isoquinolin-7-amine To a cooled (0° C.) solution of N-[1-(7-azaspiro[3.5]nonan-2-yl)pyrazolo[3,4-d]pyrimidin-6-yl]-6-methoxy-2-methyl-3,4-dihydro-1H-isoquinolin-7-amine 2,2,2-trifluoroacetate (EXAMPLE 81, Step 3) (40.mg, 0.07 mmol) in DCM (1 mL) was added DIEA (0.24 mL, 1.4 mmol) followed by methanesulfonyl chloride (8.5 µL, 0.11 mmol). Upon completion of the reaction, the crude product was purified by reverse phase HPLC (Phenomenex, Gemini-NX, 10 um, 250×30 mm, C18 column; gradient of 20% MeCN/0.1% TFA-water to 100% MeCN/0.1% TFA) to provide the title compound (18 mg). $^1$H NMR (400 MHz, Chloroform-d, HCl salt) δ 8.89 (s, 1H), 8.11 (s, 1H), 7.92 (s, 1H), 6.70 (s, 1H), 5.22 (s, 1H), 4.49 (s, 1H), 4.02 (s, 1H), 3.83 (s, 3H), 2.92 (s, 4H), 2.74 (s, 4H), 2.44 (s, 3H), 1.82 (d, 4H), 1.16 (m, 7H). LCMS [M+H]: 512.3.

Example 83

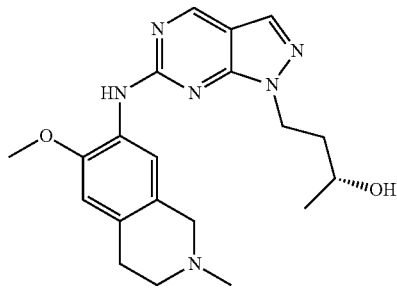 [SMILES: COc1cc2c(cc1Nc1ncc3cnn(CC[C@@H](C)O)c3n1)CN(C)CC2]

(2R)-4-[6-[(6-methoxy-2-methyl-3,4-dihydro-1H-isoquinolin-7-yl)amino]pyrazolo[3,4-d]pyrimidin-1-yl]butan-2-ol Step 1. Preparation of methyl (3R)-3-[tert-butyl(diphenyl)silyl]oxybutanoate. To a cooled (0° C.) solution of methyl®-(−)-3-hydroxybutyrate (1.9 g, 16.9 mmol) in DMF (16.9 mL) was added imidazole (3.2 g, 46.6 mmol) and tert-butylchlorodiphenylsilane (4.8 mL, 18.6 mmol). The reaction mixture was stirred for 16 h then diluted with hexanes and water. The phases were separated, and the organic phase was washed with 1 M HCl, neutralized with saturated sodium bicarbonate, dried over anhydrous sodium sulfate, filtered, and concentrated to provide the title compound (6.5 g), which was used without further purification.

Step 2. Preparation of (3R)-3-[tert-butyl(diphenyl)silyl]oxybutan-1-ol. To a cooled (0° C.) solution of methyl (3R)-3-[tert-butyl(diphenyl)silyl]oxybutanoate (6.5 g, 18.2 mmol) in THF (61 mL) was added a 4 M solution of lithium aluminum hydride (6.8 mL, 27.3 mmol) dropwise. The reaction mixture was stirred for 1 h. EtOAc was slowly added to quench any remaining LAH followed by the slow sequential addition of water (1 mL), 3 M NaOH (2 mL), and water (3 mL). The mixture was stirred for 1 h then anhydrous magnesium sulfate, filtered through Celite, and concentrated to afford the crude product (4.8 g), which was taken forward without further purification.

Step 3. Tert-butyl-diphenyl-[(1R)-3-(6-chloropyrazolo[3,4-d]pyrimidin-1-yl)-1-methyl-propoxy]silane. Prepared according to general procedure D using 6-chloro-1H-pyrazolo[3,4-d]pyrimidine (500 mg, 3.2 mmol), (3R)-3-[tert-butyl(diphenyl)silyl]oxybutan-1-ol (1.6 g, 4.8 mmol), and triphenylphosphine (1.7 g, 6.5 mmol) in THF (16.2 mL) with DEAD (40% solution in toluene, 3.0 mL, 6.5 mmol). The reaction mixture was stirred for 3 h at rt, then quenched with water and extracted with EtOAc. The combined organic phase was dried over anhydrous sodium sulfate, filtered, and concentrated. The crude product was purified by silica gel chromatography (0-50% EtOAc in hexanes) to afford the title compound (81 mg).

Step 4. Preparation of 6-methoxy-2-methyl-N-[1-[(3R)-3-[tert-butyl(diphenyl)silyl]oxybutyl]pyrazolo[3,4-d]pyrimidin-6-yl]-3,4-dihydro-1H-isoquinolin-7-amine. Prepared according to general procedure B using 6-methoxy-2-methyl-3,4-dihydro-1H-isoquinolin-7-amine (33.0 mg, 0.17 mmol), tert-butyl-diphenyl-[(1R)-3-(6-chloropyrazolo[3,4-d]pyrimidin-1-yl)-1-methyl-propoxy]silane (80.0 mg, 0.17 mmol), cesium carbonate (168 mg, 0.52 mmol), and Pd-PEPPSI-iPent catalyst (27 mg, 0.034 mmol, 20 mol %) in degassed 1,2-dimethoxyethane (1.7 mL) heated to 80° C. and stirred for 3 h. The reaction mixture was cooled to ambient temperature, filtered through Celite, and concentrated. The crude product was adsorbed onto silica gel and purified by silica gel chromatography (0-10% MeOH in DCM) to afford 6-methoxy-2-methyl-N-[1-[(3R)-3-[tert-butyl(diphenyl)silyl]oxybutyl]pyrazolo[3,4-d]pyrimidin-6-yl]-3,4-dihydro-1H-isoquinolin-7-amine (61 mg).

Step 5. Preparation of (2R)-4-[6-[(6-methoxy-2-methyl-3,4-dihydro-1H-isoquinolin-7-yl)amino]pyrazolo[3,4-d]pyrimidin-1-yl]butan-2-ol. To a solution of N-[1-[(3R)-3-[tert-butyl(diphenyl)silyl]oxybutyl]pyrazolo[3,4-d]pyrimidin-6-yl]-3,4-dihydro-1H-isoquinolin-7-amine (61 mg, 0.10 mmol) in MeOH (1.0 mL) was added a 4 M solution of HCl in 1,4-dioxane (0.20 mL, 0.80 mmol) and the reaction mixture was stirred for 3 h. The reaction mixture was concentrated and the crude product was purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (8.7 mg). ¹H NMR (400 MHz, Methanol-d₄, TFA salt) δ 8.96 (s, 1H), 8.51 (s, 1H), 8.11 (s, 1H), 6.95 (s, 1H), 4.65-4.43 (m, 3H), 4.38-4.26 (m, 1H), 3.96 (s, 3H), 3.86-3.65 (m, 2H), 3.42 (td, J=11.9, 5.2 Hz, 1H), 3.29-3.21 (m, 1H), 3.20-3.10 (m, 1H), 3.08 (s, 3H), 2.16-2.05 (m, 1H), 2.02-1.90 (m, 1H), 1.22 (d, J=6.2 Hz, 3H). LCMS [M+H]: 383.1.

Example 84

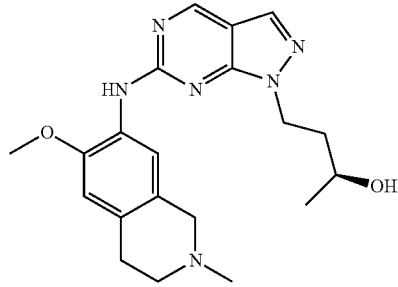 [SMILES: COc1cc2c(cc1Nc1ncc3cnn(CC[C@H](C)O)c3n1)CN(C)CC2]

(S)-4-(6-((6-methoxy-2-methyl-1,2,3,4-tetrahydroisoquinolin-7-yl)amino)-1H-pyrazolo[3,4-d]pyrimidin-1-yl)butan-2-ol The above compound was prepared according to Steps 1 to 5 from EXAMPLE 83 substituting methyl (S)-(−)-3-hydroxybutyrate for methyl (R)-(−)-3-hydroxybutyrate to afford the title compound (19 mg). ¹H NMR (400 MHz, Methanol-d₄) δ 8.84 (s, 1H), 8.36 (s, 1H), 7.99 (s, 1H), 6.76 (s, 1H), 4.54-4.37 (m, 2H), 3.90 (s, 3H), 3.78-3.66 (m, 1H), 3.62 (s, 2H), 2.92 (t, J=5.9 Hz, 2H), 2.79-2.67 (m, 2H), 2.46 (s, 3H), 2.13-2.01 (m, 1H), 2.01-1.89 (m, 1H), 1.21 (d, J=6.2 Hz, 3H). LCMS [M+H]: 383.1.

Example 85

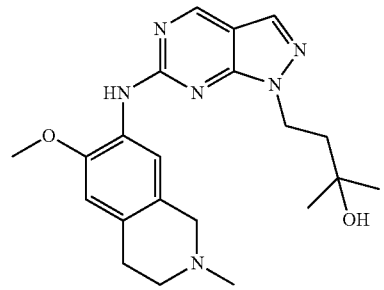 [SMILES: COc1cc2c(cc1Nc1ncc3cnn(CCC(C)(C)O)c3n1)CN(C)CC2]

4-[6-[(6-methoxy-2-methyl-3,4-dihydro-1H-isoquinolin-7-yl)amino]pyrazolo[3,4-d]pyrimidin-1-yl]-2-methyl-butan-2-ol Step 1. Preparation of 4-(6-chloropyrazolo[3,4-d]pyrimidin-1-yl)-2-methyl-butan-2-ol. Prepared according to general procedure C using 6-chloro-1H-pyrazolo[3,4-d]pyrimidine (100 mg, 0.65 mmol), 4-bromo-2-methyl-butan-2-ol (140 mg, 0.84 mmol), cesium carbonate (274 mg, 0.84 mmol), and potassium iodide (54 mg, 0.32 mmol, 50 mol %)

in MeCN (3.2 mL) stirred at 22° C. for 48 h. The reaction mixture was diluted with water and extracted with EtOAc. The combined organic phase was dried over anhydrous sodium sulfate, filtered, and concentrated. The crude product was purified by silica gel chromatography (0-50% EtOAc in hexanes) to afford the title compound (80 mg).

Step 2. Preparation of 4-[6-[(6-methoxy-2-methyl-3,4-dihydro-1H-isoquinolin-7-yl)amino]pyrazolo[3,4-d]pyrimidin-1-yl]-2-methyl-butan-2-ol. Prepared according to general procedure B using 6-methoxy-2-methyl-3,4-dihydro-1H-isoquinolin-7-amine (64.0 mg, 0.33 mmol), 4-(6-chloropyrazolo[3,4-d]pyrimidin-1-yl)-2-methyl-butan-2-ol (80.0 mg, 0.33 mmol), cesium carbonate (325 mg, 1.0 mmol), and Pd-PEPPSI-iPent catalyst (53.0 mg, 0.067 mmol, 20 mol %) in 1,2-dimethoxyethane (3.3 mL) heated to 80° C. for 3 h. The reaction mixture was cooled to ambient temperature then filtered through Celite and concentrated. The crude product was purified by silica gel chromatography (0-10% MeOH in DCM), followed by purification by reverse phase HPLC (Phenomenex, Gemini-NX, 10 um, 250×30 mm, C18 column; gradient of 20% MeCN/0.1% TFA-water to 100% MeCN/0.1% TFA) to the title compound (55 mg). $^1$H NMR (400 MHz, Methanol-$d_4$) δ 8.85 (s, 1H), 8.40 (s, 1H), 7.99 (s, 1H), 6.76 (s, 1H), 4.56-4.46 (m, 2H), 3.92 (s, 3H), 3.62 (s, 2H), 2.93 (t, J=6.0 Hz, 2H), 2.75 (t, J=6.0 Hz, 2H), 2.46 (s, 3H), 2.15-2.03 (m, 2H), 1.30 (s, 6H). LCMS [M+H]: 397.2.

Example 86

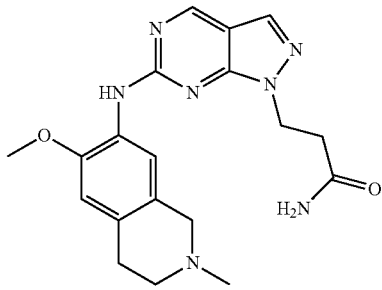 [SMILES: COc1cc2c(cc1Nc1ncc3cnn(CCC(N)=O)c3n1)CN(C)CC2]

3-[6-[(6-methoxy-2-methyl-3,4-dihydro-1H-isoquinolin-7-yl)amino]pyrazolo[3,4-d]pyrimidin-1-yl] 210ropenamide Step 1. Preparation of 3-(6-chloropyrazolo[3,4-d]pyrimidin-1-yl)210ropenamide. Prepared according to general procedure C using 6-chloro-1H-pyrazolo[3,4-d]pyrimidine (100 mg, 0.65 mmol), 3-bromopropanamide (118 mg, 0.78 mmol), cesium carbonate (316 mg, 1.0 mmol), and potassium iodide (54 mg, 0.32 mmol, 50 mol %) in MeCN (2.2 mL) stirred at 22° C. for 48 h. The reaction mixture was diluted with water and extracted with EtOAc. The combined organic phase was dried over anhydrous sodium sulfate, filtered, and concentrated. The crude product was purified by silica gel chromatography (0-20% MeOH in DCM) to afford 3-(6-chloropyrazolo[3,4-d]pyrimidin-1-yl)propenamide (33 mg).

Step 2. Preparation of 3-[6-[(6-methoxy-2-methyl-3,4-dihydro-1H-isoquinolin-7-yl)amino]pyrazolo[3,4-d]pyrimidin-1-yl]211ropenamide. Prepared according to general procedure B using 6-methoxy-2-methyl-3,4-dihydro-1H-isoquinolin-7-amine (28 mg, 0.15 mmol), 3-(6-chloropyrazolo[3,4-d]pyrimidin-1-yl)211ropenamide (33 mg, 0.15 mmol), cesium carbonate (142 mg, 0.44 mmol), and Pd-PEPPSI-iPent catalyst (23 mg, 0.029 mmol, 20 mol %) in 1,2-dimethoxyethane (1.4 mL) heated to 80° C. for 3 h. The reaction mixture was cooled to ambient temperature then filtered through Celite and concentrated. The crude product was purified by silica gel chromatography (0-20% 0.1% ammonia in MeOH in DCM), then repurified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (1.3 mg). $^1$H NMR (400 MHz, Methanol-$d_4$) δ 8.86 (s, 1H), 8.39 (s, 1H), 8.00 (s, 1H), 6.77 (s, 1H), 4.65 (t, J=7.1 Hz, 2H), 3.92 (s, 3H), 3.66 (s, 2H), 2.94 (t, J=6.0 Hz, 2H), 2.87 (t, J=7.1 Hz, 2H), 2.76 (t, J=6.0 Hz, 2H), 2.49 (s, 3H). LCMS [M+H]: 382.1.

Example 87

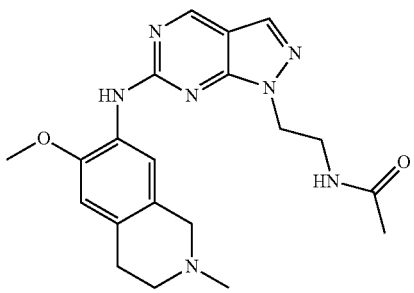 [SMILES: COc1cc2c(cc1Nc1ncc3cnn(CCNC(C)=O)c3n1)CN(C)CC2]

N-[2-[6-[(6-methoxy-2-methyl-3,4-dihydro-1H-isoquinolin-7-yl)amino]pyrazolo[3,4-d]pyrimidin-1-yl] ethyl]acetamide Step 1. Preparation of tert-butyl N-[2-(6-chloropyrazolo[3,4-d]pyrimidin-1-yl)ethyl]carbamate. Prepared according to general procedure D using 6-chloro-1H-pyrazolo[3,4-d]pyrimidine (2.0 g, 12.9 mmol), tert-butyl N-(2-hydroxyethyl)carbamate (2.4 mL 15.5 mmol), and triphenylphosphine (5.1 g, 19.4 mmol) in THF (65 mL) with DIAD (3.8 mL, 19.4 mmol). The reaction mixture was stirred for 3 h, then quenched with water and extracted with EtOAc. The combined organic phase was dried over anhydrous sodium sulfate, filtered, and concentrated. The crude product was purified by silica gel chromatography (0-50% EtOAc in hexanes) to afford the crude product which was used without further purification.

Step 2. Preparation of 2-(6-chloropyrazolo[3,4-d]pyrimidin-1-yl)ethanamine 2,2,2-trifluoroacetate. To a solution of tert-butyl N-[2-(6-chloropyrazolo[3,4-d]pyrimidin-1-yl)ethyl]carbamate (1.0 g, 3.4 mmol) in DCM (10 mL) was added trifluoroacetic acid (1.0 mL, 5.9 mmol) and the reaction mixture was stirred for 4 h. The reaction mixture was concentrated then diluted with DCM and concentrated again three additional times to afford the title compound as a crude solid (827 mg).

Step 3. Preparation of N-[2-(6-chloropyrazolo[3,4-d]pyrimidin-1-yl)ethyl]acetamide. To a cooled (0° C.) solution of 2-(6-chloropyrazolo[3,4-d]pyrimidin-1-yl)ethanamine 2,2,2-trifluoroacetate (150 mg, 0.48 mmol) in DCM (1.6 mL) was added DIEA (0.42 mL, 2.4 mmol) and acetyl chloride (45 µL, 0.63 mmol). The reaction mixture was warmed to ambient temperature and stirred for 48 h, then diluted with water and DCM. The phases were separated and the combined organic phase was washed with 1 M HCl, neutralized with saturated aqueous sodium bicarbonate, dried over anhydrous sodium sulfate, filtered, and concentrated. The crude product was purified by silica gel chromatography (0-20% MeOH in DCM) to afford the title compound (31 mg).

Step 4. Preparation of N-[2-[6-[(6-methoxy-2-methyl-3,4-dihydro-1H-isoquinolin-7-yl)amino]pyrazolo[3,4-d]pyrimidin-1-yl]ethyl]acetamide. Prepared according to general procedure B using 6-methoxy-2-methyl-3,4-dihydro-1H-isoquinolin-7-amine (25.0 mg, 0.13 mmol), N-[2-(6-chloropyrazolo[3,4-d]pyrimidin-1-yl)ethyl]acetamide (31.0 mg, 0.13 mmol), cesium carbonate (125.0 mg, 0.38 mmol), and Pd-PEPPSI-iPent catalyst (20.0 mg, 0.026 mmol, 20 mol %) in 1,2-dimethoxyethane (1.3 mL) heated to 80° C. for 3 h. The reaction mixture was cooled to ambient temperature then filtered through Celite and concentrated. The crude product was purified by silica gel chromatography (0-20% 0.1% ammonia in MeOH in DCM), then repurified by reverse phase HPLC (Phenomenex, Gemini-NX, 10 um, 250×30 mm, C18 column; gradient of 20% MeCN/0.1% TFA-water to 100% MeCN/0.1% TFA) to the title compound (18 mg). $^1$H NMR (400 MHz, Methanol-$d_4$) δ 8.87 (s, 1H), 8.33 (s, 1H), 8.03 (s, 1H), 6.78 (s, 1H), 4.56-4.46 (m, 2H), 3.92 (s, 3H), 3.71 (s, 2H), 3.68-3.61 (m, 2H), 2.93 (t, J=6.0 Hz, 2H), 2.76 (t, J=6.0 Hz, 2H), 2.50 (s, 3H), 1.72 (s, 3H). LCMS [M+H]: 396.1.

Example 88

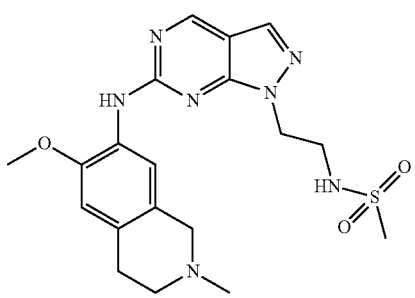 [SMILES: COc1cc2c(cc1Nc1ncc3cnn(CCNS(C)(=O)=O)c3n1)CN(C)CC2]

N-[2-[6-[(6-methoxy-2-methyl-3,4-dihydro-1H-isoquinolin-7-yl)amino]pyrazolo[3,4-d]pyrimidin-1-yl]ethyl]methanesulfonamide The above compound was prepared according to Steps 3 and 4 in EXAMPLE 87 substituting methanesulfonyl chloride for acetyl chloride to afford the title compound (13 mg). $^1$H NMR (400 MHz, Methanol-$d_4$) δ 8.87 (s, 1H), 8.36 (s, 1H), 8.03 (s, 1H), 6.78 (s, 1H), 4.52 (t, J=6.2 Hz, 2H), 3.91 (s, 3H), 3.69 (s, 2H), 3.62 (t, J=6.2 Hz, 2H), 2.98-2.91 (m, 2H), 2.87 (s, 3H), 2.76 (t, J=6.0 Hz, 2H), 2.48 (s, 3H). LCMS [M+H]: 432.1.

Example 89

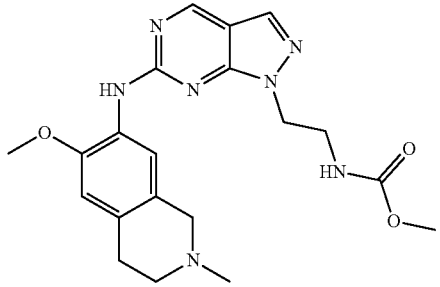

methyl N-[2-[6-[(6-methoxy-2-methyl-3,4-dihydro-1H-isoquinolin-7-yl)amino]pyrazolo[3,4-d]pyrimidin-1-yl]ethyl]carbamate The above compound was prepared according to Steps 3 and 4 in EXAMPLE 87 substituting methyl chloroformate for acetyl chloride to afford the title compound (23 mg). $^1$H NMR (400 MHz, Methanol-$d_4$) δ 8.84 (s, 1H), 8.38 (s, 1H), 8.00 (s, 1H), 6.76 (s, 1H), 4.50 (t, J=5.8 Hz, 2H), 3.91 (s, 3H), 3.73 (s, 2H), 3.56 (t, J=5.7 Hz, 2H), 3.44 (s, 3H), 2.93 (t, J=6.1 Hz, 2H), 2.75 (t, J=6.0 Hz, 2H), 2.50 (s, 3H). LCMS [M+H]: 412.1.

Example 90

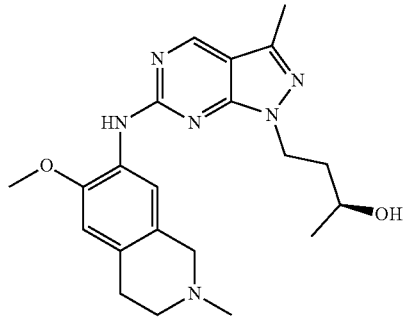 [SMILES: COc1cc2c(cc1Nc1ncc3c(C)nn(CC[C@H](C)O)c3n1)CN(C)CC2]

(2S)-4-[6-[(6-methoxy-2-methyl-3,4-dihydro-1H-isoquinolin-7-yl)amino]-3-methyl-pyrazolo[3,4-d]pyrimidin-1-yl]butan-2-ol The above compound was prepared according to Steps 3 to 5 in EXAMPLE 83 using 6-chloro-3-methyl-1H-pyrazolo[3,4-d]pyrimidine and (3S)-3-[tert-butyl(diphenyl)silyl]oxybutan-1-ol to afford (2S)-4-[6-[(6-methoxy-2-methyl-3,4-dihydro-1H-isoquinolin-7-yl)amino]-3-methyl-pyrazolo[3,4-d]pyrimidin-1-yl]butan-2-ol (4.5 mg). $^1$H NMR (400 MHz, Methanol-$d_4$) δ 8.82 (s, 1H), 8.37 (s, 1H), 6.78 (s, 1H), 4.49-4.32 (m, 2H), 3.91 (s, 3H), 3.77-3.66 (m, 1H), 3.63 (s, 2H), 2.93 (t, J=6.0 Hz, 2H), 2.76 (t, J=6.0 Hz, 2H), 2.50 (s, 3H), 2.48 (s, 3H), 2.11-1.89 (m, 2H), 1.22 (d, J=6.2 Hz, 3H). LCMS [M+H]: 397.2.

Example 91

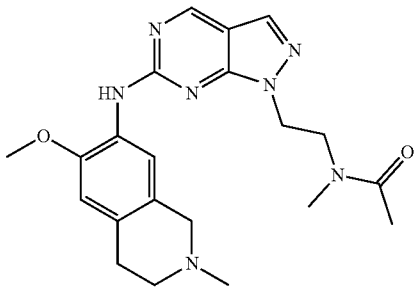 [SMILES: COc1cc2c(cc1Nc1ncc3cnn(CCN(C)C(C)=O)c3n1)CN(C)CC2]

N-[2-[6-[(6-methoxy-2-methyl-3,4-dihydro-1H-iso-
quinolin-7-yl)amino]pyrazolo[3,4-d]pyrimidin-1-yl]
ethyl]-N-methyl-acetamide The above compound was prepared according to Steps 1-4 in EXAMPLE 87 using tert-butyl N-(2-hydroxyethyl)-N-methyl-carbamate instead of tert-butyl N-(2-hydroxyethyl)carbamate to afford the title compound (36 mg). $^1$H NMR (400 MHz, Methanol-$d_4$, 1.8:1.0 mixture of rotomers) δ 8.92-8.79 (m, 2H), 8.36-8.28 (m, 2H), 8.28-8.20 (m, 1H), 8.06 (d, J=2.0 Hz, 1H), 8.02 (d, J=2.1 Hz, 1H), 6.79 (d, J=3.2 Hz, 3H), 4.66-4.48 (m, 6H), 3.94-3.90 (m, 8H), 3.88 (t, J=5.7 Hz, 2H), 3.84-3.77 (m, 4H), 3.70 (s, 4H), 3.61 (s, 2H), 2.93 (t, J=6.0 Hz, 6H), 2.89 (s, 3H), 2.75 (t, J=6.1 Hz, 6H), 2.67 (d, J=1.1 Hz, 6H), 2.50 (s, 5H), 2.47 (s, 3H), 1.78 (s, 5H), 1.68 (s, 3H). LCMS [M+H]: 410.1.

Example 92

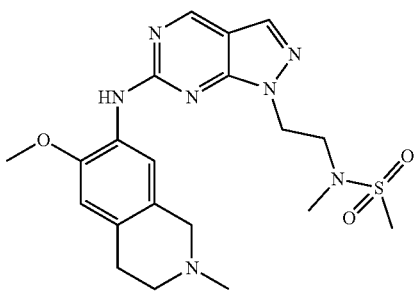 [SMILES: COc1cc2c(cc1Nc1ncc3cnn(CCN(C)S(C)(=O)=O)c3n1)CN(C)CC2]

N-[2-[6-[(6-methoxy-2-methyl-3,4-dihydro-1H-iso-
quinolin-7-yl)amino]pyrazolo[3,4-d]pyrimidin-1-yl]
ethyl]-N-methyl-methanesulfonamide The above compound was prepared according to Steps 3 and 4 in EXAMPLE 91substituting methanesulfonyl chloride for acetyl chloride to provide the title compound (26 mg). $^1$H NMR (400 MHz, Methanol-$d_4$) δ 8.88 (s, 1H), 8.37 (s, 1H), 8.04 (s, 1H), 6.79 (s, 11H), 4.59 (t, J=6.0 Hz, 2H), 3.92 (s, 3H), 3.71-3.62 (m, 4H), 2.93 (t, J=6.9, 5.2 Hz, 2H), 2.79 (s, 3H), 2.75 (t, J=5.8 Hz, 2H), 2.73 (s, 3H), 2.47 (s, 3H). LCMS [M+H]: 446.1.

Example 93

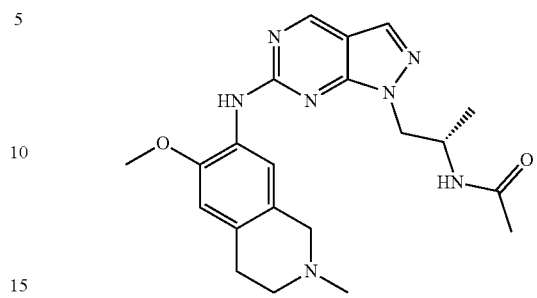

N-[(1S)-2-[6-[(6-methoxy-2-methyl-3,4-dihydro-1H-
isoquinolin-7-yl)amino]pyrazolo[3,4-d]pyrimidin-1-
yl]-1-methyl-ethyl]acetamide The above compound was prepared according to Steps 1 to 4 in EXAMPLE 87substituting Boc-L-alaninol for tert-butyl N-(2-hydroxyethyl)carbamate to afford the title compound (8.5 mg). $^1$H NMR (400 MHz, Methanol-$d_4$) δ 8.87 (s, 1H), 8.32 (s, 1H), 8.00 (s, 1H), 6.79 (s, 1H), 4.54 (dd, J=13.7, 5.1 Hz, 1H), 4.51-4.40 (m, 1H), 4.33 (dd, J=13.8, 5.7 Hz, 1H), 3.92 (s, 3H), 3.73 (d, J=14.6 Hz, 1H), 3.65 (d, J=14.6 Hz, 1H), 2.94 (t, J=6.0 Hz, 2H), 2.76 (t, J=6.0 Hz, 2H), 2.50 (s, 3H), 1.75 (s, 3H), 1.20 (d, J=6.8 Hz, 3H). LCMS [M+H]: 410.1.

Example 94

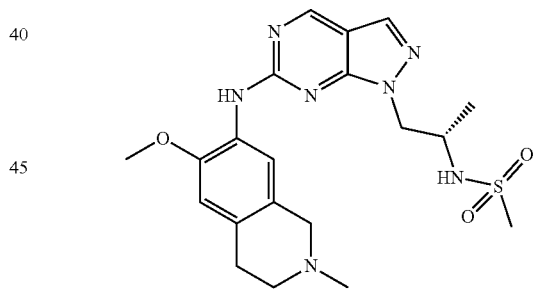

N-[(1S)-2-[6-[(6-methoxy-2-methyl-3,4-dihydro-1H-
isoquinolin-7-yl]amino]pyrazolo[3,4-d]pyrimidin-1-
yl]-1-methyl-ethyl]methanesulfonamide The above compound was prepared according to Steps 3 and 4 in EXAMPLE 93substituting methanesulfonyl chloride for acetyl chloride to afford the title compound (2 mg). H NMR (400 MHz, Methanol-$d_4$) δ 8.89 (s, 1H), 8.31 (s, 1H), 8.03 (s, 1H), 6.80 (s, 1H), 4.50 (dd, J=14.0, 6.7 Hz, 1H), 4.33 (dd, J=14.0, 6.7 Hz, 1H), 4.13-4.04 (m, 1H), 3.92 (s, 3H), 3.73 (d, J=14.5 Hz, 1H), 3.66 (d, J=14.7 Hz, 1H), 2.95 (t, J=6.1 Hz, 2H), 2.77 (t, J=5.9 Hz, 2H), 2.74 (s, 3H), 2.49 (s, 3H), 1.26 (d, J=6.7 Hz, 3H). LCMS [M+H]: 446.1.

Example 95

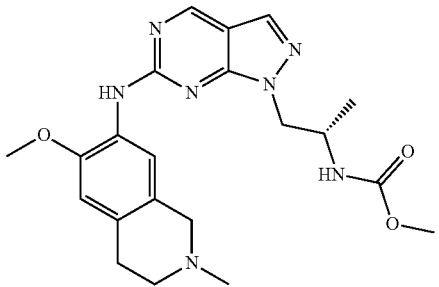

methyl N-[(1S)-2-[6-[(6-methoxy-2-methyl-3,4-dihydro-1H-isoquinolin-7-yl)amino]pyrazolo[3,4-d]pyrimidin-1-yl]-1-methyl-ethyl]carbamate The above compound was prepared according to Steps 3 and 4 in EXAMPLE 93 substituting methylchloroformate for acetyl chloride to afforded the title compound (20 mg); $^1$H NMR (400 MHz, Methanol-$d_4$) δ 8.86 (s, 1H), 8.36 (s, 1H), 7.99 (s, 1H), 6.78 (s, 1H), 4.47 (dd, J=14.1, 5.9 Hz, 1H), 4.39 (dd, J=13.9, 5.9 Hz, 1H), 4.25-4.14 (m, 1H), 3.91 (s, 3H), 3.77-3.63 (m, 2H), 3.47 (s, 3H), 2.93 (t, J=6.0 Hz, 2H), 2.75 (t, J=6.0 Hz, 2H), 2.49 (s, 3H), 1.19 (d, J=6.9 Hz, 3H). LCMS [M+H]: 426.1.

Example 96

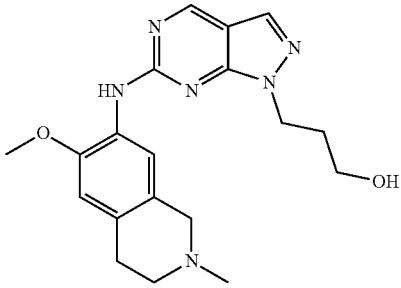 [SMILES: COc1cc2c(cc1Nc1ncc3cnn(CCCO)c3n1)CN(C)CC2]

3-[6-[(6-methoxy-2-methyl-3,4-dihydro-1H-isoquinolin-7-yl)amino]pyrazolo[3,4-d]pyrimidin-1-yl]propan-1-ol Step 1. Preparation of 3-(6-chloropyrazolo[3,4-d]pyrimidin-1-yl)propan-1-ol. Prepared according to general procedure C using 6-chloro-1H-pyrazolo[3,4-d]pyrimidine (150 mg, 0.97 mmol), 3-bromopropan-1-ol (0.11 mL, 1.3 mmol), cesium carbonate (411 mg, 1.3 mmol), and potassium iodide (81 mg, 0.49 mmol, 50 mol %) in MeCN (4.8 mL, 0.20 M) stirred at 22° C. for 48 h. The reaction mixture was diluted with water and extracted with EtOAc. The combined organic phase was dried over anhydrous sodium sulfate, filtered, and concentrated. The crude product was purified by silica gel chromatography (0-30% EtOAc in hexanes) to afford the title compound (85 mg).

Step 2. Preparation of 3-[6-[(6-methoxy-2-methyl-3,4-dihydro-1H-isoquinolin-7-yl)amino]pyrazolo[3,4-d]pyrimidin-1-yl]propan-1-ol. Prepared according to general procedure B using 6-methoxy-2-methyl-3,4-dihydro-1H-isoquinolin-7-amine (77 mg, 0.40 mmol), 3-(6-chloropyrazolo[3,4-d]pyrimidin-1-yl)propan-1-ol (85 mg, 0.40 mmol), cesium carbonate (391 mg, 1.2 mmol), and Pd-PEPPSI-iPent catalyst (63 mg, 0.080 mmol, 20 mol %) in 1,2-dimethoxyethane (4.0 mL) heated to 80° C. for 3 h. The reaction mixture was cooled to ambient temperature then filtered through Celite and concentrated. The crude product was purified by silica gel chromatography (0-10% MeOH in DCM), then repurified by reverse phase HPLC (Phenomenex, Gemini-NX, 10 um, 250×30 mm, C18 column; gradient of 20% MeCN/0.1% TFA-water to 100% MeCN/0.1% TFA) to afford 3-[6-[(6-methoxy-2-methyl-3,4-dihydro-1H-isoquinolin-7-yl)amino]pyrazolo[3,4-d]pyrimidin-1-yl]propan-1-ol (8.9 mg). $^1$H NMR (400 MHz, Methanol-$d_4$) δ 8.87 (s, 1H), 8.37 (s, 1H), 8.01 (s, 1H), 6.78 (s, 1H), 4.48 (t, J=6.9 Hz, 2H), 3.91 (s, 3H), 3.63 (s, 2H), 3.59 (t, J=6.2 Hz, 2H), 2.93 (t, J=6.0 Hz, 2H), 2.75 (t, J=6.1 Hz, 2H), 2.47 (s, 3H), 2.19-2.09 (m, 2H). LCMS [M+H]: 369.1.

Example 97

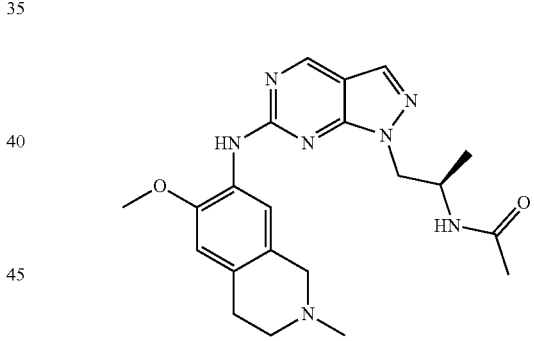

N-[(1R)-2-[6-[(6-methoxy-2-methyl-3,4-dihydro-1H-isoquinolin-7-yl)amino]pyrazolo[3,4-d]pyrimidin-1-yl]-1-methyl-ethyl]acetamide The above compound was prepared according to Steps 1 to 4 in EXAMPLE 87 substituting Boc-D-alaninol for tert-butyl N-(2-hydroxyethyl)carbamate to afford the title compound (3.6 mg). $^1$H NMR (400 MHz, Methanol-$d_4$) δ 8.87 (s, 1H), 8.32 (s, 1H), 8.00 (s, 1H), 6.79 (s, 1H), 4.54 (dd, J=13.8, 5.0 Hz, 1H), 4.50-4.40 (m, 1H), 4.32 (dd, J=13.8, 5.6 Hz, 1H), 3.92 (s, 3H), 3.73 (d, J=14.6 Hz, 1H), 3.65 (d, J=14.6 Hz, 1H), 2.94 (t, J=6.0 Hz, 2H), 2.76 (t, J=6.0 Hz, 2H), 2.49 (s, 3H), 1.75 (s, 3H), 1.20 (d, J=6.9 Hz, 3H). LCMS [M+H]: 410.1.

Example 98

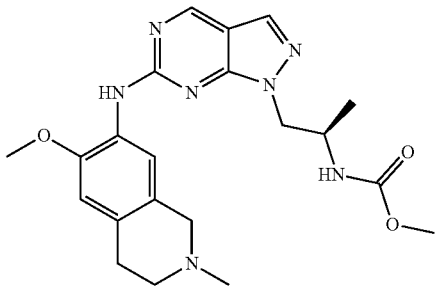

methyl N-[(1R)-2-[6-[(6-methoxy-2-methyl-3,4-dihydro-1H-isoquinolin-7-yl)amino]pyrazolo[3,4-d]pyrimidin-1-yl]-1-methyl-ethyl]carbamate The above compound was prepared according to Steps 3 and 4 in EXAMPLE 97 substituting methylchloroformate for acetyl chloride to afford the title compound (25 mg). $^1$H NMR (400 MHz, Methanol-$d_4$) δ 8.87 (s, 1H), 8.36 (s, 1H), 8.00 (s, 1H), 6.78 (s, 1H), 4.47 (dd, J=13.6, 5.8 Hz, 11H), 4.39 (dd, J=13.9, 5.8 Hz, 1H), 4.28-4.13 (m, 1H), 3.92 (d, J=1.2 Hz, 3H), 3.77-3.62 (m, 2H), 3.47 (s, 3H), 2.93 (t, J=6.0 Hz, 2H), 2.76 (t, J=6.0 Hz, 2H), 2.49 (s, 3H), 1.20 (d, J=6.8 Hz, 3H). LCMS [M+H]: 426.3.

Example 99

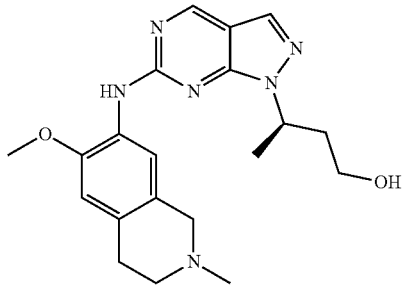 [SMILES: COc1cc2c(cc1Nc1ncc3cnn([C@H](C)CCO)c3n1)CN(C)CC2]

(3R)-3-[6-[(6-methoxy-2-methyl-3,4-dihydro-1H-isoquinolin-7-yl)amino]pyrazolo[3,4-d]pyrimidin-1-yl]butan-1-ol Step 1. Preparation of (2S)-4-[tert-butyl(dimethyl)silyl]oxybutan-2-ol. To a cooled (0° C.) solution of (S)-(+)-1,3-butanediol (1.0 mL, 11.1 mmol) in 8:1 DCM:DMF (36 mL) was added imidazole (2.1 g, 31 mmol) and tert-butyldimethylchlorosilane (1.8 g, 12.2 mmol). The reaction mixture was stirred for 16 h then diluted with hexanes and water. The phases were separated and the organic phase was washed with 1 M HCl, a saturated solution of sodium bicarbonate, dried over anhydrous sodium sulfate, filtered, and concentrated to afford the title compound as crude material (2.1 g) that was taken forward without further purification.

Step 2. Preparation of tert-butyl-[(3R)-3-(6-chloropyrazolo[3,4-d]pyrimidin-1-yl)butoxy]-dimethyl-silane. Prepared according to general procedure D using 6-chloro-1H-pyrazolo[3,4-d]pyrimidine (500 mg, 3.2 mmol), (2S)-4-[tert-butyl(dimethyl)silyl]oxybutan-2-ol (0.79 g, 3.9 mmol), and triphenylphosphine (1.3 g, 4.9 mmol), and DIAD (0.95 mL, 4.9 mmol) in THF (16.2 mL) stirred for 3 h at rt. The reaction was quenched with water and extracted with EtOAc. The combined organic phase was dried over anhydrous sodium sulfate, filtered, and concentrated. The crude product was purified by silica gel chromatography (0-50% EtOAc in hexanes) to afford the title compound (738 mg).

Step 3. Preparation of (3R)-3-[6-[(6-methoxy-2-methyl-3,4-dihydro-1H-isoquinolin-7-yl)amino]pyrazolo[3,4-d]pyrimidin-1-yl]butan-1-ol. Prepared according to general procedure B using 6-methoxy-2-methyl-3,4-dihydro-1H-isoquinolin-7-amine (34 mg, 0.18 mmol), tert-butyl-[(3R)-3-(6-chloropyrazolo[3,4-d]pyrimidin-1-yl)butoxy]-dimethyl-silane (60 mg, 0.18 mmol), cesium carbonate (172 mg, 0.53 mmol), and Pd-PEPPSI-iPent catalyst (28 mg, 0.035 mmol, 20 mol %) in degassed 1,2-dimethoxyethane (1.8 mL) heated to 80° C. and stirred for 3 h. The reaction mixture was cooled to ambient temperature, filtered through Celite, and concentrated. The crude product was adsorbed onto silica gel and purified by silica gel chromatography (0-10% MeOH in DCM). The purified product was then dissolved in DCM and treated with 4 N HCl (0.13 mL, 0.53 mmol) until desilylation was complete. The reaction mixture was concentrated and the crude product was purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (29 mg). $^1$H NMR (400 MHz, Methanol-$d_4$) δ 8.86 (d, J=1.0 Hz, 1H), 8.34 (s, 1H), 8.01 (s, 1H), 6.77 (s, 1H), 5.23-5.07 (m, 1H), 3.91 (s, 3H), 3.62 (s, 2H), 3.50 (dt, J=11.3, 5.7 Hz, 1H), 3.36 (ddd, J=10.9, 7.9, 5.5 Hz, 1H), 2.93 (t, J=6.0 Hz, 2H), 2.74 (t, J=6.0 Hz, 2H), 2.47 (s, 3H), 2.30 (ddt, J=14.7, 9.3, 5.5 Hz, 1H), 2.08 (dddd, J=14.0, 7.9, 6.0, 5.1 Hz, 1H), 1.59 (d, J=6.8 Hz, 3H). LCMS [M+H]: 383.2.

Example 100

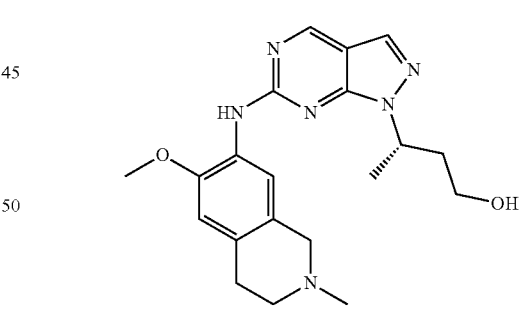

3S)-3-[6-[(6-methoxy-2-methyl-3,4-dihydro-1H-isoquinolin-7-yl)amino]pyrazolo[3,4-d]pyrimidin-1-yl]butan-1-ol The above compound was prepared according to Steps 1 to 3 from EXAMPLE 99 substituting®-(−)-1,3-butanediol for (S)-(+)-1,3-butanediol to afford the title compound (29 mg). $^1$H NMR (400 MHz, Methanol-$d_4$) δ 8.86 (s, 1H), 8.34 (s, 1H), 8.01 (s, 1H), 6.77 (s, 1H), 5.23-5.09 (m, 1H), 3.91 (s, 3H), 3.62 (s, 2H), 3.50 (dt, J=11.3, 5.8 Hz, 1H), 3.41-3.33 (m, 1H), 2.93 (t, J=6.1 Hz, 2H), 2.74 (t, J=6.0 Hz, 2H), 2.47

(s, 3H), 2.30 (ddt, J=14.6, 9.3, 5.5 Hz, 1H), 2.08 (dddd, J=14.0, 7.9, 6.0, 5.1 Hz, 1H), 1.59 (d, J=6.8 Hz, 3H). LCMS [M+H]: 383.2.

Example 101

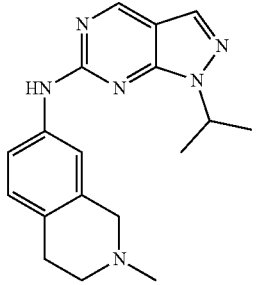 [SMILES: CC(C)n1ncc2cnc(Nc3ccc4c(c3)CN(C)CC4)nc21]

N-(1-isopropyl-1H-pyrazolo[3,4-d]pyrimidin-6-yl)-2-methyl-1,2,3,4-tetrahydroisoquinolin-7-amine The above compound was prepared according to general procedure E using Precursor 1 (50 mg, 0.22 mmol) and 2-iodopropane (35 mg, 0.22 mmol), and potassium carbonate in DMF at 80° C. and purifying directly by reverse phase HPLC (Phenomenex, Gemini-NX, 10 um, 250×30 mm, C18 column; gradient of 20% MeCN/0.1% TFA-water to 100% MeCN/0.1% TFA). $^1$H NMR (400 MHz, Acetonitrile-d3, TFA salt) δ 8.82 (s, 1H), 7.92 (s, 1H), 7.57 (s, 1H), 7.52 (d, J=8.4 Hz, 1H), 7.09 (d, J=8.2 Hz, 1H), 5.02 (m, 1H), 3.56 (s, 2H), 2.84 (t, J=6.0 Hz, 2H), 2.67 (t, J=5.9 Hz, 2H), 2.41 (s, 3H), 1.52 (d, J=6.7 Hz, 6H). LCMS [M+H]: 323.1.

Example 102

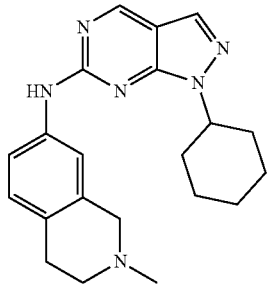 [SMILES: CN1CCc2ccc(Nc3ncc4cnn(C5CCCCC5)c4n3)cc2C1]

N-(1-cyclohexyl-1H-pyrazolo[3,4-d]pyrimidin-6-yl)-2-methyl-1,2,3,4-tetrahydroisoquinolin-7-amine The above compound was prepared according to general procedure E using Precursor 1 (25.0 mg, 0.09 mmol) and iodocylohexane (18.7 mg, 0.09 mmol), and potassium carbonate in DMF at 80° C. and purifying directly on reverse phase HPLC (Phenomenex, Gemini-NX, 10 um, 250×30 mm, C18 column; gradient of 20% MeCN/0.1% TFA-water to 100% MeCN/0.1% TFA). $^1$H NMR (400 MHz, Methanol-d4, TFA salt) δ 8.85 (s, 1H), 7.95 (s, 1H), 7.65 (s, 1H), 7.52 (d, J=8.5 Hz, 1H), 7.10 (d, J=8.4 Hz, 1H), 4.60 (m, 1H), 3.64 (s, 2H), 3.35 (s, 2H), 2.93 (t, J=6.0 Hz, 2H), 2.77 (t, J=6.0 Hz, 3H), 2.02-1.91 (m, 4H), 1.87-1.75 (m, 4H), 1.63-1.45 (m, 2H), 1.00-0.74 (m, 3H). LCMS [M+H]: 363.1.

Example 103

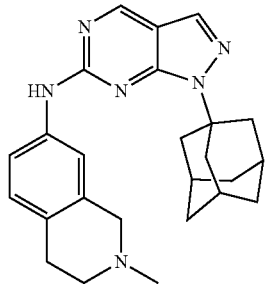 [SMILES: CN1CCc2ccc(Nc3ncc4cnn(C56CC7CC(CC(C7)C5)C6)c4n3)cc2C1]

N-(1-((3s,5s,7s)-adamantan-1-yl)-1H-pyrazolo[3,4-d]pyrimidin-6-yl)-2-methyl-1,2,3,4-tetrahydroisoquinolin-7-amine The above compound was prepared by heating Precursor 1 (27.0 mg, 0.096 mmol) and adamantan-1-ol (14.7 mg, 0.096 mmol) in acetic acid (50 mL) and phosphoric acid (200 mL) at 60° C. for 15 hours. The reaction mixture was then diluted with water (10 mL), to which was added solid sodium bicarbonate (200 mg) followed by saturated aqueous sodium bicarbonate solution until the pH reached 8. The resulting suspension was filtered to afford the crude product, which was purified by silica gel column chromatography using a mixture of 0-20% MeOH and DCM as the eluent. $^1$H NMR (400 MHz, Acetonitrile-d3, freebase) δ 9.00 (s, 1H), 8.18 (s, 1H), 7.82 (s, 1H), 7.62 (s, 1H), 7.55 (d, J=8.3 Hz, 1H), 7.07 (d, J=8.3 Hz, 1H), 3.52 (s, 2H), 2.81 (d, J=6.1 Hz, 2H), 2.62 (t, J=5.9 Hz, 2H), 2.38 (s, 3H), 2.27 (s, 3H), 1.94 (dtd, J=5.0, 2.5, 1.0 Hz, 6H), 1.81 (s, 6H). LCMS [M+H]: 415.1.

Example 104

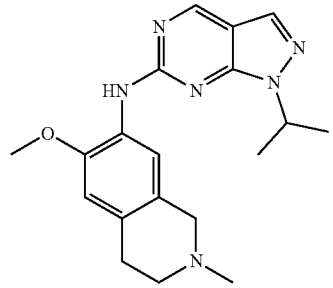 [SMILES: COc1cc2c(cc1Nc1ncc3cnn(C(C)C)c3n1)CN(C)CC2]

N-(1-isopropylpyrazolo[3,4-d]pyrimidin-6-yl)-6-methoxy-2-methyl-3,4-dihydro-1H-isoquinolin-7-amine The above compound was prepared according to general procedure A using precursor V (30.0 mg, 0.22 mmol) and 6-methoxy-2-methyl-3,4-dihydro-1H-isoquinolin-7-amine (32.3 mg, 0.22 mmol), p-TSA in 1,4-dioxane at 120° C. and purifying by silica gel column chromatographyy using a gradient of 0-20% MeOH/DCM. $^1$H NMR (400 MHz, Acetonitrile-d3, freebase) δ 8.83 (s, 1H), 8.28 (s, 1H), 7.93 (s, 1H), 7.78 (s, 1H), 6.77 (s, 1H), 5.03 (p, J=6.7 Hz, 1H), 3.88 (s, 3H), 3.55 (s, 2H), 2.85 (t, J=6.0 Hz, 2H), 2.66 (t, J=5.9 Hz, 2H), 2.41 (s, 3H), 1.54 (d, J=6.6 Hz, 6H). LCMS [M+H]: 353.1.

Example 105

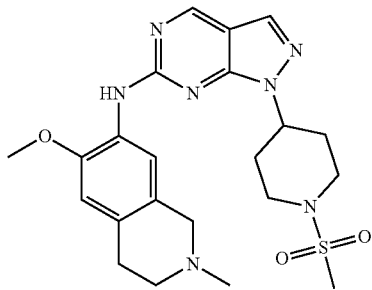 [SMILES: COc1cc2c(cc1Nc1ncc3cnn(C4CCN(S(C)(=O)=O)CC4)c3n1)CN(C)CC2]

6-methoxy-2-methyl-N-(1-(1-(methylsulfonyl)piperidin-4-yl)-1H-pyrazolo[3,4-d]pyrimidin-6-yl)-1,2,3,4-tetrahydroisoquinolin-7-amine Step 1: Preparation of tert-butyl 4-(6-chloropyrazolo[3,4-d]pyrimidin-1-yl)piperidine-1-carboxylate. Prepared according to general procedure D using 1-tert-butoxycarbonyl-4-hydroxypiperidine (0.906 g, 4.50 mmol), 6-chloro-1H-pyrazolo[3,4-d]pyrimidine (0.580 g, 3.75 mmol), triphenylphosphine (1.97 g, 7.51 mmol), and DEAD (40% solution, 3.42 mL, 7.51 050935-51800US mmol) at rt for 1.5 h. The crude product was purified by silica column chromatography eluting with 0% to 60% EtOAc in hexanes to afford the title compound (1.190 g).

Step 2: Preparation of tert-butyl 4-[6-[(6-methoxy-2-methyl-3,4-dihydro-1H-isoquinolin-7-yl)amino]pyrazolo[3,4-d]pyrimidin-1-yl]piperidine-1-carboxylate. Prepared according to general procedure B using 6-methoxy-2-methyl-3,4-dihydro-1H-isoquinolin-7-amine (273.2 mg, 1.42 mmol), tert-butyl 4-(6-chloropyrazolo[3,4-d]pyrimidin-1-yl)piperidine-1-carboxylate (400.0 mg, 1.18 mmol), Pd2(dba)3 (108.4 mg, 0.120 mmol), (S)-BINAP (147.5 mg, 0.240 mmol), and cesium carbonate (1.157 g, 3.55 mmol) in toluene (4.0 mL) and tert-butanol (4.0 mL) at 120° C. for 1 h. The crude product was purified by silica column chromatography eluting with 0% to 20% MeOH in DCM to afford the title compound (380 mg).

Step 3: Preparation of 6-methoxy-2-methyl-N-[1-(4-piperidyl)pyrazolo[3,4-d]pyrimidin-6-yl]-3,4-dihydro-1H-isoquinolin-7-amine trifluoroacetate. Trifluoroacetic acid (0.28 mL, 3.65 mmol) was added to a solution of tert-butyl 4-[6-[(6-methoxy-2-methyl-3,4-dihydro-1H-isoquinolin-7-yl)amino]pyrazolo[3,4-d]pyrimidin-1-yl]piperidine-1-carboxylate (180.0 mg, 0.360 mmol) in DCM (2.4 mL) at 23° C. The mixture was stirred for 48 h. The crude reaction mixture concentrated to afford the title compound (185.0 mg).

Step 4: Preparation of 6-methoxy-2-methyl-N-[1-(1-methylsulfonyl-4-piperidyl)pyrazolo[3,4-d]pyrimidin-6-yl]-3,4-dihydro-1H-isoquinolin-7-amine trifluoroacetate. Methanesulfonyl chloride (0.010 mL, 0.120 mmol) was added to a solution of 6-methoxy-2-methyl-N-[1-(4-piperidyl)pyrazolo[3,4-d]pyrimidin-6-yl]-3,4-dihydro-1H-isoquinolin-7-amine trifluoroacetate (40.0 mg, 0.080 mmol) and DIEA (0.270 mL, 1.58 mmol) in DCM (0.600 mL). The reaction mixture was stirred at 23° C. for 10 min. The crude product was purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (21.0 mg). 1H NMR (400 MHz, Methanol-d4, TFA salt) δ 8.92 (s, 1H), 8.46 (s, 1H), 8.00 (s, 1H), 6.95 (s, 1H), 4.69 (ddt, J=11.8, 8.0, 4.1 Hz, 1H), 4.56 (d, J=15.1 Hz, 1H), 4.39 (d, J=15.2 Hz, 1H), 4.01-3.95 (m, 2H), 3.90 (s, 3H), 3.79-3.70 (m, 1H), 3.40 (td, J=11.8, 5.1 Hz, 1H), 3.28-3.18 (m, 1H), 3.12 (s, 3H), 3.01 (dd, J=13.0, 11.0 Hz, 2H), 2.95 (s, 3H), 2.87 (td, J=12.5, 4.0 Hz, 2H), 2.16 (d, J=12.5 Hz, 2H). LCMS [M+H]: 471.9

Examples 106 and 107

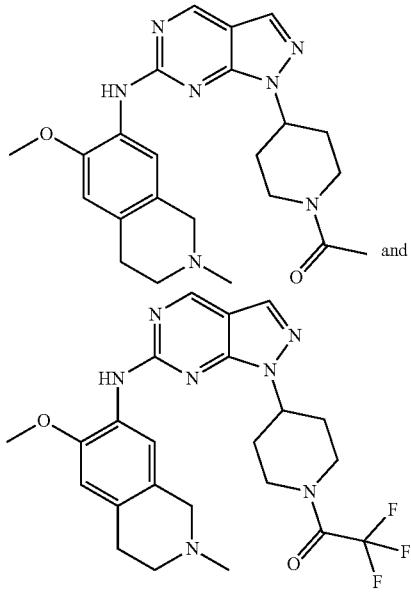

1-(4-(6-(((6-methoxy-2-methyl-1,2,3,4-tetrahydroisoquinolin-7-yl)amino)-1H-pyrazolo[3,4-d]pyrimidin-1-yl)piperidin-1-yl)ethan-1-one trifluoroacetate (EXAMPLE 106) and 2,2,2-trifluoro-1-(4-(6-((6-methoxy-2-methyl-1,2,3,4-tetrahydroisoquinolin-7-yl)amino)-1H-pyrazolo[3,4-d]pyrimidin-1-yl)piperidin-1-yl)ethan-1-one trifluroacetate (EXAMPLE 107)

Acetyl chloride (0.01 mL, 0.120 mmol) was added to a solution of 6-methoxy-2-methyl-N-[1-(4-piperidyl)pyrazolo[3,4-d]pyrimidin-6-yl]-3,4-dihydro-1H-isoquinolin-7-amine trifluoroacetate (40.0 mg, 0.080 mmol, EXAMPLE 105, Step 3) and DIEA (0.27 mL, 1.58 mmol) in DCM (0.600 mL) at 23° C. for 1 h. The crude products were purified by reverse phase HPLC (Phenomenex, Gemini-NX, 10 um, 250×30 mm, C18 column; gradient of 20% MeCN/0.1% TFA-water to 100% MeCN/0.1% TFA) to provide the title compounds EXAMPLE 106: 4.0 mg, 1H NMR (400 MHz, Methanol-d$_4$) δ 8.92 (s, 1H), 8.34 (d, J=8.3 Hz, 1H), 8.03 (s, 1H), 6.95 (s, 1H), 4.75 (d, J=13.2 Hz, 1H), 4.61-4.43 (m, 1H), 4.39-4.26 (m, 1H), 4.18-4.08 (m, 1H), 3.97 (s, 3H), 3.78 (s, 1H), 3.45-3.35 (m, 2H), 3.28-3.14 (m, 2H), 3.12 (s, 3H), 2.96 (t, J=12.6 Hz, 1H), 2.53-2.35 (m, 1H), 2.18 (d, J=6.2 Hz, 3H), 2.06-2.30 (m, 3H). LCMS [M+H]: 436.0

EXAMPLE 107: 6.0 mg, 1H NMR (400 MHz, Methanol-d₄) δ 8.93 (s, 11H), 8.29 (d, J=17.3 Hz, 1H), 8.06 (d, J=3.4 Hz, 1H), 6.95 (s, 1H), 4.66 (d, J=13.5 Hz, 1H), 4.51 (d, J=14.9 Hz, 11H), 4.32 (t, J=13.7 Hz, 1H), 4.20 (d, J=14.2 Hz, 11H), 3.96 (s, 3H), 3.81-3.72 (m, 11H), 3.56 (t, J=12.7 Hz, 1H), 3.49-3.37 (m, 1H), 3.28-3.20 (m, 2H), 3.21-3.14 (m, 1H), 3.11 (s, 3H), 2.54-2.38 (m, 1H), 2.32-2.13 (m, 3H). LCMS [M+H]: 489.9

Example 108

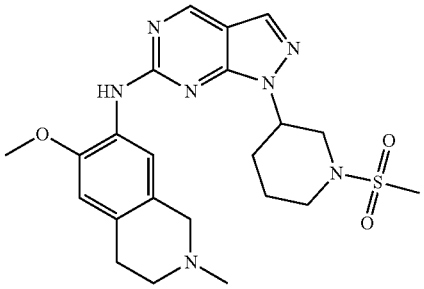

6-methoxy-2-methyl-N-(1-(1-(methylsulfonyl)piperidin-3-yl)-1H-pyrazolo[3,4-d]pyrimidin-6-yl)-1,2,3,4-tetrahydroisoquinolin-7-amine The above compound was prepared by using the preparation of EXAMPLE 105substituting 1-BOC-3-hydroxypiperidine for 1-tert-butoxycarbonyl-4-hydroxypiperidine in Step 1. 1H NMR (400 MHz, Methanol-d4, mixture of rotamers, TFA salt) δ 8.93 (s, 1H), 8.66 (s, 0.7H), 8.50 (s, 0.6H), 8.05 (s, 1H), 6.94 (s, 1H), 4.78 (d, J=14.9 Hz, 1.1H), 4.59 (d, J=15.4 Hz, 0.6H), 4.44-4.27 (m, 1H), 4.20-4.08 (m, 1H), 3.97 (s, 3H), 3.85 (d, J=11.9 Hz, 1H), 3.80-3.71 (m, 1H), 3.45-3.35 (m, 1H), 3.24 (s, 1H), 3.16 (s, 1H), 3.07 (s, 3H), 2.90 (s, 3H), 2.39 (d, J=13.0 Hz, 1H), 2.24 (s, 1H), 2.10 (s, 1H), 1.90 (s, 1H). LCMS [M+H]: 471.9

Example 109

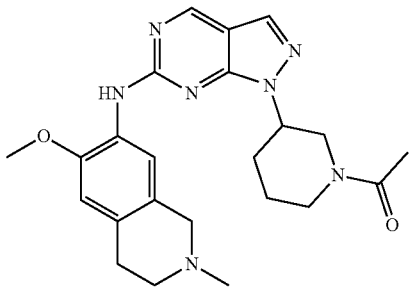 [SMILES: COc1cc2c(cc1Nc1ncc3cnn(C4CCCN(C(C)=O)C4)c3n1)CN(C)CC2]

1-(3-(6-(((6-methoxy-2-methyl-1,2,3,4-tetrahydroisoquinolin-7-yl)amino)-1H-pyrazolo[3,4-d]pyrimidin-1-yl)piperidin-1-yl)ethan-1-one The above compound was prepared by using the preparation of EXAMPLE 105substituting 1-BOC-3-hydroxypiperidine for 1-tert-butoxycarbonyl-4-hydroxypiperidine in Step 1 and acetyl chloride for methansulfonyl chloride in Step 4. 1H NMR (400 MHz, Methanol-d4) δ 8.91 (s, 1H), 8.46 (d, J=15.2 Hz, 1H), 8.04 (s, 1H), 6.92 (s, 1H), 4.32 (d, J=34.9 Hz, 2H), 3.95 (s, 3H), 3.81-3.35 (m, 2H), 3.26-3.19 (m, 2H), 3.19-3.09 (m, 1H), 3.07 (s, 3H), 3.04-2.96 (m, 1H), 2.55-2.30 (m, 1H), 2.20 (s, 3H), 2.13-1.89 (m, 11H), 1.72 (s, 1H). LCMS [M+H]: 435.9

Example 110

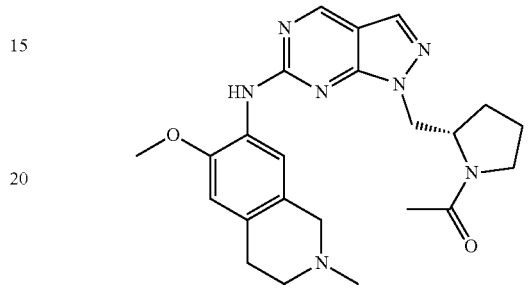

(S)-1-(2-((6-(((6-methoxy-2-methyl-1,2,3,4-tetrahydroisoquinolin-7-yl)amino)-1H-pyrazolo[3,4-d]pyrimidin-1-yl)methyl)pyrrolidin-1-yl)ethan-1-one Step 1: Preparation of tert-butyl-(2S)-2-[(6-chloropyrazolo[3,4-d]pyrimidin-1-yl)methyl]pyrrolidine-1-carboxylate. Prepared according to general procedure D using N-Boc-L-prolinol (0.72 g, 3.56 mmol), 6-chloro-1H-pyrazolo[3,4-d]pyrimidine (0.500 g, 3.23 mmol), triphenylphosphine (1.70 g, 6.47 mmol), and DEAD (40% solution in toluene, 2.95 mL, 6.47 mmol) in THF at rt for 1 h. The crude product was purified by silica column chromatography eluting with 20% to 80% EtOAc in hexanes to afford the title compound (1.390 g)

Step 2: Preparation of tert-butyl (2S)-2-[[6-[(6-methoxy-2-methyl-3,4-dihydro-1H-isoquinolin-7-yl)amino]pyrazolo[3,4-d]pyrimidin-1-yl]methyl]pyrrolidine-1-carboxylate. Prepared according to general procedure B using methoxy-2-methyl-3,4-dihydro-1H-isoquinolin-7-amine (204.9 mg, 1.07 mmol), tert-butyl (2S)-2-[(6-chloropyrazolo[3,4-d]pyrimidin-1-yl)methyl]pyrrolidine-1-carboxylate (300.0 mg, 0.890 mmol), Pd2(dba)3 (81.3 mg, 0.0900 mmol), (S)-BINAP (110.6 mg, 0.180 mmol), and cesium carbonate (868.1 mg, 2.66 mmol) in toluene (3 mL) and tert-butanol (3 mL) at 120° C. for 1 h. The crude product was purified by silica column chromatography eluting with 0% to 20% MeOH in DCM to afford the title compound (147.0 mg).

Step 3: Preparation of 6-methoxy-2-methyl-N-[1-[[(2S)-pyrrolidin-2-yl]methyl]pyrazolo[3,4-d]pyrimidin-6-yl]-3,4-dihydro-1H-isoquinolin-7-amine trifluoroacetate. Trifluoroacetic acid (0.23 mL, 2.98 mmol) was added to a solution of tert-butyl (2S)-2-[[6-[(6-methoxy-2-methyl-3,4-dihydro-1H-isoquinolin-7-yl)amino]pyrazolo[3,4-d]pyrimidin-1-yl]methyl]pyrrolidine-1-carboxylate (147.0 mg, 0.300 mmol) in DCM (2 mL) at 23° C. and stirred for 48 h. The reaction mixture was concentrated to afford the title compound (117.0 mg).

Step 4. Preparation of (S)-1-(2-((6-(((6-methoxy-2-methyl-1,2,3,4-tetrahydroisoquinolin-7-yl)amino)-1H-pyrazolo[3,4-d]pyrimidin-1-yl)methyl)pyrrolidin-1-yl)ethan-1-one. Acetyl chloride (0.010 mL, 0.120 mmol) was added to a solution of 6-methoxy-2-methyl-N-[1-[[(2S)-pyrrolidin-2-yl]methyl]pyrazolo[3,4-d]pyrimidin-6-yl]-3,4-dihydro-1H-isoquinolin-7-amine trifluoroacetate (40.0 mg, 0.080 mmol) and DIEA (0.27 mL, 1.58 mmol) in DCM (0.540 mL) at 0° C. for 3 h. The reaction was concentrated, and the crude product was purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (36.0 mg). 1H NMR (400 MHz, Methanol-d4, TFA salt) δ 8.93 (s, 1H), 8.57 (d, J=16.0 Hz, 1H), 8.06 (s, 1H), 6.93 (s, 1H), 4.80-4.23 (m, 5H), 3.97 (s, 3H), 3.85-3.70 (m, 1H), 3.51-3.34 (m, 2H), 3.28-3.19 (m, 1H), 3.17-2.96 (m, 2H), 3.10 (s, 3H), 2.26-2.11 (m, 1H), 2.08-1.89 (m, 1H), 1.87-1.81 (m, 1H), 1.82 (s, 1.5H), 1.79 (s, 1.5H) LCMS [M+H]: 435.9

Example 111

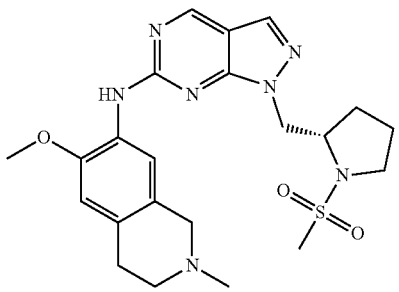 [SMILES: COc1cc2c(cc1Nc1ncc3cnn(C[C@@H]4CCCN4S(C)(=O)=O)c3n1)CN(C)CC2]

(S)-6-methoxy-2-methyl-N-(1-((1-(methylsulfonyl)228yrrolidine-2-yl)methyl)-1H-pyrazolo[3,4-d]pyrimidin-6-yl)-1,2,3,4-tetrahydroisoquinolin-7-amine Methanesulfonyl chloride (0.01 mL, 0.120 mmol) was added to a solution of 6-methoxy-2-methyl-N-[1-[[(2S)-pyrrolidin-2-yl]methyl]pyrazolo[3,4-d]pyrimidin-6-yl]-3,4-dihydro-1H-isoquinolin-7-amine trifluoroacetate (40.mg, 0.0800 mmol) (EXAMPLE 110, Step 3), and DIEA (0.27 mL, 1.58 mmol) in DCM (0.5400 mL) at 0° C. The reaction was warmed to rt. The crude product was purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (17.0 mg). 1H NMR (400 MHz, Methanol-d4) δ 8.92 (s, 11H), 8.70 (d, J=16.1 Hz, 1H), 8.06 (s, 1H), 6.93 (s, 1H), 4.85-4.67 (m, 2H), 4.42-4.29 (m, 2H), 4.21-4.08 (m, 1H), 3.98 (s, 3H), 3.80-3.70 (m, 1H), 3.46-3.33 (m, 3H), 3.27-3.20 (m, 1H), 3.18-3.10 (m, 1H), 3.07 (s, 3H), 2.92 (d, J=2.4 Hz, 3H), 2.26 (s, 1H), 1.93 (d, J=6.7 Hz, 3H). LCMS [M+H]: 471.9

Example 112

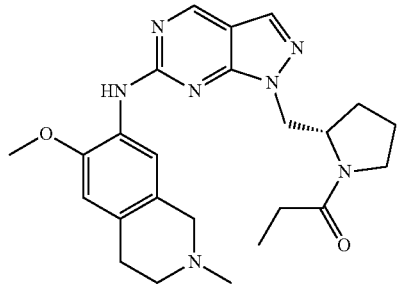 [SMILES: CCC(=O)N1CCC[C@H]1Cn1ncc2cnc(Nc3cc4c(cc3OC)CCN(C)C4)nc21]

(S)-1-(2-((6-((6-methoxy-2-methyl-1,2,3,4-tetrahydroisoquinolin-7-yl)amino)-1H-pyrazolo[3,4-d]pyrimidin-1-yl)methyl)pyrrolidin-1-yl)propan-1-one trifluoroacetate Propanoyl chloride (0.01 mL, 0.120 mmol) was added to a solution of 6-methoxy-2-methyl-N-[1-[[(2S)-pyrrolidin-2-yl]methyl]pyrazolo[3,4-d]pyrimidin-6-yl]-3,4-dihydro-1H-isoquinolin-7-amine trifluoroacetate (EXAMPLE 110, Step 3) (40.mg, 0.080 mmol) and DIEA (0.27 mL, 1.58 mmol) in DCM (0.540 mL) at 0° C. Upon completion of the reaction, the reaction mixture was concentrated. The crude product was purified by reverse phase HPLC (Phenomenex, Gemini-NX, 10 um, 250×30 mm, C18 column; gradient of 20% MeCN/0.1% TFA-water to 100% MeCN/0.1% TFA over 30 minutes) to afford the title compound (16.0 mg). 1H NMR (400 MHz, Methanol-d4, TFA salt) δ 8.93 (s, 1H), 8.60 (s, 1H), 8.07 (s, 1H), 6.94 (s, 1H), 4.78-4.29 (m, 5H), 3.97 (s, 3H), 3.83-3.70 (m, 1H), 3.49-3.36 (m, 2H), 3.28-3.14 (m, 3H), 3.10 (s, 3H), 2.27 (ddd, J=15.8, 7.8, 4.1 Hz, 1H), 2.14 (dt, J=15.9, 7.6 Hz, 2H), 2.05-1.79 (m, 2H), 1.61-1.44 (m, 1H), 0.95 (t, J=7.5 Hz, 3H). LCMS [M+H]: 449.9

Example 113

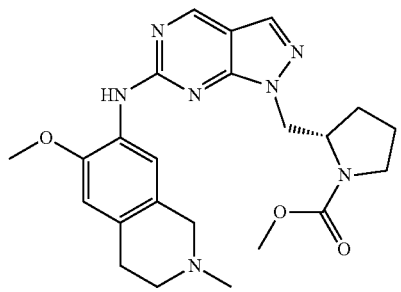 [SMILES: COC(=O)N1CCC[C@H]1Cn1ncc2cnc(Nc3cc4c(cc3OC)CCN(C)C4)nc21]

methyl (S)-2-((6-((6-methoxy-2-methyl-1,2,3,4-tetrahydroisoquinolin-7-yl)amino)-1H-pyrazolo[3,4-d]pyrimidin-1-yl)methyl)pyrrolidine-1-carboxylate trifluoroacetate Methyl chloroformate (0.01 mL, 0.120 mmol) was added to a solution of 6-methoxy-2-methyl-N-[1-[[(2S)-pyrrolidin-2-yl]methyl]pyrazolo[3,4-d]pyrimidin-6-yl]-3,4-dihydro-1H-isoquinolin-7-amine trifluoroacetate (EXAMPLE 110, Step 3) (40.mg, 0.080 mmol) and DIEA (0.27 mL, 1.58 mmol) in DCM (0.540 mL) in DCM (0.5400 mL) at 0° C. Upon completion of the reaction, the reaction mixture was concentrated. The crude product was purified by reverse phase HPLC (Phenomenex, Gemini-NX, 10 um, 250×30 mm, C18 column; gradient of 20% MeCN/0.1% TFA-water to 100% MeCN/0.1% TFA over 30 minutes) to afford the title compound (16.0 mg). 1H NMR (400 MHz, Methanol-d4) δ 8.93 (s, 1H), 8.68 (s, 1H), 8.06 (s, 1H), 6.94 (s, 1H), 4.73-4.59 (m, 2H), 4.53-4.32 (m, 2H), 3.98 (s, 3H), 3.76 (dd, J=12.4, 5.9 Hz, 1H), 3.53 (d, J=9.1 Hz, 2H), 3.50-3.35 (m, 2H), 3.27 (d, J=6.8 Hz, 3H), 3.13 (s, 1H), 3.10 (s, 3H), 2.16-1.67 (m, 2H). LCMS [M+H]: =452.0

Example 114

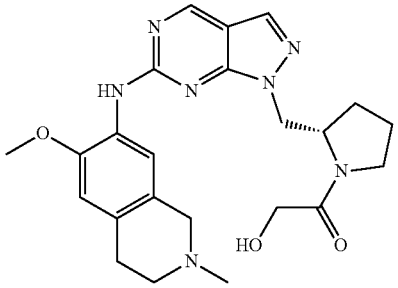 [SMILES: COc1cc2c(cc1Nc1ncc3cnn(C[C@@H]4CCCN4C(=O)CO)c3n1)CN(C)CC2]

(S)-2-hydroxy-1-(2-((6-((6-methoxy-2-methyl-1,2,3,4-tetrahydroisoquinolin-7-yl)amino)-1H-pyrazolo[3,4-d]pyrimidin-1-yl)methyl)230yrrolidine-1-yl)ethan-1-one 2,2,2-trifluoroacetate Step 1: Preparation of (S)-2-(2-((6-((6-methoxy-2-methyl-1,2,3,4-tetrahydroisoquinolin-7-yl)amino)-1H-pyrazolo[3,4-d]pyrimidin-1-yl)methyl)230yrrolidine-1-yl)-2-oxoethyl acetate. Acetoxyacetyl chloride (0.030 mL, 0.240 mmol) was added to a solution of 6-methoxy-2-methyl-N-[1-[[(2S)-pyrrolidin-2-yl]methyl]pyrazolo[3,4-d]pyrimidin-6-yl]-3,4-dihydro-1H-isoquinolin-7-amine trifluoroacetate (EXAMPLE 110, Step 3) (40.mg, 0.080 mmol) and DIEA (0.275 mL, 1.58 mmol) in DCM (0.540 mL) at 0° C. Upon completion of the reaction, the reaction mixture was concentrated. The crude product was purified by reverse phase HPLC (Phenomenex, Gemini-NX, 10 um, 250×30 mm, C18 column; gradient of 20% MeCN/0.1% TFA-water to 100% MeCN/0.1% TFA over 30 minutes) to afford the title compound as a TFA salt. The salt was free-based using a PL-HCO3 column eluting with MeOH to afford the title compound (10.0 mg).

Step 2: Preparation of (S)-2-hydroxy-1-(2-((6-((6-methoxy-2-methyl-1,2,3,4-tetrahydroisoquinolin-7-yl)amino)-1H-pyrazolo[3,4-d]pyrimidin-1-yl)methyl)231yrrolidine-1-yl)ethan-1-one 2,2,2-trifluoroacetate. Potassium carbonate (11.2 mg, 0.080 mmol) was added to a solution of (S)-2-(2-((6-((6-methoxy-2-methyl-1,2,3,4-tetrahydroisoquinolin-7-yl)amino)-1H-pyrazolo[3,4-d]pyrimidin-1-yl)methyl)231yrrolidine-1-yl)-2-oxoethyl acetate (10.0 mg, 0.020 mmol) in MeOH (2.0 mL) and the mixture was stirred at rt for 1 h. The reaction was concentrated and the crude product was purified by reverse phase HPLC (Phenomenex, Gemini-NX, 10 um, 250×30 mm, C18 column; gradient of 20% MeCN/0.1% TFA-water to 100% MeCN/0.1% TFA over 30 minutes) to afford the title compound (9.0 mg). 1H NMR (400 MHz, Methanol-d4, mixture of rotamers) δ 8.93 (s, 1H), 8.64 (s, 0.5H), 8.58 (s, 0.5H), 8.06 (s, 1H), 6.92 (s, 1H), 4.87-4.77 (m, 1H), 4.73-4.40 (m, 3H), 4.32 (d, J=14.9 Hz, 1H), 4.27-3.99 (m, 2H), 3.97 (s, 1H), 3.95 (s, 2H), 3.83 (d, J=15.8 Hz, 1H), 3.78-3.70 (m, 1H), 3.48-3.34 (m, 1H), 3.27-3.19 (m, 2H), 3.15 (d, J=10.3 Hz, 1H), 3.11 (s, 3H), 2.21-2.08 (m, 1H), 2.03-1.68 (m, 2H). LCMS [M+H]: 451.9

Example 115

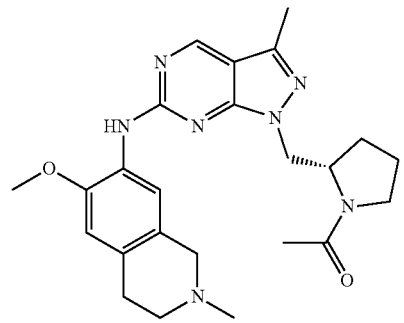 [SMILES: COc1cc2c(cc1Nc1ncc3c(C)nn(C[C@@H]4CCCN4C(C)=O)c3n1)CN(C)CC2]

(S)-1-(2-((6-((6-methoxy-2-methyl-1,2,3,4-tetrahydroisoquinolin-7-yl)amino)-3-methyl-1H-pyrazolo[3,4-d]pyrimidin-1-yl)methyl)231yrrolidine-1-yl)ethan-1-one The above compound was prepared according to EXAMPLE 110 substituting in Step 1, 6-chloro-3-methyl-1H-pyrazolo[3,4-d]pyrimidine for 6-chloro-1H-pyrazolo[3,4-d]pyrimidine. 1H NMR (400 MHz, Methanol-d4) δ 8.94 (d, J=0.9 Hz, 1H), 8.51 (s, 0.5H, rotamer), 8.47 (s, 0.5H, rotamer), 6.95 (s, 1H), 4.78-4.61 (m, 1H), 4.56-4.26 (m, 4H), 3.97 (s, 3H), 3.95 (s, 0.3 H, rotamer), 3.83-3.72 (m, 1H), 3.49-3.33 (m, 2H), 3.28-3.14 (m, 2H), 3.10 (s, 3H), 2.53 (s, 3H), 2.19-2.09 (m, 1H), 2.04-1.88 (m, 2H), 1.86 (s, 1.5H, rotamer), 1.80 (s, 1.5H, rotamer), 1.49-1.31 (m, 1H). LCMS [M+H]: 450.0

Example 116

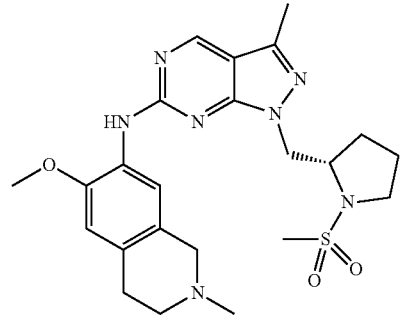 [SMILES: COc1cc2c(cc1Nc1ncc3c(C)nn(C[C@@H]4CCCN4S(C)(=O)=O)c3n1)CN(C)CC2]

(S)-6-methoxy-2-methyl-N-(3-methyl-1-((1-(methylsulfonyl)pyrrolidin-2-yl)methyl)-1H-pyrazolo[3,4-d]pyrimidin-6-yl)-1,2,3,4-tetrahydroisoquinolin-7-amine The above compound was prepared according to EXAMPLE 111 substituting in Step 1, 6-chloro-3-methyl- 1H-pyrazolo[3,4-d]pyrimidine for 6-chloro-1H-pyrazolo[3,4-d]pyrimidine. 1H NMR (400 MHz, Methanol-d4) δ 8.92 (s, 1H), 8.64 (d, J=16.1 Hz, 1H), 6.94 (s, 1H), 4.83-4.67 (m, 2H), 4.40-4.30 (m, 1H), 4.28 (dd, J=13.9, 8.6 Hz, 1H), 4.17-4.07 (m, 1H), 3.97 (s, 3H), 3.80-3.72 (m, 1H), 3.47-3.36 (m, 2H), 3.26-3.19 (m, 1H), 3.19-3.14 (m, 1H), 3.14-3.08 (m, 1H), 3.07 (s, 3H), 2.92 (d, J=2.4 Hz, 3H), 2.52 (s, 3H), 2.27-2.20 (m, 1H), 1.99-1.89 (m, 3H). LCMS [M+H]: 485.9.

Example 117

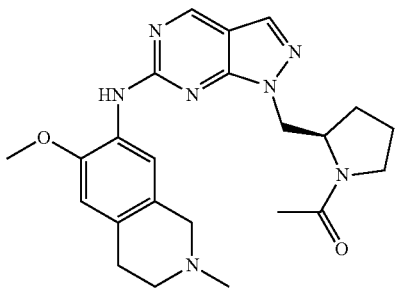 [SMILES: COc1cc2c(cc1Nc1ncc3cnn(C[C@H]4CCCN4C(C)=O)c3n1)CN(C)CC2]

(R)-1-(2-((6-((6-methoxy-2-methyl-1,2,3,4-tetrahydroisoquinolin-7-yl)amino)-1H-pyrazolo[3,4-d]pyrimidin-1-yl)methyl)pyrrolidin-1-yl)ethan-1-one trifluoroacetate Step 1: Preparation of tert-butyl (R)-2-((6-chloro-1H-pyrazolo[3,4-d]pyrimidin-1-yl)methyl)pyrrolidine-1-carboxylate. Prepared according to general procedure D using 6-chloro-1H-pyrazolo[3,4-d]pyrimidine (0.350 g, 2.26 mmol), triphenylphosphine (1.19 g, 4.53 mmol), tert-butyl (2R)-2-(hydroxymethyl)pyrrolidine-1-carboxylate (0.500 g, 2.49 mmol), and DEAD (40% solution in toluene, 2.06 mL, 4.53 mmol) in THF (15 mL) for 1 h. The crude product was purified by silica column chromatography eluting with 20% to 80% EtOAc in hexanes to afford the title compound (0.950 g).

Step 2: Preparation of tert-butyl (R)-2-((6-((6-methoxy-2-methyl-1,2,3,4-tetrahydroisoquinolin-7-yl)amino)-1H-pyrazolo[3,4-d]pyrimidin-1-yl)methyl)pyrrolidine-1-carboxylate. Prepared according to general procedure B using methoxy-2-methyl-3,4-dihydro-1H-isoquinolin-7-amine (239.0 nmg, 1.24 mmol), tert-butyl (2R)-2-[(6-chloropyrazolo[3,4-d]pyrimidin-1-yl)methyl]pyrrolidine-1-carboxylate (350.0 mg, 1.04 mmol), Pd2(dba)3 (94.9 mg, 0.10 mmol), (S)-BINAP (129.0 mg, 0.210 mmol), and cesium carbonate (1.0127 g, 3.11 mmol)) in toluene (3 mL) and tert-butanol (3 mL) at 120° C. for 1 h. The crude product was purified by silica column chromatography eluting with 0% to 20% MeOH in DCM to afford the title compound (110.0 mg).

Step 3: Preparation of (R)-6-methoxy-2-methyl-N-(1-(pyrrolidin-2-ylmethyl)-1H-pyrazolo[3,4-d]pyrimidin-6-yl)-1,2,3,4-tetrahydroisoquinolin-7-amine 2,2,2-trifluoroacetate. Trifluoroacetic acid (0.170 mL, 2.23 mmol) was added to a solution of tert-butyl (R)-2-((6-((6-methoxy-2-methyl-1,2,3,4-tetrahydroisoquinolin-7-yl)amino)-1H-pyrazolo[3,4-d]pyrimidin-1-yl)methyl)pyrrolidine-1-carboxylate (110.0 mg, 0.223 mmol) in DCM (2 mL) at 23° C. and stirred for 48 h. The reaction mixture was concentrated to afford the title compound (113.0 mg).

Step 4: Preparation of (R)-1-(2-((6-((6-methoxy-2-methyl-1,2,3,4-tetrahydroisoquinolin-7-yl)amino)-1H-pyrazolo[3,4-d]pyrimidin-1-yl)methyl)pyrrolidin-1-yl)ethan-1-one. Acetyl chloride (0.01 mL, 0.120 mmol) was added to a solution of (R)-6-methoxy-2-methyl-N-(1-(pyrrolidin-2-ylmethyl)-11H-pyrazolo[3,4-d]pyrimidin-6-yl)-1,2,3,4-tetrahydroisoquinolin-7-amine 2,2,2-trifluoroacetate (55.0 mg, 0.089 mmol) and DIEA (0.3798 mL, 2.17 mmol) in DCM (0.540 mL) at 0° C. Upon completion of the reaction, the reaction mixture was concentrated. The crude product was purified by reverse phase HPLC (Phenomenex, Gemini-NX, 10 um, 250×30 mm, C18 column; gradient of 20% MeCN/0.1% TFA-water to 100% MeCN/0.1% TFA over 30 minutes) to afford the title compound (26.0 mg). 1H NMR (400 MHz, Methanol-d4, mixture of rotamers) δ 8.95 (s, 1H), 8.52 (s, 0.5H), 8.49 (s, 0.5H), 8.13 (s, 0.1H), 8.09 (s, 0.9H), 6.93 (s, 1H), 4.86-4.66 (m, 1H), 4.60-4.47 (m, 3H), 4.30 (d, J=15.1 Hz, 1H), 3.96 (s, 3H), 3.82-3.74 (m, 1H), 3.52-3.35 (m, 2H), 3.29-3.22 (m, 1H), 3.19-3.13 (m, 11H), 3.13-3.01 (m, 1H), 3.10 (s, 3H), 2.21-2.10 (m, 1H), 2.07-1.90 (m, 2H), 1.86 (s, 1.5H), 1.80 (s, 1.5H), 1.74-1.81 (m, 1H), 1.43-1.23 (m, 1H). LCMS [M+H]: 436.0

Example 118

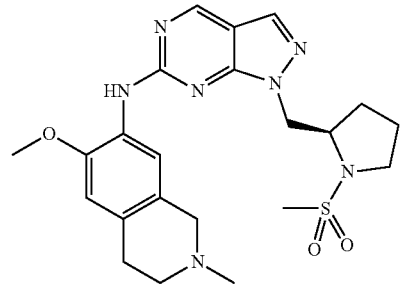 [SMILES: COc1cc2c(cc1Nc1ncc3cnn(C[C@H]4CCCN4S(C)(=O)=O)c3n1)CN(C)CC2]

(R)-6-methoxy-2-methyl-N-(1-((1-(methylsulfonyl)pyrrolidin-2-yl)methyl)-1H-pyrazolo[3,4-d]pyrimidin-6-yl)-1,2,3,4-tetrahydroisoquinolin-7-amine trifluoroacetate Methanesulfonyl chloride (0.01 mL, 0.120 mmol) was added to a solution of (R)-6-methoxy-2-methyl-N-(1-(pyrrolidin-2-ylmethyl)-1H-pyrazolo[3,4-d]pyrimidin-6-yl)-1,2,3,4-tetrahydroisoquinolin-7-amine 2,2,2-trifluoroacetate (EXAMPLE 117, Step 3) (55.0 mg, 0.108 mmol) and DIEA (0.378 mL, 2.17 mmol) in DCM (0.540 mL) at 0° C. Upon completion of the reaction, the reaction mixture was concentrated. The crude product was purified by reverse phase HPLC (Phenomenex, Gemini-NX, 10 um, 250×30 mm, C18 column; gradient of 20% MeCN/0.1% TFA-water to 100% MeCN/0.1% TFA over 30 minutes) to afford the title compound (27.0 mg). 1H NMR (400 MHz, Methanol-d4) δ 8.93 (s, 1H), 8.68 (s, 1H), 8.08 (s, 1H), 6.93 (s, 1H), 4.85-4.67 (m, 2H), 4.42-4.30 (m, 2H), 4.15 (dd, J=10.2, 6.2 Hz, 1H), 3.97 (s, 3H), 3.81-3.71 (m, 1H), 3.47-3.33 (m, 2H), 3.27-3.19 (m, 1H), 3.16 (s, 1H), 3.07 (s, 3H), 2.92 (d, J=2.4 Hz, 3H), 2.30-2.20 (m, 1H), 2.00-1.85 (m, 3H). LCMS [M+H]: 471.9

Example 119

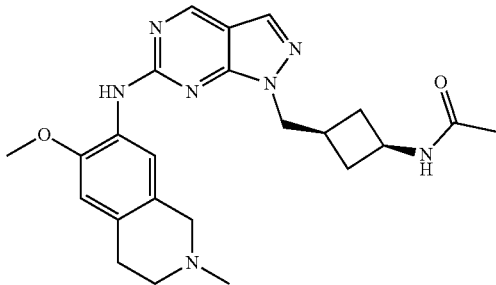 [SMILES: COc1cc2c(cc1Nc1ncc3cnn(C[C@H]4C[C@@H](NC(C)=O)C4)c3n1)CN(C)CC2]

cis N-(3-((6-((6-methoxy-2-methyl-1,2,3,4-tetrahydroisoquinolin-7-yl)amino)-1H-pyrazolo[3,4-d]pyrimidin-1-yl)methyl)cyclobutyl)acetamide Step 1: Preparation of cis tert-butyl (3-((6-chloro-1H-pyrazolo[3,4-d]pyrimidin-1-yl)methyl)cyclobutyl)carbamate. Prepared according to general procedure D using cis-tert-butyl N-[3-(hydroxymethyl)cyclobutyl]carbamate (0.55 g 2.72 mmol), 6-chloro-1H-pyrazolo[3,4-d]pyrimidine (0.40 g, 2.59 mmol), triphenylphosphine (1.36 g, 5.18 mmol), and DEAD (40% solution in toluene, 2.36 mL, 5.18 mmol) in THF at rt for 1.5 h. The crude product was purified by silica column chromatography using a gradient of 30% to 80% EtOAc in hexanes to afford the title compound (0.930 g).

Step 2: Preparation of cis-tert-butyl (3-((6-((6-methoxy-2-methyl-1,2,3,4-tetrahydroisoquinolin-7-yl)amino)-1H-pyrazolo[3,4-d]pyrimidin-1-yl)methyl)cyclobutyl)carbamate. Prepared according to general procedure B using 6-methoxy-2-methyl-3,4-dihydro-1H-isoquinolin-7-amine (225.4 mg, 1.17 mmol), cis tert-butyl N-[3-[(6-chloropyrazolo[3,4-d]pyrimidin-1-yl)methyl]cyclobutyl]carbamate (330.9 mg, 0.980 mmol), Pd2(dba)3 (89.5 mg, 0.10 mmol), (S)-BINAP (121.7 mg, 0.20 mmol), and cesium carbonate (954.9 mg, 2.93 mmol) in 1:1 toluene/tert-butanol (6 mL) at 120° C. for 1 h. The crude reaction mixture was filtered through a silica gel plug with 20% MeOH in DCM and the filtrate concentrated. The crude product was purified by silica column chromatography with a gradient of 0% to 20% MeOH in DCM to afford the title compound (126.0 mg).

Step 3: Preparation of cis N-(1-((3-aminocyclobutyl)methyl)-1H-pyrazolo[3,4-d]pyrimidin-6-yl)-6-methoxy-2-methyl-1,2,3,4-tetrahydroisoquinolin-7-amine 2,2,2-trifluoroacetate. Trifluoroacetic acid (0.2 mL, 2.57 mmol) was added to a solution of cis tert-butyl N-[3-[[6-[(6-methoxy-2-methyl-3,4-dihydro-1H-isoquinolin-7-yl)amino]pyrazolo[3,4-d]pyrimidin-1-yl]methyl]cyclobutyl]carbamate (126.0 mg, 0.260 mmol) in DCM (2 mL) at 23° C. The mixture was stirred for 48 h at rt. The reaction mixture was concentrated to provide the crude product (130 mg). This material was used without further purification.

Step 4: Preparation of cis N-(3-((6-((6-methoxy-2-methyl-1,2,3,4-tetrahydroisoquinolin-7-yl)amino)-1H-pyrazolo[3,4-d]pyrimidin-1-yl)methyl)cyclobutyl)acetamide trifluoroacetate. To a solution of cis N-(1-((3-aminocyclobutyl)methyl)-1H-pyrazolo[3,4-d]pyrimidin-6-yl)-6-methoxy-2-methyl-1,2,3,4-tetrahydroisoquinolin-7-amine 2,2,2-trifluoroacetate (40.0 mg, 0.079 mmol) and DIEA (0.27 mL, 1.58 mmol) in DCM (0.540 mL) at 0° C. was added acetyl chloride (0.01 mL, 0.120 mmol). Upon completion of the reaction, the reaction mixture was concentrated. The crude product was purified by reverse phase HPLC (Phenomenex, Gemini-NX, 10 um, 250×30 mm, C18 column; gradient of 20% MeCN/0.1% TFA-water to 100% MeCN/0.1% TFA over 30 minutes) to afford the title compound (13.0 mg). 1H NMR (400 MHz, Methanol-d4, TFA salt) δ 8.95 (s, 1H), 8.38 (s, 1H), 8.08 (s, 1H), 6.95 (s, 1H), 4.56 (d, J=14.8 Hz, 1H), 4.41 (d, J=6.1 Hz, 2H), 4.34 (d, J=15.1 Hz, 1H), 4.12-4.05 (m, 1H), 3.96 (s, 3H), 3.77 (s, 1H), 3.49-3.33 (m, 1H), 3.29-3.21 (m, 1H), 3.14-3.05 (m, 1H), 3.09 (s, 3H), 2.70-2.54 (m, 1H), 2.44-2.33 (m, 2H), 1.85 (s, 3H), 1.83-1.75 (m, 2H). LCMS [M+H]: 435.9

Example 120

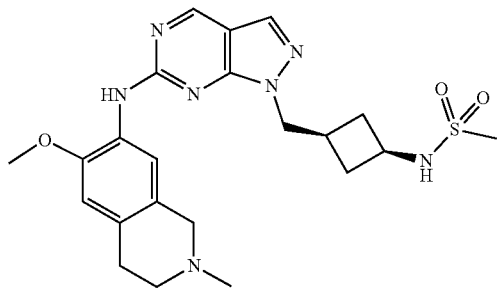

cis N-(3-((6-((6-methoxy-2-methyl-1,2,3,4-tetrahydroisoquinolin-7-yl)amino)-1H-pyrazolo[3,4-d]pyrimidin-1-yl)methyl)cyclobutyl)methanesulfonamide trifluoroacetate Methanesulfonyl chloride (0.01 mL, 0.120 mmol) was added to a solution cis N-(1-((3-aminocyclobutyl)methyl)-1H-pyrazolo[3,4-d]pyrimidin-6-yl)-6-methoxy-2-methyl-1,2,3,4-tetrahydroisoquinolin-7-amine 2,2,2-trifluoroacetate (EXAMPLE 120, Step 3) (40.0 mg, 0.079 mmol) and DIEA (0.270 mL, 1.58 mmol) in DCM (0.540 mL) at 0° C. Upon completion of the reaction, the reaction mixture was concentrated. The crude product was purified by reverse phase HPLC (Phenomenex, Gemini-NX, 10 um, 250×30 mm, C18 column; gradient of 20% MeCN/0.1% TFA-water to 100% MeCN/0.1% TFA over 30 minutes) to afford the title compound (7.0 mg). 1H NMR (400 MHz, Methanol-d4, TFA salt) δ 8.92 (s, 11H), 8.47 (s, 1H), 8.04 (s, 1H), 6.95 (s, 11H), 4.61 (d, J=14.9 Hz, 1H), 4.45 (d, J=14.9 Hz, 1H), 4.43 (dd, J=6.6, 2.3 Hz, 2H), 3.97 (s, 3H), 3.75 (t, J=7.7 Hz, 1H), 3.43 (td, J=11.9, 5.0 Hz, 11H), 3.29-3.23 (m, 1H), 3.16 (s, 2H), 3.12 (s, 3H), 2.87 (s, 3H), 2.67-2.53 (m, 1H), 2.51-2.42 (m, 2H), 1.96 (dd, J=11.3, 9.3 Hz, 2H). LCMS [M+H]: 471.9

Example 121

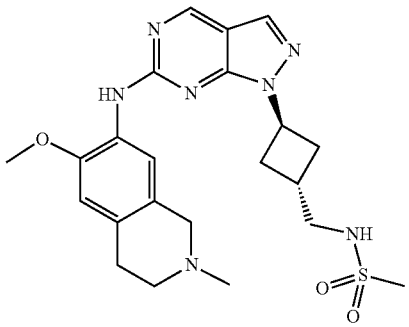

N-((trans-3-(6-(((6-methoxy-2-methyl-1,2,3,4-tetra-hydroisoquinolin-7-yl)amino)-1H-pyrazolo[3,4-d]pyrimidin-1-yl)cyclobutyl)methyl)methanesulfonamide trifluoroacetate Step 1: Preparation of tert-butyl ((trans-3-(6-chloro-1H-pyrazolo[3,4-d]pyrimidin-1-yl)cyclobutyl)methyl)carbamate. Prepared according to general procedure D using tert-butyl N-[(cis-3-hydroxycyclobutyl)methyl]carbamate (0.410 g, 2.02 mmol), 6-chloro-1H-pyrazolo[3,4-d]pyrimidine (0.26 g, 1.68 mmol), triphenylphosphine (0.88 g, 3.36 mmol), and DEAD (40% solution in toluene, 1.53 mL, 3.36 mmol) in THF (15 mL) at rt for 1.5 h. The crude product was purified by silica column chromatography using a gradient of 0% to 50% EtOAc in hexanes to afford the title compound (0.510 g).

Step 2: Preparation of tert-butyl ((trans-3-(6-(((6-methoxy-2-methyl-1,2,3,4-tetrahydroisoquinolin-7-yl)amino)-1H-pyrazolo[3,4-d]pyrimidin-1-yl)cyclobutyl)methyl)carbamate. Prepared according to general procedure B using 6-methoxy-2-methyl-3,4-dihydro-1H-isoquinolin-7-amine (187.8 mg, 0.980 mmol), tert-butyl ((trans-3-(6-chloro-1H-pyrazolo[3,4-d]pyrimidin-1-yl)cyclobutyl)methyl)carbamate (275.0 mg, 0.810 mmol), Pd2(dba)3 (74.5 mg, 0.080 mmol), (S)-BINAP (101.4 mg, 0.160 mmol), and cesium carbonate (795.7 mg, 2.44 mmol) in 1:1 toluene/tert-butanol (6 mL) at 120° C. for 1 h. The crude reaction mixture was filtered through a silica gel plug with 20% MeOH in DCM and the filtrate concentrated. The crude product was purified by silica column chromatography with a gradient of 0% to 20% MeOH in DCM to afford the title compound (100.0 mg).

Step 3: Preparation of N-(1-(trans-3-(aminomethyl)cyclobutyl)-1H-pyrazolo[3,4-d]pyrimidin-6-yl)-6-methoxy-2-methyl-1,2,3,4-tetrahydroisoquinolin-7-amine 2,2,2-trifluoroacetate. Trifluoroacetic acid (0.16 mL, 2.03 mmol) was added to a solution of of tert-butyl ((trans-3-(6-(((6-methoxy-2-methyl-1,2,3,4-tetrahydroisoquinolin-7-yl)amino)-1H-pyrazolo[3,4-d]pyrimidin-1-yl)cyclobutyl)methyl)carbamate (100.0 mg, 0.200 mmol) in DCM (3.34 mL) at 23° C. The mixture was stirred for 48 h at rt. The reaction mixture was concentrated to provide the crude product (102 mg). This material was used without further purification.

Step 4: Preparation of N-((trans-3-(6-(((6-methoxy-2-methyl-1,2,3,4-tetrahydroisoquinolin-7-yl)amino)-1H-pyrazolo[3,4-d]pyrimidin-1-yl)cyclobutyl)methyl)methanesulfonamide trifluoroacetate. Methanesulfonyl chloride (0.01 mL, 0.120 mmol) was added to a solution of N-(1-(trans-3-(aminomethyl)cyclobutyl)-1H-pyrazolo[3,4-d]pyrimidin-6-yl)-6-methoxy-2-methyl-1,2,3,4-tetrahydroisoquinolin-7-amine 2,2,2-trifluoroacetate (45.0 mg, 0.079 mmol) and DIEA (0.309 mL, 1.77 mmol) in DCM (0.540 mL) at 0° C. Upon completion of the reaction, the reaction mixture was concentrated. The crude product was purified by reverse phase HPLC (Phenomenex, Gemini-NX, 10 um, 250×30 mm, C18 column; gradient of 20% MeCN/0.1% TFA-water to 100% MeCN/0.1% TFA over 30 minutes) to afford the title compound (24.0 mg). 1H NMR (400 MHz, Methanol-d4) δ 8.92 (s, 1H), 8.49 (s, 1H), 8.09 (d, J=0.4 Hz, 1H), 6.94 (s, 1H), 5.44 (p, J=8.4 Hz, 1H), 4.69-4.57 (m, 1H), 4.39 (d, J=15.1 Hz, 1H), 3.97 (s, 3H), 3.77 (d, J=15.6 Hz, 1H), 3.42 (td, J=11.8, 5.1 Hz, 1H), 3.36-3.33 (m, 2H), 3.24 (dd, J=11.5, 5.9 Hz, 1H), 3.16-3.09 (m, 1H), 3.13 (s, 3H), 3.03 (s, 3H), 2.96 (q, J=12.2, 10.8 Hz, 2H), 2.69-2.57 (m, 1H), 2.50 (ddd, J=13.2, 8.6, 3.1 Hz, 2H). LCMS [M+H]: 471.9

Example 122

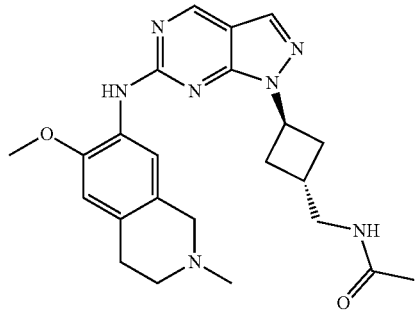 [SMILES: COc1cc2c(cc1Nc1ncc3cnn([C@H]4C[C@H](CNC(C)=O)C4)c3n1)CN(C)CC2]

N-((trans-3-(6-(((6-methoxy-2-methyl-1,2,3,4-tetrahydroisoquinolin-7-yl)amino)-1H-pyrazolo[3,4-d]pyrimidin-1-yl)cyclobutyl)methyl)acetamide 2,2,2-trifluoroacetate Acetyl chloride (0.01 mL, 0.120 mmol) was added to a N-(1-(trans-3-(aminomethyl)cyclobutyl)-1H-pyrazolo[3,4-d]pyrimidin-6-yl)-6-methoxy-2-methyl-1,2,3,4-tetrahydroisoquinolin-7-amine 2,2,2-trifluoroacetate (EXAMPLE 121, Step 3) (45.0 mg, 0.089 mmol) and DIEA (0.309 mL, 1.77 mmol) in DCM (0.540 mL) at 0° C. Upon completion of the reaction, the reaction mixture was concentrated. The crude product was purified by reverse phase HPLC (Phenomenex, Gemini-NX, 10 um, 250×30 mm, C18 column; gradient of 20% MeCN/0.1% TFA-water to 100% MeCN/0.1% TFA over 30 minutes) to afford the title compound (18.0 mg). 1H NMR (400 MHz, Methanol-d4, TFA salt) δ 8.96 (s, 1H), 8.40 (s, 1H), 8.14 (d, J=0.5 Hz, 1H), 6.96 (s, 1H), 5.47 (p, J=8.2 Hz, 1H), 4.65 (d, J=15.0 Hz, 1H), 4.39 (d, J=15.0 Hz, 1H), 3.96 (s, 3H), 3.83-3.75 (m, 1H), 3.57-3.39 (m, 3H), 3.29-3.22 (m, 1H), 3.20-3.15 (m, 1H), 3.12 (s, 3H), 2.96-2.85 (m, 2H), 2.67-2.57 (m, 1H), 2.34 (ddd, J=12.8, 8.4, 3.2 Hz, 2H), 1.99 (s, 3H). LCMS [M+H]: 436.0

Example 123

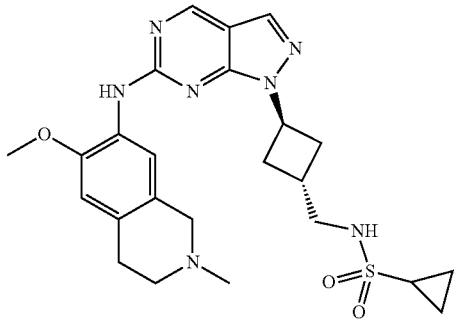 [SMILES: COc1cc2c(cc1Nc1ncc3cnn([C@H]4C[C@H](CNS(=O)(=O)C5CC5)C4)c3n1)CN(C)CC2]

N-[[3-[6-[(6-methoxy-2-methyl-3,4-dihydro-1H-isoquinolin-7-yl)amino]pyrazolo[3,4-d]pyrimidin-1-yl]cyclobutyl]methyl]cyclopropanesulfonamide Cyclopropanesulfonyl chloride (0.02 mL, 0.1500 mmol) was added to a solution of N-(1-(trans-3-(aminomethyl)cyclobutyl)-1H-pyrazolo[3,4-d]pyrimidin-6-yl)-6-methoxy-2-methyl-1,2,3,4-tetrahydroisoquinolin-7-amine 2,2,2-trifluoroacetate (EXAMPLE 121, Step 3) (30.mg, 0.0800 mmol) in DCM (0.5400 mL) along with DIEA (0.07 mL, 0.3800 mmol) at 0° C. The reaction was stirred until the LCMS exclusively showed the desired product. The reaction was then concentrated, and the crude product was purified by reverse-phase HPLC (Phenomenex, Gemini-NX, 10 um, 250×30 mm, C18 column; gradient of 20% MeCN/0.1% TFA-water to 100% MeCN/0.1% TFA over 30 minutes) yielding the title compound (3 mg, 0.0049 mmol, 6.433% yield). $^1$H NMR (400 MHz, Methanol-d4, TFA salt) δ 8.92 (s, 1H), 8.49 (s, 1H), 8.09 (s, 1H), 6.94 (s, 1H), 5.44 (t, J=8.3 Hz, 1H), 4.71-4.57 (m, 1H), 4.39 (d, J=14.8 Hz, 1H), 3.97 (m, 4H), 3.76 (s, 1H), 3.46-3.37 (m, 3H), 3.35-3.19 (m, 2H), 3.12 (s, 4H), 3.03-2.89 (m, 2H), 2.69-2.58 (m, 1H), 2.55-2.46 (m, 1H), 1.17-1.01 (m, 4H). LCMS [M+H]: 498.0.

Example 124

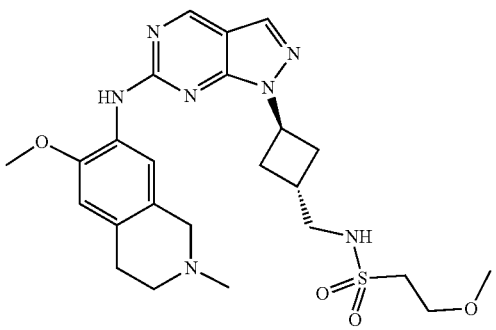

2-methoxy-N-(((1r,3r)-3-(6-(((6-methoxy-2-methyl-1,2,3,4-tetrahydroisoquinolin-7-yl)amino)-1H-pyrazolo[3,4-d]pyrimidin-1-yl)cyclobutyl)methyl)ethane-1-sulfonamide 2-Methoxy-1-ethanesulfonyl chloride (0.01 mL, 0.0800 mmol) was added to a solution of N-(1-(trans-3-(aminomethyl)cyclobutyl)-1H-pyrazolo[3,4-d]pyrimidin-6-yl)-6-methoxy-2-methyl-1,2,3,4-tetrahydroisoquinolin-7-amine 2,2,2-trifluoroacetate (EXAMPLE 121, Step 3) (20.mg, 0.0400 mmol) in DCM (0.5400 mL) along with DIEA (0.03 mL, 0.2000 mmol) at 0° C. LCMS showed the desired product. The reaction was concentrated and the crude product was purified by reverse-phase HPLC (Phenomenex, Gemini-NX, 10 um, 250×30 mm, C18 column; gradient of 20% MeCN/0.1% TFA-water to 100% MeCN/0.1% TFA over 30 minutes). $^1$H NMR (400 MHz, Methanol-d4, TFA salt) δ 8.89 (s, 1H), 8.50 (s, 11H), 8.05 (s, 11H), 6.92 (s, 1H), 5.42 (t, J=8.1 Hz, 1H), 3.96 (s, 5H), 3.81 (t, J=5.8 Hz, 4H), 3.39 (d, J=6.1 Hz, 7H), 3.34-3.31 (m, 2H), 3.18 (s, 1H), 3.12 (s, 4H), 2.96 (d, J=11.2 Hz, 1H), 2.60 (s, 1H), 2.54-2.43 (m, 1H). LCMS [M+H]: 515.9.

Example 125

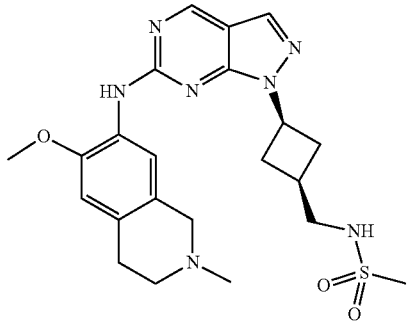

N-((cis-3-(6-(((6-methoxy-2-methyl-1,2,3,4-tetrahydroisoquinolin-7-yl)amino)-1H-pyrazolo[3,4-d]pyrimidin-1-yl)cyclobutyl)methyl)methanesulfonamide The above compound was prepared according to EXAMPLE 121, Step 1 substituting tert-butyl N-[(trans-3-hydroxycyclobutyl)methyl]carbamate for tert-butyl N-[(cis-3-hydroxycyclobutyl)methyl]carbamate. 1H NMR (400 MHz, Methanol-d4) δ 8.94 (s, 1H), 8.29 (s, 1H), 8.12 (s, 1H), 6.95 (s, 1H), 5.12 (q, J=8.7 Hz, 1H), 4.60 (d, J=14.9 Hz, 1H), 4.37 (d, J=14.9 Hz, 1H), 3.95 (s, 3H), 3.81-3.71 (m, 11H), 3.43 (td, J=11.8, 5.3 Hz, 11H), 3.28-3.22 (m, 1H), 3.21 (d, J=6.0 Hz, 2H), 3.18-3.14 (m, 1H), 3.10 (s, 3H), 2.95 (s, 3H), 2.75-2.64 (m, 2H), 2.57-2.45 (m, 3H). LCMS [M+H]: 471.9

Example 126

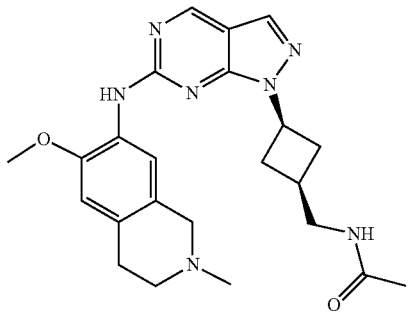 [SMILES: COc1cc2c(cc1Nc1ncc3cnn([C@H]4C[C@@H](CNC(C)=O)C4)c3n1)CN(C)CC2]

N-((cis-3-(6-((6-methoxy-2-methyl-1,2,3,4-tetrahydroisoquinolin-7-yl)amino)-1H-pyrazolo[3,4-d]pyrimidin-1-yl)cyclobutyl)methyl)acetamide The above compound was prepared according to EXAMPLE 122, Step 1, substituting tert-butyl N-[(trans-3-hydroxycyclobutyl)methyl]carbamate for tert-butyl N-[(cis-3-hydroxycyclobutyl)methyl]carbamate. 1H NMR (400 MHz, Methanol-d4) δ 8.94 (s, 1H), 8.29 (s, 1H), 8.11 (s, 1H), 6.96 (s, 1H), 5.18 (p, J=8.3 Hz, 11H), 4.60 (d, J=14.9 Hz, 11H), 4.37 (d, J=15.0 Hz, 1H), 3.96 (s, 3H), 3.82-3.73 (m, 1H), 3.44 (td, J=11.7, 5.3 Hz, 11H), 3.30-3.20 (m, 2H), 3.20-3.13 (m, 1H), 3.10 (s, 3H), 2.66-2.54 (m, 2H), 2.56-2.40 (m, 3H), 1.96 (s, 3H). LCMS [M+H]: 436.0

Example 127

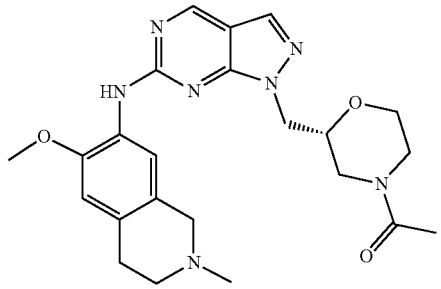 [SMILES: COc1cc2c(cc1Nc1ncc3cnn(C[C@H]4CN(C(C)=O)CCO4)c3n1)CN(C)CC2]

(R)-1-(2-((6-((6-methoxy-2-methyl-1,2,3,4-tetrahydroisoquinolin-7-yl)amino)-1H-pyrazolo[3,4-d]pyrimidin-1-yl)methyl)morpholino)ethan-1-one trifluoroacetate Step 1: Preparation of tert-butyl (R)-2-((6-chloro-1H-pyrazolo[3,4-d]pyrimidin-1-yl)methyl)morpholine-4-carboxylate. Prepared according to general procedure D using tert-butyl (2R)-2-(hydroxymethyl)morpholine-4-carboxylate (0.402 g, 1.85 mmol), 6-chloro-1H-pyrazolo[3,4-d]pyrimidine (0.26 g, 1.68 mmol), triphenylphosphine (0.88 g, 3.36 mmol), and DEAD (40% solution in toluene, 1.53 mL, 3.36 mmol) in THF (15 mL) at rt for 1 h. The crude product was purified by silica column chromatography using a gradient of 0% to 10% MeOH in DCM to afford the title compound (0.960 g).

Step 2: Preparation of tert-butyl (R)-2-((6-((6-methoxy-2-methyl-1,2,3,4-tetrahydroisoquinolin-7-yl)amino)-1H-pyrazolo[3,4-d]pyrimidin-1-yl)methyl)morpholine-4-carboxylate. Prepared according to general procedure B using 6-methoxy-2-methyl-3,4-dihydro-1H-isoquinolin-7-amine (211.9 mg, 1.10 mmol), tert-butyl (R)-2-((6-chloro-1H-pyrazolo[3,4-d]pyrimidin-1-yl)methyl)morpholine-4-carboxylate (325.0 mg, 0.920 mmol), Pd2(dba)3 (84.1 mg, 0.090 mmol), (S)-BINAP (114.4 mg, 0.180 mmol), and cesium carbonate (897.9 mg, 2.76 mmol) were dissolved in 1:1 toluene/tert-butanol (6 mL) at 120° C. for 1 h. The crude reaction mixture was filtered through a silica gel plug with 20% MeOH in DCM and the filtrate concentrated. The crude product was purified by silica column chromatography with a gradient of 0% to 20% MeOH in DCM to afford the title compound (90.0 mg).

Step 3: Preparation of (R)-6-methoxy-2-methyl-N-(1-(morpholin-2-ylmethyl)-1H-pyrazolo[3,4-d]pyrimidin-6-yl)-1,2,3,4-tetrahydroisoquinolin-7-amine trifluoroacetate. Trifluoroacetic acid (0.135 mL, 1.77 mmol) was added to a solution of tert-butyl (R)-2-((6-((6-methoxy-2-methyl-1,2,3,4-tetrahydroisoquinolin-7-yl)amino)-1H-pyrazolo[3,4-d]pyrimidin-1-yl)methyl)morpholine-4-carboxylate (90.0 mg, 0.177 mmol) in DCM (3.34 mL) at 23° C. The mixture was stirred for 48 h at rt. The reaction mixture was concentrated to provide the crude product (92 mg). This material was used without further purification.

Step 4: Preparation of (R)-1-(2-((6-((6-methoxy-2-methyl-1,2,3,4-tetrahydroisoquinolin-7-yl)amino)-1H-pyrazolo[3,4-d]pyrimidin-1-yl)methyl)morpholino)ethan-1-one trifluoroacetate. Acetyl chloride (10.4 mg, 0.133 mmol) was added to a solution of (R)-6-methoxy-2-methyl-N-(1-(morpholin-2-ylmethyl)-1H-pyrazolo[3,4-d]pyrimidin-6-yl)-1,2,3,4-tetrahydroisoquinolin-7-amine trifluoroacetate (46.4 mg, 0.089 mmol) and DIEA (0.309 mL, 1.77 mmol) in DCM (0.540 mL) at 0° C. Upon completion of the reaction, the reaction mixture was concentrated. The crude product was purified by reverse phase HPLC (Phenomenex, Gemini-NX, 10 um, 250×30 mm, C18 column; gradient of 20% MeCN/0.1% TFA-water to 100% MeCN/0.1% TFA over 30 minutes) to afford the title compound (2.8 mg). 1H NMR (400 MHz, Methanol-d4, mixture of rotamers) δ 8.94 (s, 0.3H), 8.93 (s, 0.7H), 8.51 (s, 0.7H), 8.47 (s, 0.3H), 8.10 (s, 0.3H), 8.06 (s, 0.7H), 6.94 (s, 1H), 4.70-4.31 (m, 5H), 4.29-4.16 (m, 1H), 3.97 (s, 3H), 3.94-3.85 (m, 2H), 3.74 (m, 2H), 3.51-3.39 (m, 2H), 3.27-3.16 (m, 2H), 3.13 (s, 1.5H), 3.12 (s, 1.5H), 2.17 (s, 0.5H), 2.10 (s, 2.5H). LCMS [M+H]: 451.9

Example 128

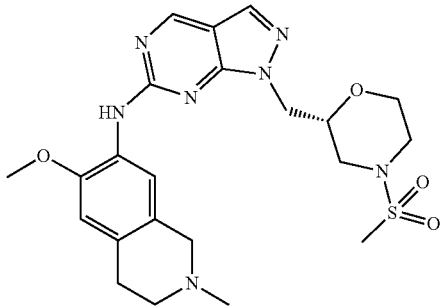 [SMILES: COc1cc2c(cc1Nc1ncc3cnn(C[C@H]4CN(S(C)(=O)=O)CCO4)c3n1)CN(C)CC2]

(S)-6-methoxy-2-methyl-N-(1-((4-(methylsulfonyl)morpholin-2-yl)methyl)-1H-pyrazolo[3,4-d]pyrimidin-6-yl)-1,2,3,4-tetrahydroisoquinolin-7-amine trifluoroacetate Methanesulfonyl chloride (15.2 mg, 0.133 mmol) was added to a solution of (R)-6-methoxy-2-methyl-N-(1-(morpholin-2-ylmethyl)-1H-pyrazolo[3,4-d]pyrimidin-6-yl)-1,2,3,4-tetrahydroisoquinolin-7-amine trifluoroacetate (46.4 mg, 0.089 mmol, EXAMPLE 127, Step 3) and DIEA (0.309 mL, 1.77 mmol) in DCM (0.540 mL) at 0° C. Upon completion of the reaction, the reaction mixture was concentrated. The crude product was purified by reverse phase HPLC (Phenomenex, Gemini-NX, 10 um, 250×30 mm, C18 column; gradient of 20% MeCN/0.1% TFA-water to 100% MeCN/0.1% TFA over 30 minutes) to afford the title compound (3.7 mg). 1H NMR (400 MHz, Methanol-d4, mixture of rotamers, TFA salt) δ 8.95 (s, 1H), 8.48 (s, 0.5H), 8.45 (s, 0.5H), 8.07 (s, 1H), 6.96 (s, 1H), 4.70-4.55 (m, 2H), 4.55-4.46 (m, 1H), 4.43-4.26 (m, 2H), 3.97 (2, 3H), 3.81-3.66 (m, 2H), 3.54 (t, J=10.9 Hz, 1H), 3.45-3.36 (m, 2H), 3.27-3.20 (m, 1H), 3.18-3.14 (m, 1H), 3.11 (s, 3H), 3.03-2.88 (m, 2H), 2.86 (s, 3H). LCMS [M+H]: 487.9

Example 129

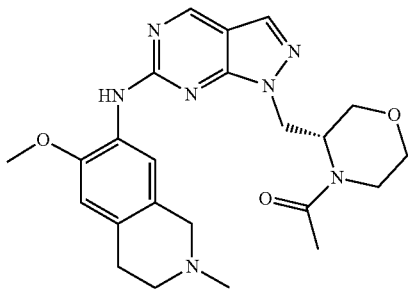 [SMILES: COc1cc2c(cc1Nc1ncc3cnn(C[C@@H]4COCCN4C(C)=O)c3n1)CN(C)CC2]

(R)-1-(3-((6-((6-methoxy-2-methyl-1,2,3,4-tetrahydroisoquinolin-7-yl)amino)-1H-pyrazolo[3,4-d]pyrimidin-1-yl)methyl)morpholino)ethan-1-one trifluoroacetate The above compound was prepared according to EXAMPLE 127, Step 1, substituting tert-butyl (3R)-3-(hydroxymethyl)morpholine-4-carboxylate for tert-butyl (2R)-2-(hydroxymethyl)morpholine-4-carboxylate. 1H NMR (400 MHz, Methanol-d4, mixture of rotamers) δ 8.94 (s, 0.5H), 8.93 (s, 0.5H), 8.45 (s, 1H), 8.12 (s, 0.5H), 8.05 (s, 0.5H), 6.96 (s, 1H), 4.77-4.48 (m, 3H), 4.35 (m, 1H), 4.04-3.89 (m, 2H), 3.96 (s, 3H), 3.84-3.71 (m, 2H), 3.62-3.36 (m, 3H), 3.27-3.19 (m, 1H), 3.20-3.11 (m, 1H), 3.09 (s, 3H), 1.92-1.84 (m, 1H), 1.79 (s, 3H). LCMS [M+H]: 451.9

Example 130

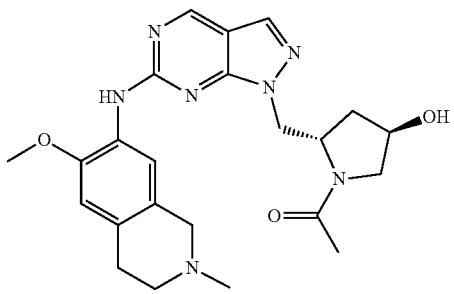 [SMILES: COc1cc2c(cc1Nc1ncc3cnn(C[C@@H]4C[C@@H](O)CN4C(C)=O)c3n1)CN(C)CC2]

1-((2S,4R)-4-hydroxy-2-((6-((6-methoxy-2-methyl-1,2,3,4-tetrahydroisoquinolin-7-yl)amino)-1H-pyrazolo[3,4-d]pyrimidin-1-yl)methyl)pyrrolidin-1-yl)ethan-1-one trifluoroacetate Step 1: Preparation of tert-butyl (2S,4R)-2-((6-chloro-1H-pyrazolo[3,4-d]pyrimidin-1-yl)methyl)-4-hydroxypyrrolidine-1-carboxylate. Prepared according to general procedure D using (2S,4R)-tert-butyl 4-hydroxy-2-(methoxymethyl)pyrrolidine-1-carboxylate (0.506 g, 2.33 mmol), 6-chloro-1H-pyrazolo[3,4-d]pyrimidine (0.300 g, 1.94 mmol), triphenylphosphine (1.02 g, 3.88 mmol), and DEAD (40% solution in toluene, 1.77 mL, 3.88 mmol) in THF (15 mL) at rt for 1 h. The crude product was purified by silica column chromatography using a gradient of 20% to 80% EtOAc in hexanes to afford the title compound (0.720 g).

Step 2: Preparation of tert-butyl (2S,4R)-4-((tert-butyldimethylsilyl)oxy)-2-((6-chloro-1H-pyrazolo[3,4-d]pyrimidin-1-yl)methyl)pyrrolidine-1-carboxylate. Tert-Butyl dimethylchlorosilane (920.1 mg, 6.11 mmol) was added to a mixture of tert-butyl (2S,4R)-2-[(6-chloropyrazolo[3,4-d]pyrimidin-1-yl)methyl]-4-hydroxy-pyrrolidine-1-carboxylate (720.0 mg, 2.04 mmol) and triethylamine (1.13 mL, 8.14 mmol) in DCM (6.60 mL) at 35° C. The mixture was stirred for 6 h. Additional tert-butyl dimethylchlorosilane (2 eq) and triethylamine (4 eq) were added and the mixture was stirred at 35° C. for 48 h. The reaction was diluted with DCM and washed with water. The combined organics was dried over anhydrous sodium sulfate and concentrated. The crude product was purified silica column chromatography eluting with a gradient of 0% to 100% EtOAc in hexanes to afford the title compound (305.0 mg).

Step 3: Preparation of (3R,5S)-5-((6-((6-methoxy-2-methyl-1,2,3,4-tetrahydroisoquinolin-7-yl)amino)-1H-pyrazolo[3,4-d]pyrimidin-1-yl)methyl)pyrrolidin-3-ol. Prepared according to general procedure A using tert-butyl (2S,4R)-4-[tert-butyl(dimethyl)silyl]oxy-2-[(6-chloropyrazolo[3,4-d]pyrimidin-1-yl)methyl]pyrrolidine-1-carboxylate (50.0 mg, 0.110 mmol), 6-methoxy-2-methyl-3,4-dihydro-1H-isoquinolin-7-amine (30.8 mg, 0.160 mmol), and p-TSA (61.0 mg, 0.320 mmol) in 2-butanol at 100° C. for 2 h. The reaction mixture was neutralized with a saturated solution of sodium bicarbonate followed by extraction with EtOAc. The combined organic layers was washed with brine, dried over anhydrous sodium sulfate, and concentrated under reduced pressure to provide the crude product (60 mg) which is taken directly to the following step.

Step 4: Preparation of 1-((2S,4R)-4-hydroxy-2-((6-((6-methoxy-2-methyl-1,2,3,4-tetrahydroisoquinolin-7-yl)amino)-1H-pyrazolo[3,4-d]pyrimidin-1-yl)methyl)pyrrolidin-1-yl)ethan-1-one trifluoroacetate. Acetyl chloride (0.01 mL, 0.160 mmol) was added to a mixture of crude (3R,5S)-5-[[6-[(6-methoxy-2-methyl-3,4-dihydro-1H-isoquinolin-7-yl)amino]pyrazolo[3,4-d]pyrimidin-1-yl]methyl]pyrrolidin-3-ol (60.0 mg, 0.150 mmol) and triethylamine (0.06 mL, 0.440 mmol) in DCM (0.980 mL). The reaction was stirred at 23° C. for 10 minutes and concentrated. The crude product was purified by reverse-phase HPLC (Phenomenex, Gemini-NX, 10 um, 250×30 mm, C18 column; gradient of 20% MeCN/0.1% TFA-water to 100% MeCN/0.1% TFA over 30 minutes) to afford the title compound (16.0 mg). 1H NMR (400 MHz, Methanol-d4, mixture of rotamers) δ 8.96 (s, 1H), 8.55 (s, 0.5H), 8.52 (s, 0.5H), 8.10 (s, 1H), 6.94 (s, 1H), 4.69-4.47 (m, 3H), 4.30 (d, J=15.1 Hz, 1H), 3.97 (s, 3H), 3.95-3.86 (m, 1H), 3.83-3.72 (m, 1H), 3.53-3.34 (m, 1H), 3.28-3.21 (m, 2H), 3.19-3.14 (m, 1H), 3.10 (d, J=1.7 Hz, 4H), 3.14-3.07 (m, 1H), 3.00 (dd, J=11.1, 5.0 Hz, 1H), 2.38 (tt, J=14.1, 5.7 Hz, 1H), 2.02-1.90 (m, 1H), 1.85 (s, 1H), 1.80 (s, 2H). LCMS [M+H]: 452.0

Example 131

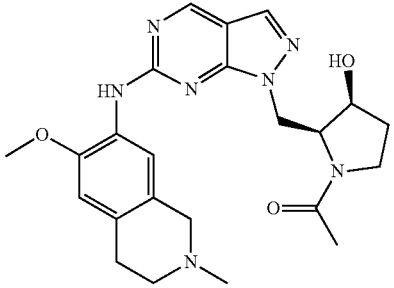 [SMILES: COc1cc2c(cc1Nc1ncc3cnn(C[C@H]4[C@@H](O)CCN4C(C)=O)c3n1)CN(C)CC2]

1-((2S,3S)-3-hydroxy-2-((6-(((6-methoxy-2-methyl-1,2,3,4-tetrahydroisoquinolin-7-yl)amino)-1H-pyrazolo[3,4-d]pyrimidin-1-ylmethyl)pyrrolidin-1-yl)ethan-1-one Step 1. Preparation of 1-(tert-butyl) 2-methyl (2R,3S)-3-((tert-butyldimethylsilyl)oxy)pyrrolidine-1,2-dicarboxylate. Tert-Butyl dimethylchlorosilane (1843.5 mg, 12.2 mmol) was added to a mixture of 1-(tert-butyl) 2-methyl (2R,3S)-3-hydroxypyrrolidine-1,2-dicarboxylate (1.000.g, 4.08 mmol) and triethylamine (2.27 mL, 16.3 mmol) in DCM (13.6 mL) at 23° C. After 4 hours, the reaction was diluted with DCM and washed with water, dried over anhydrous sodium sulfate, and concentrated under reduced pressure. The crude product was purified by silica gel column chromatography (0 to 100% EtOAc/hexanes) to provide the title compound (460 mg).

Step 2. Preparation of tert-butyl (2S,3S)-3-((tert-butyldimethylsilyl)oxy)-2-(hydroxymethyl)pyrrolidine-1-carboxylate. Lithium borohydride (66.9 mg, 3.07 mmol) was added to a solution of 1-(tert-butyl) 2-methyl (2R,3S)-3-((tert-butyldimethylsilyl)oxy)pyrrolidine-1,2-dicarboxylate (460.0 mg, 1.28 mmol) in THF (6.4 mL) and stirred at rt for 48 h. The reaction was quenched by the addition of water and extracted with DCM. The combined organic phase was washed with brine, dried over anhydrous sodium sulfate, and concentrated under reduced pressure. The crude product was purified by silica gel column chromatography (eluting with 0 to 100% EtOAc/hexanes) to provide the title compound (256 mg). This material was carried forward without any further purification.

Step 3. Preparation of tert-butyl (2S,3S)-3-((tert-butyldimethylsilyl)oxy)-2-((6-chloro-1H-pyrazolo[3,4-d]pyrimidin-1-yl)methyl)pyrrolidine-1-carboxylate. Prepared according to general procedure D. DEAD (0.310 mL, 0.680 mmol) was added dropwise to a mixture of 6-chloro-1H-pyrazolo[3,4-d]pyrimidine (70.0 mg, 0.450 mmol), triphenylphosphine (178.2 mg, 0.680 mmol), and tert-butyl (2S,3S)-3-[tert-butyl(dimethyl)silyl]oxy-2-(hydroxymethyl)pyrrolidine-1-carboxylate (165.2 mg, 0.500 mmol) in THF (2.2 mL) at 0° C. The mixture was stirred 1 h and concentrated. The crude product was purified by silica gel column chromatography (eluting with 20 to 80% EtOAc/hexanes) to provide the title compound. This material was carried forward without further purification.

Step 4. Preparation of 1-((2S,3S)-3-((tert-butyldimethylsilyl)oxy)-2-((6-chloro-1H-pyrazolo[3,4-d]pyrimidin-1-yl)methyl)pyrrolidin-1-yl)ethan-1-one. Trifluoroacetic acid (0.450 mL, 5.88 mmol) was added to a solution of tert-butyl (2S,3S)-3-[tert-butyl(dimethyl)silyl]oxy-2-[(6-chloropyrazolo[3,4-d]pyrimidin-1-yl)methyl]pyrrolidine-1-carboxylate (157.0 mg, 0.340 mmol) in DCM (1.677 mL) and stirred at 23° C. for 2 h. The mixture was concentrated and redissolved in DCM (1.7 mL). Triethylamine (0.14 mL, 1.01 mmol) and acetyl chloride (0.03 mL, 0.4000 mmol) were added and stirred for 10 min The crude product was purified by silica gel column chromatography (eluting with 0 to 80% EtOAc/hexanes then 0 to 20% MeOH/DCM) to provide the title compound (115 mg). The material was carried forward without further purification.

Step 5. Preparation of 1-((2S,3S)-3-hydroxy-2-((6-(((6-methoxy-2-methyl-1,2,3,4-tetrahydroisoquinolin-7-yl)amino)-1H-pyrazolo[3,4-d]pyrimidin-1-yl)methyl)pyrrolidin-1-yl)ethan-1-one. 1-[(2S,3S)-3-[tert-butyl(dimethyl)silyl]oxy-2-[(6-chloropyrazolo[3,4-d]pyrimidin-1-yl)methyl]pyrrolidin-1-yl]ethanone (115.0 mg, 0.280 mmol), 6-methoxy-2-methyl-3,4-dihydro-1H-isoquinolin-7-amine (80.9 mg, 0.420 mmol), and p-TSA (160.1 mg, 0.840 mmol) were heated in 2-butanol (10 mL) at 100° C. for 6 h. After cooling, the reaction was concentrated and purified by reverse-phase HPLC (Phenomenex, Gemini-NX, 10 um, 250×30 mm, C18 column; 20% to 100% MeCN/water with 0.1% TFA gradient over 30 minutes) to provide the title compound (94 mg). Mixtures of rotamers: $^1$H NMR (400 MHz, Methanol-d4, TFA salt) δ 9.15 (s, 0.3H), 9.10 (s, 0.7H), 8.95 (d, J=0.8 Hz, 1H), 8.37 (s, 0.3H), 8.26 (s, 0.7H), 8.13 (s, 0.3H), 8.10 (s, 0.7H), 6.95 (s, 1H), 4.98-4.72 (m, 1.7H), 4.72-4.55 (m, 1.7H), 4.55-4.28 (m, 1.7H), 3.97 (s, 3H), 3.78 (d, J=11.0 Hz, 1H), 3.69 (td, J=9.8, 3.6 Hz, 0.7H), 3.58-3.33 (m, 1.7H), 3.26 (s, 0.7H), 3.15 (d, J=14.7 Hz, 0.7H), 3.10 (d, J=1.4 Hz, 3H), 2.34-2.20 (m, 0.7H), 2.14-1.91 (m, 1.4H), 1.85 (s, 1H), 1.79 (s, 3H), 1.60 (dt, J=20.5, 9.6 Hz, 1H). LCMS [M+H]: 452.0.

Example 132

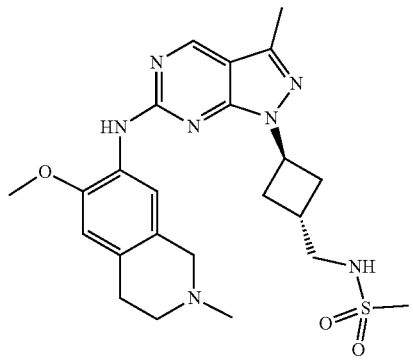

N-(((1r,3r)-3-(6-(((6-methoxy-2-methyl-1,2,3,4-tetrahydroisoquinolin-7-yl)amino)-3-methyl-1H-pyrazolo[3,4-d]pyrimidin-1-yl)cyclobutyl)methyl)methanesulfonamide Step 1. Preparation of tert-butyl (((1r,3r)-3-(6-chloro-3-methyl-1H-pyrazolo[3,4-d]pyrimidin-1-yl)cyclobutyl)methyl)carbamate. Prepared according to general procedure D. DEAD (1.89 mL, 4.15 mmol, 40% solution in toluene) was added dropwise to a mixture of 6-Chloro-3-methyl-1H-pyrazolo[3,4-d]pyrimidine (0.35 g, 2.08 mmol), triphenylphosphine (1.09 g, 4.15 mmol), and tert-butyl N-[(3-hydroxycyclobutyl)methyl]carbamate (0.5 g, 2.49 mmol) in THF (10 mL) under N2 atmosphere at 25° C. The mixture was stirred for 1.5 h and concentrated. The crude product was purified by silica gel column chromatography (0 to 50% EtOAc/hexanes) yielding the title compound (726 mg) as a mixture with diethyl hydrazine-1,2-dicarboxylate. This material was carried forward without further purification.

Step 2. Preparation of tert-butyl (((1r,3r)-3-(6-chloro-3-methyl-1H-pyrazolo[3,4-d]pyrimidin-1-yl)cyclobutyl)methyl)carbamate. tert-Butyl N-[[3-(6-chloro-3-methyl-pyrazolo[3,4-d]pyrimidin-1-yl)cyclobutyl]methyl]carbamate (260.0 mg, 0.740 mmol), 6-methoxy-2-methyl-3,4-dihydro-1H-isoquinolin-7-amine (213.12 mg, 1.11 mmol), and p-TSA (281.1 mg, 1.48 mmol) were heated in 2-butanol (2.4 mL) at 100° C. for 48 h. The reaction was quenched by the addition of saturated aqueous sodium carbonate and extracted with EtOAc. The combined organic phase was washed with brine solution, dried over anhydrous sodium sulfate, and concentrated under reduced pressure. The crude product was purified by reverse-phase HPLC (Phenomenex, Gemini-NX, 10 um, 250×30 mm, C18 column; 20% to 100% MeCN/water with 0.1% TFA gradient over 30 minutes) yielding the title compound (152 mg). The material was carried forward without any further purification.

Step 3. Preparation of N-(((1r,3r)-3-(6-((6-methoxy-2-methyl-1,2,3,4-tetrahydroisoquinolin-7-yl)amino)-3-methyl-1H-pyrazolo[3,4-d]pyrimidin-1-yl)cyclobutyl)methyl)methanesulfonamide. Methanesulfonyl chloride (0.01 mL, 0.080 mmol) was added to a solution of N-[1-[3-(aminomethyl)cyclobutyl]-3-methyl-pyrazolo[3,4-d]pyrimidin-6-yl]-6-methoxy-2-methyl-3,4-dihydro-1H-isoquinolin-7-amine (20.0 mg, 0.040 mmol) and DIEA (0.03 mL, 0.1900 mmol) in DCM (0.540 mL) at 0° C. Upon completion, the reaction was concentrated and the crude product was purified by reverse-phase HPLC (Phenomenex, Gemini-NX, 10 um, 250×30 mm, C18 column; 20% to 100% MeCN/water with 0.1% TFA gradient over 30 minutes) to provide the title compound (12 mg). $^1$H NMR (400 MHz, Methanol-d4, TFA salt) δ 8.94-8.86 (m, 1H), 8.50-8.44 (m, 1H), 6.94 (d, J=3.5 Hz, 1H), 5.45-5.31 (m, 1H), 4.62 (d, J=15.2 Hz, 2H), 4.38 (d, J=15.1 Hz, 2H), 3.97 (q, J=3.2 Hz, 3H), 3.76 (s, 2H), 3.42 (s, 1H), 3.36-3.31 (m, 1H), 3.20-3.07 (m, 3H), 3.02 (q, J=3.1 Hz, 3H), 2.99-2.88 (m, 2H), 2.62 (d, J=6.7 Hz, 1H), 2.54 (q, J=3.1 Hz, 3H), 2.52-2.41 (m, 2H). LCMS [M+H]: 485.9.

Example 133

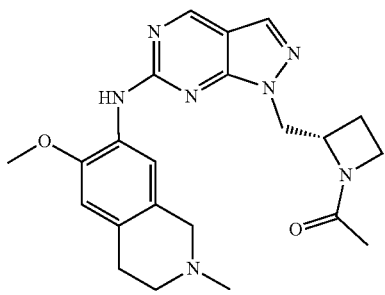 [SMILES: COc1cc2c(cc1Nc1ncc3cnn(C[C@@H]4CCN4C(C)=O)c3n1)CN(C)CC2]

(S)-1-(2-((6-((6-methoxy-2-methyl-1,2,3,4-tetrahydroisoquinolin-7-yl)amino)-1H-pyrazolo[3,4-d]pyrimidin-1-yl)methyl)azetidin-1-yl)ethan-1-one Step 1. Preparation of tert-butyl (S)-2-((6-chloro-1H-pyrazolo[3,4-d]pyrimidin-1-yl)methyl)azetidine-1-carboxylate. Prepared according to general procedure D. DIAD (1.26 mL, 6.41 mmol) was added dropwise to a mixture of 6-chloro-1H-pyrazolo[3,4-d]pyrimidine (660 mg, 4.27 mmol), triphenylphosphine (1680 mg, 6.41 mmol), and (S)-1-Boc-2-Hydroxymethylazetidine (999 mg, 5.34 mmol) in THF (14 mL) at 0° C. The mixture was warmed to rt and stirred 2 h. The reaction mixture was concentrated onto silica gel. The crude product was purified by silica gel column chromatography (eluting with 0 to 80% EtOAc/hexanes) yielding the title compound (1.260 g)

Step 2. Preparation of (S)-1-(2-((6-chloro-1H-pyrazolo[3,4-d]pyrimidin-1-yl)methyl)azetidin-1-yl)ethan-1-one. Trifluoroacetic acid (3.03 mL, 39.62 mmol) was added to a solution of tert-butyl (2S)-2-[(6-chloropyrazolo[3,4-d]pyrimidin-1-yl)methyl]azetidine-1-carboxylate (1.260 g, 3.89 mmol) in DCM and stirred for 1.5 h. The reaction was concentrated and dissolved in DCM (13 mL). Triethylamine (2.72 mL, 19.46 mmol) and acetyl chloride (0.55 mL, 7.78 mmol) were added and stirred at 23° C. for 1 hour. After concentrating, the crude product was purified by silica gel column chromatography (eluting with 0 to 100% EtOAc/hexanes then 0 to 20% MeOH/DCM) to provide the title compound (890 mg).

Step 3. Preparation of (S)-1-(2-((6-((6-methoxy-2-methyl-1,2,3,4-tetrahydroisoquinolin-7-yl)amino)-1H-pyrazolo[3,4-d]pyrimidin-1-yl)methyl)azetidin-1-yl)ethan-1-one. Prepared according to general procedure A. (S)-1-(2-((6-chloro-1H-pyrazolo[3,4-d]pyrimidin-1-yl)methyl)azetidin-1-yl)ethan-1-one (100 mg, 0.380 mmol), 6-methoxy-2-methyl-3,4-dihydro-1H-isoquinolin-7-amine (108 mg, 0.56 mmol), and p-TSA (215 mg, 1.13 mmol) were heated in 2-butanol (1.2 mL) at 100° C. for 5 h. After cooling, the reaction was quenched by the addition of saturated aqueous sodium carbonate and extracted with EtOAc). The combined organic phase was washed with brine solution, dried over anhydrous sodium sulfate, and concentrated under reduced pressure. The crude product was purified by reverse-phase HPLC (Phenomenex, Gemini-NX, 10 um, 250×30 mm, C18 column; gradient of 20% MeCN/0.1% TFA-water to 100% MeCN/0.1% TFA over 30 minutes) to provide the title compound (8 mg) $^1$H NMR (400 MHz, Methanol-d4, TFA salt) δ 8.95 (s, 1H), 8.55 (s, 11H), 8.20-8.03 (s, 1H), 6.94 (s, 1H), 4.94-4.73 (m, 2H), 4.47 (s, 1H), 4.38-4.26 (m, 1H), 3.96 (d, J=4.3 Hz, 4H), 3.81-3.70 (m, 1H), 3.51-3.37 (m, 1H), 3.35-3.22 (m, 2H), 3.09 (d, J=3.1 Hz, 5H), 2.45-2.25 (m, 2H), 1.69 (d, J=16.6 Hz, 3H). LCMS [M+H]: 422.0.

Example 134

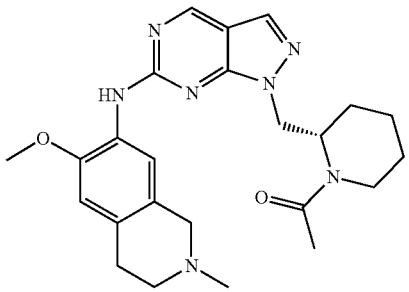 [SMILES: COc1cc2c(cc1Nc1ncc3cnn(C[C@@H]4CCCCN4C(C)=O)c3n1)CN(C)CC2]

(S)-1-(2-((6-((6-methoxy-2-methyl-1,2,3,4-tetrahydroisoquinolin-7-yl)amino)-1H-pyrazolo[3,4-d]pyrimidin-1-yl)methyl)piperidin-1-yl)ethan-1-one Step 1. tert-butyl (S)-2-((6-chloro-1H-pyrazolo[3,4-d]pyrimidin-1-yl)methyl)piperidine-1-carboxylate. Prepared according to general procedure D. DIAD (1.4 mL, 7.11 mmol,) was added dropwise to a mixture of 6-chloro-1H-pyrazolo[3,4-d]pyrimidine (625 mg, 4.04 mmol), triphenylphosphine (1591 mg, 6.07 mmol), and tert-butyl (2S)-2-(hydroxymethyl)piperidine-1-carboxylate (1088 mg, 5.05 mmol) in THF (13 mL) under N2 atmosphere at 0° C. The mixture was warmed to rt and stirred for 2 hours and concentrated onto silica gel. The crude product was purified by silica gel column chromatography (eluting with 0 to 80% EtOAc/hexanes) yielding the title compound (1090 mg). This material was carried forward without further purification.

Step 2. Preparation of (S)-1-(2-((6-chloro-1H-pyrazolo[3,4-d]pyrimidin-1-yl)methyl)piperidin-1-yl)ethan-1-one. Trifluoroacetic acid (2.42 mL, 31.5 mmol) was added to a solution of tert-butyl (S)-2-((6-chloro-1H-pyrazolo[3,4-d]pyrimidin-1-yl)methyl)piperidine-1-carboxylate (1090 mg, 3.1 mmol) in DCM and stirred for 1.5 hours. The mixture was concentrated and taken up in DCM (10.3 mL). Triethylamine (2.16 mL, 15.49 mmol) and Acetyl chloride (0.44 mL, 6.2 mmol) were added and the mixture was stirred at 23° C. for 1 hour. After concentrating, the crude product was purified by silica gel column chromatography (eluting with 0 to 100% EtOAc/hexanes then 0 to 20% MeOH/DCM) to provide the title compound (265 mg).

Step 3. Preparation of tert-butyl (S)-2-((6-chloro-1H-pyrazolo[3,4-d]pyrimidin-1-yl)methyl)piperidine-1-carboxylate. (S)-1-(2-((6-chloro-1H-pyrazolo[3,4-d]pyrimidin-1-yl)methyl)piperidin-1-yl)ethan-1-one (135 mg, 0.4600 mmol), 6-methoxy-2-methyl-3,4-dihydro-1H-isoquinolin-7-amine (133 mg, 0.6900 mmol), and p-TSA (262 mg, 1.38 mmol) were heated in 2-butanol (1.2 mL) at 100° C. for 5 h. After cooling, the reaction was quenched by the addition of saturated aqueous sodium carbonate and extracted with EtOAc. The combined organic phase was washed with brine solution, dried over anhydrous sodium sulfate, and concentrated under reduced pressure. The crude product was purified by reverse-phase HPLC (Phenomenex, Gemini-NX, 10 um, 250×30 mm, C18 column; gradient of 20% MeCN/0.1% TFA-water to 100% MeCN/0.1% TFA over 30 minutes) to provide the title compound (73 mg). $^1$H NMR (400 MHz, Methanol-d4, TFA salt) δ 8.93 (d, J=4.0 Hz, 1H), 8.11 (s, 1H), 8.05 (s, 1H), 7.00-6.90 (m, 1H), 5.23 (d, J=7.3 Hz, 2H), 4.78-4.59 (m, 1H), 4.54 (m, 2H), 4.48-4.25 (m, 2H), 3.96 (d, J=1.6 Hz, 3H), 3.85-3.63 (m, 2H), 3.56-3.37 (m, 2H), 3.31 (p, J=1.6 Hz, 2H), 3.08 (s, 3H), 1.84 (dd, J=39.0, 13.7 Hz, 5H), 1.69 (s, 2H). LCMS [M+H]: 450.0

Example 135

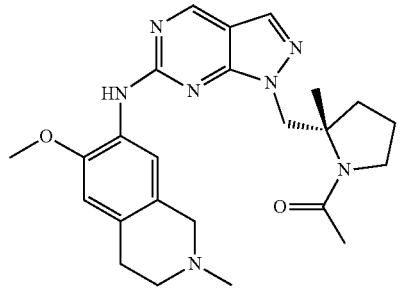 [SMILES: COc1cc2c(cc1Nc1ncc3cnn(C[C@]4(C)CCCN4C(C)=O)c3n1)CN(C)CC2]

(S)-1-(2-((6-((6-methoxy-2-methyl-1,2,3,4-tetrahydroisoquinolin-7-yl)amino)-1H-pyrazolo[3,4-d]pyrimidin-1-yl)methyl)-2-methylpyrrolidin-1-yl)ethan-1-one Step 1. tert-butyl (S)-2-((6-chloro-1H-pyrazolo[3,4-d]pyrimidin-1-yl)methyl)-2-methylpyrrolidine-1-carboxylate. Prepared according to general procedure D. DIAD (1.15 mL, 5.82 mmol) was added dropwise to a mixture of 6-chloro-1H-pyrazolo[3,4-d]pyrimidine (600 mg, 3.88 mmol), triphenylphosphine (1527 mg, 5.82 mmol), and tert-butyl (2S)-2-(hydroxymethyl)-2-methyl-pyrrolidine-1-carboxylate (1045 mg, 4.85 mmol) in THF (11.9 mL) under N2 atmosphere at 0° C. The mixture was warmed to rt and stirred for 2 hr and concentrated onto silica gel. The crude product was purified by silica gel column chromatography (20 to 80% EtOAc/hexanes) to provide the title compound (1.740 g) as a mixture with diisopropyl hydrazine-1,2-dicarboxylate. This material was carried forward without any further purification.

Step 2. Preparation of (S)-1-(2-((6-chloro-1H-pyrazolo[3,4-d]pyrimidin-1-yl)methyl)-2-methylpyrrolidin-1-yl)ethan-1-one. Trifluoroacetic acid (3.77 mL, 49.19 mmol) was added to a solution of tert-butyl (S)-2-((6-chloro-1H-pyrazolo[3,4-d]pyrimidin-1-yl)methyl)-2-methylpyrrolidine-1-carboxylate (1700 mg, 4.83 mmol) in DCM and stirred for 1.5 hours. The mixture was concentrated and redissolved in DCM (16.1 mL). Triethylamine (3.37 mL, 24.16 mmol) and acetyl chloride (0.69 mL, 9.66 mmol) were added and the mixture stirred at 23° C. for 1 hour. After concentrating, the crude product was purified by silica gel column chromatography (0 to 100% EtOAc/hexanes then 0 to 20% MeOH/DCM) to provide the title compound (1490 mg). This material was carried forward without further purification.

Step 3. Preparation of (S)-1-(2-((6-((6-methoxy-2-methyl-1,2,3,4-tetrahydroisoquinolin-7-yl)amino)-1H-pyrazolo[3,4-d]pyrimidin-1-yl)methyl)-2-methylpyrrolidin-1-yl)ethan-1-one. (S)-1-(2-((6-chloro-1H-pyrazolo[3,4-d]pyrimidin-1-yl)methyl)-2-methylpyrrolidin-1-yl)ethan-1-one (300 mg, 1.02 mmol), 6-methoxy-2-methyl-3,4-dihydro-1H-isoquinolin-7-amine (295 mg, 1.53 mmol), and p-TSA (583 mg, 3.06 mmol) were heated in 2-butanol (1.2 mL) at 100° C. for 5 h. After cooling, the reaction was quenched by the addition of saturated aqueous sodium carbonate and extracted with EtOAc. The combined organic phase was washed with brine solution, dried over anhydrous sodium sulfate, and concentrated under reduced pressure. The crude product was purified by reverse-phase HPLC (Phenomenex, Gemini-NX, 10 um, 250×30 mm, C18 column; gradient of 20% MeCN/0.1% TFA-water to 100% MeCN/0.1% TFA over 30 minutes) to provide the title compound (77 mg). 1H NMR (400 MHz, Methanol-d4, TFA salt) δ 8.96 (d, J=0.8 Hz, 1H), 8.50 (d, J=12.2 Hz, 1H), 8.11 (s, 1H), 6.93 (s, 1H), 4.95-4.69 (m, 3H), 4.49 (d, J=15.2 Hz, 1H), 4.31 (d, J=15.1 Hz, 1H), 3.96 (s, 3H), 3.77 (d, J=5.1 Hz, 1H), 3.54-3.35 (m, 2H), 3.35-3.19 (m, 2H), 3.10 (d, J=1.5 Hz, 4H), 2.54-2.46 (m, 1H), 1.90 (d, J=17.0 Hz, 3H), 1.80-1.63 (m, 2H), 1.55 (d, J=15.2 Hz, 3H). LCMS [M+H]: 450.0.

Example 136

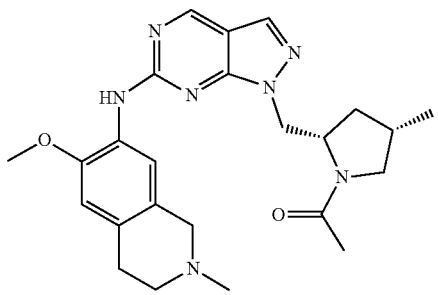

1-((2S,4S)-2-((6-((6-methoxy-2-methyl-1,2,3,4-tetrahydroisoquinolin-7-yl)amino)-1H-pyrazolo[3,4-d]pyrimidin-1-yl)methyl)-4-methylpyrrolidin-1-yl)ethan-1-one Step 1. tert-butyl (2S,4S)-2-((6-chloro-1H-pyrazolo[3,4-d]pyrimidin-1-yl)methyl)-4-methylpyrrolidine-1-carboxylate. DIAD (1.15 mL, 5.82 mmol) was added dropwise to a mixture of 6-chloro-1H-pyrazolo[3,4-d]pyrimidine (600 mg, 3.88 mmol), triphenylphosphine (1527 mg, 5.82 mmol), and tert-butyl (2S,4S)-2-(hydroxymethyl)-4-methyl-pyrrolidine-1-carboxylate (1045 mg, 4.85 mmol) in THF (11.9 mL) under N2 atmosphere at 0° C. The mixture was warmed to rt and stirred for 2 hours and concentrated onto silica gel. The crude product was purified by silica gel column chromatography (20 to 80% EtOAc/hexanes) to provide the title compound (2700 mg) as a mixture with diisopropyl hydrazine-1,2-dicarboxylate. This material was taken forward without further purification.

Step 2. Preparation of 1-((2S,4S)-2-((6-chloro-1H-pyrazolo[3,4-d]pyrimidin-1-yl)methyl)-4-methylpyrrolidin-1-yl)ethan-1-one. Trifluoroacetic acid (3.10 mL, 40.5 mmol) was added to a solution of tert-butyl (2S,4S)-2-((6-chloro-1H-pyrazolo[3,4-d]pyrimidin-1-yl)methyl)-4-methylpyrrolidine-1-carboxylate (1400 mg, 3.98 mmol) in DCM and stirred for 1.5 hours. The reaction mixture was concentrated and redissolved in DCM (16.1 mL). Triethylamine (2.78 mL, 19.9 mmol) and acetyl chloride (0.57 mL, 7.96 mmol) were added and the mixture stirred at 23° C. for 1 hour. After concentrating, the crude product was purified by silica gel column chromatography (0 to 100% EtOAc/hexanes then 0 to 20% MeOH/DCM) to provide the title compound (2490 mg) as a mixture with diisopropyl hydrazine-1,2-dicarboxylate. The material was carried forward without further purification.

Step 3. Preparation of 1-((2S,4S)-2-((6-((6-methoxy-2-methyl-1,2,3,4-tetrahydroisoquinolin-7-yl)amino)-1H-pyrazolo[3,4-d]pyrimidin-1-yl)methyl)-4-methylpyrrolidin-1-yl)ethan-1-one. 1-((2S,4S)-2-((6-chloro-1H-pyrazolo[3,4-d]pyrimidin-1-yl)methyl)-4-methylpyrrolidin-1-yl)ethan-1-one (300 mg, 1.02 mmol), 6-methoxy-2-methyl-3,4-dihydro-1H-isoquinolin-7-amine (294.53 mg, 1.53 mmol), and p-toluenesulfonic acid monohydrate (582.79 mg, 3.06 mmol) were heated in 2-butanol (1.2 mL) at 100° C. for 5 hours. After cooling, the reaction was quenched by the addition of saturated aqueous sodium carbonate and extracted with EtOAc. The combined organic phase was washed with brine solution, dried over anhydrous sodium sulfate, and concentrated under reduced pressure. The crude product was purified by reverse-phase HPLC (Phenomenex, Gemini-NX, 10 um, 250×30 mm, C18 column; gradient of 20% MeCN/0.1% TFA-water to 100% MeCN/0.1% TFA over 30 minutes) to provide the title compound as a mixture of atropisomers (174 mg): $^1$H NMR (400 MHz, DMSO-d6, TFA salt) δ 8.96 (d, J=2.5 Hz, 1H), 8.56 (d, J=10.5 Hz, 1H), 8.09 (q, J=1.9, 1.2 Hz, 1H), 6.93 (s, 1H), 4.90-4.79 (m, 1H), 4.79-4.61 (m, 2H), 4.50 (d, J=13.8 Hz, 2H), 4.30 (d, J=15.1 Hz, 0.5H), 3.97 (s, J=2.0, 1.2 Hz, 3H), 3.77 (s, 1H), 3.59 (d, J=9.9 Hz, 1H), 3.41 (td, J=11.8, 5.0 Hz, 1H), 3.31 (dq, J=3.0, 1.5 Hz, 1H), 3.16 (s, 0.5H), 3.10 (d, J=1.7 Hz, 3H), 2.46-2.34 (m, 0.5H), 2.27 (t, J=10.4 Hz, 0.5H), 2.14 (s, 2H), 1.88 (s, 1.5H), 1.85-1.70 (m, 2.5H), 0.98-0.85 (m, 3H). LCMS [M+H]: 450.0

Example 137

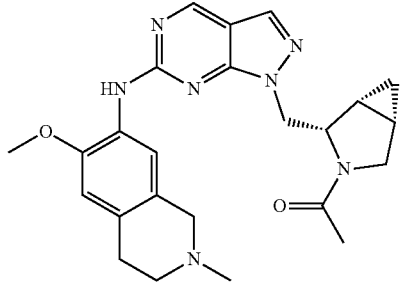 [SMILES: COc1cc2c(cc1Nc1ncc3cnn(C[C@@H]4[C@@H]5C[C@@H]5CN4C(C)=O)c3n1)CN(C)CC2]

1-((1R,2S,5S)-2-((6-((6-methoxy-2-methyl-1,2,3,4-tetrahydroisoquinolin-7-yl)amino)-1H-pyrazolo[3,4-d]pyrimidin-1-yl)methyl)-3-azabicyclo[3.1.0]hexan-3-yl)ethan-1-one Step 1. Preparation of tert-butyl (1R,2S,5S)-2-((6-chloro-1H-pyrazolo[3,4-d]pyrimidin-1-yl)methyl)-3-azabicyclo[3.1.0]hexane-3-carboxylate. DIAD (0.91 mL, 4.61 mmol) was added dropwise to a mixture of 6-chloro-1H-pyrazolo[3,4-d]pyrimidine (475.0 mg, 3.07 mmol), triphenylphosphine (1209.1 mg, 4.61 mmol), and tert-butyl (1R,2S,5S)-2-(hydroxymethyl)-3-azabicyclo[3.1.0]hexane-3-carboxylate (819.3 mg, 3.84 mmol) in THF (12 mL) under a nitrogen atmosphere at 0° C. The mixture was warmed to rt and stirred for 2 h. The reaction mixture was concentrated onto silica gel and purified by silica gel column chromatography (20 to 80% EtOAc/hexanes) to provide the title compound (1.250 g) as a crude mixture with diisopropyl hydrazine-1,2-dicarboxylate. This material was taken forward without further purification.

Step 2. Preparation of 1-((1R,2S,5S)-2-((6-chloro-1H-pyrazolo[3,4-d]pyrimidin-1-yl)methyl)-3-azabicyclo[3.1.0]hexan-3-yl)ethan-1-one. Trifluoroacetic acid (2.79 mL, 36.38 mmol) was added to a solution of tert-butyl (1R,2S,5S)-2-((6-chloro-1H-pyrazolo[3,4-d]pyrimidin-1-yl)methyl)-3-azabicyclo[3.1.0]hexane-3-carboxylate (1250 mg, 3.57 mmol) in DCM and stirred for 1.5 h. The mixture was concentrated and redissolved in DCM (11.9 mL). Triethylamine (2.49 mL, 17.87 mmol) and acetyl chloride (0.51 mL, 7.15 mmol) were added and the reaction stirred at 23° C. for 1 hour. After concentrating, the crude product was purified by silica gel column chromatography (0 to 100% EtOAc/hexanes then 0 to 20% MeOH/DCM) to provide the title compound (750 mg) as a mixture with diisopropyl hydrazine-1,2-dicarboxylate. The material was taken forward without any further purification.

Step 3. Preparation of 1-((1R,2S,5S)-2-((6-((6-methoxy-2-methyl-1,2,3,4-tetrahydroisoquinolin-7-yl)amino)-1H-pyrazolo[3,4-d]pyrimidin-1-yl)methyl)-3-azabicyclo[3.1.0]hexan-3-yl)ethan-1-one. 1-((1R,2S,5S)-2-((6-((6-chloro-1H-pyrazolo[3,4-d]pyrimidin-1-yl)methyl)-3-azabicyclo[3.1.0]hexan-3-yl)ethan-1-one (250 mg, 0.86 mmol), 6-methoxy-2-methyl-3,4-dihydro-1H-isoquinolin-7-amine (247 mg, 1.29 mmol), and p-TSA (489 mg, 2.57 mmol) were heated in 2-butanol (1.2 mL) at 100° C. for 5 hours. After cooling, the reaction was quenched by the addition of saturated aqueous sodium carbonate and extracted with EtOAc. The combined organic phase was washed with brine solution, dried over anhydrous sodium sulfate, and concentrated under reduced pressure. The crude product was purified by reverse-phase HPLC (Phenomenex, Gemini-NX, 10 um, 250×30 mm, C18 column; gradient of 20% MeCN/0.1% TFA-water to 100% MeCN/0.1% TFA over 30 minutes) to provide the title compound (95 mg). $^1$H NMR (400 MHz, Methanol-d4, TFA salt) δ 8.94 (s, 11H), 8.52 (d, J=7.4 Hz, 1H), 8.09 (s, 1H), 6.88 (s, 1H), 5.45 (dt, J=13.2, 3.6 Hz, 1H), 4.73 (dd, J=15.3, 12.3 Hz, 1H), 4.52 (dq, J=10.0, 4.9 Hz, 1H), 4.30 (dd, J=15.2, 6.9 Hz, 1H), 4.05 (ddd, J=13.3, 9.7, 1.9 Hz, 1H), 3.91 (s, 3H), 3.73 (dd, J=10.0, 5.2 Hz, 2H), 3.61 (d, J=10.0 Hz, 1H), 3.38 (tt, J=11.6, 5.7 Hz, 11H), 3.25-3.17 (m, 1H), 3.14-3.05 (m, 11H), 3.04 (s, 3H), 2.05 (d, J=0.5 Hz, 3H), 1.64 (t, J=6.7 Hz, 1H), 1.35 (tt, J=7.4, 4.8 Hz, 11H), 0.72-0.65 (m, 1H), 0.49 (p, J=4.9 Hz, 1H). LCMS [M+H]: 448.0.

Example 138

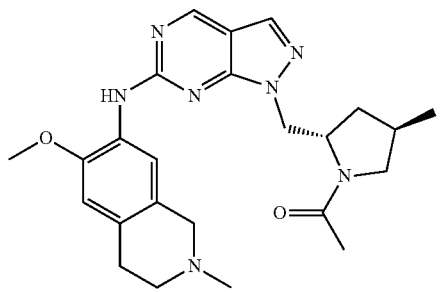

1-((2S,4R)-2-((6-((6-methoxy-2-methyl-1,2,3,4-tetrahydroisoquinolin-7-yl)amino)-1H-pyrazolo[3,4-d]pyrimidin-1-yl)methyl)-4-methylpyrrolidin-1-yl)ethan-1-one Step 1. Preparation of tert-butyl (2S,4R)-2-((6-chloro-1H-pyrazolo[3,4-d]pyrimidin-1-yl)methyl)-4-methylpyrrolidine-1-carboxylate. DIAD (1.10 mL, 5.58 mmol) was added dropwise to a mixture of 6-chloro-1H-pyrazolo[3,4-d]pyrimidine (575 mg, 3.72 mmol), triphenylphosphine (1.464 mg, 5.58 mmol), and tert-butyl (2S,4R)-2-(hydroxymethyl)-4-methylpyrrolidine-1-carboxylate (1.001 g, 4.65 mmol) in THF (12.4 mL) under N2 atmosphere at 0° C. The mixture was waned to rt and stirred for 2 hours and concentrated onto silica gel. The crude product was purified by silica gel column chromatography (20 to 80% EtOAc/hexanes) to provide the title compound (2360 mg) as a mixture with diisopropyl hydrazine-1,2-dicarboxylate. This material was carried forward without further purification.

Step 2. Preparation of 1-((2S,4R)-2-((6-chloro-1H-pyrazolo[3,4-d]pyrimidin-1-yl)methyl)-4-methylpyrrolidin-1-yl)ethan-1-one. Trifluoroacetic acid (3.10 mL, 40.51 mmol) was added to a solution of tert-butyl (2S,4R)-2-((6-chloro-1H-pyrazolo[3,4-d]pyrimidin-1-yl)methyl)-4-methylpyrrolidine-1-carboxylate (1.400 g, 3.98 mmol) in DCM and stirred for 1.5 h at rt. The mixture was concentrated and redissolved in DCM (16.1 mL), triethylamine (2.78 mL, 19.9 mmol), and acetyl chloride (0.57 mL, 7.96 mmol) were added at 0° C. and the mixture stirred at 23° C. for 1 hour. After concentrating, the crude product was purified by silica gel column chromatography (0 to 100% EtOAc/hexanes then 0 to 40% MeOH/DCM) to provide the title compound (500 mg). The material was carried forward without further purification.

Step 3. Preparation of 1-((2S,4R)-2-((6-((6-methoxy-2-methyl-1,2,3,4-tetrahydroisoquinolin-7-yl)amino)-1H-pyrazolo[3,4-d]pyrimidin-1-yl)methyl)-4-methylpyrrolidin-1-yl)ethan-1-one. 1-((2S,4R)-2-((6-chloro-1H-pyrazolo[3,4-d]pyrimidin-1-yl)methyl)-4-methylpyrrolidin-1-yl)ethan-1-one (70 mg, 0.24 mmol), 6-methoxy-2-methyl-3,4-dihydro-1H-isoquinolin-7-amine (69 mg, 0.36 mmol), and p-TSA (135.98 mg, 0.710 mmol) were heated in 2-butanol (1.2 mL) at 100° C. for 5 hours. After cooling, the reaction was quenched by the addition of saturated aqueous sodium carbonate and extracted with EtOAc. The combined organic phase was washed with brine solution, dried over anhydrous sodium sulfate, and concentrated under reduced pressure. The crude product was purified by reverse-phase HPLC (Phenomenex, Gemini-NX, 10 um, 250×30 mm, C18 column; gradient of 20% MeCN/0.1% TFA-water to 100% MeCN/0.1% TFA over 30 minutes). to provide the title compound (30 mg) as a mixture of rotamers: $^1$H NMR (400 MHz, Methanol-d4, TFA salt) δ 8.95 (s, 1H), 8.54 (d, J=15.5 Hz, 11H), 8.10 (d, J=12.4 Hz, 1H), 6.94 (s, 1H), 4.91-4.82 (m, 1H), 4.81-4.67 (m, 11H), 4.54 (td, J=16.7, 15.5, 6.8 Hz, 2H), 4.31 (d, J=15.1 Hz, 0.5H), 3.96 (d, J=5.1 Hz, 3.5H), 3.77 (d, J=11.7 Hz, 2H), 3.50-3.36 (m, 1H), 3.29-3.21 (m, 2H), 3.15 (dd, J=11.3, 2.4 Hz, 1H), 3.12-3.06 (m, 3H), 2.89 (q, J=10.1 Hz, 1H), 2.24 (dd, J=16.0, 6.0 Hz, 1H), 1.85 (s, 1.5H), 1.79 (s, 1.5H), 1.65-1.54 (m, 1H), 0.93 (t, J=6.3 Hz, 3H). LCMS [M+H]: 450.0.

Example 139

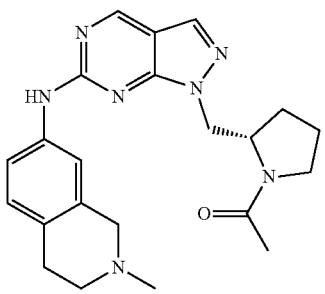 [SMILES: CC(=O)N1CCC[C@H]1Cn1ncc2cnc(Nc3ccc4c(c3)CN(C)CC4)nc21]

(S)-1-(2-((6-((2-methyl-1,2,3,4-tetrahydroisoquino-
lin-7-yl)amino)-1H-pyrazolo[3,4-d]pyrimidin-1-yl)
methyl)pyrrolidin-1-yl)ethan-1-one The above compound was prepared according to EXAMPLE 138 substituting in Step 1, N-Boc-L-prolinol for tert-butyl (2S,4R)-2-(hydroxymethyl)-4-methylpyrrolidine-1-carboxylate and substituting in Step 3, 2-methyl-3,4-dihydro-1H-isoquinolin-7-amine for 6-methoxy-2-methyl-3,4-dihydro-1H-isoquinolin-7-amine. The crude product was purified by reverse-phase HPLC (Phenomenex, Gemini-NX, 10 um, 250×30 mm, C18 column; gradient of 20% MeCN/0.1% TFA-water to 100% MeCN/0.1% TFA over 30 minutes) to provide the title compound (75 mg). Mixtures of atropisomers: $^1$H NMR (400 MHz, Methanol-d4, TFA salt) δ 8.92 (tp, J=3.4, 1.7 Hz, 1H), 8.15-8.06 (m, 1H), 8.03 (dt, J=3.3, 1.7 Hz, 1H), 7.49 (d, J=19.0 Hz, 1H), 7.26 (s, 1H), 4.87-4.64 (m, 2H), 4.51 (d, J=29.5 Hz, 3H), 4.36 (d, J=15.7 Hz, 0.5H), 3.78 (s, 2H), 3.34 (m, 2H), 3.24 (m, 0.5H), 3.16 (m, 1H), 3.09 (s, 4H), 2.11 (s, 1H), 1.99 (d, J=36.9 Hz, 3H), 1.84 (s, 1.5H), 1.79 (s, 1.5H). LCMS [M+H]: 406.0.

Example 140

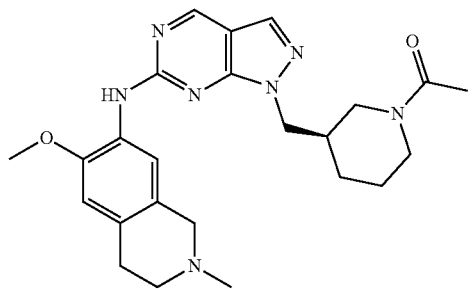 [SMILES: COc1cc2c(cc1Nc1ncc3cnn(C[C@@H]4CCCN(C(C)=O)C4)c3n1)CN(C)CC2]

1-[(3R)-3-[[6-[(6-methoxy-2-methyl-3,4-dihydro-
1H-isoquinolin-7-yl)amino]pyrazolo[3,4-d]pyrimi-
din-1-yl]methyl]-1-piperidyl]ethan-1-one Step 1: Preparation of tert-butyl rac-(3R)-3-[(6-chloropyrazolo[3,4-d]pyrimidin-1-yl)methyl]piperidine-1-carboxylate. Prepared according to general procedure D using 6-chloro-1H-pyrazolo[3,4-d]pyrimidine (300 mg, 1.94 mmol), tert-butyl (3R)-3-(hydroxymethyl)piperidine-1-carboxylate (417.88 mg, 1.94 mmol), triphenylphosphine (611 mg, 2.33 mmol) and DEAD (40% solution in toluene, 0.46 mL, 2.91 mmol) in THF (10 mL) at rt for 16 h. The crude product was purified by silica column chromatography (0-35% EtOAc in hexanes) to afford the title compound as a solid (390 mg).

Step 2: Preparation of tert-butyl (3R)-3-[[6-[(6-methoxy-2-methyl-3,4-dihydro-1H-isoquinolin-7-yl)amino]pyrazolo[3,4-d]pyrimidin-1-yl]methyl]piperidine-1-carboxylate. Prepared according to general procedure B using tert-butyl (3R)-3-[(6-chloropyrazolo[3,4-d]pyrimidin-1-yl)methyl]piperidine-1-carboxylate (390 mg, 1.11 mmol), 6-methoxy-2-methyl-3,4-dihydro-1H-isoquinolin-7-amine (320 mg, 1.66 mmol), Pd2(dba)3 (102 mg, 0.11 mmol), cesium carbonate (1.08 g, 3.33 mmol), and BINAP (138 mg, 0.22 mmol) in tert-butanol (6 mL) and toluene (6 mL) at 100° C. for 3 h. The crude product was purified by reverse phase HPLC (Phenomenex, Gemini-NX, 10 um, 250×30 mm, C18 column; gradient of 20% MeCN/0.1% TFA-water to 100% MeCN/0.1% TFA) providing the title compound as a solid (110 mg).

Step 3: Preparation of 6-methoxy-2-methyl-N-[1-[[(3R)-3-piperidyl]methyl]pyrazolo[3,4-d]pyrimidin-6-yl]-3,4-dihydro-1H-isoquinolin-7-amine. To a solution of tert-butyl (3R)-3-[[6-[(6-methoxy-2-methyl-3,4-dihydro-1H-isoquinolin-7-yl)amino]pyrazolo[3,4-d]pyrimidin-1-yl]methyl]piperidine-1-carboxylate (100 mg, 0.20 mmol) in DCM (2 mL) was added trifluoroacetic acid (0.15 mL, 1.97 mmol). The reaction mixture was stirred at rt until reaction was complete. The reaction mixture was concentrated to the title compound, which was used in the next step without further purification.

Step 4: Preparation of 1-[(3R)-3-[[6-[(6-methoxy-2-methyl-3,4-dihydro-1H-isoquinolin-7-yl)amino]pyrazolo[3,4-d]pyrimidin-1-yl]methyl]-1-piperidyl]ethan-1-one. To a cooled (0° C.) solution of 6-methoxy-2-methyl-N-[1-[[(3R)-3-piperidyl]methyl]pyrazolo[3,4-d]pyrimidin-6-yl]-3,4-dihydro-1H-isoquinolin-7-amine; 2,2,2-trifluoroacetic acid (50 mg, 0.10 mmol) in DCM (1 mL) was added DIEA (0.33 mL, 0.74 mmol) followed by acetyl chloride (10.3 µL, 0.14 mmol). The reaction mixture was monitored by LCMS until starting material was completely consumed. The crude product was purified by reverse phase HPLC (Phenomenex, Gemini-NX, 10 um, 250×30 mm, C18 column; gradient of 20% MeCN/0.1% TFA-water to 100% MeCN/0.1% TFA), providing the title compound as a solid (33 mg). $^1$H NMR (400 MHz, Methanol-d4) δ 9.15 (s, 1H), 8.35 (s, 1H), 8.17 (s, 1H), 7.05 (s, 1H), 4.72-4.24 (m, 5H), 3.96 (s, 3H), 3.78-3.70 (m, 3H), 3.70-3.62 (m, 6H), 3.58 (dd, J=5.5, 4.1 Hz, 3H), 3.12 (s, 3H), 2.05 (dd, J=7.4, 2.9 Hz, 4H). LCMS [M+H]: 450.3.

Example 141

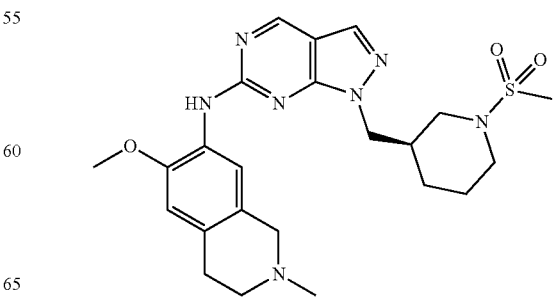

6-methoxy-2-methyl-N-[1-[[(3S)-1-methylsulfonyl-3-piperidyl]methyl]pyrazolo[3,4-d]pyrimidin-6-yl]-3,4-dihydro-1H-isoquinolin-7-amine To a cooled (0° C.) solution of 6-methoxy-2-methyl-N-[1-[[(3R)-3-piperidyl]methyl]pyrazolo[3,4-d]pyrimidin-6-yl]-3,4-dihydro-1H-isoquinolin-7-amine 2,2,2-trifluoroacetate (50 mg, 0.10 mmol, EXAMPLE 140, Step 3) in DCM (1 mL) was added DIEA (0.33 mL, 0.74 mmol) followed by methanesulfonyl chloride (11.1 μL, 0.14 mmol). The reaction mixture was monitored by LCMS until starting material was completely consumed. The crude product was by reverse phase HPLC (Phenomenex, Gemini-NX, 10 um, 250×30 mm, C18 column; gradient of 20% MeCN/0.1% TFA-water to 100% MeCN/0.1% TFA) providing the title compound as a solid (16 mg). ¹H NMR (400 MHz, Methanol-d4) δ 9.06 (s, 1H), 8.43 (d, J=10.1 Hz, 1H), 8.22 (s, 1H), 6.99 (s, 1H), 4.67-4.30 (m, 2H), 3.98 (s, 3H), 3.74 (t, J=5.6 Hz, 3H), 3.66 (q, J=5.4, 4.8 Hz, 4H), 3.62-3.54 (m, 2H), 3.10 (s, 3H), 2.81 (s, 3H), 2.56 (s, 1H), 1.88 (s, 1H), 1.64 (s, 2H), 1.29 (s, 2H). LCMS [M+H]: 486.3.

Example 142

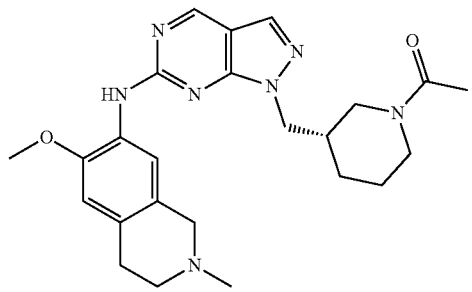 [SMILES: COc1cc2c(cc1Nc1ncc3cnn(C[C@H]4CCCN(C(C)=O)C4)c3n1)CN(C)CC2]

1-[(3S)-3-[[6-[(6-methoxy-2-methyl-3,4-dihydro-1H-isoquinolin-7-yl)amino]pyrazolo[3,4-d]pyrimidin-1-yl]methyl]-1-piperidyl]ethan-1-one Step 1: Preparation of tert-butyl (3S)-3-[(6-chloropyrazolo[3,4-d]pyrimidin-1-yl)methyl]piperidine-1-carboxylate. Prepared according to general procedure D using 6-chloro-1H-pyrazolo[3,4-d]pyrimidine (300 mg, 1.94 mmol), tert-butyl (3S)-3-(hydroxymethyl)piperidine-1-carboxylate (417.88 mg, 1.94 mmol), triphenylphosphine (611 mg, 2.33 mmol) and DEAD (40% solution in toluene, 0.46 mL, 2.91 mmol) in THF (10 mL) at rt for 16 h. The crude product was purified by silica column chromatography (0-35% EtOAc in hexanes) to afford the title compound as a solid (420 mg).

Step 2: Preparation of tert-butyl rac-(3S)-3-[[6-[(6-methoxy-2-methyl-3,4-dihydro-1H-isoquinolin-7-yl)amino]pyrazolo[3,4-d]pyrimidin-1-yl]methyl]piperidine-1-carboxylate. Prepared according to general procedure B using tert-butyl rac-(3S)-3-[(6-chloropyrazolo[3,4-d]pyrimidin-1-yl)methyl]piperidine-1-carboxylate (400 mg, 1.14 mmol), 6-methoxy-2-methyl-3,4-dihydro-1H-isoquinolin-7-amine (328 mg, 1.71 mmol), Pd2(dba)3 (104 mg, 0.11 mmol), cesium carbonate (1.11 g, 3.41 mmol) and BINAP (142 mg, 0.23 mmol) in tert-butanol (6 mL) and toluene (6 mL) at 100° C. for 3 h. The crude product was purified by reverse phase HPLC (Phenomenex, Gemini-NX, 10 um, 250×30 mm, C18 column; gradient of 20% MeCN/0.1% TFA-water to 100% MeCN/0.1% TFA) providing the title compound as a solid (300 mg).

Step 3: Preparation of 6-methoxy-2-methyl-N-[1-[[(3S)-3-piperidyl]methyl]pyrazolo[3,4-d]pyrimidin-6-yl]-3,4-dihydro-1H-isoquinolin-7-amine. To a solution of tert-butyl (3S)-3-[[6-[(6-methoxy-2-methyl-3,4-dihydro-1H-isoquinolin-7-yl)amino]pyrazolo[3,4-d]pyrimidin-1-yl]methyl]piperidine-1-carboxylate (300 mg, 0.59 mmol) in DCM (6 mL) was added trifluoroacetic acid (0.45 mL, 5.91 mmol). The reaction mixture was stirred at rt until reaction was complete. The reaction mixture was concentrated to afford the title compound, which was used in the next step without further purification.

Step 4: Preparation of 1-[(3S)-3-[[6-[(6-methoxy-2-methyl-3,4-dihydro-1H-isoquinolin-7-yl)amino]pyrazolo[3,4-d]pyrimidin-1-yl]methyl]-1-piperidyl]ethan-1-one. To a cooled (0° C.) solution of 6-methoxy-2-methyl-N-[1-[[(3S)-3-piperidyl]methyl]pyrazolo[3,4-d]pyrimidin-6-yl]-3,4-dihydro-1H-isoquinolin-7-amine; 2,2,2-trifluoroacetic acid (150 mg, 0.29 mmol) in DCM (3 mL) was added DIEA (1 mL, 5.75 mmol) followed by acetyl chloride (30.8 μL, 0.43 mmol). The reaction mixture was monitored by LCMS until starting material was completely consumed. The crude product was purified by reverse phase HPLC (Phenomenex, Gemini-NX, 10 um, 250×30 mm, C18 column; gradient of 20% MeCN/0.1% TFA-water to 100% MeCN/0.1% TFA) providing the title compound as a solid (2 mg). ¹H NMR (400 MHz, Chloroform-d) δ 9.10 (s, 1H), 8.58 (s, 1H), 8.24 (s, 1H), 6.95 (s, 1H), 4.89 (dt, J=35.6, 17.2 Hz, 2H), 4.64 (s, 1H), 4.47 (s, 2H), 4.17 (s, 3H), 3.96 (s, 4H), 3.81 (s, 1H), 3.62 (s, 1H), 3.30 (s, 3H), 2.85-2.63 (m, 1H), 2.33 (s, 2H), 2.23 (d, J=26.5 Hz, 1H), 2.14-1.96 (m, 2H), 1.63 (s, 3H). LCMS [M+H]: 450.3.

Example 143

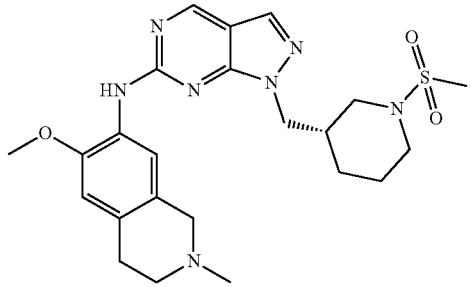

6-methoxy-2-methyl-N-[1-[[(3R)-1-methylsulfonyl-3-piperidyl]methyl]pyrazolo[3,4-d]pyrimidin-6-yl]-3,4-dihydro-1H-isoquinolin-7-amine To a cooled (0° C.) solution of 6-methoxy-2-methyl-N-[1-[[(3S)-3-piperidyl]methyl]pyrazolo[3,4-d]pyrimidin-6-yl]-3,4-dihydro-1H-isoquinolin-7-amine; 2,2,2-trifluoroacetic acid (150 mg, 0.29 mmol, EXAMPLE 142, Step 3) in DCM (3 mL) was added DIEA (1 mL, 5.75 mmol) followed by methanesulfonyl chloride (33.4 μL, 0.43 mmol). The reaction mixture was monitored by LCMS until starting material was completely consumed. The crude product was purified reversed phase eluting with 0% to 100% acetonitrile (with 0.1% TFA added) in water (with 0.1% TFA added), providing the title compound as a solid (20 mg, 12% yield).

1H NMR (400 MHz, Methanol-d4) δ 9.08 (s, 1H), 8.68 (s, 1H), 8.19 (s, 1H), 6.94 (s, 1H), 4.94-4.67 (m, 2H), 4.59 (s, 1H), 4.41 (d, J=15.7 Hz, 1H), 4.16 (s, 3H), 3.99 (s, 1H), 3.72 (d, J=11.9 Hz, 1H), 3.61 (s, 1H), 3.43 (s, 1H), 3.25 (s, 4H), 2.98 (d, J=30.4 Hz, 3H), 2.78 (s, 2H), 2.13 (s, 1H), 1.82 (s, 3H), 1.45 (d, J=17.9 Hz, 2H). LCMS [M+H]: 486.3.

MeCN/0.1% TFA), providing the title compound as a solid (59 mg). ¹H NMR (400 MHz, Methanol-d4) δ 8.94 (s, 1H), 8.57 (s, 1H), 8.07 (s, 1H), 6.93 (s, 1H), 4.74-4.27 (m, 6H), 3.97 (s, 3H), 3.84-3.71 (m, 3H), 3.50-3.37 (m, 1H), 3.10 (s, 3H), 2.76 (dt, J=37.5, 10.6 Hz, 1H), 2.50-2.28 (m, 2H), 1.85 (d, J=15.7 Hz, 4H). LCMS [M+H]: 504.0.

Example 144

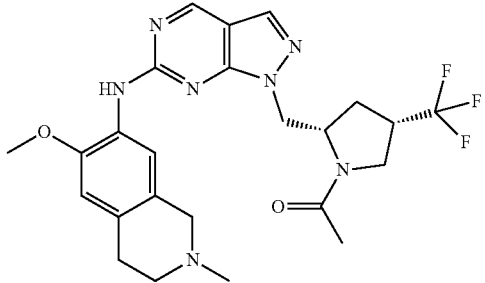 [SMILES: COc1cc2c(cc1Nc1ncc3cnn(C[C@@H]4C[C@H](C(F)(F)F)CN4C(C)=O)c3n1)CN(C)CC2]

1-[(2S,4S)-2-[[6-[(6-methoxy-2-methyl-3,4-dihydro-1H-isoquinolin-7-yl)amino]pyrazolo[3,4-d]pyrimidin-1-yl]methyl]-4-(trifluoromethyl)pyrrolidin-1-yl]ethan-1-one Step 1: Preparation of tert-butyl (2S,4S)-2-[(6-chloropyrazolo[3,4-d]pyrimidin-1-yl)methyl]-4-(trifluoromethyl)pyrrolidine-1-carboxylate. Prepared according to general procedure D using 6-chloro-1H-pyrazolo[3,4-d]pyrimidine (450 mg, 2.91 mmol), tert-butyl (2S,4S)-2-(hydroxymethyl)-4-(trifluoromethyl)pyrrolidine-1-carboxylate (980 mg, 3.64 mmol), triphenylphosphine (1.15 g, 4.37 mmol) and DIAD (0.86 mL, 4.37 mmol) in THF (10 mL) at rt for 16 h. The crude product was purified by silica column chromatography (0-35% EtOAc in hexanes) to afford the title compound as a solid (2 g).

Step 2: Preparation of 1-[(2S,4S)-2-[(6-chloropyrazolo[3,4-d]pyrimidin-1-yl)methyl]-4-(trifluoromethyl)pyrrolidin-1-yl]ethan-1-one. To a solution of tert-butyl (2S,4S)-2-[(6-chloropyrazolo[3,4-d]pyrimidin-1-yl)methyl]-4-(trifluoromethyl)pyrrolidine-1-carboxylate (2 g, 4.93 mmol) in DCM (16 mL) was added trifluoroacetic acid (3.84 mL, 1.49 mmol) and the solution was stirred at rt until reaction was complete. Triethylamine (3.44 mL, 24.6 mmol) followed by acetyl chloride (0.70 mL, 9.86 mmol) were added to the mixture at 0° C. and stirred at rt for 1 h. The reaction mixture was monitored by LCMS until starting material was completely consumed. The crude product was purified by silica column chromatography (0-100% EtOAc in hexanes, then 0-40% MeOH in DCM) to afford the title compound as a solid.

Step 3: Preparation of 1-[(2S,4S)-2-[[6-[(6-methoxy-2-methyl-3,4-dihydro-1H-isoquinolin-7-yl)amino]pyrazolo[3,4-d]pyrimidin-1-yl]methyl]-4-(trifluoromethyl)pyrrolidin-1-yl]ethan-1-one. Prepared according to general procedure A using 1-[(2S,4S)-2-[(6-chloropyrazolo[3,4-d]pyrimidin-1-yl)methyl]-4-(trifluoromethyl)pyrrolidin-1-yl]ethanone (100 mg, 0.29 mmol), 6-methoxy-2-methyl-3,4-dihydro-1H-isoquinolin-7-amine (83 mg, 0.43 mmol), and p-TSA (164 mg, 0.86 mmol) in 2-butanol (1.5 mL) at 100° C. for 3 h. The crude product was purified by reverse phase HPLC (Phenomenex, Gemini-NX, 10 um, 250×30 mm, C18 column; gradient of 20% MeCN/0.1% TFA-water to 100%

Example 145

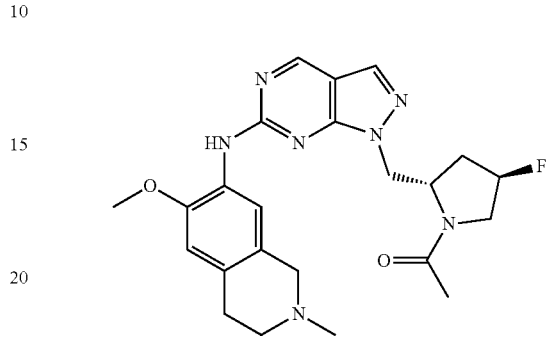

1-[(2S,4R)-4-fluoro-2-[[6-[(6-methoxy-2-methyl-3,4-dihydro-1H-isoquinolin-7-yl)amino]pyrazolo[3,4-d]pyrimidin-1-yl]methyl]pyrrolidin-1-yl]ethan-1-one Step 1: Preparation of tert-butyl (2S,4R)-2-[(6-chloropyrazolo[3,4-d]pyrimidin-1-yl)methyl]-4-fluoro-pyrrolidine-1-carboxylate. Prepared according to general procedure D using 6-chloro-1H-pyrazolo[3,4-d]pyrimidine (560 mg, 3.62 mmol), tert-butyl (2S,4R)-4-fluoro-2-(hydroxymethyl)pyrrolidine-1-carboxylate (993 mg, 4.53 mmol), triphenylphosphine (1.43 g, 5.43 mmol) and DIAD (1.07 mL, 5.43 mmol) in THF (10 mL) at rt for 16 h. The crude product was purified by silica column chromatography (0-35% EtOAc in hexanes) to afford the title compound as a solid (2 g).

Step 2: Preparation of 1-[(2S,4R)-2-[(6-chloropyrazolo[3,4-d]pyrimidin-1-yl)methyl]-4-fluoro-pyrrolidin-1-yl]ethan-1-one. To a solution of tert-butyl (2S,4R)-2-[(6-chloropyrazolo[3,4-d]pyrimidin-1-yl)methyl]-4-fluoro-pyrrolidine-1-carboxylate (1.75 g, 4.93 mmol) in DCM (16 mL) was added trifluoroacetic acid (3.84 mL, 1.49 mmol) and the solution was stirred at rt until reaction was complete. Triethylamine (3.44 mL, 24.6 mmol) followed by acetyl chloride (0.70 mL, 9.86 mmol) were added to the mixture at 0° C. and stirred at rt for until the reaction was complete. The crude product was purified by silica column chromatography (0-100% EtOAc in hexanes, then 0-40% MeOH in DCM) to afford the title compound as a solid.

Step 3: Preparation of 1-[(2S,4R)-4-fluoro-2-[[6-[(6-methoxy-2-methyl-3,4-dihydro-1H-isoquinolin-7-yl)amino]pyrazolo[3,4-d]pyrimidin-1-yl]methyl]pyrrolidin-1-yl]ethan-1-one. Prepared according to general procedure A using 1-[(2S,4R)-2-[(6-chloropyrazolo[3,4-d]pyrimidin-1-yl)methyl]-4-fluoro-pyrrolidin-1-yl]ethanone (100 mg, 0.34 mmol), 6-methoxy-2-methyl-3,4-dihydro-1H-isoquinolin-7-amine (97 mg, 0.50 mmol), and p-TSA (192 mg, 1.01 mmol) in 2-butanol (1.5 mL) at 100° C. for 3 h. The crude product was by reverse phase HPLC (Phenomenex, Gemini-NX, 10 um, 250×30 mm, C18 column; gradient of 20% MeCN/0.1% TFA-water to 100% MeCN/0.1% TFA) providing the title compound as a solid (80 mg). ¹H NMR (400 MHz, Methanol-d4) δ 8.93 (s, 1H), 8.58 (s, 1H), 8.06 (s, 1H), 6.94 (s, 1H), 4.74-4.27 (m, 6H), 3.97 (s, 4H), 3.83-3.59 (m, 3H), 3.49-3.38 (m, 11H), 3.11 (s, 2H), 2.74 (m, 3H), 1.83 (d, J=17.8 Hz, 4H). LCMS [M+H]: 454.0.

Example 146

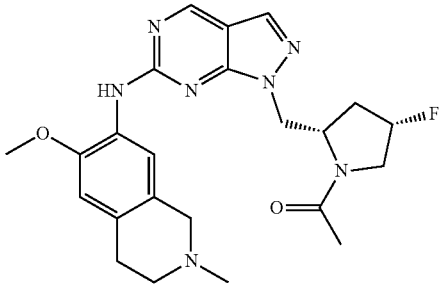 [SMILES: COc1cc2c(cc1Nc1ncc3cnn(C[C@@H]4C[C@H](F)CN4C(C)=O)c3n1)CN(C)CC2]

1-[(2S,4S)-4-fluoro-2-[[6-[(6-methoxy-2-methyl-3,4-dihydro-1H-isoquinolin-7-yl)amino]pyrazolo[3,4-d]pyrimidin-1-yl]methyl]pyrrolidin-1-yl]ethan-1-one Step 1: Preparation of tert-butyl (2S,4S)-2-[(6-chloropyrazolo[3,4-d]pyrimidin-1-yl)methyl]-4-fluoro-pyrrolidine-1-carboxylate. Prepared according to general procedure D using 6-chloro-1H-pyrazolo[3,4-d]pyrimidine (560 mg, 3.62 mmol), tert-butyl (2S,4S)-4-fluoro-2-(hydroxymethyl)pyrrolidine-1-carboxylate (993 mg, 4.53 mmol), triphenylphosphine (1.43 g, 5.43 mmol) and DIAD (1.07 mL, 5.43 mmol) in THF (10 mL) at rt for 16 h. The crude product was purified by silica column chromatography (0-35% EtOAc in hexanes) to afford the title compound as a solid (2 g).

Step 2: Preparation of 1-[(2S,4S)-2-[(6-chloropyrazolo[3,4-d]pyrimidin-1-yl)methyl]-4-fluoro-pyrrolidin-1-yl]ethan-1-one. To a solution of tert-butyl (2S,4S)-2-[(6-chloropyrazolo[3,4-d]pyrimidin-1-yl)methyl]-4-fluoro-pyrrolidine-1-carboxylate (1.75 g, 4.93 mmol) in DCM (16 mL) was added trifluoroacetic acid (3.84 mL, 1.49 mmol) and the solution was stirred at rt until reaction was complete. Triethylamine (3.44 mL, 24.6 mmol) followed by acetyl chloride (0.70 mL, 9.86 mmol) were added to the mixture at 0° C. and stirred at rt until the reaction was complete. The crude product was purified by silica column chromatography (0-100% EtOAc in hexanes, then 0-40% MeOH in DCM) to afford the title compound as a solid.

Step 3: Preparation of 1-[(2S,4S)-4-fluoro-2-[[6-[(6-methoxy-2-methyl-3,4-dihydro-1H-isoquinolin-7-yl)amino]pyrazolo[3,4-d]pyrimidin-1-yl]methyl]pyrrolidin-1-yl]ethan-1-one. Prepared according to general procedure A using 1-[(2S,4S)-2-[(6-chloropyrazolo[3,4-d]pyrimidin-1-yl)methyl]-4-fluoro-pyrrolidin-1-yl]ethanone (100 mg, 0.34 mmol), 6-methoxy-2-methyl-3,4-dihydro-1H-isoquinolin-7-amine (97 mg, 0.50 mmol), and p-TSA (192 mg, 1.01 mmol) in 2-butanol (1.5 mL) at 100° C. for 3 h. The crude product was purified by reverse phase HPLC (Phenomenex, Gemini-NX, 10 um, 250×30 mm, C18 column; gradient of 20% MeCN/0.1% TFA-water to 100% MeCN/0.1% TFA) providing the title compound as a solid (100 mg). $^1$H NMR (400 MHz, Methanol-d4) δ 8.90 (s, 1H), 8.64 (s, 1H), 8.06 (s, 1H), 6.94 (s, 1H), 4.80-4.24 (m, 6H), 3.97 (d, J=2.7 Hz, 4H), 3.88 (d, J=7.8 Hz, 1H), 3.80 (s, 1H), 3.46 (m, 1H), 3.14 (m, 1H), 3.07 (d, J=5.5 Hz, 4H), 2.37 (d, J=22.6 Hz, 1H), 1.98 (d, J=15.1 Hz, 3H), 1.67 (d, J=15.5 Hz, 1H). LCMS [M+H]: 454.0.

Examples 147 and 148

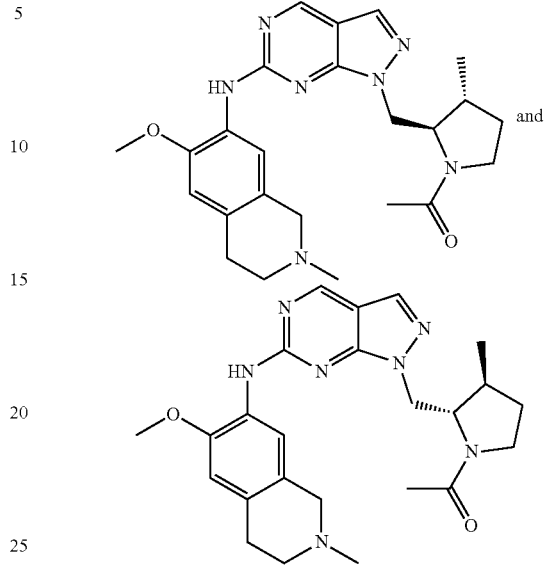

1-[(2R,3R)-2-[[6-[(6-methoxy-2-methyl-3,4-dihydro-1H-isoquinolin-7-yl)amino]pyrazolo[3,4-d]pyrimidin-1-yl]methyl]-3-methyl-pyrrolidin-1-yl]ethan-1-one (EXAMPLE 147) and 1-[(2S,3S)-2-[[6-[(6-methoxy-2-methyl-3,4-dihydro-1H-isoquinolin-7-yl)amino]pyrazolo[3,4-d]pyrimidin-1-yl]methyl]-3-methyl-pyrrolidin-1-yl]ethan-1-one (EXAMPLE 148)

Step 1. Preparation of tert-butyl 2-(hydroxymethyl)-3-methylpyrrolidine-1-carboxylate. 4-methylbenzenesulfonic acid; (3-methylpyrrolidin-2-yl)methanol (250 mg, 0.87 mmol) was charged into DCM (10 mL) under nitrogen atmosphere. Di-tert-butyl dicarbonate (208.85 mg, 0.96 mmol) was added dropwise to the reaction mixture at 0° C. and stirred for 2 hours at rt. After the completion of reaction, the reaction mixture was concentrated under reduced pressure and loaded onto silica and purified using EtOAc:Hexane to yield tert-butyl (2R,3S)-2-(hydroxymethyl)-3-methyl-pyrrolidine-1-carboxylate (184 mg).

Step 2: Preparation of tert-butyl 2-[(6-chloropyrazolo[3,4-d]pyrimidin-1-yl)methyl]-3-methyl-pyrrolidine-1-carboxylate. Prepared according to general procedure D using 6-chloro-1H-pyrazolo[3,4-d]pyrimidine (130 mg, 1.68 mmol), tert-butyl 2-(hydroxymethyl)-3-methyl-pyrrolidine-1-carboxylate (181 mg, 0.84 mmol), triphenylphosphine (441 mg, 0.84 mmol) and DEAD (40% solution in toluene, 0.77 mL, 1.68 mmol) in THF (5 mL) at rt for 3 h. The crude product was purified by silica column chromatography eluting with 0-35% EtOAc in hexanes to afford the title compound as a solid (342 mg).

Step 3: Preparation of 1-(2-((6-chloro-1H-pyrazolo[3,4-d]pyrimidin-1-yl)methyl)-3-methylpyrrolidin-1-yl)ethan-1-one. To a solution of tert-butyl 2-[(6-chloropyrazolo[3,4-d]pyrimidin-1-yl)methyl]-3-methyl-pyrrolidine-1-carboxylate (330 mg, 0.94 mmol) in DCM (5 mL) was added trifluoroacetic acid (0.72 mL, 9.38 mmol) and the solution was stirred at rt until reaction was complete. Triethylamine (0.65 mL, 4.69 mmol) followed by acetyl chloride (0.13 mL, 1.88 mmol) were added to the mixture at 0° C. and stirred at rt for 1 h. The crude product was purified by silica column chromatography (0-100% EtOAc in hexanes, then 0-40% MeOH in DCM) to afford the title compound as a solid (180 mg).

Step 4: Preparation of 1-[(2R,3R)-2-[[6-[(6-methoxy-2-methyl-3,4-dihydro-1H-isoquinolin-7-yl)amino]pyrazolo[3,4-d]pyrimidin-1-yl]methyl]-3-methyl-pyrrolidin-1-yl]ethan-1-one and 1-[(2S,3S)-2-[[6-[(6-methoxy-2-methyl-3,4-dihydro-1H-isoquinolin-7-yl)amino]pyrazolo[3,4-d]pyrimidin-1-yl]methyl]-3-methyl-pyrrolidin-1-yl]ethan-1-one. Prepared according to general procedure A using 1-[2-[(6-chloropyrazolo[3,4-d]pyrimidin-1-yl)methyl]-3-methyl-pyrrolidin-1-yl]ethan-1-one (160 mg, 0.55 mmol), 6-methoxy-2-methyl-3,4-dihydro-1H-isoquinolin-7-amine (157 mg, 0.82 mmol), and p-TSA (311 mg, 1.63 mmol) in NMP (3 mL) at 100° C. for 3 h. The crude product was by reverse phase HPLC (Phenomenex, Gemini-NX, 10 um, 250×30 mm, C18 column; gradient of 20% MeCN/0.1% TFA-water to 100% MeCN/0.1% TFA) to provide a racemic mixture which was then purified using chiral separation to give two peaks.

The first eluting peak provided 1-[(2R,3R)-2-[[6-[(6-methoxy-2-methyl-3,4-dihydro-1H-isoquinolin-7-yl)amino]pyrazolo[3,4-d]pyrimidin-1-yl]methyl]-3-methyl-pyrrolidin-1-yl]ethan-1-one (23 mg[1]H NMR (400 MHz, Methanol-d4) δ 9.20 (s, 1H), 8.39 (s, 1H), 8.24 (s, 1H), 7.05 (s, 1H), 4.88-4.28 (m, 5H), 4.09 (d, J=4.8 Hz, 11H), 3.98 (s, 3H), 3.85-3.38 (m, 4H), 3.23-3.14 (m, 1H), 3.12-3.05 (m, 3H), 2.48 (d, J=6.2 Hz, 2H), 1.86 (d, J=17.5 Hz, 3H), 1.66-1.23 (m, 1H), 1.01 (dd, J=8.7, 6.9 Hz, 3H). LCMS [M+H]: 450.1.

The second eluting peak provided 1-[(2S,3S)-2-[[6-[(6-methoxy-2-methyl-3,4-dihydro-1H-isoquinolin-7-yl)amino]pyrazolo[3,4-d]pyrimidin-1-yl]methyl]-3-methyl-pyrrolidin-1-yl]ethan-1-one (23 mg). $^1$H NMR (400 MHz, Methanol-d4) δ 9.11 (s, 1H), 8.36 (s, 1H), 8.27 (s, 1H), 7.01 (s, 1H), 4.79-4.26 (m, 5H), 4.09 (s, 1H), 3.98 (s, 3H), 3.78 (s, 1H), 3.58 (m, 3H), 3.19 (s, 1H), 3.10 (s, 3H), 2.49 (d, J=6.2 Hz, 2H), 1.87 (s, 1H), 1.82 (s, 2H), 1.29 (s, 1H), 1.00 (t, J=8.4 Hz, 3H). LCMS [M+H]: 450.1.

Example 149

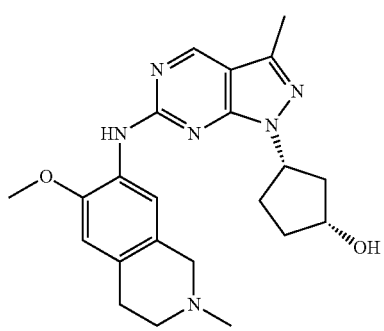 [SMILES: COc1cc2c(cc1Nc1ncc3c(C)nn([C@H]4CC[C@@H](O)C4)c3n1)CN(C)CC2]

(rel-1S,3R)-3-(6-((6-methoxy-2-methyl-1,2,3,4-tetrahydroisoquinolin-7-yl)amino)-3-methyl-1H-pyrazolo[3,4-d]pyrimidin-1-yl)cyclopentan-1-ol Step 1: Preparation of 1-((1S,3R)-3-(benzyloxy)cyclopentyl)-6-chloro-1H-pyrazolo[3,4-d]pyrimidine. Prepared according to general procedure D using (rel-1R,3R)-3-benzyloxycyclopentanol (249.0 mg, 1.26 mmol), 6-chloro-3-methyl-1H-pyrazolo[3,4-d]pyrimidine (177.0 mg, 1.05 mmol), triphenylphosphine (555.0 mg, 2.10 mmol) and DEAD (40% solution in toluene, 0.95 mL, 2.1 mmol) in THF (5.24 mL) at rt for 1 h. The crude product was purified by silica column chromatography eluting with 0% to 25% EtOAc in hexanesto afford the title compound (327.4 mg).

Step 2: Preparation of N-[1-[(rel-1S,3R)-3-benzyloxycyclopentyl]pyrazolo[3,4-d]pyrimidin-6-yl]-6-methoxy-2-methyl-3,4-dihydro-1H-isoquinolin-7-amine. Prepared according to general procedure B using 1-[(rel-1S,3R)-3-benzyloxycyclopentyl]-6-chloro-3-methyl-pyrazolo[3,4-d]pyrimidine (327.0 mg, 0.955 mmol), 6-methoxy-2-methyl-3,4-dihydro-1H-isoquinolin-7-amine (275.0 mg, 1.43 mmol), cesium carbonate (943.0 mg, 2.86 mmol), tris(dibenzylideneacetone)dipalladium(0) (45.1 mg, 0.05 mmol), and BINAP (61.3 mg, 0.095 mmol) tert-butanol (2.39 mL) and toluene (2.39 mL) at 100° C. for 1 h. The crude product was purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (196 mg).

Step 3: Preparation of (rel-1S,3R)-3-(6-(((6-methoxy-2-methyl-1,2,3,4-tetrahydroisoquinolin-7-yl)amino)-3-methyl-1H-pyrazolo[3,4-d]pyrimidin-1-yl)cyclopentan-1-ol. N-[1-[(1S,3R)-3-benzyloxycyclopentyl]-3-methyl-pyrazolo[3,4-d]pyrimidin-6-yl]-6-methoxy-2-methyl-3,4-dihydro-1H-isoquinolin-7-amine (196 mg, 0.392 mmol) in MeOH (2.0 mL) was degassed for 5 minutes. Palladium on carbon (41.7 mg, 0.0392 mmol) was added slowly to the reaction mixture. A stream of hydrogen was bubbled through the solution for 15 min. The reaction was stirred under a hydrogen atmosphere until consumption of the starting material. The reaction mixture was filtered through a pad of celite. The pad was washed with DCM followed by MeOH. The combined organics was concentrated and the crude product was purified by reverse phase HPLC (Phenomenex, Gemini-NX, 10 um, 250×30 mm, C18 column; gradient of 20% MeCN/0.1% TFA-water to 100% MeCN/0.1% TFA) to afford the title compound (52.5 mg). 1H NMR (400 MHz, Chloroform-d) δ 8.73 (s, 1H), 8.34 (s, 1H), 6.65 (s, 1H), 5.34-5.25 (m, 1H), 4.41 (s, 1H), 3.96 (s, 2H), 3.89 (s, 3H), 3.05 (s, 4H), 2.70 (s, 3H), 2.50 (s, 3H), 2.43-2.29 (m, 3H), 2.16-2.09 (m, 2H), 2.09-1.99 (m, 2H), 1.93 (ddd, J=13.7, 9.2, 4.7 Hz, 1H). LCMS [M+H]: 409.0

Example 150

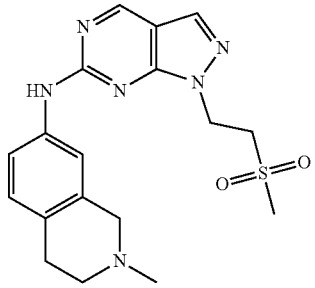 [SMILES: CN1CCc2ccc(Nc3ncc4cnn(CCS(C)(=O)=O)c4n3)cc2C1]

2-methyl-N-(1-(2-(methylsulfonyl)ethyl)-1H-pyrazolo[3,4-d]pyrimidin-6-yl)-1,2,3,4-tetrahydroisoquinolin-7-amine Step 1: Preparation of 6-chloro-1-(2-(methylsulfonyl)ethyl)-1H-pyrazolo[3,4-d]pyrimidine. Prepared according to general procedure C using 6-chloro-1 h-pyrazolo[3,4-d]pyrimidine (270.0 mg, 1.75 mmol), 1-chloro-2-methylsulfonyl-ethane (249.0 mg, 1.75 mmol), and cesium carbonate (683.0 mg, 2.10 mmol) in acetonitrile stirred at 80° C. for 18 h. The crude product was purified by silica column chromatography eluting with 0% to 100% EtOAc in DCM to provide the title compound (180 mg).

Step 2: Preparation of 2-methyl-N-(1-(2-(methylsulfonyl)ethyl)-1H-pyrazolo[3,4-d]pyrimidin-6-yl)-1,2,3,4-tetrahydroisoquinolin-7-amine. Prepared by general procedure A using 6-chloro-1-(2-methylsulfonylethyl)pyrazolo[3,4-d]pyrimidine (20.0 mg, 0.077 mmol), 2-methyl-3,4-dihydro-1H-isoquinolin-7-amine (14.9 mg, 0.092 mmol), and 4M HCl in dioxane (0.060 mL) at 120° C. for 3.5 h. The crude product was purified by reverse phase HPLC to provide the desired product. 1H NMR (400 MHz, Methanol-d4) δ 8.91 (s, 1H), 8.22 (s, 1H), 8.06 (s, 11H), 7.47 (d, J=9.0 Hz, 11H), 7.24 (d, J=8.5 Hz, 1H), 4.66 (d, J=15.5 Hz, 1H), 4.39 (d, J=15.6 Hz, 1H), 3.78 (t, J=6.8 Hz, 3H), 3.51-3.36 (m, 1H), 3.07 (s, 3H), 2.93 (s, 3H). [M+H]=387.0

Example 151

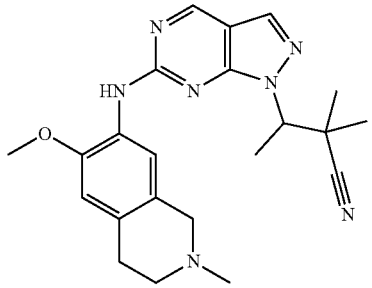 [SMILES: COc1cc2c(cc1Nc1ncc3cnn(C(C)C(C)(C)C#N)c3n1)CN(C)CC2]

3-(6-((6-methoxy-2-methyl-1,2,3,4-tetrahydroisoquinolin-7-yl)amino)-1H-pyrazolo[3,4-d]pyrimidin-1-yl)-2,2-dimethylbutanenitrile hydrochloride Step 1: Preparation of 3-(6-chloro-1H-pyrazolo[3,4-d]pyrimidin-1-yl)-2,2-dimethylbutanenitrile. Prepared according to general procedure D using 3-hydroxy-2,2-dimethylbutanenitrile (150 mg, 1.99 mmol), 6-chloro-1H-pyrazolo[3,4-d]pyrimidine (307 mg, 1.99 mmol), triphenylphosphine (550 mg, 2.10 mmol), and DEAD (40% solution, 0.660 mL, 1.46 mmol) in THF at rt for 30 min followed by 18 h at reflux. The crude product was purified by silica column chromatography eluting with 0% to 100% EA in hex to provide the title compound (97.5 mg).

Step 2: Preparation of 3-(6-((6-methoxy-2-methyl-1,2,3,4-tetrahydroisoquinolin-7-yl)amino)-1H-pyrazolo[3,4-d]pyrimidin-1-yl)-2,2-dimethylbutanenitrile hydrochloride. Prepared according to general procedure A using 3-(6-chloro-1H-pyrazolo[3,4-d]pyrimidin-1-yl)-2,2-dimethylbutanenitrile (45 mg, 0.18 mmol), 6-methoxy-2-methyl-3,4-dihydro-1H-isoquinolin-7-amine (36.4, 0.189 mmol), and p-TSA (72 mg, 0.378 mmol) in 2-butanol at 110° C. for 18 h. The reaction mixture was concentrated and triturated with EA. The remaining crude solid was suspended in EtOAc and saturated sodium bicarbonate followed by extraction with EtOAc. The combined organics was concentrated, and the crude product was purified by silica column chromatography eluting with 0% to 100% MeOH in EA. The purified product was converted to the HCl salt using 1M EtOAc to provide the title compound (27 mg) as a mixture of diastereomers. 1H NMR (400 MHz, DMSO-d6, HCl salt) δ 10.54 (d, J=25.1 Hz, 1H), 9.01 (d, J=1.2 Hz, 1H), 8.46 (d, J=10.2 Hz, 1H), 8.21 (dd, J=1.4, 0.6 Hz, 1H), 8.04 (d, J=26.9 Hz, 1H), 6.96 (s, 1H), 4.96-4.79 (m, 1H), 4.45 (dd, J=36.2, 14.2 Hz, 1H), 4.32-4.18 (m, 2H), 3.85 (d, J=2.3 Hz, 4H), 3.64 (s, 1H), 3.31 (s, 1H), 3.24-3.11 (m, 1H), 3.00 (d, J=17.2 Hz, 1H), 2.92 (dd, J=4.8, 2.6 Hz, 3H), 1.66 (dd, J=6.9, 4.2 Hz, 3H), 1.47 (s, 3H), 1.17 (d, J=1.9 Hz, 3H). LCMS [M+H]: 406.1

Example 152

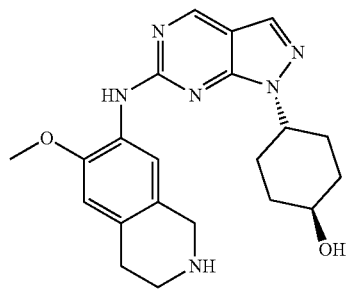

trans-4-(6-((6-methoxy-1,2,3,4-tetrahydroisoquinolin-7-yl)amino)-1H-pyrazolo[3,4-d]pyrimidin-1-yl)cyclohexan-1-ol Step 1: Preparation of tert-butyl 7-((1-(trans-4-hydroxycyclohexyl)-1H-pyrazolo[3,4-d]pyrimidin-6-yl)amino)-6-methoxy-3,4-dihydroisoquinoline-2(1H)-carboxylate. Prepared according to general procedure A using (1r,4r)-4-(6-chloro-1H-pyrazolo[3,4-d]pyrimidin-1-yl)cyclohexan-1-ol (1.27 g, 5.03 mmol), tert-butyl 7-amino-6-methoxy-3,4-dihydroisoquinoline-2(1H)-carboxylate (1.0 g, 3.59 mmol), and DIEA (1.88 mL, 10.8 mmol) in DMF (20 mL) at 100° C. for 4 days. The mixture was diluted with EtOAc (60 mL) and washed with water (3×60 mL). The organics were concentrated and purified by column chromatography (1-6% MeOH in DCM) to give tert-butyl 7-((1-(trans-4-hydroxycyclohexyl)-1H-pyrazolo[3,4-d]pyrimidin-6-yl)amino)-6-methoxy-3,4-dihydroisoquinoline-2(1H)-carboxylate (500 mg).

Step 2: Preparation of trans-4-(6-((6-methoxy-1,2,3,4-tetrahydroisoquinolin-7-yl)amino)-1H-pyrazolo[3,4-d]pyrimidin-1-yl)cyclohexan-1-ol. To a solution of -((1-(trans-4-hydroxycyclohexyl)-1H-pyrazolo[3,4-d]pyrimidin-6-yl)amino)-6-methoxy-3,4-dihydroisoquinoline-2(1H)-carboxylate (500 mg, 1.0 mmol) in 1,4-dioxane (10 mL) was added 4N HCl in dioxane (1.25 mL, 5.0 mmol). This mixture was stirred at room temperature for 2 days. The crude product was purified by reversed phase chromatography eluting with 10% to 50% acetonitrile (with 0.1% TFA added) in water (with 0.1% TFA added). Product obtained was then converted into the HCl salt (430 mg). 1H NMR (400 MHz, Methanol-d$_4$) δ 9.12 (s, 1H), 8.35 (s, 1H), 8.00 (s, 1H), 7.05 (s, 1H), 4.71-4.59 (m, 1H), 4.38 (s, 2H), 3.95 (s, 3H), 3.71 (tt, J=11.0, 10.5, 3.8 Hz, 1H), 3.54 (t, J=6.4 Hz, 2H), 3.18 (t, J=6.4 Hz, 2H), 2.20-2.05 (m, 6H), 1.62-1.43 (m, 2H). LCMS [M+H]: 395.0.

Example 153

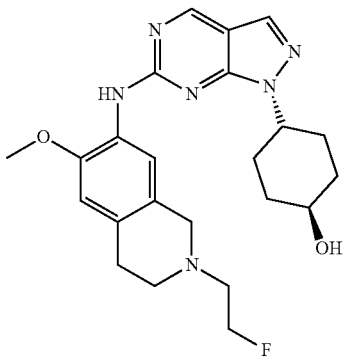

trans-4-(6-((2-(2-fluoroethyl)-6-methoxy-1,2,3,4-tetrahydroisoquinolin-7-yl)amino)-1H-pyrazolo[3,4-d]pyrimidin-1-yl)cyclohexan-1-ol To a solution of trans-4-(6-((6-methoxy-1,2,3,4-tetrahydroisoquinolin-7-yl)amino)-1H-pyrazolo[3,4-d]pyrimidin-1-yl)cyclohexan-1-ol hydrochloride (50 mg, 0.12 mmol) in acetonitrile (1.2 mL) was added potassium carbonate (48 mg, 0.35 mmol) followed by 1-fluoro-2-iodoethane (0.011 mL, 0.14 mmol). The mixture was heated to 65° C. for 4 hours. The crude product was purified by reversed phase chromatography eluting with 10% to 50% acetonitrile (with 0.1% TFA added) in water (with 0.1% TFA added). Product obtained was then converted into the HCl salt (9 mg). $^1$H NMR (400 MHz, Methanol-d$_4$) δ 9.05 (s, 1H), 8.24 (s, 1H), 8.17 (s, 1H), 7.04 (s, 1H), 5.05-5.00 (m, 1H), 4.70-4.62 (m, 2H), 4.49 (d, J=14.6 Hz, 1H), 3.96 (s, 3H), 3.96-3.86 (m, 2H), 3.78 (dd, J=5.2, 3.0 Hz, 1H), 3.75-3.68 (m, 2H), 3.55 (bs, 1H), 3.26-3.16 (m, 2H), 2.22-2.03 (m, 6H), 1.60-1.48 (m, 2H). LCMS [M+H]: 441.0.

Example 154

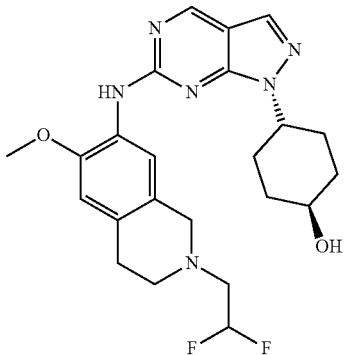

trans-4-(6-((2-(2,2-difluoroethyl)-6-methoxy-1,2,3,4-tetrahydroisoquinolin-7-yl)amino)-1H-pyrazolo[3,4-d]pyrimidin-1-yl)cyclohexan-1-ol To a solution of trans-4-(6-((6-methoxy-1,2,3,4-tetrahydroisoquinolin-7-yl)amino)-1H-pyrazolo[3,4-d]pyrimidin-1-yl)cyclohexan-1-ol hydrochloride (50 mg, 0.12 mmol) in acetonitrile (1.2 mL) was added potassium carbonate (48 mg, 0.35 mmol) followed by 2-iodo-1,1-difluoroethane (0.012 mL, 0.14 mmol). The mixture was heated to 65° C. for 24 hours. The crude product was purified by reversed phase chromatography eluting with 10% to 50% acetonitrile (with 0.1% TFA added) in water (with 0.1% TFA added). Product obtained was then converted into the HCl salt (5 mg). $^1$H NMR (400 MHz, Methanol-d$_4$) δ 9.10 (s, 1H), 8.31 (s, 11H), 8.06 (s, 1H), 7.07 (s, 11H), 6.56 (tt, J=53.4, 2.7 Hz, 1H), 4.90-4.72 (m, 1H), 4.69-4.58 (m, 2H), 4.30-4.09 (m, 2H), 3.95 (s, 3H), 3.93-3.65 (m, 3H), 2.20-2.00 (m, 6H), 1.53 (q, J=12.3, 11.7 Hz, 2H), 1.32-1.20 (m, 2H). LCMS [M+H]: 449.0.

Example 155

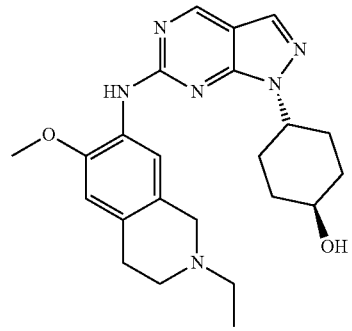

trans-4-(6-((2-ethyl-6-methoxy-1,2,3,4-tetrahydroisoquinolin-7-yl)amino)-1H-pyrazolo[3,4-d]pyrimidin-1-yl)cyclohexan-1-ol To a solution of trans-4-(6-((6-methoxy-1,2,3,4-tetrahydroisoquinolin-7-yl)amino)-1H-pyrazolo[3,4-d]pyrimidin-1-yl)cyclohexan-1-ol hydrochloride (50 mg, 0.12 mmol) in acetonitrile (1.2 mL) was added sodium triacetoxyborohydride (73 mg, 0.35 mmol) followed by ethanal (0.013 mL, 0.23 mmol). The mixture was stirred at room temperature for 2 hours. The crude mixture was quenched by 4N HCl in dioxane (0.5 mL) and purified by reversed phase chromatography eluting with 10% to 50% acetonitrile (with 0.1% TFA added) in water (with 0.1% TFA added). Product obtained was then converted into the HCl salt (28 mg). $^1$H NMR (400 MHz, Methanol-d$_4$) δ 9.07 (s, 11H), 8.27 (s, 1H), 8.11 (s, 1H), 7.05 (s, 1H), 4.71-4.62 (m, 11H), 4.59 (d, J=15.2 Hz, 11H), 4.35 (d, J=14.5 Hz, 1H), 3.95 (s, 3H), 3.85 (d, J=11.7 Hz, 1H), 3.72 (tt, J=11.0, 4.0 Hz, 1H), 3.41 (q, J=7.5 Hz, 2H), 3.36-3.31 (m, 2H), 3.19 (d, J=17.8 Hz, 11H), 2.33-2.03 (m, 6H), 1.59-1.50 (m, 2H), 1.48 (t, J=7.3 Hz, 3H). LCMS [M+H]: 423.0.

Example 156

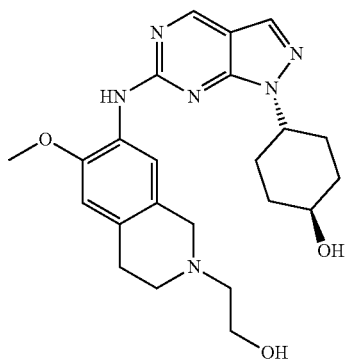

trans-4-(6-((2-(2-hydroxyethyl)-6-methoxy-1,2,3,4-tetrahydroisoquinolin-7-yl)amino)-1H-pyrazolo[3,4-d]pyrimidin-1-yl)cyclohexan-1-ol To a solution of trans-4-(6-(((6-methoxy-1,2,3,4-tetrahydroisoquinolin-7-yl)amino)-1H-pyrazolo[3,4-d]pyrimidin-1-yl)cyclohexan-1-ol hydrochloride (50 mg, 0.12 mmol) in acetonitrile (1.2 mL) was added sodium triacetoxyborohydride (73 mg, 0.35 mmol) followed by (tert-butyldimethylsiloxy)acetaldehyde (0.033 mL, 0.17 mmol). The mixture was stirred at room temperature for 1 hour. Then, 4N HCl in dioxane (0.5 mL) was added and continued stirring for an additional 1 h. The crude mixture was purified by reversed phase chromatography eluting with 10% to 50% acetonitrile (with 0.1% TFA added) in water (with 0.1% TFA added). Product obtained was then converted into the HCl salt (28 mg). $^1$H NMR (400 MHz, Methanol-d$_4$) δ 9.09 (s, 1H), 8.29 (s, 1H), 8.11 (s, 11H), 7.05 (s, 11H), 4.71-4.61 (m, 2H), 4.45 (d, J=14.9 Hz, 11H), 4.00 (t, J=5.1 Hz, 2H), 3.96 (s, 3H), 3.93-3.85 (m, 1H), 3.72 (tt, J=10.5, 3.7 Hz, 1H), 3.54-3.43 (m, 3H), 3.37-3.32 (m, 1H), 3.24-3.15 (m, 1H), 2.22-2.03 (m, 6H), 1.54 (s, 2H). LCMS [M+H]: 439.0.

Example 157

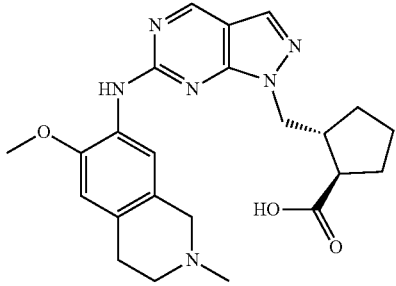 [SMILES: COc1cc2c(cc1Nc1ncc3cnn(C[C@@H]4CCC[C@H]4C(=O)O)c3n1)CN(C)CC2]

(1R,2R)-2-[[6-[(6-methoxy-2-methyl-3,4-dihydro-1H-isoquinolin-7-yl)amino]pyrazolo[3,4-d]pyrimidin-1-yl]methyl]cyclopentanecarboxylic Acid Step 1: Preparation of methyl rac-trans-2-[(6-chloropyrazolo[3,4-d]pyrimidin-1-yl)methyl]cyclopentanecarboxylate. Prepared according to general procedure D using racemic methyl trans-2-(hydroxymethyl)cyclopentanecarboxylate (1.00 g, 6.32 mmol), 6-chloro-1H-pyrazolo[3,4-d]pyrimidine (1.20 g, 7.59 mmol), triphenylphosphine (2.09 g, 7.90 mmol), and DIAD (1.56 mL, 7.90 mmol) in THF (20 mL) at rt for 1 h. The crude product was purified by silica column chromatography eluting with 0% to 100% EtOAc in hexanes to afford the title compound (1.50 g). The racemic mixture was then purified using chiral separation to give two peaks (MG II preparative SFC (SFC-14), 10 um, 250×30 mm, ChiralPak AD; 40% MeOH/CO$_2$). The first peak eluted at 1.15 min as methyl (1R,2R)-2-[(6-chloropyrazolo[3,4-d]pyrimidin-1-yl)methyl]cyclopentanecarboxylate (409 mg) and the second peak eluted at 2.10 min as methyl (1S,2S)-2-[(6-chloropyrazolo[3,4-d]pyrimidin-1-yl)methyl]cyclopentanecarboxylate (399 mg).

Step 2: Preparation of (1R,2R)-2-[[6-[(6-methoxy-2-methyl-3,4-dihydro-1H-isoquinolin-7-yl)amino]pyrazolo[3,4-d]pyrimidin-1-yl]methyl]cyclopentanecarboxylic acid. Prepared according to general procedure A using methyl (1R,2R)-2-[(6-chloropyrazolo[3,4-d]pyrimidin-1-yl)methyl]cyclopentanecarboxylate (100 mg, 0.339 mmol), 6-methoxy-2-methyl-3,4-dihydro-1H-isoquinolin-7-amine (98 mg, 0.509 mmol), and p-TSA (142 mg, 0.746 mmol) in NMP (3 mL) at 90° C. for 3 days. The mixture was cooled to rt, then added LiOH (3M aqueous soln, 0.6 mL, 1.8 mmol) and stirred at rt for 24 h. The crude product was purified by reverse phase HPLC (Phenomenex, Gemini-NX, 10 um, 250×30 mm, C18 column; gradient of 0% MeCN/0.1% TFA-water to 100% MeCN/0.1% TFA). The purified product was free based and converted to the HCl salt to provide the title compound (110 mg). $^1$H NMR (400 MHz, DMSO-d6, HCl salt) δ 10.43 (bs, 1H), 8.98 (s, 1H), 8.35 (s, 1H), 8.17 (s, 1H), 8.10 (s, 1H), 6.96 (s, 1H), 4.49-4.42 (m, 1H), 4.42-4.34 (m, 1H), 4.34-4.19 (m, 2H), 3.87 (s, 3H), 3.70-3.62 (m, 11H), 3.39-3.27 (m, 11H), 3.24-3.11 (m, 1H), 3.05-2.96 (m, 11H), 2.96-2.90 (m, 3H), 2.79-2.69 (m, 1H), 2.65-2.57 (m, 1H), 1.92 (s, 1H), 1.79-1.70 (m, 1H), 1.70-1.63 (m, 1H), 1.62-1.53 (m, 2H), 1.42 (s, 1H). [M+H]=437.3.

Example 158

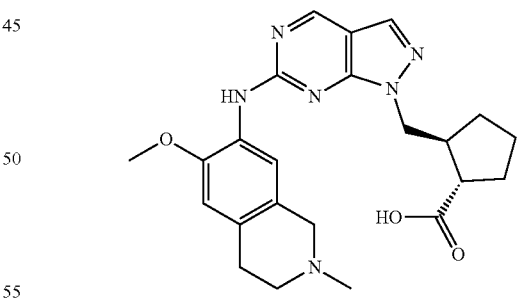

(1S,2S)-2-[[6-[(6-methoxy-2-methyl-3,4-dihydro-1H-isoquinolin-7-yl)amino]pyrazolo[3,4-d]pyrimidin-1-yl]methyl]cyclopentanecarboxylic Acid Preparation of (1S,2S)-2-[[6-[(6-methoxy-2-methyl-3,4-dihydro-1H-isoquinolin-7-yl)amino]pyrazolo[3,4-d]pyrimidin-1-yl]methyl]cyclopentanecarboxylic acid. Prepared according to general procedure A using methyl (1S,2S)-2-[(6-chloropyrazolo[3,4-d]pyrimidin-1-yl)methyl]cyclopentanecarboxylate (EXAMPLE 157 Step 1) (100 mg, 0.339 mmol), 6-methoxy-2-methyl-3,4-dihydro-1H-isoquinolin-7-amine (98 mg, 0.509 mmol), and p-TSA (142 mg, 0.746 mmol) in NMP (3 mL) at 90° C. for 4 days. The mixture was cooled to rt, then added LiOH (3M aqueous solution, 0.6 mL, 1.8 mmol) and stirred at rt for 24 h. The crude product was purified by reverse phase HPLC (Phenomenex, Gemini-NX, 10 um, 250×30 mm, C18 column; gradient of 0% MeCN/0.1% TFA-water to 100% MeCN/0.1% TFA). The purified product was free based and converted to the HCl salt to provide the title compound (104 mg). $^1$H NMR (400 MHz, DMSO-d6, HCl salt) δ 10.43 (bs, 1H), 8.98 (s, 1H), 8.35 (s, 1H), 8.17 (s, 1H), 8.10 (s, 1H), 6.96 (s, 1H), 4.49-4.42 (m, 1H), 4.42-4.34 (m, 1H), 4.34-4.19 (m, 2H), 3.87 (s, 3H), 3.70-3.62 (m, 11H), 3.39-3.27 (m, 1H), 3.24-3.11 (m, 1H), 3.05-2.96 (m, 11H), 2.96-2.90 (m, 3H), 2.79-2.69 (m, 1H), 2.65-2.57 (m, 1H), 1.92 (s, 1H), 1.79-1.70 (m, 1H), 1.70-1.63 (m, 1H), 1.62-1.53 (m, 2H), 1.42 (s, 1H). [M+H]=437.3.

Example 159

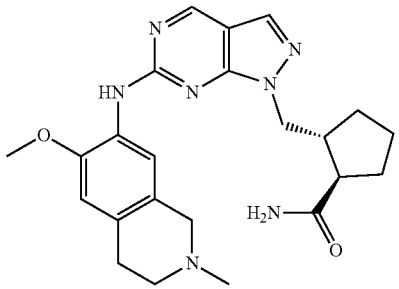 [SMILES: COc1cc2c(cc1Nc1ncc3cnn(C[C@@H]4CCC[C@H]4C(N)=O)c3n1)CN(C)CC2]

racemic trans-2-[[6-[(6-methoxy-2-methyl-3,4-dihydro-1H-isoquinolin-7-yl)amino]pyrazolo[3,4-d]pyrimidin-1-yl]methyl]cyclopentanecarboxamide Step 1: Preparation of rac-trans-2-[[6-[(6-methoxy-2-methyl-3,4-dihydro-1H-isoquinolin-7-yl)amino]pyrazolo[3,4-d]pyrimidin-1-yl]methyl]cyclopentanecarboxylic acid. Methyl rac-trans-2-[[6-[(6-methoxy-2-methyl-3,4-dihydro-1H-isoquinolin-7-yl)amino]pyrazolo[3,4-d]pyrimidin-1-yl]methyl]cyclopentanecarboxylate (408 mg, 0.723 mmol) (EXAMPLE 157, step 1] is dissolved in THF (20 mL), then added LiOH (3M aqueous solution, 2 mL, 6 mmol). The mixture was stirred at rt for 48 h, then concentrated to afford the title compound (562 mg).

Step 3: Preparation of rac-trans-2-[[6-[(6-methoxy-2-methyl-3,4-dihydro-1H-isoquinolin-7-yl)amino]pyrazolo[3,4-d]pyrimidin-1-yl]methyl]cyclopentanecarboxamide. To a mixture of racemic trans methyl 2-[[6-[(6-methoxy-2-methyl-3,4-dihydro-1H-isoquinolin-7-yl)amino]pyrazolo[3,4-d]pyrimidin-1-yl]methyl]cyclopentanecarboxylic acid (233.0 mg, 0.53 mmol), methylimidazole (0.51 mL, 6.41 mmol), and ammonium chloride (285.0 mg, 5.34 mmol) in EtOAc (3 mL) and DMF (6 mL) was added propylphosphonic anhydride (50% soln in EtOAc, 0.79 mL, 1.33 mmol). The mixture was stirred at rt for 20 h. The crude product was purified by reverse phase HPLC (Phenomenex, Gemini-NX, 10 um, 250×30 mm, C18 column; gradient of 0% MeCN/0.1% TFA-water to 100% MeCN/0.1% TFA). The purified product was free based and converted to the HCl salt to provide the title compound (8 mg). $^1$H NMR (400 MHz, DMSO-d6, HCl salt) δ 10.43 (d, J=29.9 Hz, 1H), 8.96 (s, 1H), 8.31 (s, 1H), 8.18 (d, J=11.0 Hz, 1H), 8.08 (s, 11H), 7.31 (s, 1H), 6.94 (s, 1H), 6.77 (d, J=11.1 Hz, 11H), 4.58-4.50 (m, 1H), 4.43-4.36 (m, 1H), 4.30-4.22 (m, 2H), 4.21-4.13 (m, 1H), 3.86 (s, 3H), 3.36-3.25 (m, 1H), 3.21-3.04 (m, 1H), 3.04-2.96 (m, 1H), 2.92 (s, 3H), 2.73-2.63 (m, 1H), 2.44-2.35 (m, 1H), 1.92-1.81 (m, 1H), 1.68-1.59 (m, 1H), 1.59-1.48 (m, 3H), 1.47-1.34 (m, 1H). LCMS [M+H]: 436.2.

Example 160

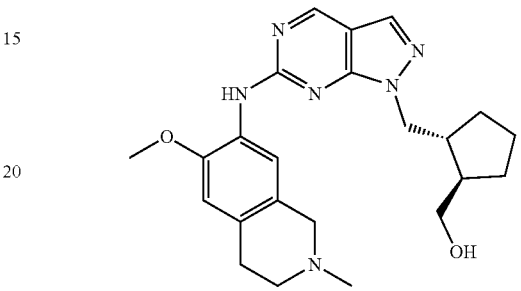

Rac-trans-2-[[6-[(6-methoxy-2-methyl-3,4-dihydro-1H-isoquinolin-7-yl)amino]pyrazolo[3,4-d]pyrimidin-1-yl]methyl]cyclopentyl]methanol Step 1: Preparation of [rac-trans-2-[(6-chloropyrazolo[3,4-d]pyrimidin-1-yl)methyl]cyclopentyl]methanol. To a cooled (0° C.) solution of methyl rac-trans-2-[(6-chloropyrazolo[3,4-d]pyrimidin-1-yl)methyl]cyclopentanecarboxylate (EXAMPLE 157, Step 1) (600 mg, 2.04 mmol) in THF (16 mL) under nitrogen was added a solution of DIBAL (20% in toluene, 4.24 mL, 5.09 mmol) dropwise. The reaction mixture was warmed to ambient temperature after 20 min and stirred for 20 min. The reaction was cooled to 0 C and quenched with excess EtOAc. An aqueous solution of Rochelle's salt (10% w/v) was added, and the mixture was stirred for 10 min. The phases were separated, the organic phase dried over anhydrous sodium sulfate, filtered, and concentrated. The crude product was purified by silica column chromatography eluting with 0% to 20% MeOH in DCM to afford the title compound (500 mg).

Step 2: Preparation of [rac-trans-2-[[6-[(6-methoxy-2-methyl-3,4-dihydro-1H-isoquinolin-7-yl)amino]pyrazolo[3,4-d]pyrimidin-1-yl]methyl]cyclopentyl]methanol. Prepared according to general procedure A using [rac-trans-2-[(6-chloropyrazolo[3,4-d]pyrimidin-1-yl)methyl]cyclopentyl]methanol (184 mg, 0.69 mmol), 6-methoxy-2-methyl-3,4-dihydro-1H-isoquinolin-7-amine (172 mg, 0.897 mmol), and p-TSA (262 mg, 1.38 mmol) in NMP (3 mL) at 90° C. for 19 h. The crude product was purified by reverse phase HPLC (Phenomenex, Gemini-NX, 10 um, 250×30 mm, C18 column; gradient of 0% MeCN/0.1% TFA-water to 100% MeCN/0.1% TFA). The purified product was free based and converted to the HCl salt to provide the title compound (157 mg). $^1$H NMR (400 MHz, DMSO-d6, HCl salt) δ 10.53 (bs, 1H), 9.03 (d, J=1.4 Hz, 1H), 8.40 (s, 1H), 8.22 (d, J=3.8 Hz, 1H), 8.15 (d, J=1.4 Hz, 1H), 7.00 (s, 11H), 5.35 (bs, 1H), 4.55-4.38 (m, 2H), 4.34-4.16 (m, 2H), 3.92 (s, 3H), 3.76-3.65 (m, 1H), 3.43-3.33 (m, 1H), 3.33-3.26 (m, 2H), 3.27-3.15 (m, 1H), 3.09-3.00 (m, 1H), 2.96 (s, 3H), 2.33-2.23 (m, 1H), 1.96-1.84 (m, 1H), 1.84-1.71 (m, 1H), 1.66-1.49 (m, 3H), 1.49-1.37 (m, 2H). LCMS [M+H]: 423.3.

Example 161

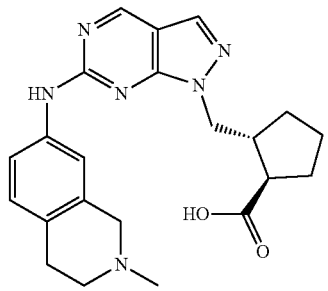 [SMILES: CN1CCc2ccc(Nc3ncc4cnn(C[C@@H]5CCC[C@H]5C(=O)O)c4n3)cc2C1]

Rac-trans-2-[[6-[(2-methyl-3,4-dihydro-1H-isoquinolin-7-yl)amino]pyrazolo[3,4-d]pyrimidin-1-yl]methyl]cyclopentanecarboxylic Acid Preparation of Rac-trans-[[6-[(2-methyl-3,4-dihydro-1H-isoquinolin-7-yl)amino]pyrazolo[3,4-d]pyrimidin-1-yl]methyl]cyclopentanecarboxylic acid. Prepared according to general procedure A using methyl rac-trans-2-[(6-chloropyrazolo[3,4-d]pyrimidin-1-yl)methyl]cyclopentanecarboxylate (EXAMPLE 157, Step 1) (100 mg, 0.339 mmol), 2-methyl-3,4-dihydro-1H-isoquinolin-7-amine (72 mg, 0.441 mmol), and p-TSA (142 mg, 0.746 mmol) in NMP (3 mL) at 90° C. for 24 h. The mixture was cooled to rt, then added LiOH (3M aqueous solution, 0.6 mL, 1.7 mmol) and stirred at rt for 3 d. The crude product was purified by reverse phase HPLC (Phenomenex, Gemini-NX, 10 um, 250×30 mm, C18 column; gradient of 0% MeCN/0.1% TFA-water to 100% MeCN/0.1% TFA). The purified product was free based and converted to the HCl salt to provide the title compound (74 mg). $^1$H NMR (400 MHz, DMSO-d6, HCl salt) δ 10.59 (bs, 1H), 10.00 (s, 1H), 8.99 (s, 11H), 8.08 (s, 1H), 7.79 (s, 1H), 7.75 (d, J=8.5 Hz, 1H), 7.21 (d, J=8.4 Hz, 1H), 4.52-4.44 (m, 1H), 4.43-4.34 (m, 1H), 4.34-4.24 (m, 2H), 3.73-3.62 (m, 1H), 3.40-3.24 (m, 1H), 3.21-3.08 (m, 1H), 3.02-2.97 (m, 1H), 2.92 (s, 3H), 2.81-2.71 (m, 1H), 2.67-2.57 (m, 1H), 1.99-1.88 (m, 1H), 1.80-1.67 (m, 1H), 1.69-1.55 (m, 3H), 1.44 (s, 1H). [M+H]=407.3.

Example 162

Rac-cis-2-[[6-[(6-methoxy-2-methyl-3,4-dihydro-1H-isoquinolin-7-yl)amino]pyrazolo[3,4-d]pyrimidin-1-yl]methyl]cyclopentanecarboxylic Acid Step 1: Preparation of methyl rac-cis-2-(hydroxymethyl)cyclopentanecarboxylate. To a cooled (0° C.) solution of rac-cis-2-(methoxycarbonyl)cyclopentanecarboxylic acid (500 mg, 2.9 mmol) in THF (28 mL) was added borane (1 M in THF, 8 mL, 8 mmol). The mixture was stirred at 0° C. for 1 h, then at rt for 2 h. The mixture was quenched with water (14 mL), stirred at rt for 16 h, then concentrated. The mixture was vigorously stirred in MeOH (15 mL) for 1 h, then azeotroped with THF (2×15 mL). The crude product was concentrated to afford the title compound (425 mg).

Step 2: Preparation of methyl rac-cis-2-[(6-chloropyrazolo[3,4-d]pyrimidin-1-yl)methyl]cyclopentanecarboxylate. Prepared according to general procedure D using methyl rac-cis-2-(hydroxymethyl)cyclopentanecarboxylate (417 mg, 2.64 mmol), 6-chloro-1H-pyrazolo[3,4-d]pyrimidine (500 mg, 3.16 mmol), triphenylphosphine (873 mg, 3.3 mmol), and DIAD (0.65 mL, 3.3 mmol) in THE (10 mL) at rt for 1 h. The crude product was purified by silica column chromatography (0% to 100% EtOAc in hexanes) to afford the title compound (891 mg).

Step 3: Preparation of rac-cis-2-[[6-[(6-methoxy-2-methyl-3,4-dihydro-1H-isoquinolin-7-yl)amino]pyrazolo[3,4-d]pyrimidin-1-yl]methyl]cyclopentanecarboxylic acid. Prepared according to general procedure A using methyl rac-cis-2-[(6-chloropyrazolo[3,4-d]pyrimidin-1-yl)methyl]cyclopentanecarboxylate (100 mg, 0.339 mmol), 6-methoxy-2-methyl-3,4-dihydro-1H-isoquinolin-7-amine (85 mg, 0.441 mmol), and p-TSA (142 mg, 0.746 mmol) in NMP (3 mL) at 90° C. for 48 h. The mixture was cooled to rt, then added LiOH (3M aqueous solution, 0.9 mL, 2.71 mmol) and stirred at rt for 16 h. The crude product was purified by reverse phase HPLC (Phenomenex, Gemini-NX, 10 um, 250×30 mm, C18 column; gradient of 0% MeCN/ 0.1% TFA-water to 100% MeCN/0.1% TFA). The purified product was free based and converted to the HCl salt to provide the title compound (36 mg). $^1$H NMR (400 MHz, DMSO-d6, HCl salt) δ 10.38 (bs, 1H), 8.98 (s, 1H), 8.40-8.34 (m, 1H), 8.21 (d, J=10.6 Hz, 11H), 8.12 (s, 1H), 6.96 (s, 1H), 4.51-4.35 (m, 1H), 4.35-4.20 (m, 3H), 3.88 (s, 3H), 3.72-3.62 (m, 1H), 3.41-3.27 (m, 1H), 3.22-3.09 (m, 11H), 3.06-2.98 (m, 1H), 2.93 (s, 3H), 2.91-2.87 (m, 1H), 2.83-2.75 (m, 1H), 1.96-1.84 (m, 2H), 1.83-1.73 (m, 1H), 1.61-1.50 (m, 1H), 1.50-1.42 (m, 2H). [M+H]=437.3.

Example 163

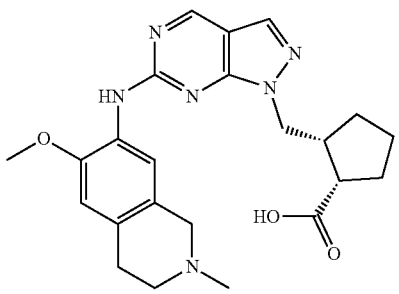 [SMILES: COc1cc2c(cc1Nc1ncc3cnn(C[C@@H]4CCC[C@@H]4C(=O)O)c3n1)CN(C)CC2]

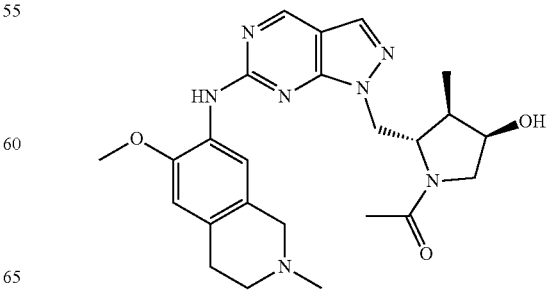

1-[(2S,3R,4S)-4-hydroxy-2-[[6-[(6-methoxy-2-methyl-3,4-dihydro-1H-isoquinolin-7-yl)amino]pyrazolo[3,4-d]pyrimidin-1-yl]methyl]-3-methyl-pyrrolidin-1-yl]ethenone Step 1: Preparation of methyl (3S)-3-[tert-butyl(dimethyl)silyl]oxy-3,4-dihydro-2H-pyrrole-5-carboxylate. To a cooled solution (at 0° C.) of methyl (2R,4S)-4-[tert-butyl(dimethyl)silyl]oxypyrrolidine-2-carboxylate (12.3 g, 47.4 mmol) in toluene (50 mL) was added water (25 mL), then (3,5-dichloro-2,4,6-trioxo-1,3,5-triazinan-1-yl)sodium (11 g, 49.8 mmol). The mixture was stirred at 0° C. for 30 min, then at rt for 1 h. The mixture was filtered over Celite, then rinsed with toluene. The organic layer was washed with water and brine. Cooled the organic layer to 0° C., then added triethylamine (9.32 mL, 66.8 mmol). The mixture was stirred at 0° C. for 40 min, then at rt for 16 h. The mixture was washed with water twice, then dried over anhydrous sodium sulfate, filtered, and concentrated to provide the title compound (10 g).

Step 2: Preparation of 01-benzyl 05-methyl (3S)-3-[tert-butyl(dimethyl)silyl]oxy-2,3-dihydropyrrole-1,5-dicarboxylate. To a cooled solution (at 0° C.) of methyl (3S)-3-[tert-butyl(dimethyl)silyl]oxy-3,4-dihydro-2H-pyrrole-5-carboxylate (10 g, 38.9 mmol) in DCM (60 mL) was added 2,6-lutidine (17 mL, 147 mmol), then benzyl chloroformate (14 mL, 98.2 mmol) dropwise. The mixture was stirred at 0° C. for 15 min, then at rt for 16 h. N,N'-Dimethylethylenediamine (0.5 mL, 4.7 mmol) was stirred into the mixture for 45 min, then concentrated. The mixture was extracted with hexanes and washed with citric acid (1 M aqueous), saturated aqueous sodium bicarbonate, and brine. The organic layer was dried over anhydrous sodium sulfate, filtered, and concentrated. The crude product was purified by silica column chromatography eluting with 0% to 20% EtOAc in hexanes to afford the title compound (3.2 g).

Step 3: Preparation of 01-benzyl 02-methyl (2S,3R,4S)-4-[tert-butyl(dimethyl)silyl]oxy-3-methyl-pyrrolidine-1,2-dicarboxylate. Into a cooled solution (at −60° C.) of copper (I) bromide dimethyl sulfide (1.62 g, 7.87 mmol) in diethyl ether (18 mL) was added methyl lithium (1.6 M in diethyl ether, 9.8 mL, 15.7 mmol) dropwise. The mixture was stirred at −30° C. for 20 min. Cooled the solution to −60° C., then added 01-benzyl 05-methyl (3S)-3-[tert-butyl(dimethyl)silyl]oxy-2,3-dihydropyrrole-1,5-dicarboxylate (2.8 g, 7.17 mmol) in diethyl ether (6 mL) dropwise. Stirred mixture at −40° C. for 45 min. Transferred mixture into saturated aqueous ammonium chloride (100 mL) and stirred at rt for 16 h. The aqueous layer was extracted with hexanes three times. The combined organic layer was dried over anhydrous sodium sulfate, filtered, and concentrated. The crude product was purified by silica column chromatography eluting with 0% to 30% EtOAc in hexanes to afford the title compound (1.05 g).

Step 4: Preparation of benzyl (2S,3R,4S)-4-[tert-butyl(dimethyl)silyl]oxy-2-(hydroxymethyl)-3-methyl-pyrrolidine-1-carboxylate. 1-benzyl 2-methyl (2S,3R,4S)-4-[tert-butyl(dimethyl)silyl]oxy-3-methyl-pyrrolidine-1,2-dicarboxylate (673 mg, 1.65 mmol), sodium borohydride (312 mg, 8.26 mmol), and calcium chloride (733 mg, 6.6 mmol) were suspended in THF (5 mL). The mixture is stirred at rt for 16 h, then poured over saturated aqueous sodium bicarbonate and DCM. Filtered mixture over Celite and rinsed with DCM. Dried organic layer over anhydrous sodium sulfate, filtered, and concentrated to afford the title compound (625 mg).

Step 5: Preparation of [(2S,3R,4S)-4-[tert-butyl(dimethyl)silyl]oxy-3-methyl-pyrrolidin-2-yl]methanol. Benzyl (2S,3R,4S)-4-[tert-butyl(dimethyl)silyl]oxy-2-(hydroxymethyl)-3-methyl-pyrrolidine-1-carboxylate (620 mg, 1.63 mmol) and Pd/C (10%, 173 mg, 0.16 mmol) were suspended in MeOH (16 mL) with a hydrogen balloon (1 atm). The mixture was stirred at rt for 16 h, then added EtOH (10 mL). The mixture was filtered over Celite and concentrated to afford the title compound (400 mg).

Step 6: Preparation of 1-[(2S,3R,4S)-4-[tert-butyl(dimethyl)silyl]oxy-2-(hydroxymethyl)-3-methyl-pyrrolidin-1-yl]ethenone. Into a cooled solution (at 0° C.) of [(2S,3R,4S)-4-[tert-butyl(dimethyl)silyl]oxy-3-methyl-pyrrolidin-2-yl]methanol in DCM (7 mL) was added triethylamine (0.46 mL, 3.27 mmol). Acetyl chloride (0.12 mL, 1.63 mmol) was dissolved in DCM (1 mL) and introduced into the mixture dropwise. The mixture was stirred at rt for 16 h, then washed with sodium acetate/acetic acid (pH 4 aqueous solution). Extracted aqueous layer with EtOAc twice. The combined organic layers were dried over anhydrous sodium sulfate, filtered, and concentrated to afford the title compound (329 mg).

Step 7: Preparation of 1-[(2S,3R,4S)-4-[tert-butyl(dimethyl)silyl]oxy-2-[(6-chloropyrazolo[3,4-d]pyrimidin-1-yl)methyl]-3-methyl-pyrrolidin-1-yl]ethenone. Prepared according to general procedure D using 1-[(2S,3R,4S)-4-[tert-butyl(dimethyl)silyl]oxy-2-(hydroxymethyl)-3-methyl-pyrrolidin-1-yl]ethanone (320 mg, 1.11 mmol), 6-chloro-1H-pyrazolo[3,4-d]pyrimidine (211 mg, 1.34 mmol), triphenylphosphine (369 mg, 1.39 mmol), and DIAD (0.27 mL, 1.39 mmol) in THF (6 mL) at rt for 1 h. The crude product was purified by silica column chromatography (0% to 100% EtOAc in hexanes) to afford the title compound (185 mg).

Step 8: Preparation of 1-[(2S,3R,4S)-4-hydroxy-2-[[6-[(6-methoxy-2-methyl-3,4-dihydro-1H-isoquinolin-7-yl)amino]pyrazolo[3,4-d]pyrimidin-1-yl]methyl]-3-methyl-pyrrolidin-1-yl]ethenone. Prepared according to general procedure A using 1-[(2S,3R,4S)-4-[tert-butyl(dimethyl)silyl]oxy-2-[(6-chloropyrazolo[3,4-d]pyrimidin-1-yl)methyl]-3-methyl-pyrrolidin-1-yl]ethanone (180 mg, 0.425 mmol), 6-methoxy-2-methyl-3,4-dihydro-1H-isoquinolin-7-amine (122 mg, 0.637 mmol), and p-TSA (242 mg, 1.27 mmol) in NMP (3 mL) at 90° C. for 3 days. The crude product was purified by reverse phase HPLC (Phenomenex, Gemini-NX, 10 um, 250×30 mm, C18 column; gradient of 0% MeCN/0.1% TFA-water to 100% MeCN/0.1% TFA). The purified product was free based and converted to the HCl salt to provide the title compound (90 mg). $^1$H NMR (400 MHz, Methanol-d4, HCl salt) δ 9.10 (s, 1H), 8.45 (d, J=13.1 Hz, 1H), 8.30 (s, 1H), 7.01 (s, 1H), 5.03-4.91 (m, 1H), 4.85-4.69 (m, 2H), 4.45-4.35 (m, 1H), 4.22-4.17 (m, 1H), 4.04-3.92 (m, 1H), 3.99 (s, 3H), 3.86-3.76 (m, 2H), 3.53-3.39 (m, 1H), 3.29-3.22 (m, 1H), 3.22-3.17 (m, 1H), 3.17-3.12 (m, 1H), 3.08 (s, 3H), 2.31-2.26 (m, 1H), 1.87 (s, 3H), 0.98 (t, J=8.0 Hz, 3H). [M+H]=466.2.

Example 164

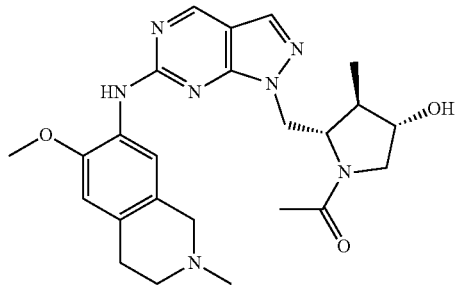 [SMILES: COc1cc2c(cc1Nc1ncc3cnn(C[C@@H]4[C@@H](C)[C@H](O)CN4C(C)=O)c3n1)CN(C)CC2]

1-[(2S,3R,4R)-4-hydroxy-2-[[6-[(6-methoxy-2-methyl-3,4-dihydro-1H-isoquinolin-7-yl)amino]pyrazolo[3,4-d]pyrimidin-1-yl]methyl]-3-methyl-pyrrolidin-1-yl]ethenone Step 1: Preparation of 1-[(2S,3R,4S)-2-[(6-chloropyrazolo[3,4-d]pyrimidin-1-yl)methyl]-4-hydroxy-3-methyl-pyrrolidin-1-yl]ethenone. To a solution of 1-[(2S,3R,4S)-4-[tert-butyl(dimethyl)silyl]oxy-2-[(6-chloropyrazolo[3,4-d]pyrimidin-1-yl)methyl]-3-methyl-pyrrolidin-1-yl]ethenone (EXAMPLE 163, Step 7) (160 mg, 0.377 mmol) in THF (4 mL) was added tetra-n-butylammonium fluoride (1 M in THF, 0.4 mL, 0.4 mmol). The mixture was stirred at rt for 90 min, then extracted in DCM, washed with water, and brine. The organic layer was dried over anhydrous sodium sulfate, filtered, and concentrated. The crude product was purified by silica column chromatography (0% to 10% MeOH in DCM) to afford the title compound (24 mg).

Step 2: Preparation of [(3R,4R,5S)-1-acetyl-5-[(6-chloropyrazolo[3,4-d]pyrimidin-1-yl)methyl]-4-methyl-pyrrolidin-3-yl] benzoate. Prepared according to general procedure D using 1-[(2S,3R,4S)-2-[(6-chloropyrazolo[3,4-d]pyrimidin-1-yl)methyl]-4-hydroxy-3-methyl-pyrrolidin-1-yl]ethenone (24 mg, 0.078 mmol), benzoic acid (11 mg, 0.093 mmol), triphenylphosphine (26 mg, 0.097 mmol), and DIAD (0.019 mL, 0.097 mmol) in THF (3 mL) at rt for 3 h. The crude product was purified by silica column chromatography (0% to 10% MeOH in DCM) to afford the title compound (32 mg).

Step 3: Preparation of 1-[(2S,3R,4R)-4-hydroxy-2-[[6-[(6-methoxy-2-methyl-3,4-dihydro-1H-isoquinolin-7-yl)amino]pyrazolo[3,4-d]pyrimidin-1-yl]methyl]-3-methyl-pyrrolidin-1-yl]ethenone. Prepared according to general procedure A using [(3R,4R,5S)-1-acetyl-5-[(6-chloropyrazolo[3,4-d]pyrimidin-1-yl)methyl]-4-methyl-pyrrolidin-3-yl] benzoate (32 mg, 0.077 mmol), 6-methoxy-2-methyl-3,4-dihydro-1H-isoquinolin-7-amine (45 mg, 0.232 mmol), and p-TSA (88 mg, 0.47 mmol) in NMP (3 mL) at 90° C. for 3 d. The mixture was cooled to rt, then add water (0.5 mL) and LiOH (3M aqueous solution, 0.26 mL, 0.775 mmol) and stirred at rt for 5 h. The crude product was purified by reverse phase HPLC (Phenomenex, Gemini-NX, 10 um, 250×30 mm, C18 column; gradient of 0% MeCN/0.1% TFA-water to 100% MeCN/0.1% TFA). The purified product was free based and converted to the HCl salt to provide the title compound (14 mg). $^1$H NMR (400 MHz, CD$_3$OD, HCl salt) δ 9.18 (s, 1H), 8.34 (s, 2H), 7.04 (s, 1H), 5.09-4.91 (m, 1H), 4.74-4.61 (m, 1H), 4.53 (d, J=15.4 Hz, 1H), 4.32 (d, J=15.1 Hz, 1H), 4.12-4.06 (m, 1H), 3.99 (s, 3H), 3.98-3.92 (m, 1H), 3.83-3.75 (m, 1H), 3.57-3.39 (m, 2H), 3.24-3.12 (m, 2H), 3.10 (s, 3H), 2.42-2.27 (m, 1H), 2.13-1.92 (m, 1H), 1.84 (d, J=16.3 Hz, 3H), 1.03 (dd, J=14.0, 6.8 Hz, 3H). [M+H]=466.3.

Example 165

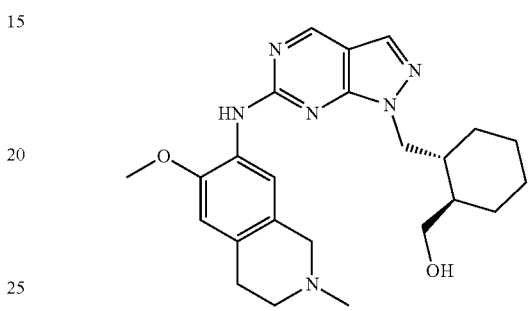

[rac-trans-2-[[6-[(6-methoxy-2-methyl-3,4-dihydro-1H-isoquinolin-7-yl)amino]pyrazolo[3,4-d]pyrimidin-1-yl]methyl]cyclohexyl]methanol Step 1: Preparation of [rac-trans-2-[(6-chloropyrazolo[3,4-d]pyrimidin-1-yl)methyl]cyclohexyl]methanol. Prepared according to general procedure D using rac-trans-1,2-cyclohexanedimethanol (214 mg, 1.48 mmol), 6-chloro-1h-pyrazolo[3,4-d]pyrimidine (229 mg, 1.48 mmol), and triphenylphosphine (486 mg, 1.85 mmol), and DIAD (0.36 mL, 1.85 mmol) in THF (5 mL) at rt for 1 h. The crude product was purified by silica column chromatography eluting with 0% to 20% MeOH in DCM to afford the title compound (76 mg).

Step 2: Preparation of [rac-trans-2-[[6-[(6-methoxy-2-methyl-3,4-dihydro-1H-isoquinolin-7-yl)amino]pyrazolo[3,4-d]pyrimidin-1-yl]methyl]cyclohexyl]methanol. Prepared according to general procedure A using [rac-trans-2-[(6-chloropyrazolo[3,4-d]pyrimidin-1-yl)methyl]cyclohexyl]methanol (230 mg, 0.82 mmol), 6-methoxy-2-methyl-3,4-dihydro-1H-isoquinolin-7-amine (236 mg, 1.23 mmol), and p-TSA (342 mg, 1.8 mmol) in NMP (3 mL) at 90° C. for 4 d. The crude product was purified by reverse phase HPLC (Phenomenex, Gemini-NX, 10 um, 250×30 mm, C18 column; gradient of 0% MeCN/0.1% TFA-water to 100% MeCN/0.1% TFA). The purified product was free based and converted to the HCl salt to provide the title compound (20 mg). $^1$H NMR (400 MHz, DMSO-d6, HCl salt) δ 10.38 (s, 1H), 8.98 (d, J=2.5 Hz, 1H), 8.33 (s, 1H), 8.18 (s, 11H), 8.10 (d, J=2.3 Hz, 1H), 6.96 (s, 1H), 4.61-4.51 (m, 1H), 4.49-4.41 (m, 1H), 4.30-4.22 (m, 11H), 4.21-4.11 (m, 2H), 3.71-3.63 (m, 2H), 3.58 (s, 3H), 3.40-3.28 (m, 1H), 3.22-3.09 (m, 1H), 3.05-3.01 (m, 1H), 3.01-2.97 (m, 11H), 2.93 (s, 3H), 1.96-1.83 (m, 1H), 1.79-1.71 (m, 1H), 1.65-1.54 (m, 2H), 1.39-1.27 (m, 1H), 1.25-1.13 (m, 2H), 1.13-0.94 (m, 2H). [M+H]=437.2.

Example 166

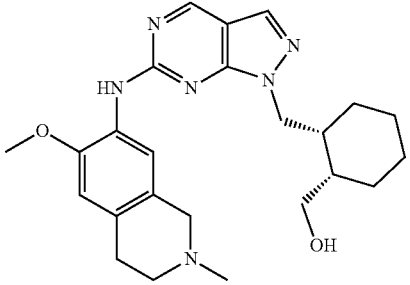 [SMILES: COc1cc2c(cc1Nc1ncc3cnn(C[C@@H]4CCCC[C@@H]4CO)c3n1)CN(C)CC2]

[rac-cis-2-[[6-[(6-methoxy-2-methyl-3,4-dihydro-1H-isoquinolin-7-yl)amino]pyrazolo[3,4-d]pyrimidin-1-yl]methyl]cyclohexyl]methanol Step 1: Preparation of [rac-cis-2-(hydroxymethyl)cyclohexyl]methyl benzoate. To a cooled (0° C.) solution of cis-cyclohexane-1,2-diyldimethanol (1000 mg, 6.93 mmol) in DCM (20 mL) was added TEA (1.45 mL, 10.4 mmol). A solution of benzoyl chloride (0.81 mL, 6.93 mmol) in DCM (4 mL) was added dropwise into the reaction mixture. Let stirred at 0° C. for 10 min, then at rt for 24 h. The mixture was washed with saturated aqueous sodium bicarbonate and extracted with DCM twice. Combined the organic layers, dried over sodium sulfate, filtered, and concentrated. The crude product was purified by silica column chromatography (0% to 20% MeOH in DCM) to afford the title compound (856 mg).

Step 2: Preparation of [rac-cis-2-[(6-chloropyrazolo[3,4-d]pyrimidin-1-yl)methyl]cyclohexyl]methyl benzoate. Prepared according to general procedure D using [rac-cis-2-(hydroxymethyl)cyclohexyl]methyl benzoate (856 mg, 3.45 mmol), 6-chloro-1 h-pyrazolo[3,4-d]pyrimidine (500 mg, 3.23 mmol), and triphenylphosphine (1.02 g, 3.88 mmol), and DIAD (0.76 mL, 3.88 mmol) in THF (15 mL) at rt for 1 h. The crude product was purified by silica column chromatography (0% to 100% EtOAc) in hexanes to afford the title compound (1.28 g).

Step 3: Preparation of [rac-2-[(6-chloropyrazolo[3,4-d]pyrimidin-1-yl)methyl]cyclohexyl]methanol. Into a solution of [Rac-cis-2-[(6-chloropyrazolo[3,4-d]pyrimidin-1-yl)methyl]cyclohexyl]methyl benzoate (1.28 g, 3.32 mmol) in THF (10 mL) is added LiOH (3M aqueous solution, 6 mL, 18 mmol) and stirred at rt for 48 h. The biphasic layer were separated and the crude product was concentrated to afford the title compound (1.25 g).

Step 4: Preparation of [rac-cis-2-[[6-[(6-methoxy-2-methyl-3,4-dihydro-1H-isoquinolin-7-yl)amino]pyrazolo[3,4-d]pyrimidin-1-yl]methyl]cyclohexyl]methanol. Prepared according to general procedure A using [rac-2-[(6-chloropyrazolo[3,4-d]pyrimidin-1-yl)methyl]cyclohexyl]methanol (163 mg, 0.581 mmol), 6-methoxy-2-methyl-3,4-dihydro-1H-isoquinolin-7-amine (112 mg, 0.581 mmol), and p-TSA (552 mg, 2.9 mmol) in NMP (3 mL) at 90° C. for 3 d. The crude product was purified by reverse phase HPLC (Phenomenex, Gemini-NX, 10 um, 250×30 mm, C18 column; gradient of 0% MeCN/0.1% TFA-water to 100% MeCN/0.1% TFA). The purified product was free based and converted to the HCl salt to provide the title compound (4 mg). $^1$H NMR (400 MHz, $CD_3OD$, HCl salt) δ 9.13 (s, 1H), 8.51 (s, 1H), 8.34 (s, 1H), 8.21 (d, J=9.2 Hz, 1H), 8.12 (d, J=1.1 Hz, 1H), 7.05 (s, 1H), 4.65-4.58 (m, 1H), 4.58-4.46 (m, 1H), 4.45-4.32 (m, 1H), 3.97 (s, 3H), 3.83-3.72 (m, 1H), 3.69 (s, 1H), 3.67-3.52 (m, 1H), 3.50-3.37 (m, 1H), 3.24-3.11 (m, 2H), 3.09 (s, 3H), 2.74 (s, 2H), 2.56 (s, 2H), 1.91-1.79 (m, 1H), 1.79-1.66 (m, 1H), 1.65-1.56 (m, 1H), 1.46-1.40 (m, 1H), 1.39-1.34 (m, 1H), 1.34-1.22 (m, 2H). [M+H]=437.3.

Example 167

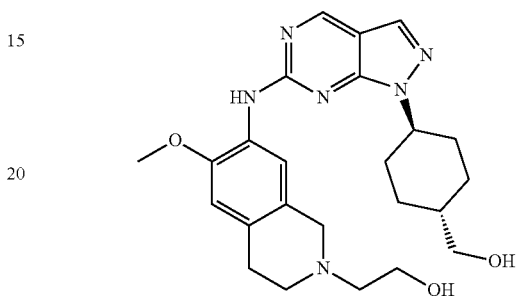

2-[7-[[1-[4-(hydroxymethyl)cyclohexyl]pyrazolo[3,4-d]pyrimidin-6-yl]amino]-6-methoxy-3,4-dihydro-1H-isoquinolin-2-yl]ethanol Step 1: Preparation of tert-butyl 6-methoxy-7-[[1-[4-(triisopropylsilyloxymethyl)cyclohexyl]pyrazolo[3,4-d]pyrimidin-6-yl]amino]-3,4-dihydro-1H-isoquinoline-2-carboxylate. Prepared following general procedure B using tert-butyl 7-amino-6-methoxy-3,4-dihydro-1H-isoquinoline-2-carboxylate (141.4 mg, 0.51 mmol), [4-(6-chloropyrazolo[3,4-d]pyrimidin-1-yl)cyclohexyl]methoxy-triisopropyl-silane (215 mg, 0.51 mmol), Pd-PEPPSI-iPent catalyst (81 mg, 0.10 mmol, 20 mol %), and cesium carbonate (496.7 mg, 1.52 mmol) to a 2-dram reaction vial. Added 1,2 dimethoxyethane (5.1 mL) then degassed the mixture with argon. Heated to 80° C. and stirred for 3 h. Cooled reaction. Filtered through Celite then concentrated under reduced pressure. The crude product was adsorbed onto silica gel and purified by silica gel chromatography, 0-50% EtOAc in hexanes to afford the titled compound (203 mg).

Step 2: Preparation of [4-[6-[(6-methoxy-1,2,3,4-tetrahydroisoquinolin-7-yl)amino]pyrazolo[3,4-d]pyrimidin-1-yl]cyclohexyl]methanol hydrochloride. To a solution of tert-butyl 6-methoxy-7-[[1-[4-(triisopropylsilyloxymethyl)cyclohexyl]pyrazolo[3,4-d]pyrimidin-6-yl]amino]-3,4-dihydro-1H-isoquinoline-2-carboxylate (200 mg, 0.30 mmol) in DCM (2.0 mL, 0.15 M) was added a solution of 4 N HCl in dioxane (0.38 mL, 1.5 mmol) and the reaction mixture was stirred for 2 h. The reaction mixture was concentrated, then additional DCM was added, and the solution was concentrated again to give crude product (138 mg). This material was carried on as is.

Step 3: Preparation of 2-[7-[[1-[4-(hydroxymethyl)cyclohexyl]pyrazolo[3,4-d]pyrimidin-6-yl]amino]-6-methoxy-3,4-dihydro-1H-isoquinolin-2-yl]ethanol. To a solution of [4-[6-[(6-methoxy-1,2,3,4-tetrahydroisoquinolin-7-yl)amino]pyrazolo[3,4-d]pyrimidin-1-yl]cyclohexyl]methanol hydrochloride (50 mg, 0.11 mmol) in DCM (2.2 mL, 0.05 M) was added (tert-butyldimethylsiloxy)acetaldehyde (0.032 mL, 0.17 mmol) and STAB-H (71 mg, 0.34 mmol).

The reaction mixture was stirred for 3 days then the reaction mixture was treated with a solution of 4 N HCl in dioxane (0.14 mL, 0.56 mmol) and stirred for 3 h. The solution was neutralized with saturated aqueous sodium bicarbonate and extracted with DCM. The combined organic phase was dried over anhydrous sodium sulfate, filtered, and concentrated under reduced pressure. The crude product was purified by silica gel chromatography (0-20% MeOH/DCM) and then repurified by reverse-phase HPLC, 0-100% 0.1% TFA/MeCN in 0.1% aqueous TFA to afford the titled compound (2.4 mg). $^1$H NMR (400 MHz, Methanol-d4) δ 8.87 (s, 1H), 8.34 (s, 1H), 7.97 (s, 1H), 6.79 (s, 1H), 4.67-4.51 (m, 1H), 3.92 (s, 3H), 3.82 (t, J=6.0 Hz, 2H), 3.75 (s, 2H), 3.49 (d, J=6.4 Hz, 2H), 2.97-2.89 (m, 2H), 2.86 (t, J=5.8 Hz, 2H), 2.75 (t, J=6.0 Hz, 2H), 2.31-2.16 (m, 2H), 2.16-1.98 (m, 4H), 1.66 (s, 1H), 1.37-1.19 (m, 2H). LCMS [M+H]$^+$: 453.3

Example 168

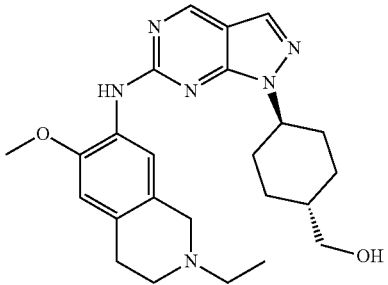 [SMILES: CCN1CCc2cc(OC)c(Nc3ncc4cnn([C@H]5CC[C@H](CO)CC5)c4n3)cc2C1]

[4-[6-[(2-ethyl-6-methoxy-3,4-dihydro-1H-isoquinolin-7-yl)amino]pyrazolo[3,4-d]pyrimidin-1-yl]cyclohexyl]methanol Prepared according to EXAMPLE 167 substituting acetaldehyde for (tert-butyldimethylsiloxy)acetaldehyde (step 3) to afford the title compound (2.6 mg). $^1$H NMR (400 MHz, Methanol-d4) δ 8.87 (s, 1H), 8.35 (s, 1H), 7.98 (s, 1H), 6.80 (s, 1H), 4.66-4.53 (m, 1H), 3.92 (s, 3H), 3.66 (s, 2H), 3.47 (d, J=6.3 Hz, 2H), 2.94 (t, J=6.0 Hz, 2H), 2.80 (t, J=6.1 Hz, 2H), 2.65 (q, J=7.2 Hz, 2H), 2.29-1.99 (m, 6H), 1.73-1.57 (m, 1H), 1.35-1.18 (m, 5H). LCMS [M+H]$^+$: 437.3

Example 169

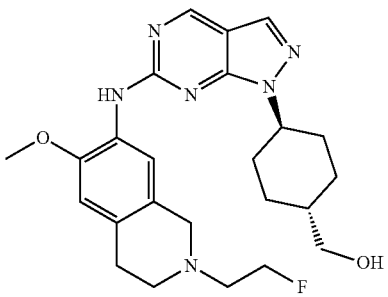 [SMILES: COc1cc2c(cc1Nc1ncc3cnn([C@H]4CC[C@H](CO)CC4)c3n1)CN(CCF)CC2]

[4-[6-[[2-(2-fluoroethyl)-6-methoxy-3,4-dihydro-1H-isoquinolin-7-yl]amino]pyrazolo[3,4-d]pyrimidin-1-yl]cyclohexyl]methanol To a solution of [4-[6-[(6-methoxy-1,2,3,4-tetrahydroisoquinolin-7-yl)amino]pyrazolo[3,4-d]pyrimidin-1-yl]cyclohexyl]methanol hydrochloride (50 mg, 0.12 mmol) (EXAMPLE 167, step 2) in MeCN (0.61 mL, 0.2 M) was added potassium carbonate (51 mg, 0.37 mmol) and 1-fluoro-2-iodoethane (12 μL, 0.15 mmol). The reaction mixture was stirred at 65° C. for 18 h then cooled, diluted with 10% MeOH in DCM, filtered, and concentrated under reduced pressure. The crude product was purified by reverse-phase HPLC, 0-100% 0.1% TFA/MeCN in 0.1% aqueous TFA. The fractions containing the product were concentrated to one-third volume, basified with saturated aqueous sodium bicarbonate and 1 M sodium carbonate, then extracted with 10% MeOH in DCM. The combined organic phase was dried over anhydrous sodium sulfate, filtered, and concentrated under reduced pressure to afford the title compound (18 mg). $^1$H NMR (400 MHz, Methanol-d4) δ 8.84 (d, J=1.0 Hz, 1H), 8.34 (s, 1H), 7.95 (s, 1H), 6.77 (s, 1H), 4.76 (t, J=4.7 Hz, 1H), 4.64 (t, J=4.7 Hz, 1H), 4.62-4.49 (m, 1H), 3.91 (s, 3H), 3.76 (s, 2H), 3.46 (d, J=6.3 Hz, 2H), 3.01-2.84 (m, 6H), 2.26-1.98 (m, 6H), 1.71-1.56 (m, 1H), 1.36-1.15 (m, 2H). LCMS [M+H]$^+$: 455.3

Example 170

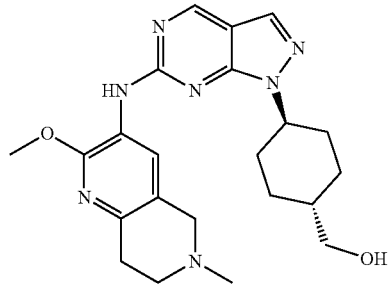 [SMILES: COc1nc2c(cc1Nc1ncc3cnn([C@H]4CC[C@H](CO)CC4)c3n1)CN(C)CC2]

[4-[6-(2-methoxy-6-methyl-7,8-dihydro-5H-1,6-naphthyridin-3-yl)amino]pyrazolo[3,4-d]pyrimidin-1-yl]cyclohexyl]methanol Step 1: Preparation of 6-methyl-3-nitro-5,6,7,8-tetrahydro-1,6-naphthyridine. A mixture of 1-methyl-3,5-dinitropyridin-2-one (5 g, 25.11 mmol) and 1-methylpiperidin-4-one (3.41 g, 30.13 mmol, 3.50 mL) in NH$_3$ (7 M in MeOH, 40.00 mL) was stirred at 50° C. for 12 hr. Upon completion, the reaction mixture was diluted with DCM (50 mL) and water (50 mL). The organic layer was separated, and the aqueous layer was extracted with DCM (3×50 mL). The combined organic extracts were washed with brine (100 mL), dried over sodium sulfate, filtered, and concentrated under reduced pressure to give the title compound (2.7 g) as a yellow solid.

Step 2: Preparation of 6-methyl-5,6,7,8-tetrahydro-1,6-naphthyridin-3-amine. To a solution of 6-methyl-3-nitro-7,8-dihydro-5H-1,6-naphthyridine (1.5 g, 7.76 mmol) in THF (40 mL) was added Pd/C (1.2 g, 0.155 mmol, 10% purity) under nitrogen atmosphere, and then the reaction mixture was stirred at rt under H$_2$ atmosphere (H$_2$ balloon) for 12 hr.

The reaction mixture was filtered and concentrated under reduced pressure to give the title compound (1.2 g) as yellow oil.

Step 3: Preparation of 2-bromo-6-methyl-5,6,7,8-tetrahydro-1,6-naphthyridin-3-amine. To a solution of 6-methyl-7,8-dihydro-5H-1,6-naphthyridin-3-amine (410 mg, 2.51 mmol) and pyridinium tribromide (843.54 mg, 2.64 mmol) in acetic acid (10 mL) was added sodium acetate (412.13 mg, 5.02 mmol) at 25° C., and then the reaction mixture was stirred at 25° C. for 1 hr. Upon completion, the reaction mixture was diluted with DCM (50 mL) and neutralized with saturated bicarbonate to pH=8. The organic layer was separated and the aqueous layer back-extracted with DCM (3×50 mL). The combined organic layers were washed with brine, dried over Na$_2$SO$_4$, filtered, and concentrated under reduced pressure. The residue was purified by flash silica gel chromatography (0-10% DCM/MeOH) to give 2-bromo-6-methyl-7,8-dihydro-5H-1,6-naphthyridin-3-amine (350 mg, 1.45 mmol) as yellow solid.

Step 4: Preparation of 2-methoxy-6-methyl-5,6,7,8-tetrahydro-1,6-naphthyridin-3-amine. A mixture of 2-bromo-6-methyl-7,8-dihydro-5H-1,6-naphthyridin-3-amine (600 mg, 2.48 mmol) and cesium carbonate (1.61 g, 4.96 mmol) in MeOH (10 mL) was purged with nitrogen. After copper(I) iodide (47.2 mg, 0.248 mmol) and 3,4,7,8-tetramethyl-1,10-phenanthroline (117.1 mg, 0.496 mmol) were added, the mixture was purged again with nitrogen. The mixture was heated at 100° C. under microwave heating for 1 hr. Upon completion, the reaction mixture was filtered and concentrated. The residue was purified by silica gel chromatography (0-10% DCM in MeOH) to give the title compound (420 mg) as yellow solid Step 5: Preparation of [4-[6-[(2-methoxy-6-methyl-7,8-dihydro-5H-1,6-naphthyridin-3-yl)amino]pyrazolo[3,4-d]pyrimidin-1-yl]cyclohexyl]methanol. Prepared following the procedure in EXAMPLE 64 using 2-methoxy-6-methyl-5,6,7,8-dihydro-1,6-naphthyridin-3-amine (54.8 mg, 0.28 mmol) (EXAMPLE 170), trans-[4-(6-chloropyrazolo[3,4-d]pyrimidin-1-yl)cyclohexyl]methoxy-triisopropyl-silane (120.0 mg, 0.28 mmol), Pd-PEPPSI-iPent catalyst (45.0 mg, 0.06 mmol, 20 mol %), and cesium carbonate (277.3 mg, 0.85 mmol) in 1,2 dimethoxyethane (2.8 mL, 0.1 M) stirring at 80° C. for 3 h. The crude product was purified by silica gel chromatography eluting with 0-20% MeOH in DCM to give a crude brown solid. The crude product was dissolved in 1.5 mL of DCM and treated with 4N hydrochloric acid (0.28 mL, 1.13 mmol) in dioxane and stirred for 3 h. The reaction mixture was concentrated under reduced pressure, then added DCM and concentrated again. Repeated the DCM addition and concentration twice more to get a tan solid. The crude product was suspended in 1:1 MeCN:water. Purified by reverse-phase HPLC (Phenomenex, Gemini-NX, 10 um, 250×30 mm, C18 column; gradient of 10% MeCN/0.1% TFA-water to 100% MeCN/0.1% TFA). Combined fractions concentrated to one third volume then poured into a separatory funnel with 20 mL of 20% MeOH in DCM. Treated with saturated sodium bicarbonate and 1 M sodium carbonate to give the free-base material. The organic phase was separated and the aqueous phase was back extracted once with 20% MeOH in DCM. The combined organic phases were dried over anhydrous sodium sulfate, filtered, and concentrated under reduced pressure to give a yellow residue (8.9 mg): $^1$H NMR (400 MHz, Methanol-d4) δ 8.88 (s, 1H), 8.54 (s, 1H), 7.99 (s, 1H), 4.58 (td, J=11.8, 5.9 Hz, 1H), 4.01 (s, 3H), 3.61 (s, 2H), 3.47 (d, J=6.2 Hz, 2H), 2.91 (t, J=6.1 Hz, 2H), 2.83 (t, J=6.0 Hz, 2H), 2.50 (s, 3H), 2.27-1.96 (m, 6H), 1.72-1.55 (m, 1H), 1.36-1.17 (m, 2H). [M+H]$^+$: 424.3.

Example 171

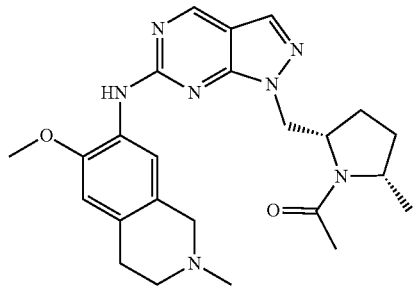

1-[(2S,5S)-2-[[6-[(6-methoxy-2-methyl-3,4-dihydro-1H-isoquinolin-7-yl)amino]pyrazolo[3,4-d]pyrimidin-1-yl]methyl]-5-methyl-pyrrolidin-1-yl]ethanone Step 1: Preparation of tert-butyl (2S,5S)-2-(hydroxymethyl)-5-methyl-pyrrolidine-1-carboxylate To a cooled 0° C. solution of (2S,5S)-1-tert-butoxycarbonyl-5-methyl-pyrrolidine-2-carboxylic acid (1.00 g, 4.36 mmol) in THF (21.8 mL, 0.2 M) under nitrogen was added 2 M dimethylsulfide borane in THF (4.36 mL, 8.72 mmol) dropwise. The reaction mixture was stirred at 0° C. for 2 h then warmed to ambient temperature and stirred for 3 h. The reaction mixture was cooled to 0° C. and quenched with saturated aqueous potassium carbonate then stirred overnight. Extracted with EtOAc. The combined organic extracts were dried over anhydrous sodium sulfate, filtered, and concentrated under reduced pressure to give an oil that was taken forward as the crude material (800 mg).

Step 2: Preparation of tert-butyl (2S,5S)-2-[(6-chloropyrazolo[3,4-d]pyrimidin-1-yl)methyl]-5-methyl-pyrrolidine-1-carboxylate. Prepared following general procedure D using tert-butyl (2S,5S)-2-(hydroxymethyl)-5-methyl-pyrrolidine-1-carboxylate (407 mg, 1.9 mmol), 6-chloro-1 h-pyrazolo[3,4-d]pyrimidine (225 mg, 1.46 mmol), triphenylphosphine (763.6 mg, 2.91 mmol) in THF (8.8 mL, 0.17 M) at 0° C. Added DIAD (0.57 mL, 2.91 mmol) dropwise over 1 h and stirred the reaction mixture at ambient temperature for 1 h. Added saturated aqueous sodium bicarbonate solution. The phases were separated, and the aqueous phase was extracted with EtOAc. The combined organic phase was dried over anhydrous sodium sulfate, filtered, and concentrated under reduced pressure. The crude product was adsorbed onto silica gel and purified by silica gel chromatography, 0-30% EtOAc in hexanes to give impure tert-butyl (2S,5S)-2-[(6-chloropyrazolo[3,4-d]pyrimidin-1-yl)methyl]-5-methyl-pyrrolidine-1-carboxylate (888 mg).

Step 3: Preparation of 6-chloro-1-[[(2S,5S)-5-methylpyrrolidin-2-yl]methyl]pyrazolo[3,4-d]pyrimidine hydrochloride. To a solution of tert-butyl (2S,5S)-2-[(6-chloropyrazolo[3,4-d]pyrimidin-1-yl)methyl]-5-methyl-pyrrolidine-1-carboxylate (888 mg, 2.52 mmol) in DCM (12.62 mL, 0.2 M) was added 4 N hydrochloric acid (0.63 mL, 2.52 mmol). The reaction mixture was stirred for 18 h. Concentrated under reduced pressure, then added more DCM and concentrated again. Repeated two more times to give the title compound as a crude solid (787 mg).

Step 4: Preparation of 1-[(2S,5S)-2-[(6-chloropyrazolo[3,4-d]pyrimidin-1-yl)methyl]-5-methyl-pyrrolidin-1-yl]ethenone. To a 0° C. solution of crude 6-chloro-1-[[(2S,5S)-5-methylpyrrolidin-2-yl]methyl]pyrazolo[3,4-d]pyrimidine; hydrochloride (400 mg, 1.39 mmol) in DCM (13.9 mL, 0.1 M) was added triethylamine (0.58 mL, 4.16 mmol) followed by acetyl chloride (0.15 mL, 2.08 mmol). The reaction mixture was warmed to ambient temperature and stirred for 18 h. The reaction mixture was quenched with water and then acidified with 1 M HCl. The phases were separated then the aqueous was extracted with DCM. The combined organic extract was washed with saturated aqueous sodium bicarbonate, dried over anhydrous sodium sulfate, filtered, and concentrated under reduced pressure. The crude product was adsorbed onto silica gel and purified by silica gel chromatography, 0-100% EtOAc in hexanes to afford 1-[(2S,5S)-2-[(6-chloropyrazolo[3,4-d]pyrimidin-1-yl)methyl]-5-methyl-pyrrolidin-1-yl]ethenone (124 mg).

Step 5: Preparation of 1-[(2S,5S)-2-[[6-[(6-methoxy-2-methyl-3,4-dihydro-1H-isoquinolin-7-yl)amino]pyrazolo[3,4-d]pyrimidin-1-yl]methyl]-5-methyl-pyrrolidin-1-yl]ethenone. Prepared according to general procedure B using 6-methoxy-2-methyl-3,4-dihydro-1H-isoquinolin-7-amine (96.6 mg, 0.5 mmol), 1-[(2S,5S)-2-[(6-chloropyrazolo[3,4-d]pyrimidin-1-yl)methyl]-5-methyl-pyrrolidin-1-yl]ethanone (123 mg, 0.42 mmol), cesium carbonate (409.3 mg, 1.26 mmol), and Pd-PEPPSI-iPent catalyst (66.4 mg, 0.08 mmol) to a 2-dram reaction vial. Added 1,2 dimethoxyethane (4.2 mL) then degassed the mixture with argon. Heated to 80° C. and stirred for 2 h. The reaction mixture was cooled, filtered through Celite, and concentrated under reduced pressure. The crude product was adsorbed onto silica gel and purified by silica gel chromatography (0-10% MeOH/DCM). The isolated product was repurified by reverse-phase HPLC, 0-100% 0.1% TFA/MeCN in 0.1% aqueous TFA. The fractions containing the product were concentrated to one-third volume, basified with saturated aqueous sodium bicarbonate and 1 M sodium carbonate, then extracted with 10% MeOH in DCM. The combined organic phase was dried over anhydrous sodium sulfate, filtered, and concentrated under reduced pressure to give the product as a colorless residue (71 mg). Characterized as a mixture of rotamers, a ratio of 1:0.6, ¹H NMR (400 MHz, Methanol-d4) δ 8.92-8.84 (m, 1.5H), 8.39 (s, 1H), 8.23 (s, 0.6H), 8.06 (s, 0.6H), 8.02 (s, 1H), 6.83-6.76 (m, 1.6H), 4.87-4.78 (m, 1.6H), 4.58 (dd, J=14.0, 3.6 Hz, 1H), 4.56-4.40 (m, 3H), 4.15-3.96 (m, 1.6H), 3.96-3.89 (m, 5H), 3.89-3.79 (m, 1H), 3.71-3.57 (m, 2.3H), 2.94 (t, J=6.0 Hz, 3.4H), 2.76 (t, J=6.3 Hz, 3.4H), 2.54-2.44 (m, 5H), 2.28-2.08 (m, 1.8H), 2.06-1.75 (m, 9H), 1.62-1.50 (m, 1H), 1.33 (d, J=6.2 Hz, 1.9H), 0.77 (d, J=6.5 Hz, 3H). LCMS [M+H]⁺: 450.3

Example 172

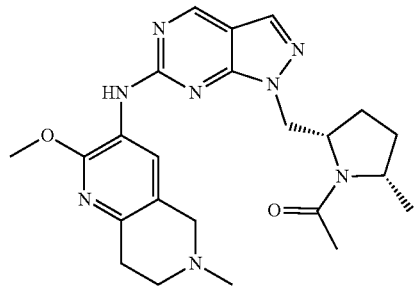

1-[(2S,5S)-2-[[6-[(2-methoxy-6-methyl-7,8-dihydro-5H-1,6-naphthyridin-3-yl)amino]pyrazolo[3,4-d]pyrimidin-1-yl]methyl]-5-methyl-pyrrolidin-1-yl]ethenone Prepared according to EXAMPLE 171 substituting 2-methoxy-6-methyl-7,8-dihydro-5H-1,6-naphthyridin-3-amine (EXAMPLE 170, step 4) for 6-methoxy-2-methyl-3,4-dihydro-1H-isoquinolin-7-amine to afford the title compound (71 mg). Characterized as a mixture of rotamers, ¹H NMR (400 MHz, Methanol-d4) δ 9.00-8.91 (m, 2H), 8.14-8.07 (m, 1H), 5.14-4.94 (m, 1.4H), 4.80-4.68 (m, 0.6H), 4.65-4.49 (m, 2H), 4.49-4.31 (m, 2H), 4.14-4.02 (m, 3.6H), 4.02-3.90 (m, 11H), 3.90-3.77 (m, 1H), 3.64-3.48 (m, 1H), 3.28-3.19 (m, 1H), 3.19-3.04 (m, 5H), 2.69 (s, 3H), 2.46-2.28 (m, 1H), 2.11-1.94 (m, 2H), 1.89 (d, J=11.4 Hz, 3.8H), 1.58-1.44 (m, 1H), 0.49 (dd, J=32.3, 6.5 Hz, 3H). LCMS [M+H]⁺: 451.3

Example 173

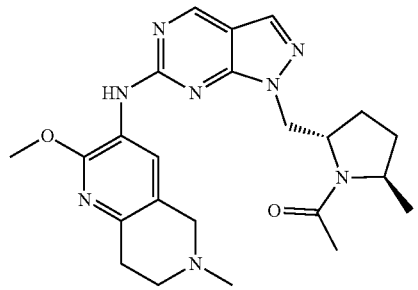

1-[(2S,5R)-2-[[6-[(2-methoxy-6-methyl-7,8-dihydro-5H-1,6-naphthyridin-3-yl)amino]pyrazolo[3,4-d]pyrimidin-1-yl]methyl]-5-methyl-pyrrolidin-1-yl]ethenone Methanesulfonic Acid The above compound was prepared according to Steps 1 to 5 from EXAMPLE 171 substituting (2S,5R)-1-tert-butoxycarbonyl-5-methyl-pyrrolidine-2-carboxylic acid for (2S,5S)-1-tert-butoxycarbonyl-5-methyl-pyrrolidine-2-carboxylic acid and substituting in Step 6, 2-methoxy-6-methyl-7,8-dihydro-5H-1,6-naphthyridin-3-amine (EXAMPLE 170, step 4) for 6-methoxy-2-methyl-3,4-dihydro-1H-isoquinolin-7-amine. The free base was converted to the mesylate salt using methanesulfonic acid (1 equiv in DCM) to afford the title compound (32 mg). Characterized as a mixture of rotamers, ¹H NMR (400 MHz, HOMs salt, Methanol-d4) δ 8.99-8.89 (m, 2H), 8.13-8.05 (m, 1H), 4.96 (d, 0.5H), 4.86-4.73 (m, 1H), 4.70-4.46 (m, 2.6H), 4.38 (d, J=15.3 Hz, 0.8H), 4.15-4.02 (m, 3H), 3.92-3.72 (m, 2H), 3.66-3.46 (m, 1H), 3.29-3.19 (m, 1H), 3.19-3.05 (m, 4H), 2.69 (d, J=0.9 Hz, 3H), 2.25-2.05 (m, 2.5H), 1.97 (d, J=14.7 Hz, 3H), 1.55-1.23 (m, 2H), 1.23-1.10 (m, 3H). LCMS [M+H]⁺: 451.2

Example 174

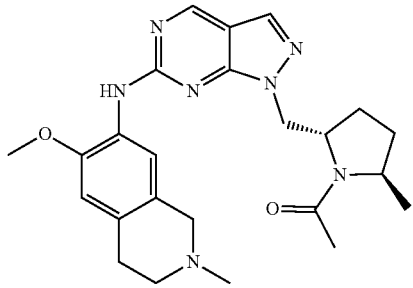

Preparation of 1-[(2S,5R)-2-[r6-[(6-methoxy-2-methyl-3,4-dihydro-1H-isoquinolin-7-yl)amino]pyrazolo[3,4-d]pyrimidin-1-yl]methyl]-5-methyl-pyrrolidin-1-yl]ethenone Prepared according to EXAMPLE 173 substituting in Step 5 with 6-methoxy-2-methyl-3,4-dihydro-1H-isoquinolin-7-amine for 2-methoxy-6-methyl-7,8-dihydro-5H-1,6-naphthyridin-3-amine to afford the title compound (34 mg). ¹H NMR (400 MHz, Methanol-d4, mixture of rotamers) δ 8.91-8.85 (m, 1H), 8.37 (s, 0.8H), 8.17 (s, 0.3H) 8.05 (m, 0.3H), 8.01 (m, 0.H), 6.82-6.76 (m, 1H), 4.80-4.70 (m, 1H), 4.56 (d, J=12.9 Hz, 2H), 4.44 (s, 1H), 3.91 (m, 3.6H), 3.90-3.78 (m, 1.8H), 3.71-3.58 (m, 6H), 2.95 (t, J=6.1 Hz, 2.5H), 2.77 (t, J=6.1 Hz, 2.5H), 2.49 (d, J=7.4 Hz, 3.7H), 2.06 (m, 5.6H), 1.51-1.37 (m, 1.7H), 1.17 (m, 3.6H). LCMS [M+H]⁺: 450.2

Example 175

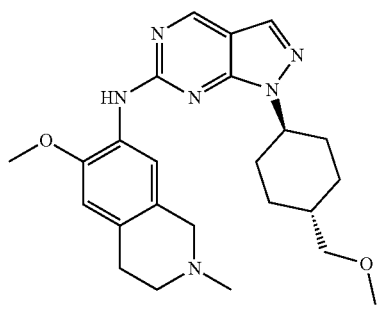

6-methoxy-N-[trans-1-[4-(methoxymethyl)cyclohexyl]pyrazolo[3,4-d]pyrimidin-6-yl]-2-methyl-3,4-dihydro-1H-isoquinolin-7-amine Step 1: Preparation of cis-methyl 4-tetrahydropyran-2-yloxycyclohexanecarboxylate. To a 20-mL reaction vial containing methyl cis-4-hydroxycyclohexanecarboxylate (2.5 g, 15.8 mmol) was added dihydropyran (2.9 mL, 31.6 mmol) followed by Amberlyst 15 hydrogen (250 mg, 0.8 mmol). the reaction mixture was stirred for 18 h and monitored by TLC using KMnO₄ stain. The reaction mixture was diluted with DCM, filtered, and concentrated under reduced pressure. The crude product was adsorbed onto silica gel and purified by silica gel chromatography (0-50% EtOAc/hexanes) to provide the title compound (1.7 g).

Step 2: Preparation of cis (4-tetrahydropyran-2-yloxycyclohexyl)methanol. To a cooled (0° C.) solution of methyl 4-tetrahydropyran-2-yloxycyclohexanecarboxylate (1.7 g, 7.1 mmol) in THF (71 mL, 0.1 M) was added a solution of 4 M LAH in ether (2.7 mL, 10.6 mmol) dropwise. The reaction mixture was warmed to ambient temperature and stirred for 30 min and TLC analysis in 50% EtOAc in hexanes with KMnO₄ staining indicated starting material was consumed. The reaction mixture was cooled back to 0° C. and treated with EtOAc to quench excess reagent then 0.4 mL water, 0.8 mL of 3 M NaOH, and 1.2 mL of water were sequentially added. The mixture was stirred for 2 h then magnesium sulfate was added, and the mixture was filtered and concentrated under reduced pressure. The crude product was adsorbed onto silica gel and purified by silica gel chromatography (0-50% EtOAc/hexanes) to afford the title compound (855 mg).

Step 3: Preparation of cis 2-[4-(methoxymethyl)cyclohexoxy]tetrahydropyran. To a cooled (0° C.) solution of cis (4-tetrahydropyran-2-yloxycyclohexyl)methanol (855 mg, 4.0 mmol) in THF (20 mL, 0.2 M) was added sodium hydride (192 mg, 4.8 mmol, 60% w/w) and the mixture was stirred for 30 min. Added methyl iodide (0.35 mL, 5.6 mmol) to the reaction mixture and stirred for 30 min. TLC analysis in 50% EtOAc in hexanes with KMnO₄ staining was used to monitor the reaction progress. Additional sodium hydride (192 mg, 4.8 mmol, 60% w/w) followed by methyl iodide (0.35 mL, 5.6 mmol) were added and stirred for 30 min. The reaction mixture was quenched with saturated aqueous ammonium chloride solution. Additional water was added and the mixture was extracted with EtOAc. The combined organic extracts were dried over anhydrous sodium sulfate, filtered, and concentrated under reduced pressure to give the title compound as a crude solid (960 mg). This material was taken forward as is.

Step 4: Preparation of cis 4-(methoxymethyl)cyclohexanol. To a solution of cis 2-[4-(methoxymethyl)cyclohexoxy]tetrahydropyran (960 mg, 4.2 mmol) in MeOH (4.2 mL, 1.0 M) was added catalytic p-TSA (40 mg, 0.21 mmol) and the reaction mixture was stirred for 2 days. TLC analysis in 50% EtOAc in hexanes with KMnO₄ staining to monitor reaction progress. The acid was quenched with saturated aqueous sodium bicarbonate and partially concentrated to remove methanol. The mixture was then diluted with water and extracted with EtOAc. The combined organic extract was dried over anhydrous sodium sulfate, filtered, and concentrated under reduced pressure. The crude product was adsorbed onto silica gel and purified by silica gel chromatography chromatography (0-50% EtOAc/hexanes) afford the title compound (303 mg).

Step 5: 6-chloro-1-[4-(methoxymethyl)cyclohexyl]pyrazolo[3,4-d]pyrimidine. Prepared according to general procedure D using using cis 4-(methoxymethyl)cyclohexanol (303 mg, 2.1 mmol), 6-chloro-1 h-pyrazolo[3,4-d]pyrimidine (250 mg, 1.62 mmol), triphenylphosphine (848 mg, 3.23 mmol), and DIAD (0.64 mL, 3.23 mmol) in THE (9.7 mL, 0.17 M) at rt for 1 h. Added saturated aqueous sodium bicarbonate solution. The phases were separated, and the aqueous phase was extracted with EtOAc. The combined organic phase was dried over anhydrous sodium sulfate, filtered, and concentrated under reduced pressure. The crude product was adsorbed onto silica gel and purified by silica gel chromatography, 0-30% EtOAc in hexanes to give impure 6-chloro-1-[4-(methoxymethyl)cyclohexyl]pyrazolo [3,4-d]pyrimidine (603 mg). NMR analysis indicated the product is ~12% purity. This material was taken forward without further purification.

Step 6: 6-methoxy-N-[1-[4-(methoxymethyl)cyclohexyl] pyrazolo[3,4-d]pyrimidin-6-yl]-2-methyl-3,4-dihydro-1H-isoquinolin-7-amine. Prepared following general procedure B using 6-methoxy-2-methyl-3,4-dihydro-1H-isoquinolin-7-amine (52 mg, 0.27 mmol), 6-chloro-1-[4-(methoxymethyl)cyclohexyl]pyrazolo[3,4-d]pyrimidine (530 mg, 0.23 mmol), cesium carbonate (221 mg, 0.68 mmol), and Pd-PEPPSI-iPent catalyst (36 mg, 0.05 mmol) in 1,2 dimethoxyethane (2.3 mL, 0.1 M). The degassed mixture was stirred at 80° C. for 2 h. The reaction mixture was cooled, filtered through Celite, and concentrated under reduced pressure. The crude product was adsorbed onto silica gel and purified by silica gel chromatography (0-10% MeOH/DCM). The isolated product was repurified by reverse-phase HPLC, 0-100% 0.1% TFA/MeCN in 0.1% aqueous TFA. The fractions containing the product were concentrated to one-third volume, basified with saturated aqueous sodium bicarbonate and 1 M sodium carbonate, then extracted with 10% MeOH in DCM. The combined organic phase was dried over anhydrous sodium sulfate, filtered, and concentrated under reduced pressure to afford the title compound (9.7 mg). $^1$H NMR (400 MHz, Methanol-d4) δ 8.84 (s, 1H), 8.30 (s, 11H), 7.95 (s, 1H), 6.78 (s, 1H), 4.62-4.48 (m, 1H), 3.91 (s, 3H), 3.60 (s, 2H), 3.35 (s, 3H), 3.30-3.27 (m, 2H), 2.93 (t, J=6.0 Hz, 2H), 2.74 (t, J=6.0 Hz, 2H), 2.47 (s, 3H), 2.32-2.15 (m, 2H), 2.14-1.97 (m, 4H), 1.86-1.70 (m, 1H), 1.36-1.17 (m, 2H). LCMS [M+H]$^+$: 437.3.

Example 176

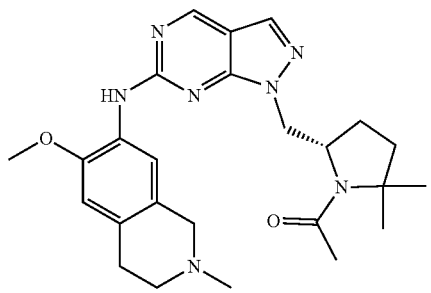

1-[(5S)-5-[[6-[(6-methoxy-2-methyl-3,4-dihydro-1H-isoquinolin-7-yl)amino]pyrazolo[3,4-d]pyrimidin-1-yl]ymethyl]-2,2-dimethyl-pyrrolidin-1-yl]ethenone The above compound was prepared according to EXAMPLE 171 substituting (2S,5S)-1-tert-butoxycarbonyl-5-methyl-pyrrolidine-2-carboxylic acid for (2S)-1-tert-butoxycarbonyl-5,5-dimethyl-pyrrolidine-2-carboxylic acid to afford the title compound (4 mg). Characterized as a mixture of rotamers, $^1$H NMR (400 MHz, Methanol-d4) δ 8.91-8.85 (m, 1H), 8.23 (s, 1H), 8.08-8.03 (m, 1H), 6.80 (s, 1H), 4.55 (dd, J=13.6, 9.5 Hz, 1H), 4.49-4.39 (m, 1H), 4.35 (dd, J=13.6, 3.7 Hz, 1H), 3.92 (s, 3H), 3.63 (s, 2H), 2.94 (t, J=6.1 Hz, 2H), 2.76 (t, J=6.0 Hz, 2H), 2.53-2.43 (m, 3H), 2.22-2.14 (m, 4H), 2.03-1.93 (m, 1H), 1.85 (dd, J=12.3, 6.6 Hz, 1H), 1.73 (dd, J=12.7, 6.4 Hz, 1H), 1.63 (s, 3H), 1.40 (s, 3H). LCMS [M+H]$^+$: 464.4

Example 177

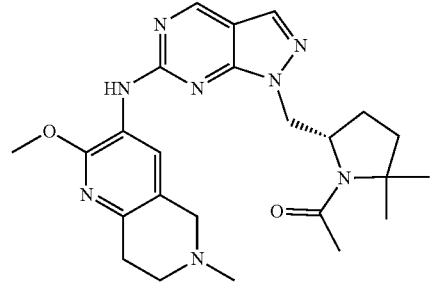

1-[(5S)-5-[[6-[(2-methoxy-6-methyl-7,8-dihydro-5H-1,6-naphthyridin-3-yl)amino]pyrazolo[3,4-d] pyrimidin-1-yl]methyl]-2,2-dimethyl-pyrrolidin-1-yl]ethenone Prepared according to EXAMPLE 176 substituting 2-methoxy-6-methyl-5,6,7,8-tetrahydro-1,6-naphthyridin-3-amine (EXAMPLE 170, step 4) for 6-methoxy-2-methyl-1,2,3,4-tetrahydroisoquinolin-7-amine to afford the title compound (42 mg). Characterized as a mixture of rotamers, $^1$H NMR (400 MHz, mesylate salt, Methanol-d4) δ 9.01-8.91 (m, 1.4H), 8.62 (d, J=19.6 Hz, 0.5H), 8.11 (d, 1H), 5.01-4.94 (m, 1H), 4.80-4.73 (m, 0.5H), 4.69-4.45 (m, 3H), 4.45-4.31 (m, 1.5H), 4.07 (d, J=5.9 Hz, 3H), 3.91-3.78 (m, 1H), 3.57 (td, J=11.4, 5.3 Hz, 11H), 3.28-3.19 (m, 1H), 3.19-3.06 (m, 4H), 2.69 (d, J=1.1 Hz, 3H), 2.15 (d, J=9.2 Hz, 2H), 2.09-1.95 (m, 3H), 1.91-1.79 (m, 1H), 1.76-1.64 (m, 0.5H), 1.59 (d, J=3.4 Hz, 2H), 1.40 (s, 2H), 1.32 (d, J=5.2 Hz, 2H), 1.04 (s, 0.7H), 0.97 (s, 0.7H). LCMS [M+H]$^+$: 465.3

Example 178

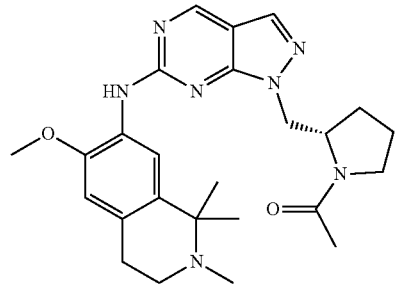 [SMILES: COc1cc2c(cc1Nc1ncc3cnn(C[C@@H]4CCCN4C(C)=O)c3n1)C(C)(C)N(C)CC2]

(S)-1-(2-((6-((6-methoxy-1,1,2-trimethyl-1,2,3,4-tetrahydroisoquinolin-7-yl)amino)-1H-pyrazolo[3,4-d]pyrimidin-1-yl)methyl)pyrrolidin-1-yl)ethan-1-one Step 1: Preparation of N-(3-methoxyphenethyl)acetamide. To a solution of 2-(3-methoxyphenyl)ethanamine (4.0 g, 26.4 mmol, 3.88 mL) in DCM (80 mL) was added acetic anhydride (3.24 g, 31.74 mmol, 2.97 mL) and the resultant mixture was stirred at 20° C. for 16 h. The reaction mixture was diluted with DCM (10 mL), washed with NaHCO$_3$ (saturated, 20 mL) solution. The separated organic layer was dried over Na$_2$SO$_4$, filtered, and concentrated under reduced pressure to give the desired product (5.1 g). $^1$H NMR (400 MHz, CDCl3) δ: 7.26-7.22 (t, J=8.0 Hz, 1H), 6.81-6.74 (m, 3H), 5.48 (br s, 1H), 3.81 (s, 3H), 3.55-3.49 (t, J=6.4 Hz, 2H), 2.82-2.78 (q, J=7.2 Hz, 2H), 1.95 (s, 3H). LCMS [M+H].: 194.2

Step 2: Preparation of 6-methoxy-1-methyl-3,4-dihydroisoquinoline. To a solution of N-[2-(3-methoxyphenyl)ethyl]acetamide (5.1 g, 26.39 mmol) in toluene (60 mL) was added POCl$_3$ (20.23 g, 131.96 mmol, 12.26 mL). The reaction mixture was stirred at 120° C. for 5 h. The reaction mixture was cooled and poured into H$_2$O (100 mL) in portions. The aqueous layer was basified with 15% NaOH to about pH 9 and extracted with EtOAc (3×100 mL). The combined organic layer was dried over Na2SO$_4$, filtered, and concentrated under reduced pressure to give the product (4.4 g), which was used for next step without further purification. $^1$H NMR (400 MHz, CDCl3) δ: 7.45-7.41 (d, J=8.8 Hz, 1H), 6.81-6.78 (dd, J=8.8 Hz, 2.8 Hz, 1H), 6.72-6.70 (d, J=2.8 Hz, 1H), 3.84 (s, 3H), 3.66-3.62 (m, 2H), 2.71-2.67 (t, J=7.2 Hz, 2H), 2.36 (s, 3H). LCMS [M+H]: 176.1

Step 3: Preparation of 6-methoxy-1,2-dimethyl-3,4-dihydroisoquinolin-2-ium iodide. To a solution of 6-methoxy-1-methyl-3,4-dihydroisoquinoline (160 mg, 0.913 mmol) in acetone (3 mL) was added MeI (129.61 mg, 0.913 mmol, 0.056 mL) at 20° C. and then the solution was stirred for 16 h. The reaction mixture was concentrated under reduced pressure to give the product (250 mg), which can be used for next step without further purification. $^1$H NMR (400 MHz, DMSO-d6) δ: 8.07-8.03 (m, 1H), 7.08-7.01 (m, 2H), 3.99-3.95 (t, J=7.2 Hz, 2H), 3.91 (s, 3H), 3.65 (s, 3H), 3.13-3.08 (t, J=7.6 Hz, 2H), 2.74 (s, 3H). LCMS [M+H]: m/z 190.2.

Step 4: Preparation of 6-methoxy-1,1,2-trimethyl-1,2,3,4-tetrahydroisoquinoline. To a solution of 2-iodo-6-methoxy-1,2-dimethyl-3,4-dihydroisoquinoline (250 mg, 0.788 mmol) in THF (3 mL) was added methyl magnesium bromide (3 M, 1.05 mL) at −70° C. under N2 atmosphere. After being stirred for 1 h, the reaction mixture was warmed to 20° C. and stirred for another 12 h. The reaction mixture was quenched by H$_2$O (10 mL) at 0° C. and extracted with EtOAc (3×15 mL). The combined organic layer was dried over Na$_2$SO$_4$, filtered, and concentrated under reduced pressure to give the desired product (110 mg). 1H NMR (400 MHz, CDCl3) δ: 7.19-7.16 (d, J=8.4 Hz, 1H), 6.77-6.74 (dd, J=12.8 Hz, 2.8 Hz, 1H), 6.59-6.58 (d, J=2.8 Hz, 1H), 3.79 (s, 3H), 2.89 (brs, 4H), 2.48 (s, 3H), 1.45-1.42 (m, 6H). LCMS [M+H].: 206.2

Step 5: Preparation of 6-methoxy-1,1,2-trimethyl-7-nitro-1,2,3,4-tetrahydroisoquinoline. To a solution of 6-methoxy-1,1,2-trimethyl-3,4-dihydroisoquinoline (1 g, 4.87 mmol) in DME (10 mL) was added nitronium tetrafluoroborate (970.4 mg, 7.31 mmol, 0.752 mL) at −40° C. Then the reaction mixture was stirred for 3 h at −40° C. The reaction mixture was quenched with sat. NaHCO$_3$ (10 mL) and extracted with EtOAc (3×20 mL). The combined organic layer was dried over Na$_2$SO$_4$, filtered, and concentrated under reduced pressure to give a residue. The residue was purified by prep-HPLC (column: Xtimate C18 150*40 mm*5 um; mobile phase: [water(0.05% NH3H2O)-ACN]; B %: 31%-61%,8 min) to give the desired product 6-methoxy-1,1,2-trimethyl-7-nitro-3,4-dihydroisoquinoline (350 mg). 1H NMR (400 MHz, CDCl3) δ: 7.82 (s, 1H), 6.73 (s, 1H), 3.93 (s, 2H), 2.93-2.87 (m, 4H), 2.45 (s, 1H), 1.41 (s, 6H). LCMS [M+H]: 251.2.

Prep-HPLC also gave the by-product 6-methoxy-1,1,2-trimethyl-5-nitro-3,4-dihydroisoquinoline (300 mg). 1H NMR (400 MHz, CDCl3) δ: 7.35-7.32 (d, J=8.8 Hz, 1H), 6.91-6.88 (d, J=9.2 Hz, 1H), 3.88 (s, 3H), 2.90-2.86 (t, J=6.0 Hz, 1H), 2.77-2.73 (t, J=6.0 Hz, 2H), 2.43 (s, 3H), 1.40 (s, 6H). LCMS [M+H]: 251.1

Step 6: Preparation of 66-methoxy-1,1,2-trimethyl-1,2,3,4-tetrahydroisoquinolin-7-amine. To a solution of 6-methoxy-1,1,2-trimethyl-7-nitro-3,4-dihydroisoquinoline (200 mg, 0.799 mmol) in THF (20 mL) was added Pd/C (50 mg, 10% purity). Then the reaction mixture was stirred under H$_2$ atmosphere at 20° C. for 2 h. The reaction mixture was filtered and concentrated under reduced pressure to give a crude product (170 mg). $^1$H NMR (400 MHz, CDCl3) δ: 6.61 (s, 1H), 6.45 (s, 1H), 3.82 (s, 3H), 3.66 (brs, 1H), 2.88-2.84 (t, J=6.0 Hz, 2H), 4.78-4.74 (t, J=6.0 Hz, 2H), 2.43 (s, 3H), 1.37 (s, 6H). LCMS [M+H]: 221.2

Step 7: Preparation of (S)-1-(2-((6-((6-methoxy-1,1,2-trimethyl-1,2,3,4-tetrahydroisoquinolin-7-yl)amino)-1H-pyrazolo[3,4-d]pyrimidin-1-yl)methyl)pyrrolidin-1-yl)ethan-1-one. Prepared according to general procedure A using 6-methoxy-1,1,2-trimethyl-3,4-dihydroisoquinolin-7-amine (60.0 mg, 0.272 mmol), 1-[(2S)-2-[(6-chloropyrazolo[3,4-d]pyrimidin-1-yl]methyl]pyrrolidin-1-yl]ethanone (83.8 mg, 0.300 mmol) and p-TsOH (117.2 mg, 0.681 mmol) in 2-butanol (2 mL) stirred at 100° C. for 48 h. The reaction mixture was poured to sat.NaHCO$_3$ (10 mL) and extracted with DCM (3×10 mL). The combined organic layer was dried over Na$_2$SO$_4$, filtered, and concentrated under reduced pressure to give a residue. The residue was purified by prep-HPLC (column: Boston Prime C18 150*30 mm*5 um; mobile phase: [water(0.05% NH3H2O+10 mM NH4HCO3)-ACN]; B %: 35%-65%,7 min). After lyophilization, the desired product was taken up with water and 3 drops of HCl (1 M) solution was added. The solution was lyophilized to give the HCl salt of desired product (24.3 mg). $^1$H NMR (400 MHz, Deuterium oxide) δ: 8.72-8.62 (m, 1H), 8.01-7.83 (m, 2H), 6.83-6.76 (m, 1H), 4.38-4.17 (m, 1H), 4.21-3.99 (m, 2H), 3.79 (s, 3H), 3.42-3.14 (m, 4H), 3.09-3.02 (m, 2H), 2.79 (s, 3H), 1.95-1.64 (m, 5.5 H), 1.60-1.58 (m, 6H), 1.45-1.34 (m, 1.5H). LCMS [M+H]: 464.3

Example 179

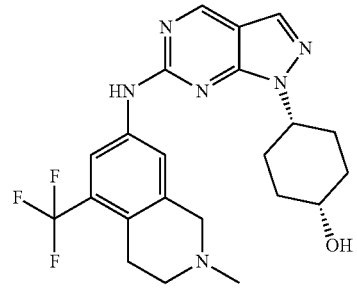 [SMILES: CN1CCc2c(cc(Nc3ncc4cnn([C@H]5CC[C@@H](O)CC5)c4n3)cc2C(F)(F)F)C1]

(1s,4s)-4-(6-((2-methyl-5-(trifluoromethyl)-1,2,3,4-tetrahydroisoquinolin-7-yl)amino)-1H-pyrazolo[3,4-d]pyrimidin-1-yl)cyclohexan-1-ol Step 1: Preparation of 1-((1s,4s)-4-((tert-butyldimethylsilyl)oxy)cyclohexyl)-6-chloro-1H-pyrazolo[3,4-d]pyrimidine. Prepared according to general procedure D using 6-chloro-1H-pyrazolo[3,4-d]pyrimidine (150 mg, 0.971 mmol), 4-[tert-butyl(dimethyl)silyl]oxycyclohexanol (335.44 mg, 1.46 mmol), triphenylphospine (458.2 mg, 1.75 mmol), and DEAD (304.2 mg, 1.75 mmol) in THF (5 mL) stirred at 10° C. for 4 h. The crude product was purified by flash silica gel chromatography (0-18% EtOAc/petroleum ether gradient) to give the title compound (280 mg). LCMS [M+H]: 367.2

Step 2: Preparation of (1s,4s)-4-(6-((2-methyl-5-(trifluoromethyl)-1,2,3,4-tetrahydroisoquinolin-7-yl)amino)-1H-pyrazolo[3,4-d]pyrimidin-1-yl)cyclohexan-1-ol. Prepared according to general procedure A using 2-methyl-5-(trifluoromethyl)-3,4-dihydro-1H-isoquinolin-7-amine (50 mg, 0.217 mmol) (EXAMPLE 58, 1-((1s,4s)-4-((tert-butyldimethylsilyl)oxy)cyclohexyl)-6-chloro-1H-pyrazolo[3,4-d]pyrimidine (103.6 mg, 0.282 mmol), and p-TSA (123.9 mg, 0.651 mmol) in 2-butanol (1 mL) and stirred 100° C. for 15 h. The crude residue was purified by reverse phase HPLC (column: Boston Prime C18 150*30 mm*5 um; mobile phase: [water(0.05% NH$_3$H$_2$O+10 mM NH$_4$HCO$_3$)-ACN]; B %: 40%-70%, 7 min). After lyophlization the residue was diluted with H$_2$O (10 mL) and treated with HCl (1M, 3 drops). Then the solution was submitted to lyophilization again to give the HCl salt of the title compound (76 mg). $^1$H NMR (400 MHz, DMSO-d6) δ: 10.69 (br s, 1H), 10.32 (s, 1H), 9.04 (s, 1H), 8.50 (s, 1H), 8.12 (s, 1H), 7.86 (s, 1H), 4.62-4.55 (m, 2H), 4.42-4.36 (m, 1H), 3.93 (s, 1H), 3.72-3.68 (m, 1H), 3.31-3.09 (m, 3H), 2.95-2.93 (d, J=4.0 Hz, 3H), 2.45-2.35 (m, 2H), 1.87-1.84 (m, 2H), 1.73-1.58 (m, 5H). LCMS [M+H]: 447.2

Example 180

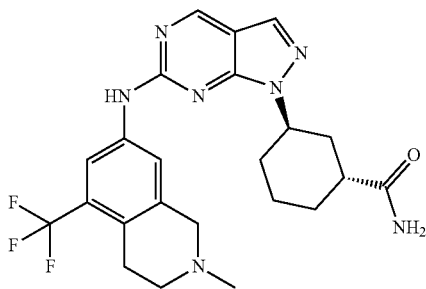 [SMILES: CN1CCc2c(cc(Nc3ncc4cnn([C@@H]5CCC[C@@H](C(N)=O)C5)c4n3)cc2C(F)(F)F)C1]

(1R,3R)-3-(6-((2-methyl-5-(trifluoromethyl)-1,2,3,4-tetrahydroisoquinolin-7-yl)amino)-1H-pyrazolo[3,4-d]pyrimidin-1-yl)cyclohexane-1-carboxamide Step 1: Preparation of methyl (1R,3R)-3-(6-((2-methyl-5-(trifluoromethyl)-1,2,3,4-tetrahydroisoquinolin-7-yl)amino)-1H-pyrazolo[3,4-d]pyrimidin-1-yl)cyclohexane-1-carboxylate Prepared according to general procedure B using methyl (1R,3R)-3-(6-chloropyrazolo[3,4-d]pyrimidin-1-yl)cyclohexanecarboxylate (100.0 mg, 0.339 mmol) (EXAMPLE 40, 2-methyl-5-(trifluoromethyl)-3,4-dihydro-1H-isoquinolin-7-amine (85.9 mg, 0.373 mmol) (EXAMPLE 58), Pd$_2$(dba)$_3$ (15.5 mg, 0.017 mmol), XPhos (16.2 mg, 0.034 mmol) and K$_2$CO$_3$ (103.16 mg, 0.746 mmol) in t-BuOH (2.5 mL) and stirred at. 90° C. under N$_2$ for 4 h. The residue was purified by flash silica gel chromatography (0-5% MeOH/DCM gradien) to give the title product (80 mg). LCMS [M+H]: 489.2

Step 2: Preparation of (1R,3R)-3-(6-((2-methyl-5-(trifluoromethyl)-1,2,3,4-tetrahydroisoquinolin-7-yl)amino)-1H-pyrazolo[3,4-d]pyrimidin-1-yl)cyclohexane-1-carboxylic acid. Methyl (1R,3R)-3-[6-[[2-methyl-5-(trifluoromethyl)-3,4-dihydro-1H-isoquinolin-7-yl]amino]pyrazolo[3,4-d]pyrimidin-1-yl]cyclohexanecarboxylate (80 mg, 0.164 mmol) was dissolved in THF (1.0 mL) and treated with LiOH monohydrate (48.1 mg, 1.15 mmol) in water (0.5 mL) and stirred at 35° C. for 16 h. The mixture was acidified with HCl (2 N in water) to pH 4 and concentrated to remove the volatiles. The aqueous layer was extracted with 10% MeOH/DCM (3×10 mL). The combined organic layers were dried over anhydrous Na$_2$SO$_4$, filtered, and concentrated. The residue was triturated with MeCN (2 mL) and stirred for 10 min. The suspension was filtered, and the crude product was dried under reduced pressure (48 mg). This crude material was taken forward without further purification. LCMS [M+H]: 475.2

Step 3: Preparation of (1R,3R)-3-(6-((2-methyl-5-(trifluoromethyl)-1,2,3,4-tetrahydroisoquinolin-7-yl)amino)-1H-pyrazolo[3,4-d]pyrimidin-1-yl)cyclohexane-1-carboxamide. (1R,3R)-3-[6-[[2-methyl-5-(trifluoromethyl)-3,4-dihydro-1H-isoquinolin-7-yl]amino]pyrazolo[3,4-d]pyrimidin-1-yl]cyclohexanecarboxylic acid (40 mg, 0.084 mmol) and NH$_4$Cl (22.55 mg, 0.421 mmol) were dissolved in DMSO (0.6 mL) and treated with TEA (59.71 mg, 0.590 mmol, 0.082 uML) and HATU (48.08 mg, 0.126 mmol). Then the mixture was stirred at 25° C. for 16 h. The mixture was diluted with MeOH (2 mL) and purified using reverse phase HPLC (column: Xtimate C18 150*40 mm*5 um; mobile phase: [water (0.05% NH$_3$H2O)-ACN]; B %: 34%-64%, 8 min). After lyophilization, the product was dissolved in water and treated with HCl (1 M, 3 drops). Then the solution was lyophilized again to give the HCl salt of the title compound (5.2 mg). $^1$H NMR (400 MHz, deuterium oxide-d) δ ppm 8.72-8.70 (d, 1H), 8.00-7.96 (d, 1H), 7.94-7.92 (d, 1H), 7.46-7.42 (d, 1H), 4.57-4.52 (d, 1H), 4.34-4.26 (m, 1H), 3.78-3.74 (m, 1H), 3.41-3.25 (m, 3H), 3.03 (s, 3H), 2.81-2.72 (d, 1H), 2.18-2.08 (m, 1H), 2.00-1.70 (m, 5H), 1.66-1.49 (m, 3H). LCMS [M+H]: 474.3

Example 181

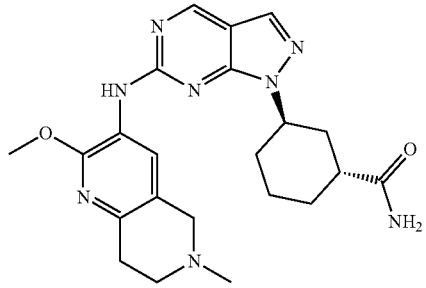 [SMILES: COc1nc2c(cc1Nc1ncc3cnn([C@@H]4CCC[C@@H](C(N)=O)C4)c3n1)CN(C)CC2]

(1R,3R)-3-(6-((2-methoxy-6-methyl-5,6,7,8-tetrahydro-1,6-naphthyridin-3-yl)amino)-1H-pyrazolo[3,4-d]pyrimidin-1-yl)cyclohexane-1-carboxamide Mesylate Prepared according to EXAMPLE 40 substituting 2-methoxy-6-methyl-5,6,7,8-tetrahydro-1,6-naphthyridin-3- amine (EXAMPLE 170) for 6-methoxy-2-methyl-3,4-dihydro-1H-isoquinolin-7-amine in Step 2 to provide the desired compound as the TFA salt as a solid. This material was basified using $Na_2CO_3$, extracted with EtOAc, and the combined organic layers concentrated under reduced pressure to provide title compound as the free base. The free base was converted into the mesylate salt by adding 1 equiv. of methanesulfonic acid, providing the desire product as a solid (17 mg). 1H NMR (400 MHz, Methanol-d4, mesylate salt) δ 8.95 (s, 1H), 8.88 (d, J=19.1 Hz, 1H), 8.08 (s, 1H), 5.49-5.37 (m, 11H), 4.77 (dd, J=31.8, 15.3 Hz, 1H), 4.53-4.38 (m, 1H), 4.17-4.08 (m, 1H), 4.07 (s, 3H), 3.90-3.76 (m, 1H), 3.64-3.51 (m, $^1$H), 3.28-3.20 (m, 1H), 3.15 (s, 3H), 3.12-3.05 (m, 1H), 3.00-2.89 (m, 1H), 2.69 (s, 3H), 2.26-2.19 (m, 1H), 2.17-2.08 (m, 2H), 2.01-1.92 (m, 2H), 1.91-1.81 (m, 2H). LCMS [M+H]: 437.2

Example 182

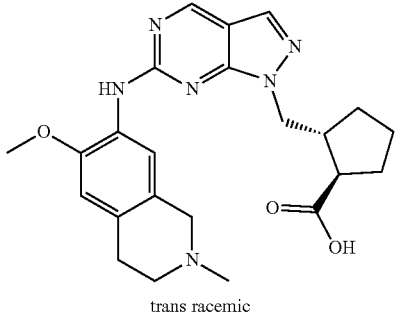 [SMILES: COc1cc2c(cc1Nc1ncc3cnn(C[C@@H]4CCC[C@H]4C(=O)O)c3n1)CN(C)CC2]

racemic trans-2-((6-((6-methoxy-2-methyl-1,2,3,4-tetrahydroisoquinolin-7-yl)amino)-1H-pyrazolo[3,4-d]pyrimidin-1-yl)methyl)cyclopentane-1-carboxylic Acid Step 1: Preparation of racemic methyl trans-2-((6-chloro-1H-pyrazolo[3,4-d]pyrimidin-1-yl)methyl)cyclopentane-1-carboxylate. Prepared by general procedure D using 6-chloro-1H-pyrazolo[3,4-d]pyrimidine (1.00 g, 6.32 mmol), racemic methyl trans-2-(hydroxymethyl)cyclopentane-1-carboxylate (1.00 g, 6.32 mmol), triphenylphosphine (2.09 g, 7.90 mmol) and DEAD (3.60 mL, 7.90 mmol, 40% soln in toluene) in THF (20 mL) stirring at rt for 1 h. The crude product was purified by silica column chromatography (0%-100% EtOAc/hexane gradient) to provide the desired product as a solid (553 mg). This material was taken directly to the next step without further purification. LCMS [M+H]: 295.1

Step 2: Preparation of racemic trans-2-((6-((6-methoxy-2-methyl-1,2,3,4-tetrahydroisoquinolin-7-yl)amino)-1H-pyrazolo[3,4-d]pyrimidin-1-yl)methyl)cyclopentane-1-carboxylic acid. Prepared by general procedure A using racemic methyl trans-2-((6-chloro-1H-pyrazolo[3,4-d]pyrimidin-1-yl)methyl)cyclopentane-1-carboxylate (125.0 mg, 0.34 mmol), 6-methoxy-2-methyl-1,2,3,4-tetrahydroisoquinolin-7-amine (97.0 mg, 0.51 mmol), and p-TSA (142.0 mg, 0.74 mmol) in NMP (1.6 mL) at 110° C. for 48 h. The reaction mixture was purified using preparative HPLC providing the desired product as a solid (16 mg). $^1$H NMR (400 MHz, Methanol-d4) δ 8.92 (s, 1H), 8.44 (s, 1H), 8.05 (s, 1H), 6.93 (s, 1H), 4.61 (d, J=15.0 Hz, 1H), 4.53 (dd, J=14.0, 6.4 Hz, 1H), 4.40-4.29 (m, 2H), 3.96 (s, 3H), 3.82-3.72 (m, 1H), 3.42 (td, J=11.4, 5.1 Hz, 1H), 3.29-3.20 (m, 1H), 3.19-3.11 (m, 1H), 3.09 (s, 3H), 2.95-2.82 (m, 1H), 2.63 (q, J=8.3 Hz, 1H), 2.10-1.98 (m, 1H), 1.89-1.81 (m, 1H), 1.81-1.74 (m, 1H), 1.72-1.63 (m, 2H), 1.61-1.49 (m, 1H). LCMS [M+H]: 437.2

Example 183

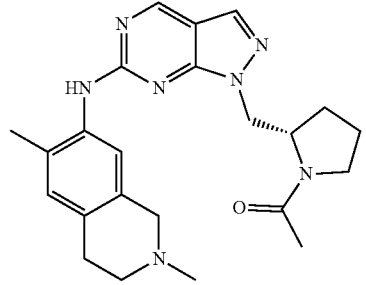 [SMILES: CC(=O)N1CCC[C@H]1Cn1ncc2cnc(Nc3cc4c(cc3C)CCN(C)C4)nc21]

(S)-1-(2-((6-((2,6-dimethyl-1,2,3,4-tetrahydroisoquinolin-7-yl)amino)-1H-pyrazolo[3,4-d]pyrimidin-1-yl)methyl)pyrrolidin-1-yl)ethan-1-one Step 1: Preparation of 6-methyl-3,4-dihydroisoquinolin-1(2H)-one. To a solution of 6-bromo-3,4-dihydro-2H-isoquinolin-1-one (3.0 g, 13.27 mmol) and 2,4,6-trimethyl-1,3,5,2,4,6-trioxatriborinane (3.00 g, 23.9 mmol, 3.34 mL) in dioxane (30 mL) were added Pd(dppf)Cl$_{12}$ (485.5 mg, 0.663 mmol) and a solution of Na2CO$_3$ (3.52 g, 33.18 mmol) in water (15 mL). Then the mixture was stirred at 80° C. under $N_2$ for 8 h. The mixture was cooled to rt, poured onto water (20 mL), and extracted with EtOAc (3×20 mL). The combined organic layers were dried over anhydrous $Na_2SO_4$, filtered, and concentrated under reduced pressure. The crude product was purified by flash silica gel chromatography (0-40% EtOAc/Petroleum ether) to give the title compound (1.6 g). LCMS [M+H]: 162.1

Step 2: Preparation of 2,6-dimethyl-3,4-dihydroisoquinolin-1(2H)-one. To a solution of 6-methyl-3,4-dihydroisoquinolin-1(2H)-one (1.50 g, 9.31 mmol) in THF (30 mL) was added sodium hydride (930.4 mg, 23.3 mmol, 60% purity) at 0° C. The mixture was then stirred at 20° C. for 30 min, followed by cooling to 0° C. A solution of iodomethane (3.30 g, 23.26 mmol, 1.45 mL) in THF (15 mL) was added dropwise at 0° C. The resulting mixture was stirred at 30° C. for 2 h. The reaction was quenched by the addition of water (50 mL), then extracted with EtOAc (3×50 mL). The combined organic layers were dried over anhydrous $Na_2SO_4$, filtered and concentrated under reduced pressure. The residue was purified by flash silica gel chromatography (0-40% EtOAc/Petroleum ether gradient) to give the title compound (1.4 g). LCMS: 176.2

Step 3: Preparation of 2,6-dimethyl-7-nitro-3,4-dihydroisoquinolin-1(2H)-one. To a solution of 2,6-dimethyl-3,4-dihydroisoquinolin-1(2H)-one (700.0 mg, 3.99 mmol) in sulfuric acid (9 mL) was added nitric acid (251.7 mg, 3.99 mmol, 0.180 mL) at 0° C. dropwise. The mixture was stirred at 0° C. for 1 h. The reaction was quenched by the addition of NaOH to pH 9 and extracted with EtOAc (3×80 mL). The combined organic layer was dried over anhydrous Na2SO$_4$, filtered, and concentrated under reduced pressure. The residue was purified by flash silica gel chromatography (0-50% EtOAc/Petroleum ether gradient) to give the title compound (720 mg). LCMS: 221.1

Step 4: Preparation of 2,6-dimethyl-7-nitro-1,2,3,4-tetrahydroisoquinoline. To a solution of 2,6-dimethyl-7-nitro-3,4-dihydroisoquinolin-1(2H)-one (720.0 mg, 3.27 mmol) in THF (15 mL) was added $BH_3$ THF (1 M, 8.17 mL) at 0° C. The mixture was stirred at 65° C. for 16 h. The reaction was quenched by MeOH (5 mL) and concentrated under reduced pressure. The residue was adjusted by 1N HCl to pH ~1 and stirred at 65° C. for 6 h. Then the mixture was adjusted by aqueous sodium carbonate to pH ~9 and extracted with DCM (3×20 mL). The combined organic layer was dried over anhydrous $Na_2SO_4$, filtered and concentrated under reduced pressure. The residue was purified by flash silica gel chromatography (0-0.6% MeOH/DCM gradient) to give the title compound (650 mg). LCMS [M+H]: 207.2

Step 5: Preparation of 2,6-dimethyl-1,2,3,4-tetrahydroisoquinolin-7-amine. To a solution of 2,6-dimethyl-7-nitro-1,2,3,4-tetrahydroisoquinoline (300 mg, 1.45 mmol) in EtOH (6 mL) was added iron (649.9 mg, 11.6 mmol) and ammonium chloride (466.8 mg, 8.73 mmol) in water (2 mL). The mixture was stirred at 80° C. for 2 h. The reaction was then diluted with water (3 mL) and extracted with EtOAc (3×10 mL). The combined organic layers were dried over anhydrous $Na_2SO_4$, filtered, and concentrated under reduce pressure. The residue was purified by flash silica gel chromatography (0-4% MeOH/DCM gradient) to give the title compound (147 mg). LCMS [M+H]: 177.2

Step 6: Preparation of (S)-1-(2-((6-((2,6-dimethyl-1,2,3,4-tetrahydroisoquinolin-7-yl)amino)-1H-pyrazolo[3,4-d]pyrimidin-1-yl)methyl)pyrrolidin-1-yl)ethan-1-one. Prepared according to general procedure A using 2,6-dimethyl-3,4-dihydro-1H-isoquinolin-7-amine (50 mg, 0.284 mmol), 1-[(2S)-2-[(6-chloropyrazolo[3,4-d]pyrimidin-1-yl)methyl]pyrrolidin-1-yl]ethanone (87.3 mg, 0.312 mmol) (EXAMPLE 62, Step 2) and p-TsOH (122.2 mg, 0.709 mmol) in 2-butanol (1.2 mL) and stirred at 100° C. for 16 h. under $N_2$. The reaction mixture was combined with another batch (20 mg). The combined mixture was basified with aqueous sodium bicarbonate to pH 8 and extracted with DCM (3×30 mL). The combined organic layers were dried over $Na_2SO_4$ and filtered. The filtrate was evaporated to give a crude product, which was then purified by reverse phase HPLC (column: Boston Prime C18 150*30 mm*5 um; mobile phase: [water(0.05% $NH_3H_2O$+10 mM $NH_4HCO_3$)-ACN]; B %: 30%-60%, 7 min). After lyophilization the free amine was dissolved in $H_2O$ (10 mL) and treated with HCl (1 M, 4 drops). The solution was lyophilized to give the HCl salt of the title compound (56.8 mg). $^1$H NMR (400 MHz, Deuterium oxide) δ ppm 8.70-8.62 (d, 1H), 7.94-7.87 (d, 1H), 7.31-7.16 (d, 1H), 7.04-7.01 (d, 1H), 4.35-4.00 (m, 3H), 3.73-3.55 (m, 2H), 3.31-3.19 (m, 1H), 3.17-3.04 (m, 1H), 2.87 (br s, 4H), 2.56-2.42 (d, 3H), 2.11-2.02 (d, 3H), 1.90-1.68 (m, 3.5 H), 1.64 (s, 2H), 1.46 (s, 1H), 1.46-1.43 (m, 0.5 H). LCMS [M+H]: 420.1

Example 184

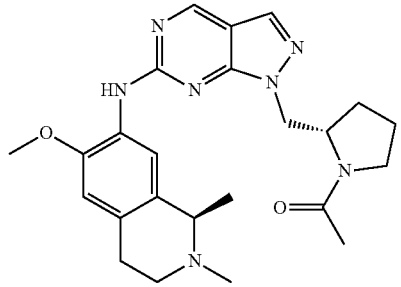 [SMILES: COc1cc2c(cc1Nc1ncc3cnn(C[C@@H]4CCCN4C(C)=O)c3n1)[C@@H](C)N(C)CC2]

1-((S)-2-((6-(((R)-6-methoxy-1,2-dimethyl-1,2,3,4-tetrahydroisoquinolin-7-yl)amino)-1H-pyrazolo[3,4-d]pyrimidin-1-yl)methyl)pyrrolidin-1-yl)ethan-1-one Step 1: Preparation of (R)-1-(4-methoxyphenyl)-N-(2-(phenylthio)ethyl)ethan-1-amine. A mixture of (1R)-1-(4-methoxyphenyl)ethanamine (5 g, 33.07 mmol), 2-chloroethylsulfanylbenzene (6.85 g, 39.68 mmol), $Na_2CO_3$ (3.50 g, 33.07 mmol) and NaI (2.48 g, 16.53 mmol) and TBAB (1.07 g, 3.31 mmol) in toluene (80 mL) was refluxed (115° C.) for 24 h. After being cooled to ambient temperature, the mixture was combined with another batch reaction (3 g of compound 1). The combined mixture was filtered and concentrated. The residue was purified by flash silica gel chomatography (ISCO®; 80 g SepaFlash® Silica Flash Column, Eluent of 0-40% EtOAc (1% NH3)/Petroleum ether gradient @ 60 mL/min) to give the desired compound (4.3 g, for two batches). $^1$H NMR (400 MHz, CDCl3) δ: 7.24-7.09 (m, 7H), 6.79-6.76 (m, 1H), 3.72 (s, 3H), 3.67-3.62 (q, J=6.4 Hz, 1H), 2.97-2.93 (t, J=6.4 Hz, 2H), 2.69-2.55 (m, 2H), 1.27-1.24 (d, J=6.4 Hz, 3H). LCMS [M+H]: 288.1

Step 2: Preparation of (R)—N-(1-(4-methoxyphenyl)ethyl)-N-(2-(phenylthio)ethyl)formamide. A mixture of formic acid (19.05 g, 396.6 mmol) and acetic anhydride (13.50 g, 132.2 mmol, 12.3 mL) were stirred at 50° C. for 15 min and then poured to a flask charged with (1R)-1-(4-methoxyphenyl)-N-(2-phenylsulfanylethyl)ethanamine (3.8 g, 13.2 mmol). The solution was stirred at 70° C. for 30 min. Then the reaction mixture was combined with another batch (0.5 g). The combined mixture was concentrated under reduced pressure. The residue was diluted with EtOAc (30 mL) and basified with saturated sodium carbonate aqueous solution. The organic layer was separated and extracted with EtOAc (3×30 mL). The combined organic layer was dried over anhydrous sodium sulfate, filtered, and concentrated under reduced pressure. The residue was purified by flash silica gel chomatography (0-50% EtOAc/petroleum ether) to give the desired product (4.16 g). $^1$H NMR (400 MHz, CDCl3) δ: 8.39 (s, 0.7H), 8.15 (s, 0.3H), 7.29-7.15 (m, 7H), 6.91-6.86 (m, 2H), 5.77-5.70 (q, J=6.8 Hz, 0.25H), 4.78-4.72 (q, J=6.8 Hz, 0.75H), 3.84-3.83 (m, 3H), 3.40-3.33 (m, 0.7H), 3.29-3.16 (m, 1.3H), 3.05-2.96 (m, 0.7H), 2.82-2.74 (m, 0.8H), 2.65-2.60 (m, 0.5H), 1.61-1.58 (d, J=7.2 Hz, 2H), 1.52-1.49 (d, J=7.2 Hz, 1H). LCMS [M+H]: 338.1

Step 3: Preparation of N-((R)-1-(4-methoxyphenyl)ethyl)-N-(2-(phenylsulfinyl)ethyl)formamide. A solution of sodium periodate (3.36 g, 15.69 mmol, 869.58 uL) in $H_2O$ (25 mL) was added to the solution of N-[(1R)-1-(4-methoxyphenyl)ethyl]-N-(2-phenylsulfanylethyl)formamide (3.3 g, 10.46 mmol) in MeOH (125 mL) and the reaction mixture was stirred at 20° C. for 4 h. The mixture was combined with another batch of reaction (0.8 g of compound 3). The combined mixture was filtered and concentrated under reduced pressure. The residue was purified by flash silica gel chomatography (0-90% EtOAc/Petroleum ether gradient) to give the desired product (3.1 g). $^1$H NMR (400 MHz, CDCl3) δ: 8.31-8.03 (m, 1H), 7.51-7.36 (m, 5H), 7.27-7.09 (m, 2H), 6.84-6.77 (m, 2H), 5.77-5.60 (m, 0.2H), 6.75-4.64 (m, 0.8H), 3.76-3.74 (m, 3H), 3.52-3.16 (m, 2H), 3.08-2.15 (m, 2H), 1.60-1.54 (m, 2.4H), 1.45-1.39 (m, 0.6H). LCMS [M+H]: 332.1

Step 4: Preparation of (1R)-6-methoxy-1-methyl-4-(phenylthio)-3,4-dihydroisoquinoline-2(1H)-carbaldehyde. N-[2-(Benzenesulfinyl)ethyl]-N-[(1R)-1-(4-methoxyphenyl)ethyl]formamide (3.00 g, 9.05 mmol) was dissolved in toluene (75 mL) and treated with TFAA (9.51 g, 45.26 mmol, 6.30 mL) at 20° C. and the mixture was stirred for 1 h. Then BF$_3$·Et$_2$O (3.85 g, 27.2 mmol, 3.35 mL) was added to the reaction mixture and the resultant mixture was stirred at 20° C. for another 1 h. The reaction was combined with another batch of Pummerer reaction (800 mg of N-[2-(benzenesulfinyl)ethyl]-N-[(1R)-1-(4-methoxyphenyl) ethyl]formamide. The mixture was diluted with water/NaHCO$_3$ (20 mL, saturated) and extracted with EtOAc (2×70 mL). The combined organic layer was dried over anhydrous Na2SO$_4$, filtered and concentrated under reduced pressure. The residue was purified by flash silica gel chomatography (0-40% EtOAc/Petroleum ether gradient) to give the desired product (3.0 g). $^1$H NMR (400 MHz, CDCl3) δ: 8.44 (s, 0.2H), 7.99 (s, 0.8H), 7.66-7.63 (m, 0.4H), 7.48-7.43 (m, 1.6H), 7.39-7.30 (m, 3H), 7.10-7.04 (m, 1H), 63.88-6.80 (m, 2H), 5.49-5.43 (q, J=6.8 Hz, 0.8H), 4.83-4.77 (q, J=6.8 Hz, 0.3H), 4.60-4.56 (d, J=13.2 Hz, 0.2H), 4.46 (s, 0.8H), 4.31 (s, 0.2H), 3.83 (s, 0.2H), 3.80-3.79 (m, 2.8H), 3.75-3.70 (dd, J=14.0 Hz, 2.4 Hz, 0.8H), 3.56-3.51 (d, J=14 Hz, 0.8H), 3.27-3.22 (dd, J=14 Hz, 3.2 Hz), 1.51-1.48 (d, J=6.8 Hz, 0.8H), 1.45-1.42 (d, J=6.8 Hz, 2.2H). LCMS [M+H]: 314.1

Step 5: Preparation of (R)-6-methoxy-1-methyl-3,4-dihydroisoquinoline-2(1H)-carbaldehyde. Sodium borohydride (2.90 g, 76.6 mmol) was added in portions to a solution of (1R)-6-methoxy-1-methyl-4-phenylsulfanyl-3,4-dihydro-1H-isoquinoline-2-carbaldehyde (2.40 g, 7.66 mmol) and NiCl$_2$·6H$_2$O (6.37 g, 26.8 mmol) in MeOH (88 mL) and THF (32 mL) at 0° C. The mixture was stirred at 20° C. for 2 h. This batch was combined with another batch of reduction material (600 mg, 1.91 mmol). The combined mixture was filtered and concentrated. The residue was diluted with water (20 mL) and extracted with DCM (2×20 mL). The combined organic layer was dried over anhydrous Na$_2$SO$_4$, filtered and concentrated. The residue was purified by flash silica gel chomatography (0-80% EtOAc/Petroleum ether gradient) to give the desired product (1.41 g). 1H NMR (400 MHz, CDCl3) δ: 8.31 (s, 0.4H), 8.16 (s, 0.6H), 7.10-7.04 (m, 1H), 6.83-6.78 (m, 1H), 6.68-6.64 (dd, J=10. 4 Hz, 2.4 Hz, 1H), 5.46-5.40 (q, J=6.8 Hz, 0.6H), 4.80-4.74 (q, J=6.8 Hz, 0.4H), 4.49-4.42 (m, 0.4H), 3.82-3.80 (m, 3H), 3.73-3.68 (m, 0.6H), 3.60-3.52 (td, J=12.4 Hz, 3.6 Hz, 0.6H), 3.21-3.13 (m, 0.4H), 3.01-2.90 (m, 1H), 2.85-2.74 (m, 1H). LCMS [M+H]: 206.2

Step 6: Preparation of (R)-6-methoxy-1-methyl-7-nitro-3,4-dihydroisoquinoline-2(1H)-carbaldehyde. To a solution of (1R)-6-methoxy-1-methyl-4,4-dihydro-1H-isoquinoline-2-carbaldehyde (1.0 g, 4.87 mmol) in TFA (15 mL) was added a solution of HNO3 (337.70 mg, 5.36 mmol, 241.22 uL) in TFA (3.0 mL) dropwise at 0° C. The reaction mixture was stirred at 0° C. for 1 h. The mixture was combined with another batch of nitration of compound 6 (400 mg, 1.95 mmol). The combined mixture was poured to aqueous NaHCO$_3$ (200 mL) and extracted with DCM (2×100 mL). The combined organic layer was dried over anhydrous Na2SO$_4$, filtered and concentrated under reduced pressure. The residue was sent to prep-HPLC (column: Xtimate C18 150*40 mm*5 um; mobile phase: [water(0.05% NH3H2O)-ACN]; B %: 22%-52%,8 min) to give the desired product (630 mg, for the combined batch). $^1$H NMR (400 MHz, CDCl3) δ: 8.29 (s, 0.4H), 8.15 (s, 0.6H), 7.70 (s, 1H), 6.83-6.80 (d, J=11.6 Hz, 1H), 5.49-5.43 (q, J=6.4 Hz, 0.6H), 4.83-4.77 (q, J=6.4 Hz, 0.4H), 4.54-4.48 (dd, J=13.2 Hz, 6.0 Hz, 0.4H), 3.95-3.93 (m, 3H), 3.78-3.72 (dd, J=13.2 Hz, 5.6 Hz, 0.6H), 3.57-3.50 (m, 0.6H), 3.18-3.10 (m, 0.4H), 3.05-2.81 (m, 2H). LCMS [M+H]: 251.1

Step 7: Preparation of (R)-6-methoxy-1,2-dimethyl-7-nitro-1,2,3,4-tetrahydroisoquinoline. (1R)-6-methoxy-1-methyl-7-nitro-3,4-dihydro-1H-isoquinoline-2-carbaldehyde (250 mg, 0.999 nmol) was dissolved in THF (8 mL) and treated with borane/THF (1 M, 3.00 mL). The mixture was stirred at 60° C. for 3 h. The reaction mixture was quenched with MeOH (2 mL) and concentrated. The residue was diluted with MeOH (2 mL) and acidified with HCl (1 M) to pH=1. The mixture was stirred at 70° C. for 6 h. After being cooled to ambient temperature, the solution was concentrated. The residue was diluted with saturated sodium carbonate (aq, 10 mL) and extracted with DCM (2×20). The combined DCM layer was dried over anhydrous sodium sulfate, filtered, and concentrated under reduced pressure. The residue was combined with another batch of crude product (20 mg, 0.080 mmol) and purified by flash silica gel chomatography (0-2% MeOH/DCM gradient) to give the desired product (230 mg for the combined batches). $^1$H NMR (400 MHz, CDCl3) δ: 7.70 (s, 1H), 6.78 (s, 1H), 3.94 (s, 1H), 3.62-3.56 (q, J=6.4 Hz, 1H), 3.08-2.83 (m, 3H), 2.70-2.63 (m, 1H), 2.49 (s, 3H), 1.42-1.39 (d, J=6.8 Hz, 3H). LCMS [M+H]: 237.1

Step 8: Preparation of (R)-6-methoxy-1,2-dimethyl-1,2,3,4-tetrahydroisoquinolin-7-amine. (1R)-6-methoxy-1,2-dimethyl-7-nitro-3,4-dihydro-1H-isoquinoline (200 mg, 0.846 mmol) was dissolved in EtOH (4.0 mL) and treated with iron (236.4 mg, 4.23 mmol) and NH$_4$Cl (226.4 mg, 4.23 mmol) in water (0.8 mL). The mixture was stirred at 80° C. for 2 h. The mixture was combined with another batch of reduced material (30 mg, 0.127 mmol). The combined mixture was filtered and concentrated under reduced pressure. The residue was purified by flash silica gel chomatography (0-6% MeOH/DCM gradient) to give the desired product (1R)-6-methoxy-1,2-dimethyl-3,4-dihydro-1H-isoquinolin-7-amine (160 mg). LCMS [M+H]: 207.1

Step 9: Preparation of 1-((S)-2-((6-(((R)-6-methoxy-1,2-dimethyl-1,2,3,4-tetrahydroisoquinolin-7-yl)amino)-1H-pyrazolo[3,4-d]pyrimidin-1-yl)methyl)pyrrolidin-1-yl) ethan-1-one. Prepared according to general procedure A using 1-[(2S)-2-[(6-chloropyrazolo[3,4-d]pyrimidin-1-yl) methyl]pyrrolidin-1-yl]ethanone (50 mg, 0.179 mmol) (EXAMPLE 62, Step 2), (1R)-6-methoxy-1,2-dimethyl-3,4-dihydro-1H-isoquinolin-7-amine (36.9 mg, 0.179 mmol), and p-TSA (67.7 mg, 0.393 mmol) in dissolved in 2-butanol (1.5 mL) stirred at 100° C. for 30 h. The mixture was diluted with water/NaHCO$_3$ (10 mL) and extracted with DCM (2×20 mL). The combined organic layer was dried over anhydrous sodium sulfate, filtered, and concentrated under reduced pressure. The residue was purified by flash silica gel chomatography (0-16% MeOH/DCM gradient). The obtained product was further purified using reverse phase HPLC (column: Welch Xtimate C18 150*30 mm*5 um; mobile phase: [water(0.05% NH3H2O+10 mM NH4HCO3)-ACN]; B %: 35%-65%,9 min). After lyophilization the solid was dissolved in water (10 mL) and 3 drops of HCl solution (1 M) was added. The solution was submitted to lyophilization again to give the desired product (18 mg). $^1$H NMR (400 MHz, Deuterium oxide, mixture of rotomers) δ: 8.86-8.82 (m, 1H), 8.10 (s, 0.2H), 8.04-8.02 (d, J=2.4 Hz, 0.8H), 7.87 (s, 0.8H), 7.61-7.60 (d, J=2.0 Hz, 0.2H), 6.97-6.90 (m, 1H), 4.60-4.15 (m, 4H), 3.84-3.81 (m, 3H), 3.76-3.69 (m, 0.6H), 3.58-3.52 (m, 0.8H), 3.44-3.37 (m, 0.6H), 3.30-3.07 (m, 3H), 3.05-2.94 (m, 3H), 2.91-2.89 (m, 3H), 2.01-1.81 (m, 2H), 1.79-1.65 (m, 4H), 1.62-1.56 (m, 2.3H), 1.50 (s, 0.7H), 1.26-1.13 (m, 1H). LCMS [M+H]: 450.3

Example 185

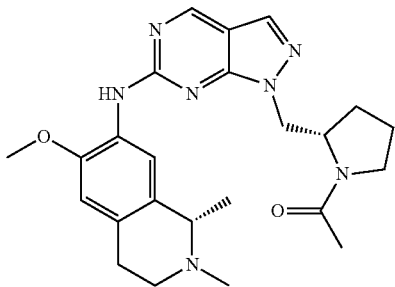 [SMILES: COc1cc2c(cc1Nc1ncc3cnn(C[C@@H]4CCCN4C(C)=O)c3n1)[C@H](C)N(C)CC2]

1-((S)-2-((6-(((S)-6-methoxy-1,2-dimethyl-1,2,3,4-tetrahydroisoquinolin-7-yl)amino)-1H-pyrazolo[3,4-d]pyrimidin-1-yl)methyl)pyrrolidin-1-yl)ethan-1-one hydrochloride Prepared according to EXAMPLE 184 substituting (1S)-1-(4-methoxyphenyl)ethanamine for (1R)-1-(4-methoxyphenyl)ethanamine to provide the title compound (47 mg). [M+H]: 450.3

Example 186

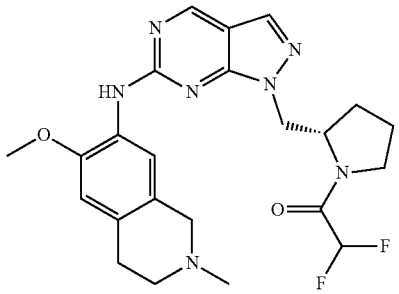 [SMILES: COc1cc2c(cc1Nc1ncc3cnn(C[C@@H]4CCCN4C(=O)C(F)F)c3n1)CN(C)CC2]

(S)-2,2-difluoro-1-(2-((6-(((6-methoxy-2-methyl-1,2,3,4-tetrahydroisoquinolin-7-yl)amino)-1H-pyrazolo[3,4-d]pyrimidin-1-yl)methyl)pyrrolidin-1-yl)ethan-1-one Step 1: Preparation of (S)-6-chloro-1-(pyrrolidin-2-ylmethyl)-1H-pyrazolo[3,4-d]pyrimidine. To a solution of tert-butyl (S)-2-((6-chloro-1H-pyrazolo[3,4-d]pyrimidin-1-yl)methyl)pyrrolidine-1-carboxylate (EXAMPLE 110, Step 1) (13.9 gram, 36.5 mmol) in DCM (50 mL) was added 4M soln of HCl in dioxane (22 mL, 88.0 mmol) at room temperature. The reaction mixture was stirred at room temperature overnight and then heated at 50° C. for 2 h. The reaction was concentrated, filtered and washed with DCM to give (S)-6-chloro-1-(pyrrolidin-2-ylmethyl)-1H-pyrazolo[3,4-d]pyrimidine as HCl salt (3.91 gram). This material was taken directly to the next step without further purification.

Step 2: Preparation of (S)-1-(2-((6-chloro-1H-pyrazolo[3,4-d]pyrimidin-1-yl)methyl)pyrrolidin-1-yl)-2,2-difluoroethan-1-one. To a solution of (S)-6-chloro-1-(pyrrolidin-2-ylmethyl)-1H-pyrazolo[3,4-d]pyrimidine (300 mg, 1.09 mmol) and 2,2-difluoroacetic acid (0.103 mL, 1.64 mmol) in DMF (4.0 mL) and EtOAc (1.0 mL) were added methylimidazole (898 mg, 10.9 mmol) and 1-propylphosphonic acid cyclic anhydride, 50+% soln. in EtOAc (1.63 mL, 2.74 mmol). The mixture was stirred at rt for 0.5 h before being purified by silica gel chromatography (0% to 100% EtOAc in hexane) providing the desire product a as free base (402 mg). LCMS [M+H]: 316.0. This material was taken directly to the next step without further purification.

Step 3: Preparation of (S)-2,2-difluoro-1-(2-((6-((6-methoxy-2-methyl-1,2,3,4-tetrahydroisoquinolin-7-yl)amino)-1H-pyrazolo[3,4-d]pyrimidin-1-yl)methyl)pyrrolidin-1-yl)ethan-1-one. Prepared by general procedure A using (S)-1-(2-((6-chloro-1H-pyrazolo[3,4-d]pyrimidin-1-yl)methyl)pyrrolidin-1-yl)-2,2-difluoroethan-1-one (80.0 mg, 0.250 mmol), 6-methoxy-2-methyl-1,2,3,4-tetrahydroisoquinolin-7-amine (73.1 mg, 0.38 mmol), and p-TSA (106 mg, 0.56 mmol) in 2-butanol (0.80 mL) at 120° C. overnight. The reaction was concentrated in vacuo to remove solvent and the mixture was purified using preparative HPLC providing the desired product as the HCl salt (53 mg). $^1$H NMR (400 MHz, Methanol-d4) δ 9.01 (s, 1H), 8.62 (d, J=11.8 Hz, 1H), 8.16 (s, 1H), 6.95 (s, 1H), 6.26 (td, J=53.3, 4.6 Hz, 1H), 4.89-4.80 (m, 2H), 4.65-4.45 (m, 2H), 4.45-4.29 (m, 1H), 3.98 (s, 3H), 3.82-3.72 (m, 1H), 3.64-3.53 (m, 1H), 3.53-3.37 (m, 2H), 3.29-3.23 (m, 1H), 3.19-3.11 (m, 1H), 3.08 (s, 3H), 2.31-2.16 (m, 1H), 2.06-1.90 (m, 2H), 1.87-1.74 (m, 1H). LCMS [M+H]: 472.2

Example 187

(1r,4r)-4-(6-((2-methoxy-6-methyl-5,6,7,8-tetrahydro-1,6-naphthyridin-3-yl)amino)-1H-pyrazolo[3,4-d]pyrimidin-1-yl)cyclohexan-1-ol Prepared by general procedure B using 1-((1r,4r)-4-((tert-butyldimethylsilyl)oxy)cyclohexyl)-6-chloro-1H-pyrazolo[3,4-d]pyrimidine (100 mg, 0.27 mmol) (EXAMPLE 58, Step 2), 2-methoxy-6-methyl-5,6,7,8-tetrahydro-1,6-naphthyridin-3-amine (68.5 mg, 0.35 mmol) (EXAMPLE 170, step 4), Pd₂(dba)₃ (37 mg, 0.15 mmol), potassium tert-butoxide (40 mg, 0.35 mmol), and (S)-BINAP (59 mg, 0.10 mmol) in THF (1.6 mL) and 2-butanol at 80° C. using a microwave reactor for 2 h. The reaction mixture was purified using preparative HPLC providing the desired product (1r,4r)-4-(6-((2-methoxy-6-methyl-5,6,7,8-tetrahydro-1,6-naphthyridin-3-yl)amino)-1H-pyrazolo[3,4-d]pyrimidin-1-yl)cyclohexan-1-ol as a solid TFA salt. The TFA salt obtained was basified using Na₂CO₃, extracted with EtOAc, and the combined organic extracts were concentrated to provide the free base. The free base was converted into the mesylate by adding 1 equiv. of methanesulfonic acid, providing the desire product as a solid (3.6 mg). ¹H NMR (400 MHz, Methanol-d4) δ 8.95 (s, 1H), 8.69 (s, 1H), 8.06 (s, 1H), 4.77-4.64 (m, 1H), 4.57 (d, J=14.9 Hz, 1H), 4.41 (d, J=14.8 Hz, 11H), 4.07 (s, 3H), 3.89-3.80 (m, 1H), 3.78-3.68 (m, 1H), 3.61-3.48 (m, 1H), 3.28-3.20 (m, 1H), 3.12 (s, 3H), 2.70-2.68 (m, 4H), 2.23-2.11 (m, 4H), 2.10-2.01 (m, 2H), 1.63-1.51 (m, 2H). LCMS [M+H]: 410.2

Example 188

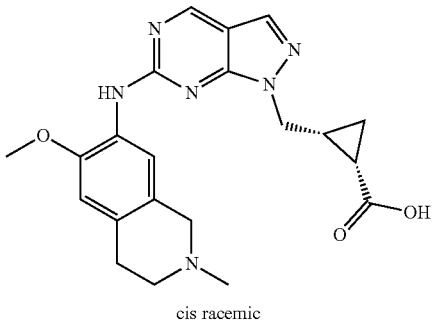 [SMILES: COc1cc2c(cc1Nc1ncc3cnn(C[C@@H]4C[C@@H]4C(=O)O)c3n1)CN(C)CC2]

cis racemic (cis)-2-((6-(((6-methoxy-2-methyl-1,2,3,4-tetrahydroisoquinolin-7-yl)amino)-1H-pyrazolo[3,4-d]pyrimidin-1-yl)methyl)cyclopropane-1-carboxylic Acid Step 1: Preparation of racemic ethyl (cis)-2-((6-chloro-1H-pyrazolo[3,4-d]pyrimidin-1-yl)methyl)cyclopropane-1-carboxylate. Prepared by general procedure D using 6-chloro-1H-pyrazolo[3,4-d]pyrimidine (0.88 gram, 5.69 mmol), racemic ethyl (cis)-2-(hydroxymethyl)cyclopropane-1-carboxylate (0.82 g, 5.69 mmol), triphenylphosphine (2.99 g, 11.40 mmol) and DIAD (2.24 mL, 11.40 mmol) in THF (30 mL) with stirring at rt for 1 h. The crude product was purified by silica column chromatography eluting with 0% to 100% EtOAc in hexane and then purified again using reverse phase HPLC with 0% to 100% MeCN (with 0.1% TFA added) in water (with 0.1% TFA added), to provide the desired product as TFA salt (493 mg). LCMS [M+H]: 281.1. This material was taken directly to the next step without further purification.

Step 2: Preparation of racemic ethyl (cis)-2-((6-((6-methoxy-2-methyl-1,2,3,4-tetrahydroisoquinolin-7-yl)amino)-1H-pyrazolo[3,4-d]pyrimidin-1-yl)methyl)cyclopropane-1-carboxylate. Prepared by general procedure A using racemic ethyl (cis)-2-((6-chloro-1H-pyrazolo[3,4-d]pyrimidin-1-yl)methyl)cyclopropane-1-carboxylate (109 mg, 0.27 mmol), 6-methoxy-2-methyl-1,2,3,4-tetrahydroisoquinolin-7-amine (79.6 mg, 0.41 mmol), and p-TSA (116 mg, 0.60 mmol) in NMP (1.5 mL) with stirring at 110° C. overnight. The reaction mixture was diluted with EtOH (0.60 mL) and stirred for an additional 6 h. The crude product was purified using reversed phase HPLC eluting with 0% to 100% MeCN (with 0.1% TFA added) in water (with 0.1% TFA added), to provide the desired product as the TFA salt. The TFA salt obtained was basified using Na2CO3 and extracted with DCM to provide the desired product as the free base (87 mg). ¹H NMR (400 MHz, Methanol-d4) δ 8.77 (s, 1H), 8.42 (s, 1H), 7.93 (s, 1H), 6.70 (s, 1H), 4.68 (ddd, J=14.4, 7.6, 1.6 Hz, 1H), 4.40 (ddd, J=14.5, 6.6, 1.6 Hz, 1H), 4.15-4.06 (m, 2H), 3.88 (d, J=1.6 Hz, 3H), 3.74-3.59 (m, 2H), 2.88 (t, J=6.2 Hz, 2H), 2.70 (t, J=6.0 Hz, 2H), 2.44 (d, J=1.6 Hz, 3H), 2.00-1.80 (m, 2H), 1.28-1.22 (m, 1H), 1.17 (td, J=7.1, 1.5 Hz, 3H), 1.13-1.06 (m, 1H). LCMS [M+H]: 437.2

Step 3: Preparation of racemic (cis)-2-((6-(((6-methoxy-2-methyl-1,2,3,4-tetrahydroisoquinolin-7-yl)amino)-1H-pyrazolo[3,4-d]pyrimidin-1-yl)methyl)cyclopropane-1-carboxylic acid. To a solution of racemic ethyl (1S,2R)-2-((6-(((6-methoxy-2-methyl-1,2,3,4-tetrahydroisoquinolin-7-yl)amino)-1H-pyrazolo[3,4-d]pyrimidin-1-yl)methyl)cyclopropane-1-carboxylate (74 mg, 0.17 mmol) in THF (1.5 mL) and water (0.75 mL) was added lithium hydroxide (32 mg, 1.36 mmol). The reaction mixture was stirred at room temperature overnight. The reaction was concentrated in vacuo to remove solvent and the mixture was purified using preparative HPLC to provide the title compound (44 mg). ¹H NMR (400 MHz, Methanol-d4) δ 9.07 (s, 11H), 8.48 (s, 1H), 8.27 (s, 11H), 6.97 (s, 1H), 4.87-4.65 (m, 3H), 4.61-4.44 (m, 1H), 4.42-4.21 (m, 1H), 3.96 (s, 3H), 3.83-3.64 (m, 1H), 3.53-3.35 (m, 11H), 3.21-3.13 (m, 11H), 3.07 (s, 3H), 2.10-1.80 (m, 2H), 1.37-0.93 (m, 2H). LCMS [M+H]: 409.3

Example 189

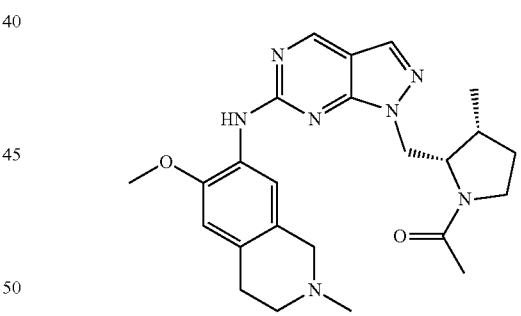

1-((2S,3R)-2-((6-(((6-methoxy-2-methyl-1,2,3,4-tetrahydroisoquinolin-7-yl)amino)-1H-pyrazolo[3,4-d]pyrimidin-1-yl)methyl)-3-methylpyrrolidin-1-yl)ethan-1-one Step 1: Preparation of (S)—N-(1-phenylethyl)but-3-en-1-amine. A mixture of 4-bromobut-1-ene (5 g, 37.04 mmol, 3.76 mL), K₂CO₃ (15.36 g, 111.1 mmol), sodium iodide (16.65 g, 111.1 mmol) and (1S)-1-phenylethanamine (5.83 g, 48.15 mmol, 6.13 mL) in DMF (50 mL) was heated to 100° C. for 16 h. The mixture was diluted with water (200 mL) and extracted with EtOAc (3×30 mL). The combined organic layers were washed with water (3×20 mL), then brine (20 mL), dried over anhydrous Na2SO4, and filtered.

The filtrate was evaporated to give a crude product, which was purified by flash silica gel chromatography (0-10% EtOAc/Petroleum ether gradient) to give the title compound (4.3 g). LCMS [M+H]: 176.2

Step 2: Preparation of ethyl (S)—N-(but-3-en-1-yl)-N-(1-phenylethyl)glycinate. To a mixture of (S)—N-(1-phenylethyl)but-3-en-1-amine (4.3 g, 24.53 mmol) in dry DMSO (45 mL) was slowly added ethyl 2-bromoacetate (4.92 g, 29.44 mmol, 3.26 mL) and Et$_3$N (2.98 g, 29.44 mmol, 4.10 mL). The mixture was heated to 50° C. and stirred for 16 h. The reaction mixture combined with a second batch (300 mg) and the combined batches were diluted with water (50 mL) and extracted with EtOAc (3×100 mL). The combined organic layer was washed with water (3×30 mL) and brine (30 mL), dried over Na2SO$_4$ and filtered. The filtrate was evaporated to give a crude product. The crude product was purified by flash silica gel chromatography (0-2% EtOAc/Petroleum ether gradient) to give a mixture of the title compound (3.5 g) and starting material (1.3 g). This mixture was taken forward without further purification. LCMS [M+H]: 262.2

Step 3: Preparation of ethyl (2S,3R)-3-methyl-1-((S)-1-phenylethyl)pyrrolidine-2-carboxylate. N-isopropylpropan-2-amine (1.01 g, 9.95 mmol, 1.41 mL) was dissolved in THF (10 mL) and the solution was treated with n-butyl lithium (2.5 M, 3.98 mL) at −40° C. under N$_2$. The mixture was warmed to 0° C. and stirred for 10 min. Then the mixture was cooled back to −40° C. and treated with ethyl 2-[but-3-enyl-[(1S)-1-phenylethyl]amino]acetate (2 g, 7.65 mmol) in THF (10 mL) dropwise. Then the mixture was warmed to 0° C. and stirred for 10 min. The mixture was cooled to −40° C. and ZnBr$_2$ (3.79 g, 16.84 mmol, 0.843 mL) in THF (10 mL) was added dropwise. Then the mixture was warmed to rt and stirred for 3 h. The mixture was cooled to 0° C. and a solution of 1:1 NH$_4$Cl (10 g)/ammonia hydroxide (10 mL) was added slowly to the reaction mixture, followed by sodium sulfide hydrate (500 mg). The mixture was stirred for 12 hr at rt. Water (20 mL) was added and the mixture was extracted with EtOAc (3×50 mL). The combined organic layers were washed with brine (50 mL), dried over Na$_2$SO$_4$, filtered, and concentrated to give a crude product. The crude product was purified by flash silica gel chromatography (0-10% EtOAc/Petroleum ether gradient) to give the title compound (1.2 g) and residual starting material (500 mg). The mixture was taken forward without further purification. LCMS [M+H]: 262.2

Step 4: Preparation of ethyl (2S,3R)-3-methylpyrrolidine-2-carboxylate. To a solution of ethyl (2S, 3R)-3-methyl-1-[(1S)-1-phenylethyl]pyrrolidine-2-carboxylate (800 mg, 3.06 mmol) in EtOH (5 mL) was added Pd/C (50 mg, 10% purity) under N$_2$. The suspension was degassed under vacuum and purged with H$_2$ several times. The mixture was stirred under H2 (balloon, 15 PSI) at 20° C. for 16 h. The reaction mixture combined with another batch (500 mg) was filtered and the filtrate was concentrated to give the title compound (600 mg), which was used in the next step directly. LCMS [M+H]: 158.1

Step 5: Preparation of ethyl (2S,3R)-1-acetyl-3-methylpyrrolidine-2-carboxylate. A mixture of ethyl (2S, 3R)-3-methylpyrrolidine-2-carboxylate (600 mg, 3.82 mmol), Ac$_2$O (467.55 mg, 4.58 mmol, 0.430 uL) and TEA (772.39 mg, 7.63 mmol, 1.06 mL) in DCM (7 mL) was stirred at rt for 16 h. The reaction mixture was evaporated to give a crude product. The crude product was purified by flash silica gel chromatography (0-4% MeOH/DCM gradient) to give the title compound (460 mg). LCMS [M+H]: 200.2

Step 6: Preparation of 1-((2S,3R)-2-(hydroxymethyl)-3-methylpyrrolidin-1-yl)ethan-1-one. To a mixture of ethyl (2S,3R)-1-acetyl-3-methyl-pyrrolidine-2-carboxylate (420 mg, 2.11 mmol) and calcium chloride (701.84 mg, 6.32 mmol) in THF (5 mL) was added sodium borohydride (318.9 mg, 8.43 mmol) in portions at 20° C. Then the reaction mixture was stirred at 20° C. for 16 h. The reaction mixture was diluted with THF (20 mL) and filtered. The filtrate was evaporated to give a crude product, which was then purified by HPLC (column: Xtimate C18 150*40 mm*5 um; mobile phase: [water (0.05% NH$_3$H$_2$O)-ACN]; B %: 3%-33%, 8 min) to give the title compound as a colorless oil. LCMS [M+H]: 158.1

Step 7: Preparation of 1-((2S,3R)-2-((6-chloro-1H-pyrazolo[3,4-d]pyrimidin-1-yl)methyl)-3-methylpyrrolidin-1-yl)ethan-1-one. Prepared by using general procedure D with 1-[(2S,3R)-2-(hydroxymethyl)-3-methyl-pyrrolidin-1-yl]ethanone (110 mg, 0.700 mmol), 6-chloro-1H-pyrazolo[3,4-d]pyrimidine (119.0 mg, 0.770 mmol), triphenylphosphine (367.0 mg, 1.40 mmol), and DEAD (243.71 mg, 1.40 mmol, 0.254 mL) in THF stirring at rt for 16 h. The crude product was combined with a second crude batch (30.0 mg). The combined batches were purified by flash silica gel chromatography (0-5% MeOH/DCM gradient) to give the title compound (80 mg). LCMS [M+H]: 294.2

Step 8: Preparation of 1-((2S,3R)-2-((6-((6-methoxy-2-methyl-1,2,3,4-tetrahydroisoquinolin-7-yl)amino)-1H-pyrazolo[3,4-d]pyrimidin-1-yl)methyl)-3-methylpyrrolidin-1-yl)ethan-1-one. Prepared according to general procedure A using a mixture of 1-[(2S,3R)-2-[(6-chloropyrazolo[3,4-d]pyrimidin-1-yl)methyl]-3-methyl-pyrrolidin-1-yl]ethanone (65.0 mg, 0.221 mmol), 6-methoxy-2-methyl-3,4-dihydro-1H-isoquinolin-7-amine (85.1 mg, 0.443 mmol) and p-TSA (114.3 mg, 0.666 mmol) in 2-butanol (4 mL) stirred at 100° C. for 16 h. The crude product, was purified by HPLC (column: Boston Prime C18 150*30 mm*5 um; mobile phase: [water (0.05% NH3H2O+10 mM NH$_4$HCO$_3$)-ACN]; B %: 35%-65%,7 min) to give the desired product. The product was diluted with MeCN (2 mL) and water (20 mL) and then 1N HCl (3 to 4 drops) was added. The solution was lyophilized to give the title compound (50.2 mg, HCl salt). $^1$H NMR (400 MHz, Deuterium oxide) δ: 8.85-8.81 (m, 1H), 8.13-8.04 (m, 1H), 7.78-7.67 (m, 11H), 6.95-6.93 (m, 1H), 4.48-4.08 (m, 5H), 3.84 (s, 1.5H), 3.83 (s, 1.5H), 3.77-3.72 (m, 1H), 3.36-3.13 (m, 5H), 3.05-3.03 (m, 3H), 2.47-2.25 (m, 1H), 2.16-2.05 (m, 1H), 1.71-1.60 (m, 1H), 1.48-1.46 (d, J=5.2 Hz, 2H), 1.16-1.11 (m, 3H), 1.07-1.05 (m, 1H). LCMS [M+H]: 450.3

Example 190

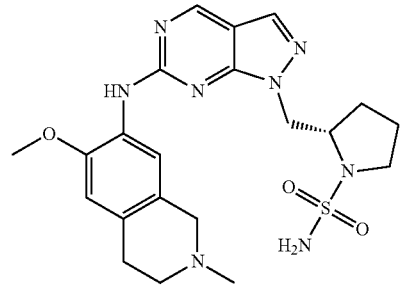 [SMILES: COc1cc2c(cc1Nc1ncc3cnn(C[C@@H]4CCCN4S(N)(=O)=O)c3n1)CN(C)CC2]

(S)-2-((6-((6-methoxy-2-methyl-1,2,3,4-tetrahydroisoquinolin-7-yl)amino)-1H-pyrazolo[3,4-d]pyrimidin-1-yl)methyl)pyrrolidine-1-sulfonamide hydrochloride Step 1: Preparation of 6-chloro-1-[[(2S)-pyrrolidin-2-yl]methyl]pyrazolo[3,4-d]pyrimidine hydrochloride. Prepared according to general procedure D using 6-chloro-1 h-pyrazolo[3,4-d]pyrimidine (5.00 g, 32.35 mmol), N-Boc-L-prolinol (7.81 g, 38.8 mmol), triphenylphosphine (12.73 g, 48.5 mmol), and DIAD (9.55 mL, 48.5 mmol) in dry THF (100 mL). The reaction was stirred at rt for 30 min. Upon completion, the volatiles were removed under reduced pressure and hexanes (200 mL) was added to precipitate triphenylphosphine oxide and DIAD byproduct. The mixture was filtered through a pad of celite. The filtrate was concentrated to give a crude oil which was suspended in dry DCM (100 mL) and HCl 4 N in dioxane (40.4 mL, 161.7 mmol). The mixture was stirred at room temperature for 18 h. The product was collected by filtration as an off-white solid (8.28 g). This crude product was taken on without further purification.

Step 2: Preparation of 6-methoxy-2-methyl-N-[1-[[(2S)-pyrrolidin-2-yl]methyl]pyrazolo[3,4-d]pyrimidin-6-yl]-3,4-dihydro-1H-isoquinolin-7-amine 2,2,2-trifluoroacetate. Prepared according to general procedure A using 6-chloro-1-[[(2S)-pyrrolidin-2-yl]methyl]pyrazolo[3,4-d]pyrimidine hydrochloride (250 mg, 0.912 mmol), 6-methoxy-2-methyl-3,4-dihydro-1H-isoquinolin-7-amine (404 mg, 2.1 mmol), and HCl 4 N in dioxane (0.68 mL, 2.74 mmol) in isopropyl alcohol (4.56 mL). The mixture was stirred at 110° C. for 18 h. The mixture was cooled to room temperature, diluted with DMF:MeOH (4:1) to 5 mL, and purified by reverse-phase HPLC (Phenomenex, Gemini-NX, 10 um, 250×30 mm, C18 column; gradient of 20% MeCN/0.1% TFA-water to 100% MeCN/0.1% TFA) to provide the desired product. This material was taken directly to the next step.

Step 3: Preparation of (S)-2-((6-((6-methoxy-2-methyl-1,2,3,4-tetrahydroisoquinolin-7-yl)amino)-1H-pyrazolo[3,4-d]pyrimidin-1-yl)methyl)pyrrolidine-1-sulfonamide hydrochloride. Sulfamoyl chloride (9.29 uL, 0.14 mmol) was added to a solution of DIEA (0.42 mL, 2.41 mmol) and 6-methoxy-2-methyl-N-[1-[[(2S)-pyrrolidin-2-yl]methyl]pyrazolo[3,4-d]pyrimidin-6-yl]-3,4-dihydro-1H-isoquinolin-7-amine 2,2,2-trifluoroacetate (75 mg, 0.121 mmol) in MeCN (1.2 mL) at 0° C. The reaction was allowed to come to room temperature and stirred at 80° C. for 4 h. The crude was purified directly via reverse phase HPLC (Phenomenex, Gemini-NX, 10 um, 250×30 mm, C18 column; gradient of 20% MeCN/0.1% TFA-water to 100% MeCN/0.1% TFA). It was then converted to the HCl salt to give the title compound (10 mg) as a yellow solid. $^1$H NMR (400 MHz, Methanol-$d_4$, HCl salt) δ 9.11 (s, 1H), 8.36 (d, J=19.6 Hz, 1H), 8.28 (s, 1H), 6.92 (s, 1H), 4.76-4.58 (m, 4H), 4.34-4.25 (m, 2H), 4.02 (s, 1H), 3.90 (s, 3H), 3.69 (s, 1H), 3.33 (d, J=13.0 Hz, 1H), 3.08 (d, J=17.5 Hz, 1H), 3.00 (s, 3H), 2.21-2.09 (m, 1H), 1.84 (ddd, J=40.7, 18.3, 8.6 Hz, 3H), 1.20 (s, 1H). LCMS [M+H]: 473.2

Example 191

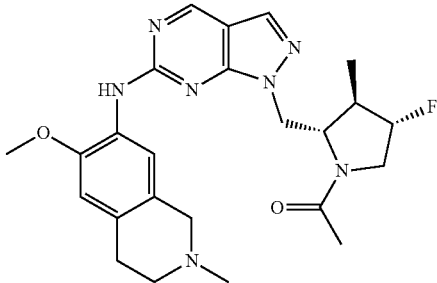 [SMILES: COc1cc2c(cc1Nc1ncc3cnn(C[C@@H]4[C@@H](C)[C@H](F)CN4C(C)=O)c3n1)CN(C)CC2]

1-((2S,3R,4S)-4-fluoro-2-((6-((6-methoxy-2-methyl-1,2,3,4-tetrahydroisoquinolin-7-yl)amino)-1H-pyrazolo[3,4-d]pyrimidin-1-yl)methyl)-3-methylpyrrolidin-1-yl)ethan-1-one Step 1: Preparation of 1-((2S,3R,4S)-4-fluoro-2-(hydroxymethyl)-3-methylpyrrolidin-1-yl)ethan-1-one. A suspension of 1-benzyl 2-methyl (2S,3R,4S)-4-fluoro-3-methylpyrrolidine-1,2-dicarboxylate (prepared according to EXAMPLE 118, WO214078609) (112 mg, 0.38 mmol) and palladium on carbon (5%, 40.4 mg, 0.019 mmol) in methanol (4 mL) was placed under hydrogen gas and stirred at rt for 24 h. The reaction mixture was filtered through a pad of celite and the filtrate concentrated. The isolated residue and DMAP (76.4 mg, 0.63 mmol) was suspended in DCM (1 mL). The reaction mixture was placed under nitrogen and cooled in an ice bath. Acetyl chloride (0.03 mL, 0.42 mmol) was added dropwise. The reaction mixture was stirred in the cooling bath for 2 h then at rt for 1 h. The reaction was quenched by the addition of 1M HCl (0.22 mL, 0.22 mmol). The reaction mixture was washed with water, brine, dried on Na2SO$_4$, and concentrated. The crude residue was suspended in THF (1 mL). Followed by the addition of sodium borohydride (37.2 mg, 0.98 mmol), and calcium chloride (87.3 mg, 0.79 mmol). The reaction mixture is stirred at rt for 24 h. Upon completion of the reaction, the reaction was quenched with saturated sodium bicarbonate and extracted exhaustively with DCM. The combined organics was concentrated to provide the crude product which was taken forward without purification.

Step 2: Preparation of 1-((2S,3R,4S)-2-((6-chloro-11H-pyrazolo[3,4-d]pyrimidin-1-yl)methyl)-4-fluoro-3-methylpyrrolidin-1-yl)ethan-1-one. Prepared according to general procedure D using DIAD (0.03 mL, 0.16 mmol), 1-((2S,3R,4S)-4-fluoro-2-(hydroxymethyl)-3-methylpyrrolidin-1-yl)ethan-1-one (22.8 mg, 0.13 mmol), 6-chloro-1 h-pyrazolo[3,4-d]pyrimidine (30.0 mg, 0.19 mmol), and triphenylphosphine (90 mg, 0.34 mmol) in THF (0.5 mL). The reaction mixture was purified by silica column chromatography (4 g silica column, eluting with 50% to 100% EA in hex followed by 0% to 100% MeOH in EA) to provide the title compound as a crude solid (5 mg). This material was taken directly to the next step without further purification.

Step 3: Preparation of 1-((2S,3R,4S)-4-fluoro-2-((6-((6-methoxy-2-methyl-1,2,3,4-tetrahydroisoquinolin-7-yl)amino)-1H-pyrazolo[3,4-d]pyrimidin-1-yl)methyl)-3-methylpyrrolidin-1-yl)ethan-1-one. Prepared according to general procedure A using 1-((2S,3R,4S)-2-((6-chloro-1H-pyrazolo[3,4-d]pyrimidin-1-yl)methyl)-4-fluoro-3-methylpyrrolidin-1-yl)ethan-1-one (5.0 mg, 0.016 mmol), 6-methoxy-2-methyl-3,4-dihydro-1H-isoquinolin-7-amine (3.1 mg, 0.016 mmol), pTSA (6.1 mg, 0.03 mmol), and sec-butanol (0.2 mL). The reaction was stirred at 80° C. for 32 h. The reaction was cooled to rt, diluted with water (5 mL), and purified directly on reverse phase HPLC (Phenomenex, Gemini-NX, 10 um, 250×30 mm, C18 column; gradient of 20% MeCN/0.1% TFA-water to 100% MeCN/ 0.1% TFA) to afford the title compound as an amorphous solid (1.3 mg). Characterized as a mixture of rotomers. $^1$H NMR (400 MHz, Methanol-d$_4$) δ 8.93 (s, 0.3H), 8.92 (s, 0.7H), 8.67 (s, 0.45H), 8.64 (s, 0.40 H), 8.51 (s, 0.35H), 8.13 (s, 0.3H), 8.05 (s, 0.7H), 6.94 (s, 1H), 5.09-5.00 (m, 1H), 4.79-4.58 (m, 1H), 4.51 (dd, J=13.8, 7.9 Hz, 1H), 4.43-4.21 (m, 2H), 3.98 (s, 3H), 3.85-3.68 (m, 2H), 3.50-3.38 (m, 1H), 3.28-3.20 (m, 1H), 3.15 (d, J=14.5 Hz, 1H), 3.08 (s, 2.4H), 3.07 (s, 0.6H) 2.73-2.60 (m, 1H), 1.98 (d, J=16.0 Hz, 2H), 1.63 (d, J=16.1 Hz, 1H), 1.32 (d, J=16.2 Hz, 1H), 0.99 (d, J=7.5 Hz, 1H), 0.92 (app t, J=8.1 Hz, 2H), 0.21-0.09 (m, 1H). LCMS [M+H]: 468.3

Example 192

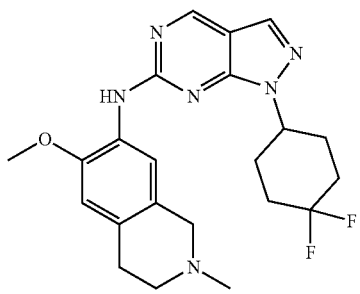 [SMILES: COc1cc2c(cc1Nc1ncc3cnn(C4CCC(F)(F)CC4)c3n1)CN(C)CC2]

N-[1-(4,4-difluorocyclohexyl)pyrazolo[3,4-d]pyrimidin-6-yl]-6-methoxy-2-methyl-3,4-dihydro-1H-isoquinolin-7-amine Hydrochloride Step 1: 6-chloro-1-(4,4-difluorocyclohexyl)pyrazolo[3,4-d]pyrimidine. Prepared according to general procedure D using 6-chloro-1 h-pyrazolo[3,4-d]pyrimidine (100 mg, 0.65 mmol), 4,4-difluorocyclohexan-1-ol (106 mg, 0.78 mmol), triphenylphosphine (339 mg, 1.3 mmol) and DIAD (0.255 mL, 1.3 mmol) in THF (3 mL). The crude product was purified using silica gel chromatography (eluting with 0% to 30% EA in hex) providing the title compound as a solid (164 mg). This material was taken directly to the next step without further purification.

Step 2: Preparation of (cis)-4-(6-((6-methoxy-2-methyl-1,2,3,4-tetrahydroisoquinolin-7-yl)amino)-3-methyl-1H-pyrazolo[3,4-d]pyrimidin-1-yl)cyclohexan-1-ol. Prepared according to general procedure A using 6-chloro-1-(4,4-difluorocyclohexyl)pyrazolo[3,4-d]pyrimidine (164 mg, 0.60 mmol), 6-methoxy-2-methyl-3,4-dihydro-1H-isoquinolin-7-amine (173 mg, 0.90 mmol), and p-TSA (260 mg, 1.37 mmol) in NMP (3 mL) in a sealed reaction vessel at 100° C. for 3 h. The reaction was quenched with 3M NaOH (0.8 mL) followed by purification using reverse phase HPLC (Phenomenex, Gemini-NX, 10 um, 250×30 mm, C18 column; gradient of 20% MeCN/0.1% TFA-water to 100% MeCN/0.1% TFA), providing the title compound as a solid (28 mg). $^1$H NMR (400 MHz, DMSO-d$_6$) δ 10.80 (s, 1H), 9.00 (s, 1H), 8.43 (s, 1H), 8.13 (s, 1H), 8.04 (s, 1H), 6.96 (s, 1H), 4.81 (s, 1H), 4.23 (dd, J=15.1, 8.2 Hz, 1H), 3.87 (s, 3H), 3.70-3.59 (m, 1H), 3.40-3.10 (m, 2H), 2.99 (d, J=18.3 Hz, 1H), 2.90 (d, J=4.6 Hz, 3H), 2.15 (d, J=57.5 Hz, 9H). LCMS: [M+H]: 429.1

Example 193

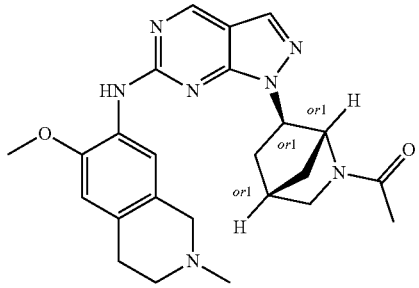 [SMILES: COc1cc2c(cc1Nc1ncc3cnn([C@@H]4C[C@@H]5C[C@H]4N(C(C)=O)C5)c3n1)CN(C)CC2]

rel-1-((1R,4S,6R)-6-(6-((6-methoxy-2-methyl-1,2,3,4-tetrahydroisoquinolin-7-yl)amino)-1H-pyrazolo[3,4-d]pyrimidin-1-yl]-2-azabicyclo[2.2.1]heptan-2-yl)ethan-1-one Step 1: Preparation of rel-tert-butyl (1R,4S,6S)-6-(6-chloro-1H-pyrazolo[3,4-d]pyrimidin-1-yl)-2-azabicyclo[2.2.1]heptane-2-carboxylate. Prepared according to general procedure D using 6-chloro-1 h-pyrazolo[3,4-d]pyrimidine (362 mg, 2.34 mmol), (1r,4s,6s)-rel-tert-butyl 6-hydroxy-2-azabicyclo[2.2.1]heptane-2-carboxylate (500 mg, 2.3 mmol), triphenylphosphine (1.23 g, 4.7 mmol) and DIAD (0.92 mL, 4.7 mmol) in THF (12 mL). The crude product was purified using silica gel chromatography (eluting with 0% to 10% MeOH in DCM) providing the title compound as a solid (500 mg). This material was taken directly to the next step without further purification.

Step 2: Preparation of rel-1-((1R,4S,6S)-6-(6-chloro-1H-pyrazolo[3,4-d]pyrimidin-1-yl)-2-azabicyclo[2.2.1]heptan-2-yl)ethan-1-one. A solution rel-tert-butyl (1R,4S,6S)-6-(6-chloro-1H-pyrazolo[3,4-d]pyrimidin-1-yl)-2-azabicyclo[2.2.I]heptane-2-carboxylate (500 mg, 1.4 mmol) and 4M HCl in dioxane (6 mL) in DCM (6 mL) was stirred at rt for 2 h then concentrated under reduced pressure. The residue was taken up in DCM (6 mL) and MeOH (1 mL) followed by the sequential addition of Et3N (0.80 mL, 5.7 mmol) and acetyl chloride (0.20 mL, 2.9 mmol). The reaction mixture was stirred for 30 min at rt. The reaction mixture pre-loaded onto celite and the crude product was purified by silica gel chromatography (eluting with 0% to 10% MeOH in DCM) to provide the title compound as a solid (300 mg).

Step 3: Preparation of rel-1-((1R,4S,6R)-6-(6-((6-methoxy-2-methyl-1,2,3,4-tetrahydroisoquinolin-7-yl) amino)-1H-pyrazolo[3,4-d]pyrimidin-1-yl)-2-azabicyclo [2.2.1]heptan-2-yl)ethan-1-one.Prepared by general procedure A using rel-1-((1R,4S,6S)-6-(6-chloro-1H-pyrazolo[3,4-d]pyrimidin-1-yl)-2-azabicyclo[2.2.1]heptan-2-yl) ethan-1-one (200 mg, 0.69 mmol), 6-methoxy-2-methyl-3, 4-dihydro-1H-isoquinolin-7-amine (198 mg, 1.03 mmol), p-TSA (261 mg, 1.37 mmol) in 2-butanol (3 mL) at 100° C. for 2 days. The crude was purified by reverse phase HPLC (Phenomenex, Gemini-NX, 10 um, 250×30 mm, C18 column; gradient of 20% MeCN/0.1% TFA-water to 100% MeCN/0.1% TFA), providing the title compound as the TFA salt. This material was converted to the HCl salt to provide the title compound (250 mg) as an off-white powder. Characterized as a mixture containing rotomers. $^1$H NMR (400 MHz, Deuterium Oxide) δ 8.92 (s, 1H), 8.85 (d, J=8.5 Hz, 1H), 8.15 (s, 1H), 8.09 (d, J=7.6 Hz, 1H), 7.87 (d, J=8.5 Hz, 1H), 7.62 (d, J=11.3 Hz, 1H), 7.03 (s, 1H), 6.96 (d, J=5.1 Hz, 1H), 4.61-4.34 (m, 4H), 4.39-4.17 (m, 3H), 3.87 (s, 3H), 3.84 (s, 3H), 3.81-3.72 (m, 2H), 3.53 (d, J=9.0 Hz, 1H), 3.49-3.35 (m, 3H), 3.29 (d, J=9.6 Hz, 3H), 3.14 (d, J=10.0 Hz, 3H), 3.06 (s, 6H), 2.87 (d, J=13.6 Hz, 2H), 2.61 (d, J=13.6 Hz, 1H), 2.52-2.38 (m, 1H), 2.21-2.02 (m, 7H), 1.95 (d, J=11.0 Hz, 1H), 1.85 (s, 3H), 1.71 (d, J=10.9 Hz, 1H), 1.65 (d, J=11.1 Hz, 1H). LCMS: [M+H]:448.1

Example 194

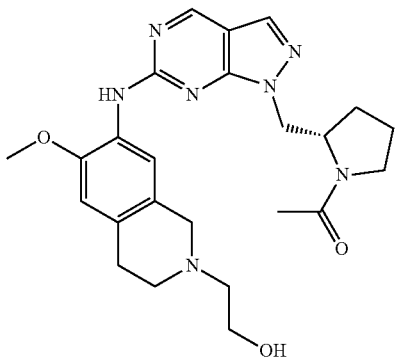 [SMILES: COc1cc2c(cc1Nc1ncc3cnn(C[C@@H]4CCCN4C(C)=O)c3n1)CN(CCO)CC2]

(S)-1-(2-((6-((2-(2-hydroxyethyl)-6-methoxy-1,2,3,4-tetrahydroisoquinolin-7-yl)amino)-1H-pyrazolo[3,4-d]pyrimidin-1-yl)methyl)pyrrolidin-1-yl)ethan-1-one Step 1: Preparation of (S)-6-chloro-1-(pyrrolidin-2-ylmethyl)-1H-pyrazolo[3,4-d]pyrimidine hydrochloride. A solution of 6-chloro-1H-pyrazolo[3,4-d]pyrimidine (3.00 g, 19.0 mmol), N-Boc-S-prolinol (4.69 g, 22.8 mmol) and triphenylphosphine (7.56 g, 28.5 mmol) in THF (76.087 mL) was cooled to 0° C. followed by dropwise addition of DIAD (5.67 mL, 28.53 mmol). The reaction mixture was stirred at 0° C. for 30 min. The volatiles were removed under reduced pressure and the crude was purified by silica column chromatography (0-80% EtOAc in hexanes gradient) to provide a crude mixture of desired product and a DIAD byproduct. The crude mixture was dissolved in 38 mL of dichloromethane at rt and a 4 N HCl soln in dioxane (23.78 mL, 95.11 mmol) was added dropwise. The mixture was stirred at rt for 8 hr. The white precipitate collected by filtration, rinsed with DCM, and then dried under reduced pressure to provide the title compound (4.65) as an off-white solid.

Step 3: Preparation of (S)-1-(2-((6-chloro-1H-pyrazolo[3,4-d]pyrimidin-1-yl)methyl)pyrrolidin-1-yl)ethan-1-one. (S)-6-chloro-1-(pyrrolidin-2-ylmethyl)-1H-pyrazolo[3,4-d]pyrimidine hydrochloride (2.0 g, 7.3 mmol) and TEA (3.05 mL, 21.89 mmol) were dissolved in DCM (15 mL) at rt and then acetic anhydride (1.03 mL, 10.9 mmol) was added dropwise. The reaction was stirred at rt for 30 min. The mixture was diluted with DCM (50 mL) and washed with a saturated aqueous sodium carbonate solution (50 mL). The organic layer was dried over sodium sulfate, filtered, and concentrated under reduced pressure to afford the title compound (1.94 g) as a light-yellow viscous oil.

Step 4: Preparation of tert-butyl (S)-7-((1-((1-acetylpyrrolidin-2-yl)methyl)-1H-pyrazolo[3,4-d]pyrimidin-6-yl)amino)-6-methoxy-3,4-dihydroisoquinoline-2(1H)-carboxylate. Prepared according to general procedure A using a degassed solution of tert-butyl 7-amino-6-methoxy-3,4-dihydro-1H-isoquinoline-2-carboxylate (746.3 mg, 2.68 mmol), (S)-1-(2-((6-chloro-1H-pyrazolo[3,4-d]pyrimidin-1-yl)methyl)pyrrolidin-1-yl)ethan-1-one (500 mg, 1.79 mmol) and DIEA (0.62 mL, 3.57 mmol) in DMF (8.9 mL) with stirring at 100° C. for 20 hr. The mixture was cooled to rt and then mixture was purified directly by reversed phase HPLC (Phenomenex Gemini-NX, 10 mm, 250×30 mm, C18 column, eluent: 0 to 100% MeCN in water, both eluents containing 0.1% TFA, gradient elution over 30 minutes) to provide the title compound (614 mg) as an off-white solid. LCMS [M+H]: 522.2

Step 5: Preparation of (S)-1-(2-((6-((6-methoxy-1,2,3,4-tetrahydroisoquinolin-7-yl)amino)-1H-pyrazolo[3,4-d]pyrimidin-1-yl)methyl)pyrrolidin-1-yl)ethan-1-one hydrochloride. tert-butyl 7-[[1-[[(2S)-1-acetylpyrrolidin-2-yl]methyl]pyrazolo[3,4-d]pyrimidin-6-yl]amino]-6-methoxy-3,4-dihydro-1H-isoquinoline-2-carboxylate (600 mg, 1.15 mmol) was dissolved in DCM (12 mL) and then a 4 M HCl solution in dioxane (1.44 mL, 5.75 mmol) was added dropwise. The mixture was stirred at rt for 2 hr. All the volatiles were removed under reduced pressure to provide the title compound (517 mg) as an off-white solid.

Step 6: Preparation of (S)-1-(2-((6-((2-(2-hydroxyethyl)-6-methoxy-1,2,3,4-tetrahydroisoquinolin-7-yl)amino)-1H-pyrazolo[3,4-d]pyrimidin-1-yl)methyl)pyrrolidin-1-yl)ethan-1-one. To a solution of (S)-1-(2-((6-((6-methoxy-1,2,3,4-tetrahydroisoquinolin-7-yl)amino)-1H-pyrazolo[3,4-d]pyrimidin-1-yl)methyl)pyrrolidin-1-yl)ethan-1-one hydrochloride (80 mg, 0.17 mmol) in MeCN (3 mL) was added STAB-H (184.2 mg, 0.87 mmol). The reaction was stirred at rt for 5 min followed by the dropwise addition of. (tert-butyldimethylsiloxy) acetaldehyde (0.08 mL, 0.44 mmol). The reaction mixture was vigorously stirred at rt for 2 h. The reaction was quenched by adding a solution of HCl in dioxane (4M, 0.22 mL, 0.87 mmol). The resulting mixture was stirred at rt for 2 h. All volatiles were removed under reduced pressure to provide the crude product. The residue was purified directly by reversed phase preparative HPLC (Geminix, 10 mm, 250×30 mm, C18 column (Phenomenex, Torrance, CA), eluent: 0 to 100% MeCN in water, both eluents containing 0.1% TFA, gradient elution over 30 minutes) to provide the title compound as the TFA salt. The TFA salt was free based using a sodium carbonate SPE cartridge and DCM/MeOH (1:1) as eluent, and then concentrated under reduced pressure. The residue was further purified by silica column chromatography (0-20% MeOH/DCM, with 0.1% TEA) to provide the desired compound as the free base. The free base was dissolved in MeOH (5 mL) and HCl (2 M in diethyl ether, 1 equiv) and the resultant mixture was concentrated to afford the title compound as the corresponding HCl salt (77.4 mg). $^1$H NMR (400 MHz, Methanol-d4, HCl salt, mixture of rotamers) δ 9.14 (s, 1H), 8.32 (s, 1H), 8.22 (s, 1H), 6.98 (s, 1H), 4.70-4.54 (m, 2H), 4.54-4.45 (m, 1H), 4.44-4.33 (m, 1H), 4.01-3.92 (m, 2H), 3.92 (s, 3H), 3.89-3.77 (m, 1H), 3.50-3.32 (m, 4H), 3.32-3.26 (m, 1H), 3.18-3.03 (m, 1H), 2.14-2.00 (m, 1H), 2.00-1.88 (m, 2H), 1.87-1.82 (m, 2H), 1.81 (s, 1.5H), 1.80 (s, 1.5H), 1.62-1.41 (m, 1H). LCMS [M+H]: 466.3

Example 195

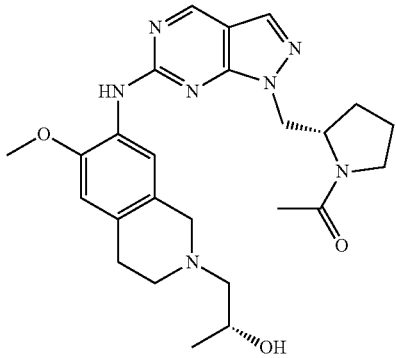 [SMILES: COc1cc2c(cc1Nc1ncc3cnn(C[C@@H]4CCCN4C(C)=O)c3n1)CN(C[C@@H](C)O)CC2]

1-((S)-2-((6-((2-((R)-2-hydroxypropyl)-6-methoxy-1,2,3,4-tetrahydroisoquinolin-7-yl)amino)-1H-pyrazolo[3,4-d]pyrimidin-1-yl)methyl)pyrrolidin-1-yl)ethan-1-one Prepared according to EXAMPLE 194, Step 6 using (S)-1-(2-((6-(((6-methoxy-1,2,3,4-tetrahydroisoquinolin-7-yl)amino)-1H-pyrazolo[3,4-d]pyrimidin-1-yl)methyl)pyrrolidin-1-yl)ethan-1-one hydrochloride (50 mg, 0.11 mmol), (2R)-2-[tert-butyl(dimethyl)silyl]oxypropanal (51.4 mg, 0.28 mmol), and STAB-H (116.0 mg, 0.55 mmol) in MeCN. The crude product was purified by HPLC (Phenomenex, Gemini-NX, 10 um, 250×30 mm, C18 column; gradient of 10% MeCN/0.1% TFA-water to 100% MeCN/0.1% TFA) to provide the title compound (30.9 mg, TFA salt). $^1$H NMR (400 MHz, DMSO-$d_6$) δ 9.67 (s, 1H), 8.90 (s, 11H), 8.39 (s, 0.6H), 8.33 (d, J=11.5 Hz, 0.4H), 8.15 (s, 1H), 8.05 (s, 1H), 6.85 (s, 1H), 4.55-4.17 (m, 5H), 3.80 (s, 2.5H), 3.77 (s, 0.5H), 3.66-3.55 (m, 1H), 3.36-3.18 (m, 2H), 3.18-2.83 (m, 5H), 1.92-1.73 (m, 5H), 1.73-1.59 (m, 2H), 1.34 (s, 1H), 1.14 (s, 1H), 1.08 (d, J=5.7 Hz, 2H). LCMS [M+H]: 480.1

Example 196

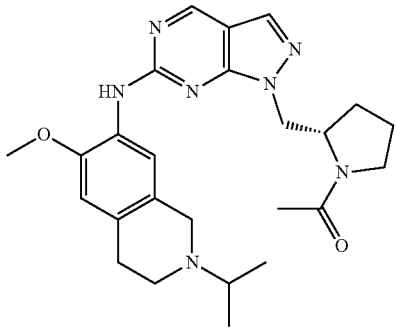 [SMILES: COc1cc2c(cc1Nc1ncc3cnn(C[C@@H]4CCCN4C(C)=O)c3n1)CN(C(C)C)CC2]

(S)-1-(2-((6-(((2-isopropyl-6-methoxy-1,2,3,4-tetrahydroisoquinolin-7-yl)amino)-1H-pyrazolo[3,4-d]pyrimidin-1-yl)methyl)pyrrolidin-1-yl)ethan-1-one hydrochloride Prepared according to EXAMPLE 194 by substituting (S)-1-(2-((6-(((6-methoxy-1,2,3,4-tetrahydroisoquinolin-7-yl)amino)-1H-pyrazolo[3,4-d]pyrimidin-1-yl)methyl)pyrrolidin-1-yl)ethan-1-one hydrochloride (80 mg, 0.17 mmol) and acetone (0.03 mL, 0.44 mmol) in step 6 to provide the title compound (21 mg, HCl salt). $^1$H NMR (400 MHz, Methanol-d4, HCl salt, mixture of rotamers) δ 9.05 (s, 1H), 8.35 (d, J=5.6 Hz, 11H), 8.21 (s, 11H), 6.93 (s, 11H), 4.74 (s, 1H), 4.62-4.57 (m, 1H), 4.57-4.43 (m, 2H), 4.45-4.33 (m, 1H), 3.90 (s, 3H), 3.74-3.61 (m, 2H), 3.41-3.28 (m, 3H), 3.16-3.02 (m, 2H), 2.15-2.01 (m, 1H), 1.99-1.83 (m, 2H), 1.79 (s, 1.5H), 1.77 (s, 1.5H), 1.47-1.40 (m, 7H). LCMS [M+H]: 464.3

Example 197

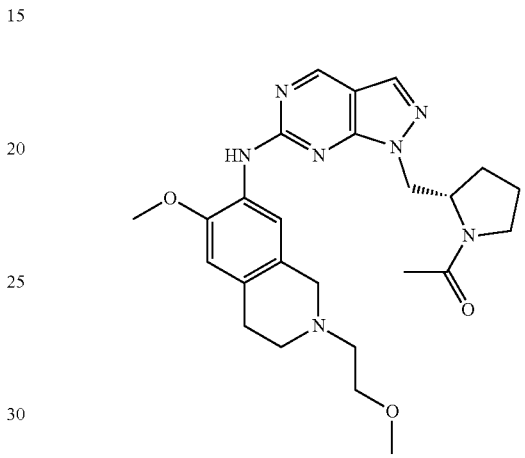

(S)-1-(2-((6-(((6-methoxy-2-(2-methoxyethyl)-1,2,3,4-tetrahydroisoquinolin-7-yl)amino)-1H-pyrazolo[3,4-d]pyrimidin-1-yl)methyl)pyrrolidin-1-yl)ethan-1-one Hydrochloride A solution of (S)-1-(2-((6-(((6-methoxy-1,2,3,4-tetrahydroisoquinolin-7-yl)amino)-1H-pyrazolo[3,4-d]pyrimidin-1-yl)methyl)pyrrolidin-1-yl)ethan-1-one hydrochloride (50 mg, 0.11 mmol) (EXAMPLE 194, Step 5) in MeCN (3 mL) at rt was treated with cesium carbonate (106.7 mg, 0.33 mmol). The reaction mixture was stirred at rt for 5 min, followed by the dropwise addition of 2-chloroethyl methyl ether (0.02 mL, 0.22 mmol). The reaction was stirred at rt for 12 h. The volatiles were removed under reduced pressure and the residue was purified by silica column chromatography (0-20% MeOH/DCM gradient, with 0.1% TEA). The product was converted into the corresponding HCl salt, by dissolving it in MeOH (5 mL) and adding HCl (2 M in diethyl ether, 1 equiv) followed by concentration under reduced pressure to afforded the title compound as the corresponding HCl salt (18 mg). $^1$H NMR (400 MHz, Methanol-d4, HCl salt, mixture of rotamers) δ 9.25 (s, 1H), 8.43 (s, 1H), 8.20 (s, 1H), 7.05 (s, 1H), 4.95-4.84 (m, 1H), 4.81-4.71 (m, 1H), 4.71-4.50 (m, 3H), 4.49-4.39 (m, 1H), 3.97 (s, 3H), 3.94-3.81 (m, 3H), 3.60-3.48 (m, 3H), 3.47 (s, 3H), 3.45-3.35 (m, 2H), 3.26-3.13 (m, 1H), 2.21-2.07 (m, 1H), 2.07-1.94 (m, 2H), 1.90 (s, 1.5H), 1.87 (s, 1.5H), 1.73-1.50 (m, 1H). LCMS [M+H]: 480.3

Example 198

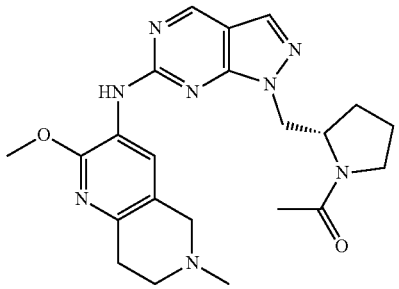 [SMILES: COc1nc2c(cc1Nc1ncc3cnn(C[C@@H]4CCCN4C(C)=O)c3n1)CN(C)CC2]

(S)-1-(2-((6-(((6-methoxy-2-(2-methoxyethyl)-1,2,3,4-tetrahydroisoquinolin-7-yl)amino)-1H-pyrazolo[3,4-d]pyrimidin-1-yl)methyl)pyrrolidin-1-yl)ethan-1-one Prepared according to general procedure B using (S)-1-(2-((6-chloro-1H-pyrazolo[3,4-d]pyrimidin-1-yl)methyl)pyrrolidin-1-yl)ethan-1-one (200 mg, 0.71 mmol) (EXAMPLE 62), 2-methoxy-6-methyl-7,8-dihydro-5H-1,6-naphthyridin-3-amine (207.3 mg, 1.07 mmol) (EXAMPLE 170), Pd$_2$(dba)$_3$ (65.5 mg, 0.07 mmol), potassium tert-butoxide (160.46 mg, 1.43 mmol), and BINAP (133.6 mg, 0.21 mmol) in THF (5.4 mL) and tert-butanol (1.8 mL). The mixture was degassed under vacuum and then flushed with nitrogen. The mixture was stirred 100° C. for 8 h. The reaction was cooled to rt and filtered through a celite pad using DCM/MeOH (4:1) as eluent, and concentrated under reduced pressure. The residue was purified reverse phase preparative HPLC (Phnomenex Gemini-NX, 10 mm, 250×30 mm, C18 column, eluent: 0 to 100% MeCN in water, both eluents containing 0.1% TFA, gradient elution over 30 minutes). The fractions containing the desired product were concentrated under reduced pressure and afforded the corresponding TFA salt. The TFA salt was free based using a Carbonate SPE Cartridge and DCM/MeOH (1:1) as eluent, and then concentrated under reduced pressure. The free base was converted to the corresponding mesylate salt by dissolution in methanol, addition of methanesulfonic acid (47.3 mg) and concentrated under reduced pressure to provide the title compound as the corresponding mesylate salt (215 mg). $^1$H NMR (400 MHz, Methanol-d4, Mesylate salt, mixture of rotamers) δ 8.98 (s, 1H), 8.73 (d, J=12.4 Hz, 1H), 8.10 (d, J=5.2 Hz, 1H), 4.76-4.61 (m, 2H), 4.59-4.27 (m, 4H), 4.00 (s, 3H), 3.83-3.69 (m, 1H), 3.55-3.40 (m, 1H), 3.35-3.25 (m, 2H), 3.20-3.08 (m, 1H), 3.05 (s, 3H), 2.61 (s, 3H), 2.16-2.04 (m, 1H), 2.02-1.83 (m, 1H), 1.82 (s, 1.5H), 1.78 (s, 1.5H), 1.76-1.67 (m, 1H), 1.48-1.19 (m, 1H). LCMS [M+H]: 437.2

Example 199

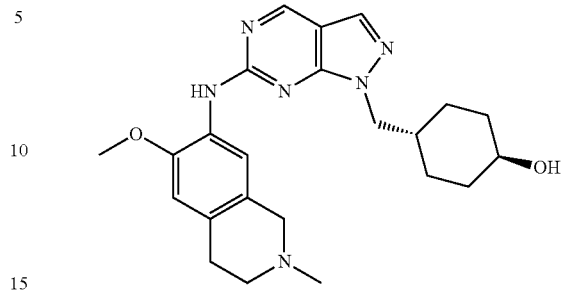

(trans)-4-((6-(((6-methoxy-2-methyl-1,2,3,4-tetrahydroisoquinolin-7-yl)amino)-1H-pyrazolo[3,4-d]pyrimidin-1-yl)methyl)cyclohexan-1-ol hydrochloride Step 1: Preparation of (trans)-4-((6-chloro-1H-pyrazolo[3,4-d]pyrimidin-1-yl)methyl)cyclohexan-1-ol. Prepared according to general procedure D using 6-chloro-1H-pyrazolo[3,4-d]pyrimidine (1.0 g, 6.34 mmol), trans-4-(hydroxymethyl)cyclohexanol (825.4 mg, 6.34 mmol), triphenylphosphine (2.0 g, 7.6 mmol), and DIAD (1.5 mL, 7.6 mmol) in THF (32 mL) at −78° C. for 2 h. The mixture was allowed to warm up to rt and then all the volatiles were removed under reduced pressure. The crude product was directly purified by silica column chromatography (0-20% MeOH/DCM) to afford the title compound (1.19 g) as a light yellow viscous oil.

Step 2: Preparation of (trans)-4-((6-(((6-methoxy-2-methyl-1,2,3,4-tetrahydroisoquinolin-7-yl)amino)-1H-pyrazolo[3,4-d]pyrimidin-1-yl)methyl)cyclohexan-1-ol. Prepared according to general procedure A using 6-methoxy-2-methyl-3,4-dihydro-1H-isoquinolin-7-amine (108.1 mg, 0.56 mmol), (trans)-4-((6-chloro-1H-pyrazolo[3,4-d]pyrimidin-1-yl)methyl)cyclohexan-1-ol (100 mg, 0.37 mmol) and p-TSA hydrate (213.9 mg, 1.12 mmol) in NMP (2 mL) at 100° C. for 36 h. The crude product was purified directly by reversed phase preparative HPLC (Phenomenex Gemini-NX, 10 mm, 250×30 mm, C18 column, eluent: 0 to 100% MeCN in water, both eluents containing 0.1% TFA, gradient elution over 30 minutes). The fractions containing the desired product were concentrated under reduced pressure and afforded the corresponding TFA salt. The TFA salt was free based using a carbonate SPE Cartridge and DCM/MeOH (1:1) as eluent, and then concentrated under reduced pressure. The free base was converted into the corresponding HCl salt, by dissolving it in MeOH (5 mL) and adding HCl (2 M in diethyl ether, 1 equiv) and then concentrated under reduced pressure to afforded the title compound as the corresponding HCl salt (49.5 mg). $^1$H NMR (400 MHz, DMSO-d6, HCl salt) δ 10.59 (bs, 1H), 8.97 (s, 1H), 8.40 (s, 1H), 8.10 (s, 1H), 8.08 (s, 1H), 6.94 (s, 1H), 4.41 (bs, 1H), 4.27-4.17 (m, 1H), 4.12 (d, J=7.0 Hz, 2H), 3.85 (s, 3H), 3.68-3.59 (m, 1H), 3.38-3.25 (m, 2H), 3.22-3.09 (m, 1H), 3.02-2.93 (m, 1H), 2.90 (d, J=4.8 Hz, 3H), 2.35-2.30 (m, 1H), 1.93-1.75 (m, 3H), 1.62-1.47 (m, 2H), 1.16-0.97 (m, 4H). LCMS [M+H]: 423.2

Example 200

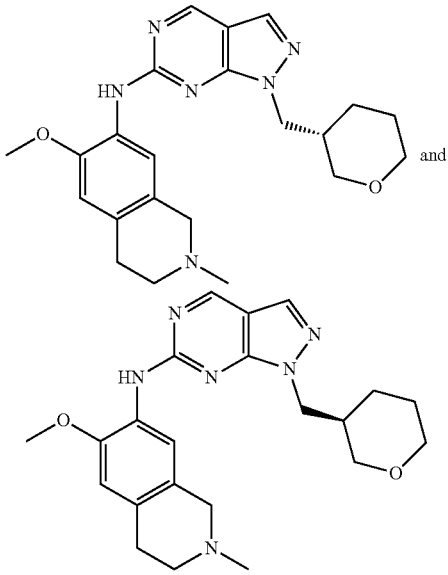

(S)-6-methoxy-2-methyl-N-(1-((tetrahydro-2H-pyran-3-yl)methyl)-1H-pyrazolo[3,4-d]pyrimidin-6-yl)-1,2,3,4-tetrahydroisoquinolin-7-amine and (R)-6-methoxy-2-methyl-N-(1-((tetrahydro-2H-pyran-3-yl)methyl)-1H-pyrazolo[3,4-d]pyrimidin-6-yl)-1,2,3,4-tetrahydroisoquinolin-7-amine racemic mixture Step 1: Preparation of rac-6-chloro-1-((tetrahydro-2H-pyran-3-yl)methyl)-1H-pyrazolo[3,4-d]pyrimidine. Prepared according to general procedure D using 6-chloro-1H-pyrazolo[3,4-d]pyrimidine (1.0 g, 6.34 mmol), rac-oxan-3-ylmethanol (736.5 mg, 6.34 mmol), triphenylphosphine (2.0 g, 7.6 mmol) and DIAD (1.5 mL, 7.6 mmol) in THF (32 mL) at 0° C. for 2 h. The mixture was warmed to rt and then all volatiles were removed under reduced pressure and the residue was directly by silica column chromatography (0-20% MeOH/DCM gradient) to afford the title compound (1.3 g) as a light-yellow viscous oil.

Step 2: Preparation of (S)-6-methoxy-2-methyl-N-(1-((tetrahydro-2H-pyran-3-yl)methyl)-1H-pyrazolo[3,4-d]pyrimidin-6-yl)-1,2,3,4-tetrahydroisoquinolin-7-amine and (R)-6-methoxy-2-methyl-N-(1-((tetrahydro-2H-pyran-3-yl)methyl)-1H-pyrazolo[3,4-d]pyrimidin-6-yl)-1,2,3,4-tetrahydroisoquinolin-7-amine. Prepared according to general procedure A using 6-methoxy-2-methyl-3,4-dihydro-1H-isoquinolin-7-amine (110, mg, 0.59 mmol), racemic 6-chloro-1-((tetrahydro-2H-pyran-3-yl)methyl)-1H-pyrazolo[3,4-d]pyrimidine (100 mg, 0.4 mmol) and p-TSA hydrate (230 mg, 1.19 mmol) in NMP (2 mL) with stirring at 100° C. for 36 h. The crude product was purified directly by reversed phase preparative HPLC (Gemini-NX, 10 mm, 250×30 mm, C18 column, eluent: 0 to 100% MeCN in water, both eluents containing 0.1% TFA, gradient elution over 30 minutes). The fractions containing the desired product were concentrated under reduced pressure and afforded the corresponding TFA salt. The TFA salt was free based using a carbonate SPE Cartridge and DCM/MeOH (1:1) as eluent, and then concentrated under reduced pressure. The free base was converted into the corresponding HCl salt, by dissolving it in MeOH (5 mL) and adding HCl (2 M in diethyl ether, 1 equiv) and then concentrated afforded the title racemic compound as the corresponding HCl salt (49 mg). $^1$H NMR (400 MHz, Methanol-d4, HCl salt) δ 8.95 (s, 1H), 8.23 (d, J=8.3 Hz, 1H), 8.12 (s, 1H), 6.92 (s, 1H), 4.48 (d, J=14.9 Hz, 1H), 4.38-4.19 (m, 3H), 3.88 (s, 3H), 3.76-3.66 (m, 4H), 3.52-3.43 (m, 1H), 3.41-3.30 (m, 2H), 3.14-3.03 (m, 1H), 3.00 (s, 3H), 2.32-2.20 (m, 1H), 1.83-1.61 (m, 2H), 1.57-1.43 (m, 1H), 1.40-1.27 (m, 1H). LCMS [M+H]: 409.3

Example 201

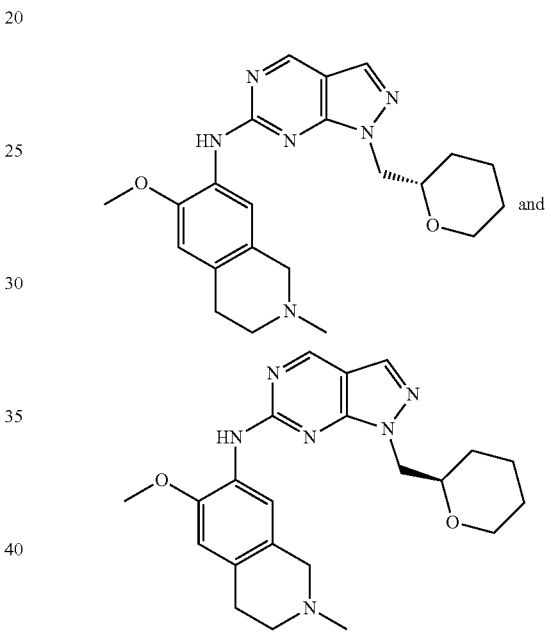

(S)-6-methoxy-2-methyl-N-(1-((tetrahydro-2H-pyran-2-yl)methyl)-1H-pyrazolo[3,4-d]pyrimidin-6-yl)-1,2,3,4-tetrahydroisoquinolin-7-amine and (R)-6-methoxy-2-methyl-N-(1-((tetrahydro-2H-pyran-2-yl methyl)-1H-pyrazolo[3,4-d]pyrimidin-6-yl)-1,2,3, 4-tetrahydroisoquinolin-7-amine Hydrochloride, Racemic Mixture Prepared according to Example 200 substituting rac-tetrahydropyran-2-methanol (736.5 mg, 6.34 mmol) for rac-oxan-3-ylmethanol (736.5 mg, 6.34 mmol) to afford the title compound as the corresponding HCl salt (85.4 mg. $^1$H NMR (400 MHz, Methanol-d4, HCl salt) δ 9.02 (s, 1H), 8.23 (s, 11H), 8.11 (s, 1H), 6.96 (s, 11H), 4.48 (d, J=14.6 Hz, 11H), 4.44-4.35 (m, 1H), 4.33-4.19 (m, 3H), 3.89 (s, 3H), 3.87-3.76 (m, 2H), 3.76-3.67 (m, 1H), 3.43-3.26 (m, 2H), 3.16-3.06 (m, 1H), 3.01 (s, 3H), 1.88-1.77 (m, 1H), 1.67-1.60 (m, 1H), 1.56-1.42 (m, 3H), 1.39-1.28 (m, 1H). LCMS [M+H]: 409.2

Example 202

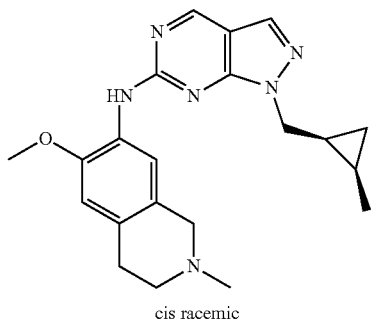

cis racemic

6-methoxy-2-methyl-N-(1-((cis-2-methylcyclopropyl)methyl)-1H-pyrazolo[3,4-d]pyrimidin-6-yl)-1,2,3,4-tetrahydroisoquinolin-7-amine, Trifluoroacetate Salt Step 1: Preparation of 6-chloro-1-(((cis)-2-methylcyclopropyl)methyl)-1H-pyrazolo[3,4-d]pyrimidine. Prepared according to general procedure D using (cis-2-methylcyclopropyl)methanol (234 mg, 2.72 mmol), 6-chloro-1H-pyrazolo[3,4-d]pyrimidine (300 mg, 1.94 mmol), triphenylphosphine (764 mg, 2.91 mmol), and DIAD (0.573 mL, 589 mg, 2.91 mmol) in THF (0.2 M). The crude product was purified by silica gel chromatography (eluting with 0 to 100% EtOAc in hexanes). To provide the title compound (350 mg).

Step 2: Preparation of 6-methoxy-2-methyl-N-(1-(((cis)-2-methylcyclopropyl)methyl)-1H-pyrazolo[3,4-d]pyrimidin-6-yl)-1,2,3,4-tetrahydroisoquinolin-7-amine, trifluoroacetate salt. Prepared according to general procedure A using 6-chloro-1-(((cis)-2-methylcyclopropyl)methyl)-1H-pyrazolo[3,4-d]pyrimidine (350 mg, 1.57 mmol), 6-methoxy-2-methyl-1,2,3,4-tetrahydroisoquinolin-7-amine (544 mg, 2.83 mmol), and p-TSA (897 mg, 4.72 mmol) in 2-butanol (0.26 M). The reaction mixture was stirred for 48 h at 120° C. The crude product was first purified by silica gel chromatography (eluting with 0 to 20% MeOH in DCM), then by reverse phase HPLC (Phenomenex, Gemini-NX, 10 um, 250×30 mm, C18 column; gradient of 20% MeCN/0.1% TFA-water to 100% MeCN/0.1% TFA) to provide the title compound 300 mg (50%). 1H NMR (400 MHz, Methanol-d4, TFA salt): 8.88 (s, 1H), 8.44 (s, 11H), 8.02 (s, 11H), 6.82 (s, 1H), 4.41-4.52 (m, 1H), 4.38 (d, J=7.6 Hz, 2H), 4.18-4.29 (m, 1H), 3.95 (m, 3H), 3.64-3.80 (m, 0.5H), 3.32-3.45 (m, 0.5H), 3.17-3.27 (m, 1H), 3.06-3.16 (m, 1H), 3.02-3.05 (m, 4H), 1.39-1.51 (m, 1H), 1.22 (d, J=6.3 Hz, 3H), 0.98 (p, J=7.2 Hz, 1H), 0.71-0.81 (m, 1H), 0.16 (q, J=5.3 Hz, 1H) ppm. LCMS [M+H]$^+$: 379.0

Example 203

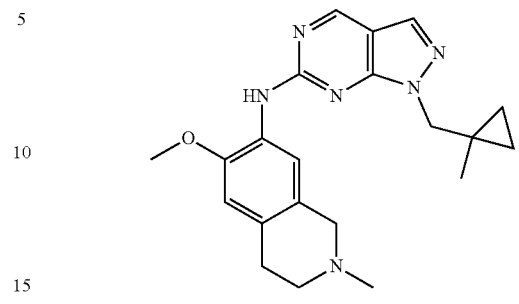

6-methoxy-2-methyl-N-(1-((1-methylcyclopropyl)methyl)-1H-pyrazolo[3,4-d]pyrimidin-6-yl)-1,2,3,4-tetrahydroisoquinolin-7-amine Step 1: Preparation of 6-chloro-1-((1-methylcyclopropyl)methyl)-1H-pyrazolo[3,4-d]pyrimidine. Prepared according to general procedure D using (1-methylcyclopropyl)methanol (234 mg, 2.72 mmol), 6-chloro-1H-pyrazolo[3,4-d]pyrimidine (300 mg, 1.94 mmol), triphenylphosphine (764 mg, 2.91 mmol), and DIAD (0.573 mL, 2.91 mmol) in THF (0.2 M). The reaction was stirred for 1.5 h at rt. The crude product was purified by silica gel chromatography (eluting with 0 to 100% EtOAc in hex) to provide the title compound.

Step 2: Preparation of 6-methoxy-2-methyl-N-(1-((1-methylcyclopropyl)methyl)-1H-pyrazolo[3,4-d]pyrimidin-6-yl)-1,2,3,4-tetrahydroisoquinolin-7-amine. Prepared according to general procedure A using 6-chloro-1-((1-methylcyclopropyl)methyl)-1H-pyrazolo[3,4-d]pyrimidine (322 mg, 1.50 mmol), 6-methoxy-2-methyl-1,2,3,4-tetrahydroisoquinolin-7-amine (518 mg, 2.69 mmol), and p-TSA (853 mg, 4.49 mmol) in 2-butanol (0.18 M) for 48 h at 120° C. The crude product was first purified by silica gel chromatography (eluting with 0 to 20% MeOH in DCM), then by reverse phase HPLC (Phenomenex, Gemini-NX, 10 um, 250×30 mm, C18 column; gradient of 20% MeCN/0.1% TFA-water to 100% MeCN/0.1% TFA) to provide the title compound (120 mg). 1H NMR (400 MHz, Methanol-d4, TFA salt): 8.89 (s, 1H), 8.48 (s, $^1$H), 8.01 (s, 1H), 6.85 (s, 1H), 4.38-4.59 (m, 1H), 4.19-4.38 (m, 3H), 3.95 (s, 3H), 3.60-3.83 (m, 0.5H), 3.33-3.49 (m, 0.5H), 3.08-3.28 (m, 2H), 3.06 (m, 4H), 1.08 (s, 3H), 0.77-0.82 (m, 2H), 0.38-0.43 (m, 2H) ppm. LCMS [M+H]$^+$: 379.2

Example 204

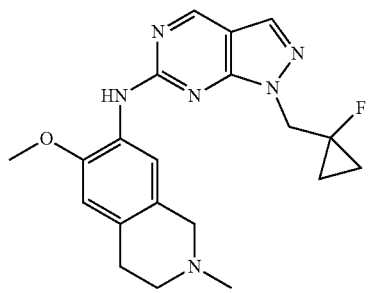 [SMILES: COc1cc2c(cc1Nc1ncc3cnn(CC4(F)CC4)c3n1)CN(C)CC2]

N-(1-((1-fluorocyclopropyl)methyl)-1H-pyrazolo[3,4-d]pyrimidin-6-yl)-6-methoxy-2-methyl-1,2,3,4-tetrahydroisoquinolin-7-amine Step 1: Preparation of 6-chloro-1-((1-fluorocyclopropyl)methyl)-1H-pyrazolo[3,4-d]pyrimidine. Prepared according to general procedure D using (1-fluorocyclopropyl)methanol (234 mg, 2.72 mmol), 6-chloro-1H-pyrazolo[3,4-d]pyrimidine (300 mg, 1.94 mmol), triphenylphosphine (764 mg, 2.91 mmol), and DIAD (0.573 mL, 2.91 mmol) in THF (0.2 M). The reaction was stirred at rt for 1.5 h. The crude product was purified by silica gel chromatography (eluting with 0 to 100% EtOAC in hexanes) to provide the title compound (430 mg).

Step 2: Preparation of N-(1-((1-fluorocyclopropyl)methyl)-1H-pyrazolo[3,4-d]pyrimidin-6-yl)-6-methoxy-2-methyl-1,2,3,4-tetrahydroisoquinolin-7-amine. Prepared according to general procedure A using 6-chloro-1-((1-fluorocyclopropyl)methyl)-11H-pyrazolo[3,4-d]pyrimidine (430 mg, 1.9 mmol), 6-methoxy-2-methyl-1,2,3,4-tetrahydroisoquinolin-7-amine (657 mg, 3.42 mmol), and p-TSA (1.080 g, 5.69 mmol) in 2-butanol (0.24 M). The reaction was stirred for 48 hrs at 120° C. The crude product was first purified by silica gel chromatography (eluting with 0 to 20% MeOH/DCM), then by reverse phase HPLC (Phenomenex, Gemini-NX, 10 um, 250×30 mm, C18 column; gradient of 20% MeCN/0.1% TFA-water to 100% MeCN/0.1% TFA) to provide the title compound (200 mg). 1H NMR (400 MHz, Methanol-d4, TFA salt): 8.89 (s, 1H), 8.44 (s, 1H), 8.02 (s, 1H), 6.81 (s, 1H), 4.37-4.53 (m, 1H), 4.15-4.32 (m, 1H), 3.94 (s, 3H), 3.63-3.78 (m, 1H), 3.32-3.43 (m, 1H), 3.18-3.28 (m, 1H), 2.98-3.16 (m, 6H), 1.05-1.17 (m, 2H), 0.95-1.05 (m, 2H) ppm. LCMS [M+H]$^+$: 383.1

Example 205

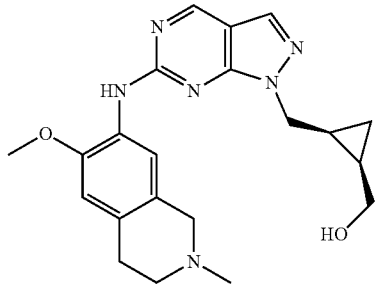 [SMILES: COc1cc2c(cc1Nc1ncc3cnn(C[C@H]4C[C@H]4CO)c3n1)CN(C)CC2]

(cis-2-((6-((6-methoxy-2-methyl-1,2,3,4-tetrahydroisoquinolin-7-yl)amino)-1H-pyrazolo[3,4-d]pyrimidin-1-yl)methyl)cyclopropyl)methanol Step 1: Preparation of 1-((cis-2-(((tert-butyldimethylsilyl)oxy)methyl)cyclopropyl)methyl)-6-chloro-1H-pyrazolo[3,4-d]pyrimidine. Prepared according to general procedure D using (cis-2-(((tert-butyldimethylsilyl)oxy)methyl)cyclopropyl)methanol (431 mg, 1.99 mmol), 6-chloro-1H-pyrazolo[3,4-d]pyrimidine (220 mg, 1.42 mmol), triphenylphosphine (560 mg, 2.14 mmol), and DIAD (0.420 mL, 2.14 mmol) in THF (0.2 M). The reaction was stirred at rt for 1.5 h. The crude product was purified by silica gel chromatography (eluting with 0 to 100% EtOAC in hexanes) to provide the title compound (485 mg).

Step 2: Preparation of (cis-2-((6-((6-methoxy-2-methyl-1,2,3,4-tetrahydroisoquinolin-7-yl)amino)-1H-pyrazolo[3,4-d]pyrimidin-1-yl)methyl)cyclopropyl)methanol. Prepared according to general procedure A using 1-((cis-2-(((tert-butyldimethylsilyl)oxy)methyl)cyclopropyl)methyl)-6-chloro-1H-pyrazolo[3,4-d]pyrimidine (485 mg, 1.37 mmol), 6-methoxy-2-methyl-1,2,3,4-tetrahydroisoquinolin-7-amine (476 mg, 2.47 mmol), and p-TSA (784 mg, 4.12 mmol) in 2-butanol (0.24 M). The reaction was stirred for 48 h at 120° C. The crude product was first purified by silica gel chromatography (eluting with 0 to 20% MeOH/DCM), then by reverse phase HPLC (Phenomenex, Gemini-NX, 10 um, 250×30 mm, C18 column; gradient of 20% MeCN/0.1% TFA-water to 100% MeCN/0.1% TFA) to provide the title compound (220 mg). 1H NMR (400 MHz, Methanol-d4, TFA salt): 8.89 (s, 1H), 8.41 (s, 1H), 8.03 (s, 1H), 6.82 (s, 1H), 4.68 (dd, J=14.7 Hz, J=6.3 Hz, 1H), 4.47-4.59 (m, 1H), 4.15-2.34 (m, 2H), 3.87-3.97 (m, 4H), 3.66-3.77 (m, 1H), 3.53 (dd, J=12.1 Hz, J=9.0 Hz, 1H), 3.20-3.41 (m, 2H), 3.00-3.14 (m, 5H), 1.37 (dp, J=37.5 Hz, J=7.6 Hz, 2H), 0.83 (td, J=8.5 Hz, J=5.1 Hz, 1H), 0.39 (q, J=5.5 Hz, 1H) ppm. LCMS [M+H]$^+$: 395.1

Example 206

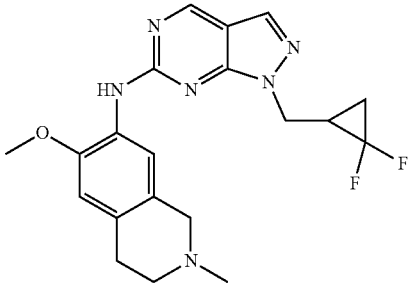 [SMILES: COc1cc2c(cc1Nc1ncc3cnn(CC4CC4(F)F)c3n1)CN(C)CC2]

N-(1-((2,2-difluorocyclopropyl)methyl)-1H-pyrazolo[3,4-d]pyrimidin-6-yl)-6-methoxy-2-methyl-1,2,3,4-tetrahydroisoquinolin-7-amine Step 1: Preparation of 6-chloro-1-((2,2-difluorocyclopropyl)methyl)-1H-pyrazolo[3,4-d]pyrimidine. Prepared according to general procedure D using (2,2-difluorocyclopropyl)methanol (349.67 mg, 3.23 mmol), 6-chloro-1 h-pyrazolo[3,4-d]pyrimidine (500.mg, 3.23 mmol), triphenylphosphine (1.7 g, 6.47 mmol), and DIAD (1.31 g, 6.47 mmol) in THF (3 mL). The reaction was stirred at rt for 4 h. The crude product was purified using silica gel chromatography (eluting with 0% to 100% EtOAc in hexanes) to provide the title compound (489.8 mg).

Step 2: Preparation of N-(1-((2,2-difluorocyclopropyl)methyl)-1H-pyrazolo[3,4-d]pyrimidin-6-yl)-6-methoxy-2-methyl-1,2,3,4-tetrahydroisoquinolin-7-amine. Prepared according to general procedure A using 6-methoxy-2-methyl-3,4-dihydro-1H-isoquinolin-7-amine (0.37 g, 1.93 mmol), 6-chloro-1-((2,2-difluorocyclopropyl)methyl)-1H-pyrazolo[3,4-d]pyrimidine (0.31 g, 1.29 mmol), and p-TSA (0.49 g, 2.58 mmol) in 2-butanol (3 mL). The reaction was stirred at 90° C. for 18 h. The crude product was purified using reverse phase HPLC (Phenomenex, Gemini-NX, 10 um, 250×30 mm, C18 column; gradient of 20% MeCN/0.1% TFA-water to 100% MeCN/0.1% TFA) to provide the title compound (214 mg). 1H NMR (400 MHz, MeOH-d4, TFA salt) δ 9.13 (s, 1H), 8.34 (s, 1H), 8.04 (s, 0.6H), 7.67 (s, 1H), 6.94 (s, 1H), 4.54 (m, 2H), 4.24 (m, 1H) 3.97 (s, 3H), 3.69 (m, 1H), 3.44-3.09 (m, 4H), 3.01 (s, 3H), 2.2 (m, 1H), 1.51 (m, 1H), 1.39 (m, 1H); LCMS [M+H]: 401.1

Example 207

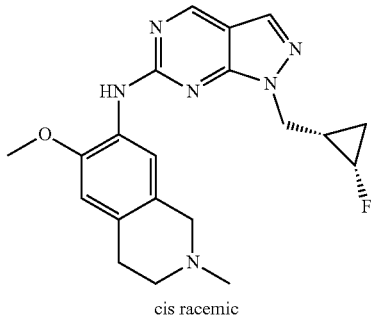 [SMILES: COc1cc2c(cc1Nc1ncc3cnn(C[C@@H]4C[C@@H]4F)c3n1)CN(C)CC2]

cis racemic

N-(1-(((cis)-2-fluorocyclopropyl)methyl)-1H-pyrazolo[3,4-d]pyrimidin-6-yl)-6-methoxy-2-methyl-1,2,3,4-tetrahydroisoquinolin-7-amine Prepared according to EXAMPLE 206 substituting (trans)-2-fluorocyclopropanol (246.09 mg, 3.23 mmol) for (2,2-difluorocyclopropyl)methanol (349.67 mg, 3.23 mmol) in step 1 to provide the title compound (214 mg). 1H NMR (400 MHz, MeOH-d4, TFA salt) δ 9.10 (s, 1H), 8.32 (s, 2H), 7.01 (s, 1H), 4.56 (d, J=8 Hz, 2H), 4.40 (m, 1H), 3.97 (s, 3H), 3.79 (m, 1H), 3.44 (m, 1H), 3.29-3.10 (m, 4H), 3.07 (s, 3H), 1.61 (m, 1H), 0.95 (m, 2H); LCMS [M+H]: 383.1

Example 208

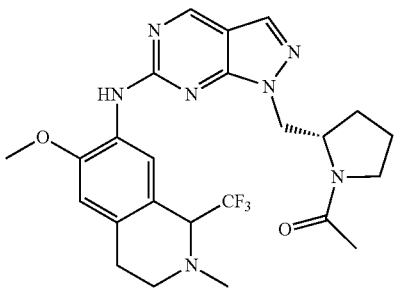 [SMILES: COc1cc2c(cc1Nc1ncc3cnn(C[C@@H]4CCCN4C(C)=O)c3n1)C(C(F)(F)F)N(C)CC2]

1-((2S)-2-((6-((6-methoxy-2-methyl-1-(trifluoromethyl)-1,2,3,4-tetrahydroisoquinolin-7-yl)amino)-1H-pyrazolo[3,4-d]pyrimidin-1-yl)methyl)pyrrolidin-1-yl)ethan-1-one Step 1: Preparation of 2,2,2-trifluoro-N-(3-methoxyphenethyl)acetamide. A solution of 2-(3-methoxyphenyl)ethylamine (15.0.g, 99.2 mmol) and triethylamine (20.1 g, 198.4 mmol) in DCM (300 mL) was cooled to 0° C. followed by dropwise addition of trifluoroacetic anhydride (20.8 g, 99.2 mmol). The reaction was stirred at rt for 1 h then poured into water and extracted with DCM. The combined organic layers were dried over magnesium sulfate, filtered, and concentrated under reduced pressure to provide the title compound as a crude solid (22.0 g). which was used without further purification. LCMS [M+H]: 248.1

Step 2: Preparation of 6-methoxy-1-(trifluoromethyl)-1,2,3,4-tetrahydroisoquinoline. 2,2,2-Trifluoro-N-[2-(3-methoxyphenyl)ethyl]acetamide (22.g, 94.34 mmol) was dissolved in phosphoryl chloride (100 mL) and refluxed for 10 h. The reaction mixture was concentrated under reduced pressure and dried on high vacuum. The residue was redissolved in 1:1 mixture of MeOH/DCM and cooled in an ice bath. Sodium borohydride (6.73 g, 178 mmol) was added portion wise, keeping the temperature below 30° C. The reaction mixture was stirred at rt for 2 h and then poured onto water. The aqueous mixture was extracted with EtOAc and the combined organic layers were discarded. The aqueous pH was adjusted to 7-8 and then extracted with DCM. The combined DCM extracts were dried over magnesium sulfate and concentrated under reduced pressure to provide the title compound (7.50 g) LCMS [M+H]: 232.1

Step 3: Preparation of 6-methoxy-1-(trifluoromethyl)-3,4-dihydroisoquinoline-2(1H)-carbaldehyde. 6-methoxy-1-(trifluoromethyl)-1,2,3,4-tetrahydroisoquinoline (7.5 g, 32.4 mmol) was dissolved in 20 mL of water, 30% formalin aqueous solution (40 mL), and 1M HCl 20 mL). The reaction mixture was stirred at 60° C. for 16 h. The reaction mixture was then poured into water and extracted with DCM. The organics was dried over magnesium sulfate and concentrated under reduced pressure to provide the title compound (7.90 g). LCMS [M+H]: 259.9

Step 4: Preparation of 6-methoxy-7-nitro-1-(trifluoromethyl)-3,4-dihydroisoquinoline-2(1H)-carbaldehyde: To a solution of 6-methoxy-1-(trifluoromethyl)-3,4-dihydro-1H-isoquinoline-2-carbaldehyde (4.g, 15.43 mmol) in nitromethane (20 mL) was added acetic anhydride (4.38 mL, 46.29 mmol). resulting solution was cooled to 0° C. In the separate vial were mixed acetic anhydride (4.38 mL, 46.29 mmol) and concentrated nitric acid (2.15 mL, 46.29 mmol). Upon cooling to rt, the acetic anhydride/nitric acid solution was added dropwise to the cooled solution of 6-methoxy-1-(trifluoromethyl)-3,4-dihydro-1H-isoquinoline-2-carbaldehyde in nitromethane. After addition, the ice bath was removed, and the reaction mixture was stirred at rt for 2 h. The reaction was quenched with careful addition of saturated sodium bicarbonate solution. The mixture was diluted with water and extracted with EtOAc. The combined organic layers were dried over magnesium sulfate and concentrated. The crude product was purified on silica gel chromatography (0% to 100% EA in hex) affording the title compound (1.7 g). LCMS [M+H]: 305.0

Step 5: Preparation of 6-methoxy-2-methyl-1-(trifluoromethyl)-1,2,3,4-tetrahydroisoquinolin-7-amine. 6-Methoxy-7-nitro-1-(trifluoromethyl)-3,4-dihydro-1H-isoquinoline-2-carbaldehyde (1.7 g, 5.59 mmol) was dissolved in a 1M solution THF-borane complex (15 mL). The reaction mixture was heated at 60° C. for 6 h. All volatiles were removed under reduced pressure and the residue was redissolved in MeOH and placed under nitrogen, then Pearlman's catalyst (200 mg, 10% wet Pd/C) was added, and the reaction was stirred under hydrogen atmosphere overnight. The reaction mixture was filtered through celite and the filtrate was concentrated under reduced pressure to provide the title compound (1.11 g) LCMS [M+H]: 261.0

Step 6: Preparation of 1-((2S)-2-((6-((6-methoxy-2-methyl-1-(trifluoromethyl)-1,2,3,4-tetrahydroisoquinolin-7-yl)amino)-1H-pyrazolo[3,4-d]pyrimidin-1-yl)methyl)pyrrolidin-1-yl)ethan-1-one. Prepared according to general procedure A using 6-methoxy-2-methyl-1-(trifluoromethyl)-

3,4-dihydro-1H-isoquinolin-7-amine (0.28 g, 1.07 mmol), 1-[(2S)-2-[(6-chloropyrazolo[3,4-d]pyrimidin-1-yl)methyl]pyrrolidin-1-yl]ethanone (0.2 g, 0.71 mmol), and p-TSA (0.27 g, 1.43 mmol) in in 2-butanol (3 mL) at 90° C. for 18 h. Upon completion, the reaction mixture was cooled to rt, concentrated under reduced pressure, and purified using reverse phase HPLC (Phenomenex, Gemini-NX, 10 um, 250×30 mm, C18 column; gradient of 20% MeCN/0.1% TFA-water to 100% MeCN/0.1% TFA) affording the title compound (200 mg). 1H NMR (400 MHz, CDCl3, TFA salt) δ 9.06 (s, 1H), 8.79 (d, J=16 Hz, 1H), 8.65 (d, J=24 Hz, 0.85H), 7.95 (s, 1H), 5.98 (m, 1H), 4.97 (m, 0.3H), 4.58 (m, 1.3H), 4.41 (m, 0.4H), 3.91 (s, 3H), 3.71 (m, 1H), 3.55 (m, 0.5H), 3.48-3.39 (m, 2H), 3.28 (m, 0.5H), 3.16-2.98 (m, 6H), 2.1 (s, 3H), 2.0-1.71 (m, 4H); LCMS [M+H]: 504.2

Example 209

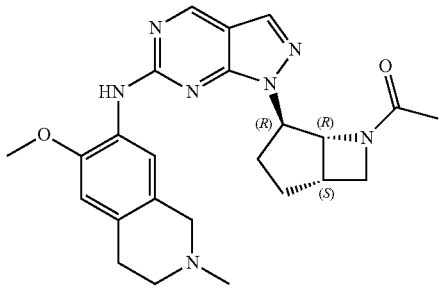

1-((1S,4R,5R)-4-(6-((6-methoxy-2-methyl-1,2,3,4-tetrahydroisoquinolin-7-yl)amino)-1H-pyrazolo[3,4-d]pyrimidin-1-yl)-6-azabicyclo[3.2.0]heptan-6-yl)ethan-1-one Step 1: Preparation of tert-butyl (1S,4R,5R)-4-(6-chloro-1H-pyrazolo[3,4-d]pyrimidin-1-yl)-6-azabicyclo[3.2.0]heptane-6-carboxylate: Prepared according to general procedure D using tert-butyl (1S,4S,5R)-4-hydroxy-6-azabicyclo[3.2.0]heptane-6-carboxylate (250.mg, 1.17 mmol), 6-chloro-1 h-pyrazolo[3,4-d]pyrimidine (181.2 mg, 1.17 mmol), triphenylphosphine (614.9 mg, 2.34 mmol), and DIAD (0.46 mL, 2.34 mmol) in THF (3 mL) at rt for 4 h. The residue was purified using silica gel chromatography (0-40% EtOAc in hexane)s to provide the title compound (300 mg).

Step 2: Preparation of 1-[(1S,4R,5R)-4-(6-chloropyrazolo[3,4-d]pyrimidin-1-yl)-6-azabicyclo[3.2.0]heptan-6-yl]ethanone. To a solution of tert-butyl (1S,4R,5R)-4-(6-chloropyrazolo[3,4-d]pyrimidin-1-yl)-6-azabicyclo[3.2.0]heptane-6-carboxylate (300.mg, 0.86 mmol) in DCM (2 mL) was added TFA (2 mL). The reaction was stirred at rt for 4 h. The reaction mixture was then concentrated and redissolved in DCM (3 mL). To this solution was added TEA (173.5 mg, 1.72 mmol) and acetic anhydride (131.3 mg, 1.29 mmol). The reaction mixture was stirred at rt for 1 h, then concentrated under reduced pressure. The crude product was purified on silica gel chromatography (0-100% EtOAc in hexanes) to afford the title compound (180 mg).

Step 3: Preparation of 1-((1S,4R,5R)-4-(6-((6-methoxy-2-methyl-1,2,3,4-tetrahydroisoquinolin-7-yl)amino)-1H-pyrazolo[3,4-d]pyrimidin-1-yl)-6-azabicyclo[3.2.0]heptan-6-yl)ethan-1-one. Prepared according to general procedure A using 6-methoxy-2-methyl-3,4-dihydro-1H-isoquinolin-7-amine (148.3 mg, 0.77 mmol), 1-[(1S,4R,5R)-4-(6-chloropyrazolo[3,4-d]pyrimidin-1-yl)-6-azabicyclo[3.2.0]heptan-6-yl]ethanone (150.mg, 0.51 mmol), and p-TSA (195.38 mg, 1.03 mmol) in 2-butanol (3 mL) at 90° C. for 16 h. Upon completion, the reaction mixture was cooled to rt, concentrated under reduced pressure, and purified on a reversed phase HPLC ('Phenomenex, Gemini-NX, 10 um, 250×30 mm, C18 column; gradient of 20% MeCN/0.1% TFA-water to 100% MeCN/0.1% TFA over 30 minutes), affording final compound (88 mg). 1H NMR (400 MHz, DMSO-d6, HCl salt) δ 9.16 (s, 1H), 8.27 (s, 1H), 7.47 (s, 1H), 6.81 (s, 1H), 5.53 (m, 1H), 4.78-4.68 (m, 1H), 4.39-4.26 (m, 2H), 3.91 (s, 3H), 3.78 (m, 1H), 3.69 (m, 1H) 3.45-3.27 (m, 4H), 3.21 (m, 1H), 3.08 (m, 1H), 2.99 (s, 3H), 2.62 (m, 1H), 2.42 (m, 1H), 2.25 (m, 1H), 2.02 (s, 3H); LCMS [M+H]: 448.3

Example 210

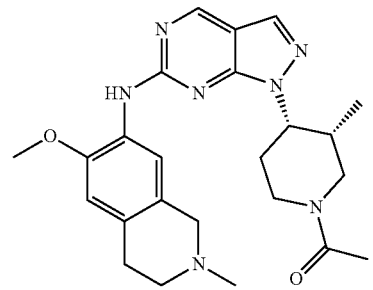 [SMILES: COc1cc2c(cc1Nc1ncc3cnn([C@H]4CCN(C(C)=O)C[C@H]4C)c3n1)CN(C)CC2]

1-((3R,4S)-4-(6-((6-methoxy-2-methyl-1,2,3,4-tetrahydroisoquinolin-7-yl)amino)-1H-pyrazolo[3,4-d]pyrimidin-1-yl)-3-methylpiperidin-1-yl)ethan-1-one Prepared according to EXAMPLE 209 substituting tert-butyl (3R,4R)-4-hydroxy-3-methylpiperidine-1-carboxylate for tert-butyl (1S,4S,5R)-4-hydroxy-6-azabicyclo[3.2.0]heptane-6-carboxylate to provide the title compound (446 mg). 1H NMR (400 MHz, Methanol-d4, HCl salt, ~1:1.5 mixture of rotomers) δ 8.91 (s, 1H), 8.19 (m, 1H), 8.05 (s, 1H), 6.88 (s, 1H), 4.52-4.03 (m, 2H), 3.87 (s, 3H), 3.69 (m, 1H), 3.56 (m, 1H), 3.39-3.15 (m, 6H), 3.1-2.99 (m, 4H), 2.56-2.29 (m, 1H); 2.1-1.99 (m, 5H), 0.66 (two d, J=4.4 Hz, 3H); LCMS [M+H]: 450.3

Example 211

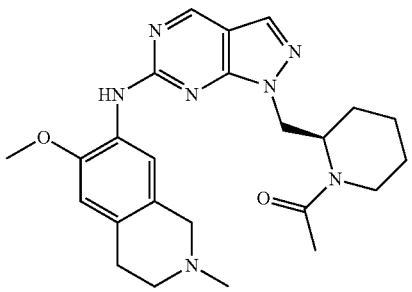 [SMILES: COc1cc2c(cc1Nc1ncc3cnn(C[C@H]4CCCCN4C(C)=O)c3n1)CN(C)CC2]

1-[(2R)-2-[[6-[(6-methoxy-2-methyl-3,4-dihydro-1H-isoquinolin-7-yl)amino]pyrazolo[3,4-d]pyrimidin-1-yl]methyl]-1-piperidyl]ethenone hydrochloride Step 1: Preparation of (R)-6-chloro-1-(piperidin-2-ylmethyl)-1H-pyrazolo[3,4-d]pyrimidine. Prepared according to general procedure D using 6-chloro-1H-pyrazolo[3,4-d]pyrimidine (400 mg, 2.59 mmol), tert-butyl (R)-2-(hydroxymethyl)piperidine-1-carboxylate (613 mg, 2.85 mmol), triphenylphosphine (1.02 g, 3.88 mmol) and DIAD (0.76 mL, 3.88 mmol) in THF (7 mL) at rt for 1.5 h. The crude product was purified by silica column chromatography (0-60% EtOAc in hexanes). To a solution of the compound in DCM (10 mL) was added 2 M HCl in diethyl ether (5.2 mL, 10.4 mmol) and the solution was stirred at rt until reaction was complete. The reaction was filtered to afford the title compound as a white solid (280 mg).

Step 2: Preparation of (R)-1-(2-((6-chloro-1H-pyrazolo[3,4-d]pyrimidin-1-yl)methyl)piperidin-1-yl)ethan-1-one. To a solution of (R)-6-chloro-1-(piperidin-2-ylmethyl)-1H-pyrazolo[3,4-d]pyrimidine (280 mg, 0.97 mmol) in DCM (5 mL) cooled to 0° C. was added triethylamine (0.68 mL, 4.86 mmol) followed by acetic anhydride (0.28 mL, 2.91 mmol) and the solution was stirred at rt for 12 h. The mixture was then stirred with saturated aqueous. sodium carbonate (2 mL), extracted twice with EtOAc (15 ml), washed with sat. aq. NaCl (15 mL), and the combined organics dried over Na₂SO₄, filtered, and concentrated. The crude title compound was taken onto step 3 without further purification.

Step 3: Preparation of 1-[(2R)-2-[[6-[(6-methoxy-2-methyl-3,4-dihydro-1H-isoquinolin-7-yl)amino]pyrazolo[3,4-d]pyrimidin-1-yl]methyl]-1-piperidyl]ethenone hydrochloride. Prepared according to general procedure A using (R)-1-(2-((6-chloro-1H-pyrazolo[3,4-d]pyrimidin-1-yl)methyl)piperidin-1-yl)ethan-1-one (125 mg, 0.43 mmol), 6-methoxy-2-methyl-3,4-dihydro-1H-isoquinolin-7-amine (98 mg, 0.51 mmol), and p-TSA (194 mg, 1.02 mmol) in 2-butanol (1.9 mL) at 110° C. for 17 h. The crude product was purified by reverse phase HPLC (Phenomenex, Gemini-NX, 10 um, 250×30 mm, C18 column; gradient of 5% MeCN/0.1% TFA-water to 50% MeCN/0.1% TFA-water) providing the purified compound as the TFA salt. The purified compound was free based and converted to the HCl salt, yielding the title compound as a solid (116 mg) The ¹H NMR (400 MHz, DMSO-d6) δ 11.16 (br s, 1H), 9.02 (s, 1H), 8.53 (m, 1H), 8.22 (m, 2H), 6.97 (s, 1H), 4.90 (m, 1H), 4.42 (m, 4H), 3.88 (s, 3H), 3.62 (br s, 2H), 3.29 (m, 3H), 2.99 (m, 1H), 2.89 (s, 3H), 1.71 (m, 8H), 1.33 (m, 1H). LCMS [M+H]: 450.2.

Example 212

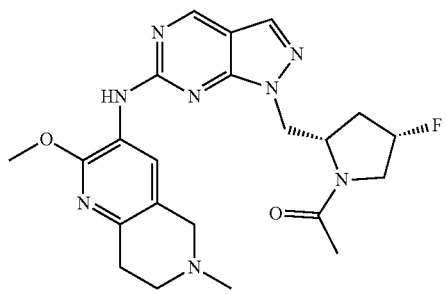 [SMILES: COc1nc2c(cc1Nc1ncc3cnn(C[C@@H]4C[C@H](F)CN4C(C)=O)c3n1)CN(C)CC2]

1-[(2S,4S)-4-fluoro-2-[[6-[(2-methoxy-6-methyl-7,8-dihydro-5H-1,6-naphthyridin-3-yl)amino]pyrazolo[3,4-d]pyrimidin-1-yl]methyl]pyrrolidin-1-yl]ethenone Prepared by general procedure B using 1-((2S,4S)-2-((6-chloro-1H-pyrazolo[3,4-d]pyrimidin-1-yl)methyl)-4-fluoropyrrolidin-1-yl)ethan-1-one (145.0 mg, 0.49 mmol) (EXAMPLE 146), 2-methoxy-6-methyl-5,6,7,8-tetrahydro-1,6-naphthyridin-3-amine (141.2 mg, 0.73 mmol) (EXAMPLE 170), Pd2(dba)3 (44.6 mg, 0.05 mmol), potassium tert-butoxide (109.3 mg, 0.97 mmol), and BINAP (91.0 mg, 0.15 mmol) in tert-butanol (0.5 mL) and THF (1.5 mL) at 100° C. for 3 h. The crude product was purified by reversed phase HPLC (Phenomenex, Gemini-NX, 10 um, 250×30 mm, C18 column; gradient of 0% MeCN/0.1% TFA-water to 100% MeCN/0.1% TFA) providing the desired product as a solid (66 mg). 1H NMR (400 MHz, Methanol-d4) δ 9.35-9.23 (m, 1H), 8.65 (d, J=11.1 Hz, 1H), 8.48-8.43 (m, 1H), 5.43 (d, J=53.3 Hz, 1H), 4.89 (dt, J=13.9, 5.6 Hz, 1H), 4.81-4.67 (m, 2H), 4.54 (dd, J=13.6, 7.9 Hz, 1H), 4.07 (d, J=5.6 Hz, 3H), 4.00-3.89 (m, 1H), 3.58 (td, J=11.7, 5.2 Hz, 1H), 3.40-3.25 (m, 6H), 3.12 (dd, J=4.5, 1.7 Hz, 3H), 2.49-2.11 (m, 1H), 2.06-1.93 (m, 3H). [M+H]⁺: 455.0.

Example 213

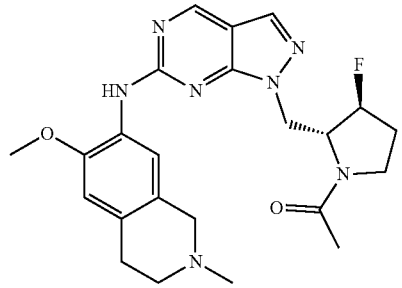 [SMILES: COc1cc2c(cc1Nc1ncc3cnn(C[C@@H]4[C@@H](F)CCN4C(C)=O)c3n1)CN(C)CC2]

1-[(2R,3S)-3-fluoro-2-[[6-[(6-methoxy-2-methyl-3,4-dihydro-1H-isoquinolin-7-yl)amino]pyrazolo[3,4-d]pyrimidin-1-yl]methyl]pyrrolidin-1-yl]ethanone Step 1: Preparation of tert-butyl (2R,3S)-3-fluoro-2-(hydroxymethyl)pyrrolidine-1-carboxylate. To a solution of 1-(tert-butyl) 2-methyl (2R,3S)-3-fluoropyrrolidine-1,2-dicarboxylate (255.mg, 1.03 mmol) in THF (7.93 mL) was added LAH (0.28 mL, 1.13 mmol) at −40° C. under nitrogen. The mixture was stirred at −40° C. for 30 min, then warm to 0° C. and the mixture was stirred at 0° C. for 30 min. The mixture was quenched with water at 0° C. and extracted with DCM. The combined organic layers were washed with brine, dried over anhydrous Na2SO₄, and concentrated under reduced pressure to give the title compound (210 mg).

Step 2: Preparation of tert-butyl (2R,3S)-2-[(6-chloropyrazolo[3,4-d]pyrimidin-1-yl)methyl]-3-fluoro-pyrrolidine-1-carboxylate. Prepared by general procedure D using 6-chloro-1 h-pyrazolo[3,4-d]pyrimidine (150.0 mg, 0.97 mmol), tert-butyl (2R,3S)-3-fluoro-2-(hydroxymethyl)pyrrolidine-1-carboxylate (212.8 mg, 0.97 mmol), triphenylphosphine (509.1 mg, 1.94 mmol) and DIAD (0.38 mL, 1.94 mmol) in THF (2 mL) at rt for 16 h. The crude product was purified by silica column chromatography (0-50% EtOAc in hexanes) to provide the desired product as a solid (340 mg).

Step 3: Preparation of 1-[(2R,3S)-2-[(6-chloropyrazolo[3,4-d]pyrimidin-1-yl)methyl]-3-fluoro-pyrrolidin-1-yl]ethenone. To a solution of tert-butyl (2R,3S)-2-[(6-chloropyrazolo[3,4-d]pyrimidin-1-yl)methyl]-3-fluoro-pyrrolidine-1-carboxylate (340.mg, 0.96 mmol) in DCM (2 mL) was added TFA (0.73 mL, 9.56 mmol). The reaction was stirred at rt until complete deprotection. Triethylamine (0.67 mL, 4.78 mmol) followed by acetyl chloride (0.14 mL, 1.91 mmol) were added to the mixture at 0° C. and then stirred at rt for 1 h. The crude product was purified by silica column chromatography (0-100% EtOAc in hexanes, then 0-40% MeOH in DCM) to provide the desired product as a solid (200 mg).

Step 4: Preparation of 1-[(2R,3S)-3-fluoro-2-[[6-[(6-methoxy-2-methyl-3,4-dihydro-1H-isoquinolin-7-yl)amino]pyrazolo[3,4-d]pyrimidin-1-yl]methyl]pyrrolidin-1-yl]ethenone. Prepared by general procedure A using 1-[(2R,3S)-2-[(6-chloropyrazolo[3,4-d]pyrimidin-1-yl)methyl]-3-fluoropyrrolidin-1-yl]ethanone (200 mg, 0.67 mmol), 6-methoxy-2-methyl-3,4-dihydro-1H-isoquinolin-7-amine (194 mg, 1 mmol), and p-TSA (256 mg, 1.34 mmol) in 2-butanol (3 mL) at 100° C. for 3 h. The crude product was purified reversed phase HPLC (Phenomenex, Gemini-NX, 10 um, 250×30 mm, C18 column; gradient of 00% MeCN/0.1% TFA-water to 100% MeCN/0.1% TFA), providing the desired product as a solid (100 mg). 1H NMR (400 MHz, DMSO) δ 8.27 (d, J=4.4 Hz, 1H), 8.18 (s, 1H), 8.04 (d, J=8.5 Hz, 1H), 6.83 (s, 1H), 4.56 (d, J=11.4 Hz, 1H), 4.44-4.19 (m, 2H), 3.77 (s, 3H), 3.25 (d, J=10.2 Hz, 1H), 2.96 (dt, J=11.4, 5.6 Hz, 4H), 2.84 (s, 3H), 1.79 (d, J=5.3 Hz, 3H), 1.04 (t, J=7.1 Hz, 6H). [M+H]$^+$: 454.2

Example 214

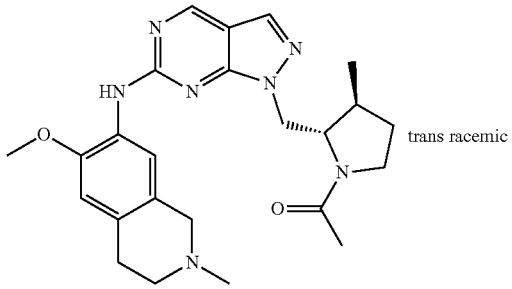 [SMILES: COc1cc2c(cc1Nc1ncc3cnn(C[C@@H]4[C@@H](C)CCN4C(C)=O)c3n1)CN(C)CC2]

1-[2-[[6-[(6-methoxy-2-methyl-3,4-dihydro-1H-isoquinolin-7-yl)amino]pyrazolo[3,4-d]pyrimidin-1-yl]methyl]-3-methyl-pyrrolidin-1-yl]ethenone Prepared by EXAMPLE 213 steps 2-4 substituting tert-butyl cis-2-(hydroxymethyl)-3-methyl-pyrrolidine-1-carboxylate for tert-butyl (2R,3S)-3-fluoro-2-(hydroxymethyl)pyrrolidine-1-carboxylate provide the desired product as a solid (80 mg). 1H NMR (400 MHz, Methanol-d4) δ 8.97-8.91 (m, 1H), 8.56 (d, J=12.2 Hz, 11H), 8.06 (s, 1H), 6.93 (s, 1H), 4.82-4.36 (m, 2H), 4.30 (d, J=14.9 Hz, 1H), 4.09 (q, J=3.8 Hz, 1H), 3.96 (d, J=5.1 Hz, 4H), 3.76 (s, 1H), 3.44 (ddt, J=23.6, 17.4, 6.5 Hz, 2H), 3.09 (d, J=5.9 Hz, 3H), 2.97 (s, $^1$H), 2.50 (s, 1H), 1.83 (d, J=20.2 Hz, 3H), 1.65-1.32 (m, 2H), 0.97 (dd, J=11.7, 7.0 Hz, 3H). [M+H]$^+$: 450.0.

Example 215

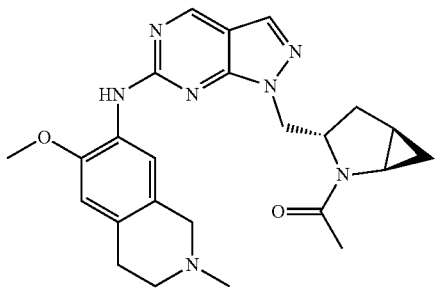 [SMILES: COc1cc2c(cc1Nc1ncc3cnn(C[C@@H]4C[C@H]5C[C@H]5N4C(C)=O)c3n1)CN(C)CC2]

1-[(1R,3S,5R)-3-[[6-[(6-methoxy-2-methyl-3,4-dihydro-1H-isoquinolin-7-yl)amino]pyrazolo[3,4-d]pyrimidin-1-yl]methyl]-2-azabicyclo[3.1.0]hexan-2-yl]ethanone Step 1: Preparation of tert-butyl (1R,3S,5R)-3-(hydroxymethyl)-2-azabicyclo[3.1.0]hexane-2-carboxylate. To (1R,3S,5R)-2-tert-butoxycarbonyl-2-azabicyclo[3.1.0]hexane-3-carboxylic acid (200.0 mg, 0.88 mmol) in anhydrous THF (4.40 mL) at rt was added dimethylsulfide borane (2M in THF, 0.48 mL, 0.97 mmol) dropwise over 15 min. The reaction was heated at reflux for 1.5 h and was then cooled by an ice-bath. Methanol (1 mL) was added dropwise during 30 min while the temperature was maintained between 4-15° C. The ice-bath was removed, and the reaction was allowed to reach rt over 35 min. The reaction mixture was concentrated under reduced pressure at 25° C. and the residue was partitioned between DCM and water. The organic layer was washed sequentially with saturated aqueous sodium bicarbonate and brine. The aqueous layer from the final wash was extracted with a small portion of DCM and the combined organic layers were dried over anhydrous sodium sulfate, filtered, and concentrated under reduced pressure to give the crude tert-butyl (1R,3S,5R)-3-(hydroxymethyl)-2-azabicyclo[3.1.0]hexane-2-carboxylate (210 mg). This material was taken forward without further purification.

Step 2: Preparation of tert-butyl (1R,3S,5R)-3-[(6-chloropyrazolo[3,4-d]pyrimidin-1-yl)methyl]-2-azabicyclo[3.1.0]hexane-2-carboxylate. Prepared by general procedure D using 6-chloro-1 h-pyrazolo[3,4-d]pyrimidine (150.0 mg, 0.97 mmol), tert-butyl (1R,3S,5R)-3-(hydroxymethyl)-2-azabicyclo[3.1.0]hexane-2-carboxylate (207.0 mg, 0.97 mmol), triphenylphosphine (509.1 mg, 1.94 mmol) DIAD (0.38 mL, 1.94 mmol) in THF (2 mL) at rt for 16 h. The crude product was purified by silica column chromatography (0-50% EtOAc in hexanes) to provide the desired product as a solid (350 mg).

Step 3: Preparation of 1-[(1R,3S,5R)-3-[(6-chloropyrazolo[3,4-d]pyrimidin-1-yl)methyl]-2-azabicyclo[3.1.0]hexan-2-yl]ethanone. To a solution of tert-butyl (1R,3S,5R)-3-[(6-chloropyrazolo[3,4-d]pyrimidin-1-yl)methyl]-2-azabicyclo[3.1.0]hexane-2-carboxylate (350.0 mg, 1 mmol) in DCM (2 mL) was added TFA (0.77 mL, 10.0 mmol) and the solution was stirred at rt until the reaction was complete. Triethylamine (0.70 mL, 5. mmol) followed by acetyl chloride (0.14 mL, 2.0 mmol) were added to the mixture at 0° C. and stirred at rt for 1 h. The crude product was purified by silica column chromatography (0-100% EtOAc in hexanes, then 0-40% MeOH in DCM) to provide the desired product as a solid (300 mg).

Step 4: Preparation of 1-[(1R,3S,5R)-3-[[6-[(6-methoxy-2-methyl-3,4-dihydro-1H-isoquinolin-7-yl)amino]pyrazolo[3,4-d]pyrimidin-1-yl]methyl]-2-azabicyclo[3.1.0]hexan-2-yl]ethanone. Prepared by general procedure A using 1-[(1R,3S,5R)-3-[(6-chloropyrazolo[3,4-d]pyrimidin-1-yl)methyl]-2-azabicyclo[3.1.0]hexan-2-yl]ethanone (300 mg, 1 mmol), 6-methoxy-2-methyl-3,4-dihydro-1H-isoquinolin-7-amine (320 mg, 1.7 mmol), and p-TSA (422 mg, 2.22 mmol) in 2-butanol (4 mL) at 100° C. for 3 h. The crude product was purified reversed phase HPLC (Phenomenex, Gemini-NX, 10 um, 250×30 mm, C18 column; gradient of 0% MeCN/0.1% TFA-water to 100% MeCN/0.1% TFA), providing the desired product as a solid (60 mg, 11% yield). 1H NMR (400 MHz, CD30 D) δ 9.13 (d, J=6.6 Hz, 1H), 8.32 (s, 2H), 7.02 (s, 1H), 4.83 (s, 1H), 4.74-4.21 (m, 4H), 3.98 (s, 3H), 3.79 (s, 1H), 3.44 (d, J=16.6 Hz, 1H), 3.17 (d, J=20.3 Hz, 1H), 3.10 (d, J=2.3 Hz, 3H), 2.89-2.41 (m, 3H), 2.04-1.95 (m, 1H), 1.88 (s, 1H), 1.83 (s, 1H), 1.64-1.14 (m, 2H), 0.88 (d, J=9.4 Hz, 1H), 0.42 (d, J=5.0 Hz, 1H). [M+H]+: 448.0

Example 216

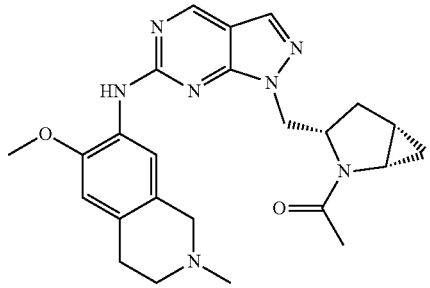 [SMILES: COc1cc2c(cc1Nc1ncc3cnn(C[C@@H]4C[C@@H]5C[C@@H]5N4C(C)=O)c3n1)CN(C)CC2]

1-[(1S,3S,5S)-3-[[6-[(6-methoxy-2-methyl-3,4-dihydro-1H-isoquinolin-7-yl)amino]pyrazolo[3,4-d]pyrimidin-1-yl]methyl]-2-azabicyclo[3.1.0]hexan-2-yl]ethanone Step 1: Preparation of tert-butyl (1S,3S,5S)-3-(hydroxymethyl)-2-azabicyclo[3.1.0]hexane-2-carboxylate. To a solution of 2-(tert-butyl) 3-ethyl (1S,3S,5S)-2-azabicyclo[3.1.0]hexane-2,3-dicarboxylate (250.0 mg, 0.98 mmol) in THF (4.8 mL) was added LAH (0.49 mL, 1.96 mmol) at 0° C. under nitrogen. The mixture was stirred at 0 C for 30 min. After completion, the mixture was quenched with sat. NH4Cl at 0° C. The reaction mixture was extracted with DCM. The combined organic layers were washed with brine, dried over anhydrous Na2SO4, concentrated under reduced pressure, to obtain the title compound (208 mg).

Step 2: Preparation of 1-[(1S,3S,5S)-3-[(6-chloropyrazolo[3,4-d]pyrimidin-1-yl)methyl]-2-azabicyclo[3.1.0]hexan-2-yl]ethanone. Prepared by general procedure D using 6-chloro-1 h-pyrazolo[3,4-d]pyrimidine (20.03 mg, 1 mmol), tert-butyl (1S,3S,5S)-3-(hydroxymethyl)-2-azabicyclo[3.1.0]hexane-2-carboxylate (280.0 mg, 1 mmol), triphenylphosphine (689 mg, 2.63 mmol) and DIAD (0.52 mL, 2.63 mmol) in THF (6 mL) at rt for 16 h. The crude product concentrated under reduced pressure and dissolved in DCM (5 mL). 4N HCl in 1,4-dioxane (2.5 mL) was added and the solution was stirred at rt until reaction was complete. Triethylamine (1.8 mL, 13 mmol) followed by acetyl chloride (0.21 mL, 2.9 mmol) were added to the mixture at 0° C. and stirred at rt for 1 h. The crude product was purified by silica column chromatography (0-100% EtOAc in hexanes, then 0-40% MeOH in DCM) to provide the desired product as a solid (150 mg).

Step 3: Preparation of 1-[(1S,3S,5S)-3-[[6-[(6-methoxy-2-methyl-3,4-dihydro-1H-isoquinolin-7-yl)amino]pyrazolo[3,4-d]pyrimidin-1-yl]methyl]-2-azabicyclo[3.1.0]hexan-2-yl]ethanone. Prepared by general procedure A using 1-[(1S,3S,5S)-3-[(6-chloropyrazolo[3,4-d]pyrimidin-1-yl)methyl]-2-azabicyclo[3.1.0]hexan-2-yl]ethanone (150 mg, 0.51 mmol), 6-methoxy-2-methyl-3,4-dihydro-1H-isoquinolin-7-amine (148 mg, 0.7 mmol), and p-TSA (196 mg, 1.03 mmol) in 2-butanol (2 mL) at 100° C. for 3 h. The crude product was purified by HPLC (Phenomenex, Gemini-NX, 10 um, 250×30 mm, C18 column; gradient of 0% MeCN/0.1% TFA-water to 100% MeCN/0.1% TFA), providing the desired product as a solid (23 mg). 1H NMR (400 MHz, DMSO-d6) δ 8.45 (s, 1H), 8.28 (s, 1H), 8.14 (s, 1H), 6.95 (s, 1H), 4.63 (d, J=12.9 Hz, 3H), 4.47-4.17 (m, 2H), 3.90 (s, 3H), 3.88 (s, 1H), 3.47 (s, 1H), 3.25 (d, J=67.5 Hz, 1H), 3.05-2.90 (m, 6H), 2.21 (t, J=6.6 Hz, 2H), 2.07 (d, J=6.5 Hz, 3H), 1.55 (s, 1H), 0.66 (d, J=8.0 Hz, 1H). [M+H]+: 448.0

Example 217

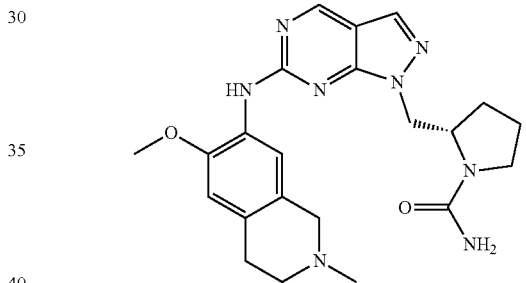

(2S)-2-[[6-[(6-methoxy-2-methyl-3,4-dihydro-1H-isoquinolin-7-yl)amino]pyrazolo[3,4-d]pyrimidin-1-yl]methyl]pyrrolidine-1-carboxamide Step 1: Preparation of (2S)-2-[(6-chloropyrazolo[3,4-d]pyrimidin-1-yl)methyl]pyrrolidine-1-carboxamide. To a mixture of 6-chloro-1-[[(2S)-pyrrolidin-2-yl]methyl]pyrazolo[3,4-d]pyrimidine hydrochloride (50 mg, 0.18 mmol) and sodium cyanate (27.9 mg, 0.36 mmol) in MeCN (0.9 mL) was added TFA (0.03 mL, 0.36 mmol). The suspension was stirred at rt for 3 h, then another 1 eq. of sodium cyanate and TFA were added and stirred at rt for an additional 18 h. The reaction was concentrated and acidified using 1M HCl. The mixture was extracted with DCM and the combined organics were concentrated under reduced pressure and carried to the next step without further purification.

Step 2: Preparation of (2S)-2-[[6-[(6-methoxy-2-methyl-3,4-dihydro-1H-isoquinolin-7-yl)amino]pyrazolo[3,4-d]pyrimidin-1-yl]methyl]pyrrolidine-1-carboxamide. Prepared by general procedure A using (2S)-2-[(6-chloropyrazolo[3,4-d]pyrimidin-1-yl)methyl]pyrrolidine-1-carboxamide (100 mg, 0.36 mmol), 6-methoxy-2-methyl-3,4-dihydro-1H-isoquinolin-7-amine (103 mg, 0.54 mmol), and p-TSA (136 mg, 0.72 mmol) in 2-butanol (2 mL) at 100° C. for 3 h. The crude product was purified by (Phenomenex, Gemini-NX, 10 um, 250×30 mm, C18 column; gradient of 0% MeCN/ 0.1% TFA-water to 100% MeCN/0.1% TFA), providing the desired product as a solid (37 mg). 1H NMR (400 MHz, DMSO-d6) δ 8.34 (s, 1H), 8.18 (s, 1H), 8.01 (s, 1H), 6.83 (s, 1H), 4.77-4.40 (m, 1H), 4.23 (d, J=11.4 Hz, 1H), 4.16 (s, 3H), 3.78 (s, 3H), 3.20 (s, 1H), 3.03 (s, 2H), 2.91-2.80 (m, 4H), 1.68 (dd, J=61.4, 26.2 Hz, 4H), 1.39 (s, 11H), 1.07 (s, 11H). [M+H]⁺: 437.1

Example 218

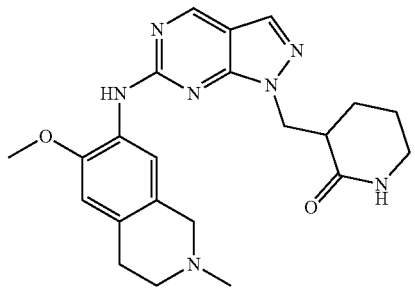 [SMILES: COc1cc2c(cc1Nc1ncc3cnn(CC4CCCNC4=O)c3n1)CN(C)CC2]

3-[[6-[(6-methoxy-2-methyl-3,4-dihydro-1H-isoquinolin-7-yl)amino]pyrazolo[3,4-d]pyrimidin-1-yl]methyl]piperidin-2-one Step 1: Preparation of 3-[(6-chloropyrazolo[3,4-d]pyrimidin-1-yl)methyl]piperidin-2-one. Prepared by general procedure D using 6-chloro-1 h-pyrazolo[3,4-d]pyrimidine (120 mg, 0.77 mmol), 3-(hydroxymethyl)piperidin-2-one (100 mg, 0.77 mmol), triphenylphosphine (406 mg, 1.55 mmol) and DIAD (0.31 mL, 1.55 mmol) in THF (3 mL) at rt for 16 h. The crude product was purified by silica column chromatography (0-100% EtOAc in hexanes, then 0-40% MeOH in DCM) to provide the desired product as a solid (200 mg).

Step 2: Preparation of 3-r[6-[(6-methoxy-2-methyl-3,4-dihydro-1H-isoquinolin-7-yl)amino]pyrazolo[3,4-d]pyrimidin-1-yl]methyl]piperidin-2-one. Prepared by general procedure A using 3-[(6-chloropyrazolo[3,4-d]pyrimidin-1-yl)methyl]piperidin-2-one (88 mg, 0.33 mmol), 6-methoxy-2-methyl-3,4-dihydro-1H-isoquinolin-7-amine (96 mg, 0.5 mmol), and p-TSA (126 mg, 0.66 mmol) in 2-butanol (2 mL) at 100° C. for 3 h. The crude product was purified reversed phase eluting with 0% to 100% MeCN (with 0.1% TFA added) in water (with 0.1% TFA added), providing the desired product as a solid (37 mg). 1H NMR (400 MHz, DMSO) δ 8.42 (d, J=4.6 Hz, 1H), 8.12 (d, J=1.4 Hz, 1H), 7.66 (s, 1H), 6.94 (s, 1H), 4.88-4.65 (m, 1H), 4.57-4.13 (m, 3H), 3.30 (s, 1H), 3.12 (d, J=6.4 Hz, 3H), 2.98 (d, J=17.7 Hz, 1H), 2.90 (dd, J=5.0, 2.5 Hz, 3H), 2.82-2.66 (m, 1H), 2.33 (s, 2H), 1.98-1.31 (m, 5H), 1.16 (d, J=6.3 Hz, 1H). [M+H]⁺: 422.0

Example 219

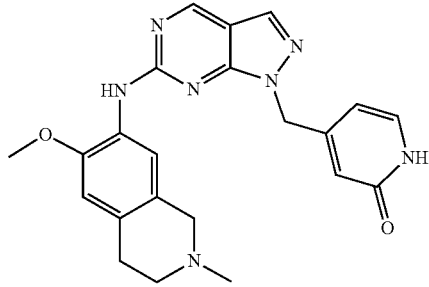 [SMILES: COc1cc2c(cc1Nc1ncc3cnn(Cc4cc[nH]c(=O)c4)c3n1)CN(C)CC2]

4-[[6-[(6-methoxy-2-methyl-3,4-dihydro-1H-isoquinolin-7-yl)amino]pyrazolo[3,4-d]pyrimidin-1-yl]methyl]-1H-pyridin-2-one Step 1: Preparation of 4-[(6-chloropyrazolo[3,4-d]pyrimidin-1-yl)methyl]-1H-pyridin-2-one. Prepared by general procedure D using 6-chloro-1 h-pyrazolo[3,4-d]pyrimidine (124 mg, 0.8 mmol), 4-(hydroxymethyl)-2(1H)-pyridinone (100 mg, 0.8 mmol), triphenylphosphine (419 mg, 1.6 mmol) and DIAD (0.31 mL, 1.6 mmol) in THF (3 mL) at rt for 16 h. The crude product was purified by silica column chromatography (0-100% EtOAc in hexanes, then 0-40% MeOH in DCM) to provide the desired product as a solid (100 mg).

Step 2: Preparation of 4-[[6-[(6-methoxy-2-methyl-3,4-dihydro-1H-isoquinolin-7-yl)amino]pyrazolo[3,4-d]pyrimidin-1-yl]methyl]-1H-pyridin-2-one. Prepared by general procedure A using 4-[(6-chloropyrazolo[3,4-d]pyrimidin-1-yl)methyl]-1H-pyridin-2-one (40 mg, 0.15 mmol), 6-methoxy-2-methyl-3,4-dihydro-1H-isoquinolin-7-amine (44 mg, 0.2 mmol), and p-TSA (58 mg, 0.31 mmol) in 2-butanol (2 mL) at 100° C. for 3 h. The crude product was purified reversed phase HPLC (Phenomenex, Gemini-NX, 10 um, 250×30 mm, C18 column; gradient of 0% MeCN/ 0.1% TFA-water to 100% MeCN/0.1% TFA), providing the desired product as a solid (12 mg). 1H NMR (400 MHz, DMSO-d6) δ 9.38 (s, 1H), 8.80 (s, 1H), 8.55 (s, 1H), 8.39 (s, 1H), 7.68 (d, J=6.8 Hz, 1H), 7.31 (s, 11H), 6.53 (s, 11H), 6.30 (d, J=6.5 Hz, 1H), 5.73 (s, 2H), 4.79 (s, 1H), 4.6 (s, 1H), 4.21 (s, 3H), 3.31 (s, 3H), 1.59 (s, 2H). [M+H]⁺: 418.0

Example 220

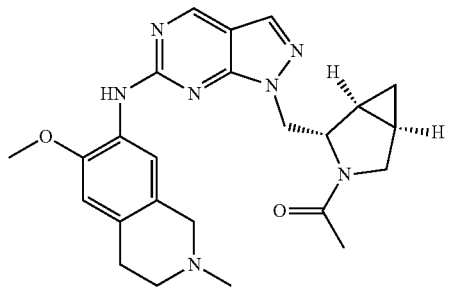 [SMILES: COc1cc2c(cc1Nc1ncc3cnn(C[C@@H]4[C@H]5C[C@H]5CN4C(C)=O)c3n1)CN(C)CC2]

1-[(1S,2S,5R)-2-[[6-[(6-methoxy-2-methyl-3,4-dihydro-1H-isoquinolin-7-yl)amino]pyrazolo[3,4-d]pyrimidin-1-yl]methyl]-3-azabicyclo[3.1.0]hexan-3-yl]ethanone Step 1: Preparation of 1-[(1S,2S,5R)-2-[(6-chloropyrazolo[3,4-d]pyrimidin-1-yl)methyl]-3-azabicyclo[3.1.0]hexan-3-yl]ethenone. Prepared by general procedure D using 6-chloro-1 h-pyrazolo[3,4-d]pyrimidine (330 mg, 2.14 mmol), tert-butyl (1S,2S,5R)-2-(hydroxymethyl)-3-azabicyclo[3.1.0]hexane-3-carboxylate (467 mg, 2.2 mmol), triphenylphosphine (1.2 g, 4.27 mmol) and DIAD (0.84 mL, 4.27 mmol) in THF (10 mL) at rt for 16 h. The crude product concentrated under reduced pressure and dissolved in DCM (5 mL). 4N HCl in 1,4-dioxane (3 mL) was added and the solution was stirred at room temperature until reaction was complete. TEA (1.2 mL, 8.81 mmol) followed by acetyl chloride (0.31 mL, 4.4 mmol) were added to the mixture at 0° C. and stirred at rt for 1 h. The crude product was purified by silica column chromatography (0-100% EtOAc in hexanes, then 0-40% MeOH in DCM) to provide the desired product as a solid (700 mg).

Step 2: Preparation of 1-[rac-(1S,2S,5R)-2-[[6-[(6-methoxy-2-methyl-3,4-dihydro-1H-isoquinolin-7-yl)amino]pyrazolo[3,4-d]pyrimidin-1-yl]methyl]-3-azabicyclo[3.1.0]hexan-3-yl]ethanone. Prepared by general procedure A using 1-[(1S,2S,5R)-2-[(6-chloropyrazolo[3,4-d]pyrimidin-1-yl)methyl]-3-azabicyclo[3.1.0]hexan-3-yl]ethanone (100 mg, 0.34 mmol), 6-methoxy-2-methyl-3,4-dihydro-1H-isoquinolin-7-amine (99 mg, 0.51 mmol), and p-TSA (130 mg, 0.68 mmol) in NMP (2 mL) at 100° C. for 3 h. The crude product was purified reversed phase eluting with 0% to 100% MeCN (with 0.1% TFA added) in water (with 0.1% TFA added), providing the desired product as a solid (30 mg). 1H NMR (400 MHz, DMSO-d6) δ 8.98 (d, J=11.1 Hz, 1H), 8.17-8.07 (m, 2H), 6.81 (s, 1H), 4.42 (t, J=13.3 Hz, 4H), 3.93-3.85 (m, 2H), 3.83 (d, J=9.6 Hz, 4H), 2.84 (s, 3H), 1.70 (s, 2H), 1.58 (s, 2H), 1.24 (s, 2H), 1.18 (d, J=6.3 Hz, $^1$H), 0.63 (d, J=7.0 Hz, 2H), 0.04 (s, 2H). [M+H]$^+$: 448.0

Example 221

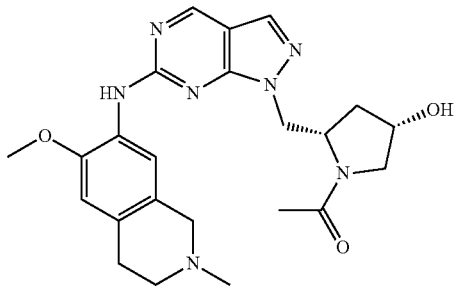 [SMILES: COc1cc2c(cc1Nc1ncc3cnn(C[C@@H]4C[C@H](O)CN4C(C)=O)c3n1)CN(C)CC2]

1-((2S,4S)-4-hydroxy-2-((6-((6-methoxy-2-methyl-1,2,3,4-tetrahydroisoquinolin-7-yl)amino)-1H-pyrazolo[3,4-d]pyrimidin-1-yl)methyl)pyrrolidin-1-yl)ethan-1-one Step 1: Preparation of 1-((2S,4S)-2-((6-chloro-1H-pyrazolo[3,4-d]pyrimidin-1-yl)methyl)-4-hydroxypyrrolidin-1-yl)ethan-1-one. To a solution of tert-butyl (2S,4R)-2-[(6-chloropyrazolo[3,4-d]pyrimidin-1-yl)methyl]-4-hydroxypyrrolidine-1-carboxylate (6.0 g, 16.9 mmol) DCM (34 mL) at rt was added HCl (4M soln in dioxane, 12.2 mL, 50.0 mmol) dropwise. The reaction mixture was stirred at rt for 8 h. The white precipitate was filtered, rinsed with DCM, and dried under reduced pressure to provide the deprotected material as an off-white solid. To a solution of this deprotected material in DCM (25 mL) was added sequentially TEA (5.19 mL, 37.2 mmol) and acetic anhydride (2.35 mL, 24.8 mmol). The reaction mixture was stirred at rt for 30 min. Upon completion of the reaction, the mixture was diluted with DCM (50 mL) and washed with a saturated aqueous sodium carbonate solution (50 mL) to give an aqueous pH=12. The organic layer was dried over sodium sulfate, filtered, and concentrated under reduced pressure to afford the title compound (3.52 g). This crude material was used as is for the next reaction without any further purification.

Step 2: Preparation of 1-((2S,4R)-4-hydroxy-2-((6-((6-methoxy-2-methyl-1,2,3,4-tetrahydroisoquinolin-7-yl)amino)-1H-pyrazolo[3,4-d]pyrimidin-1-yl)methyl)pyrrolidin-1-yl)ethan-1-one. Prepared according to general procedure A using 6-methoxy-2-methyl-3,4-dihydro-1H-isoquinolin-7-amine (0.20 g, 1.01 mmol), 1-((2S,4S)-2-((6-chloro-1H-pyrazolo[3,4-d]pyrimidin-1-yl)methyl)-4-hydroxypyrrolidin-1-yl)ethan-1-one (0.20 g, 0.68 mmol), and p-TSA (0.39 g, 2.03 mmol) in NMP (1.8 mL) at 100° C. for 36 h. The crude product was purified directly by reversed phase preparative HPLC (Gemini-NX, 10 mm, 250×30 mm, C18 column, eluent: 0 to 100% MeCN in water, both eluents containing 0.1% TFA, gradient elution over 30 minutes). The fractions containing the desired product were concentrated under reduced pressure and afforded the corresponding TFA salt. The TFA salt was free based using a Carbonate SiliaPrep SPE Cartridge (SPE-R66030B-200 mg/3 mL) and DCM/MeOH (1:1) as eluent, and then concentrated under reduced pressure to afforded the title compound (89.6 mg) as a solid.

Step 3: Preparation of (3S,5S)-1-acetyl-5-((6-chloro-1H-pyrazolo[3,4-d]pyrimidin-1-yl)methyl)pyrrolidin-3-yl benzoate. Prepared according to general procedure D using-((2S,4R)-4-hydroxy-2-((6-((6-methoxy-2-methyl-1,2,3,4-tetrahydroisoquinolin-7-yl)amino)-1H-pyrazolo[3,4-d]pyrimidin-1-yl)methyl)pyrrolidin-1-yl)ethan-1-one (1.0 g, 3.38 mmol), benzoic acid (0.45 g, 3.72 mmol), triphenylphosphine (1.34 g, 5.07 mmol), and DIAD (1.01 mL, 5.07 mmol) in THF (17 mL) at 0° C. for 30 min. Upon completion of the reaction, the volatiles were removed under reduced pressure. The crude was purified by silica gel MPLC (0-20% MeOH in DCM) to afford a mixture of the title compound (0.81 g, 60% purity) with residual triphenylphosphine oxide by-product as a light-yellow oil. This material was taken forward without further purification.

Step 4: Preparation of 1-((2S,4S)-4-hydroxy-2-((6-((6-methoxy-2-methyl-1,2,3,4-tetrahydroisoquinolin-7-yl)amino)-1H-pyrazolo[3,4-d]pyrimidin-1-yl)methyl)pyrrolidin-1-yl)ethan-1-one hydrochloride. Prepared according to general procedure A using 6-methoxy-2-methyl-3,4-dihydro-1H-isoquinolin-7-amine (0.14 g, 0.75 mmol) and (3S,5S)-1-acetyl-5-((6-chloro-1H-pyrazolo[3,4-d]pyrimidin-1-yl)methyl)pyrrolidin-3-yl benzoate (0.20 g, 0.5 mmol) and p-TSA (0.29 g, 1.5 mmol) in NMP (1.8 mL) at 100° C. for 36 h. The mixture was cooled to rt and then lithium hydroxide (57.3 mg, 2.5 mmol) and water (1 mL) was added. The reaction mixture was stirred at rt for 24 h. The crude product was purified directly by reversed phase preparative HPLC (Gemini-NX, 10 mm, 250×30 mm, C18 column, eluent: 0 to 100% MeCN in water, both eluents containing 0.1% TFA, gradient elution, 30 min). The fractions contain- Example 222

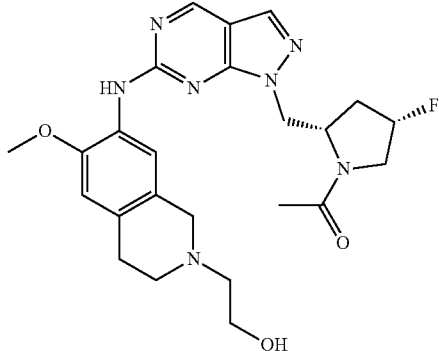 [SMILES: COc1cc2c(cc1Nc1ncc3cnn(C[C@@H]4C[C@H](F)CN4C(C)=O)c3n1)CN(CCO)CC2]

1-((2S,4S)-4-fluoro-2-((6-((2-(2-hydroxyethyl)-6-methoxy-1,2,3,4-tetrahydroisoquinolin-7-yl)amino)-1H-pyrazolo[3,4-d]pyrimidin-1-yl)methyl)pyrrolidin-1-yl)ethan-1-one Prepared according to EXAMPLE 194 substituting tert-butyl (2S,4S)-4-fluoro-2-(hydroxymethyl)pyrrolidine-1-carboxylate for N-Boc-L-prolinol (step 1) to afford the title compound (84 mg). Characterized as a mixture of rotamers, 1H NMR (400 MHz, Methanol-d4) δ 9.11 (s, 1H), 8.45 (s, 1H), 8.28 (s, 1H), 7.01 (s, 1H), 5.50-5.41 (m, 1H), 5.37-5.28 (m, 1H), 4.78-4.70 (m, 2H), 4.68-4.55 (m, 1H), 4.54-4.42 (m, 2H), 4.03-3.99 (m, 1H), 3.98 (s, 3H), 3.90-3.82 (m, 2H), 3.82-3.77 (m, 1H), 3.54-3.37 (m, 3H), 3.22-3.10 (m, 1H), 2.45-2.31 (m, 1H), 2.31-2.09 (m, 1H), 1.95 (s, 3H), 1.73 (d, J=11.3 Hz, 1H). LCMS [M+H]⁺: 484.3

Example 223

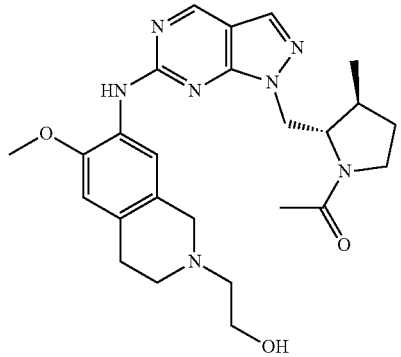 [SMILES: COc1cc2c(cc1Nc1ncc3cnn(C[C@@H]4[C@@H](C)CCN4C(C)=O)c3n1)CN(CCO)CC2]

1-((2S,3S)-2-((6-((2-(2-hydroxyethyl)-6-methoxy-1,2,3,4-tetrahydroisoquinolin-7-yl)amino)-1H-pyrazolo[3,4-d]pyrimidin-1-yl)methyl)-3-methylpyrrolidin-1-yl)ethan-1-one Prepared according to EXAMPLE 194 substituting 1-((2S,3S)-2-(hydroxymethyl)-3-methylpyrrolidin-1-yl)ethan-1-one (step 1) for N-Boc-L-prolinol to afford the title compound (84 mg). Characterized as a mixture of rotamers, 1H NMR (400 MHz, Methanol-d4) δ 9.18 (d, J=1.6 Hz, 1H), 8.36 (d, J=1.6 Hz, 1H), 8.30 (s, 1H), 7.03 (s, 1H), 4.83-4.56 (m, 3H), 4.54-4.38 (m, 1H), 4.15-4.07 (m, 1H), 4.07-3.99 (m, 2H), 3.98 (s, 3H), 3.93-3.82 (m, 1H), 3.61-3.48 (m, 1H), 3.48-3.40 (m, 3H), 3.23-3.12 (m, 3H), 2.53-2.41 (m, 1H), 1.87 (s, 1.5H), 1.86 (s, 1.5H), 1.84-1.73 (m, 1H), 1.59-1.49 (m, 1H), 1.00 (d, J=5.7 Hz, 1.5H), 0.98 (d, J=5.7 Hz, 1.5H). LCMS [M+H]⁺: 480.3

Example 224

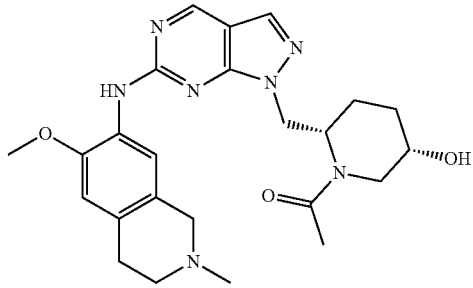 [SMILES: COc1cc2c(cc1Nc1ncc3cnn(C[C@@H]4CC[C@H](O)CN4C(C)=O)c3n1)CN(C)CC2]

1-((2S,5S)-5-hydroxy-2-((6-((6-methoxy-2-methyl-1,2,3,4-tetrahydroisoquinolin-7-yl)amino)-1H-pyrazolo[3,4-d]pyrimidin-1-yl)methyl)piperidin-1-yl)ethan-1-one Prepared according to EXAMPLE 221 substituting tert-butyl (2S,5S)-5-hydroxy-2-(hydroxymethyl)piperidine-1-carboxylate (step 1) for tert-butyl (1S,2S,5R)-2-(hydroxymethyl)-3-azabicyclo[3.1.0]hexane-3-carboxylate to afford the title compound (72 mg). Characterized as a mixture of rotamers, 1H NMR (400 MHz, Methanol-d4) δ 9.10 (s, 1H), 8.33-8.19 (m, 2H), 7.03 (d, J=12.0 Hz, 1H), 5.18-5.00

(m, 1H), 4.85-4.63 (m, 1H), 4.59-4.32 (m, 3H), 3.97 (s, 3H), 3.82-3.74 (m, 1H), 3.73-3.56 (m, 1H), 3.55-3.38 (m, 1H), 3.23-3.11 (m, 2H), 3.08 (s, 3H), 2.89-2.71 (m, 1H), 2.07-1.88 (m, 3H), 1.88-1.79 (m, 2H), 1.72 (s, 3H). LCMS [M+H]$^+$: 466.3

Example 225

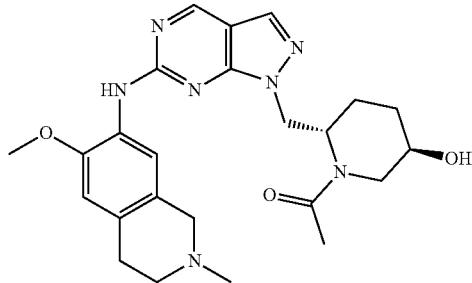 [SMILES: COc1cc2c(cc1Nc1ncc3cnn(C[C@@H]4CC[C@@H](O)CN4C(C)=O)c3n1)CN(C)CC2]

1-((2S,5R)-5-hydroxy-2-((6-((6-methoxy-2-methyl-1,2,3,4-tetrahydroisoquinolin-7-yl)amino)-1H-pyrazolo[3,4-d]pyrimidin-1-yl)methyl)piperidin-1-yl)ethan-1-one Prepared according to EXAMPLE 220 substituting 1-((2S,5S)-2-((6-chloro-1H-pyrazolo[3,4-d]pyrimidin-1-yl)methyl)-5-hydroxypiperidin-1-yl)ethan-1-one (step 1) for 1-((2S,4R)-2-((6-chloro-1H-pyrazolo[3,4-d]pyrimidin-1-yl)methyl)-4-hydroxypyrrolidin-1-yl)ethan-1-one to afford the title compound (231 mg). Characterized as a mixture of rotamers, 11H NMR (400 MHz, Methanol-d4) δ 9.15 (s, 1H), 8.34 (s, 11H), 8.03 (d, J=8.8 Hz, 11H), 7.08 (s, 1H), 5.26-5.17 (m, 1H), 4.80-4.69 (m, 1H), 4.69-4.60 (m, 1H), 4.60-4.49 (m, 1H), 4.41-4.32 (m, 1H), 4.04-3.99 (m, 11H), 3.96 (s, 3H), 3.85-3.74 (m, 11H), 3.73-3.63 (m, 11H), 3.63-3.53 (m, 1H), 3.52-3.41 (m, 1H), 3.27-3.16 (m, 1H), 3.09 (s, 3H), 2.15-1.97 (m, 2H), 1.92 (s, 1.5H), 1.91 (s, 1.5H), 1.83-1.65 (m, 2H), 1.66-1.54 (m, 1H). LCMS [M+H]$^+$: 466.3

Example 226

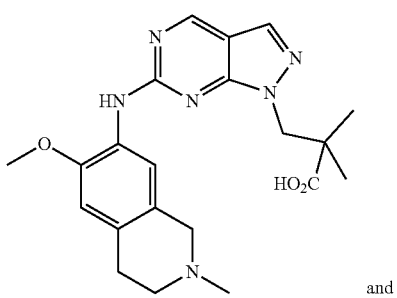

and

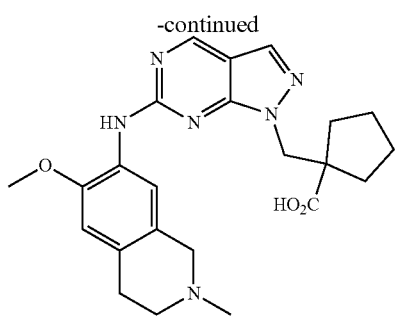

These compounds are made by the synthetic methods described earlier herein. Example 227 Biochemical Assay for Testing Compounds for Activity against HPK1

The enzymatic activity of human HPK1 (MAP4K1) was monitored in a biochemical assay in the presence or absence of compounds, using a peptide substrate (myelin basic protein, MBP), with an ADP-Glo assay kit (Promega, Cat. #V9103). An increase in phosphorylation of the peptide by HPK1 was indicative of its kinase activity.

Recombinant human HPK1 kinase domain was obtained from ThermoFisher (Cat. #PV6357) and SignalChem (Cat. #M23-11G). A 1 nM HPK1 kinase enzyme solution was prepared from the HPK1 stock received from the commercial supplier using an assay buffer containing 50 mM HEPES (4-(2-hydroxyethyl)-1-piperazineethanesulfonic acid) pH 7.5 (Fisher Scientific, Cat. #H1035), 150 mM NaCl (Fisher Scientific, Cat. #50843067), 3 mM TCEP-HCl (Tris (2-carboxyethyl)phosphine hydrochloride; Fisher Scientific, Cat. #PIPG82080), 10 mM MgCl$_2$ (Fisher Scientific, Cat. #AM9530G), 0.005% Tween-20 (Fisher Scientific, Cat. #BP337500) and 0.01% BSA (bovine serum albumin; ThermoFisher, Cat. #15260037), in ultra-pure water. The final concentration of the assay buffer was 770 nM. A 5 mM stock solution of the peptide substrate was prepared using 270 mM MBP (Myelin Basic Protein, Active Motif, Cat. #31314), 10 mM ATP (adenosine 5'-triphosphate; Sigma-Aldrich, Cat. #GE27-2056-01) and of assay buffer.

Test compounds were dissolved in DMSO (dimethyl sulfoxide) at 10 mM and then serial dilutions were prepared using a ViaFlow assist multichannel dispenser (Integra ViaFlo). 20 nL of test compounds at various concentrations were dispensed into a 1536-well assay plate (Corning Cat. #7247) using an Echo Nanoliter dispenser (Labcyte ECHO 550). 2 mL of a 1 nM solution of HPK1 kinase enzyme diluted in assay buffer was added to the compound-containing plate using a Mantis Microliter dispenser (Formulatrix Mantis), covered with a lid, and incubated for 15 minutes at room temperature. 50 nL of a 5 mM stock solution of the peptide substrate (MBP) were added using the Echo Nanoliter dispenser. The plate was covered with a lid, centrifugated at 500 rpm for 1 minute and incubated for 2 hours at room temperature. 1 mL of ADP-Glo reagent A was added using the Mantis Microliter dispenser, centrifugated at 500 rpm for 30 seconds and incubated for 40 minutes at room temperature. 2 mL of ADP-Glo reagent B was added using the Mantis Microliter dispenser, centrifugated at 500 rpm for 30 seconds and incubated for 30 minutes at room temperature. Peptide phosphorylation was measured by luminescence on an Envision plate reader (PerkinElmer).

The HPK1 biochemical IC$_{50}$ activity levels of the compounds of Examples 1-225 were tested using this assay and are shown in Table 2. A HPK1 activity of ±means an IC$_{50}$ test compound concentration ranging from 251 nM to >500 nM; a HPK1 activity of ±++ means an IC$_{50}$ test compound concentration ranging from 250 nM to 100 nM; and a HPK1 activity of +++ means an IC$_{50}$ test compound concentration of less than 100 nM.

TABLE 2

| Example | HPK1 activity |
|---|---|
| 1 | +++ |
| 2 | +++ |
| 3 | +++ |
| 4 | +++ |
| 5 | +++ |
| 6 | +++ |
| 7 | +++ |
| 8 | +++ |
| 9 | +++ |
| 10 | +++ |
| 11 | +++ |
| 12 | +++ |
| 13 | +++ |
| 14 | +++ |
| 15 | +++ |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ |
| 25 | +++ |
| 26 | +++ |
| 27 | +++ |
| 28 | +++ |
| 29 | +++ |
| 30 | ++ |
| 31 | +++ |
| 32 | +++ |
| 33 | +++ |
| 34 | +++ |
| 35 | +++ |
| 36 | +++ |
| 36 | +++ |
| 38 | +++ |
| 39 | +++ |
| 40 | +++ |
| 41 | ++ |
| 42 | +++ |
| 43 | +++ |
| 44 | +++ |
| 45 | +++ |
| 46 | +++ |
| 47 | +++ |
| 48 | +++ |
| 49 | +++ |
| 50 | +++ |
| 51 | +++ |
| 52 | +++ |
| 53 | +++ |
| 54 | +++ |
| 55 | +++ |
| 56 | +++ |
| 57 | +++ |
| 58 | +++ |
| 59 | +++ |
| 60 | +++ |
| 61 | +++ |
| 62 | +++ |
| 63 | +++ |
| 64 | +++ |
| 65 | +++ |
| 66 | +++ |
| 67 | +++ |
| 68 | +++ |
| 69 | +++ |
| 70 | +++ |
| 71 | +++ |

TABLE 2-continued

| Example | HPK1 activity |
|---|---|
| 71 | +++ |
| 73 | +++ |
| 74 | +++ |
| 75 | + |
| 76 | +++ |
| 77 | +++ |
| 78 | +++ |
| 79 | +++ |
| 80 | +++ |
| 81 | +++ |
| 82 | +++ |
| 83 | +++ |
| 84 | +++ |
| 85 | +++ |
| 86 | +++ |
| 87 | +++ |
| 88 | +++ |
| 89 | ++ |
| 90 | +++ |
| 91 | ++ |
| 92 | ++ |
| 93 | +++ |
| 94 | ++ |
| 95 | +++ |
| 96 | +++ |
| 97 | ++ |
| 98 | ++ |
| 99 | +++ |
| 100 | +++ |
| 101 | +++ |
| 102 | +++ |
| 103 | +++ |
| 104 | +++ |
| 105 | +++ |
| 106 | +++ |
| 107 | ++ |
| 108 | +++ |
| 109 | +++ |
| 110 | +++ |
| 111 | +++ |
| 112 | +++ |
| 113 | +++ |
| 114 | +++ |
| 115 | ++ |
| 116 | ++ |
| 117 | +++ |
| 118 | +++ |
| 119 | +++ |
| 120 | +++ |
| 121 | +++ |
| 122 | +++ |
| 123 | +++ |
| 124 | +++ |
| 125 | ++ |
| 126 | ++ |
| 127 | +++ |
| 128 | +++ |
| 129 | +++ |
| 130 | +++ |
| 131 | + |
| 132 | +++ |
| 133 | ++ |
| 134 | +++ |
| 135 | +++ |
| 136 | ++ |
| 137 | +++ |
| 138 | +++ |
| 139 | +++ |
| 140 | +++ |
| 141 | +++ |
| 142 | +++ |
| 143 | +++ |
| 144 | ++ |
| 145 | ++ |
| 146 | +++ |
| 147 | ++ |
| 148 | +++ |

TABLE 2-continued

| Example | HPK1 activity |
|---|---|
| 149 | +++ |
| 150 | +++ |
| 151 | +++ |
| 152 | +++ |
| 153 | +++ |
| 154 | +++ |
| 155 | +++ |
| 156 | +++ |
| 157 | +++ |
| 158 | +++ |
| 159 | +++ |
| 160 | +++ |
| 161 | +++ |
| 162 | +++ |
| 163 | +++ |
| 164 | +++ |
| 165 | +++ |
| 166 | +++ |
| 167 | +++ |
| 168 | +++ |
| 169 | +++ |
| 170 | +++ |
| 171 | +++ |
| 172 | +++ |
| 173 | +++ |
| 174 | +++ |
| 175 | +++ |
| 176 | +++ |
| 177 | +++ |
| 178 | +++ |
| 179 | +++ |
| 180 | +++ |
| 181 | +++ |
| 182 | +++ |
| 183 | +++ |
| 184 | +++ |
| 185 | +++ |
| 186 | +++ |
| 187 | +++ |
| 188 | +++ |
| 189 | +++ |
| 190 | +++ |
| 191 | +++ |
| 192 | +++ |
| 193 | +++ |
| 194 | +++ |
| 195 | +++ |
| 196 | +++ |
| 197 | +++ |
| 198 | +++ |
| 199 | +++ |
| 200 | +++ |
| 201 | +++ |
| 202 | +++ |
| 203 | +++ |
| 204 | +++ |
| 205 | +++ |
| 206 | +++ |
| 207 | +++ |
| 208 | +++ |
| 209 | +++ |
| 210 | +++ |
| 211 | ++ |
| 212 | +++ |
| 213 | +++ |
| 214 | +++ |
| 215 | +++ |
| 216 | +++ |
| 217 | +++ |
| 218 | +++ |
| 219 | +++ |
| 220 | +++ |
| 221 | +++ |
| 222 | +++ |
| 223 | +++ |
| 224 | +++ |
| 225 | +++ |

The above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

NUMBERED EMBODIMENTS

Embodiment P1. A compound of formula (I):

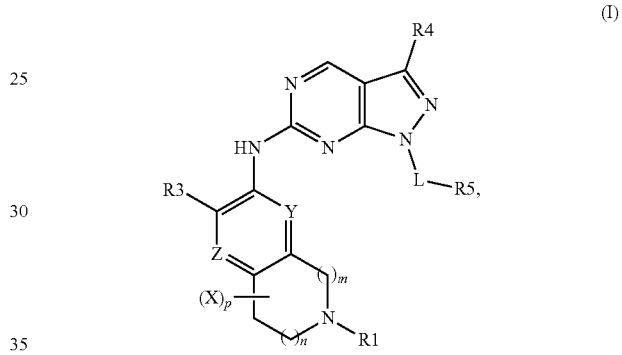

or a pharmaceutically acceptable salt thereof, wherein:
L is a bond or a substituted or unsubstituted methylene;
X is not bonded directly to the N atom of N—$R^1$ and is either absent or if present is a substituted or unsubstituted alkyl;
Y is CH or N;
Z is $CR^2$ or N;
each of n and m is 0, 1 or 2, and (n+m) equals 1, 2 or 3;
p is 0, 1, 2 or 3;
$R^1$ is H, or a substituted or unsubstituted alkyl;
$R^2$ is H, a halogen, a substituted or unsubstituted alkyl or a substituted or unsubstituted heteroalkyl;
$R^3$ is H, or a substituted or unsubstituted heteroalkyl;
$R^4$ is H, a substituted or unsubstituted alkyl or a halogen; and
$R^5$ is a substituted or unsubstituted alkyl, a substituted or unsubstituted heteroalkyl, a substituted or unsubstituted cycloalkyl or a substituted or unsubstituted heterocycloalkyl.

Embodiment P2. A compound of embodiment P1 or a pharmaceutically acceptable salt thereof, wherein n and m are each 1.

Embodiment P3. A compound of embodiment P1 or a pharmaceutically acceptable salt thereof, wherein at least one of Y is CH or Z is $CR^2$.

Embodiment P4. A compound of embodiment P1 or a pharmaceutically acceptable salt thereof, wherein Z is CH.

Embodiment P5. A compound of embodiment P1 or a pharmaceutically acceptable salt thereof, wherein $R^4$ is H.

Embodiment P6. A compound of embodiment P1 or a pharmaceutically acceptable salt thereof, wherein $R^3$ is an unsubstituted heteroalkyl.

Embodiment P7. A compound of embodiment P1 or a pharmaceutically acceptable salt thereof, wherein $R^3$ is alkoxy.

Embodiment P8. A compound of embodiment P1 or a pharmaceutically acceptable salt thereof, wherein L is a bond or —$CH_2$—.

Embodiment P9. A compound of embodiment P1 or a pharmaceutically acceptable salt thereof, wherein $R^5$ is a substituted cycloalkyl or a substituted heterocycloalkyl.

Embodiment P10. A compound of embodiment P1, having formula (Ia):

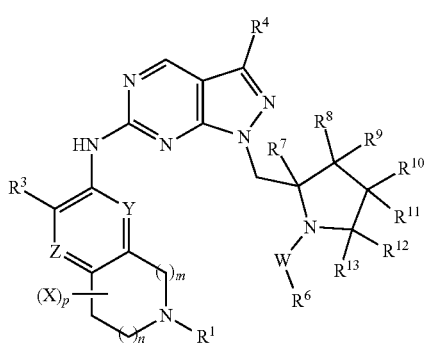

(Ia)

or a pharmaceutically acceptable salt thereof, wherein:
W is C(O), S(O), S(O)$_2$ or S(NH)(O);
$R^6$ is a substituted or unsubstituted $C_{1-3}$ alkyl, —$OCH_3$ or —$NR^{14}R^{15}$;
$R^7$ is H or —$CH_3$;
$R^8$, $R^9$, $R^{10}$ and $R^{11}$ are each independently H, substituted or unsubstituted $C_{1-3}$ alkyl, —OH or F;
$R^{12}$ and $R^{13}$ are each independently H or $C_{1-3}$ substituted or unsubstituted alkyl;
or where one of moiety pairs (i) $R^8$ and $R^9$, (ii) $R^9$ and $R^{10}$, (iii) $R^{11}$ and $R^{11}$, (iv) $R^{11}$ and $R^{12}$ and (v) $R^{12}$ and $R^{13}$ may optionally be joined to form a substituted or unsubstituted $C_{3-6}$ cycloalkyl; and
$R^{14}$ and $R^{15}$ are each independently H or substituted or unsubstituted alkyl.

Embodiment P11. The compound of embodiment P1, having formula (Ib):

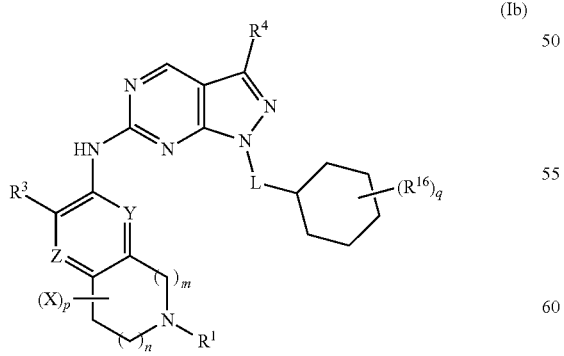

(Ib)

or a pharmaceutically acceptable salt thereof, wherein:
$R^{16}$ is —OH, a substituted or unsubstituted $C_{1-3}$ alkyl, —COOH, —$OCH_3$, —NHC(O)$CH_3$, —NHC(O) $CH_2$OH, and —NHSO$_2$CH$_3$ or —C(O)NR$^{17}$R$^{18}$;

$R^{17}$ and $R^{18}$ are each independently H or a substituted or unsubstituted $C_{1-3}$ alkyl; and
q is 0, 1 or 2.

Embodiment P12. The compound of embodiment P1, having formula (Ic):

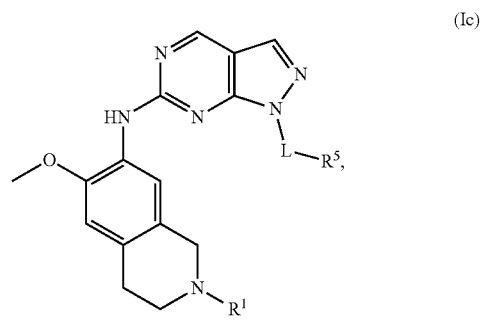

(Ic)

or a pharmaceutically acceptable salt thereof.

Embodiment P13. The compound of embodiment P12 selected from:

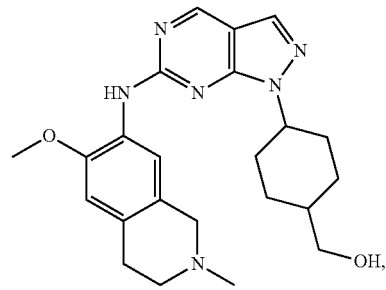

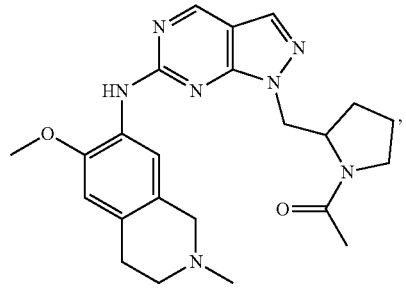

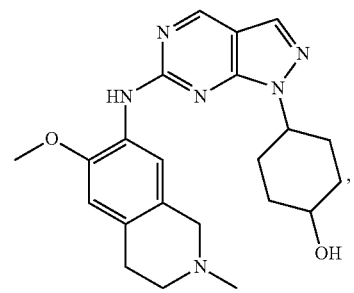

-continued

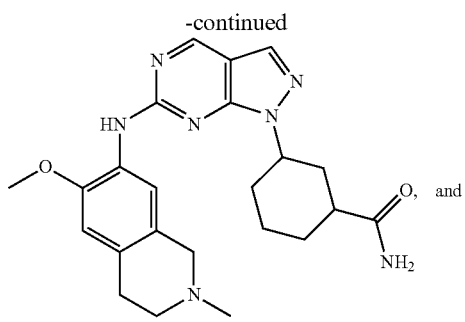
, and

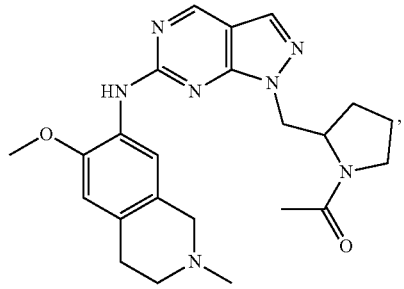

or a pharmaceutically acceptable salt thereof.

Embodiment P14. The compound of embodiment P13 selected from:

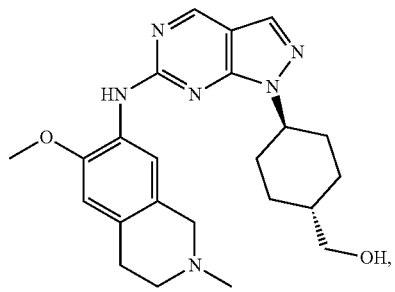

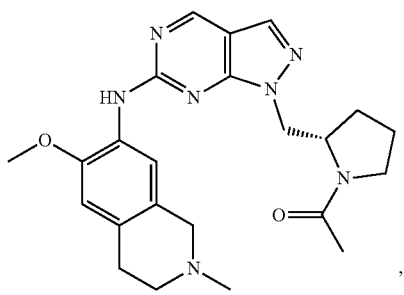

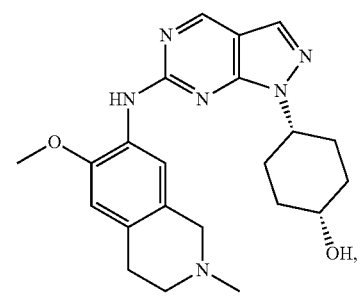

-continued

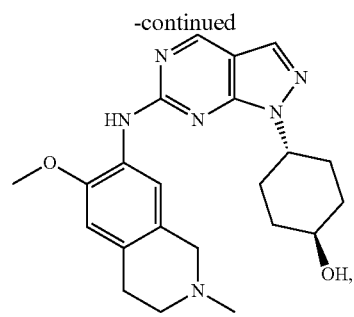

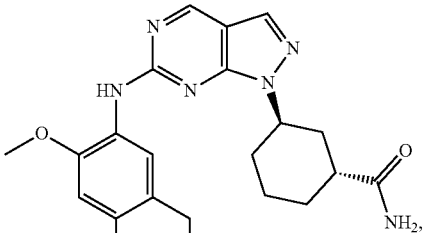

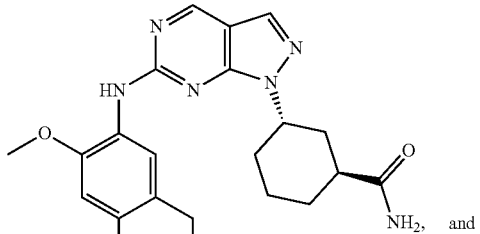
, and

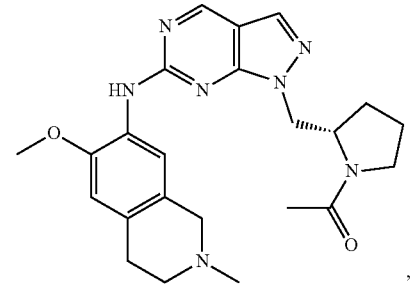

or a pharmaceutically acceptable salt thereof.

Embodiment P15. A pharmaceutical composition comprising the compound of embodiment P1 and a pharmaceutically acceptable excipient.

Embodiment P16. A method of treating a disease or disorder associated with activity of hematopoietic progenitor kinase 1 (HPK1), the method comprising administering to a patient in need thereof the compound of embodiment P1 or a pharmaceutically acceptable salt thereof.

Embodiment P17. The method of embodiment P16, wherein the disease or disorder is cancer.

Embodiment P18. The method of embodiment P17, further comprising administering to the subject a second anti-cancer drug.

Embodiment P19. The method of embodiment P18, wherein the second anti-cancer drug is an immune checkpoint inhibitor selected from an inhibitor of CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4.

Embodiment P20. The method of embodiment P17, wherein the cancer is selected from brain cancer, head and neck cancer, eye cancer, skin cancer, bladder cancer, ovarian cancer, breast cancer, gastric cancer, pancreatic cancer, liver cancer, prostate cancer, colon cancer, blood cancer, lung cancers, bone cancer, respiratory tract cancer, reproductive organ cancer, digestive tract cancer, urinary tract cancer, thyroid cancer, parathyroid cancer and its distant metastases, lymphoma, sarcoma, and leukemia.

Embodiment P21. The method of embodiment P20, wherein the cancer is selected from neuroblastoma, intestine carcinoma, rectum carcinoma, colon carcinoma, familiar adenomatous polyposis carcinoma, hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, glioblastoma, astrocytoma, meningioma, medulloblastoma, peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, large B-cell lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

Embodiment P22. The method of embodiment P16, wherein the disease or disorder is selected from viral infection, bacterial infection, chronic infection that produces exhausted immune response, infection-mediated immune suppression, age-related decline in immune response, age related decline in cognitive function, infertility and proliferative disease other than cancer.

Embodiment P23. The method of embodiment P22, wherein the disease or disorder is selected from skin infection, GI infection, urinary tract infections, genito-urinary infection, hepatitis B (HBV) and systemic infection.

FURTHER NUMBERED EMBODIMENTS

Embodiment 1. A compound of formula (I):

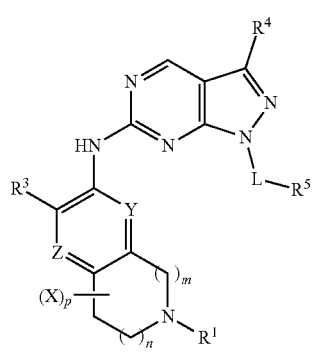

(I)

or a pharmaceutically acceptable salt thereof, wherein:

L is a bond or a substituted or unsubstituted methylene;

X is not bonded directly to the N atom of N—$R^1$ and is either absent or if present is a substituted or unsubstituted alkyl;

Y is CH or N;

Z is $CR^2$ or N;

each of n and m is 0, 1 or 2, and (n+m) equals 1, 2 or 3;

p is 0, 1, 2 or 3;

$R^1$ is H, or a substituted or unsubstituted alkyl;

$R^2$ is H, a halogen, a substituted or unsubstituted alkyl or a substituted or unsubstituted heteroalkyl;

$R^3$ is H, or a substituted or unsubstituted heteroalkyl;

$R^4$ is H, a substituted or unsubstituted alkyl or a halogen; and $R^5$ is a substituted or unsubstituted alkyl, a substituted or unsubstituted heteroalkyl, a substituted or unsubstituted cycloalkyl or a substituted or unsubstituted heterocycloalkyl.

Embodiment 2. The compound of embodiment 1 or a pharmaceutically acceptable salt thereof, provided that the compound is not N-(1-isopropylpyrazolo[3,4-d]pyrimidin-6-yl)-6-methoxy-2-methyl-3,4-dihydro-1H-isoquinolin-7-amine of formula:

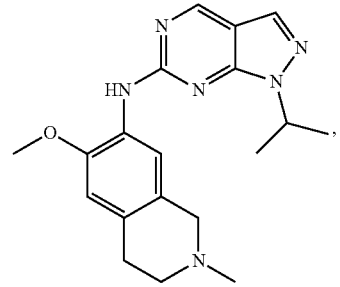 [SMILES: COc1cc2c(cc1Nc1ncc3cnn(C(C)C)c3n1)CN(C)CC2]

or a pharmaceutically acceptable salt thereof.

Embodiment 3. The compound of embodiment 1, wherein $R^5$ is a substituted or unsubstituted heteroalkyl, a substituted or unsubstituted cycloalkyl or a substituted or unsubstituted heterocycloalkyl.

Embodiment 4. The compound of embodiment 1, wherein $R^3$ is H or a substituted heteroalkyl and $R^5$ is a substituted or unsubstituted alkyl.

Embodiment 5. The compound of embodiment 1, wherein the compound is:

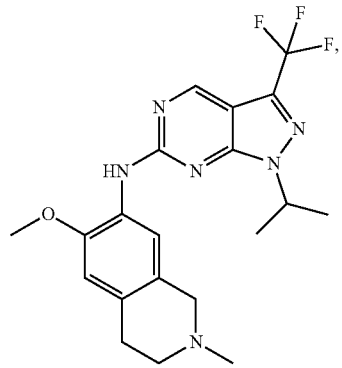

305

-continued

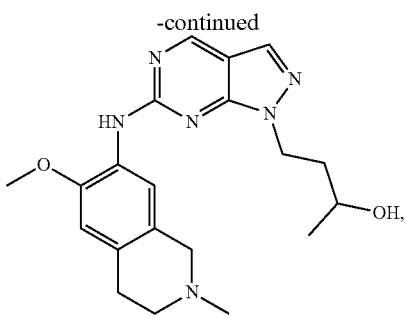

306

-continued

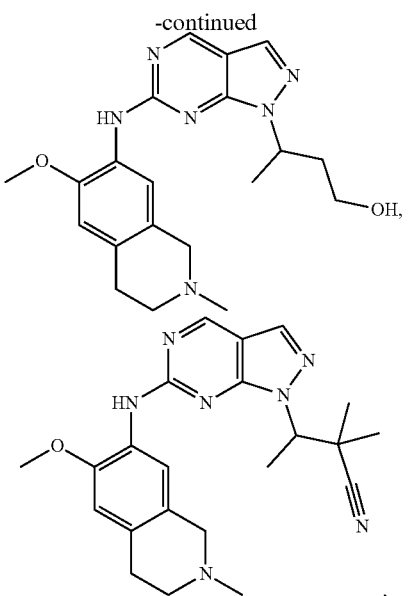

or a pharmaceutically acceptable salt thereof.

Embodiment 6. The compound of embodiment 1, wherein $R^5$ is:

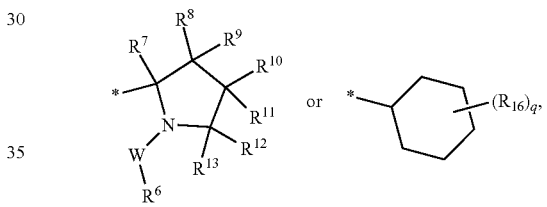

wherein:

W is —C(O), —S(O), —S(O)$_2$ or —S(NH)(O);

$R^6$ is a substituted or unsubstituted alkyl, —OCH$_3$ or —NR$^{14}$R$^{15}$;

$R^7$ is H or —CH$_3$;

$R^8$, $R^9$, $R^{10}$ and $R^{11}$ are each independently H, substituted or unsubstituted alkyl, —OH or halogen;

$R^{12}$ and $R^{13}$ are each independently H or substituted or unsubstituted alkyl, or $R^8$ and $R^9$, $R^9$ and $R^{10}$, $R^{10}$ and $R^{11}$, $R^{11}$ and $R^{12}$, and $R^{12}$ and $R^{13}$ may optionally be joined to form a substituted or unsubstituted cycloalkyl;

$R^{14}$ and $R^{15}$ are each independently H or substituted or unsubstituted alkyl;

$R^{16}$ is —OH, a substituted or unsubstituted alkyl, —COOH, —OCH$_3$, —NHC(O)CH$_3$, —NHC(O)CH$_2$OH, —NHSO$_2$CH$_3$ or —C(O)NR$^{17}$R$^{18}$;

$R^{17}$ and $R^{18}$ are each independently H or a substituted or unsubstituted alkyl; and q is 0, 1 or 2.

Embodiment 7. The compound of any one of embodiments 1 to 4 and 6, or a pharmaceutically acceptable salt thereof, wherein n and m are each 1.

Embodiment 8. The compound of any one of embodiments 1 to 4 and 6, or a pharmaceutically acceptable salt thereof, wherein at least one of Y is CH or Z is CR$^2$.

Embodiment 9. The compound of any one of embodiments 1 to 4 and 6, or a pharmaceutically acceptable salt thereof, wherein Z is CH.

Embodiment 10. The compound of any one of embodiments 1 to 4 and 6, or a pharmaceutically acceptable salt thereof, wherein $R^4$ is H.

Embodiment 11. The compound of any one of embodiments 1 to 4 and 6, or a pharmaceutically acceptable salt thereof, wherein $R^3$ is an unsubstituted heteroalkyl.

Embodiment 12. The compound of any one of embodiments 1 to 4 and 6, or a pharmaceutically acceptable salt thereof, wherein $R^3$ is alkoxy.

Embodiment 13. The compound of any one of embodiments 1 to 4 and 6, or a pharmaceutically acceptable salt thereof, wherein L is a bond or —$CH_2$—.

Embodiment 14. The compound of any one of embodiments 1 to 4 and 6, or a pharmaceutically acceptable salt thereof, wherein $R^5$ is a substituted cycloalkyl or a substituted heterocycloalkyl.

Embodiment 15. The compound of any one of embodiments 1 to 4 and 6 having formula (Ia):

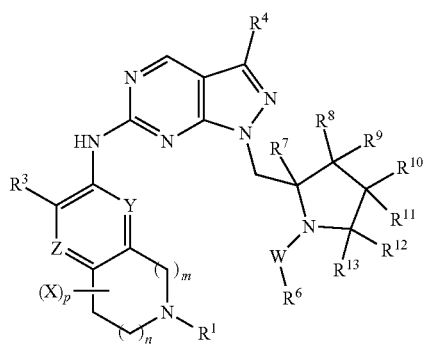

(Ia)

or a pharmaceutically acceptable salt thereof, wherein:

W is C(O), S(O), S(O)$_2$ or S(NH)(O);

$R^6$ is a substituted or unsubstituted alkyl, —$OCH_3$ or —$NR^{14}R^{15}$;

$R^7$ is H or substituted or unsubstituted alkyl;

$R^8$, $R^9$, $R^{10}$ and $R^{11}$ are each independently H, substituted or unsubstituted alkyl, —OH or halogen;

$R^{12}$ and $R^{13}$ are each independently H or $C_{1-3}$ substituted or unsubstituted alkyl; or where one of moiety pairs (i) $R^8$ and $R^9$, (ii) $R^9$ and $R^{10}$, (iii) $R^{10}$ and $R^{11}$, (iv) $R^{11}$ and $R^{12}$ and (v) $R^{12}$ and $R^{13}$ may optionally be joined to form a substituted or unsubstituted $C_{3-6}$ cycloalkyl; and $R^{14}$ and $R^{15}$ are each independently H or substituted or unsubstituted alkyl.

Embodiment 16. The compound of embodiment 15, wherein $R^7$ is —$CH_3$.

Embodiment 17. The compound of embodiment 15, wherein $R^8$, $R^9$, $R^{10}$ and $R^{11}$ are each independently —F.

Embodiment 18. The compound of any one of embodiments 1 to 4 and 6 having formula (Ib):

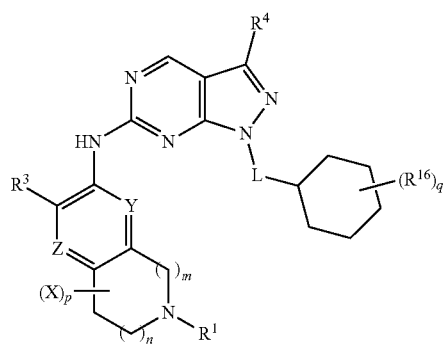

(Ib)

or a pharmaceutically acceptable salt thereof, wherein:

$R^{16}$ is —OH, a substituted or unsubstituted alkyl, —COOH, —$OCH_3$, —$NHC(O)CH_3$, —$NHC(O)CH_2OH$, —$NHSO_2CH_3$, or —$C(O)NR^{17}R^{18}$;

$R^{17}$ and $R^{18}$ are each independently H or a substituted or unsubstituted alkyl; and q is 0, 1 or 2.

Embodiment 19. The compound of any one of embodiments 1 to 4 and 6 having formula (Ic):

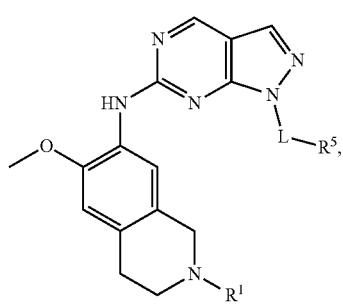

(Ic)

or a pharmaceutically acceptable salt thereof.

Embodiment 20. The compound of any one of embodiments 1-4 and 6-19 selected from:

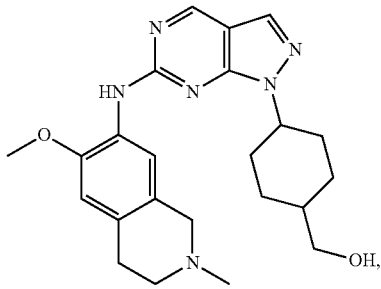

309
-continued

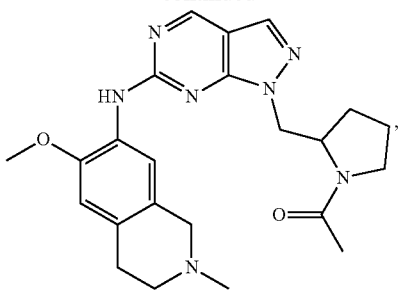

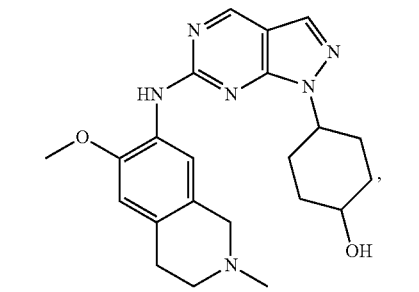

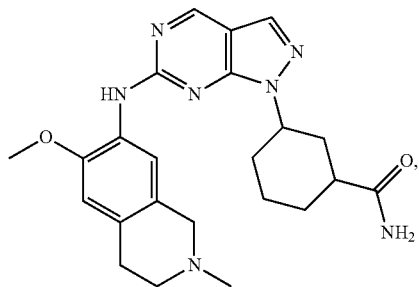

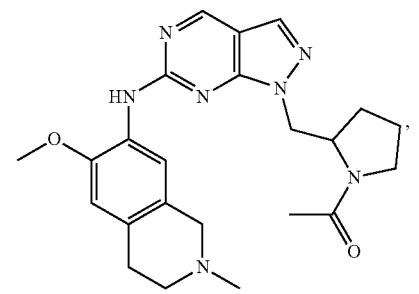

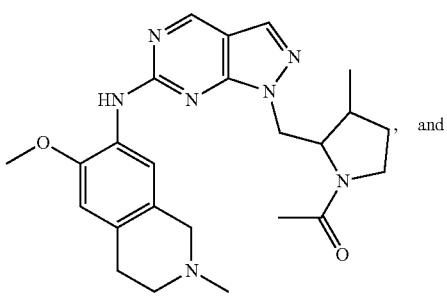 and

310
-continued

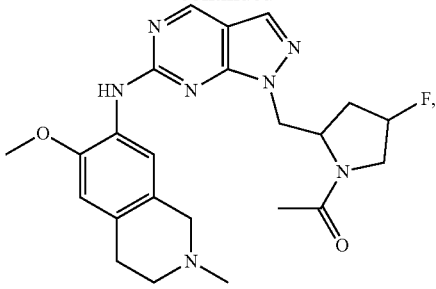

or a pharmaceutically acceptable salt thereof.

Embodiment 21. The compound of embodiment 1 having formula (II):

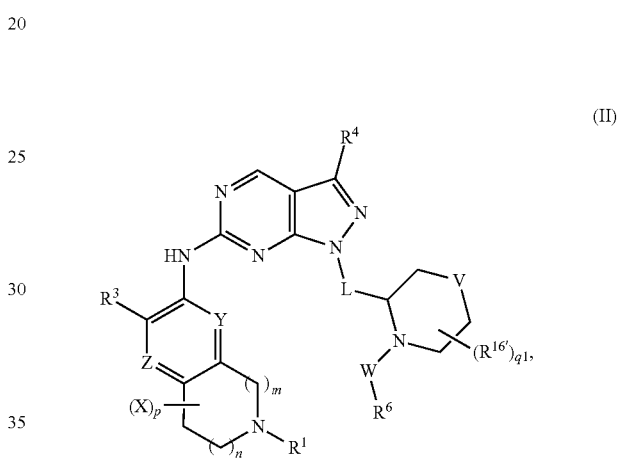

(II)

or a pharmaceutically acceptable salt thereof, wherein:

V is $CR^{19}R^{20}$, O or $NR^{21}$;

W is —C(O), —S(O), —S(O)$_2$ or —S(NH)(O);

q1 is an integer from 0 to 7;

$R^6$ is a substituted or unsubstituted alkyl, —OCH$_3$ or —NR$^{14}$R$^{15}$;

$R^{14}$ and $R^{15}$ are each independently H or substituted or unsubstituted alkyl;

$R^{19}$ and $R^{20}$ are each H, —OH, —OCH$_3$, —NR$^{14}$R$^{15}$, substituted or unsubstituted alkyl, substituted or unsubstituted heteroalkyl, or substituted or unsubstituted cycloalkyl;

$R^{21}$ is H, —OH, substituted or unsubstituted alkyl, or substituted or unsubstituted cycloalkyl; and $R^{16'}$ is independently —OH, substituted or unsubstituted alkyl, or halogen.

Embodiment 22. The compound of embodiment 21 having formula (IIa):

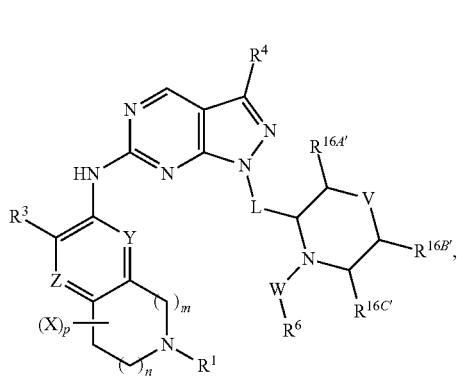

(IIa)

or a pharmaceutically acceptable salt thereof, wherein when V is O or $NR^{21}$, then each $R^{16A}$, $R^{16B}$, and $R^{16C}$ are independently a substituted or unsubstituted alkyl.

Embodiment 23. The compound of embodiment 1 having formula (III):

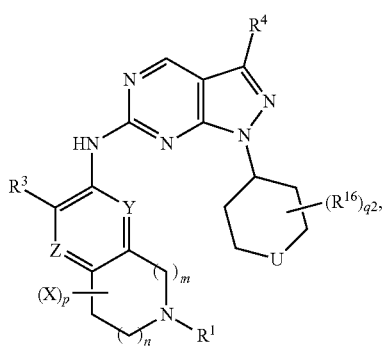

(III)

or a pharmaceutically acceptable salt thereof, wherein:

$R^{16'}$ is independently —OH, substituted or unsubstituted alkyl, or halogen;

q2 is an integer from 0 to 9;

U is O, $-NR^{23}$, $-N(CO)R^{24}$ or $-N(SO_2)R^{25}$;

$R^{23}$ and $R^{24}$ are each H, —OH, —OCH$_3$, —NR$^{14}$R$^{15}$, substituted or unsubstituted alkyl, substituted or unsubstituted heteroalkyl, or substituted or unsubstituted cycloalkyl;

$R^{14}$ and $R^{15}$ are each independently H or substituted or unsubstituted alkyl; and $R^{25}$ is H, —OH, substituted or unsubstituted alkyl, or substituted or unsubstituted cycloalkyl.

Embodiment 24. The compound of embodiment 23 having formula (IIIa):

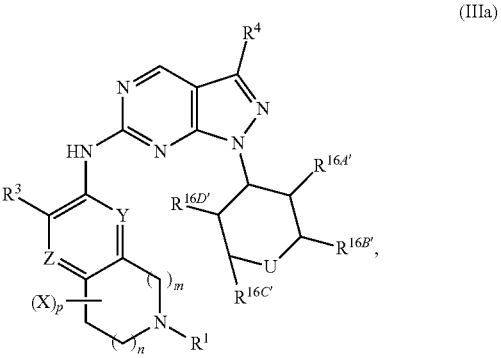

(IIIa)

or a pharmaceutically acceptable salt thereof, wherein each $R^{16B'}$ and $R^{16C'}$ is independently a substituted or unsubstituted alkyl, and each $R^{16A'}$ and $R^{16D'}$ is independently —OH, substituted or unsubstituted alkyl, or halogen.

Embodiment 25. The compound of embodiment 1 having formula (IV):

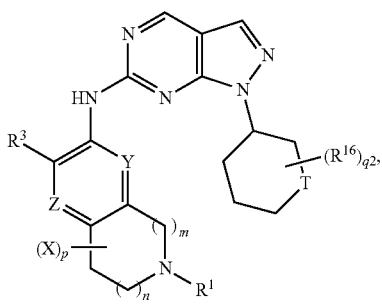

(IV)

or a pharmaceutically acceptable salt thereof, wherein:

$R^{16'}$ is independently —OH, substituted or unsubstituted alkyl, or halogen;

q2 is an integer from 0 to 9;

T is O, $-NR^{27}$, $-N(CO)R^{28}$ or $-N(SO_2)R^{29}$;

$R^{27}$ and $R^{28}$ are each H, —OH, —OCH$_3$, —NR$^{14}$R$^{15}$, substituted or unsubstituted alkyl, substituted or unsubstituted heteroalkyl, or substituted or unsubstituted cycloalkyl;

$R^{14}$ and $R^{15}$ are each independently H or substituted or unsubstituted alkyl; and $R^{29}$ is H, —OH, substituted or unsubstituted alkyl, or substituted or unsubstituted cycloalkyl.

Embodiment 26. The compound of embodiment 25 having formula (IVa):

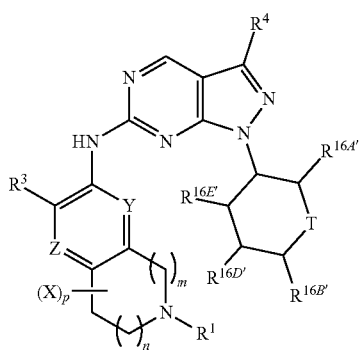

or a pharmaceutically acceptable salt thereof, wherein each $R^{16A'}$ and $R^{16B'}$ is independently a substituted or unsubstituted alkyl, and each $R^{16D'}$ and $R^{16E'}$ is independently —OH, substituted or unsubstituted alkyl, or halogen.

Embodiment 27. A pharmaceutical composition comprising the compound of any one of embodiments 1 to 26 and a pharmaceutically acceptable excipient.

Embodiment 28. A method of treating a disease or disorder associated with activity of hematopoietic progenitor kinase 1 (HPK1), the method comprising administering to a patient in need thereof the compound of any one of embodiments 1 to 26 or a pharmaceutically acceptable salt thereof.

Embodiment 29. The method of embodiment 28, wherein the disease or disorder is cancer.

Embodiment 30. The method of embodiment 29, further comprising administering to the subject an anti-cancer drug.

Embodiment 31. The method of embodiment 30, wherein the anti-cancer drug is an immune checkpoint inhibitor selected from an inhibitor of CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4.

Embodiment 32. The method of embodiment 29, wherein the cancer is selected from brain cancer, head and neck cancer, eye cancer, skin cancer, bladder cancer, ovarian cancer, breast cancer, gastric cancer, pancreatic cancer, liver cancer, prostate cancer, colon cancer, blood cancer, lung cancers, bone cancer, respiratory tract cancer, reproductive organ cancer, digestive tract cancer, urinary tract cancer, thyroid cancer, parathyroid cancer and its distant metastases, lymphoma, sarcoma, and leukemia.

Embodiment 33. The method of embodiment 32, wherein the cancer is selected from neuroblastoma, intestine carcinoma, rectum carcinoma, colon carcinoma, familiar adenomatous polyposis carcinoma, hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, glioblastoma, astrocytoma, meningioma, medulloblastoma, peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, large B-cell lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

Embodiment 34. The method of embodiment 28, wherein the disease or disorder is selected from viral infection, bacterial infection, chronic infection that produces exhausted immune response, infection-mediated immune suppression, age-related decline in immune response, age related decline in cognitive function, infertility and proliferative disease other than cancer.

Embodiment 35. The method of embodiment 34, wherein the disease or disorder is selected from skin infection, GI infection, urinary tract infections, genito-urinary infection, hepatitis B (HBV) and systemic infection.

What is claimed is:

1. A compound of formula (I):

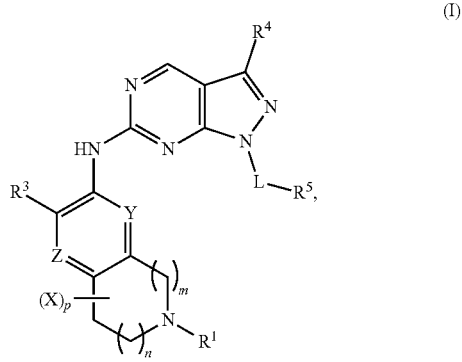

or a pharmaceutically acceptable salt thereof, wherein:
L is a bond or a substituted or unsubstituted methylene;
X is not bonded directly to the N atom of N—$R^1$ and is either absent or if present is a substituted or unsubstituted alkyl;
Y is CH or N;
Z is $CR^2$ or N;
each of n and m is 0, 1 or 2, and (n+m) equals 1, 2 or 3;
p is 0, 1, 2 or 3;
$R^1$ is H, or a substituted or unsubstituted alkyl;
$R^2$ is H, a halogen, a substituted or unsubstituted alkyl or a substituted or unsubstituted heteroalkyl;
$R^3$ is H, or a substituted or unsubstituted heteroalkyl;
$R^4$ is H, a substituted or unsubstituted alkyl or a halogen; and
$R^5$ is a substituted or unsubstituted alkyl, a substituted or unsubstituted heteroalkyl, a substituted or unsubstituted cycloalkyl or a substituted or unsubstituted heterocycloalkyl.

2. The compound of claim 1, or a pharmaceutically acceptable salt thereof, provided that the compound is not N-(1-isopropylpyrazolo[3,4-d]pyrimidin-6-yl)-6-methoxy-2-methyl-3,4-dihydro-1H-isoquinolin-7-amine of formula:

315

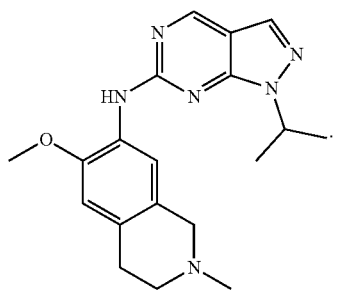 [SMILES: COc1cc2c(cc1Nc1ncc3cnn(C(C)C)c3n1)CN(C)CC2]

3. The compound of claim 1, or a pharmaceutically acceptable salt thereof, wherein $R^5$ is a substituted or unsubstituted heteroalkyl, a substituted or unsubstituted cycloalkyl or a substituted or unsubstituted heterocycloalkyl.

4. The compound of claim 1, or a pharmaceutically acceptable salt thereof, wherein $R^3$ is H or a substituted heteroalkyl and $R^5$ is a substituted or unsubstituted alkyl.

5. The compound of claim 1, wherein the compound is:

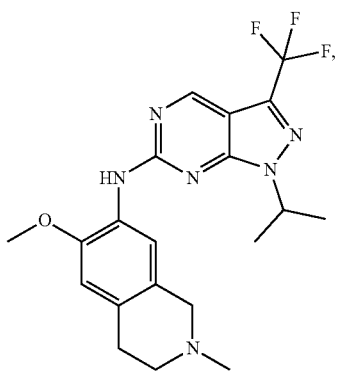

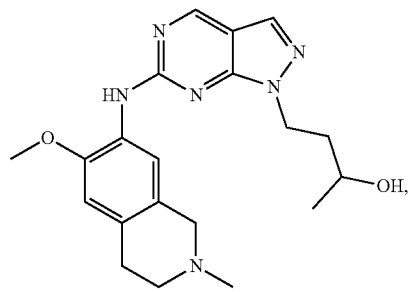

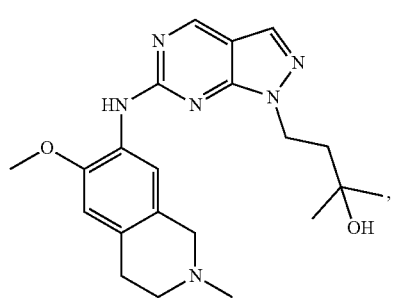

316

-continued

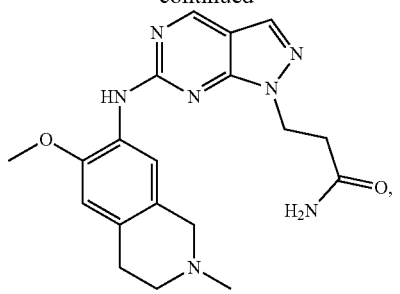

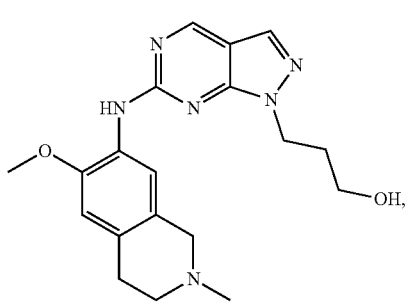

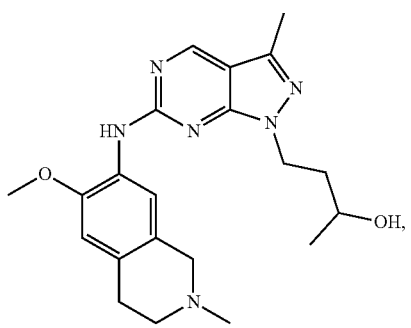

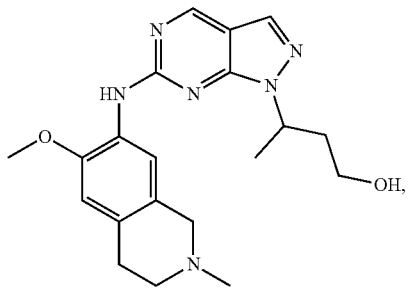

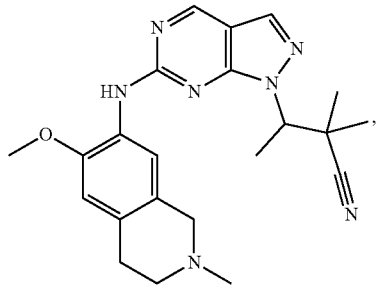

or a pharmaceutically acceptable salt thereof.

6. The compound of claim 1, or a pharmaceutically acceptable salt thereof, wherein $R^5$ is:

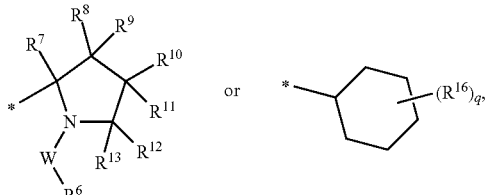

wherein:

W is —C(O), —S(O), —S(O)$_2$ or —S(NH)(O);

$R^6$ is a substituted or unsubstituted alkyl, —OCH$_3$ or —NR$^{14}$R$^{15}$;

$R^7$ is H or —CH$_3$;

$R^8$, $R^9$, $R^{10}$ and $R^{11}$ are each independently H, substituted or unsubstituted alkyl, —OH or halogen;

$R^{12}$ and $R^{13}$ are each independently H or substituted or unsubstituted alkyl, or $R^8$ and $R^9$, $R^9$ and $R^{10}$, $R^{10}$ and $R^{11}$, $R^{11}$ and $R^{12}$, and $R^{12}$ and $R^{13}$ may optionally be joined to form a substituted or unsubstituted cycloalkyl;

$R^{14}$ and $R^{15}$ are each independently H or substituted or unsubstituted alkyl;

$R^{16}$ is —OH, a substituted or unsubstituted alkyl, —COOH, —OCH$_3$, —NHC(O)CH$_3$, —NHC(O)CH$_2$OH, —NHSO$_2$CH$_3$ or —C(O)NR$^{17}$R$^{17}$;

$R^{17}$ and $R^{18}$ are each independently H or a substituted or unsubstituted alkyl; and q is 0, 1 or 2.

7. The compound of claim 1, or a pharmaceutically acceptable salt thereof, wherein n and m are each 1.

8. The compound of claim 1, or a pharmaceutically acceptable salt thereof, wherein at least one of Y is CH or Z is CR$^2$.

9. The compound of claim 1, or a pharmaceutically acceptable salt thereof, wherein Z is CH.

10. The compound of claim 1, or a pharmaceutically acceptable salt thereof, wherein $R^4$ is H.

11. The compound of claim 1, or a pharmaceutically acceptable salt thereof, wherein $R^3$ is an unsubstituted heteroalkyl.

12. The compound of claim 1, or a pharmaceutically acceptable salt thereof, wherein $R^3$ is alkoxy.

13. The compound of claim 1, or a pharmaceutically acceptable salt thereof, wherein L is a bond or —CH$_2$—.

14. The compound of claim 1, or a pharmaceutically acceptable salt thereof, wherein $R^5$ is a substituted cycloalkyl or a substituted heterocycloalkyl.

15. The compound of claim 1 having formula (Ia):

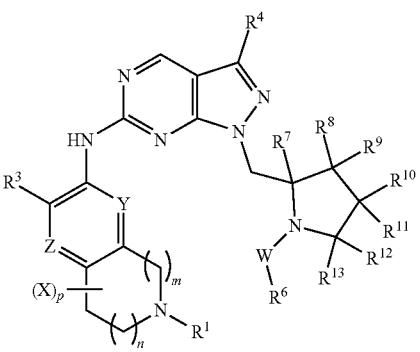

(Ia)

or a pharmaceutically acceptable salt thereof, wherein:

W is C(O), S(O), S(O)$_2$ or S(NH)(O);

$R^6$ is a substituted or unsubstituted alkyl, —OCH$_3$ or —NR$^{14}$R$^{15}$;

$R^7$ is H or substituted or unsubstituted alkyl;

$R^8$, $R^9$, $R^{10}$ and $R^{11}$ are each independently H, substituted or unsubstituted alkyl, —OH or halogen;

$R^{12}$ and $R^{13}$ are each independently H or $C_{1-3}$ substituted or unsubstituted alkyl; or where one of moiety pairs (i) $R^8$ and $R^9$, (ii) $R^9$ and $R^{10}$, (iii) $R^{10}$ and $R^{11}$, (iv) $R^{11}$ and $R^{12}$ and (v) $R^{12}$ and $R^{13}$ may optionally be joined to form a substituted or unsubstituted $C_{3-6}$ cycloalkyl; and $R^{14}$ and $R^{15}$ are each independently H or substituted or unsubstituted alkyl.

16. The compound of claim 15, or a pharmaceutically acceptable salt thereof, wherein $R^7$ is —CH$_3$.

17. The compound of claim 15, or a pharmaceutically acceptable salt thereof, wherein $R^8$, $R^9$, $R^{10}$ and $R^{11}$ are each independently —F.

18. The compound of claim 1 having formula (Ib):

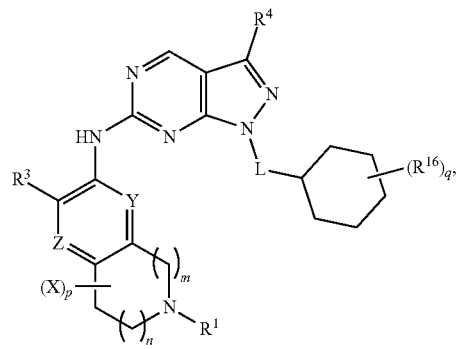

(Ib)

or a pharmaceutically acceptable salt thereof, wherein:

$R^{16}$ is —OH, a substituted or unsubstituted alkyl, —COOH, —OCH$_3$, —NHC(O)CH$_3$, —NHC(O)CH$_2$OH, —NHSO$_2$CH$_3$, or —C(O)NR$^{17}$R$^{18}$;

$R^{17}$ and $R^{18}$ are each independently H or a substituted or unsubstituted alkyl; and q is 0, 1 or 2.

19. The compound of claim 1 having formula (Ic):

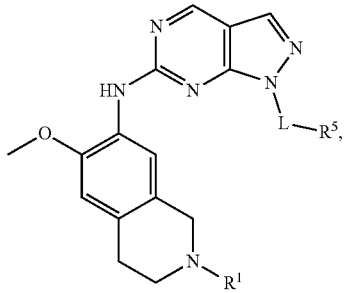

(Ic)

or a pharmaceutically acceptable salt thereof.

20. The compound of claim 1, wherein the compound is:

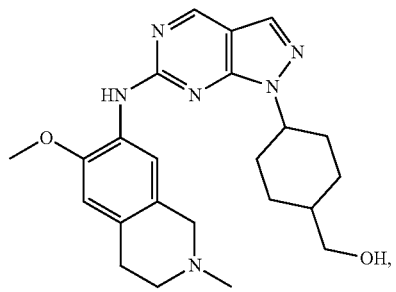

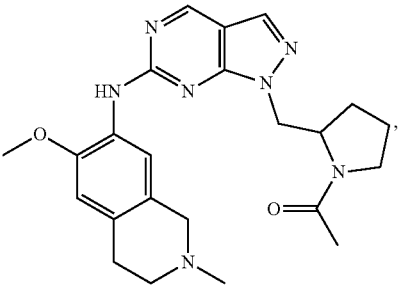

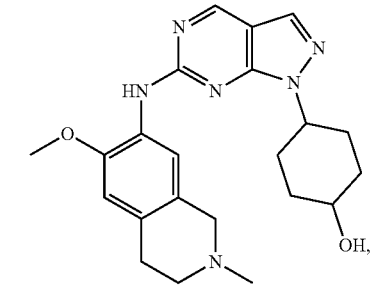

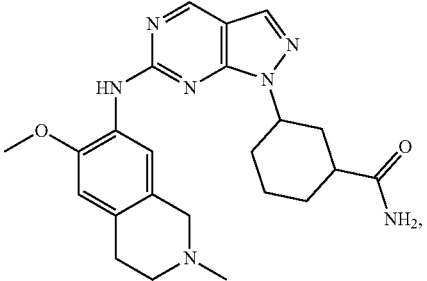

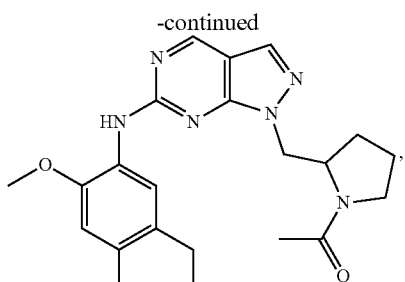

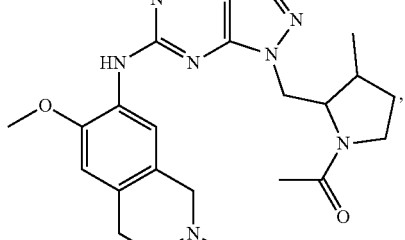

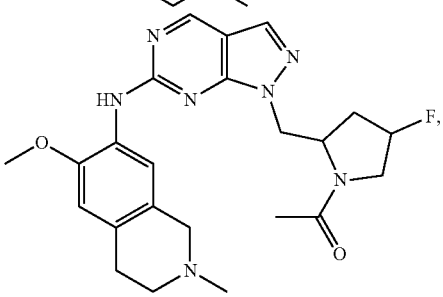

or a pharmaceutically acceptable salt thereof.

21. The compound of claim 1 having formula (II):

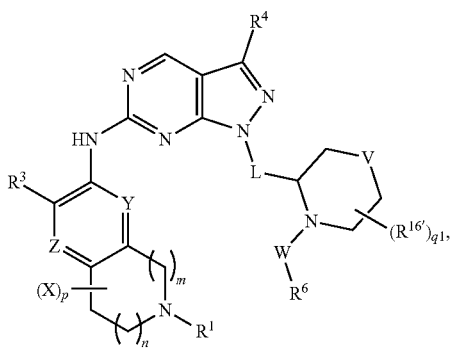

(II)

or a pharmaceutically acceptable salt thereof,
wherein:
V is $CR^{19}R^{20}$, O or $NR^{21}$;
W is —C(O), —S(O), —S(O)$_2$ or —S(NH)(O);
q1 is an integer from 0 to 7;
$R^6$ is a substituted or unsubstituted alkyl, —OCH$_3$ or —$R^{14}R^{15}$;
$R^{14}$ and $R^{15}$ are each independently H or substituted or unsubstituted alkyl;
$R^{19}$ and $R^{20}$ are each H, —OH, —OCH$_3$, —NR$^{14}$R$^{15}$, substituted or unsubstituted alkyl, substituted or unsubstituted heteroalkyl, or substituted or unsubstituted cycloalkyl;

R²¹ is H, —OH, substituted or unsubstituted alkyl, or substituted or unsubstituted cycloalkyl; and R¹⁶' is independently —OH, substituted or unsubstituted alkyl, or halogen.

22. The compound of claim 21 having formula (IIa):

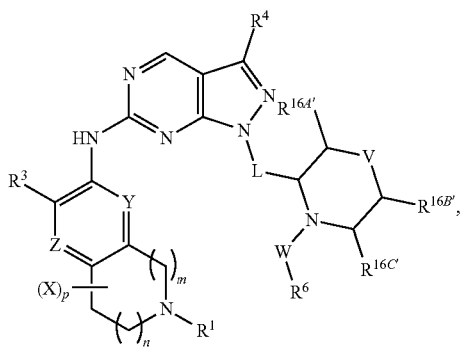

(IIa)

or a pharmaceutically acceptable salt thereof, wherein when V is O or NR²¹, then each R¹⁶ᴬ', R¹⁶ᴮ', and R¹⁶ᶜ' are independently a substituted or unsubstituted alkyl.

23. The compound of claim 1 having formula (III):

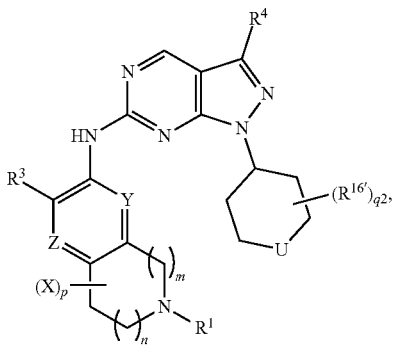

(III)

or a pharmaceutically acceptable salt thereof, wherein:

R¹⁶' is independently —OH, substituted or unsubstituted alkyl, or halogen;

q2 is an integer from 0 to 9;

U is O, —NR²³, —N(CO)R²⁴ or —N(SO₂)R²⁵;

R²³ and R²⁴ are each H, —OH, —OCH₃, —NR¹⁴R¹⁵, substituted or unsubstituted alkyl, substituted or unsubstituted heteroalkyl, or substituted or unsubstituted cycloalkyl;

R¹⁴ and R¹⁵ are each independently H or substituted or unsubstituted alkyl; and

R²⁵ is H, —OH, substituted or unsubstituted alkyl, or substituted or unsubstituted cycloalkyl.

24. The compound of claim 23 having formula (IIIa):

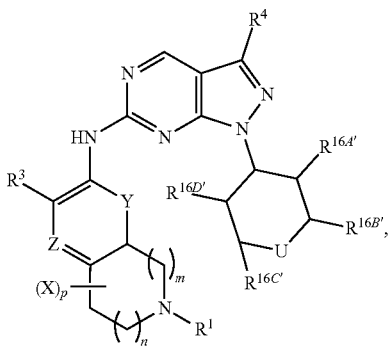

(IIIa)

or a pharmaceutically acceptable salt thereof, wherein each R¹⁶ᴮ' and R¹⁶ᶜ' is independently a substituted or unsubstituted alkyl, and each R¹⁶ᴬ' and R¹⁶ᴰ' is independently —OH, substituted or unsubstituted alkyl, or halogen.

25. The compound of claim 1 having formula (IV):

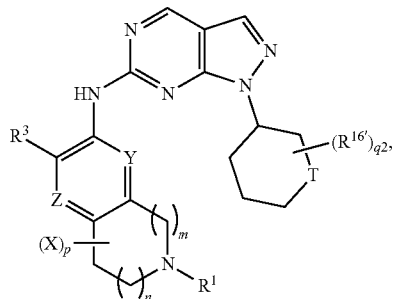

(IV)

or a pharmaceutically acceptable salt thereof, wherein:

R¹⁶' is independently —OH, substituted or unsubstituted alkyl, or halogen;

q2 is an integer from 0 to 9;

T is O, —NR²⁷, —N(CO)R²⁸ or —N(SO₂)R²⁹;

R²⁷ and R²⁸ are each H, —OH, —OCH₃, —NR¹⁴R¹⁵, substituted or unsubstituted alkyl, substituted or unsubstituted heteroalkyl, or substituted or unsubstituted cycloalkyl;

R¹⁴ and R¹⁵ are each independently H or substituted or unsubstituted alkyl; and

R²⁹ is H, —OH, substituted or unsubstituted alkyl, or substituted or unsubstituted cycloalkyl.

26. The compound of claim 25 having formula (IVa):

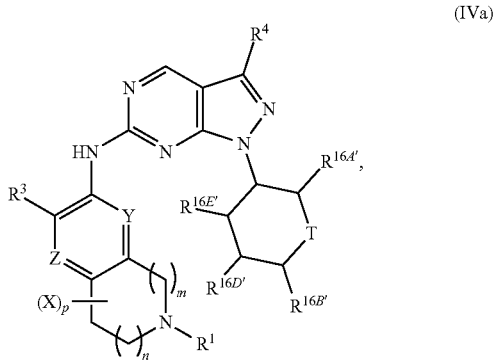

(IVa)

or a pharmaceutically acceptable salt thereof, wherein each $R^{16A'}$ and $R^{16B'}$ is independently a substituted or unsubstituted alkyl, and each $R^{16D'}$ and $R^{16E'}$ is independently —OH, substituted or unsubstituted alkyl, or halogen.

27. A pharmaceutical composition comprising the compound of claim 1, or a pharmaceutically acceptable salt thereof, and a pharmaceutically acceptable excipient.

28. A method of treating a disease or disorder associated with activity of hematopoietic progenitor kinase 1 (HPK1), the method comprising administering to a subject in need thereof the compound of claim 1 or a pharmaceutically acceptable salt thereof.

29. The method of claim 28, wherein the disease or disorder is cancer.

30. The method of claim 29, further comprising administering to the subject an anti-cancer drug.

31. The method of claim 30, wherein the anti-cancer drug is an immune checkpoint inhibitor selected from an inhibitor of CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4.

32. The method of claim 29, wherein the cancer is selected from brain cancer, head and neck cancer, eye cancer, skin cancer, bladder cancer, ovarian cancer, breast cancer, gastric cancer, pancreatic cancer, liver cancer, prostate cancer, colon cancer, blood cancer, lung cancer, bone cancer, respiratory tract cancer, reproductive organ cancer, digestive tract cancer, urinary tract cancer, thyroid cancer, parathyroid cancer and its distant metastases, lymphoma, sarcoma, and leukemia.

33. The method of claim 32, wherein the cancer is selected from neuroblastoma, intestine carcinoma, rectum carcinoma, colon carcinoma, familiar adenomatous polyposis carcinoma, hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, glioblastoma, astrocytoma, meningioma, medulloblastoma, peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, large B-cell lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

34. The method of claim 28, wherein the disease or disorder is selected from viral infection, bacterial infection, chronic infection that produces exhausted immune response, infection-mediated immune suppression, age-related decline in immune response, age related decline in cognitive function, infertility and proliferative disease other than cancer.

35. The method of claim 34, wherein the disease or disorder is selected from skin infection, GI infection, urinary tract infections, genito-urinary infection, hepatitis B (HBV) and systemic infection.

36. A compound of formula (Ia), or a pharmaceutically acceptable salt thereof, wherein:

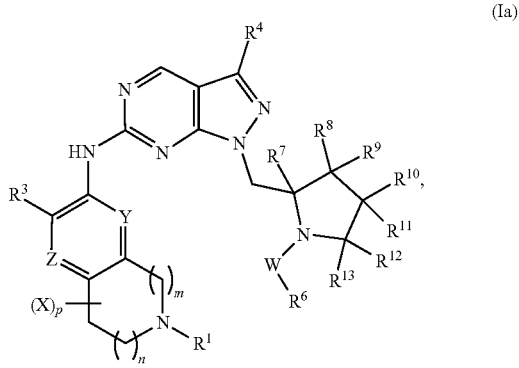

(Ia)

m and n are independently 1;

p is 0;

Y and Z are independently CH;

W is C(O);

$R^1$ is an unsubstituted alkyl;

$R^3$ is an unsubstituted heteroalkyl;

$R^4$ is H;

$R^6$ is a substituted or unsubstituted alkyl;

$R^7$ is H;

$R^8$, $R^9$, $R^{10}$ and $R^{11}$ are each independently H or unsubstituted alkyl; and $R^{12}$ and $R^{13}$ are each independently H or $C_{1-3}$ unsubstituted alkyl.

37. The compound of claim 36, wherein $R^1$ is methyl.

38. The compound of claim 36, wherein $R^3$ is methoxy.

39. The compound of claim 36, wherein one of $R^8$ and $R^9$ is methyl and the other is H.

40. The compound of claim 36, wherein $R^{10}$, $R^{11}$, $R^{12}$ and $R^{13}$ are independently H.

41. The compound of claim 36, wherein $R^6$ is methyl or —CH$_2$OH.

42. The compound of claim 36 selected from:
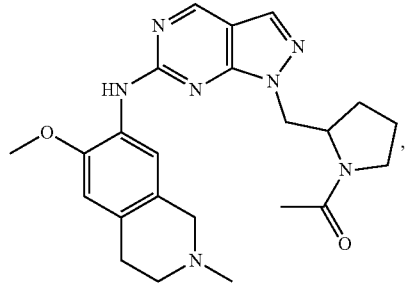
,
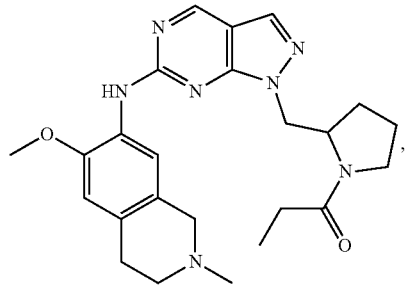
,
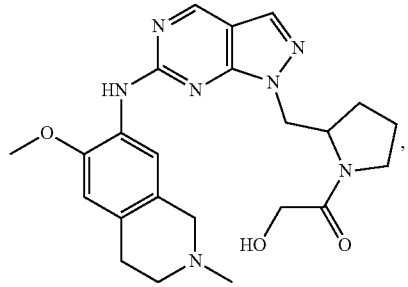
,
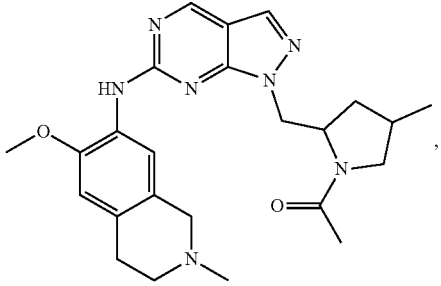
,
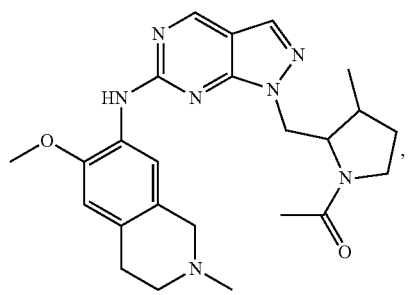
,
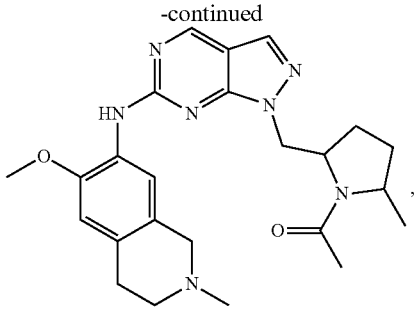
,
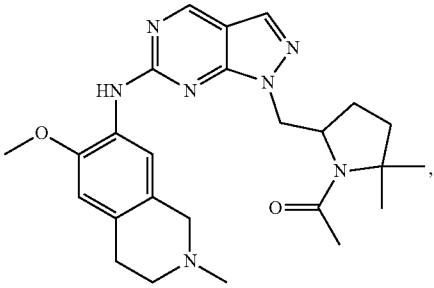
,
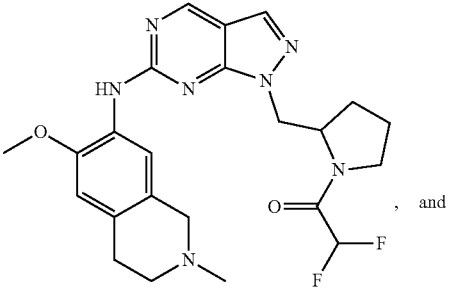
, and
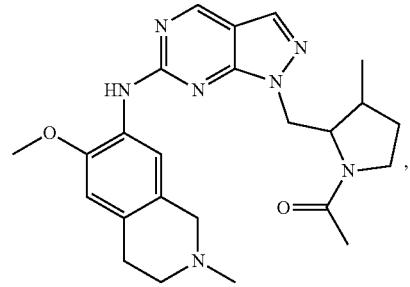
or a pharmaceutically acceptable salt thereof.
43. A compound having chemical structure:
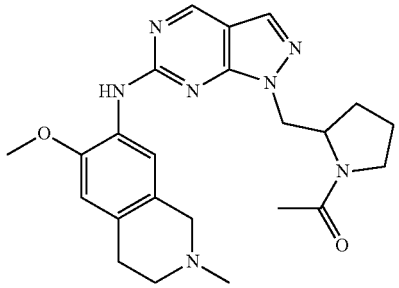 [SMILES: COc1cc2c(cc1Nc1ncc3cnn(CC4CCCN4C(C)=O)c3n1)CN(C)CC2]
or a pharmaceutically acceptable salt thereof.

44. A compound having chemical structure:

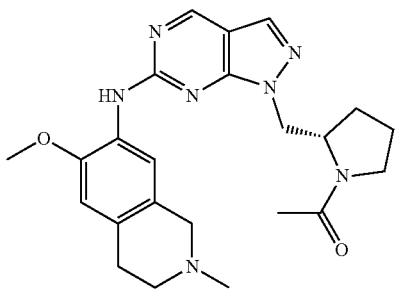 [SMILES: COc1cc2c(cc1Nc1ncc3cnn(C[C@@H]4CCCN4C(C)=O)c3n1)CN(C)CC2]

or a pharmaceutically acceptable salt thereof.

45. A compound having chemical structure:

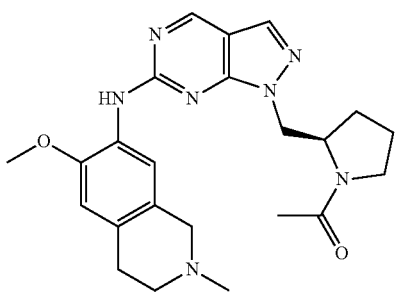 [SMILES: COc1cc2c(cc1Nc1ncc3cnn(C[C@H]4CCCN4C(C)=O)c3n1)CN(C)CC2]

or a pharmaceutically acceptable salt thereof.

46. A compound having chemical structure:

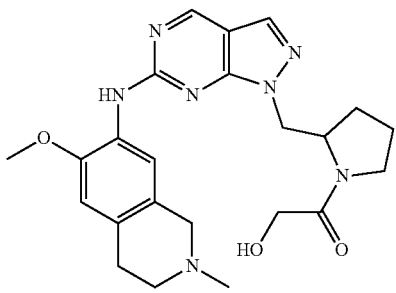

or a pharmaceutically acceptable salt thereof.

47. A compound having chemical structure:

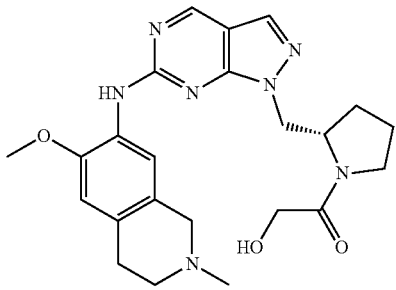 [SMILES: COc1cc2c(cc1Nc1ncc3cnn(CC4CCCN4C(=O)CO)c3n1)CN(C)CC2]

or a pharmaceutically acceptable salt thereof.

48. A compound having chemical structure:

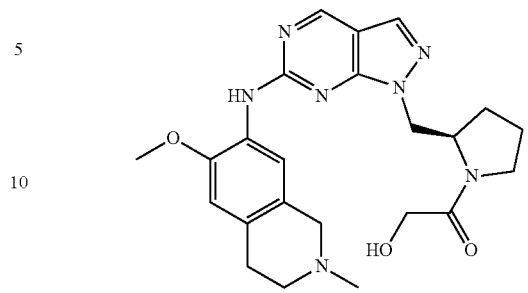

or a pharmaceutically acceptable salt thereof.

49. A compound having chemical structure:

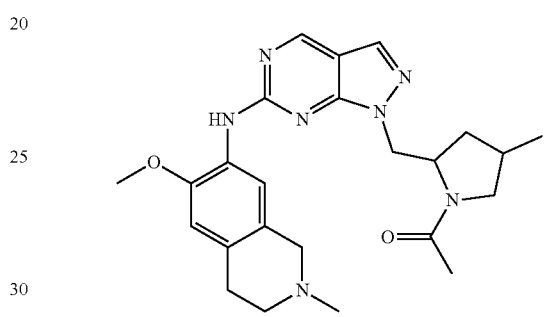

or a pharmaceutically acceptable salt thereof.

50. A compound having chemical structure:

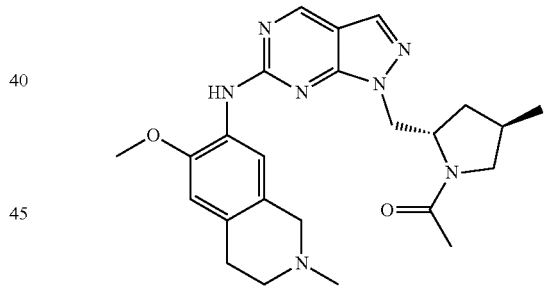

or a pharmaceutically acceptable salt thereof.

51. A compound having chemical structure:

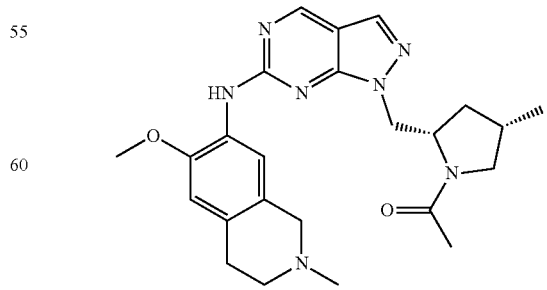

or a pharmaceutically acceptable salt thereof.

52. A compound having chemical structure:

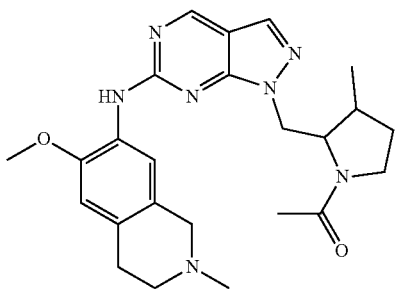 [SMILES: COc1cc2c(cc1Nc1ncc3cnn(CC4C(C)CCN4C(C)=O)c3n1)CN(C)CC2]

or a pharmaceutically acceptable salt thereof.

53. A compound having chemical structure:

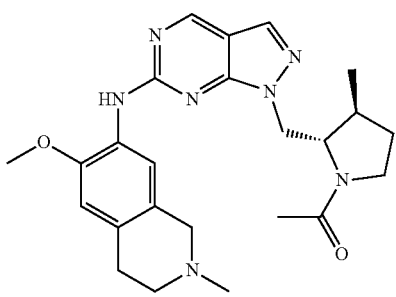 [SMILES: COc1cc2c(cc1Nc1ncc3cnn(C[C@@H]4[C@@H](C)CCN4C(C)=O)c3n1)CN(C)CC2]

or a pharmaceutically acceptable salt thereof.

54. A compound having chemical structure:

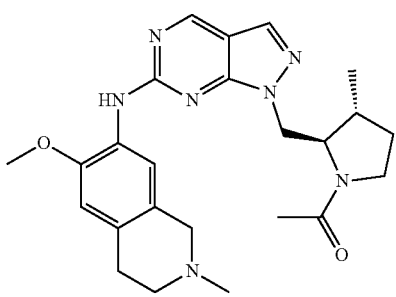 [SMILES: COc1cc2c(cc1Nc1ncc3cnn(C[C@H]4[C@H](C)CCN4C(C)=O)c3n1)CN(C)CC2]

or a pharmaceutically acceptable salt thereof.

55. A compound having chemical structure:

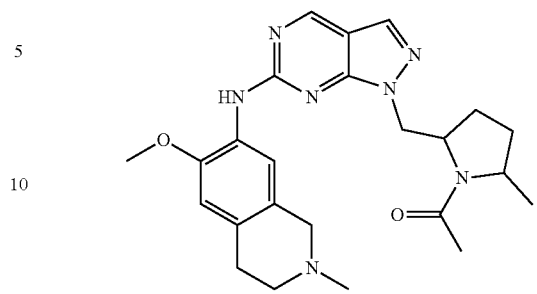

or a pharmaceutically acceptable salt thereof.

56. A compound having chemical structure:

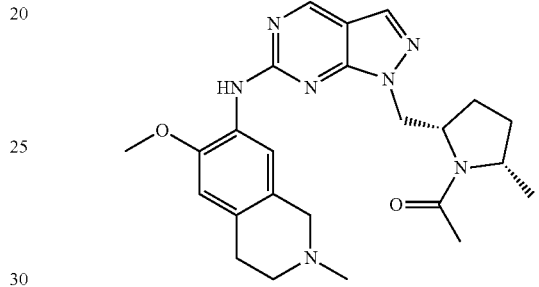

or a pharmaceutically acceptable salt thereof.

57. A compound having chemical structure:

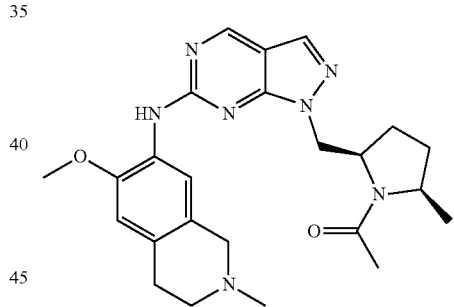

or a pharmaceutically acceptable salt thereof.

* * * * *